United States Patent
Fuchino et al.

(10) Patent No.: US 9,527,840 B2
(45) Date of Patent: Dec. 27, 2016

(54) SUBSTITUTED-QUINOXALINE-TYPE PIPERIDINE COMPOUNDS AND THE USES THEREOF

(71) Applicants: Purdue Pharma L.P., Stamford, CT (US); Shionogi & Co. Ltd., Chuo-ku, Osaka-shi (JP)

(72) Inventors: Kouki Fuchino, Osaka (JP); R. Richard Goehring, Pipersville, PA (US); Bin Shao, Richboro, PA (US); Yoshiyuki Taoda, Osaka (JP); Naoki Tsuno, Osaka (JP); John William Frank Whitehead, Newton, PA (US); Jiangchao Yao, Monmouth Junction, NJ (US)

(73) Assignees: Purdue Pharma L.P., Stamford, CT (US); Shionogi & Co. Ltd. (JP)

( * ) Notice: Subject to any disclaimer, the term of this patent is extended or adjusted under 35 U.S.C. 154(b) by 0 days.

(21) Appl. No.: 15/041,998

(22) Filed: Feb. 11, 2016

(65) Prior Publication Data

US 2016/0159785 A1 Jun. 9, 2016

Related U.S. Application Data

(60) Continuation of application No. 14/331,034, filed on Jul. 14, 2014, now Pat. No. 9,278,967, which is a division of application No. 12/712,042, filed on Feb. 24, 2010, now Pat. No. 8,846,929, which is a continuation of application No. PCT/IB2008/002291, filed on Aug. 29, 2008.

(60) Provisional application No. 61/082,464, filed on Jul. 21, 2008, provisional application No. 61/046,364, filed on Apr. 18, 2008, provisional application No. 60/989,791, filed on Nov. 21, 2007, provisional application No. 60/966,994, filed on Aug. 31, 2007.

(51) Int. Cl.
| | |
|---|---|
| *A61K 31/498* | (2006.01) |
| *C07D 451/14* | (2006.01) |
| *C07D 401/04* | (2006.01) |
| *C07D 401/14* | (2006.01) |
| *C07D 451/04* | (2006.01) |
| *C07D 471/14* | (2006.01) |
| *C07D 471/08* | (2006.01) |
| *C07D 487/04* | (2006.01) |
| *C07D 498/08* | (2006.01) |
| *C07D 519/00* | (2006.01) |

(52) U.S. Cl.
CPC .......... *C07D 451/14* (2013.01); *C07D 401/04* (2013.01); *C07D 401/14* (2013.01); *C07D 451/04* (2013.01); *C07D 471/08* (2013.01); *C07D 471/14* (2013.01); *C07D 487/04* (2013.01); *C07D 498/08* (2013.01); *C07D 519/00* (2013.01); *A61K 31/498* (2013.01)

(58) Field of Classification Search
CPC ........................ C07D 451/14; A61K 31/498
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 3,963,727 A | 6/1976 | Ueno et al. |
| 4,008,719 A | 2/1977 | Theeuwes et al. |
| 5,059,595 A | 10/1991 | Le Grazie |
| 5,073,543 A | 12/1991 | Marshall et al. |
| 5,120,548 A | 6/1992 | McClelland et al. |
| 5,283,244 A | 2/1994 | Sakamoto et al. |
| 5,354,556 A | 10/1994 | Sparks et al. |
| 5,591,767 A | 1/1997 | Mohr et al. |
| 5,639,476 A | 6/1997 | Oshlack et al. |
| 5,665,719 A | 9/1997 | Bock et al. |
| 5,674,533 A | 10/1997 | Santus et al. |
| 5,698,155 A | 12/1997 | Grosswald et al. |
| 5,733,566 A | 3/1998 | Lewis |
| 5,739,129 A | 4/1998 | Aquino et al. |
| 5,859,007 A | 1/1999 | Aquino et al. |
| 5,922,717 A | 7/1999 | Pieper et al. |
| 6,136,839 A | 10/2000 | Isakson et al. |
| 6,172,067 B1 | 1/2001 | Ito et al. |
| 6,258,825 B1 | 7/2001 | Ozaki et al. |
| 6,262,066 B1 | 7/2001 | Tulshian et al. |
| 6,340,681 B1 | 1/2002 | Ito |
| 6,423,716 B1 | 7/2002 | Matsuno et al. |

(Continued)

FOREIGN PATENT DOCUMENTS

| | | |
|---|---|---|
| CA | 1085852 A | 9/1980 |
| EP | 0990653 A1 | 4/2000 |

(Continued)

OTHER PUBLICATIONS

Bartho et al., "Involvement of Capsaicin-Sensitive Neurones in Hyperalgesia and Enhanced Opioid Antinociception in Inflammation," *Naunyn-Schmiedeberg's Archives Pharmacol.* 342:666-670 (1990).

(Continued)

*Primary Examiner* — Alexander R Pagano
(74) *Attorney, Agent, or Firm* — Dechert LLP

(57) ABSTRACT

The invention relates to Substituted-Quinoxaline-Type Piperidine Compounds, compositions comprising an effective amount of a Substituted-Quinoxaline-Type Piperidine Compound and methods to treat or prevent a condition, such as pain, comprising administering to an animal in need thereof an effective amount of a Substituted-Quinoxaline-Type Piperidine Compound.

20 Claims, No Drawings

(56) References Cited

U.S. PATENT DOCUMENTS

| | | |
|---|---|---|
| 6,423,725 B1 | 7/2002 | Ito et al. |
| 6,455,527 B2 | 9/2002 | Tulshian et al. |
| 6,576,644 B2 | 6/2003 | Bi et al. |
| 6,586,430 B1 | 7/2003 | Armour et al. |
| 6,635,653 B2 | 10/2003 | Goehring et al. |
| 6,828,440 B2 | 12/2004 | Goehring et al. |
| 6,835,737 B2 | 12/2004 | Bi et al. |
| 6,861,421 B2 | 3/2005 | Goehring et al. |
| 6,861,425 B2 | 3/2005 | Ito et al. |
| 6,867,222 B2 | 3/2005 | Sun et al. |
| 6,872,733 B2 | 3/2005 | Goehring et al. |
| 6,989,393 B2 | 1/2006 | Burrows et al. |
| 7,001,901 B2 | 2/2006 | Yang |
| 7,041,667 B1 | 5/2006 | Armour et al. |
| 7,217,714 B1 | 5/2007 | Armour et al. |
| 7,300,947 B2 | 11/2007 | Hashimoto et al. |
| 7,456,198 B2 | 11/2008 | Kyle et al. |
| 7,459,556 B2 | 12/2008 | Mergelsberg et al. |
| 7,495,109 B2 | 2/2009 | Sun et al. |
| 7,538,115 B2 | 5/2009 | Hurnaus et al. |
| 7,563,809 B2 | 7/2009 | Goehring et al. |
| 7,678,809 B2 | 3/2010 | Kyle et al. |
| 7,851,630 B2 | 12/2010 | Den Hartog et al. |
| 7,858,635 B2* | 12/2010 | Makings ............... A61K 31/438 514/212.02 |
| 7,939,670 B2 | 5/2011 | Sun et al. |
| 8,110,602 B2* | 2/2012 | Brown ................. C07D 401/04 514/549 |
| 8,252,815 B2 | 8/2012 | Sun et al. |
| 8,476,271 B2* | 7/2013 | Tsuno ................... C07D 403/04 514/249 |
| 8,637,502 B2* | 1/2014 | Brown ................. C07D 401/04 514/221 |
| 8,846,929 B2* | 9/2014 | Fuchino ............... C07D 401/04 546/184 |
| 9,040,533 B2* | 5/2015 | Marra ................... C07D 451/04 514/249 |
| 9,145,408 B2* | 9/2015 | Tsuno ................... C07D 403/04 |
| 9,278,967 B2* | 3/2016 | Fuchino ............... C07D 401/04 |
| 2003/0134846 A1 | 7/2003 | Windsor et al. |
| 2003/0149027 A1 | 8/2003 | Oi et al. |
| 2003/0207886 A1 | 11/2003 | Plucker et al. |
| 2004/0082784 A1 | 4/2004 | Sielecki-Dzurdz et al. |
| 2004/0087641 A1 | 5/2004 | Goehring et al. |
| 2004/0220177 A1 | 11/2004 | Kath et al. |
| 2005/0119308 A1 | 6/2005 | Teshima et al. |
| 2005/0215546 A1 | 9/2005 | Hurnaus et al. |
| 2005/0228023 A1 | 10/2005 | Zaveri et al. |
| 2006/0264638 A1 | 11/2006 | Kyle et al. |
| 2008/0015214 A1 | 1/2008 | Bignan et al. |
| 2008/0214827 A1 | 9/2008 | Goehring et al. |
| 2010/0022519 A1* | 1/2010 | Brown ................. C07D 401/04 514/221 |
| 2010/0120841 A1 | 5/2010 | Nakano et al. |
| 2010/0173935 A1 | 7/2010 | Cheng et al. |
| 2010/0216726 A1* | 8/2010 | Fuchino ............... C07D 401/04 514/1.1 |
| 2011/0178090 A1* | 7/2011 | Fuchino ............... C07D 403/04 514/249 |
| 2012/0108575 A1* | 5/2012 | Brown ................. C07D 401/04 514/221 |
| 2013/0274265 A1* | 10/2013 | Fuchino ............... C07D 403/04 514/249 |
| 2014/0187544 A1* | 7/2014 | Marra ................... C07D 451/04 514/230.5 |
| 2015/0141643 A1* | 5/2015 | Fuchino ............... C07D 401/04 544/105 |
| 2015/0238485 A1* | 8/2015 | Marra ................... C07D 451/04 514/230.5 |
| 2016/0002203 A1* | 1/2016 | Tadesse ............... C07D 401/04 514/266.21 |
| 2016/0009717 A1* | 1/2016 | Fuchino ............... C07D 403/04 514/249 |
| 2016/0159785 A1* | 6/2016 | Fuchino ............... C07D 401/04 514/249 |

FOREIGN PATENT DOCUMENTS

| | | |
|---|---|---|
| EP | 1067123 A1 | 1/2001 |
| EP | 2128154 A1 | 12/2009 |
| EP | 2324013 B1 | 9/2012 |
| EP | 2537844 A1 | 12/2012 |
| GB | 1542514 A | 3/1979 |
| JP | 51-136673 A | 11/1976 |
| JP | 51-146473 A | 12/1976 |
| JP | 51-146474 A | 12/1976 |
| JP | 2006/327947 A | 12/2006 |
| WO | WO 95/02405 A1 | 1/1995 |
| WO | WO 95/03299 A1 | 2/1995 |
| WO | WO 99/32481 A1 | 7/1999 |
| WO | WO 99/46260 A1 | 9/1999 |
| WO | WO 00/06545 A1 | 2/2000 |
| WO | WO 00/08013 A2 | 2/2000 |
| WO | WO 01/34571 A1 | 5/2001 |
| WO | WO 02/080895 A2 | 10/2002 |
| WO | WO 02/085361 A1 | 10/2002 |
| WO | WO 03/062234 A1 | 7/2003 |
| WO | WO 03/076432 A1 | 9/2003 |
| WO | WO 2006/038112 A1 | 4/2006 |
| WO | WO 2006/101245 A1 | 9/2006 |
| WO | WO 2008/089201 A2 | 7/2008 |
| WO | WO 2008/105497 A1 | 9/2008 |
| WO | WO 2008/122510 A1 | 10/2008 |
| WO | WO 2008/089201 A3 | 12/2008 |

OTHER PUBLICATIONS

Berdini et al., "A modified palladium catalysed reductive amination procedure," *Tetrahedron* 58:5669-5674 (2002).

Bignan et al., "Recent advances towards the discovery of ORL-1 receptor agonists and antagonists," *Expert Opin. Ther. Patents* 15(4):357-388 (2005).

Bingham et al.,"Over one hundred solvates of sulfathiazole," *Chem. Comm.*, pp. 603-604 (2001).

Buchwald et al., "Long-term, Continuous Intravenous Heparin Administration by an Implantable Infusion Pump in Ambulatory Patients with Recurrent Venous Thrombosis," *Surgery* 88:507-516 (1980).

Bundgaard et al.,"Glycolamide Esters as Biolabile Prodrugs of Carboxylic Acid Agents: Synthesis, Stability, Bioconversion, and Physicochemical Properties," *J. Pharmaceut. Sci.* 77(4):285-298 (1988).

Bundgaard, "(C) Means to Enhance Penetration (1) Prodrugs as a means to improve the delivery of peptide drugs," *Advanced Drug Delivery Revs.* 8:1-38 (1992).

Bundgaard, "Design and Application of Prodrugs," in a *Textbook of Drug Design and Development*, P. Krogsgaard-Larsen and H. Bundgaard, eds., Harwood Academic Publishers, Chapter 5, pp. 113-191 (1991).

Bundgaard, ed., *Design of Prodrugs*, Elsevier, Amsterdam (1985).

Caira et al., "Preparation and Crystal Characterization of a Polymorph, a Monohydrate, and an Ethyl Acetate Solvate of the Antifungal Fluconazole," *J. Pharmaceut. Sci.* 93(3):601-611 (2004).

Carroll et al., "N-Substituted 4-beta-Methyl-5-(3-hydroxyphenyl)-7-alpha-amidomorphans are Potent, Selective Kappa Opioid Receptor Antagonists" *J. Med. Chem.* 49:1781-1791 (2006).

Colowick et al., "Drug and Enzyme Targeting, Part A," in J. Widder et al., eds., *Methods in Enzymology*, vol. 112, Academic Press (1985).

Communication Pursuant to Article 94(3) EPC for EP application No. 08806986.9 dated Nov. 13, 2009.

(56) References Cited

OTHER PUBLICATIONS

Communication Pursuant to Article 94(3) EPC for EP application No. 08806986.9 dated Jul. 22, 2011.
Communication Pursuant to Article 94(3) EPC for EP application No. 08806986.9 dated Oct. 8, 2012.
Communication Pursuant to Article 94(3) EPC for EP application No. 08806986.9 dated May 14, 2013.
Communication Pursuant to Article 94(3) EPC for EP application No. 11188195.9 dated Sep. 16, 2013.
Cramer et al., "Enantioselective Desymmetrization of Tropinone Derivatives by Hydroboration," *Synlett.* 14:2175-2177 (2003).
D'Amour et al., "A Method for Determining Loss of Pain Sensation," *J. Pharmacol. Exp. Ther.* 72:74-79 (1941).
Dudash et al., "Synthesis and evaluation of 3-anilino-quinoxalinones as glycogen phosphorylase inhibitors," *Bioorg. Med. Chem. Lett.* 15:4790-4793 (2005).
During et al., "Controlled Release of Dopamine from a Polymeric Brain Implant: In Vivo Characterization," *Ann. Neurol.* 25:351-356 (1989).
Extended European Search Report for EP application No. 11188189.2 dated Feb. 27, 2012.
Extended European Search Report for EP application No. 11188205.6 dated Feb. 27, 2012.
Extended European Search Report for EP application No. 11188195.9 dated Feb. 27, 2012.
Filer, "The Preparation and Characterization of Tritiated Neurochemicals," *Isotopes in the Physical and Biomedical Sciences*, vol. 1, Labeled Compounds (Part A), E. Buncel et al, eds., Chapter 6, pp. 155-192 (1987).
"Flunitrazepam," National Library of Medicine—Medical Subject Headings, 2009, entry at http://www.nlm.nih.gov/cgi/mesh/2009/MB_cgi?mode=&term=Flunitrazepam.
Ghaffar et al., "A New Homogeneous Platinum Containing Catalyst for the Hydrolysis of Nitriles," *Tetrahedron Lett.* 36(47):8657-8660 (1995).
Goodson, "Dental Applications," in *Medical Applications of Controlled Release*, vol. 2, Applications and Evaluation, R.S. Langer and D.L. Wise, eds., CRC Press, Chapter 6, pp. 115-138 (1984).
Greene et al., "Protective Groups in Organic Synthesis," 3$^{rd}$ Ed., John Wiley & Sons, Inc., New York, pp. 531-535 & 556-557 (1999).
Grupp et al., "Protection against Hypoxia-reoxygenation in the Absence of Poly (ADP-ribose) Synthetase in Isolated Working Hearts," *J. Mol. Cell Cardiol.* 31:297-303 (1999).
Hall, "Synthesis and Polymerization of 3-Azabicyclo-[4.3.1]decan-4-one and 7,7-Dimethyl-2-azabicyclo[4.1.1]octan-3-one," *J. Org. Chem.* 28:3213-3214 (1963).
*Handbook of Pharmaceutical Excipients*, American Pharmaceutical Association, Washington, D.C. (1986).
Hanson, "Analgesic, Antipyretic and Anti-Inflammatory Drugs," *Remington: The Science and Practice of Pharmacy*, vol. II 1196-1221 (Gennaro ed. 19$^{th}$ ed. 1995).
Hargreaves et al., "A New and Sensitive Method for Measuring Thermal Nociception in Cutaneous Hyperalgesia," *Pain* 32(1):77-88 (1988).
Hey et al., "The Guinea Pig Model for Assessing Cardiotoxic Proclivities of Second Generation Antihistamines," *Arzneim.-Forsch./Drug Res.* 46(8):834-837 (1996).
Howard et al., "Intracerebral Drug Delivery in Rats With Lesion-Induced Memory Deficits," *J. Neurosurg.* 71:105-112 (1989).
Insel, "Analgesic-Antipyretic and Anti-inflammatory Agents and Drugs Employed in the Treatment of Gout," in *Goodman & Gilman's The Pharmacological Basis of Therapeutics* pp. 617-657 (Goodman et al., eds., 9$^{th}$ ed., McGraw-Hill, New York 1996).
International Search Report and Written Opinion of the International Searching Authority for PCT/IB2008/002291 dated Feb. 6, 2009.
Japanese Official Action dated Oct. 2, 2012 (English translation) for Japanese Patent Application No. 2010-522469.
Japanese Official Action dated Sep. 24, 2013 (English translation) for Japanese Patent Application No. 2010-522469.
Kakeya et al., "Studies on Prodrugs of Cephalosporins. I. Synthesis and Biological Properties of Glycyloxygenzoyloxymethyl and Glycylaminobenzoyloxymethyl Esters of 7β-[2-(2-Aminothiazol-4-yl)-(Z)-2-methoxyiminoacetam ido]-3-methyl-3-cephem-4-carboxylic Acid," *Chem. Pharm. Bull.* 32(2):692-698 (1984).
Keeton et al., "Specific and Sensitive Radioimmunoassay for 3-Methoxy-4-hydroxyphenylethyleneglycol (MOPEG)," *Science* 211:586-588 (1981).
Kim, "An Experimental Model for Peripheral Neuropathy Produced by Segmental Spinal Nerve Ligation in the Rat," *Pain* 50(3):355-363 (1992).
King, "Tablets, Capsules, and Pills," in A. Osol, ed., *Remington's Pharmaceutical Sciences*, 16$^{th}$ Ed., Mack Publishing, Easton, PA, Ch. 89, pp. 1553-1584 (1980).
Langer et al., "Chemical and Physical Structure of Polymers as Carriers for Controlled Release of Bioactive Agents: A Review," *J. Macramol. Sci. Rev. Macromol. Chem.* C23(1):61-126 (1983).
Langer et al., "Classes of Systems," *Medical Applications of Controlled Release* vol. I, CRC Press, Boca Raton, FL (1984).
Langer, "New Methods of Drug Delivery," *Science* 249:1527-1533 (1990).
Lazareno, "Measurement of agonist-stimulated [$^{35}$S]GTPγS binding to cell membranes" in M. Keen, ed., *Methods in Molecular Biology*, vol. 106, pp. 231-245, Humana Press (1999).
Levy et al., "Inhibition of Calcification of Bioprosthetic Heart Valves by Local Controlled-Release Diphosphonate," *Science* 228:190-192 (1985).
Lewin et al., "Molecular Features Associated with Polyamine Modulation of NMDA Receptors," *J. Med. Chem.* 41:988-995 (1998).
Lieberman et al., *Pharmaceutical Dosage Forms: Disperse Systems*, 2$^{nd}$ Ed., Marcel Dekker, Inc. (1996 & 1998).
Lieberman et al., *Pharmaceutical Dosage Forms: Tablets*, 2$^{nd}$ Ed., Marcel Dekker, Inc., New York (1989 & 1990).
Milligan, "Principles: Extending the utility of [$^{35}$S]GTPγS binding assays," *Trends Pharmacol. Sci.* 24(2):87-90 (2003).
Momose et al.,"Bicyclo[3.3.1]nonanes as Synthetic Intermediates. I. Improved Synthetic Methods for Bicyclo[3.3.1]nonan-3-one," *Chem. Pharm. Bull.* 26(1):288-295 (1978).
Narita et al., "Identification of the G-protein coupled ORL1 receptor in the mouse spinal cord by [$^{35}$S]-GTPγS binding and immunohistochemistry," *Brit. J. Pharmacol.* 128:1300-1306 (1999).
Olofson et al., "A New Reagent for the Selective, High-Yield N-Dealkylation of Tertiary Amines: Improved Syntheses of Naltrexone and Nalbuphine," *J. Org. Chem.* 49(11):2081-2082(1984).
Olofson et al., "Value of the Vinyloxycarbonyl Unit in Hydroxyl Protection: Application to the Synthesis of Nalorphin," *Tetrahedron Lett.* 18:1571-1574 (1977).
Perregaard et al., "Studies on Organophosphorus Compounds XVIII. Oxidation of Tertiary Alicyclic Amines with Elem ental Sulfur in Hexamethylphosphoric Triamide (HMPA). Oxidative Rearrangements of Hexahydroazepines and Octahydroazocines to Bis(3-Pyrrolyl)Polysulfides.," *Bull. Soc. Chim. Belg.* 86(9):679-691 (1977).
Porter, "The Zinin Reduction of Nitroarenes," *Org. Reactions* 20:455-481 (1973).
Poulain et al., "From Hit to Lead. Analyzing Structure-Profile Relationships," *J. Med. Chem.* 44:3391-3401 (2001).
Poulain et al., "From Hit to Lead. Combining Two Complementary Methods for Focused Library Design. Application to μ Opiate Ligands," *J. Med. Chem.* 44:3378-3390 (2001).
Radebough et al., "Preformulation," pp. 1447-1676 in *Remington's Pharmaceutical Sciences* vol. 2 (Gennaro, ed., 19$^{th}$ ed., Mack Publishing, Easton, PA, 1995).
Robinson, "Coating of Pharmaceutical Dosage Forms," in A. Osol, ed., *Remington's Pharmaceutical Sciences*, 16$^{th}$ Ed., Mack Publishing, Easton, PA, Ch. 89, pp. 1585-1593 (1980).
Ronzoni et al., "Lead generation and lead optimization approaches in the discovery of selective, non-peptide ORL-1 receptor agonists and antagonists," *Expert Opin. Ther. Patents* 11(4):525-546 (2001).

(56) References Cited

OTHER PUBLICATIONS

Ross et al., "Pharmacodynamics: Mechanisms of Drug Action and the Relationship Between Drug Concentration and Effect," in *Goodman & Gilman's the Pharmacological Basis of Therapeutics* pp. 31-43 (Goodman et al., eds., 10th ed., McGraw-Hill, New York 2001).
Rylander, "Hydrogenation of Nitro Compounds," in *Hydrogenation Methods* pp. 104-116 (Academic Press, London, 1985).
Sato et al., "Psychotropic Agents. 3. 4-(4-Substituted piperidinyl)-1-(4-fluorophenyl)-1-butanones with Potent Neuroleptic Activity," *J. Med. Chem.* 21(11):1116-1120(1978).
Saudek et al., "A Preliminary Trial of the Programmable Implantable Medication System for Insulin Delivery," *New Engl. J. Med.* 321:574-579 (1989).
Sefton, "Implantable Pumps," *CRC Crit. Rev. Biomed. Eng.* 14(3):201-240 (1987).
Seltzer et al., "A Novel Behavioral Model of Neuropathic Pain Disorders Produced in Rats by Partial Sciatic Nerve Injury," *Pain* 43:205-218 (1990).
Shimohigashi et al., "Sensitivity of opioid receptor-like receptor ORL1 for chemical modification on nociceptin, a naturally occurring nociceptive peptide," *J. Biol. Chem.* 271(39):23642-23645 (1996).
Smolen et al., "Drug Product Design and Performance," *Controlled Drug Bioavailability* vol. 1, John Wiley & Sons, New York (1984).
Stein, "Unilateral Inflammation of the Hindpaw in Rats as a Model of Prolonged Noxious Stimulation: Alterations in Behavior and Nociceptive Thresholds," *Pharmacol. Biochem. Behavior* 31:451-455 (1988).
Stradomskii et al., "Molecular Mechanisms of the Psychotropic Action of Trimethidon," *Pharma. Chem. J.* 31(1):7-8 (1997).
Sweet et al., "Synthesis of an Affinity Chromatography Column Designed for Recovery of Labile Proteins," *Biochem. Biophys. Res. Comm.* 63(1):99-105 (1975).
"Tofranil-PM," Physicians' Desk Reference, 51st Ed., Montvale, NJ, pp. 876-878 (1997).
Tortolani et al., "A Convenient Synthesis to N-Aryl-Substituted 4-Piperidones," *Org. Lett.* 1(8):1261-1262 (1999).
Treat et al., "Liposome encapsulated doxorubicin—preliminary results of phase I and phase II trials" *Liposomes in the Therapy of Infectious Disease and Cancer*, pp. 317-327 and 353-365 (1989).
Van Tonder et al., "Preparation and Physicochemical Characterization of 5 Niclosamide Solvates and 1 Hemisolvate," *AAPS Pharm. Sci. Tech.* 5(1):Article 12, pp. 1-10 (2004).
Webb, "A Mild, Inexpensive and Practical Oxidation of Sulfides," *Tetrahedron Lett.* 35(21):3457-3460 (1994).
Zhou et al., "Properties of HERG Channels Stably Expressed in HEK 293 Cells Studied at Physiological Temperature," *Biophys. J.* 74:230-241 (1998).
Zirkle et al., "The Isomeric 3-Oxa- and 3-Thiagranatanin-7-ols and Their Derivatives; Reduction of Bicyclic Amino Ketones Related to Tropinone" *J. Org. Chem.* 26:395-407 (1961).

\* cited by examiner

US 9,527,840 B2

SUBSTITUTED-QUINOXALINE-TYPE PIPERIDINE COMPOUNDS AND THE USES THEREOF

CROSS REFERENCE TO RELATED APPLICATIONS

This application is a continuation of application Ser. No. 14/331,034, filed Jul. 14, 2014, now U.S. Pat. No. 9,278, 967, which is a divisional of application Ser. No. 12/712, 042, filed Feb. 24, 2010, now U.S. Pat. No. 8,846,929, which is a continuation of PCT application serial no. PCT/IB2008/ 002291, filed Aug. 29, 2008 which claims the benefit under 35 U.S.C. 119(e) of provisional application no. 61/082 464 filed Jul. 21, 2008, provisional application no. 61/046,364, filed Apr. 18, 2008, provisional application no. 60/989,791, filed Nov. 21, 2007, and provisional application no. 60/966, 994, filed Aug. 31, 2007, the contents of all of which are incorporated herein by reference.

1. FIELD OF THE INVENTION

The invention relates to Substituted-Quinoxaline-Type Piperidine Compounds, compositions comprising an effective amount of a Substituted-Quinoxaline-Type Piperidine Compound and methods to treat or prevent a condition, such as pain, comprising administering to an animal in need thereof an effective amount of a Substituted-Quinoxaline-Type Piperidine Compound.

2. BACKGROUND OF THE INVENTION

Chronic pain is a major contributor to disability and is the cause of much suffering. The successful treatment of severe and chronic pain is a primary goal of the physician, with opioid analgesics being preferred drugs for doing so.

Until recently, there was evidence of three major classes of opioid receptors in the central nervous system (CNS), with each class having subtype receptors. These receptor classes are known as μ, κ and δ. As opiates have a high affinity for these receptors while not being endogenous to the body, research followed in order to identify and isolate the endogenous ligands to these receptors. These ligands were identified as endorphins, dynorphins and enkephalins, respectively.

Recent experimentation has led to the identification of a cDNA encoding an opioid receptor-like (ORL-1) receptor with a high degree of homology to the known receptor classes. The ORL-1 receptor was classified as an opioid receptor based only on structural grounds, as the receptor did not exhibit pharmacological homology. It was initially demonstrated that non-selective ligands having a high affinity for μ, κ and δ receptors had low affinity for the ORL-1 receptor. This characteristic, along with the fact that an endogenous ligand had not yet been discovered, led to the term "orphan receptor".

Subsequent research led to the isolation and structure of the endogenous ligand of the ORL-1 receptor (i.e., nociceptin; also known as orphanin FQ (OFQ)). This ligand is a seventeen amino acid peptide structurally similar to members of the opioid peptide family.

The discovery of the ORL-1 receptor presents an opportunity in drug discovery for novel compounds that can be administered for pain management or other syndromes modulated by this receptor.

International PCT Publication No. WO 99/46260 A1 describes quinoxalinone derivatives as inhibitors of protein kinase C.

International PCT Publication No. WO 99/50254 A1 describes quinoxalinone derivatives as serine protease inhibitors.

International PCT Publication No. WO 01/90102 A2 describes 6-heterocyclyl-3-oxo-3,4-dihydro-quinoxalines for use as herbicides.

International PCT Publication No. WO 2005/028451 A1 describes tetrahydroquinoxaline derivatives for use as M2 acetylcholine receptor agonists.

International PCT Publication No. WO 2003/062234 A1 describes quinoxaline derivatives for use in remedying diseases in which poly(ADP-ribose) polymerase (PARP) participates.

U.S. published patent application No. US 2005/0256000 by Schaper et al. describes quinoxaline-2-one derivatives for use as safeners for plants.

Citation of any reference in Section 2 of this application is not to be construed as an admission that such reference is prior art to the present application.

3. SUMMARY OF THE INVENTION

It is an object of the invention to provide new compounds that exhibit affinity for the ORL-1 receptor.

In certain embodiments of the invention, such new compounds exhibit agonist activity at the ORL-1 receptor.

In certain embodiments of the invention, such new compounds exhibit partial agonist activity at the ORL-1 receptor.

In certain other embodiments of the invention, such new compounds exhibit antagonist activity at the ORL-1 receptor.

In certain embodiments of the invention, such new compounds exhibit affinity for the ORL-1 receptor, and also for one or more of the μ, κ or δ receptors. In a particular embodiment, a new compound of the invention exhibits affinity for both the ORL-1 receptor and the μ receptor. In another embodiment, a new compound of the invention acts as an ORL-1 receptor agonist and as a μ receptor agonist. In another embodiment, a new compound of the invention acts as an ORL-1 receptor partial agonist and as a μ receptor agonist. In another embodiment, a new compound of the invention acts as an ORL-1 receptor partial agonist and as a μ receptor antagonist. In another embodiment, a new compound of the invention acts as an ORL-1 receptor antagonist and as a μ receptor agonist.

Certain new compounds of the invention can be used to treat an animal suffering from chronic or acute pain.

It is a further object of the invention to provide methods of treating chronic or acute pain in an animal by administering one or more Substituted-Quinoxaline-Type Piperidine Compounds of the invention to an animal in need of such treatment. In certain embodiments, such new Substituted-Quinoxaline-Type Piperidine Compounds effectively treat chronic or acute pain in the animal, while producing fewer or reduced side effects compared to previously available compounds.

The invention encompasses compounds of Formula (I) and Formula (II):

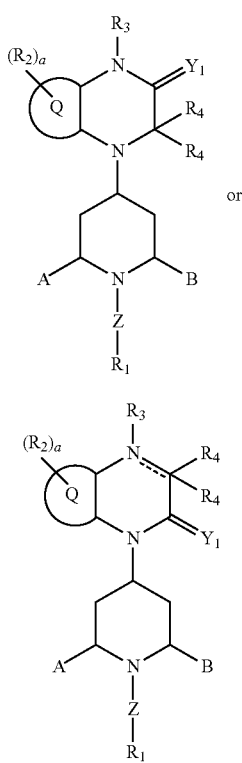

and pharmaceutically acceptable derivatives thereof wherein:

$Y_1$ is O or S;

Q is selected from fused benzo or (5- or 6-membered)heteroaryl;

each $R_2$ is independently selected from:
(a) -halo, —CN, —NO$_2$, —OT$_3$, —C(=O)T$_3$, —C(=O)OT$_3$, —C(=O)N(T$_1$)(T$_2$), —S(=O)$_2$OH, —S(=O)T$_3$, —S(=O)$_2$T$_3$, —S(=O)$_2$N(T$_1$)(T$_2$), —N(T$_1$)(T$_2$), —N(T$_3$)C(=O)T$_3$, —N(T$_3$)C(=O)N(T$_1$)(T$_2$), —N(T$_3$)S(=O)$_2$T$_3$, or —N(T$_3$)S(=O)$_2$N(T$_1$)(T$_2$); or
(b) —(C$_1$-C$_6$)alkyl, —(C$_2$-C$_6$)alkenyl, —(C$_2$-C$_6$)alkynyl, —(C$_3$-C$_7$)cycloalkyl, —(C$_1$-C$_6$)alkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(5- or 6-membered)heterocycle, or -(7- to 10-membered)bicycloheterocycle, each of which is unsubstituted or substituted with 1, 2 or 3 independently selected $R_8$ groups; or
(c) -phenyl, -naphthalenyl, —(C$_{14}$)aryl, or -(5- or 6-membered)heteroaryl, each of which is unsubstituted or substituted with 1, 2 or 3 independently selected $R_7$ groups;

a is an integer selected from 0, 1 or 2;

the dashed line in the 6-membered, nitrogen-containing ring that is fused to the Q group denotes the presence or absence of a bond, and when that dashed line denotes the presence of a bond then $R_3$ and one $R_4$ are absent;

$R_3$ is selected from:
(a) —H; or
(b) —(C$_1$-C$_4$)alkyl which is unsubstituted or substituted with 1, 2 or 3 groups independently selected from —OH, —(C$_1$-C$_4$)alkoxy, —N(R$_6$)$_2$, —C(=O)OR$_9$, or —C(=O)N(R$_6$)$_2$; or
(c) —(C$_3$-C$_7$)cycloalkyl which is unsubstituted or substituted with 1, 2 or 3 groups independently selected from —OH, —(C$_1$-C$_4$)alkyl, —(C$_1$-C$_4$)alkoxy, —N(R$_6$)$_2$, —C(=O)OR$_9$, or —C(=O)N(R$_6$)$_2$;

each $R_4$ is independently selected from:
(a) —H; or
(b) -halo, —CN, or —NO$_2$; or
(c) —X, —CH$_2$X, —CH$_2$CH$_2$X, —(C$_1$-C$_6$)alkyl-X, -(5- or 6-membered)heterocycle-X, -(5- or 6-membered)heterocycle-(C$_1$-C$_6$)alkyl-X, or -(5- or 6-membered)heterocycle-(C$_1$-C$_6$)alkyl-R$_8$; or
(d) —C(=Y)CN, —C(=Y)X, —C(=Y)T$_3$, —C(=Y)YX, —C(=Y)YT$_3$, —C(=Y)N(T$_1$)(T$_2$), —C(=Y)N(R$_9$)CN, —C(=Y)N(R$_9$)X, —C(=Y)N(R$_9$)CH$_2$CH$_2$N(T$_1$)(T$_2$), —C(=Y)N(R$_9$)YH, —C(=Y)N(R$_9$)YX, —C(=Y)N(R$_9$)YCH$_2$X, —C(=Y)N(R$_9$)YCH$_2$CH$_2$X, or —C(=Y)N(R$_9$)S(=O)$_2$T$_3$; or
(e) —N(R$_9$)X, —N(R$_9$)—CH$_2$X, —N(R$_9$)—CH$_2$CH$_2$X, —N(R$_9$)—CH$_2$CH$_2$N(R$_9$)X, —N(R$_9$)CH$_2$CH$_2$N(T$_1$)(T$_2$), —N(R$_9$)CH$_2$C(=Y)X, —N((C$_1$-C$_6$)alkyl-C(=O)OR$_9$)$_2$, —N(R$_9$)CH$_2$N(R$_9$)C(=N(R$_{12}$))N(R$_{12}$)$_2$, —N(R$_9$)—CH$_2$CH$_2$N(R$_9$)C(=N(R$_{12}$))N(R$_{12}$)$_2$, —N(T$_1$)(T$_2$), —N(T$_3$)C(=Y)T$_3$, —N(T$_3$)C(=Y)YT$_3$, —N(T$_3$)C(=Y)N(T$_1$)(T$_2$), —N(T$_3$)S(=O)$_2$T$_3$, or —N(T$_3$)S(=O)$_2$N(T$_1$)(T$_2$); or
(f) —YH, —CH$_2$YH, —CH$_2$CH$_2$YH, —YX, or —YT$_3$; or
(g) —S(=O)T$_3$, —S(=O)$_2$T$_3$, —S(=O)T$_3$, —S(=O)N(T$_1$)(T$_2$), —S(=O)$_2$N(T$_1$)(T$_2$), —S(=O)X, or —S(=O)$_2$X;

X is:
(a) —H, —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(5- or 6-membered)heterocycle, or -(7- to 10-membered)bicycloheterocycle, each of which is unsubstituted or substituted with 1, 2 or 3 independently selected $R_8$ groups; or
(b) -phenyl, -benzyl, -naphthalenyl, —(C$_{14}$)aryl, —(C$_1$-C$_6$)alkyl-(5- or 6-membered)heteroaryl or -(5- or 6-membered)heteroaryl, each of which is unsubstituted or substituted with 1, 2 or 3 independently selected $R_7$ groups;

each Y is independently selected from O or S;

A and B are independently selected from:
(a) —H, —CN, —C(=O)OT$_3$, or —C(=O)N(T$_1$)(T$_2$); or
(b) —(C$_3$-C$_{12}$)cycloalkyl, —(C$_3$-C$_{12}$)cycloalkoxy, —(C$_1$-C$_6$)alkyl, —(C$_2$-C$_6$)alkenyl, —(C$_2$-C$_6$)alkynyl, or —(C$_1$-C$_6$)alkoxy, each of which is unsubstituted or substituted with 1 or 2 substituents independently selected from —OH, —S(=O)$_2$NH$_2$, —N(R$_6$)$_2$, =NR$_6$, —C(=O)OT$_3$, —C(=O)N(R$_6$)$_2$, —N(R$_6$)C(=O)R$_9$, and -(5- or 6-membered)heterocycle, or 1, 2 or 3 independently selected -halo; or
(c) A-B can together form a (C$_2$-C$_6$)bridge, which is unsubstituted or substituted with 1, 2, 3, 4, 5, 6, 7 or 8 substituents independently selected from —OH, —(C$_1$-C$_4$)alkyl, -halo, and —C(halo)$_3$, and which bridge optionally contains —HC=CH— or —O— within the (C$_2$-C$_6$)bridge; wherein the 6-membered, nitrogen-containing ring that is fused to the Q group can be in the endo- or exo-configuration with respect to the A-B bridge; or
(d) A-B can together form a —CH$_2$—N(R$_a$)—CH$_2$— bridge, a

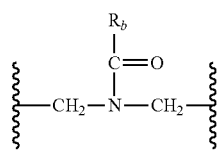

bridge, or a

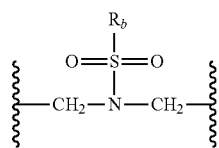

bridge;

wherein the 6-membered, nitrogen-containing ring that is fused to the Q group can be in the endo- or exo- configuration with respect to the A-B bridge;

$R_a$ is selected from —H, —$(C_1$-$C_6)$alkyl, —$(C_3$-$C_7)$cycloalkyl, —$CH_2$—$C(=O)$—$R_c$, —$(CH_2)$—$C(=O)$—$OR_c$, —$(CH_2)$—$C(=O)$—$N(R_c)_2$, —$(CH_2)_2$—$O$—$R_c$, —$(CH_2)_2$—$S(=O)_2$—$N(R_c)_2$, $R_c$, or —$(CH_2)_2$—$N(R_c)S(=O)_2$—$R_c$;

$R_b$ is selected from:

(a) —H, —$(C_1$-$C_6)$alkyl, —$(C_3$-$C_7)$cycloalkyl, -(3- to 7-membered)heterocycle, —$N(R_c)_2$, —$N(R_c)$—$(C_3$-$C_7)$cycloalkyl, or —$N(R_c)$-(3- to 7-membered)heterocycle; or (b) -phenyl, -naphthalenyl, or -(5- or 6-membered)heteroaryl, each of which is unsubstituted or substituted with 1, 2 or 3 independently selected $R_7$ groups; or (c) —$N(R_c)$-phenyl, —$N(R_c)$-naphthalenyl, —$N(R_c)$—$(C_{14})$aryl, or —$N(R_c)$-(5- to 10-membered)heteroaryl, each of which is unsubstituted or substituted with 1, 2 or 3 independently selected $R_7$ groups;

each $R_c$ is independently selected from —H or —$(C_1$-$C_4)$alkyl;

Z is —$[(C_1$-$C_{10})$alkyl optionally substituted by $R_1]_h$—, wherein h is 0 or 1; [$(C_2$-$C_{10})$alkenyl optionally substituted by $R_1$]—; or —$(C_1$-$C_{10})$alkyl-$NR_6C(=Y)$—;

each $R_1$ is independently selected from:

(a) —H, -halo, —CN, —OH, —$CH_2OH$, —$CH_2CH_2OH$, —$NO_2$, —$N(R_6)_2$, —$S(=O)NH_2$, —$S(=O)_2NH_2$, —$C(=O)OV_1$, or —$C(=O)CN$; or (b) —$(C_1$-$C_{10})$alkyl, —$(C_2$-$C_{10})$alkenyl, —$(C_2$-$C_{10})$alkynyl, —$O(C_1$-$C_6)$alkyl, —$(C_3$-$C_7)$cycloalkoxy, —$(C_6$-$C_{14})$bicycloalkyl, —$(C_8$-$C_{20})$tricycloalkyl, —$(C_5$-$C_{10})$cycloalkenyl, —$(C_7$-$C_{14})$bicycloalkenyl, —$(C_8$-$C_{20})$tricycloalkenyl, -(3- to 7-membered)heterocycle, -(7- to 10-membered)bicycloheterocycle, each of which is unsubstituted or substituted with 1, 2 or 3 independently selected $R_8$ groups; or (c)

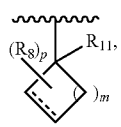

(i)

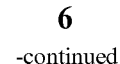

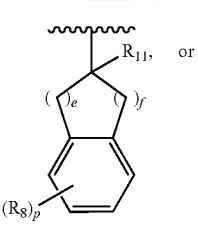

(ii)

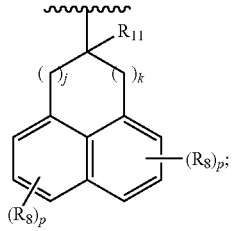

(iii)

or (d) -phenyl, -naphthalenyl, —$(C_{14})$aryl, or -(5- to 10-membered)heteroaryl, each of which is unsubstituted or substituted with an $R_7$ group; or —Z—$R_1$ is 3,3-diphenylpropyl- optionally substituted at the 3 carbon of the propyl with —CN, —$C(=O)N(R_6)_2$, —$C(=O)OV_1$, or -tetrazolyl; or —Z—$R_1$ is —$(C_1$-$C_4)$alkyl substituted with tetrazolyl;

each $R_6$ is independently selected from —H, —$(C_1$-$C_6)$alkyl, or —$(C_3$-$C_7)$cycloalkyl, or two $R_6$ groups attached to the same nitrogen atom can together form a 5- to 8-membered ring, wherein the number of atoms in the ring includes the nitrogen atom, and in which one of the 5- to 8-membered ring carbon atoms is optionally replaced by O, S, or $N(T_3)$;

each $R_7$ is independently selected from —$(C_1$-$C_4)$alkyl, —$(C_2$-$C_6)$alkenyl, —$(C_2$-$C_6)$alkynyl, —$OR_9$, —$SR_9$, —$C(halo)_3$, —$CH(halo)_2$, —$CH_2(halo)$, —CN, -halo, —$N_3$, —$NO_2$, —$CH=N(R_9)$, —$N(R_9)_2$, —$N(R_9)OH$, —$N(R_9)S(=O)R_{12}$, —$N(R_9)S(=O)_2R_{12}$, —$N(R_9)C(=O)R_{12}$, —$N(R_9)C(=O)N(T_1)(T_2)$, —$N(R_9)C(=O)OR_{12}$, —$C(=O)R_9$, —$C(=O)N(T_1)(T_2)$, —$C(=O)OR_9$, —$OC(=O)R_9$, —$OC(=O)N(T_1)(T_2)$, —$OC(=O)OR_9$, —$S(=O)R_9$, or —$S(=O)_2R_9$;

each $R_8$ is independently selected from —$(C_1$-$C_4)$alkyl, —$(C_2$-$C_6)$alkenyl, —$(C_2$-$C_6)$alkynyl, -(5- or 6-membered)heteroaryl, -phenyl, —$(C_1$-$C_6)$alkyl-$C(=O)OR_9$, —$OR_9$, —$SR_9$, —$C(halo)_3$, —$CH(halo)_2$, —$CH_2(halo)$, —CN, =O, =S, -halo, —$N_3$, —$NO_2$, —$CH=N(R_9)$, —$NR_9(C_1$-$C_6)$alkyl-$C(=O)OR_9$, —$N(R_9)_2$, —$N(R_9)OH$, —$N(R_9)S(=O)R_{12}$, —$N(R_9)S(=O)_2R_{12}$, —$N(R_9)C(=O)R_{12}$, —$N(R_9)C(=O)N(T_1)(T_2)$, —$N(R_9)C(=O)OR_{12}$, —$C(=O)R_9$, —$C(=O)$—$C(=O)OR_9$, —$C(=O)N(T_1)(T_2)$, —$C(=O)OR_9$, —$OC(=O)R_9$, —$OC(=O)N(T_1)(T_2)$, —$OC(=O)OR_9$, —$S(=O)R_9$, or —$S(=O)_2R_9$;

each $R_9$ is independently selected from —H, —$(C_1$-$C_6)$alkyl, —$(C_2$-$C_6)$alkenyl, —$(C_2$-$C_6)$alkynyl, —$(C_1$-$C_6)$alkoxy, —$(C_3$-$C_8)$cycloalkyl, —$(C_5$-$C_8)$cycloalkenyl, -phenyl, -benzyl, -(3- to 6-membered)heterocycle, -(5- to 10-membered)heteroaryl, —$C(halo)_3$, —$CH(halo)_2$, or —$CH_2(halo)$;

if h is 0, then $R_{11}$ can be selected from —H, —CN, —$C(=O)OR_9$, or —$C(=O)N(R_6)_2$ or $R_{11}$ can be —$(C_1$-$C_4)$ alkyl which is unsubstituted or substituted with —OH, —$(C_1$-$C_4)$alkoxy, —$N(R_6)_2$, —$C(=O)OR_9$, or —$C(=O)N(R_6)_2$;

if h is 1, then $R_{11}$ can be —H, —CN, —OH, -halo, —C(=O)OR$_9$, or —C(=O)N(R$_6$)$_2$ or $R_{11}$ can be —(C$_1$-C$_4$)alkyl which is unsubstituted or substituted with —OH, —(C$_1$-C$_4$)alkoxy, —N(R$_6$)$_2$, —C(=O)OR$_9$, or —C(=O)N(R$_6$)$_2$;

otherwise, where Z is —(C$_1$-C$_{10}$)alkyl-NR$_6$C(=Y)—, then $R_{11}$ can be selected from —H, —CN, —C(=O)OR$_9$, or —C(=O)N(R$_6$)$_2$ or $R_{11}$ can be —(C$_1$-C$_4$)alkyl which is unsubstituted or substituted with —OH, —(C$_1$-C$_4$)alkoxy, —N(R$_6$)$_2$, —C(=O)OR$_9$, or —C(=O)N(R$_6$)$_2$;

each $R_{12}$ is independently selected from —H or —(C$_1$-C$_4$)alkyl;

m is an integer selected from 0, 1, 2, 3, 4, 5, 6, 7, 8, 9, 10, or 11;

e and f are each an integer independently selected from 0, 1, 2, 3, 4, or 5 provided that 2≤(e+f)≤5;

j and k are each an integer independently selected from 0, 1, 2, 3, or 4 provided that 1≤(j+k)≤4;

each p is an integer independently selected from 0, 1, 2, 3, or 4;

each $T_1$, $T_2$, and $T_3$ is independently —H or —(C$_1$-C$_{10}$)alkyl which is unsubstituted or substituted with 1, 2 or 3 independently selected $R_8$ groups and, optionally, in which any —(C$_1$-C$_{10}$)alkyl carbon atom except the carbon atom bonded directly to the atom to which $T_1$, $T_2$, or $T_3$ is attached is independently replaced by O, S, or N(R$_6$), or $T_1$ and $T_2$ can together form a 5- to 8-membered ring where the number of atoms in the ring includes the nitrogen atom to which $T_1$ and $T_2$ are bonded, said 5- to 8-membered ring is unsubstituted or substituted with 1, 2 or 3 independently selected $R_8$ groups and, optionally, any carbon atom in said 5- to 8-membered ring is independently replaced by O, S, or N(R$_6$);

each $V_1$ is independently selected from —H, —(C$_1$-C$_6$)alkyl, —(C$_3$-C$_7$)cycloalkyl, -phenyl, or -benzyl; and each halo is independently selected from —F, —Cl, —Br, or —I.

A compound of Formula (I) or Formula (II) or a pharmaceutically acceptable derivative thereof (a "Substituted-Quinoxaline-Type Piperidine Compound") is useful, e.g., as an analgesic, anti-inflammatory, diuretic, anesthetic agent, neuroprotective agent, anti-hypertensive, an anxiolytic agent, an agent for appetite control, hearing regulator, anti-tussive, anti-asthmatic, modulator of locomotor activity, modulator of learning and memory, regulator of neurotransmitter release, regulator of hormone release, kidney function modulator, anti-depressant, agent to treat memory loss due to Alzheimer's disease and/or other dementias, anti-epileptic, anti-convulsant, agent to treat withdrawal from alcohol, agent to treat withdrawal from drug(s) of addiction, agent to control water balance, agent to control sodium excretion, and/or agent to control arterial blood pressure disorder(s).

A Substituted-Quinoxaline-Type Piperidine Compound is useful for treating and/or preventing pain, anxiety, cough, diarrhea, high blood pressure, epilepsy, anorexia/cachexia, urinary incontinence, drug abuse, a memory disorder, obesity, constipation, depression, dementia, or Parkinsonism (each being a "Condition") in an animal.

The invention also relates to compositions comprising an effective amount of a Substituted-Quinoxaline-Type Piperidine Compound and a pharmaceutically acceptable carrier or excipient. The compositions are useful for treating or preventing a Condition in an animal.

The invention further relates to methods for treating a Condition, comprising administering to an animal in need thereof an effective amount of a Substituted-Quinoxaline-Type Piperidine Compound.

The invention further relates to methods for preventing a Condition, comprising administering to an animal in need thereof an effective amount of a Substituted-Quinoxaline-Type Piperidine Compound.

The invention further relates to the use of a Substituted-Quinoxaline-Type Piperidine Compound, e.g., of Formulas (I) and/or (II), for the manufacture of a medicament useful for treating a Condition.

The invention further relates to the use of a Substituted-Quinoxaline-Type Piperidine Compound, e.g., of Formulas (I) and/or (II), for the manufacture of a medicament useful for preventing a Condition.

The invention still further relates to methods for inhibiting ORL-1 receptor function in a cell, comprising contacting a cell capable of expressing the ORL-1 receptor with an ORL-1 receptor function inhibiting amount of a Substituted-Quinoxaline-Type Piperidine Compound.

The invention still further relates to methods for activating ORL-1 receptor function in a cell, comprising contacting a cell capable of expressing the ORL-1 receptor with an ORL-1 receptor function activating amount of a Substituted-Quinoxaline-Type Piperidine Compound.

The invention still further relates to methods for preparing a composition, comprising the step of admixing a Substituted-Quinoxaline-Type Piperidine Compound and a pharmaceutically acceptable carrier or excipient.

The invention still further relates to a kit comprising a container containing an effective amount of a Substituted-Quinoxaline-Type Piperidine Compound.

The invention also provides novel intermediates for use in making the Substituted-Quinoxaline-Type Piperidine Compounds.

The invention can be understood more fully by reference to the following detailed description and illustrative examples, which are intended to exemplify non-limiting embodiments of the invention. Other objects and advantages of the invention will become apparent from the following detailed description thereof.

4. DETAILED DESCRIPTION OF THE INVENTION

The invention encompasses compounds of Formula (I.1) and Formula (II.1):

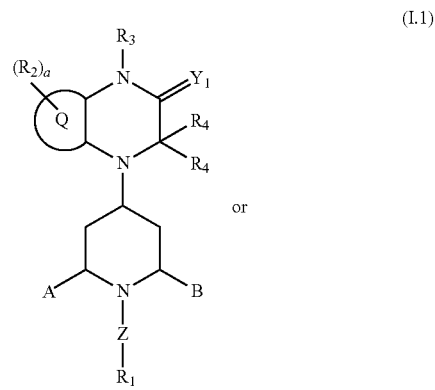

(I.1)

or

-continued

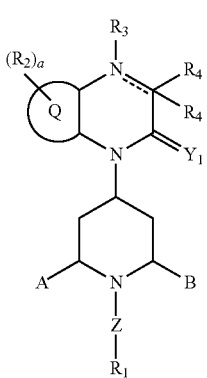
(II.1)

or a pharmaceutically acceptable derivative thereof wherein:

$Y_1$ is O or S;

Q is selected from fused benzo or (5- or 6-membered) heteroaryl;

each $R_2$ is independently selected from:
- (a) -halo, —CN, —NO$_2$, —OT$_3$, —C(=O)T$_3$, —C(=O)OT$_3$, —C(=O)N(T$_1$)(T$_2$), —S(O)$_2$OH, —S(O)T$_3$, —S(O)$_2$T$_3$, —S(O)$_2$N(T$_1$)(T$_2$), —N(T$_1$)(T$_2$), —N(T$_3$)C(=O)T$_3$, —N(T$_3$)C(=O)N(T$_1$)(T$_2$), —N(T$_3$)S(O)$_2$T$_3$, or —N(T$_3$)S(O)$_2$N(T$_1$)(T$_2$); or
- (b) —(C$_1$-C$_6$)alkyl, —(C$_2$-C$_6$)alkenyl, —(C$_2$-C$_6$)alkynyl, —(C$_3$-C$_2$)cycloalkyl, —(C$_6$-C$_{14}$)bicycloalkyl, —(C$_8$-C$_{20}$)tricycloalkyl, —(C$_5$-C$_{10}$)cycloalkenyl, —(C$_2$-C$_{14}$)bicycloalkenyl, —(C$_8$-C$_{20}$)tricycloalkenyl, -(5- or 6-membered)heterocycle, or -(7- to 10-membered)bicycloheterocycle, each of which is unsubstituted or substituted with 1, 2 or 3 $R_8$ groups; or
- (c) -phenyl, -naphthalenyl, —(C$_{14}$)aryl, or -(5- or 6-membered)heteroaryl, each of which is unsubstituted or substituted with 1, 2 or 3 $R_7$ groups;

a is an integer from 0 to 2;

the dashed line in the fused piperazine ring denotes the presence or absence of a bond, and when that dashed line denotes the presence of a bond then $R_3$ and one $R_4$ are absent;

$R_3$ is independently selected from —H or —(C$_1$-C$_4$)alkyl which is unsubstituted or substituted with 1, 2, or 3 of —OH, —(C$_1$-C$_4$)alkoxy, —N(R$_6$)$_2$, —C(=O)OR$_9$, or —C(=O)N(R$_6$)$_2$;

each $R_4$ is independently selected from:
- (a) —H; or
- (b) -halo, —CN, or —NO$_2$; or
- (c) —X, —CH$_2$X, or —CH$_2$CH$_2$X; or
- (d) —C(Y)CN, —C(Y)X, —C(Y)T$_3$, —C(Y)YX, —C(Y)YT$_3$, —C(Y)N(T$_1$)(T$_2$), —C(Y)N(R$_9$)CN, —C(Y)N(R$_9$)X, —C(Y)N(R$_9$)YH, —C(Y)N(R$_9$)YX, —C(Y)N(R$_9$)YCH$_2$X, —C(Y)N(R$_9$)YCH$_2$CH$_2$X, or —C(Y)N(R$_9$)S(O)$_2$T$_3$; or
- (e) —N(R$_9$)X, —N(R$_9$)—CH$_2$X, —N(R$_9$)—CH$_2$CH$_2$X, —N(R$_9$)CH$_2$N(R$_9$)C(=N(R$_{12}$))N(R$_{12}$)$_2$, —N(R$_9$)—CH$_2$CH$_2$N(R$_9$)C(=N(R$_{12}$))N(R$_{12}$)$_2$, —N(T$_1$)(T$_2$), —N(T$_3$)C(Y)T$_3$, —N(T$_3$)C(Y)YT$_3$, —N(T$_3$)C(Y)N(T$_1$)(T$_2$), —N(T$_3$)S(O)$_2$T$_3$, or —N(T$_3$)S(O)$_2$N(T$_1$)(T$_2$); or
- (f) —YH, —CH$_2$YH, —CH$_2$CH$_2$YH, —YX, or —YT$_3$; or
- (g) —S(O)T$_3$, —S(O)$_2$T$_3$, —S(O)N(T$_1$)(T$_2$), —S(O)$_2$N(T$_1$)(T$_2$), —S(O)X, or —S(O)$_2$X;

X is:
- (a) —(C$_1$-C$_6$)alkyl, —(C$_2$-C$_6$)alkenyl, —(C$_2$-C$_6$)alkynyl, —(C$_3$-C$_7$)cycloalkyl, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(5- or 6-membered)heterocycle, or -(7- to 10-membered)bicycloheterocycle, each of which is unsubstituted or substituted with 1, 2 or 3 $R_8$ groups; or
- (b) -phenyl, -naphthalenyl, —(C$_{14}$)aryl, or -(5- or 6-membered)heteroaryl, each of which is unsubstituted or substituted with 1, 2 or 3 $R_7$ groups;

each Y is independently selected from O or S;

A and B are independently selected from:
- (a) —H, —CN, —C(=O)OT$_3$, —C(=O)N(T$_1$)(T$_2$), —(C$_3$-C$_{12}$)cycloalkyl, —(C$_3$-C$_{12}$)cycloalkoxy, —(C$_1$-C$_6$)alkyl, —(C$_2$-C$_6$)alkenyl, or —(C$_2$-C$_6$)alkynyl, each of which —(C$_1$-C$_6$)alkyl, —(C$_2$-C$_6$)alkenyl or —(C$_2$-C$_6$)alkynyl is unsubstituted or substituted with 1 or 2 substituents selected from —OH, —S(O)$_2$NH$_2$, —N(R$_6$)$_2$, =NR$_6$, —C(=O)OT$_3$, —C(=O)N(R$_6$)$_2$, —N(R$_6$)C(=O)R$_9$ and -(5- or 6-membered)heterocycle or from 1 to 3 independently selected -halo; or
- (b) A-B can together form a (C$_2$-C$_6$)bridge, which is unsubstituted or optionally substituted with from 1 to 3 —OH or optionally contains —HC=CH— within the (C$_2$-C$_6$)bridge; or
- (c) A-B can together form a —CH$_2$—N(R$_a$)—CH$_2$— bridge, a

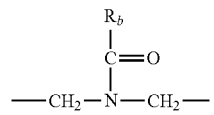

bridge, or a

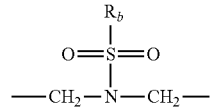

bridge;

$R_a$ is selected from —H, —(C$_1$-C$_6$)alkyl, —(C$_3$-C$_7$)cycloalkyl, —CH$_2$—C(=O)—R$_c$, —(CH$_2$)—C(=O)—OR$_c$, —(CH$_2$)—C(=O)—N(R$_c$)$_2$, —(CH$_2$)$_2$—O—R$_c$, —(CH$_2$)$_2$—S(O)$_2$—N(R$_c$)$_2$, R$_c$, or —(CH$_2$)$_2$—N(R$_c$)S(O)$_2$—R$_c$;

$R_b$ is selected from:
- (a) —H, —(C$_1$-C$_6$)alkyl, —(C$_3$-C$_7$)cycloalkyl, -(3- to 7-membered)heterocycle, —N(R$_c$)$_2$, —N(R$_c$)—(C$_3$-C$_7$)cycloalkyl, or —N(R$_c$)-(3- to 7-membered)heterocycle; or
- (b) -phenyl, -naphthalenyl, or -(5- or 6-membered)heteroaryl, each of which is unsubstituted or substituted with 1, 2 or 3 $R_7$ groups; or
- (c) —N(R$_c$)-phenyl, —N(R$_c$)-naphthalenyl, —N(R$_c$)—(C$_{14}$)aryl, or —N(R$_c$)-(5- to 10-membered)heteroaryl, each of which is unsubstituted or substituted with 1, 2 or 3 $R_7$ groups;

each $R_c$ is independently selected from —H or —(C$_1$-C$_4$)alkyl;

Z is —[(C$_1$-C$_{10}$)alkyl]$_h$-, wherein h is 0 or 1; or —(C$_1$-C$_{10}$)alkyl-NR$_6$C(=Y)—;

$R_1$ is selected from:
(a) —H, -halo, —CN, —OH, —CH$_2$OH, —CH$_2$CH$_2$OH, —NO$_2$, —N(R$_6$)$_2$, —S(O)NH$_2$, —S(O)$_2$NH$_2$, —C(=O)OV$_1$, or —C(=O)CN; or
(b) —(C$_1$-C$_6$)alkyl, —(C$_2$-C$_6$)alkenyl, —(C$_2$-C$_6$)alkynyl, —O(C$_1$-C$_6$)alkyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(3- to 7-membered)heterocycle, -(7- to 10-membered)bicycloheterocycle, each of which is unsubstituted or substituted with an R$_8$ group, or

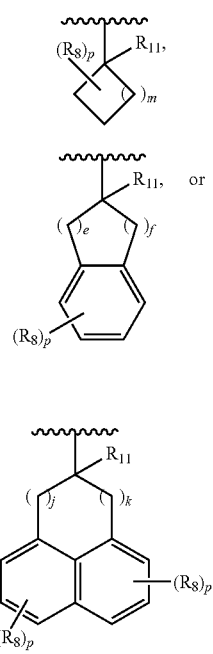

or
(c) -phenyl, -naphthalenyl, —(C$_{14}$)aryl, or -(5- to 10-membered)heteroaryl, each of which is unsubstituted or substituted with an R$_7$ group; or
—Z—R$_1$ is 3,3-diphenylpropyl- optionally substituted at the 3 carbon of the propyl with —CN, —C(=O)N(R$_6$)$_2$, —C(=O)OV$_1$, or -tetrazolyl; or
—Z—R$_1$ is —(C$_1$-C$_4$)alkyl substituted with tetrazolyl;
each R$_6$ is independently selected from —H, —(C$_1$-C$_6$)alkyl, or —(C$_3$-C$_7$)cycloalkyl, or two R$_6$ groups attached to the same nitrogen atom can form a 5- to 8-membered ring, the number of atoms in the ring including the nitrogen atom, in which one of the ring carbon atoms is optionally replaced by O, S, or N(T$_3$);
each R$_7$ is independently selected from —(C$_1$-C$_4$)alkyl, —(C$_2$-C$_6$)alkenyl, —(C$_2$-C$_6$)alkynyl, —OR$_9$, —SR$_9$, —C(halo)$_3$, —CH(halo)$_2$, —CH$_2$(halo), —CN, -halo, —N$_3$, —NO$_2$, —CH=N(R$_9$), —N(R$_9$)$_2$, —N(R$_9$)OH, —N(R$_9$)S(O)R$_{12}$, —N(R$_9$)S(O)$_2$R$_{12}$, —N(R$_9$)C(=O)R$_{12}$, —N(R$_9$)C(=O)N(T$_1$)(T$_2$), —N(R$_9$)C(=O)OR$_{12}$, —C(=O)R$_9$, —C(=O)N(T$_1$)(T$_2$), —C(=O)OR$_9$, —OC(=O)R$_9$, —OC(=O)N(T$_1$)(T$_2$), —OC(=O)OR$_9$, —S(O)R$_9$, or —S(O)$_2$R$_9$;
each R$_8$ is independently selected from —(C$_1$-C$_4$)alkyl, —(C$_2$-C$_6$)alkenyl, —(C$_2$-C$_6$)alkynyl, —OR$_9$, —SR$_9$, —C(halo)$_3$, —CH(halo)$_2$, —CH$_2$(halo), —CN, =O, =S, -halo, —N$_3$, —NO$_2$, —CH=N(R$_9$), —N(R$_9$)$_2$, —N(R$_9$)OH, —N(R$_9$)S(O)R$_{12}$, —N(R$_9$)S(O)$_2$R$_{12}$, —N(R$_9$)C(=O)R$_{12}$, —N(R$_9$)C(=O)N(T$_1$)(T$_2$), —N(R$_9$)C(=O)OR$_{12}$, —C(=O)R$_9$, —C(=O)N(T$_1$)(T$_2$), —C(=O)OR$_9$, —OC(=O)R$_9$, —OC(=O)N(T$_1$)(T$_2$), —OC(=O)OR$_9$, —S(O)R$_9$, or —S(O)$_2$R$_9$;

each R$_9$ is independently selected from —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -benzyl, -(3- to 6-membered)heterocycle, —C(halo)$_3$, —CH(halo)$_2$, or —CH$_2$(halo);

if h is 0, R$_{11}$ is selected from —H, —C(=O)OR$_9$, or —C(=O)N(R$_6$)$_2$ or —(C$_1$-C$_4$)alkyl which is unsubstituted or substituted with —OH, —(C$_1$-C$_4$)alkoxy, —N(R$_6$)$_2$, —C(=O)OR$_9$, or —C(=O)N(R$_6$)$_2$;

if h is 1, R$_{11}$ is selected from —H, —OH, -halo, —C(=O)OR$_9$, or —C(=O)N(R$_6$)$_2$ or —(C$_1$-C$_4$)alkyl which is unsubstituted or substituted with —OH, —(C$_1$-C$_4$)alkoxy, —N(R$_6$)$_2$, —C(=O)OR$_9$, or —C(=O)N(R$_6$)$_2$;

each R$_{12}$ is independently selected from —H or —(C$_1$-C$_4$)alkyl;

m is an integer from 1 to 7;

e and f are independently an integer from 0 to 5 provided that 2≤(e+f)≤5;

j and k are independently an integer from 0 to 4 provided that 1≤(j+k)≤4;

each p is independently 0 or 1;

each T$_1$, T$_2$, and T$_3$ is independently —H or —(C$_1$-C$_{10}$)alkyl which is unsubstituted or substituted with 1, 2 or 3 R$_8$ groups and, optionally, in which any —(C$_1$-C$_{10}$)alkyl carbon atom except the carbon atom bonded directly to the atom to which T$_1$, T$_2$, or T$_3$ is attached is independently replaced by O, S, or N(R$_6$), or T$_1$ and T$_2$ together can form a 5- to 8-membered ring where the number of atoms in the ring includes the nitrogen atom to which T$_1$ and T$_2$ are bonded, said 5- to 8-membered ring is unsubstituted or substituted with 1, 2 or 3 R$_8$ groups and, optionally, any carbon atom in said 5- to 8-membered ring is independently replaced by O, S, or N(R$_6$);

each V$_1$ is independently selected from —H, —(C$_3$-C$_7$)cycloalkyl, -phenyl, or -benzyl; and each halo is independently selected from —F, —Cl, —Br, or —I.

The invention encompasses compounds of Formula (I.2) and Formula (II.2):

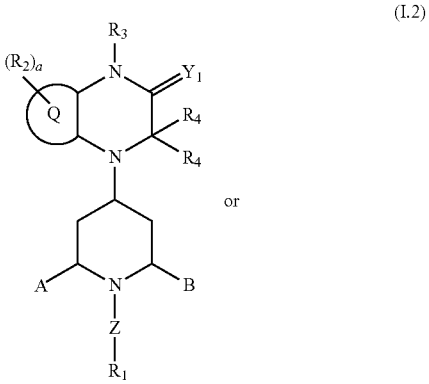

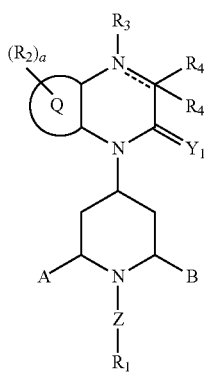

(II.2)

or a pharmaceutically acceptable derivative thereof wherein:
$Y_1$ is O or S;
Q is selected from fused benzo or (5- or 6-membered) heteroaryl;
each $R_2$ is independently selected from:
(a) -halo, —CN, —NO$_2$, —OT$_3$, —C(=O)T$_3$, —C(=O)OT$_3$, —C(=O)N(T$_1$)(T$_2$), —S(O)$_2$OH, —S(O)T$_3$, —S(O)$_2$T$_3$, —S(O)$_2$N(T$_1$)(T$_2$), —N(T$_1$)(T$_2$), —N(T$_3$)C(=O)T$_3$, —N(T$_3$)C(=O)N(T$_1$)(T$_2$), —N(T$_3$)S(O)$_2$T$_3$, or —N(T$_3$)S(O)$_2$N(T$_1$)(T$_2$); or
(b) —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(5- or 6-membered)heterocycle, or -(7- to 10-membered)bicycloheterocycle, each of which is unsubstituted or substituted with 1, 2 or 3 independently selected $R_8$ groups; or
(c) -phenyl, -naphthalenyl, —(C$_{14}$)aryl, or -(5- or 6-membered)heteroaryl, each of which is unsubstituted or substituted with 1, 2 or 3 independently selected $R_7$ groups;
a is an integer selected from 0, 1 or 2;
the dashed line in the fused piperazine ring denotes the presence or absence of a bond, and when that dashed line denotes the presence of a bond then $R_3$ and one $R_4$ are absent;
$R_3$ is selected from —H, —(C$_1$-C$_4$)alkyl which is unsubstituted or substituted with 1, 2, or 3 of independently selected —OH, —(C$_1$-C$_4$)alkoxy, —N(R$_6$)$_2$, —C(=O)OR$_9$, or —C(=O)N(R$_6$)$_2$, or —(C$_3$-C$_7$)cycloalkyl which is unsubstituted or substituted with 1, 2, or 3 of independently selected —OH, —(C$_1$-C$_4$)alkyl, —(C$_1$-C$_4$)alkoxy, —N(R$_6$)$_2$, —C(=O)OR$_9$, or —C(=O)N(R$_6$)$_2$;
each $R_4$ is independently selected from:
(a) —H; or
(b) -halo, —CN, or —NO$_2$; or
(c) —X, —CH$_2$X, or —CH$_2$CH$_2$X; or
(d) —C(Y)CN, —C(Y)T$_3$, —C(Y)YX, —C(Y)YT$_3$, —C(Y)N(T$_1$)(T$_2$), —C(Y)N(R$_9$)CN, —C(Y)N(R$_9$)X, —C(Y)N(R$_9$)YH, —C(Y)N(R$_9$)YX, —C(Y)N(R$_9$)YCH$_2$X, —C(Y)N(R$_9$)YCH$_2$CH$_2$X, or —C(Y)N(R$_9$)S(O)$_2$T$_3$; or
(e) —N(R$_9$)X, —N(R$_9$)—CH$_2$X, —N(R$_9$)—CH$_2$CH$_2$X, —N(R$_9$)CH$_2$N(R$_9$)C(=N(R$_{12}$))N(R$_{12}$)$_2$, —N(R$_9$)—CH$_2$CH$_2$N(R$_9$)C(=N(R$_{12}$))N(R$_{12}$)$_2$, —N(T$_1$)(T$_2$), —N(T$_3$)C(Y)T$_3$, —N(T$_3$)C(Y)YT$_3$, —N(T$_3$)C(Y)N(T$_1$)(T$_2$), —N(T$_3$)S(O)$_2$T$_3$, or —N(T$_3$)S(O)$_2$N(T$_1$)(T$_2$); or
(f) —YH, —CH$_2$YH, —CH$_2$CH$_2$YH, —YX, or —YT$_3$; or
(g) —S(O)T$_3$, —S(O)$_2$T$_3$, —S(O)N(T$_1$)(T$_2$), —S(O)$_2$N(T$_1$)(T$_2$), —S(O)X, or —S(O)$_2$X;
X is:
(a) —H, —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(5- or 6-membered)heterocycle, or -(7- to 10-membered)bicycloheterocycle, each of which is unsubstituted or substituted with 1, 2 or 3 independently selected $R_8$ groups; or
(b) -phenyl, -naphthalenyl, —(C$_{14}$)aryl, or -(5- or 6-membered)heteroaryl, each of which is unsubstituted or substituted with 1, 2 or 3 independently selected $R_7$ groups;
each Y is independently selected from O or S;
A and B are independently selected from:
(a) —H, —CN, —C(=O)OT$_3$, —C(=O)N(T$_1$)(T$_2$), —(C$_3$-C$_{12}$)cycloalkyl, —(C$_3$-C$_{12}$)cycloalkoxy, —(C$_1$-C$_6$)alkyl, —(C$_2$-C$_6$)alkenyl, —(C$_2$-C$_6$)alkynyl or —(C$_1$-C$_6$)alkoxy, each of which —(C$_3$-C$_{12}$)cycloalkyl, —(C$_3$-C$_{12}$)cycloalkoxy, —(C$_1$-C$_6$)alkyl, —(C$_2$-C$_6$)alkenyl or —(C$_2$-C$_6$)alkynyl is unsubstituted or substituted with 1 or 2 substituents independently selected from —OH, —S(O)$_2$NH$_2$, —N(R$_6$)$_2$, =NR$_6$, —C(=O)OT$_3$, —C(=O)N(R$_6$)$_2$, —N(R$_6$)C(=O)R$_9$ and -(5- or 6-membered)heterocycle or 1, 2 or 3 independently selected -halo; or
(b) A-B can together form a (C$_2$-C$_6$)bridge, which is unsubstituted or substituted with 1, 2 or 3 —OH groups, and which bridge optionally contains —HC=CH— within the (C$_2$-C$_6$)bridge; wherein the piperazine ring that is fused to the Q group can be in the endo- or exo- configuration with respect to the A-B bridge;
or
(c) A-B can together form a —CH$_2$—N(R$_a$)—CH$_2$— bridge, a

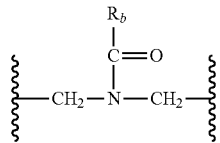

bridge, or a

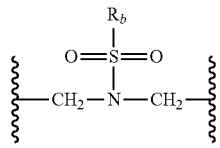

bridge;
wherein the piperazine ring that is fused to the Q group can be in the endo- or exo-configuration with respect to the A-B bridge;
$R_a$ is selected from —H, —(C$_1$-C$_6$)alkyl, —(C$_3$-C$_7$)cycloalkyl, —CH$_2$—C(=O)—R$_c$, —(CH$_2$)—C(=O)—OR$_c$, —(CH$_2$)—C(=O)—N(R$_c$)$_2$, —(CH$_2$)$_2$—O—R$_c$, —(CH$_2$)$_2$—S(O)$_2$—N(R$_c$)$_2$, R$_c$, or —(CH$_2$)$_2$—N(ROS(O)$_2$—R$_9$;

$R_b$ is selected from:
(a) —H, —$(C_1$-$C_6)$alkyl, —$(C_3$-$C_7)$cycloalkyl, -(3- to 7-membered)heterocycle, —$N(R_c)_2$, —$N(R_c)$—$(C_3$-$C_7)$cycloalkyl, or —$N(R_c)$-(3- to 7-membered)heterocycle; or
(b) -phenyl, -naphthalenyl, or -(5- or 6-membered)heteroaryl, each of which is unsubstituted or substituted with 1, 2 or 3 independently selected $R_7$ groups; or
(c) —$N(R_c)$-phenyl, —$N(R_c)$-naphthalenyl, —$N(R_c)$—$(C_{14})$aryl, or —$N(R_c)$-(5- to 10-membered)heteroaryl, each of which is unsubstituted or substituted with 1, 2 or 3 independently selected $R_7$ groups;
each $R_c$ is independently selected from —H or —$(C_1$-$C_4)$alkyl;
Z is —[$(C_1$-$C_{10})$alkyl optionally substituted by $R_1$]$_h$—, wherein h is 0 or 1; or —$(C_1$-$C_{10})$alkyl-$NR_6C(=Y)$—;
each $R_1$ is independently selected from:
(a) —H, -halo, —CN, —OH, —$CH_2OH$, —$CH_2CH_2OH$, —$NO_2$, —$N(R_6)_2$, —$S(O)NH_2$, —$S(O)_2NH_2$, —$C(=O)OV_1$, or —$C(=O)CN$; or
(b) —$(C_1$-$C_6)$alkyl, —$(C_2$-$C_6)$alkenyl, —$(C_2$-$C_6)$alkynyl, —$O(C_1$-$C_6)$alkyl, —$(C_3$-$C_7)$cycloalkoxy, —$(C_6$-$C_{14})$bicycloalkyl, —$(C_8$-$C_{20})$tricycloalkyl, —$(C_5$-$C_{10})$cycloalkenyl, —$(C_7$-$C_{14})$bicycloalkenyl, —$(C_8$-$C_{20})$tricycloalkenyl, -(3- to 7-membered)heterocycle, -(7- to 10-membered)bicycloheterocycle, each of which is unsubstituted or substituted with 1, 2 or 3 independently selected $R_8$ groups; or

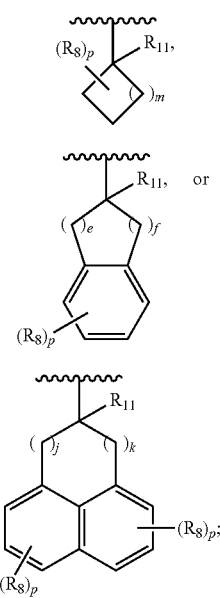

or
(d) -phenyl, -naphthalenyl, —$(C_{14})$aryl, or -(5- to 10-membered)heteroaryl, each of which is unsubstituted or substituted with an $R_7$ group; or
—Z—$R_1$ is 3,3-diphenylpropyl- optionally substituted at the 3 carbon of the propyl with —CN, —$C(=O)N(R_6)_2$, —$C(=O)OV_1$, or -tetrazolyl; or
—Z—$R_1$ is —$(C_1$-$C_4)$alkyl substituted with tetrazolyl;
each $R_6$ is independently selected from —H, —$(C_1$-$C_6)$alkyl, or —$(C_3$-$C_7)$cycloalkyl, or two $R_6$ groups attached to the same nitrogen atom can together form a 5- to 8-membered ring, wherein the number of atoms in the ring includes the nitrogen atom, and in which one of the 5- to 8-membered ring carbon atoms is optionally replaced by O, S, or $N(T_3)$;
each $R_7$ is independently selected from —$(C_1$-$C_4)$alkyl, —$(C_2$-$C_6)$alkenyl, —$(C_2$-$C_6)$alkynyl, —$OR_9$, —$SR_9$, —$C(halo)_3$, —$CH(halo)_2$, —$CH_2(halo)$, —CN, -halo, —$N_3$, —$NO_2$, —CH=$N(R_9)$, —$N(R_9)_2$, —$N(R_9)OH$, —$N(R_9)S(O)R_{12}$, —$N(R_9)S(O)_2R_{12}$, —$N(R_9)(C=O)R_{12}$, —$N(R_9)C(=O)N(T_1)(T_2)$, —$N(R_9)C(=O)OR_{12}$, —$C(=O)R_9$, —$C(=O)N(T_1)(T_2)$, —$C(=O)OR_9$, —$OC(=O)R_9$, —$OC(=O)N(T_1)(T_2)$, —$OC(=O)OR_9$, —$S(O)R_9$, or —$S(O)_2R_9$;
each $R_8$ is independently selected from —$(C_1$-$C_4)$alkyl, —$(C_2$-$C_6)$alkenyl, —$(C_2$-$C_6)$alkynyl, $(C_1$-$C_6)$alkyl-$C(=O)OR_9$, —$OR_9$, —$SR_9$, —$C(halo)_3$, —$CH(halo)_2$, —$CH_2(halo)$, —CN, =O, =S, -halo, —$N_3$, —$NO_2$, —CH=$N(R_9)$, —$N(R_9)(C_1$-$C_6)$alkyl-$C(=O)OR_9$, —$N(R_9)_2$, —$N(R_9)OH$, —$N(R_9)S(O)R_{12}$, —$N(R_9)S(O)_2R_{12}$, —$N(R_9)C(=O)R_{12}$, —$N(R_9)C(=O)N(T_1)(T_2)$, —$N(R_9)C(=O)OR_{12}$, —$C(=O)R_9$, —$C(=O)N(T_1)(T_2)$, —$C(=O)OR_9$, —$OC(=O)R_9$, —$OC(=O)N(T_1)(T_2)$, —$OC(=O)OR_9$, —$S(O)R_9$, or —$S(O)_2R_9$;
each $R_9$ is independently selected from —H, —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$cycloalkenyl, -phenyl, -benzyl, -(3- to 6-membered)heterocycle, —$C(halo)_3$, —$CH(halo)_2$, or —$CH_2(halo)$;
if h is 0, then $R_{11}$ can be selected from —H, —$C(=O)OR_9$, or —$C(=O)N(R_6)_2$ or $R_{11}$ can be —$(C_1$-$C_4)$alkyl which is unsubstituted or substituted with —OH, —$(C_1$-$C_4)$alkoxy, —$N(R_6)_2$, —$C(=O)OR_9$, or —$C(=O)N(R_6)_2$;
if h is 1, then $R_{11}$ can be selected from —H, —OH, -halo, —$C(=O)OR_9$, or —$C(=O)N(R_6)_2$ or $R_{11}$ can be —$(C_1$-$C_4)$alkyl which is unsubstituted or substituted with —OH, —$(C_1$-$C_4)$alkoxy, —$N(R_6)_2$, —$C(=O)OR_9$, or —$C(=O)N(R_6)_2$;
otherwise, where Z is —$(C_1$-$C_{10})$alkyl-$NR_6C(=Y)$—, then $R_{11}$ can be selected from —H, —$C(=O)OR_9$, or —$C(=O)N(R_6)_2$ or $R_{11}$ can be —$(C_1$-$C_4)$alkyl which is unsubstituted or substituted with —OH, —$(C_1$-$C_4)$alkoxy, —$N(R_6)_2$, —$C(=O)OR_9$, or —$C(=O)N(R_6)_2$;
each $R_{12}$ is independently selected from —H or —$(C_1$-$C_4)$alkyl;
m is an integer selected from 0, 1, 2, 3, 4, 5, 6 or 7;
e and f are each an integer independently selected from 0, 1, 2, 3, 4 or 5 provided that 2≤(e+f)≤5;
j and k are each an integer independently selected from 0, 1, 2, 3 or 4 provided that 1≤(j+k)≤4;
each p is an integer independently selected from 0 or 1;
each $T_1$, $T_2$, and $T_3$ is independently —H or —$(C_1$-$C_{10})$alkyl which is unsubstituted or substituted with 1, 2 or 3 independently selected $R_8$ groups and, optionally, in which any —$(C_1$-$C_{10})$alkyl carbon atom except the carbon atom bonded directly to the atom to which $T_1$, $T_2$, or $T_3$ is attached is independently replaced by O, S, or $N(R_6)$, or $T_1$ and $T_2$ can together form a 5- to 8-membered ring where the number of atoms in the ring includes the nitrogen atom to which $T_1$ and $T_2$ are bonded, said 5- to 8-membered ring is unsubstituted or substituted with 1, 2 or 3 independently selected $R_8$ groups and, optionally, any carbon atom in said 5- to 8-membered ring is independently replaced by O, S, or $N(R_6)$;
each $V_1$ is independently selected from —H, —$(C_1$-$C_6)$alkyl, —$(C_3$-$C_7)$cycloalkyl, -phenyl, or -benzyl; and
each halo is independently selected from —F, —Cl, —Br, or —I.
The invention encompasses compounds of Formula (I.3) and Formula (II.3):

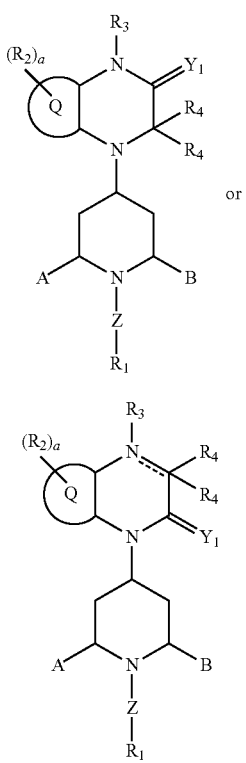

or a pharmaceutically acceptable derivative thereof wherein:
$Y_1$ is O or S;
Q is selected from fused benzo or (5- or 6-membered) heteroaryl;
each $R_2$ is independently selected from:
(a) -halo, —CN, —NO$_2$, —OT$_3$, —C(=O)T$_3$, —C(=O)OT$_3$, —C(=O)N(T$_1$)(T$_2$), —S(O)$_2$OH, —S(O)T$_3$, —S(O)$_2$T$_3$, —S(O)$_2$N(T$_1$)(T$_2$), —N(T$_1$)(T$_2$), —N(T$_3$)C(=O)T$_3$, —N(T$_3$)C(=O)N(T$_1$)(T$_2$), —N(T$_3$)S(O)$_2$T$_3$, or —N(T$_3$)S(O)$_2$N(T$_1$)(T$_2$); or
(b) —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(5- or 6-membered)heterocycle, or -(7- to 10-membered)bicycloheterocycle, each of which is unsubstituted or substituted with 1, 2 or 3 independently selected $R_8$ groups; or
(c) -phenyl, -naphthalenyl, —(C$_{14}$)aryl, or -(5- or 6-membered)heteroaryl, each of which is unsubstituted or substituted with 1, 2 or 3 independently selected $R_7$ groups;
a is an integer selected from 0, 1 or 2;
the dashed line in the fused piperazine ring denotes the presence or absence of a bond, and when that dashed line denotes the presence of a bond then $R_3$ and one $R_4$ are absent;
$R_3$ is selected from —H, —(C$_1$-C$_4$)alkyl which is unsubstituted or substituted with 1, 2, or 3 of independently selected —OH, —(C$_1$-C$_4$)alkoxy, —N(R$_6$)$_2$, —C(=O)OR$_9$, or —C(=O)N(R$_6$)$_2$, or —(C$_3$-C$_7$)cycloalkyl which is unsubstituted or substituted with 1, 2, or 3 of independently selected —OH, —(C$_1$-C$_4$)alkyl, —(C$_1$-C$_4$)alkoxy, —N(R$_6$)$_2$, —C(=O)OR$_9$, or —C(=O)N(R$_6$)$_2$;

each $R_4$ is independently selected from:
(a) —H; or
(b) -halo, —CN, or —NO$_2$; or
(c) —X, —CH$_2$X, or —CH$_2$CH$_2$X; or
(d) —C(Y)CN, —C(Y)X, —C(Y)T$_3$, —C(Y)YX, —C(Y)YT$_3$, —C(Y)N(T$_1$)(T$_2$), —C(Y)N(R$_9$)CN, —C(Y)N(R$_9$)X, —C(Y)N(R$_9$)YH, —C(Y)N(R$_9$)YX, —C(Y)N(R$_9$)YCH$_2$X, —C(Y)N(R$_9$)YCH$_2$CH$_2$X, or —C(Y)N(R$_9$)S(O)$_2$T$_3$; or
(e) —N(R$_9$)X, —N(R$_9$)—CH$_2$X, —N(R$_9$)—CH$_2$CH$_2$X, —N(R$_9$)CH$_2$N(R$_9$)C(=N(R$_{12}$))N(R$_{12}$)$_2$, —N(R$_9$)—CH$_2$CH$_2$N(R$_9$)C(=N(R$_{12}$))N(R$_{12}$)$_2$, —N(T$_1$)(T$_2$), —N(T$_3$)C(Y)T$_3$, —N(T$_3$)C(Y)YT$_3$, —N(T$_3$)C(Y)N(T$_1$)(T$_2$), —N(T$_3$)S(O)$_2$T$_3$, or —N(T$_3$)S(O)$_2$N(T$_1$)(T$_2$); or
(f) —CH$_2$YH, —CH$_2$CH$_2$YH, —YX, or —YT$_3$; or
(g) —S(O)T$_3$, —S(O)$_2$T$_3$, —S(O)N(T$_1$)(T$_2$), —S(O)$_2$N(T$_1$)(T$_2$), —S(O)X, or —S(O)$_2$X;
X is:
(a) —H, —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(5- or 6-membered)heterocycle, or -(7- to 10-membered)bicycloheterocycle, each of which is unsubstituted or substituted with 1, 2 or 3 independently selected $R_8$ groups; or
(b) -phenyl, -naphthalenyl, —(C$_{14}$)aryl, or -(5- or 6-membered)heteroaryl, each of which is unsubstituted or substituted with 1, 2 or 3 independently selected $R_7$ groups;
each Y is independently selected from O or S;
A and B are independently selected from:
(a) —H, —CN, —C(=O)OT$_3$, —C(=O)N(T$_1$)(T$_2$), —(C$_3$-C$_{12}$)cycloalkyl, —(C$_3$-C$_{12}$)cycloalkoxy, —(C$_1$-C$_6$)alkyl, —(C$_2$-C$_6$)alkenyl, —(C$_2$-C$_6$)alkynyl or —(C$_1$-C$_6$)alkoxy, each of which —(C$_3$-C$_{12}$)cycloalkyl, —(C$_3$-C$_{12}$)cycloalkoxy, —(C$_1$-C$_6$)alkyl, —(C$_2$-C$_6$)alkenyl or —(C$_2$-C$_6$)alkynyl is unsubstituted or substituted with 1 or 2 substituents independently selected from —OH, —S(O)$_2$NH$_2$, —N(R$_6$)$_2$, =NR$_6$, —C(=O)OT$_3$, —C(=O)N(R$_6$)$_2$, —N(R$_6$)C(=O)R$_9$ and -(5- or 6-membered)heterocycle or 1, 2 or 3 independently selected -halo; or
(b) A-B can together form a (C$_2$-C$_6$)bridge, which is unsubstituted or substituted with 1, 2 or 3 —OH groups, and which bridge optionally contains —HC=CH— or —O— within the (C$_2$-C$_6$)bridge; wherein the piperazine ring that is fused to the Q group can be in the endo- or exo- configuration with respect to the A-B bridge;
or
(c) A-B can together form a —CH$_2$—N(R$_a$)—CH$_2$— bridge, a

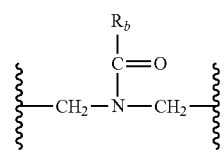

bridge, or a

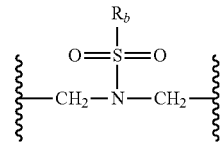

bridge;

wherein the piperazine ring that is fused to the Q group can be in the endo- or exo-configuration with respect to the A-B bridge;

$R_a$ is selected from —H, —$(C_1-C_6)$alkyl, —$(C_3-C_7)$cycloalkyl, —$CH_2$—$C(=O)$—$R_c$, —$(CH_2)$—$C(=O)$—$OR_c$, —$(CH_2)$—$C(=O)$—$N(R_c)_2$, —$(CH_2)_2$—$O$—$R_c$, —$(CH_2)_2$—$S(O)_2$—$N(R_c)_2$, $R_c$, or —$(CH_2)_2N(R_c)S(O)_2$—$R_c$;

$R_b$ is selected from:

(a) —H, —$(C_1-C_6)$alkyl, —$(C_3-C_7)$cycloalkyl, -(3- to 7-membered)heterocycle, —$N(R_c)_2$, —$N(R_c)$—$(C_3-C_7)$cycloalkyl, or —$N(R_c)$-(3- to 7-membered)heterocycle; or (b) -phenyl, -naphthalenyl, or -(5- or 6-membered)heteroaryl, each of which is unsubstituted or substituted with 1, 2 or 3 independently selected $R_7$ groups; or (c) —$N(R_c)$-phenyl, —$N(R_c)$-naphthalenyl, —$N(R_c)$—$(C_{14})$aryl, or —$N(R_c)$-(5- to 10-membered)heteroaryl, each of which is unsubstituted or substituted with 1, 2 or 3 independently selected $R_7$ groups;

each $R_c$ is independently selected from —H or —$(C_1-C_4)$alkyl;

Z is —$[(C_1-C_{10})$alkyl optionally substituted by $R_1]_h$—, wherein h is 0 or 1; or —$(C_1-C_{10})$alkyl-$NR_6C(=Y)$—;

each $R_1$ is independently selected from:

(a) —H, -halo, —CN, —OH, —$CH_2OH$, —$CH_2CH_2OH$, —$NO_2$, —$N(R_6)_2$, —$S(O)NH_2$, —$S(O)_2NH_2$, —$C(=O)OV_1$, or —$C(=O)CN$; or (b) —$(C_1-C_6)$alkyl, —$(C_2-C_6)$alkenyl, —$(C_2-C_6)$alkynyl, —$O(C_1-C_6)$alkyl, —$(C_3-C_7)$cycloalkoxy, —$(C_6-C_{14})$bicloalkyl, —$(C_8-C_{20})$tricycloalkyl, —$(C_5-C_{10})$cycloalkenyl, —$(C_7-C_{14})$bicycloalkenyl, —$(C_8-C_{20})$tricycloalkenyl, -(3- to 7-membered)heterocycle, -(7- to 10-membered)bicycloheterocycle, each of which is unsubstituted or substituted with 1, 2 or 3 independently selected $R_8$ groups; or

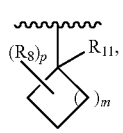

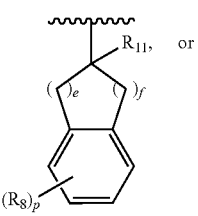

or

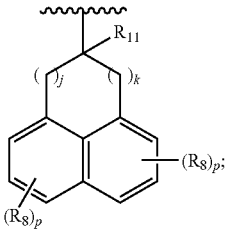

or (d) -phenyl, -naphthalenyl, —$(C_{14})$aryl, or -(5- to 10-membered)heteroaryl, each of which is unsubstituted or substituted with an $R_7$ group; or —Z—$R_1$ is 3,3-diphenylpropyl- optionally substituted at the 3 carbon of the propyl with —CN, —$C(=O)N(R_6)_2$, —$C(=O)OV_1$, or -tetrazolyl; or —Z—$R_1$ is —$(C_1-C_4)$alkyl substituted with tetrazolyl;

each $R_6$ is independently selected from —H, —$(C_1-C_6)$alkyl, or —$(C_3-C_7)$cycloalkyl, or two $R_6$ groups attached to the same nitrogen atom can together form a 5- to 8-membered ring, wherein the number of atoms in the ring includes the nitrogen atom, and in which one of the 5- to 8-membered ring carbon atoms is optionally replaced by O, S, or $N(T_3)$;

each $R_7$ is independently selected from —$(C_1-C_4)$alkyl, —$(C_2-C_6)$alkenyl, —$(C_2-C_6)$alkynyl, —$OR_9$, —$SR_9$, —$C(halo)_3$, —$CH(halo)_2$, —$CH_2(halo)$, —CN, -halo, —$N_3$, —$NO_2$, —$CH=N(R_9)$, —$N(R_9)_2$, —$N(R_9)OH$, —$N(R_9)S(O)R_{12}$, —$N(R_9)S(O)_2R_{12}$, —$N(R_9)C(=O)R_{12}$, —$N(R_9)C(=O)N(T_1)(T_2)$, —$N(R_9)C(=O)OR_{12}$, —$C(=O)R_9$, —$C(=O)N(T_1)(T_2)$, —$C(=O)OR_9$, —$OC(=O)R_9$, —$OC(=O)N(T_1)(T_2)$, —$OC(=O)OR_9$, —$S(O)R_9$, or —$S(O)_2R_9$;

each $R_8$ is independently selected from —$(C_1-C_4)$alkyl, —$(C_2-C_6)$alkenyl, —$(C_2-C_6)$alkynyl, $(C_1-C_6)$alkyl-$C(=O)OR_9$, —$OR_9$, —$SR_9$, —$C(halo)_3$, —$CH(halo)_2$, —$CH_2(halo)$, —CN, =O, =S, -halo, —$N_3$, —$NO_2$, —$CH=N(R_9)$, —$N(R_9)(C_1-C_6)$alkyl-$C(=O)OR_9$, —$N(R_9)_2$, —$N(R_9)OH$, —$N(R_9)S(O)R_{12}$, —$N(R_9)S(O)_2R_{12}$, —$N(R_9)C(=O)R_{12}$, —$N(R_9)C(=O)N(T_1)(T_2)$, —$N(R_9)C(=O)OR_{12}$, —$C(=O)R_9$, —$C(=O)N(T_1)(T_2)$, —$C(=O)OR_9$, —$OC(=O)R_9$, —$OC(=O)N(T_1)(T_2)$, —$OC(=O)OR_9$, —$S(O)R_9$, or —$S(O)_2R_9$;

each $R_9$ is independently selected from —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, -benzyl, -(3- to 6-membered)heterocycle, —$C(halo)_3$, —$CH(halo)_2$, or —$CH_2(halo)$;

if h is 0, then $R_{11}$ can be selected from —H, —$C(=O)OR_9$, or —$C(=O)N(R_6)_2$ or $R_{11}$ can be —$(C_1-C_4)$alkyl which is unsubstituted or substituted with —OH, —$(C_1-C_4)$alkoxy, —$N(R_6)_2$, —$C(=O)OR_9$, or —$C(=O)N(R_6)_2$;

if h is 1, then $R_{11}$ can be selected from —H, —OH, -halo, —$C(=O)OR_9$, or —$C(=O)N(R_6)_2$ or $R_{11}$ can be —$(C_1-C_4)$alkyl which is unsubstituted or substituted with —OH, —$(C_1-C_4)$alkoxy, —$N(R_6)_2$, —$C(=O)OR_9$, or —$C(=O)N(R_6)_2$;

otherwise, where Z is —$(C_1-C_{10})$alkyl-$NR_6C(=Y)$—, then $R_{11}$ can be selected from —H, —$C(=O)OR_9$, or —$C(=O)N(R_6)_2$ or $R_{11}$ can be —$(C_1-C_4)$alkyl which is unsubstituted or substituted with —OH, —$(C_1-C_4)$alkoxy, —$N(R_6)_2$, —$C(=O)OR_9$, or —$C(=O)N(R_6)_2$;

each $R_{12}$ is independently selected from —H or —$(C_1-C_4)$alkyl;

m is an integer selected from 0, 1, 2, 3, 4, 5, 6 or 7;

e and f are each an integer independently selected from 0, 1, 2, 3, 4 or 5 provided that 2≤(e+f)≤5;

j and k are each an integer independently selected from 0, 1, 2, 3 or 4 provided that 1≤(j+k)≤4;

each p is an integer independently selected from 0 or 1;

each $T_1$, $T_2$, and $T_3$ is independently —H or —($C_1$-$C_{10}$)alkyl which is unsubstituted or substituted with 1, 2 or 3 independently selected $R_8$ groups and, optionally, in which any —($C_1$-$C_{10}$)alkyl carbon atom except the carbon atom bonded directly to the atom to which $T_1$, $T_2$, or $T_3$ is attached is independently replaced by O, S, or N($R_6$), or $T_1$ and $T_2$ can together form a 5- to 8-membered ring where the number of atoms in the ring includes the nitrogen atom to which $T_1$ and $T_2$ are bonded, said 5- to 8-membered ring is unsubstituted or substituted with 1, 2 or 3 independently selected $R_8$ groups and, optionally, any carbon atom in said 5- to 8-membered ring is independently replaced by O, S, or N($R_6$);

each $V_1$ is independently selected from —H, —($C_1$-$C_6$)alkyl, —($C_3$-$C_7$)cycloalkyl, -phenyl, or -benzyl; and each halo is independently selected from —F, —Cl, —Br, or —I.

The invention encompasses compounds of Formula (I.4) and Formula (II.4):

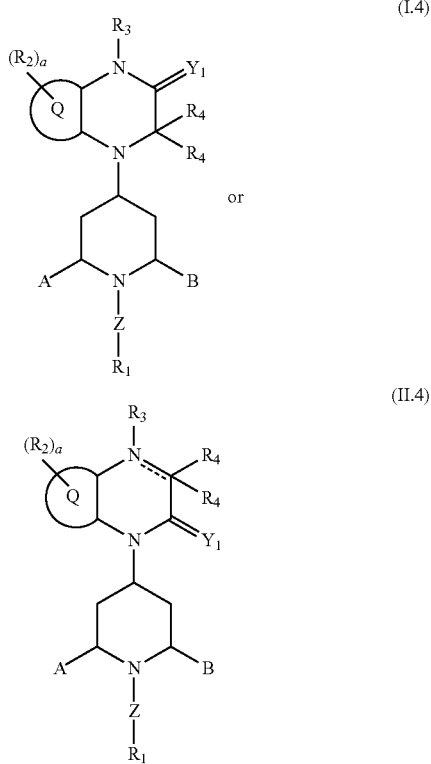

or a pharmaceutically acceptable derivative thereof wherein:
$Y_1$ is O or S;
Q is selected from fused benzo or (5- or 6-membered) heteroaryl;
each $R_2$ is independently selected from:
(a) -halo, —CN, —NO$_2$, —OT$_3$, —C(═O)T$_3$, —C(═O)OT$_3$, —C(═O)N(T$_1$)(T$_2$), —S(═O)$_2$OH, —S(═O)T$_3$, —S(═O)$_2$T$_3$, —S(═O)$_2$N(T$_1$)(T$_2$), —N(T$_1$)(T$_2$), —N(T$_3$)C(═O)T$_3$, —N(T$_3$)C(═O)N(T$_1$)(T$_2$), —N(T$_3$)S(═O)$_2$T$_3$, or —N(T$_3$)S(═O)$_2$N(T$_1$)(T$_2$); or (b) —($C_1$-$C_6$)alkyl, —($C_2$-$C_6$)alkenyl, —($C_2$-$C_6$)alkynyl, —($C_1$-$C_6$)alkoxy, —($C_3$-$C_7$)cycloalkyl, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(5- or 6-membered)heterocycle, or -(7- to 10-membered)bicycloheterocycle, each of which is unsubstituted or substituted with 1, 2 or 3 independently selected $R_8$ groups; or (c) -phenyl, -naphthalenyl, —($C_{14}$)aryl, or -(5- or 6-membered)heteroaryl, each of which is unsubstituted or substituted with 1, 2 or 3 independently selected $R_7$ groups;

a is an integer selected from 0, 1 or 2;

the dashed line in the 6-membered, nitrogen-containing ring that is fused to the Q group denotes the presence or absence of a bond, and when that dashed line denotes the presence of a bond then $R_3$ and one $R_4$ are absent;

$R_3$ is selected from:
(a) —H; or
(b) —($C_1$-$C_4$)alkyl which is unsubstituted or substituted with 1, 2 or 3 groups independently selected from —OH, —($C_1$-$C_4$)alkoxy, —N($R_6$)$_2$, —C(═O)OR$_9$, or —C(═O)N($R_6$)$_2$; or
(c) —($C_3$-$C_7$)cycloalkyl which is unsubstituted or substituted with 1, 2 or 3 groups independently selected from —OH, —($C_1$-$C_4$)alkyl, —($C_1$-$C_4$)alkoxy, —N($R_6$)$_2$, —C(═O)OR$_9$, or —C(═O)N($R_6$)$_2$;

each $R_4$ is independently selected from:
(a) —H; or
(b) -halo, —CN, or —NO$_2$; or
(c) —X, —($C_1$-$C_6$)alkyl-X, -(5- or 6-membered)heterocycle-X, or -(5- or 6-membered)heterocycle-($C_1$-$C_6$)alkyl-X; or
(d) —C(═Y)CN, —C(═Y)X, —C(═Y)T$_3$, —C(═Y)YX, —C(═Y)YT$_3$, —C(═Y)N(T$_1$)(T$_2$), —C(═Y)N(R$_9$)CN, —C(═Y)N(R$_9$)X, —C(═Y)N(R$_9$)YH, —C(═Y)N(R$_9$)YX, —C(═Y)N(R$_9$)YCH$_2$X, —C(═Y)N(R$_9$)YCH$_2$CH$_2$X, or —C(═Y)N(R$_9$)S(═O)$_2$T$_3$; or
(e) —N(R$_9$)X, —N(R$_9$)—CH$_2$X, —N(R$_9$)—CH$_2$CH$_2$X, —N(R$_9$)CH$_2$N(R$_9$)C(═N(R$_{12}$))N(R$_{12}$)$_2$, —N(R$_9$)—CH$_2$CH$_2$N(R$_9$)C(═N(R$_{12}$))N(R$_{12}$)$_2$, —N(T$_1$)(T$_2$), —N(T$_3$)C(═Y)T$_3$, —N(T$_3$)C(═Y)YT$_3$, —N(T$_3$)C(═Y)N(T$_1$)(T$_2$), —N(T$_3$)S(═O)$_2$T$_3$, or —N(T$_3$)S(═O)$_2$N(T$_1$)(T$_2$); or
(f) —YH, —CH$_2$YH, —CH$_2$CH$_2$YH, —YX, or —YT$_3$; or
(g) —S(═O)T$_3$, —S(═O)$_2$T$_3$, —S(═O)N(T$_1$)(T$_2$), —S(═O)$_2$N(T$_1$)(T$_2$), —S(═O)X, or —S(═O)$_2$X;

X is:
(a) —H, —($C_1$-$C_6$)alkyl, —($C_2$-$C_6$)alkenyl, —($C_2$-$C_6$)alkynyl, —($C_1$-$C_6$)alkoxy, —($C_3$-$C_7$)cycloalicyl, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(5- or 6-membered)heterocycle, or -(7- to 10-membered)bicycloheterocycle, each of which is unsubstituted or substituted with 1, 2 or 3 independently selected $R_8$ groups; or
(b) -phenyl, -naphthalenyl, —($C_{14}$)aryl, or -(5- or 6-membered)heteroaryl, each of which is unsubstituted or substituted with 1, 2 or 3 independently selected $R_7$ groups;

each Y is independently selected from O or S;

A and B are independently selected from:
(a) —H, —CN, —C(═O)OT$_3$, or —C(═O)N(T$_1$)(T$_2$); or
(b) —($C_3$-$C_{12}$)cycloalkyl, —($C_3$-$C_{12}$)cycloalkoxy, —($C_1$-$C_6$)alkyl, —($C_2$-$C_6$)alkenyl, —($C_2$-$C_6$)alkynyl, or —($C_1$-$C_6$)alkoxy, each of which is unsubstituted or substituted with 1 or 2 substituents independently selected from —OH, —S(=O)$_2$NH$_2$, —N(R$_6$)$_2$, =NR$_6$, —C(=O)OT$_3$, —C(=O)N(R$_6$)$_2$, —N(R$_6$)C(=O)R$_9$, and -(5- or 6-membered)heterocycle, or 1, 2 or 3 independently selected -halo; or (c) A-B can together form a (C$_2$-C$_6$)bridge, which is unsubstituted or substituted with 1, 2, 3, 4, 5, 6, 7 or 8 substituents independently selected from —OH, —(C$_1$-C$_4$)alkyl, -halo, and —C(halo)$_3$, and which bridge optionally contains —HC=CH— or —O— within the (C$_2$-C$_6$)bridge; wherein the 6-membered, nitrogen-containing ring that is fused to the Q group can be in the endo- or exo-configuration with respect to the A-B bridge; or (d) A-B can together form a —CH$_2$—N(R$_a$)—CH$_2$— bridge, a

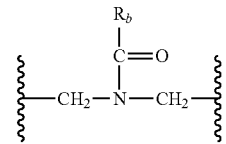

bridge, or a

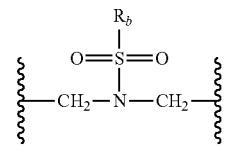

bridge;

wherein the 6-membered, nitrogen-containing ring that is fused to the Q group can be in the endo- or exo- configuration with respect to the A-B bridge;

R$_a$ is selected from —H, —(C$_1$-C$_6$)alkyl, —(C$_3$-C$_7$)cycloalkyl, —CH$_2$—C(=O)—R$_c$, —(CH$_2$)—C(=O)—OR$_c$, —(CH$_2$)—C(=O)—N(R$_c$)$_2$, —(CH$_2$)$_2$—O—R$_c$, —(CH$_2$)$_2$—S(=O)$_2$—N(R$_c$)$_2$, R$_c$, or —(CH$_2$)$_2$—N(R$_c$)S(O)$_2$—R$_c$;

R$_b$ is selected from:

(a) —H, —(C$_1$-C$_6$)alkyl, —(C$_3$-C$_7$)cycloalkyl, -(3- to 7-membered)heterocycle, —N(R$_c$)$_2$, —N(R$_c$)—(C$_3$-C$_7$)cycloalkyl, or —N(R$_c$)-(3- to 7-membered)heterocycle; or (b) -phenyl, -naphthalenyl, or -(5- or 6-membered)heteroaryl, each of which is unsubstituted or substituted with 1, 2 or 3 independently selected R$_7$ groups; or (c) —N(R$_c$)-phenyl, —N(R$_c$)-naphthalenyl, —N(R$_c$)—(C$_{14}$)aryl, or —N(R$_c$)-(5- to 10-membered)heteroaryl, each of which is unsubstituted or substituted with 1, 2 or 3 independently selected R$_7$ groups;

each R$_c$ is independently selected from —H or —(C$_1$-C$_4$)alkyl;

Z is —[(C$_1$-C$_{10}$)alkyl optionally substituted by R$_1$]$_h$—, wherein h is 0 or 1; or —(C$_1$-C$_{10}$)alkyl-NR$_6$C(=Y)—;

each R$_1$ is independently selected from:

(a) —H, -halo, —CN, —OH, —CH$_2$OH, —CH$_2$CH$_2$OH, —NO$_2$, —N(R$_6$)$_2$, —S(=O)NH$_2$, —S(=O)$_2$NH$_2$, —C(=O)OV$_1$, or —C(=O)CN; or (b) —(C$_1$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(3- to 7-membered)heterocycle, -(7- to 10-membered)bicycloheterocycle, each of which is unsubstituted or substituted with 1, 2 or 3 independently selected R$_8$ groups; or (c)

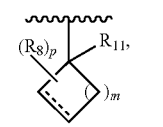

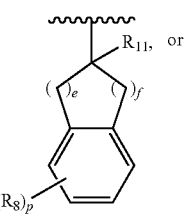

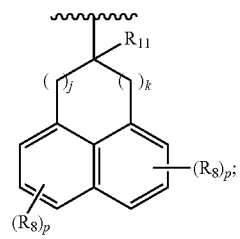

or (d) -phenyl, -naphthalenyl, —(C$_{14}$)aryl, or -(5- to 10-membered)heteroaryl, each of which is unsubstituted or substituted with an R$_7$ group; or —Z—R$_1$ is 3,3-diphenylpropyl- optionally substituted at the 3 carbon of the propyl with —CN, —C(=O)N(R$_6$)$_2$, —C(=O)OV$_1$, or -tetrazolyl; or —Z—R$_1$ is —(C$_1$-C$_4$)alkyl substituted with tetrazolyl;

each R$_6$ is independently selected from —H, —(C$_1$-C$_6$)alkyl, or —(C$_3$-C$_7$)cycloalkyl, or two R$_6$ groups attached to the same nitrogen atom can together form a 5- to 8-membered ring, wherein the number of atoms in the ring includes the nitrogen atom, and in which one of the 5- to 8-membered ring carbon atoms is optionally replaced by O, S, or N(T$_3$);

each R$_7$ is independently selected from —(C$_1$-C$_4$)alkyl, —(C$_2$-C$_6$)alkenyl, —(C$_2$-C$_6$)alkynyl, —OR$_9$, —SR$_9$, —C(halo)$_3$, —CH(halo)$_2$, —CH$_2$(halo), —CN, -halo, —N$_3$, —NO$_2$, —CH=N(R$_9$), —N(R$_9$)$_2$, —N(R$_9$)OH, —N(R$_9$)S(=O)R$_{12}$, —N(R$_9$)S(=O)$_2$R$_{12}$, —N(R$_9$)C(=O)R$_{12}$, —N(R$_9$)C(=O)N(T$_1$)(T$_2$), —N(R$_9$)C(=O)OR$_{12}$, —C(=O)R$_9$, —C(=O)N(T$_1$)(T$_2$), —C(=O)OR$_9$, —OC(=O)R$_9$, —OC(=O)N(T$_1$)(T$_2$), —OC(=O)OR$_9$, —S(=O)R$_9$, or —S(=O)$_2$R$_9$;

each R$_8$ is independently selected from —(C$_1$-C$_4$)alkyl, —(C$_2$-C$_6$)alkenyl, —(C$_2$-C$_6$)alkynyl, -(5- or 6-membered)heteroaryl, —(C$_1$-C$_6$)alkyl-C(=O)OR$_9$, —OR$_9$, —SR$_9$, —C(halo)$_3$, —CH(halo)$_2$, —CH$_2$(halo), —CN, =O, =S, -halo, —N$_3$, —NO$_2$, —CH=N(R$_9$), —N(R$_9$)(C$_1$-C$_6$)alkyl-C(=O)OR$_9$, —N(R$_9$)$_2$, —N(R$_9$)OH, —N(R$_9$)S(=O)R$_{12}$, —N(R$_9$)S(=O)$_2$R$_{12}$, —N(R$_9$)C(=O)R$_{12}$, —N(R$_9$)C(=O)N(T$_1$)(T$_2$), —N(R$_9$)C(=O)OR$_{12}$, —C(=O)R$_9$, —C(=O)N(T$_1$)(T$_2$), —C(=O)OR$_9$, —OC(=O)R$_9$, —OC(=O)N(T$_1$)(T$_2$), —OC(=O)OR$_9$, —S(=O)R$_9$, or —S(=O)$_2$R$_9$;

each $R_9$ is independently selected from —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -benzyl, -(3- to 6-membered)heterocycle, —C(halo)$_3$, —CH(halo)$_2$, or —CH$_2$(halo);

if h is 0, then $R_{11}$ can be selected from —H, —CN, —C(=O)OR$_9$, or —C(=O)N(R$_6$)$_2$ or $R_{11}$ can be —($C_1$-$C_4$)alkyl which is unsubstituted or substituted with —OH, —($C_1$-$C_4$)alkoxy, —N(R$_6$)$_2$, —C(=O)OR$_9$, or —C(=O)N(R$_6$)$_2$;

if h is 1, then $R_{11}$ can be selected from —H, —CN, —OH, -halo, —C(=O)OR$_9$, or —C(=O)N(R$_6$)$_2$ or $R_{11}$ can be —($C_1$-$C_4$)alkyl which is unsubstituted or substituted with —OH, —($C_1$-$C_4$)alkoxy, —N(R$_6$)$_2$, —C(=O)OR$_9$, or —C(=O)N(R$_6$)$_2$;

otherwise, where Z is —($C_1$-$C_{10}$)alkyl-NR$_6$C(=Y)—, then $R_{11}$ can be selected from —H, —CN, —C(=O)OR$_9$, or —C(=O)N(R$_6$)$_2$ or $R_{11}$ can be —($C_1$-$C_4$)alkyl which is unsubstituted or substituted with —OH, —($C_1$-$C_4$)alkoxy, —N(R$_6$)$_2$, —C(=O)OR$_9$, or —C(=O)N(R$_6$)$_2$;

each $R_{12}$ is independently selected from —H or —($C_1$-$C_4$)alkyl;

m is an integer selected from 0, 1, 2, 3, 4, 5, 6, 7, 8, 9, 10, or 11;

e and f are each an integer independently selected from 0, 1, 2, 3, 4, or 5 provided that $2 \leq (e+f) \leq 5$;

j and k are each an integer independently selected from 0, 1, 2, 3, or 4 provided that $1 \leq (j+k) \leq 4$;

each p is an integer independently selected from 0 or 1;

each $T_1$, $T_2$, and $T_3$ is independently —H or —($C_1$-$C_{10}$)alkyl which is unsubstituted or substituted with 1, 2 or 3 independently selected $R_8$ groups and, optionally, in which any —($C_1$-$C_{10}$)alkyl carbon atom except the carbon atom bonded directly to the atom to which $T_1$, $T_2$, or $T_3$ is attached is independently replaced by O, S, or N(R$_6$), or $T_1$ and $T_2$ can together form a 5- to 8-membered ring where the number of atoms in the ring includes the nitrogen atom to which $T_1$ and $T_2$ are bonded, said 5- to 8-membered ring is unsubstituted or substituted with 1, 2 or 3 independently selected $R_8$ groups and, optionally, any carbon atom in said 5- to 8-membered ring is independently replaced by O, S, or N(R$_6$);

each $V_1$ is independently selected from —H, —($C_1$-$C_6$)alkyl, —($C_3$-$C_7$)cycloalkyl, -phenyl, or -benzyl; and each halo is independently selected from —F, —Cl, —Br, or —I.

4.1 Substituted-Quinoxaline-Type Piperidine Compounds of Formula (I)

As stated above, the invention encompasses Substituted-Quinoxaline-Type Piperidine Compounds of Formula (I):

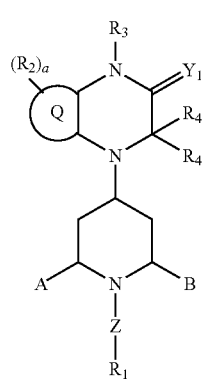

(I)

or a pharmaceutically acceptable derivative thereof where $R_1$, $R_2$, $R_3$, $R_4$, Q, $Y_1$, Z, A, B, and a are defined above for the Substituted-Quinoxaline-Type Piperidine Compounds.

In one embodiment, $Y_1$ is O.
In another embodiment, $Y_1$ is S.
In another embodiment, A is H.
In another embodiment, B is H.
In another embodiment, a is 0 or 1.
In another embodiment, a is 0.
In another embodiment, a is 1.
In another embodiment, a is 2.
In another embodiment, h is 0.
In another embodiment, h is 1.
In another embodiment, h is 1 and Z is a ($C_1$-$C_3$)alkyl.
In another embodiment, h is 1, Z is a ($C_1$-$C_3$)alkyl, $R_1$ is phenyl, the ($C_1$-$C_3$)alkyl is substituted by another $R_1$, and the other $R_1$ is phenyl.

In another embodiment, $R_1$ is —($C_1$-$C_6$)alkyl, —($C_2$-$C_6$)alkenyl, —($C_2$-$C_6$)alkynyl, —O($C_1$-$C_6$)alkyl, —($C_3$-$C_7$)cycloalkoxy, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(3- to 7-membered)heterocycle, -(7- to 10-membered)bicycloheterocycle, each of which is unsubstituted or substituted with 1, 2 or 3 independently selected $R_8$ groups.

In another embodiment, $R_1$ is optionally substituted cyclooctyl.
In another embodiment, $R_1$ is optionally substituted cyclooctenyl.
In another embodiment, $R_1$ is optionally substituted anthryl.
In another embodiment, h is 0 and $R_1$ is optionally substituted cyclooctyl.
In another embodiment, h is 0 and $R_1$ is optionally substituted cyclooctenyl.
In another embodiment, h is 0 and $R_1$ is optionally substituted anthryl.
In another embodiment, $Y_1$ is O, A and B are each H, and a is 0 or 1.
In another embodiment, $Y_1$ is S, A and B are each H, and a is 0 or 1.
In another embodiment, $Y_1$ is O, A and B are each H, and a is 0.
In another embodiment, $Y_1$ is S, A and B are each H, and a is 0.
In another embodiment, $Y_1$ is O, A and B are each H, and a is 1.
In another embodiment, $Y_1$ is S, A and B are each H, and a is 1.
In another embodiment, $R_3$ is —H, —($C_1$-$C_4$)alkyl, or —($C_3$-$C_7$)cycloalkyl.
In another embodiment, $R_3$ is —H.
In another embodiment, $R_3$ is —($C_1$-$C_4$)alkyl.
In another embodiment, $R_3$ is methyl, ethyl, n-propyl or iso-propyl, each optionally substituted with one —OH, —($C_1$-$C_4$)alkoxy, —N(R$_6$)$_2$, —C(=O)OR$_9$, or —C(=O)N(R$_6$)$_2$ group.
In another embodiment, $R_3$ is —($C_3$-$C_7$)cycloalkyl.
In another embodiment, $R_3$ is cyclopropyl, cyclobutyl, cyclopentyl, cyclohexyl, or cycloheptyl, each optionally substituted with 1 or 2 —CH$_3$ groups.
In another embodiment, $R_3$ is cyclopentyl, cyclohexyl, or cycloheptyl, each optionally substituted with one —OH, —($C_1$-$C_4$)alkyl, —($C_1$-$C_4$)alkoxy, —N(R$_6$)$_2$, —C(=O)OR$_9$, or —C(=O)N(R$_6$)$_2$ group.
In another embodiment, $R_{11}$ is not —COOH.

In another embodiment, $Y_1$ is O, A and B are each H, $R_3$ is —H, —($C_1$-$C_4$)alkyl, or —($C_3$-$C_7$)cycloalkyl, and a is 0 or 1.

In another embodiment, $Y_1$ is S, A and B are each H, $R_3$ is —H, —($C_1$-$C_4$)alkyl, or —($C_3$-$C_7$)cycloalkyl, and a is 0 or 1.

In another embodiment, $Y_1$ is O, A and B are each H, $R_3$ is —H, —($C_1$-$C_4$)alkyl, or —($C_3$-$C_7$)cycloalkyl, and a is 0.

In another embodiment, $Y_1$ is S, A and B are each H, $R_3$ is —H, —($C_1$-$C_4$)alkyl, or —($C_3$-$C_7$)cycloalkyl, and a is 0.

In another embodiment, $Y_1$ is O, A and B are each H, $R_3$ is —H, —($C_1$-$C_4$)alkyl, or —($C_3$-$C_7$)cycloalkyl, and a is 1.

In another embodiment, $Y_1$ is S, A and B are each H, $R_3$ is —H, —($C_1$-$C_4$)alkyl, or —($C_3$-$C_7$)cycloalkyl, and a is 1.

In another embodiment, each $R_2$ is independently selected from -halo, —OH, —$NH_2$, —CN, —($C_1$-$C_6$)alkyl, —($C_3$-$C_7$)cycloalkyl, -(5- or 6-membered)heterocycle, -phenyl, -naphthalenyl or -(5- or 6-membered)heteroaryl.

In another embodiment, a is 2 and each $R_2$ is independently selected from -halo, —OH, —$NH_2$, —CN, —($C_1$-$C_6$)alkyl, —($C_3$-$C_7$)cycloalkyl, -(5- or 6-membered)heterocycle, -phenyl, -naphthalenyl or -(5- or 6-membered)heteroaryl.

In another embodiment, a is 1 and $R_2$ is selected from -halo, —OH, —$NH_2$, —CN, —($C_1$-$C_6$)alkyl, —($C_3$-$C_7$)cycloalkyl, -(5- or 6-membered)heterocycle, -phenyl, -naphthalenyl or -(5- or 6-membered)heteroaryl.

In another embodiment, a is 2 and each $R_2$ is independently selected from -halo, —OH, —$NH_2$, —CN, methyl, ethyl, n-propyl, iso-propyl, cyclopentyl, cyclohexyl, cycloheptyl, or phenyl.

In another embodiment, a is 1 and $R_2$ is selected from -halo, —OH, —$NH_2$, —CN, methyl, ethyl, n-propyl, iso-propyl, cyclopentyl, cyclohexyl, cycloheptyl, or phenyl.

In another embodiment, Q is selected from benzo, pyridino, pyrimidino, pyrazino, pyridazino, pyrrolino, imidazolino, pyrazolino, triazolino, furano, oxazolino, isoxazolino, oxadiazolino, thiopheno, thiazolino, isothiazolino, or thiadiazolino.

In another embodiment, Q is selected from benzo or pyridino.

In another embodiment, Q is benzo.

In another embodiment, Q is pyridino.

In another embodiment, Q is pyridino and the 2- and 3-positions of the pyridino are fused to the 6-membered, nitrogen-containing ring.

In another embodiment, each Y is O.

In another embodiment, each Y is S.

In another embodiment, the Substituted-Quinoxaline-Type Piperidine Compound of Formula (I) is a Substituted-Quinoxaline-Type Piperidine Compound of Formula (IA):

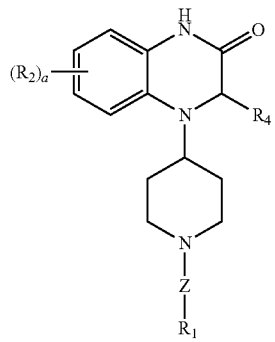

(IA)

wherein $R_1$, $R_2$, $R_4$, Z and a are as defined above for the Substituted-Quinoxaline-Type Piperidine Compounds of Formula (I).

In another embodiment, the Substituted-Quinoxaline-Type Piperidine Compound of Formula (I) is a Substituted-Quinoxaline-Type Piperidine Compound of Formula (IB):

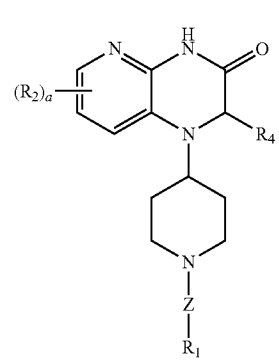

(IB)

wherein $R_1$, $R_2$, $R_4$, Z and a are as defined above for the Substituted-Quinoxaline-Type Piperidine Compounds of Formula (I).

In another embodiment, the Substituted-Quinoxaline-Type Piperidine Compound of Formula (I) is a Substituted-Quinoxaline-Type Piperidine Compound of Formula (IC):

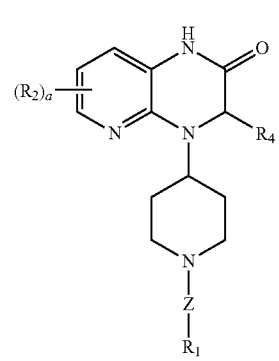

(IC)

wherein $R_1$, $R_2$, $R_4$, Z and a are as defined above for the Substituted-Quinoxaline-Type Piperidine Compounds of Formula (I).

In another embodiment, the Substituted-Quinoxaline-Type Piperidine Compound of Formula (I) is a Substituted-Quinoxaline-Type Piperidine Compound of Formula (ID):

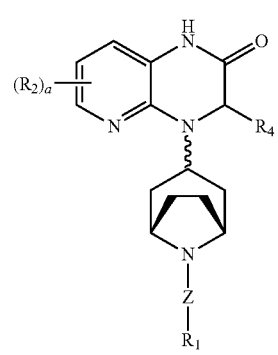

(ID)

wherein $R_1$, $R_2$, $R_4$, Z and a are as defined above for the Substituted-Quinoxaline-Type Piperidine Compounds of Formula (I).

In another embodiment, the Substituted-Quinoxaline-Type Piperidine Compound of Formula (I) is a Substituted-Quinoxaline-Type Piperidine Compound of Formula (ID1):

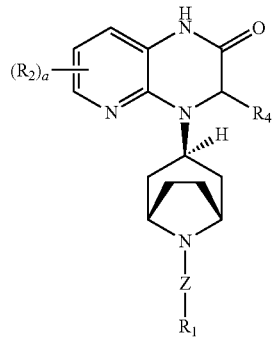

(ID1)

i.e., a Substituted-Quinoxaline-Type Piperidine Compound of Formula (ID) wherein the 6-membered, nitrogen-containing ring that is fused to the benzo is in the endo- configuration with respect to the (—CH$_2$—CH$_2$—) bridge.

In another embodiment, the Substituted-Quinoxaline-Type Piperidine Compound of Formula (I) is a Substituted-Quinoxaline-Type Piperidine Compound of Formula (ID2):

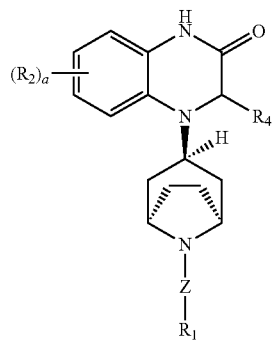

(ID2)

i.e., a Substituted-Quinoxaline-Type Piperidine Compound of Formula (ID) wherein the 6-membered, nitrogen-containing ring that is fused to the benzo is in the exo- configuration with respect to the (—CH$_2$—CH$_2$—) bridge.

In another embodiment, the Substituted-Quinoxaline-Type Piperidine Compound of Formula (I) is a Substituted-Quinoxaline-Type Piperidine Compound of Formula (IE):

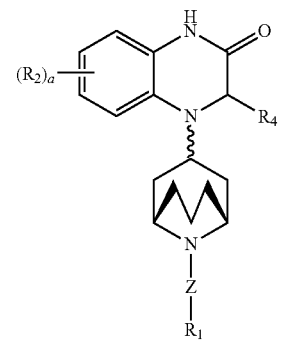

(IE)

wherein R$_1$, R$_2$, R$_4$, Z and a are as defined above for the Substituted-Quinoxaline-Type Piperidine Compounds of Formula (I).

In another embodiment, the Substituted-Quinoxaline-Type Piperidine Compound of Formula (I) is a Substituted-Quinoxaline-Type Piperidine Compound of Formula (IE1):

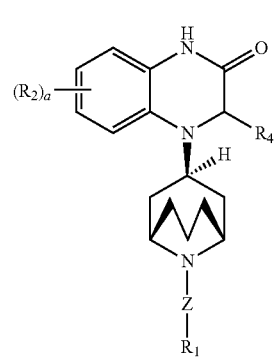

(IE1)

i.e., a Substituted-Quinoxaline-Type Piperidine Compound of Formula (IE) wherein the 6-membered, nitrogen-containing ring that is fused to the benzo is in the endo- configuration with respect to the (—CH$_2$—CH$_2$—CH$_2$—) bridge.

In another embodiment, the Substituted-Quinoxaline-Type Piperidine Compound of Formula (I) is a Substituted-Quinoxaline-Type Piperidine Compound of Formula (IE2):

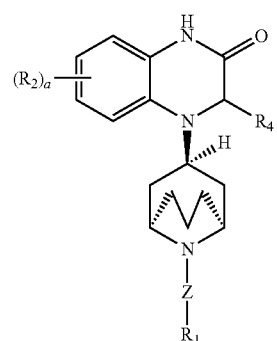

(IE2)

i.e., a Substituted-Quinoxaline-Type Piperidine Compound of Formula (IE) wherein the 6-membered, nitrogen-containing ring that is fused to the benzo is in the exo- configuration with respect to the (—CH$_2$—CH$_2$—CH$_2$—) bridge.

In another embodiment, the Substituted-Quinoxaline-Type Piperidine Compound of Formula (I) is a Substituted-Quinoxaline-Type Piperidine Compound of Formula (IF):

(IF)

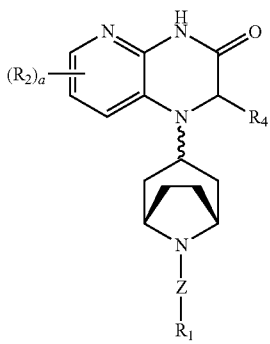

wherein R₁, R₂, R₄, Z and a are as defined above for the Substituted-Quinoxaline-Type Piperidine Compounds of Formula (I).

In another embodiment, the Substituted-Quinoxaline-Type Piperidine Compound of Formula (I) is a Substituted-Quinoxaline-Type Piperidine Compound of Formula (IF1):

(IF1)

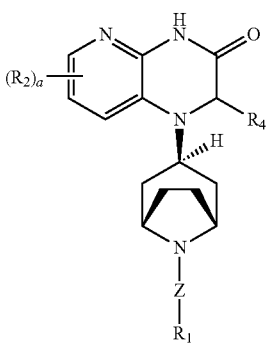

i.e., a Substituted-Quinoxaline-Type Piperidine Compound of Formula (IF) wherein the 6-membered, nitrogen-containing ring that is fused to the pyridino is in the endo-configuration with respect to the (—CH₂—CH₂—) bridge.

In another embodiment, the Substituted-Quinoxaline-Type Piperidine Compound of Formula (I) is a Substituted-Quinoxaline-Type Piperidine Compound of Formula (IF2):

(IF2)

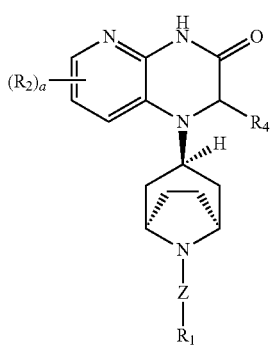

i.e., a Substituted-Quinoxaline-Type Piperidine Compound of Formula (IF) wherein the 6-membered, nitrogen-containing ring that is fused to the pyridino is in the exo- configuration with respect to the (—CH₂—CH₂—) bridge.

In another embodiment, the Substituted-Quinoxaline-Type Piperidine Compound of Formula (I) is a Substituted-Quinoxaline-Type Piperidine Compound of Formula (IG):

(IG)

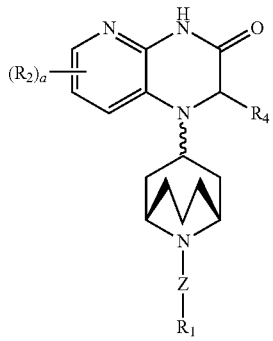

wherein R₁, R₂, R₄, Z and a are as defined above for the Substituted-Quinoxaline-Type Piperidine Compounds of Formula (I).

In another embodiment, the Substituted-Quinoxaline-Type Piperidine Compound of Formula (I) is a Substituted-Quinoxaline-Type Piperidine Compound of Formula (IG1):

(IG1)

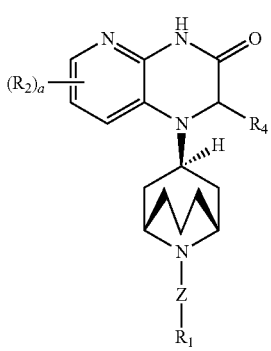

i.e., a Substituted-Quinoxaline-Type Piperidine Compound of Formula (IG) wherein the 6-membered, nitrogen-containing ring that is fused to the pyridino is in the endo-configuration with respect to the (—CH₂—CH₂—CH₂—) bridge.

In another embodiment, the Substituted-Quinoxaline-Type Piperidine Compound of Formula (I) is a Substituted-Quinoxaline-Type Piperidine Compound of Formula (IG2):

(IG2)

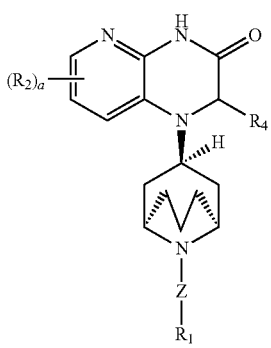

i.e., a Substituted-Quinoxaline-Type Piperidine Compound of Formula (IG) wherein the 6-membered, nitrogen-containing ring that is fused to the pyridino is in the exo- configuration with respect to the (—CH₂—CH₂—CH₂—) bridge.

In another embodiment, the Substituted-Quinoxaline-Type Piperidine Compound of Formula (I) is a Substituted-Quinoxaline-Type Piperidine Compound of Formula (IH):

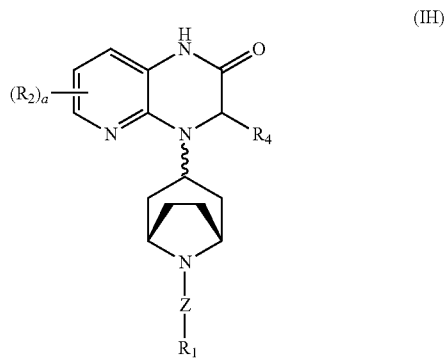

(IH)

wherein R₁, R₂, R₄, Z and a are as defined above for the Substituted-Quinoxaline-Type Piperidine Compounds of Formula (I).

In another embodiment, the Substituted-Quinoxaline-Type Piperidine Compound of Formula (I) is a Substituted-Quinoxaline-Type Piperidine Compound of Formula (IH1):

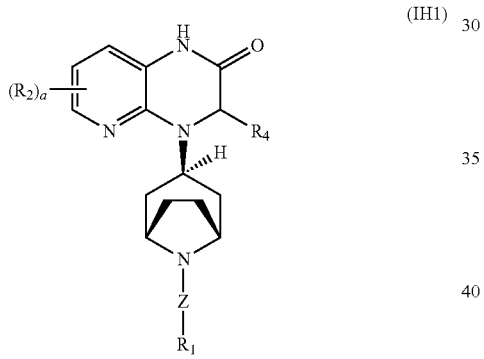

(IH1)

i.e., a Substituted-Quinoxaline-Type Piperidine Compound of Formula (IH) wherein the 6-membered, nitrogen-containing ring that is fused to the pyridino is in the endo-configuration with respect to the (—CH₂—CH₂—) bridge.

In another embodiment, the Substituted-Quinoxaline-Type Piperidine Compound of Formula (I) is a Substituted-Quinoxaline-Type Piperidine Compound of Formula (IH2):

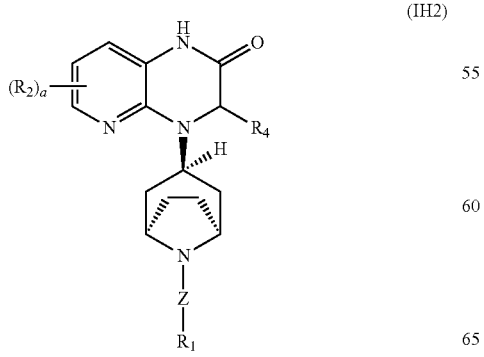

(IH2)

i.e., a Substituted-Quinoxaline-Type Piperidine Compound of Formula (IH) wherein the 6-membered, nitrogen-containing ring that is fused to the pyridino is in the exo- configuration with respect to the (—CH₂—CH₂—) bridge.

In another embodiment, the Substituted-Quinoxaline-Type Piperidine Compound of Formula (I) is a Substituted-Quinoxaline-Type Piperidine Compound of Formula (IJ):

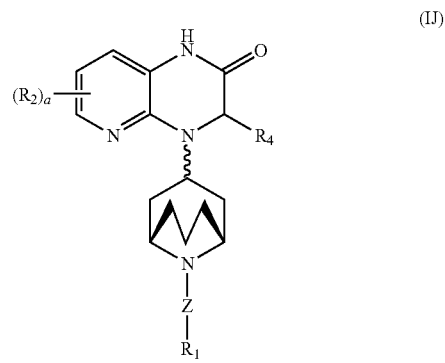

(IJ)

wherein R₁, R₂, R₄, Z and a are as defined above for the Substituted-Quinoxaline-Type Piperidine Compounds of Formula (I).

In another embodiment, the Substituted-Quinoxaline-Type Piperidine Compound of Formula (I) is a Substituted-Quinoxaline-Type Piperidine Compound of Formula (IJ1):

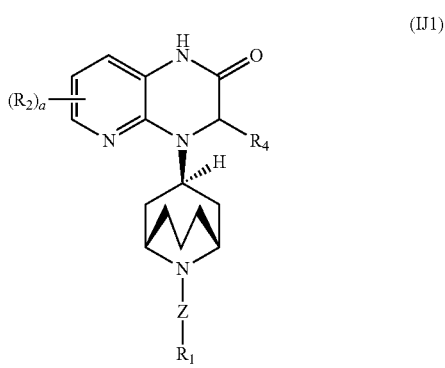

(IJ1)

i.e., a Substituted-Quinoxaline-Type Piperidine Compound of Formula (IJ) wherein the 6-membered, nitrogen-containing ring that is fused to the pyridino is in the endo-configuration with respect to the (—CH₂—CH₂—CH₂—) bridge.

In another embodiment, the Substituted-Quinoxaline-Type Piperidine Compound of Formula (I) is a Substituted-Quinoxaline-Type Piperidine Compound of Formula (IJ2):

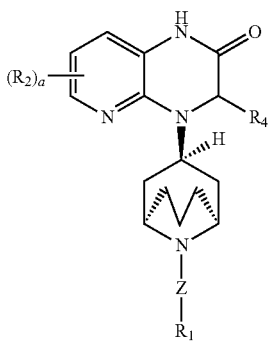

(IJ2)

i.e., a Substituted-Quinoxaline-Type Piperidine Compound of Formula (IJ) wherein the 6-membered, nitrogen-containing ring that is fused to the pyridino is in the exo- configuration with respect to the (—$CH_2$—$CH_2$—$CH_2$—) bridge.

4.2 Substituted-Quinoxaline-Type Piperidine Compounds of Formula (II)

As stated above, the invention encompasses Substituted-Quinoxaline-Type Piperidine Compounds of Formula (II):

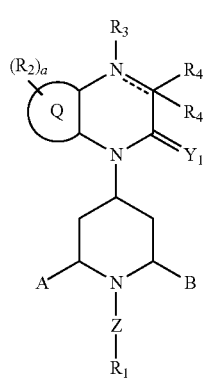

(II)

or a pharmaceutically acceptable derivative thereof where $R_1$, $R_2$, $R_3$, $R_4$, Q, $Y_1$, Z, A, B, a, and the dashed line are defined above for the Substituted-Quinoxaline-Type Piperidine Compounds.

In one embodiment, the dashed line (representing a bond) in the 6-membered, nitrogen-containing ring that is fused to the Q group is absent and $R_3$ is present.

In another embodiment, the dashed line (representing one bond of a double bond) in the 6-membered, nitrogen-containing ring that is fused to the Q group is present, and $R_3$ and one $R_4$ are absent.

In another embodiment, $Y_1$ is O.
In another embodiment, $Y_1$ is S.
In another embodiment, A is H.
In another embodiment, B is H.
In another embodiment, a is 0 or 1.
In another embodiment, a is 0.
In another embodiment, a is 1.
In another embodiment, a is 2.
In another embodiment, h is 0.
In another embodiment, h is 1.
In another embodiment, h is 1 and Z is a ($C_1$-$C_3$)alkyl.

In another embodiment, h is 1, Z is a ($C_1$-$C_3$)alkyl, $R_1$ is phenyl, the ($C_1$-$C_3$)alkyl is substituted by another $R_1$, and the other $R_1$ is phenyl.

In another embodiment, $R_1$ is —($C_1$-$C_6$)alkyl, —($C_2$-$C_6$)alkenyl, —($C_2$-$C_6$)alkynyl, —O($C_1$-$C_6$)alkyl, —($C_3$-$C_7$)cycloalkoxy, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(3- to 7-membered)heterocycle, -(7- to 10-membered)bicycloheterocycle, each of which is unsubstituted or substituted with 1, 2 or 3 independently selected $R_8$ groups.

In another embodiment, h is 1 and Z is a ($C_2$-$C_{10}$)alkenyl.
In another embodiment, h is 1 and Z is a ($C_2$-$C_6$)alkenyl.
In another embodiment, h is 1 and Z is a propenyl.
In another embodiment h is 1, Z is propenyl and $R_1$ is an optionally substituted —($C_6$-$C_{14}$)bicycloalkyl or —($C_8$-$C_{20}$)tricycloalkyl.

In another embodiment h is 1, and Z—R1 is

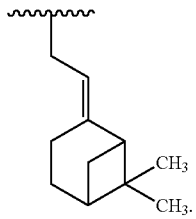 [SMILES: *C/C=C1\CCC2CC1C2(C)C]

In another embodiment, $R_1$ is optionally substituted cyclooctyl.
In another embodiment, $R_1$ is optionally substituted cyclooctenyl.
In another embodiment, $R_1$ is optionally substituted anthryl.
In another embodiment, h is 0 and $R_1$ is optionally substituted cyclooctyl.
In another embodiment, h is 0 and $R_1$ is optionally substituted cycloundecyl.
In another embodiment, h is 0 and $R_1$ is optionally substituted cyclooctenyl.
In another embodiment, h is 0 and $R_1$ is optionally substituted anthryl.
In another embodiment, h is 0 and $R_1$ is optionally substituted —($C_6$-$C_{14}$)bicycloalkyl.
In another embodiment, h is 0 and $R_1$ is optionally substituted bicyclo[3.3.1]nonyl.
In another embodiment, h is 0 and $R_1$ is optionally substituted bicyclo[2.2.1]hepyl.
In another embodiment, h is 0 and $R_1$ is optionally substituted —($C_8$-$C_{20}$)tricycloalkyl.
In another embodiment, h is 0 and $R_1$ is optionally substituted adamantyl.
In another embodiment, h is 0 and $R_1$ is optionally substituted noradamantyl.
In another embodiment, if Z is —[($C_1$-$C_{10}$)alkyl optionally substituted by $R_1$]$_h$— and h is 0 then $R_4$ is not COOH.
In another embodiment, $Y_1$ is O, A and B are each H, and a is 0 or 1.
In another embodiment, $Y_1$ is S, A and B are each H, and a is 0 or 1.
In another embodiment, $Y_1$ is O, A and B are each H, and a is 0.
In another embodiment, $Y_1$ is S, A and B are each H, and a is 0.

In another embodiment, $Y_1$ is O, A and B are each H, and a is 1.

In another embodiment, $Y_1$ is S, A and B are each H, and a is 1.

In another embodiment, the double bond in the 6-membered, nitrogen-containing ring that is fused to the Q group is present and $R_3$ is absent.

In another embodiment, $R_3$ is —H, —($C_1$-$C_4$)alkyl, or —($C_3$-$C_7$)cycloalkyl.

In another embodiment, $R_3$ is —H.

In another embodiment, $R_3$ is —($C_1$-$C_4$)alkyl.

In another embodiment, $R_3$ is methyl, ethyl, n-propyl or iso-propyl, each optionally substituted with one —OH, —($C_1$-$C_4$)alkoxy, —N($R_6$)$_2$, —C(═O)O$R_9$, or —C(═O)N($R_6$)$_2$ group.

In another embodiment, $R_3$ is —($C_3$-$C_7$)cycloalkyl.

In another embodiment, $R_3$ is cyclopropyl, cyclobutyl, cyclopentyl, cyclohexyl, or cycloheptyl, each optionally substituted with 1 or 2 —$CH_3$ groups.

In another embodiment, $R_3$ is cyclopentyl, cyclohexyl, or cycloheptyl, each optionally substituted with one —OH, —($C_1$-$C_4$)alkyl, —($C_1$-$C_4$)alkoxy, —N($R_6$)$_2$, —C(═O)O$R_9$, or —C(═O)N($R_6$)$_2$ group.

In another embodiment, $R_{11}$ is not —COOH.

In another embodiment, $Y_1$ is O, A and B are each H, the double bond in the 6-membered, nitrogen-containing ring that is fused to the Q group is present, $R_3$ is absent, and a is 0 or 1.

In another embodiment, $Y_1$ is S, A and B are each H, the double bond in the 6-membered, nitrogen-containing ring that is fused to the Q group is present, $R_3$ is absent, and a is 0 or 1.

In another embodiment, $Y_1$ is O, A and B are each H, the double bond in the 6-membered, nitrogen-containing ring that is fused to the Q group is present, $R_3$ is absent, and a is 0.

In another embodiment, $Y_1$ is S, A and B are each H, the double bond in the 6-membered, nitrogen-containing ring that is fused to the Q group is present, $R_3$ is absent, and a is 0.

In another embodiment, $Y_1$ is O, A and B are each H, the double bond in the 6-membered, nitrogen-containing ring that is fused to the Q group is present, $R_3$ is absent, and a is 1.

In another embodiment, $Y_1$ is S, A and B are each H, the double bond in the 6-membered, nitrogen-containing ring that is fused to the Q group is present, $R_3$ is absent, and a is 1.

In another embodiment, $Y_1$ is O, A and B are each H, $R_3$ is —H, —($C_1$-$C_4$)alkyl, or —($C_3$-$C_7$)cycloalkyl, and a is 0 or 1.

In another embodiment, $Y_1$ is S, A and B are each H, $R_3$ is —H, —($C_1$-$C_4$)alkyl, or —($C_3$-$C_7$)cycloalkyl, and a is 0 or 1.

In another embodiment, $Y_1$ is O, A and B are each H, $R_3$ is —H, —($C_1$-$C_4$)alkyl, or —($C_3$-$C_7$)cycloalkyl, and a is 0.

In another embodiment, $Y_1$ is S, A and B are each H, $R_3$ is —H, —($C_1$-$C_4$)alkyl, or —($C_3$-$C_7$)cycloalkyl, and a is 0.

In another embodiment, $Y_1$ is O, A and B are each H, $R_3$ is —H, —($C_1$-$C_4$)alkyl, or —($C_3$-$C_7$)cycloalkyl, and a is 1.

In another embodiment, $Y_1$ is S, A and B are each H, $R_3$ is —H, —($C_1$-$C_4$)alkyl, or —($C_3$-$C_7$)cycloalkyl, and a is 1.

In another embodiment, each $R_2$ is independently selected from -halo, —OH, —$NH_2$, —CN, —($C_1$-$C_6$)alkyl, —($C_3$-$C_7$)cycloalkyl, -(5- or 6-membered)heterocycle, -phenyl, -naphthalenyl or -(5- or 6-membered)heteroaryl.

In another embodiment, a is 2 and each $R_2$ is independently selected from -halo, —OH, —$NH_2$, —CN, —($C_1$-$C_6$)alkyl, —($C_3$-$C_7$)cycloalkyl, -(5- or 6-membered)heterocycle, -phenyl, -naphthalenyl or -(5- or 6-membered) heteroaryl.

In another embodiment, a is 1 and $R_2$ is selected from -halo, —OH, —$NH_2$, —CN, —($C_1$-$C_6$)alkyl, —($C_3$-$C_7$)cycloalkyl, -(5- or 6-membered)heterocycle, -phenyl, -naphthalenyl or -(5- or 6-membered)heteroaryl.

In another embodiment, a is 2 and each $R_2$ is independently selected from -halo, —OH, —$NH_2$, —CN, methyl, ethyl, n-propyl, iso-propyl, cyclopentyl, cyclohexyl, cycloheptyl, or phenyl.

In another embodiment, a is 1 and $R_2$ is selected from -halo, —OH, —$NH_2$, —CN, methyl, ethyl, n-propyl, iso-propyl, cyclopentyl, cyclohexyl, cycloheptyl, or phenyl.

In another embodiment, a is 1 and $R_2$ is selected from -halo, optionally —F.

In another embodiment, Q is selected from benzo, pyridino, pyrimidino, pyrazino, pyridazino, pyrrolino, imidazolino, pyrazolino, triazolino, furano, oxazolino, isoxazolino, oxadiazolino, thiopheno, thiazolino, isothiazolino, or thiadiazolino.

In another embodiment, Q is selected from benzo or pyridino.

In another embodiment, a is 1, Q is benzo or pyridino, and $R_2$ is attached at the 6-position of the benzo or pyridino, e.g., as illustrated for the —F substituted benzo of Substituted-Quinoxaline-Type Piperidine Compound 133.

In another embodiment, a is 1, Q is benzo or pyridino, $R_2$ is selected from -halo, optionally —F, and $R_2$ is attached at the 6-position of the benzo or pyridino, e.g., as illustrated for the —F substituted benzo of Substituted-Quinoxaline-Type Piperidine Compound 133.

In another embodiment, Q is benzo.

In another embodiment, Q is pyridino.

In another embodiment, Q is pyridino and the 2- and 3-positions of the pyridino are fused to the 6-membered, nitrogen-containing ring, e.g. as illustrated for compounds according to Formula (JIB).

In another embodiment, each Y is O.

In another embodiment, each Y is S.

In another embodiment, the pharmaceutically acceptable derivative of compounds of Formula (II) is a pharmaceutically acceptable salt.

In another embodiment, the pharmaceutically acceptable salt is a hydrochloride salt.

In another embodiment, the pharmaceutically acceptable salt is a sodium salt.

In another embodiment, the pharmaceutically acceptable salt is a potassium salt.

In another embodiment, the Substituted-Quinoxaline-Type Piperidine Compound of Formula (II) is a Substituted-Quinoxaline-Type Piperidine Compound of Formula (IIA):

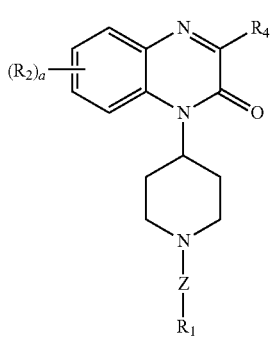

(IIA)

wherein $R_1$, $R_2$, $R_4$, Z and a are as defined above for the Substituted-Quinoxaline-Type Piperidine Compounds of Formula (II).

In another embodiment, the Substituted-Quinoxaline-Type Piperidine Compound of Formula (II) is a Substituted-Quinoxaline-Type Piperidine Compound of Formula (IIB):

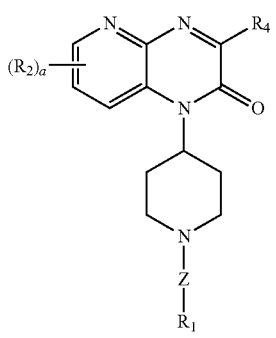

(IIB)

wherein $R_1$, $R_2$, $R_4$, Z and a are as defined above for the Substituted-Quinoxaline-Type Piperidine Compounds of Formula (II).

In another embodiment, the Substituted-Quinoxaline-Type Piperidine Compound of Formula (II) is a Substituted-Quinoxaline-Type Piperidine Compound of Formula (IIC):

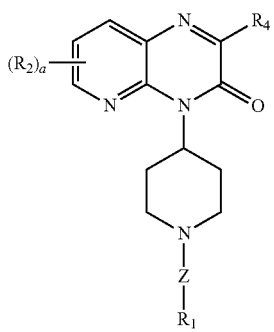

(IIC)

wherein $R_1$, $R_2$, $R_4$, Z and a are as defined above for the Substituted-Quinoxaline-Type Piperidine Compounds of Formula (II).

In another embodiment, the Substituted-Quinoxaline-Type Piperidine Compound of Formula (II) is a Substituted-Quinoxaline-Type Piperidine Compound of Formula (IID):

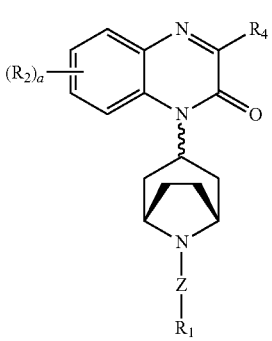

(IID)

wherein $R_1$, $R_2$, $R_4$, Z and a are as defined above for the Substituted-Quinoxaline-Type Piperidine Compounds of Formula (II).

In another embodiment, the Substituted-Quinoxaline-Type Piperidine Compound of Formula (II) is a Substituted-Quinoxaline-Type Piperidine Compound of Formula (IID1):

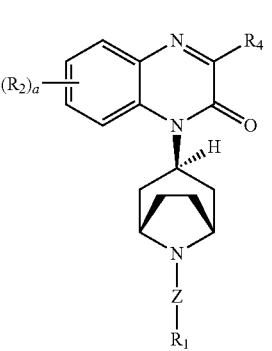

(IID1)

i.e., a Substituted-Quinoxaline-Type Piperidine Compound of Formula (IID) wherein the 6-membered, nitrogen-containing ring that is fused to the benzo is in the endo-configuration with respect to the (—$CH_2$—$CH_2$—) bridge.

In another embodiment, the Substituted-Quinoxaline-Type Piperidine Compound of Formula (II) is a Substituted-Quinoxaline-Type Piperidine Compound of Formula (IID2):

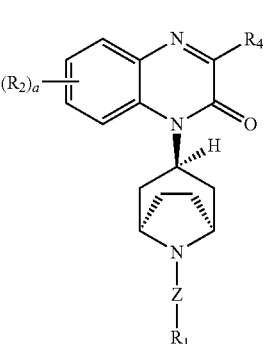

(IID2)

i.e., a Substituted-Quinoxaline-Type Piperidine Compound of Formula (IID) wherein the 6-membered, nitrogen-containing ring that is fused to the benzo is in the exo-configuration with respect to the (—$CH_2$—$CH_2$—) bridge.

In another embodiment, the Substituted-Quinoxaline-Type Piperidine Compound of Formula (II) is a Substituted-Quinoxaline-Type Piperidine Compound of Formula (IIE):

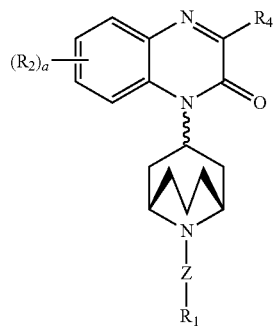

wherein $R_1$, $R_2$, $R_4$, Z and a are as defined above for the Substituted-Quinoxaline-Type Piperidine Compounds of Formula (II).

In another embodiment, the Substituted-Quinoxaline-Type Piperidine Compound of Formula (II) is a Substituted-Quinoxaline-Type Piperidine Compound of Formula (IIE1):

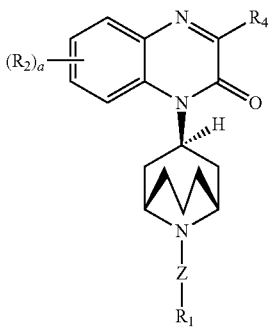

i.e., a Substituted-Quinoxaline-Type Piperidine Compound of Formula (IIE) wherein the 6-membered, nitrogen-containing ring that is fused to the benzo is in the endo-configuration with respect to the (—$CH_2$—$CH_2$—$CH_2$—) bridge.

In another embodiment, the Substituted-Quinoxaline-Type Piperidine Compound of Formula (II) is a Substituted-Quinoxaline-Type Piperidine Compound of Formula (IIE2):

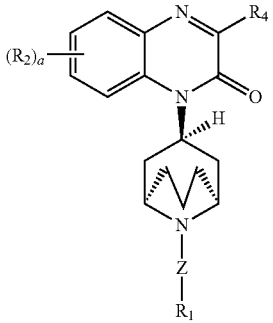

i.e., a Substituted-Quinoxaline-Type Piperidine Compound of Formula (IIE) wherein the 6-membered, nitrogen-containing ring that is fused to the benzo is in the exo-configuration with respect to the (—$CH_2$—$CH_2$—$CH_2$—) bridge.

In another embodiment, the Substituted-Quinoxaline-Type Piperidine Compound of Formula (II) is a Substituted-Quinoxaline-Type Piperidine Compound of Formula (IIF):

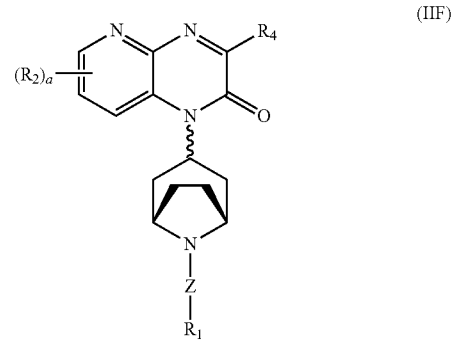

wherein $R_1$, $R_2$, $R_4$, Z and a are as defined above for the Substituted-Quinoxaline-Type Piperidine Compounds of Formula (II).

In another embodiment, the Substituted-Quinoxaline-Type Piperidine Compound of Formula (II) is a Substituted-Quinoxaline-Type Piperidine Compound of Formula (IIF1):

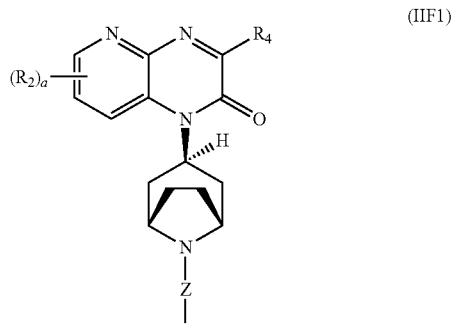

i.e., a Substituted-Quinoxaline-Type Piperidine Compound of Formula (IIF) wherein the 6-membered, nitrogen-containing ring that is fused to the pyridino is in the endo-configuration with respect to the (—$CH_2$—$CH_2$—) bridge.

In another embodiment, the Substituted-Quinoxaline-Type Piperidine Compound of Formula (II) is a Substituted-Quinoxaline-Type Piperidine Compound of Formula (IIF2):

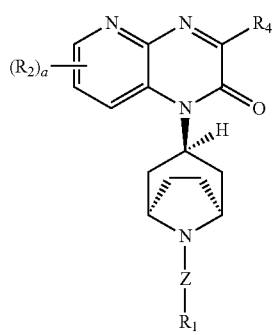
(IIF2)

i.e., a Substituted-Quinoxaline-Type Piperidine Compound of Formula (IIF) wherein the 6-membered, nitrogen-containing ring that is fused to the pyridino is in the exo-configuration with respect to the (—CH$_2$—CH$_2$—) bridge.

In another embodiment, the Substituted-Quinoxaline-Type Piperidine Compound of Formula (II) is a Substituted-Quinoxaline-Type Piperidine Compound of Formula (IIG):

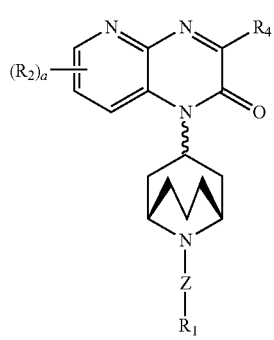
(IIG)

wherein R$_1$, R$_2$, R$_4$, Z and a are as defined above for the Substituted-Quinoxaline-Type Piperidine Compounds of Formula (II).

In another embodiment, the Substituted-Quinoxaline-Type Piperidine Compound of Formula (II) is a Substituted-Quinoxaline-Type Piperidine Compound of Formula (IIG1):

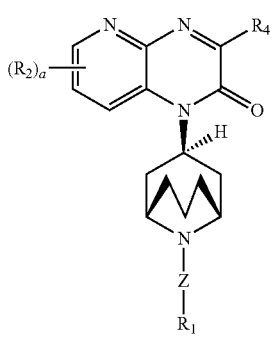
(IIG1)

i.e., a Substituted-Quinoxaline-Type Piperidine Compound of Formula (IIG) wherein the 6-membered, nitrogen-containing ring that is fused to the pyridino is in the endo-configuration with respect to the (—CH$_2$—CH$_2$—CH$_2$—) bridge.

In another embodiment, the Substituted-Quinoxaline-Type Piperidine Compound of Formula (II) is a Substituted-Quinoxaline-Type Piperidine Compound of Formula (IIG2):

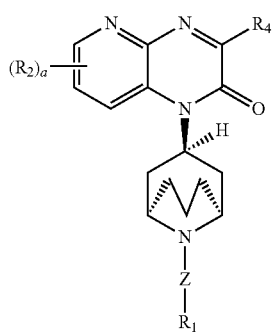
(IIG2)

i.e., a Substituted-Quinoxaline-Type Piperidine Compound' ompound of Formula (IIG) wherein the 6-membered, nitrogen-containing ring that is fused to the pyridino is in the exo-configuration with respect to the (—CH$_2$—CH$_2$—CH$_2$—) bridge.

In another embodiment, the Substituted-Quinoxaline-Type Piperidine Compound of Formula (II) is a Substituted-Quinoxaline-Type Piperidine Compound of Formula (IIH):

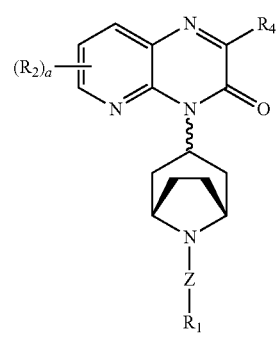
(IIH)

wherein R$_1$, R$_2$, R$_4$, Z and a are as defined above for the Substituted-Quinoxaline-Type Piperidine Compounds of Formula (II).

In another embodiment, the Substituted-Quinoxaline-Type Piperidine Compound of Formula (II) is a Substituted-Quinoxaline-Type Piperidine Compound of Formula (IIH1):

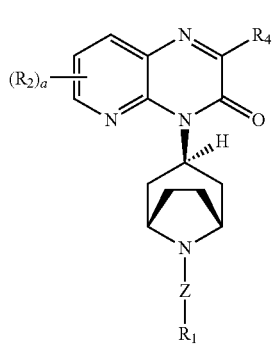
(IIH1)

i.e., a Substituted-Quinoxaline-Type Piperidine Compound of Formula (IIH) wherein the 6-membered, nitrogen-containing ring that is fused to the pyridino is in the endo-configuration with respect to the (—CH$_2$—CH$_2$—) bridge.

In another embodiment, the Substituted-Quinoxaline-Type Piperidine Compound of Formula (II) is a Substituted-Quinoxaline-Type Piperidine Compound of Formula (IIH2):

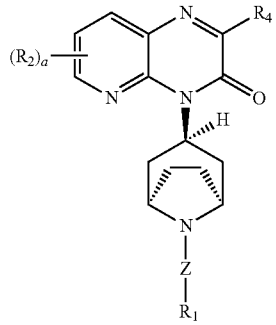

(IIH2)

i.e., a Substituted-Quinoxaline-Type Piperidine Compound of Formula (IIH) wherein the 6-membered, nitrogen-containing ring that is fused to the pyridino is in the exo-configuration with respect to the (—CH$_2$—CH$_2$—) bridge.

In another embodiment, the Substituted-Quinoxaline-Type Piperidine Compound of Formula (II) is a Substituted-Quinoxaline-Type Piperidine Compound of Formula (IIJ):

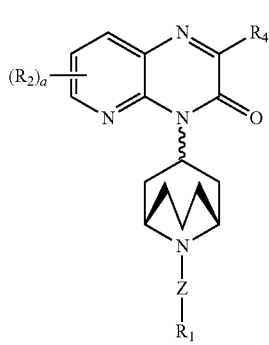

(IIJ)

wherein R$_1$, R$_2$, R$_4$, Z and a are as defined above for the Substituted-Quinoxaline-Type Piperidine Compounds of Formula (II).

In another embodiment, the Substituted-Quinoxaline-Type Piperidine Compound of Formula (II) is a Substituted-Quinoxaline-Type Piperidine Compound of Formula (IIJ1):

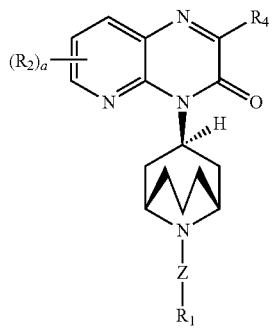

(IIJ1)

i.e., a Substituted-Quinoxaline-Type Piperidine Compound of Formula (IIJ) wherein the 6-membered, nitrogen-containing ring that is fused to the pyridino is in the endo-configuration with respect to the (—CH$_2$—CH$_2$—CH$_2$—) bridge.

In another embodiment, the Substituted-Quinoxaline-Type Piperidine Compound of Formula (II) is a Substituted-Quinoxaline-Type Piperidine Compound of Formula (IIJ1):

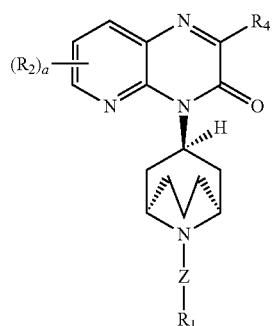

(IIJ2)

i.e., a Substituted-Quinoxaline-Type Piperidine Compound of Formula (III) wherein the 6-membered, nitrogen-containing ring that is fused to the pyridino is in the exo- configuration with respect to the (—CH$_2$—CH$_2$—CH$_2$—) bridge.

In another embodiment, the Substituted-Quinoxaline-Type Piperidine Compound of Formula (II) is a Substituted-Quinoxaline-Type Piperidine Compound of Formula (IIK):

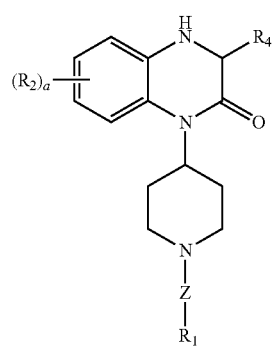

(IIK)

wherein R$_1$, R$_2$, R$_4$, Z and a are as defined above for the Substituted-Quinoxaline-Type Piperidine Compounds of Formula (II).

In another embodiment, the Substituted-Quinoxaline-Type Piperidine Compound of Formula (II) is a Substituted-Quinoxaline-Type Piperidine Compound of Formula (IIL):

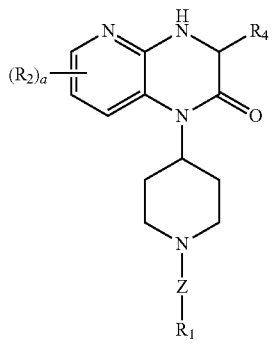
(IIL)

wherein $R_1$, $R_2$, $R_4$, Z and a are as defined above for the Substituted-Quinoxaline-Type Piperidine Compounds of Formula (II).

In another embodiment, the Substituted-Quinoxaline-Type Piperidine Compound of Formula (II) is a Substituted-Quinoxaline-Type Piperidine Compound of Formula (IIM):

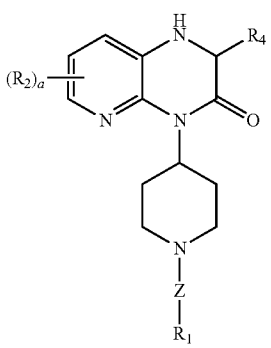
(IIM)

wherein $R_1$, $R_2$, $R_4$, Z and a are as defined above for the Substituted-Quinoxaline-Type Piperidine Compounds of Formula (II).

In another embodiment, the Substituted-Quinoxaline-Type Piperidine Compound of Formula (II) is a Substituted-Quinoxaline-Type Piperidine Compound of Formula (IIN):

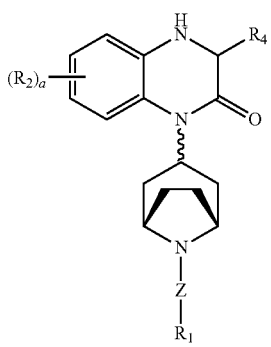
(IIN)

wherein $R_1$, $R_2$, $R_4$, Z and a are as defined above for the Substituted-Quinoxaline-Type Piperidine Compounds of Formula (II).

In another embodiment, the Substituted-Quinoxaline-Type Piperidine Compound of Formula (II) is a Substituted-Quinoxaline-Type Piperidine Compound of Formula (IIN1):

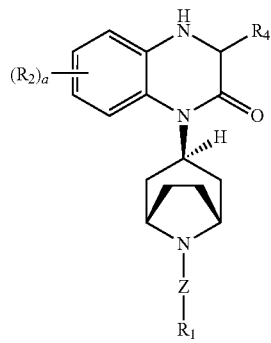
(IIN1)

i.e., a Substituted-Quinoxaline-Type Piperidine Compound of Formula (IIN) wherein the 6-membered, nitrogen-containing ring that is fused to the benzo is in the endo-configuration with respect to the (—CH$_2$—CH$_2$—) bridge.

In another embodiment, the Substituted-Quinoxaline-Type Piperidine Compound of Formula (II) is a Substituted-Quinoxaline-Type Piperidine Compound of Formula (IIN2):

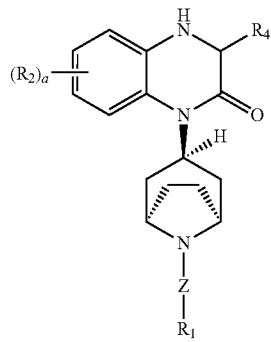
(IIN2)

i.e., a Substituted-Quinoxaline-Type Piperidine Compound of Formula (IIN) wherein the 6-membered, nitrogen-containing ring that is fused to the benzo is in the exo-configuration with respect to the (—CH$_2$—CH$_2$—) bridge.

In another embodiment, the Substituted-Quinoxaline-Type Piperidine Compound of Formula (II) is a Substituted-Quinoxaline-Type Piperidine Compound of Formula (IIO):

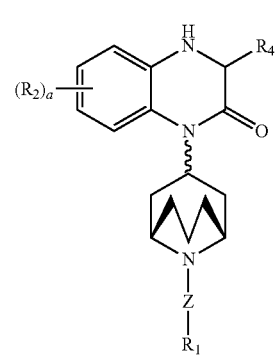
(IIO)

wherein $R_1$, $R_2$, $R_4$, Z and a are as defined above for the Substituted-Quinoxaline-Type Piperidine Compounds of Formula (II).

In another embodiment, the Substituted-Quinoxaline-Type Piperidine Compound of Formula (II) is a Substituted-Quinoxaline-Type Piperidine Compound of Formula (IIO1):

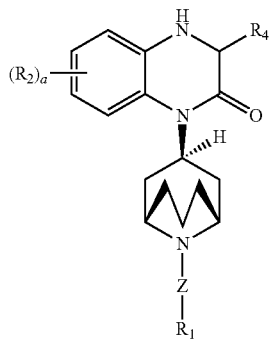

(IIO1)

i.e., a Substituted-Quinoxaline-Type Piperidine Compound of Formula (IIO) wherein the 6-membered, nitrogen-containing ring that is fused to the benzo is in the endo-configuration with respect to the (—CH₂—CH₂—CH₂—) bridge.

In another embodiment, the Substituted-Quinoxaline-Type Piperidine Compound of Formula (II) is a Substituted-Quinoxaline-Type Piperidine Compound of Formula (IIO2):

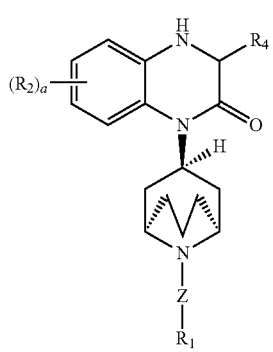

(IIO2)

i.e., a Substituted-Quinoxaline-Type Piperidine Compound of Formula (IIO) wherein the 6-membered, nitrogen-containing ring that is fused to the benzo is in the exo-configuration with respect to the (—CH₂—CH₂—CH₂—) bridge.

In another embodiment, the Substituted-Quinoxaline-Type Piperidine Compound of Formula (II) is a Substituted-Quinoxaline-Type Piperidine Compound of Formula (IIP):

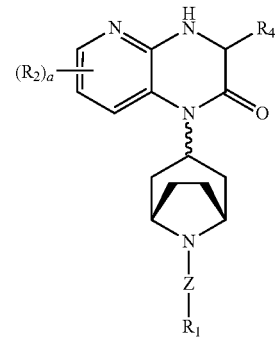

(IIP)

wherein $R_1$, $R_2$, $R_4$, Z and a are as defined above for the Substituted-Quinoxaline-Type Piperidine Compounds of Formula (H).

In another embodiment, the Substituted-Quinoxaline-Type Piperidine Compound of Formula (II) is a Substituted-Quinoxaline-Type Piperidine Compound of Formula (IIP1):

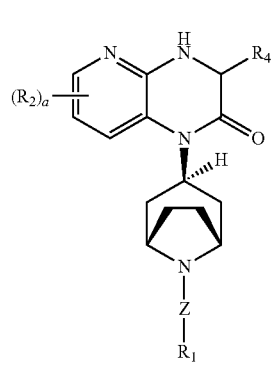

(IIP1)

i.e., a Substituted-Quinoxaline-Type Piperidine Compound of Formula (BP) wherein the 6-membered, nitrogen-containing ring that is fused to the pyridino is in the endo-configuration with respect to the (—CH₂—CH₂—) bridge.

In another embodiment, the Substituted-Quinoxaline-Type Piperidine Compound of Formula (II) is a Substituted-Quinoxaline-Type Piperidine Compound of Formula (IIP2):

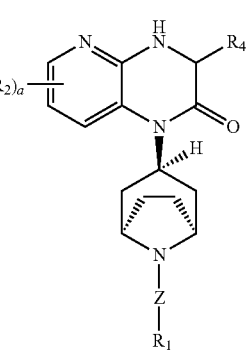

(IIP2)

i.e., a Substituted-Quinoxaline-Type Piperidine Compound of Formula (BP) wherein the 6-membered, nitrogen-containing ring that is fused to the pyridino is in the exo-configuration with respect to the (—CH₂—CH₂—) bridge.

In another embodiment, the Substituted-Quinoxaline-Type Piperidine Compound of Formula (II) is a Substituted-Quinoxaline-Type Piperidine Compound of Formula (IIQ):

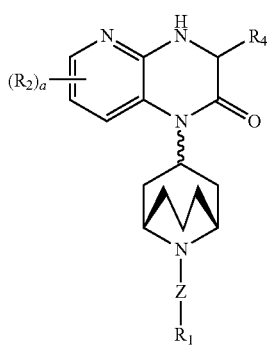

(IIQ)

wherein $R_1$, $R_2$, $R_4$, Z and a are as defined above for the Substituted-Quinoxaline-Type Piperidine Compounds of Formula (II).

In another embodiment, the Substituted-Quinoxaline-Type Piperidine Compound of Formula (II) is a Substituted-Quinoxaline-Type Piperidine Compound of Formula (IIQ1):

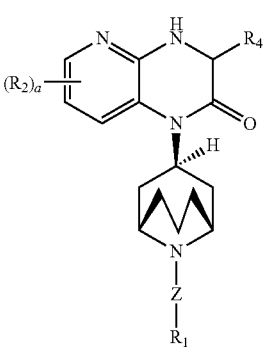

(IIQ1)

i.e., a Substituted-Quinoxaline-Type Piperidine Compound of Formula (IIQ) wherein the 6-membered, nitrogen-containing ring that is fused to the pyridino is in the endo-configuration with respect to the (—CH$_2$—CH$_2$—CH$_2$—) bridge.

In another embodiment, the Substituted-Quinoxaline-Type Piperidine Compound of Formula (II) is a Substituted-Quinoxaline-Type Piperidine Compound of Formula (IIQ2):

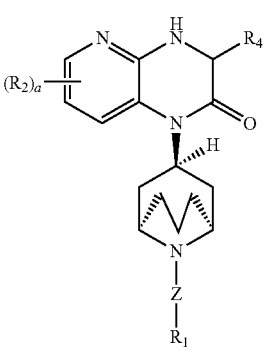

(IIQ2)

i.e., a Substituted-Quinoxaline-Type Piperidine Compound of Formula (IIQ) wherein the 6-membered, nitrogen-containing ring that is fused to the pyridino is in the exo-configuration with respect to the (—CH$_2$—CH$_2$—CH$_2$—) bridge.

In another embodiment, the Substituted-Quinoxaline-Type Piperidine Compound of Formula (II) is a Substituted-Quinoxaline-Type Piperidine Compound of Formula (IIR):

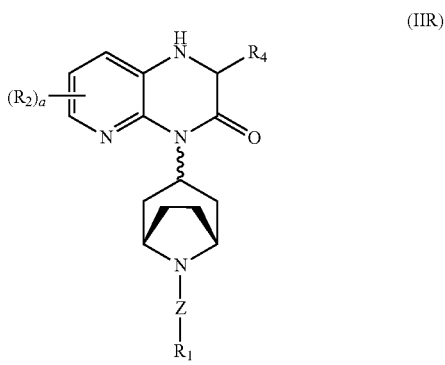

(IIR)

wherein $R_1$, $R_2$, $R_4$, Z and a are as defined above for the Substituted-Quinoxaline-Type Piperidine Compounds of Formula (II).

In another embodiment, the Substituted-Quinoxaline-Type Piperidine Compound of Formula (II) is a Substituted-Quinoxaline-Type Piperidine Compound of Formula (IIR1):

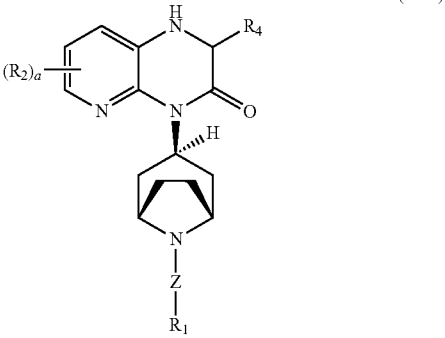

(IIR1)

i.e., a Substituted-Quinoxaline-Type Piperidine Compound of Formula (IIR) wherein the 6-membered, nitrogen-containing ring that is fused to the pyridino is in the endo-configuration with respect to the (—CH$_2$—CH$_2$—) bridge.

In another embodiment, the Substituted-Quinoxaline-Type Piperidine Compound of Formula (II) is a Substituted-Quinoxaline-Type Piperidine Compound of Formula (IIR2):

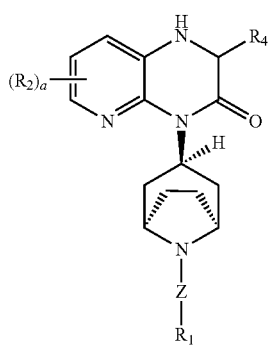

(IIR2)

i.e., a Substituted-Quinoxaline-Type Piperidine Compound of Formula (IIR) wherein the 6-membered, nitrogen-containing ring that is fused to the pyridino is in the exo-configuration with respect to the (—$CH_2$—$CH_2$—) bridge.

In another embodiment, the Substituted-Quinoxaline-Type Piperidine Compound of Formula (II) is a Substituted-Quinoxaline-Type Piperidine Compound of Formula (IIS):

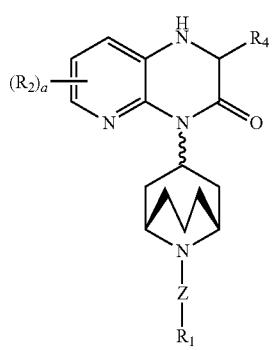

(IIS)

wherein $R_1$, $R_2$, $R_4$, Z and a are as defined above for the Substituted-Quinoxaline-Type Piperidine Compounds of Formula (II).

In another embodiment, the Substituted-Quinoxaline-Type Piperidine Compound of Formula (II) is a Substituted-Quinoxaline-Type Piperidine Compound of Formula (IIS1):

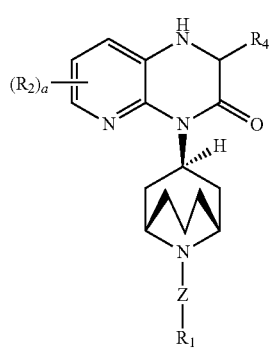

(IIS1)

i.e., a Substituted-Quinoxaline-Type Piperidine Compound of Formula (IIS) wherein the 6-membered, nitrogen-containing ring that is fused to the pyridino is in the endo-configuration with respect to the (—$CH_2$—$CH_2$—$CH_2$—) bridge.

In another embodiment, the Substituted-Quinoxaline-Type Piperidine Compound of Formula (II) is a Substituted-Quinoxaline-Type Piperidine Compound of Formula (IIS2):

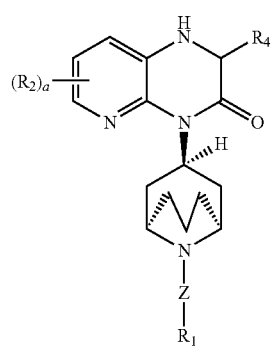

(IIS2)

i.e., a Substituted-Quinoxaline-Type Piperidine Compound of Formula (IIS) wherein the 6-membered, nitrogen-containing ring that is fused to the pyridino is in the exo-configuration with respect to the (—$CH_2$—$CH_2$—$CH_2$—) bridge.

In another embodiment, the Substituted-Quinoxaline-Type Piperidine Compound of Formula (II) is

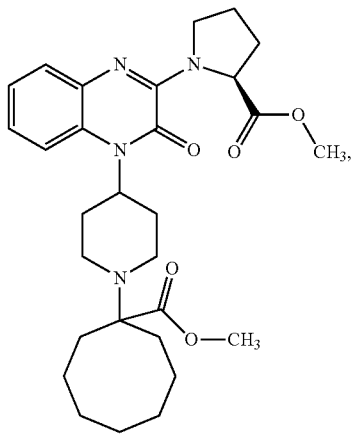

35

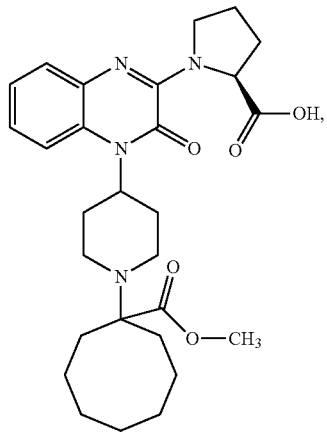

36

96
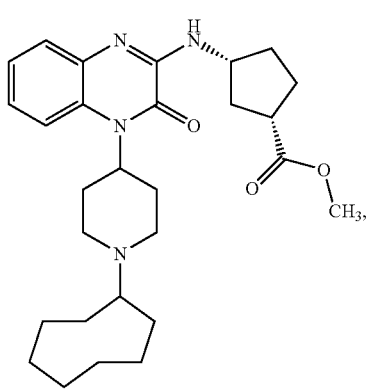
132
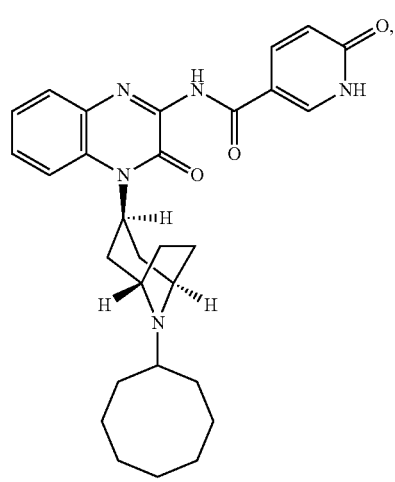
338
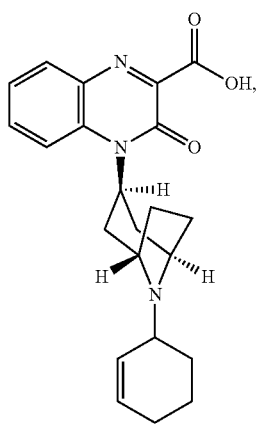
339
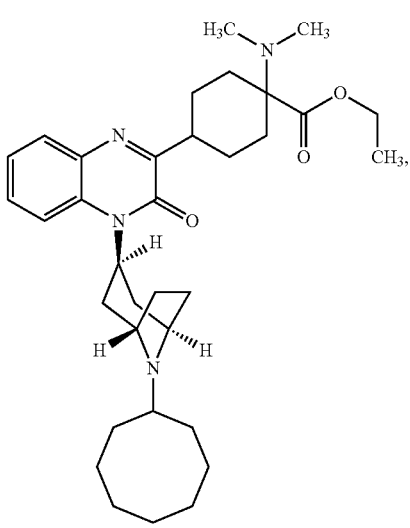
341
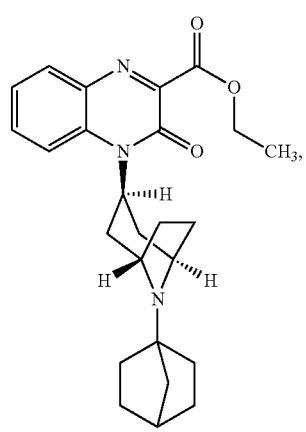
348
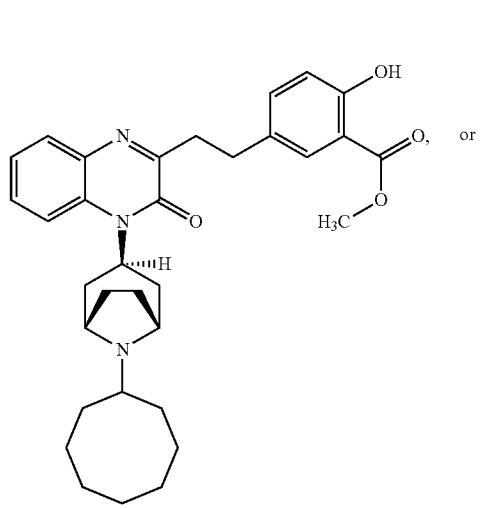
or

349

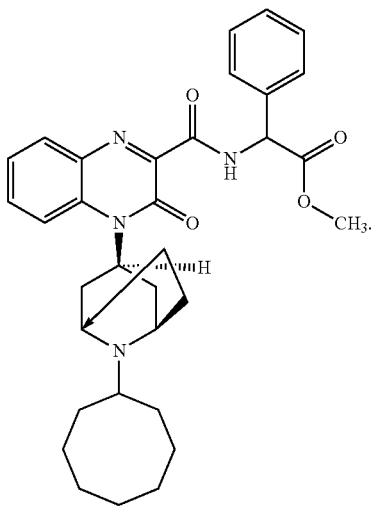

4.3 Definitions

As used in connection with the Substituted-Quinoxaline-Type Piperidine Compounds herein, the terms used herein having following meaning:

"—$(C_1-C_{10})$alkyl" means a straight chain or branched non-cyclic hydrocarbon having from 1 to 10 carbon atoms. Representative straight chain —$(C_1-C_{10})$alkyls include -methyl, -ethyl, -n-propyl, -n-butyl, -n-pentyl, -n-hexyl, -n-heptyl, -n-octyl, -n-nonyl, and -n-decyl. A branched alkyl means that one or more straight chain —$(C_1-C_8)$alkyl groups, such as methyl, ethyl or propyl, replace one or both hydrogens in a —$CH_2$— group of a straight chain alkyl. A branched non-cyclic hydrocarbon means that one or more straight chain —$(C_1-C_{10})$alkyl groups, such as methyl, ethyl or propyl, replace one or both hydrogens in a —$CH_2$— group of a straight chain non-cyclic hydrocarbon. Representative branched —$(C_1-C_{10})$alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

"—$(C_1-C_6)$alkyl" means a straight chain or branched non-cyclic hydrocarbon having from 1 to 6 carbon atoms. Representative straight chain —$(C_1-C_6)$alkyls include -methyl, -ethyl, -n-propyl, -n-butyl, -n-pentyl, and -n-hexyl. Representative branched —$(C_1-C_6)$alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, and 3,3-dimethylbutyl.

"—$(C_1-C_4)$alkyl" means a straight chain or branched non-cyclic hydrocarbon having from 1 to 4 carbon atoms. Representative straight chain —$(C_1-C_4)$alkyls include -methyl, -ethyl, -n-propyl, and -n-butyl. Representative branched —$(C_1-C_4)$alkyls include -iso-propyl, -sec-butyl, -iso-butyl, and -tert-butyl.

"—$(C_1-C_3)$alkyl" means a straight chain or branched non-cyclic hydrocarbon having from 1 to 3 carbon atoms. Representative straight chain —$(C_1-C_3)$alkyls include -methyl, -ethyl, and -n-propyl. Representative branched —$(C_1-C_3)$alkyls include -iso-propyl.

"—$(C_1-C_2)$alkyl" means a straight chain non-cyclic hydrocarbon having 1 or 2 carbon atoms. Representative straight chain —$(C_1-C_2)$alkyls include -methyl and -ethyl.

"—$(C_2-C_{10})$alkenyl" means a straight chain or branched non-cyclic hydrocarbon having from 2 to 10 carbon atoms and including at least one carbon-carbon double bond. A branched alkenyl means that one or more straight chain —$(C_1-C_8)$alkyl groups, such as methyl, ethyl or propyl, replace one or both hydrogens in a —$CH_2$— or —CH= group of a straight chain alkenyl. Representative straight chain and branched $(C_2-C_{10})$alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl, and the like.

"—$(C_2-C_6)$alkenyl" means a straight chain or branched non-cyclic hydrocarbon having from 2 to 6 carbon atoms and including at least one carbon-carbon double bond. Representative straight chain and branched $(C_2-C_6)$alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, 2-hexenyl, 3-hexenyl, and the like.

"—$(C_2-C_{10})$alkynyl" means a straight chain or branched non-cyclic hydrocarbon having from 2 to 10 carbon atoms and including at least one carbon-carbon triple bond. A branched alkynyl means that one or more straight chain —$(C_1-C_8)$alkyl groups, such as methyl, ethyl or propyl, replace one or both hydrogens in a —$CH_2$— group of a straight chain alkynyl. Representative straight chain and branched —$(C_2-C_{10})$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like.

"—$(C_2-C_6)$alkynyl" means a straight chain or branched non-cyclic hydrocarbon having from 2 to 6 carbon atoms and including at least one carbon-carbon triple bond. Representative straight chain and branched $(C_2-C_6)$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, and the like.

"—$(C_1-C_6)$alkoxy" means a straight chain or branched non-cyclic hydrocarbon having one or more ether groups and from 1 to 6 carbon atoms. Representative straight chain and branched $(C_1-C_6)$alkoxys include -methoxy, -ethoxy, methoxymethyl, 2-methoxyethyl, -5-methoxypentyl, 3-ethoxybutyl and the like.

"—$(C_3-C_{14})$cycloalkyl" means a saturated monocyclic hydrocarbon having from 3 to 14 carbon atoms. Representative $(C_3-C_{14})$cycloalkyls are -cyclopropyl, -cyclobutyl, -cyclopentyl, -cyclohexyl, -cycloheptyl, -cyclooctyl, -cyclononyl, -cyclodecyl, cycloundecyl, and -cyclododecyl, and -cyclotetradecyl.

"—($C_3$-$C_{12}$)cycloalkyl" means a saturated monocyclic hydrocarbon having from 3 to 12 carbon atoms. Representative ($C_3$-$C_{12}$)cycloalkyls are -cyclopropyl, -cyclobutyl, -cyclopentyl, -cyclohexyl, -cycloheptyl, -cyclooctyl, -cyclononyl, -cyclodecyl, cycloundecyl, and -cyclododecyl.

"—($C_6$-$C_{12}$)cycloalkyl" means a saturated monocyclic hydrocarbon having from 6 to 12 carbon atoms. Representative ($C_6$-$C_{12}$)cycloalkyls are -cyclohexyl, -cycloheptyl, -cyclooctyl, -cyclononyl, -cyclodecyl, cycloundecyl, and -cyclododecyl.

"—($C_4$-$C_8$)cycloalkyl" or "4- to 8-member cycloalkyl ring" means a saturated monocyclic hydrocarbon having from 4 to 8 carbon atoms. Representative —($C_4$-$C_8$)cycloalkyls are -cyclobutyl, -cyclopentyl, -cyclohexyl, -cycloheptyl, and -cyclooctyl.

"—($C_3$-$C_8$)cycloalkyl" means a saturated monocyclic hydrocarbon having from 3 to 8 carbon atoms. Representative ($C_3$-$C_8$)cycloalkyls include -cyclopropyl, -cyclobutyl, -cyclopentyl, -cyclohexyl, -cycloheptyl, and -cyclooctyl.

"—($C_3$-$C_7$)cycloalkyl" means a saturated monocyclic hydrocarbon having from 3 to 7 carbon atoms. Representative ($C_3$-$C_7$)cycloalkyls include cyclopropyl, -cyclobutyl, -cyclopentyl, -cyclohexyl, and -cycloheptyl.

"—($C_6$-$C_{14}$)bicycloalkyl" means a bi-cyclic hydrocarbon ring system having from 6 to 14 carbon atoms and at least one saturated cyclic alkyl ring. Representative —($C_6$-$C_{14}$) bicycloalkyls include -indanyl, -norbornyl, -1,2,3,4-tetrahydronaphthalenyl, -5,6,7,8-tetrahydronaphthalenyl, -perhydronaphthalenyl, bicyclo[2.2.1]hexyl, bicyclo[2.2.1]heptyl, bicyclo[2.2.2]octyl, bicyclo[3.3.1]heptyl, bicyclo[3.2.1]octyl, bicyclo[3.3.1]nonyl, bicyclo[3.3.2]decyl, bicyclo[3.3.3] undecyl, bicyclo[4.2.2]decyl, bicyclo[4.3.2]undecyl, bicyclo[4.3.1]decyl, and the like.

"—($C_8$-$C_{20}$)tricycloalkyl" means a tri-cyclic hydrocarbon ring system having from 8 to 20 carbon atoms and at least one saturated cyclic alkyl ring. Representative —($C_8$-$C_{20}$) tricycloalkyls include -pyrenyl, -adamantyl, noradamantyl, -1,2,3,4-tetrahydroanthracenyl, -perhydroanthracenyl -aceanthrenyl, -1,2,3,4-tetrahydropenanthrenyl, -5,6,7,8-tetrahydrophenanthrenyl, -perhydrophenanthrenyl, tetradecahydro-1H-cyclohepta[a]naphthalenyl, tetradecahydro-1H-cycloocta[e]indenyl, tetradecahydro-1H-cyclohepta[e] azulenyl, hexadecahydrocycloocta[b]naphthalenyl, hexadecahydrocyclohepta[a]heptalenyl, tricyclo-pentadecanyl, tricyclo-octadecanyl, tricyclo-nonadecanyl, tricyclo-icosanyl, and the like.

"—($C_3$-$C_{14}$)cycloalkenyl" means a cyclic non-aromatic hydrocarbon having at least one carbon-carbon double bond in the cyclic system and from 3 to 14 carbon atoms. Representative ($C_3$-$C_{14}$)cycloalkenyls include -cyclopropenyl, -cyclobutenyl, -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -cyclotetradecenyl, -cyclododecadienyl, and the like.

"—($C_5$-$C_{14}$)cycloalkenyl" means a cyclic non-aromatic hydrocarbon having at least one carbon-carbon double bond in the cyclic system and from 5 to 14 carbon atoms. Representative ($C_5$-$C_{14}$)cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, and the like.

"—($C_6$-$C_{12}$)cycloalkenyl" means a cyclic non-aromatic hydrocarbon having at least one carbon-carbon double bond in the cyclic system and from 6 to 12 carbon atoms. Representative ($C_6$-$C_{12}$)cycloalkenyls include -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -cyclododecadienyl, and the like.

"—($C_5$-$C_{10}$)cycloalkenyl" means a cyclic non-aromatic hydrocarbon having at least one carbon-carbon double bond in the cyclic system and from 5 to 10 carbon atoms. Representative ($C_5$-$C_{10}$)cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, and the like.

"—($C_5$-$C_8$)cycloalkenyl" means a cyclic non-aromatic hydrocarbon having at least one carbon-carbon double bond in the cyclic system and from 5 to 8 carbon atoms. Representative ($C_5$-$C_8$)cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, and the like.

"—($C_7$-$C_{14}$)bicycloalkenyl" means a bi-cyclic hydrocarbon ring system having at least one carbon-carbon double bond in each ring and from 7 to 14 carbon atoms. Representative —($C_7$-$C_{14}$)bicycloalkenyls include -bicyclo[3.2.0] hept-2-enyl, -indenyl, -pentalenyl, -naphthalenyl, -azulenyl, -heptalenyl, -1,2,7,8-tetrahydronaphthalenyl, norbornenyl, and the like.

"—($C_8$-$C_{20}$)tricycloalkenyl" means a tri-cyclic hydrocarbon ring system having at least one carbon-carbon double bond in each ring and from 8 to 20 carbon atoms. Representative —($C_8$-$C_{20}$)tricycloalkenyls include -anthracenyl, -phenanthrenyl, -phenalenyl, -acenaphthalenyl, as-indacenyl, s-indacenyl, 2,3,6,7,8,9,10,11-octahydro-1H-cycloocta [e]indenyl, 2,3,4,7,8,9,10,11-octahydro-1H-cyclohepta[a] naphthalenyl, 8,9,10,11-tetrahydro-7H-cyclohepta[a] naphthalenyl, 2,3,4,5,6,7,8,9,10,11,12,13-dodecahydro-1H-cyclohepta[a]heptalenyl, 1,2,3,4,5,6,7,8,9,10,11,12,13,14-tetradecahydro-dicyclohepta[a,c]cyclooctenyl, 2,3,4,5,6,7,8, 9,10,11,12,13-dodecahydro-1H-dibenzo[a,d]cyclononenyl, and the like.

"-(3- to 7-membered)heterocycle" or "-(3- to 7-membered)heterocyclo" means a 3- to 7-membered monocyclic heterocyclic ring which is either saturated, unsaturated non-aromatic, or aromatic. A 3-membered heterocycle can contain up to 1 heteroatom, a 4-membered heterocycle can contain up to 2 heteroatoms, a 5-membered heterocycle can contain up to 4 heteroatoms, a 6-membered heterocycle can contain up to 4 heteroatoms, and a 7-membered heterocycle can contain up to 5 heteroatoms. Each heteroatom is independently selected from nitrogen, which can be quaternized; oxygen; and sulfur, including sulfoxide and sulfone. The -(3- to 7-membered)heterocycle can be attached via a nitrogen or carbon atom. Representative -(3- to 7-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

"-(5- or 6-membered)heterocycle" or "-(5- or 6-membered)heterocyclo" means a 5- or 6-membered monocyclic heterocyclic ring which is either saturated, unsaturated non-aromatic, or aromatic. A 5-membered heterocycle can contain up to 4 heteroatoms and a 6-membered heterocycle can contain up to 4 heteroatoms. Each heteroatom is independently selected from nitrogen, which can be quaternized; oxygen; and sulfur, including sulfoxide and sulfone. The -(5- or 6-membered)heterocycle can be attached via a nitrogen or carbon atom. Representative -(5- or 6-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, tetrahydrofuranyl, tetrahydropyranyl, dihydropyridinyl, tetrahydropyridinyl, tetrahydropyrimidinyl, tetrahydrothiophenyl, tetrahydrothiopyranyl, tetrazolyl, and the like.

"-(3- to 5-membered)heterocycle" or "-(3- to 5-membered)heterocyclo" means a 3- to 5-membered monocyclic heterocyclic ring which is either saturated, unsaturated non-aromatic, or aromatic. A 3-membered heterocycle can contain up to 1 heteroatom, a 4-membered heterocycle can contain up to 2 heteroatoms, and a 5-membered heterocycle can contain up to 4 heteroatoms. Each heteroatom is independently selected from nitrogen, which can be quaternized; oxygen; and sulfur, including sulfoxide and sulfone. The -(3- to 5-membered)heterocycle can be attached via a nitrogen or carbon atom. Representative -(3- to 5-membered)heterocycles include furyl, thiophenyl, pyrrolyl, oxazolyl, imidazolyl, thiazolidinyl, thiadiazolyl, thiazolyl, isoxazolyl, pyrazolyl, isothiazolyl, triazinyl, pyrrolidinonyl, pyrrolidinyl, 2,3-dihydrofuranyl, hydantoinyl, oxiranyl, oxetanyl, tetrahydrofuranyl, tetrahydrothiophenyl, pyrazolidinyl and the like.

"-(7- to 10-membered)bicycloheterocycle" or "-(7- to 10-membered)bicycloheterocyclo" means a 7- to 10-membered bicyclic, heterocyclic ring which is either saturated, unsaturated non-aromatic, or aromatic. A -(7- to 10-membered)bicycloheterocycle contains from 1 to 4 heteroatoms independently selected from nitrogen, which can be quaternized; oxygen; and sulfur, including sulfoxide and sulfone. The -(7- to 10-membered)bicycloheterocycle can be attached via a nitrogen or carbon atom. Representative -(7- to 10-membered)bicycloheterocycles include -quinolinyl, -isoquinolinyl, -chromonyl, -coumarinyl, -indolyl, -indolizinyl, -benzo[b]furanyl, -benzo[b]thiophenyl, -indazolyl, -purinyl, -4H-quinolizinyl, -isoquinolyl, -quinolyl, -phthalazinyl, -naphthyridinyl, -carbazolyl, carbolinyl, -indolinyl, -isoindolinyl, -1,2,3,4-tetrahydroquinolinyl, -1,2,3,4-tetrahydroisoquinolinyl, pyrrolopyrrolyl and the like.

"—($C_3$-$C_{12}$)cycloalkoxy" means a saturated monocyclic hydrocarbon having from 3 to 12 carbon atoms where at least one of the carbon atoms is replaced by an oxygen atom. Representative ($C_3$-$C_{12}$)cycloalkoxy are -oxiranyl, -oxetanyl, -tetrahydrofuranyl, -tetrahydro-2H-pyranyl, -1,4-dioxanyl, -oxepanyl, -1,4-dioxepanyl, -oxocanyl, -1,5-dioxocanyl, -1,3,5-trioxocanyl, -oxonanyl, -1,5-dioxonanyl, -1,4,7-trioxonanyl, -oxacyclododecanyl, -1,7-dioxacyclododecanyl, and -1,5,9-trioxacyclododecanyl.

"—($C_3$-$C_7$)cycloalkoxy" means a saturated monocyclic hydrocarbon having from 3 to 7 carbon atoms where at least one of the carbon atoms is replaced by an oxygen atom. Representative ($C_3$-$C_7$)cycloalkoxy are -oxiranyl, -oxetanyl, -tetrahydrofuranyl, -tetrahydro-2H-pyranyl, -1,4-dioxanyl, -oxepanyl, and -1,4-dioxepanyl.

"—($C_{14}$)aryl" means a 14-membered aromatic carbocyclic moiety such as -anthryl or -phenanthryl.

"-(5- to 10-membered)heteroaryl" means an aromatic heterocycle ring of 5 to 10 members, including both mono- and bicyclic ring systems, where at least one carbon atom of one or both of the rings is replaced with a heteroatom independently selected from nitrogen, oxygen, and sulfur, or at least two carbon atoms of one or both of the rings are replaced with a heteroatom independently selected from nitrogen, oxygen, and sulfur. In one embodiment, one of the -(5- to 10-membered)heteroaryl's rings contain at least one carbon atom. In another embodiment, both of the -(5- to 10-membered)heteroaryl's rings contain at least one carbon atom. Representative -(5- to 10-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, cinnolinyl, phthalazinyl, and quinazolinyl.

"-(5- or 6-membered)heteroaryl" means a monocyclic aromatic heterocycle ring of 5 or 6 members where at least one carbon atom is replaced with a heteroatom independently selected from nitrogen, oxygen, and sulfur. In one embodiment, one of the -(5- or 6-membered)heteroaryl's ring contains at least one carbon atom. Representative -(5- or 6-membered)heteroaryls include pyridyl, furyl, pyrrolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, and thiophenyl.

"—$CH_2$(halo)" means a methyl group where one of the hydrogens of the methyl group has been replaced with a halogen. Representative —$CH_2$(halo) groups include —$CH_2F$, —$CH_2Cl$, —$CH_2Br$, and —$CH_2I$.

"—CH(halo)$_2$" means a methyl group where two of the hydrogens of the methyl group have been replaced with a halogen. Representative —CH(halo)$_2$ groups include —$CHF_2$, —$CHCl_2$, —$CHBr_2$, —CHBrCl, —CHClI, and —$CHI_2$.

"—C(halo)$_3$" means a methyl group where each of the hydrogens of the methyl group has been replaced with a halogen. Representative —C(halo)$_3$ groups include —$CF_3$, —$CCl_3$, —$CBr_3$, and —$Cl_3$.

"—Halogen" or "-halo" means —F, —Cl, —Br, or —I.

"Oxo", "=O", and the like as used herein mean an oxygen atom doubly bonded to carbon or another element.

"Thiooxo", "thioxo", "=S", and the like as used herein mean a sulfur atom doubly bonded to carbon or another element.

As used herein in connection with Formula (II), when the dashed line in the 6-membered, nitrogen-containing ring that is fused to the Q group is absent, then Formula (II) is understood to appear as follows

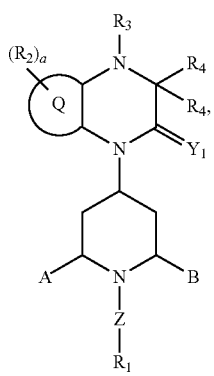

(II)

i.e., the 6-membered, nitrogen-containing ring that is fused to the Q group contains no double bond between the ring-carbon to which the $R_4$ groups are attached and the adjacent ring-nitrogen.

As used herein in connection with Formula (II), when the dashed line in the 6-membered, nitrogen-containing ring that is fused to the Q group indicates the presence of a bond, then Formula (II) is understood to appear as follows

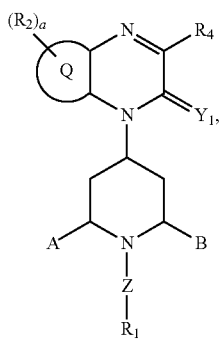

(II)

i.e., the 6-membered, nitrogen-containing ring that is fused to the Q group contains a double bond between the ring-carbon to which the $R_4$ group is attached and the adjacent ring-nitrogen.

As used herein in connection with the $R_1$ group

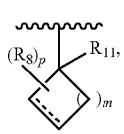

(i)

when the dashed line in the ring indicates the presence of a bond, then that group is understood to appear as follows

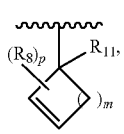

(i)

and when the dashed line in the ring indicates the absence of a bond, then that group is understood to appear as follows

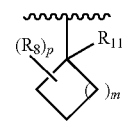

(i)

"—[($C_1$-$C_{10}$)alkyl optionally substituted by $R_1$]$_h$—" as used herein in connection with Z means that, when h is 0, Z is a bond. When h is 1, Z—$R_1$, as attached to the piperidine ring bearing A and B substituents, is

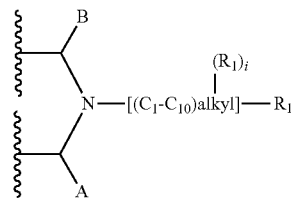

where; when i is 0, the ($C_1$-$C_{10}$)alkyl is unsubstituted by an $R_1$ group at any position other than at the carbon atom furthest removed from the piperidine ring bearing A and B substituents; and, when i is 1, (the ($C_1$-$C_{10}$)alkyl is substituted by an $R_1$ group at the carbon atom furthest removed from the piperidine ring bearing A and B substituents and substituted by another independently selected $R_1$ group at any carbon atom of the ($C_1$-$C_{10}$)alkyl including at the carbon atom furthest removed from the piperidine ring bearing A and B substituents.

"($C_2$-$C_{10}$)alkenyl optionally substituted by $R_1$]—" as used herein in connection with Z means that the piperidine ring bearing A and B substituents, is

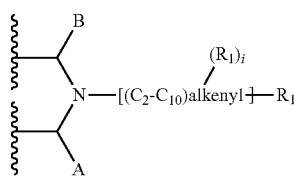

where; when i is 0, the ($C_2$-$C_{10}$)alkenyl is unsubstituted by an $R_1$ group at any position other than at the carbon atom furthest removed from the piperidine ring bearing A and B substituents; and, when i is 1, the ($C_2$-$C_{10}$)alkenyl is substituted by an $R_1$ group at the carbon atom furthest removed from the piperidine ring bearing A and B substituents and substituted by another independently selected $R_1$ group at any carbon atom of the ($C_2$-$C_{10}$)alkenyl including at the carbon atom furthest removed from the piperidine ring bearing A and B substituents.

"($C_2$-$C_6$)bridge" as used herein means a hydrocarbon chain containing 2 to 6 carbon atoms joining two atoms of the piperidine ring of Formula (I) or Formula (II) to form a fused bicyclic ring system. For example, compounds of the invention can comprise a ($C_2$-$C_6$)bridge joining positions 2 and 6 of the piperidine ring (A-B can together form a ($C_2$-$C_6$)bridge). Exemplary compounds of the invention include those with an unsubstituted ($C_2$)bridge, —$CH_2$—

CH$_2$—, joining positions 2 and 6 of the piperidine ring (A-B can together form a (C$_2$)bridge); an unsubstituted (C$_3$) bridge, —CH$_2$—CH$_2$—CH$_2$—, joining positions 2 and 6 of the piperidine ring (A-B can together form a (C$_3$)bridge); an unsubstituted (C$_4$)bridge, —CH$_2$—CH$_2$—CH$_2$—CH$_2$—, joining positions 2 and 6 of the piperidine ring (A-B can together form a (C$_4$)bridge); an unsubstituted (C$_5$)bridge, —CH$_2$—CH$_2$—CH$_2$—CH$_2$—CH$_2$—, joining positions 2 and 6 of the piperidine ring (A-B can together form a (C$_5$)bridge); or an unsubstituted (C$_6$)bridge, —CH$_2$—CH$_2$—CH$_2$—CH$_2$—CH$_2$—CH$_2$—, joining positions 2 and 6 of the piperidine ring (A-B can together form a (C$_6$) bridge). Examples of compounds where A-B can together form a (C$_2$-C$_6$)bridge include compounds comprising the following ring systems: 8-aza-bicyclo[3.2.1]octane; 9-aza-bicyclo[3.3.1]nonane; 10-aza-bicyclo[4.3.1]decane; 11-aza-bicyclo[5.3.1]undecane; and 12-aza-bicyclo[6.3.1]dodecane. Examples of a (C$_2$-C$_6$)bridge which optionally contains —HC═CH— within the (C$_2$-C$_6$)bridge include —HC═CH—, —CH$_2$—HC═CH—, —HC═CH—CH$_2$—, —CH$_2$—HC═CH—CH$_2$—, and the like. Examples of a (C$_2$-C$_6$)bridge which optionally contains —O— within the (C$_2$-C$_6$)bridge include —CH$_2$—O—CH$_2$— (containing 2 carbon atoms), —CH$_2$—O—CH$_2$—CH$_2$— and —CH$_2$—CH$_2$—O—CH$_2$— (each containing 3 carbon atoms), —CH$_2$—CH$_2$—O—CH$_2$—CH$_2$—, —CH$_2$—O—CH$_2$—CH$_2$—CH$_2$— and —CH$_2$—CH$_2$—CH$_2$—O—CH$_2$— (each containing 4 carbon atoms), and the like.

In compounds of the invention comprising a bridge joining positions 2 and 6 of the piperidine ring (e.g., A-B can together form a (C$_2$-C$_6$)bridge), for, e.g., a compound of Formula (II), the exemplary endo bridge

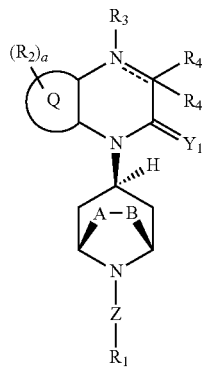

is equivalent to

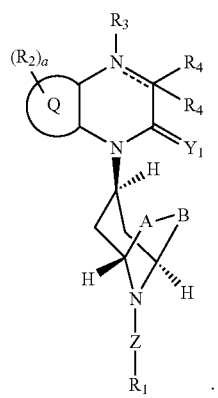

In compounds of the invention comprising a bridge joining positions 2 and 6 of the piperidine ring (e.g., A-B can together form a (C$_2$-C$_6$)bridge), for, e.g., a compound of Formula (II), the exemplary exo bridge

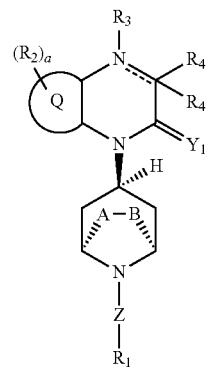

is equivalent to

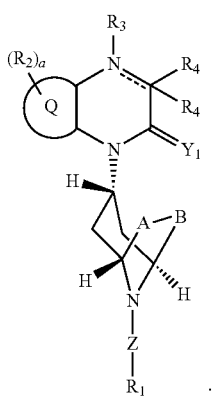

In compounds of the invention where the —Z—R$_1$ group comprises a bicyclic group, that bicyclic group can have two orientations. For example, for a —Z—R$_1$ group that is a —(C$_6$-C$_{14}$)bicycloalkyl, e.g., bicyclo[3.3.1]nonanyl, attached directly to the piperidine ring nitrogen, the following orientations are possible:

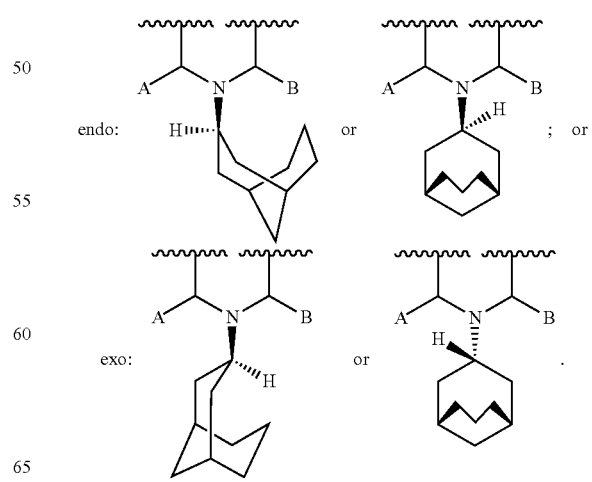

When a first group is "substituted with one or more" second groups, one or more hydrogen atoms of the first group is replaced with a corresponding number of second groups. When the number of second groups is two or greater, each second group can be the same or different.

In one embodiment, a first group is substituted with up to three second groups.

In another embodiment, a first group is substituted with one or two second groups.

In another embodiment, a first group is substituted with only one second group.

The phrase "benzo", "benzo group" and the like, when used in connection with the optionally-substituted Q group, means

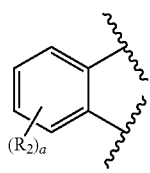

where $R_2$ and a are defined above for the Substituted-Quinoxaline-Type Piperidine Compounds of Formulas (I) and (II).

The phrase "pyridino", "pyridino group" and the like, when used in connection with the optionally-substituted Q group, means

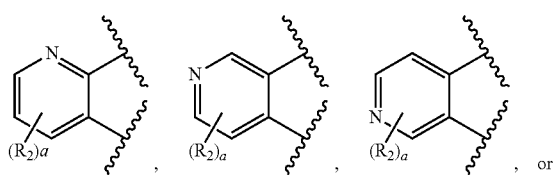, or

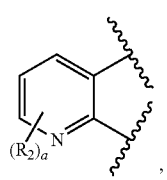, where $R_2$ and a are defined above for the Substituted-Quinoxaline-Type Piperidine Compounds of Formulas (I) and (II). In one embodiment, the optionally-substituted pyridino Q group is

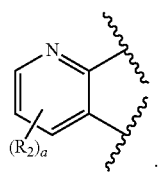.

In another embodiment, the optionally-substituted pyridino Q group is

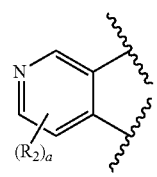.

In another embodiment, the optionally-substituted pyridino Q group is

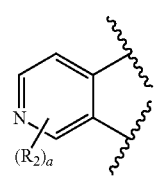.

In another embodiment, the optionally-substituted pyridino Q group is

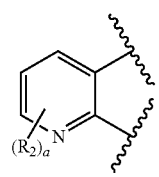.

The phrase "pyrimidino", "pyrimidino group" and the like, when used in connection with the optionally-substituted Q group, means

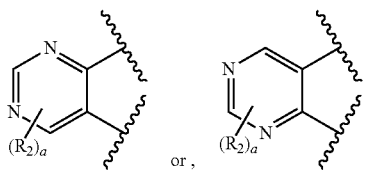

where $R_2$ and a are defined above for the Substituted-Quinoxaline-Type Piperidine Compounds of Formulas (I) and (II). In one embodiment, the optionally-substituted pyrimidino Q group is

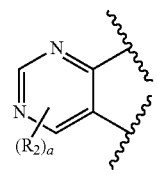.

In another embodiment, the optionally-substituted pyrimidino Q group is

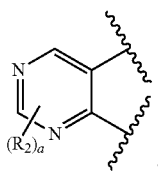

The phrase "pyrazino", "pyrazino group" and the like, when used in connection with the optionally-substituted Q group, means

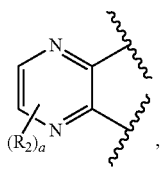

where $R_2$ and a are defined above for the Substituted-Quinoxaline-Type Piperidine Compounds of Formulas (I) and (II).

The phrase "pyridazino", "pyridazino group" and the like, when used in connection with the optionally-substituted Q group, means

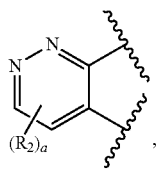 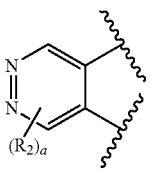 or, 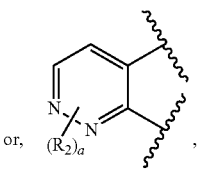

where $R_2$ and a are defined above for the Substituted-Quinoxaline-Type Piperidine Compounds of Formulas (I) and (II). In one embodiment, the optionally-substituted pyridazino Q group is

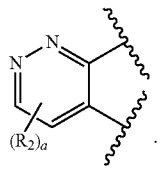

In another embodiment, the optionally-substituted pyridazino Q group is

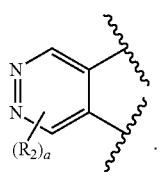

In another embodiment, the optionally-substituted pyridazino Q group is

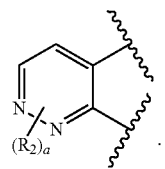

In one embodiment, the phrase "optionally substituted bicyclo[3.3.1]nonyl", when used in connection with the optionally-substituted $R_1$ group, means

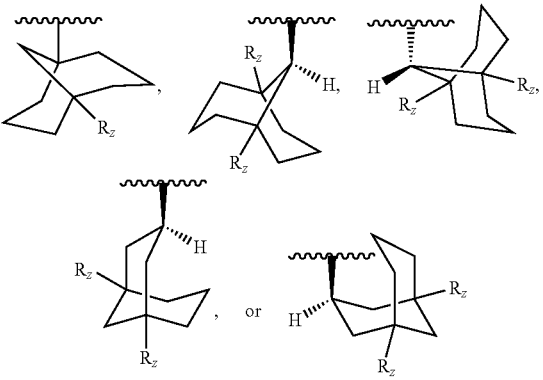

where $R_z$ is defined above for the Substituted-Quinoxaline-Type Piperidine Compounds of Formulas (I) and (II).

In one embodiment the optionally substituted bicyclo [3.3.1]nonyl is

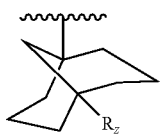

In another embodiment the optionally substituted bicyclo [3.3.1]nonly is

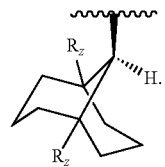

In another embodiment the optionally substituted bicyclo [3.3.1]nonly is

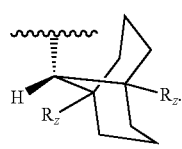

In another embodiment the optionally substituted bicyclo [3.3.1]nonly is

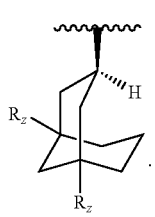

In another embodiment the optionally substituted bicyclo[3.3.1]nonly is

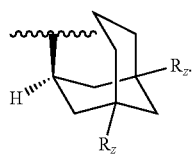

In one embodiment the phrase "optionally substituted —(C$_6$-C$_{14}$)bicycloalkyl" means

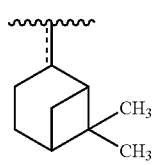

wherein the dashed line denotes the presence or absence of a bond.

The phrase "pyrrolino", "pyrrolino group" and the like, when used in connection with the optionally-substituted Q group, means

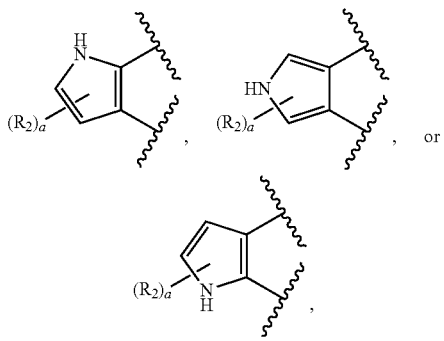

where R$_2$ and a are defined above for the Substituted-Quinoxaline-Type Piperidine Compounds of Formulas (I) and (II). In one embodiment, the optionally-substituted pyrrolino Q group is

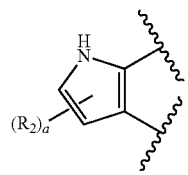

In another embodiment, the optionally-substituted pyrrolino. Q group is

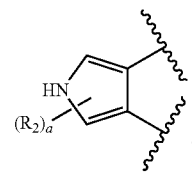

In another embodiment, the optionally-substituted pyrrolino Q group is

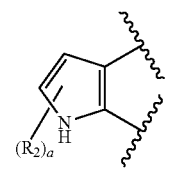

The phrase "imidazolino", "imidazolino group" and the like, when used in connection with the optionally-substituted Q group, means

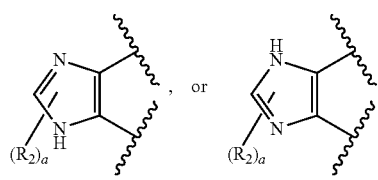

where R$_2$ and a are defined above for the Substituted-Quinoxaline-Type Piperidine Compounds of Formulas (I) and (II). In one embodiment, the optionally-substituted imidazolino Q group is

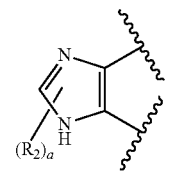

In another embodiment, the optionally-substituted imidazolino Q group is

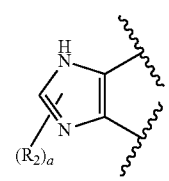

The phrase "pyrazolino", "pyrazolino group" and the like, when used in connection with the optionally-substituted Q group, means

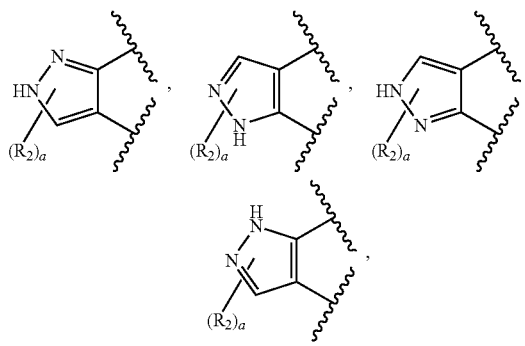

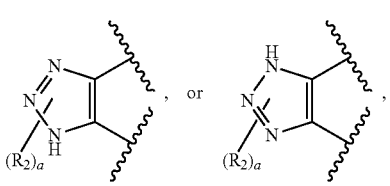

where R₂ and a are defined above for the Substituted-Quinoxaline-Type Piperidine Compounds of Formulas (I) and (II). In one embodiment, the optionally-substituted triazolino Q group is

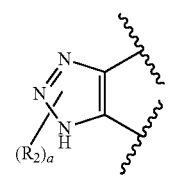

In another embodiment, the optionally-substituted triazolino Q group is

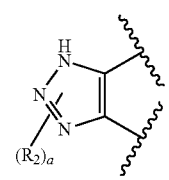

The phrase "furano", "furano group" and the like, when used in connection with the optionally-substituted Q group, means where R₂ and a are defined above for the Substituted-Quinoxaline-Type Piperidine Compounds of Formulas (I) and (II). In one embodiment, the optionally-substituted pyrazolino Q group is

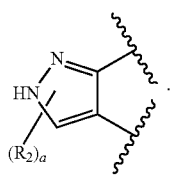

In another embodiment, the optionally-substituted pyrazolino Q group is

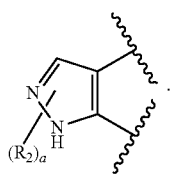

In another embodiment, the optionally-substituted pyrazolino Q group is

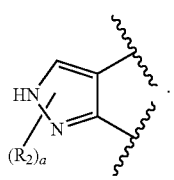

In another embodiment, the optionally-substituted pyrazolino Q group is

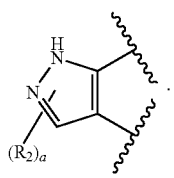

The phrase "triazolino", "triazolino group" and the like, when used in connection with the optionally-substituted Q group, means where R₂ and a are defined above for the Substituted-Quinoxaline-Type Piperidine Compounds of Formulas (I) and (II). In one embodiment, the optionally-substituted furano Q group is In another embodiment, the optionally-substituted furano Q group is

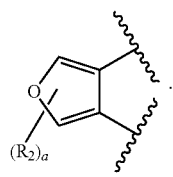

In another embodiment, the optionally-substituted furano Q group is

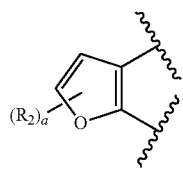

The phrase "oxazolino", "oxazolino group" and the like, when used in connection with the optionally-substituted Q group, means

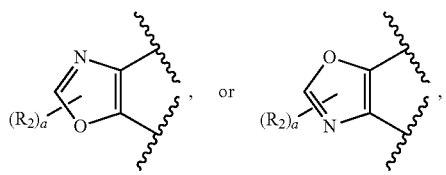

where $R_2$ and a are defined above for the Substituted-Quinoxaline-Type Piperidine Compounds of Formulas (I) and (II). In one embodiment, the optionally-substituted oxazolino Q group is

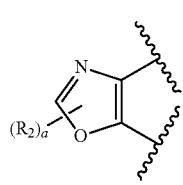

In another embodiment, the optionally-substituted oxazolino Q group is

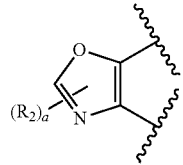

The phrase "isoxazolino", "isoxazolino group" and the like, when used in connection with the optionally-substituted Q group, means

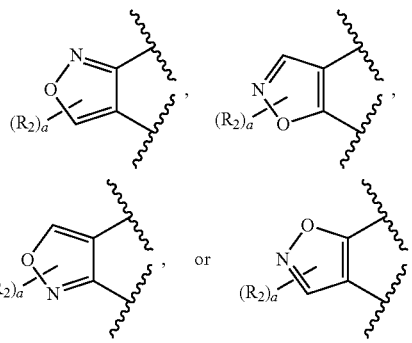

where $R_2$ and a are defined above for the Substituted-Quinoxaline-Type Piperidine Compounds of Formulas (I) and (II). In one embodiment, the optionally-substituted isoxazolino Q group is

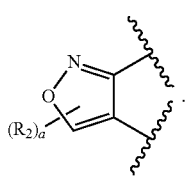

In another embodiment, the optionally-substituted isoxazolino Q group is

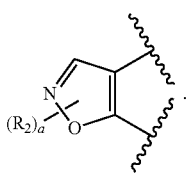

In another embodiment, the optionally-substituted isoxazolino Q group is

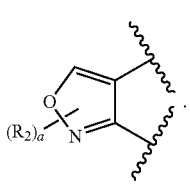

In another embodiment, the optionally-substituted isoxazolino Q group is

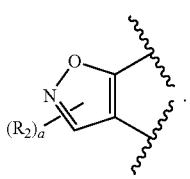

The phrase "oxadiazolino", "oxadiazolino group" and the like, when used in connection with the optionally-substituted Q group, means

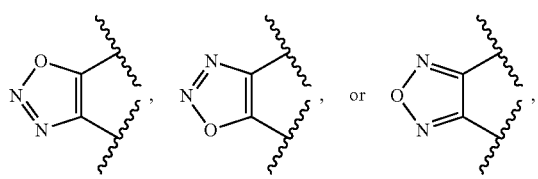

where $R_2$ and a are defined above for the Substituted-Quinoxaline-Type Piperidine Compounds of Formulas (I) and (II). In one embodiment, the optionally-substituted oxadiazolino Q group is

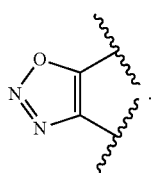 [SMILES: *c1nnoc1*]

In another embodiment, the optionally-substituted oxadiazolino Q group is

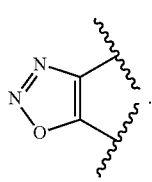 [SMILES: *c1nnoc1*]

In another embodiment, the optionally-substituted oxadiazolino Q group is

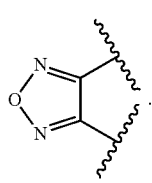

The phrase "thiopheno", "thiopheno group" and the like, when used in connection with the optionally-substituted Q group, means

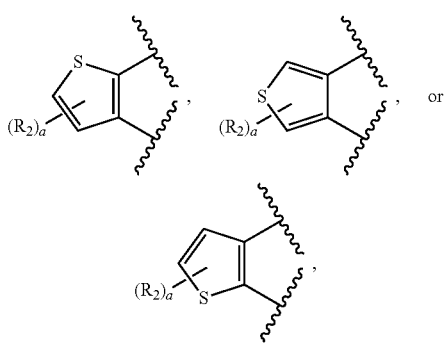

where $R_2$ and a are defined above for the Substituted-Quinoxaline-Type Piperidine Compounds of Formulas (I) and (II). In one embodiment, the optionally-substituted thiopheno Q group is

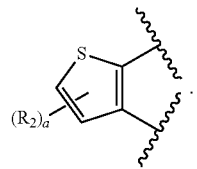

In another embodiment, the optionally-substituted thiopheno Q group is

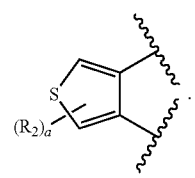

In another embodiment, the optionally-substituted thiopheno Q group is

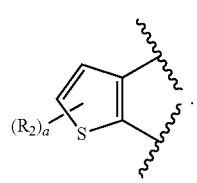

The phrase "thiazolino", "thiazolino group" and the like, when used in connection with the optionally-substituted Q group, means

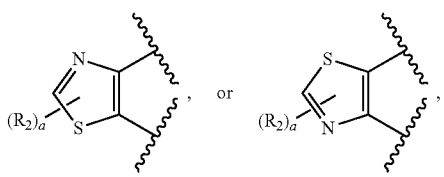

where $R_2$ and a are defined above for the Substituted-Quinoxaline-Type Piperidine Compounds of Formulas (I) and (II). In one embodiment, the optionally-substituted thiazolino Q group is

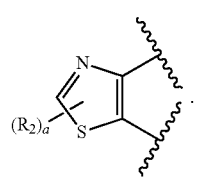

In another embodiment, the optionally-substituted thiazolino Q group is

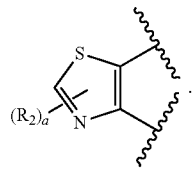

The phrase "isothiazolino", "isothiazolino group" and the like, when used in connection with the optionally-substituted Q group, means

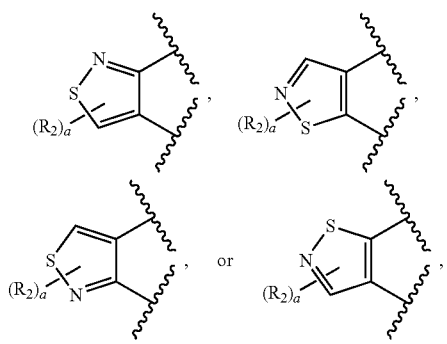

where R$_2$ and a are defined above for the Substituted-Quinoxaline-Type Piperidine Compounds of Formulas (I) and (II). In one embodiment, the optionally-substituted isothiazolino Q group is

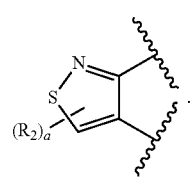

In another embodiment, the optionally-substituted isothiazolino Q group is

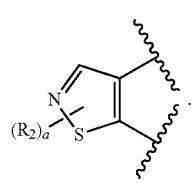

In another embodiment, the optionally-substituted isothiazolino Q group is

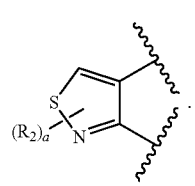

In another embodiment, the optionally-substituted isothiazolino Q group is

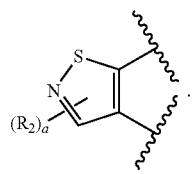

The phrase "thiadiazolino", "thiadiazolino group" and the like, when used in connection with the optionally-substituted Q group, means

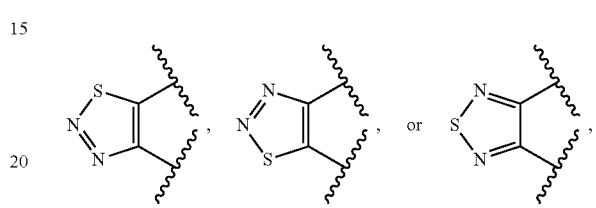

where R$_2$ and a are defined above for the Substituted-Quinoxaline-Type Piperidine Compounds of Formulas (I) and (II). In one embodiment, the optionally-substituted thiadiazolino Q group is

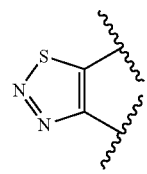

In another embodiment, the optionally-substituted thiadiazolino Q group is

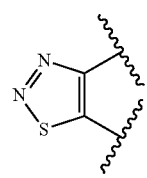

In another embodiment, the optionally-substituted thiadiazolino Q group is

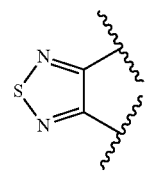

The phrase "3,3-diphenylpropyl-" and the like, when used in connection with the —Z—R$_1$ group, means

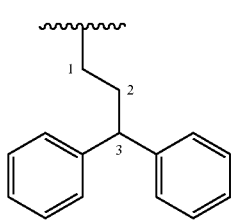 [SMILES: *CCC(c1ccccc1)c1ccccc1]

where the 3 carbon of the propyl is indicated by the number 3 in the structure above.

The phrase "tetrazolyl group" means

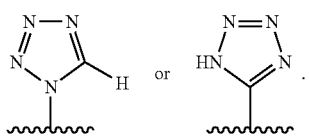

In one embodiment, the tetrazolyl group is

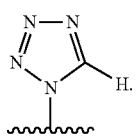

In another embodiment, the tetrazolyl group is

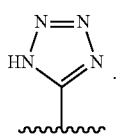

The term "animal" includes, but is not limited to, a human or a non-human animal, such as a companion animal or livestock, e.g., a cow, monkey, baboon, chimpanzee, horse, sheep, pig, chicken, turkey, quail, cat, dog, mouse, rat, rabbit or guinea pig.

The phrase "pharmaceutically acceptable derivative", as used herein, includes any pharmaceutically acceptable salt, solvate, prodrug, radiolabeled, stereoisomer, enantiomer, diastereomer, other stereoisomeric form, racemic mixture, geometric isomer, and/or tautomer, e.g., of a Substituted-Quinoxaline-Type Piperidine Compound of the invention. In one embodiment, the pharmaceutically acceptable derivative is a pharmaceutically acceptable salt, solvate, radiolabeled, stereoisomer, enantiomer, diastereomer, other stereoisomeric form, racemic mixture, geometric isomer, and/or tautomer, e.g., of a Substituted-Quinoxaline-Type Piperidine Compound of the invention. In another embodiment, the pharmaceutically acceptable derivative is a pharmaceutically acceptable salt, e.g., of a Substituted-Quinoxaline-Type Piperidine Compound of the invention.

The phrase "pharmaceutically acceptable salt", as used herein, is any pharmaceutically acceptable salt that can be prepared from a Substituted-Quinoxaline-Type Piperidine Compound including a salt formed from an acid and a basic functional group, such as a nitrogen group, of a Substituted-Quinoxaline-Type Piperidine Compound. Illustrative salts include, but are not limited, to sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt prepared from a Substituted-Quinoxaline-Type Piperidine Compound having an acidic functional group, such as a carboxylic acid functional group, and a pharmaceutically acceptable inorganic or organic base. Suitable bases include, but are not limited to, hydroxides of alkali metals such as sodium, potassium, cesium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; picoline; N-methyl,N-ethylamine; diethylamine; triethylamine; mono-, bis-, or tris-(2-hydroxy-($C_1$-$C_3$)alkyl amines), such as mono-, bis-, or tris-(2-hydroxyethyl)amine, 2-hydroxy-tert-butylamine, or tris-(hydroxymethyl)methylamine, N,N-di-[($C_1$-$C_3$)alkyl]-N-(hydroxy-($C_1$-$C_3$)alkyl)-amines, such as N,N-dimethyl-N-(2-hydroxyethyl)amine, or tri-(2-hydroxyethyl)amine; N-methyl-D-glucamine; and amino acids such as arginine, lysine, and the like. One skilled in the art will recognize that, e.g., acid addition salts of a Substituted-Quinoxaline-Type Piperidine Compound can be prepared by reaction of the compounds with the appropriate acid via a variety of known methods.

The invention disclosed herein is also meant to encompass all solvates of the Substituted-Quinoxaline-Type Piperidine Compounds. "Solvates" are known in the art and are considered to be a combination, physical association and/or solvation of a Substituted-Quinoxaline-Type Piperidine Compound with a solvent molecule, e.g., a disolvate, monosolvate or hemisolvate when the solvent molecule: Substituted-Quinoxaline-Type Piperidine Compound molecule ratio is 2:1, 1:1 or 1:2, respectively. This physical association involves varying degrees of ionic and covalent bonding, including hydrogen bonding. In certain instances, the solvate can be isolated, for example when one or more solvent molecules are incorporated into the crystal lattice of a crystalline solid. Thus, "solvate", as used herein, encompasses both solution-phase and isolatable solvates. A Substituted-Quinoxaline-Type Piperidine Compound of the invention can be present as a solvated form with a pharmaceutically acceptable solvent, such as water, methanol, ethanol, and the like, and it is intended that the invention include both solvated and unsolvated Substituted-Quinoxaline-Type Piperidine Compound forms. As "hydrate" relates to a particular subgroup of solvates, i.e., where the solvent molecule is water, hydrates are included within the solvates of the invention. Preparation of solvates is known in the art. For example, M. Caira et al., *J. Pharmaceut. Sci.,* 93(3): 601-611 (2004), describes the preparation of solvates of fluconazole with ethyl acetate and with water. Similar preparations of solvates, hemisolvate, hydrates, and the like are described by E. C. van Tonder et al., *AAPS Pharm. Sci. Tech.,* 5(1):Article 12 (2004), and A. L. Bingham et al., *Chem. Commun.,* 603-604 (2001). A typical, non-limiting, process involves dissolving the Substituted-Quinoxaline-Type Piperidine Compound in a desired amount of the desired solvent (organic, water or mixtures thereof) at temperatures above about 20° C. to about 25° C., cooling the solution at a rate sufficient to form crystals, and isolating the crystals by known methods, e.g., filtration. Analytical techniques, for example, infrared spectroscopy, can be used to show the presence of the solvent in a crystal of the solvate.

The invention disclosed herein is also meant to encompass all prodrugs of the Substituted-Quinoxaline-Type Piperidine Compounds. "Prodrugs" are known in the art and, while not necessarily possessing any pharmaceutical activity as such, are considered to be any covalently bonded carrier(s) that releases the active parent drug in vivo. In general, such prodrugs will be a functional derivative of a Substituted-Quinoxaline-Type Piperidine Compound of Formula (I) or Formula (II) which is readily convertible in vivo, e.g., by being metabolized, into the required Substituted-Quinoxaline-Type Piperidine Compound of Formula (I) or Formula (II). Conventional procedures for the selection and preparation of suitable prodrug derivatives are described in, for example, *Design of Prodrugs*, H. Bundgaard ed., Elsevier (1985); "Drug and Enzyme Targeting, Part A," K. Widder et al. eds., Vol. 112 in *Methods in Enzymology*, Academic Press (1985); Bundgaard, "Design and Application of Prodrugs," Chapter 5 (pp. 113-191) in *A Textbook of Drug Design and Development*, P. Krogsgaard-Larsen and H. Bundgaard eds., Harwood Academic Publishers (1991); Bundgaard et al., *Adv. Drug Delivery Revs.* 8:1-38 (1992); Bundgaard et al., *J. Pharmaceut. Sci.* 77:285 (1988); and Kakeya et al., *Chem. Pharm. Bull.* 32:692 (1984).

In addition, one or more hydrogen, carbon or other atoms of a Substituted-Quinoxaline-Type Piperidine Compound can be replaced by an isotope of the hydrogen, carbon or other atoms. Such a "radiolabeled", "radiolabeled form", and the like of a Substituted-Quinoxaline-Type Piperidine Compound, each of which is encompassed by the invention, is useful as a research and/or diagnostic tool in metabolism pharmacokinetic studies and in binding assays. Examples of isotopes that can be incorporated into a Substituted-Quinoxaline-Type Piperidine Compound of the invention include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Radiolabeled compounds of the invention can be prepared by methods known in the art. For example, tritiated compounds of Formula I can be prepared by introducing tritium into the particular compound of Formula I, for example, by catalytic dehalogenation with tritium. This method can include reacting a suitably halogen-substituted precursor of a compound of Formula (I) or Formula (II) with tritium gas in the presence of a suitable catalyst, for example, Pd/C, in the presence or absence of a base. Other suitable methods for preparing tritiated compounds can be found in Filer, *Isotopes in the Physical and Biomedical Sciences, Vol. 1, Labeled Compounds (Part A)*, Chapter 6 (1987). $^{14}C$-labeled compounds can be prepared by employing starting materials having a $^{14}C$ carbon.

A Substituted-Quinoxaline-Type Piperidine Compound can contain one or more asymmetric centers and can thus give rise to enantiomers, diastereomers, and other stereoisomeric forms. The invention is also meant to encompass all such possible forms as well as their racemic and resolved forms or any mixture thereof. When a Substituted-Quinoxaline-Type Piperidine Compound contains an olefinic double bond or other center of geometric asymmetry, and unless specified otherwise, it is intended to include all "geometric isomers", e.g., both E and Z geometric isomers. All "tautomers", e.g., ketone-enol, amide-imidic acid, lactam-lactim, enamine-imine, amine-imine, and enamine-enimine tautomers, are intended to be encompassed by the invention as well.

As used herein, the terms "stereoisomer", "stereoisomeric form", and the like are general terms for all isomers of individual molecules that differ only in the orientation of their atoms in space. It includes enantiomers and isomers of compounds with more than one chiral center that are not mirror images of one another ("diastereomers").

The term "chiral center" refers to a carbon atom to which four different groups are attached.

The term "enantiomer" or "enantiomeric" refers to a molecule that is nonsuperimposeable on its mirror image and hence optically active where the enantiomer rotates the plane of polarized light in one direction and its mirror image rotates the plane of polarized light in the opposite direction.

The term "racemic" refers to a mixture of equal parts of enantiomers which is optically inactive.

The term "resolution" refers to the separation or concentration or depletion of one of the two enantiomeric forms of a molecule.

Optical isomers of a Substituted-Quinoxaline-Type Piperidine Compound can be obtained by known techniques such as chiral chromatography or formation of diastereomeric salts from an optically active acid or base.

The phrase "effective amount", when used in connection with a Substituted-Quinoxaline-Type Piperidine Compound, means an amount effective for: (a) treating or preventing a Condition; (b) detectably inhibiting ORL-1 receptor function in a cell; or (c) detectably activating ORL-1 receptor function in a cell.

The phrase "effective amount", when used in connection with a second therapeutic agent means an amount for providing the therapeutic effect of the therapeutic agent.

The terms "modulate", "modulating", and the like as used herein with respect to the ORL-1 receptor mean the mediation of a pharmacodynamic response (e.g., analgesia) in an animal from (i) inhibiting or activating the receptor, or (ii) directly or indirectly affecting the normal regulation of the receptor activity. Compounds that modulate the receptor activity include agonists, partial agonists, antagonists, mixed agonists/antagonists, mixed partial agonists/antagonists and compounds which directly or indirectly affect regulation of the receptor activity.

As used herein, a compound that binds to a receptor and mimics the regulatory effect(s) of an endogenous ligand is defined as an "agonist". As used herein, a compound that binds to a receptor and is only partly effective as an agonist is defined as a "partial agonist". As used herein, a compound that binds to a receptor but produces no regulatory effect, but rather blocks binding of another agent to the receptor is defined as an "antagonist". (See Ross and Kenakin, *Pharmacodynamics: Mechanisms of Drug Action and the Relationship Between Drug Concentration and Effect*, Chapter 2 in. *Goodman & Gilman's The Pharmacological Basis of Therapeutics* 31-32 (J. G. Hardman, L. E. Limbird and A. Goodman-Gilman eds., 10$^{th}$ ed 2001).

The term "MeOH" means methanol, i.e., methyl alcohol.
The term "EtOH" means ethanol, i.e., ethyl alcohol.
The term "Et$_2$O" means diethyl ether, i.e., ethoxyethane.
The term "THF" means tetrahydrofuran.
The term "DMF" means N,N-dimethylformamide.
The term "DCM" means methylene chloride, i.e., dichloromethane or CH$_2$Cl$_2$.
The term "DCE" means dichloroethane.
The term "EtOAc" means ethyl acetate.
The term "MeCN" means acetonitrile.
The term "DMSO" means dimethylsulfoxide, i.e., methylsulfinylmethane.
The term "AcOH" means acetic acid.

The term "NH₄Cl" means ammonium chloride.
The term "NH₄OH" means ammonium hydroxide.
The term "TEA" means triethylamine.
The term "TMA" means trimethylamine.
The term "DIEA" means N,N-di-iso-propylethylamine or N-ethyl-N-iso-propylpropan-2-amine.
The term "NaH" means sodium hydride.
The term "DMAP" means 4-dimethylaminopyridine.
The term "HOBT" means 1-hydroxybenzotriazole.
The term "WSCI" means a water soluble carbodiimide, for example, N-ethyl-N-(3-dimethylaminopropyl)carbodiimide.
The term "DIC" means 1,3-diisopropylcarbodiimide, i.e., N,N'-methanediylidenedipropan-2-amine.
The term "TMSCl" means trimethylsilylchloride or (CH₃)₃SiCl.
The term "TFFA" means trifluoroacetic anhydride or 2,2,2-trifluoroacetic anhydride.
The term "Bn" means benzyl or

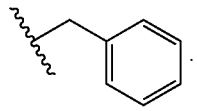

The term "BOC" means tert-butyloxycarbonyl or

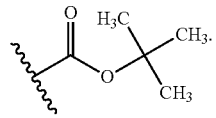

The term "CBZ" means benzyloxycarbonyl or

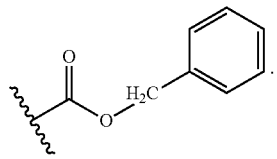 [SMILES: *C(=O)OCc1ccccc1]

The term "IBD" means inflammatory-bowel disease.
The term "IBS" means irritable-bowel syndrome.
The term "ALS" means amyotrophic lateral sclerosis.
The phrases "treatment of", "treating", and the like include the amelioration or cessation of a Condition or a symptom thereof. In one embodiment, treating includes inhibiting, for example, decreasing the overall frequency of episodes of a Condition or a symptom thereof.
The phrases "prevention of", "preventing", and the like include the avoidance of the onset of a Condition or a symptom thereof.
A "disorder" includes, but is not limited to, the Conditions defined above.

4.4 Methods for Making the Substituted-Quinoxaline-Type Piperidine Compounds

The Substituted-Quinoxaline-Type Piperidine Compounds can be made using conventional organic synthesis, in view of the present disclosure, and including the following illustrative methods shown in the schemes below where $R_1$, $R_2$, $R_3$, $R_4$, $T_1$, $T_2$, $T_3$, Q, $Y_1$, Y, Z, A, B, a, and the dashed line are defined above, L is a halogen leaving group such as Br or I, L' is F or Cl, R is —($C_1$-$C_4$)alkyl or —$CF_3$, R' is —($C_1$-$C_4$)alkyl, and u is the integer 1 or 2.

Scheme A

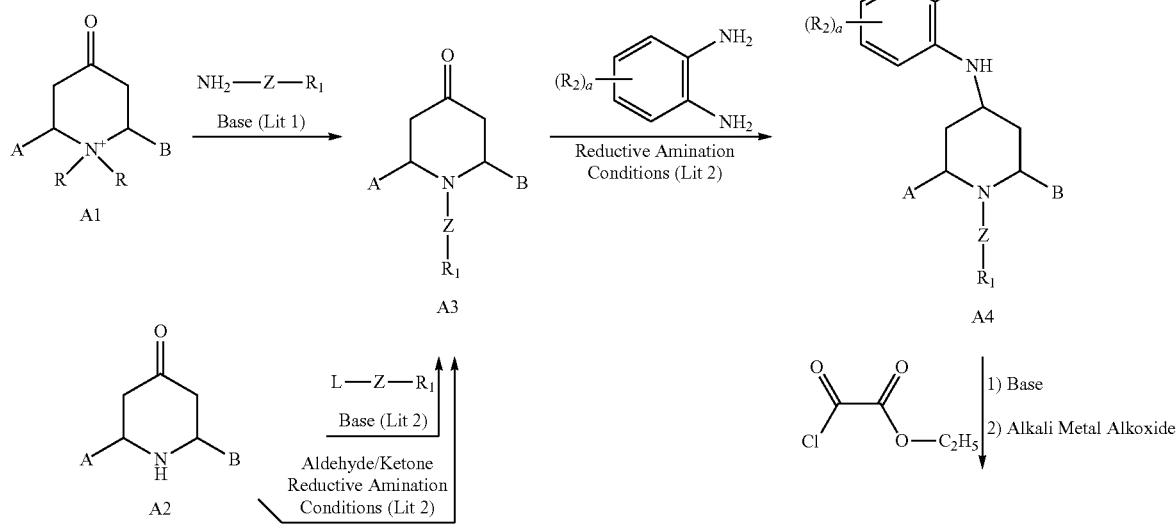

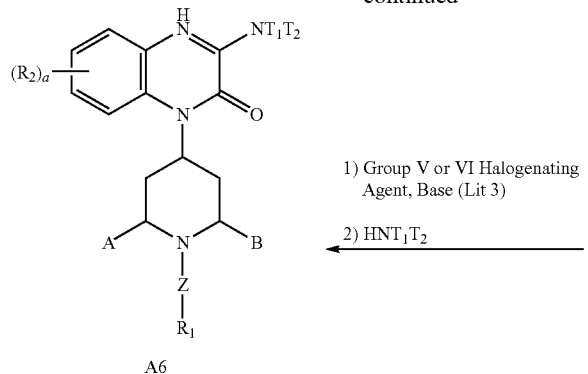

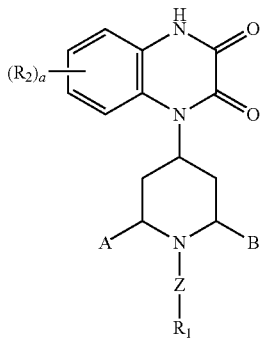

In Scheme A and the other schemes, "Lit 1" refers to the procedures described in the publications D. A. Tortolani and M. A. Poss, *Org. Lett.* 1: 1261 (1999) and/or International PCT Publication No. WO 2005/075459 A1 of Euro-Celtique S. A., "Lit 2" refers to the procedures described in U.S. Pat. No. 6,635,653 by Goehring et al., and "Lit 3" refers to the procedures described in the publication J. Dudash et al., *Bioorg. Med. Chem. Let.*, 15(21): 4790-4793 (2005).

Compounds of formula A1 and A2 are commercially available or can be prepared by methods known to the art.

A piperidinium salt of structure A1 can be reacted with a primary amine in a suitable solvent such as ethanol under reflux conditions in the presence of a base such as potassium carbonate as described in reference "Lit 1" to provide the 1-(substituted)piperidine-4-one compound A3. As described in reference "Lit 2," compound A3 can also be prepared by alkylation of a piperidine-4-one of structure A2 with an alkyl bromide or alkyl iodide in a suitable solvent such as dimethyl formamide, acetonitrile or dimethyl sulfoxide in the presence of an inorganic base such as potassium carbonate or an organic base such as diisopropylethylamine. As described in reference "Lit 2," compound A3 can also be prepared by reductive amination of compound A2 with an aldehyde or ketone using either sodium triacetoxyborohydride or sodium cyanoborohydride in a suitable solvent such as dichloromethane or methanol, respectively. Compound A3 can then be reductively aminated with a substituted or unsubstituted 1,2-phenylenediamine using sodium triacetoxyborohydride or sodium cyanoborohydride in a suitable solvent such as dichloromethane or methanol, respectively, to provide compound A4, as described in reference "Lit 2." Compound A4 can be dissolved in a suitable solvent such as toluene and reacted with ethyl 2-chloro-2-oxoacetate in the presence of a base such as triethylamine followed by treatment with an alkali metal alkoxide such as sodium ethoxide in a suitable solvent such as methanol or ethanol to provide compound A5. Compound A5 can be dissolved in a suitable solvent such as toluene and, as described in reference "Lit 3," reacted with a group V or VI halogenating agent, such as thionyl chloride, phosphorus oxychloride or phosphorus pentachloride, and a base such as diisopropylethylamine in which an intermediate, believed to comprise a 3-chloroquinoxalin-2-one, is formed then reacted with the desired amine, e.g., HNT$_1$T$_2$, to give compound A6, as shown in Scheme A.

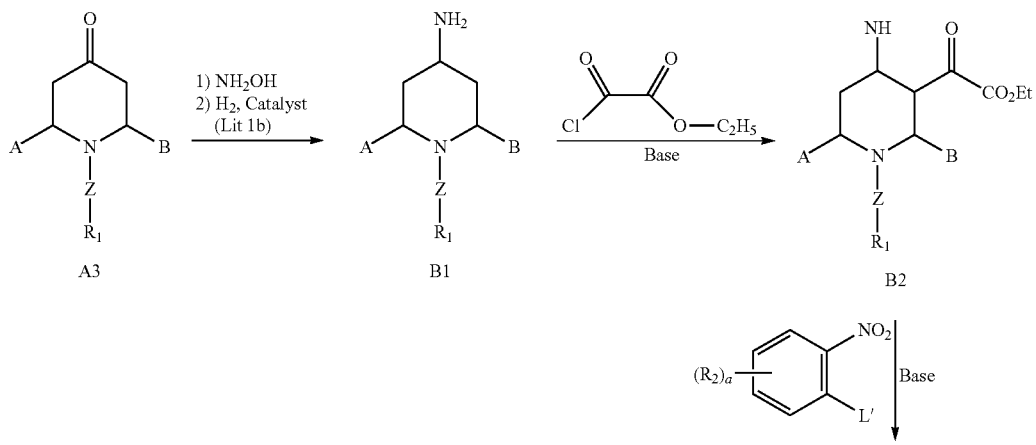

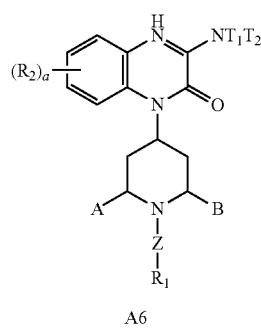

A6

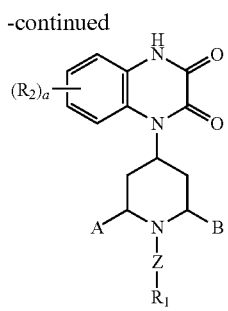

A5

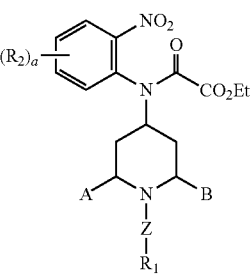

B3

In Scheme B and the other schemes, "Lit 1b" refers to the procedures described in International PCT Publication No. WO 2005/075459 A1 of Euro-Celtique S. A.

As described in reference "Lit 1b," compound A3 can be reacted with 50% aqueous hydroxylamine in a suitable solvent such as hexanes to provide an intermediate hydroxylamine which can be converted to an oxime by dehydration in a suitable solvent such as toluene under reflux conditions using a Dean-Stark apparatus. The oxime intermediate can be reduced to the primary amine compound B1 by catalytic hydrogenation using a catalyst such as rhodium on alumina in a suitable solvent such as ethanol under a hydrogen atmosphere at a pressure of 1 atm or greater in a suitable apparatus such as a Parr Hydrogenator according to reference "Lit 1b." Compound B1 can be reacted with ethyl 2-chloro-2-oxoacetate in the presence of a base such as triethylamine to provide compound B2. Compound B2 can be reacted with a substituted or unsubstituted 2-halo-1-nitrobenzene (where the halo is fluoride or chloride) in the presence of a base such as potassium carbonate in a suitable solvent such as acetonitrile under reflux conditions to provide compound B3. Compound B3 can be treated with a hydrogenation catalyst such as Raney nickel in a suitable solvent such as ethanol under a hydrogen atmosphere, and the product immediately treated with an alkali metal alkoxide such as sodium ethoxide in a suitable solvent such as methanol or ethanol to provide compound A5, which can be converted to compound A6 as described in Scheme A.

Scheme C

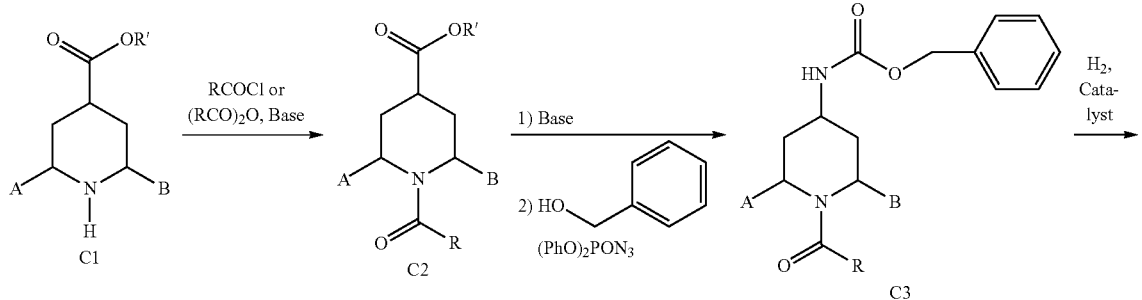

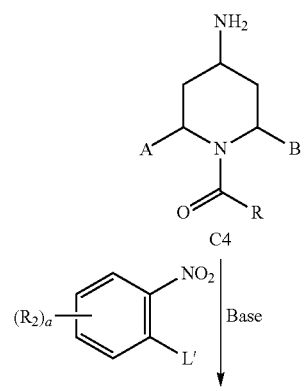

C4

-continued

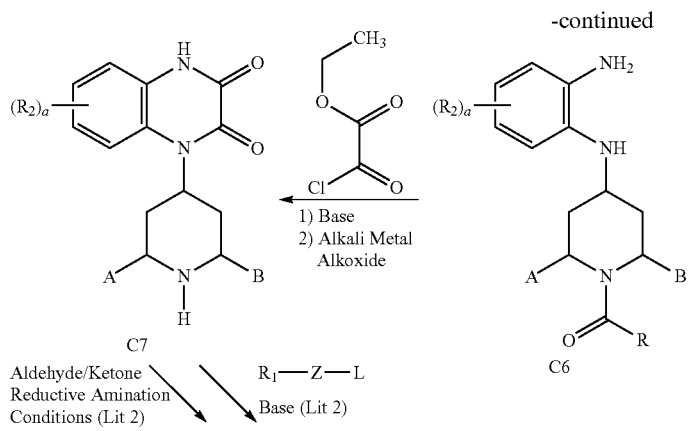

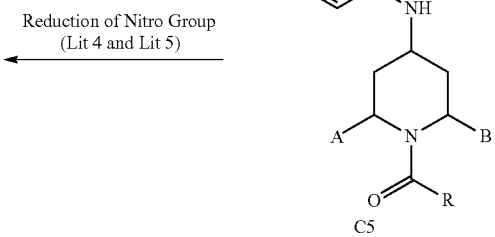

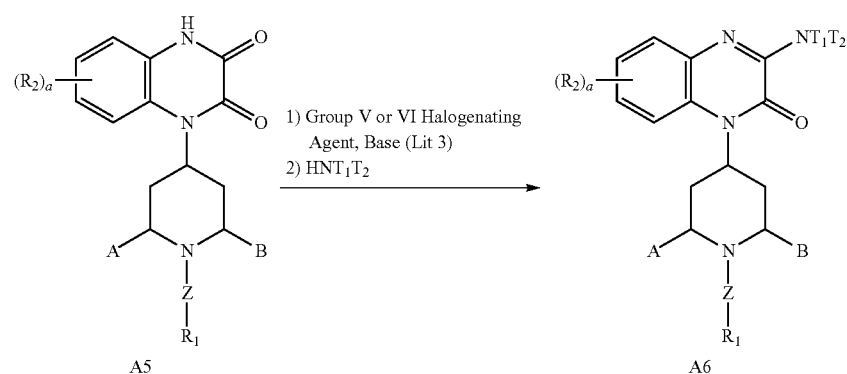

In Scheme C and the other schemes, "Lit 4" refers to the reference P.N. Rylander, *Hydrogenation Methods*, Academic Press, 104-116 (1985), which provides a review of the methods available for the reduction of nitro groups, and "Lit 5" refers to the Zinin reduction procedures described in the reference Porter, *Organic Reactions*, 20:455-481 (1973).

The compound of formula C1 is commercially available or can be prepared by methods known to the art. Compound C1 can be reacted with an acid chloride RCOCl, such as 2,2,2-trifluoroacetyl chloride, or anhydride (RCO)$_2$O, such as 2,2,2-trifluoroacetic anhydride, and a base such as triethylamine in a suitable solvent such as dichloromethane or tetrahydrofuran to provide compound C2. Compound C2 can be converted to compound C3 in a two step procedure by hydrolysis of the ester to the carboxylic acid using an appropriate base such as aqueous NaOH, followed by treatment with diphenyl phosphorazidate ("(PhO)$_2$P(=O)N$_3$") and phenylmethanol ("BnOH") under Curtius rearrangement conditions. The benzyloxycarbonyl group of compound C3 can then be removed under hydrogenolysis conditions using a noble metal catalyst, e.g., palladium on carbon, under a hydrogen atmosphere, to provide compound C4. Compound C4 can be reacted with a substituted or unsubstituted 2-halo-1-nitrobenzene (where the halo is fluoride or chloride) (similar to steps described in Scheme B) to provide compound C5. In the next step, compound C5 can be converted to compound C6 using a catalyst such as Raney nickel in a suitable solvent such as ethanol under a hydrogen atmosphere as described in reference "Lit 4." Compound C5 can also be converted to compound C6 by chemical means, such as with Zn, Sn(II) chloride or Fe, or using sulfides or polysulfides by the Zinin Reduction as described in reference "Lit 5." Compound C6 can then be treated with ethyl 2-chloro-2-oxoacetate and a base such as triethylamine in a suitable solvent such as toluene, followed by treatment with an alkali metal alkoxide such as sodium ethoxide in a suitable solvent such as ethanol to provide compound C7. Compound A5 can be prepared by alkylation of compound C7 with an alkyl bromide or alkyl iodide or by reductive amination of compound C7 with an aldehyde or ketone, each as described in Scheme A. Thereafter, compound A5 can be converted to compound A6 as described in Scheme A.

Scheme D

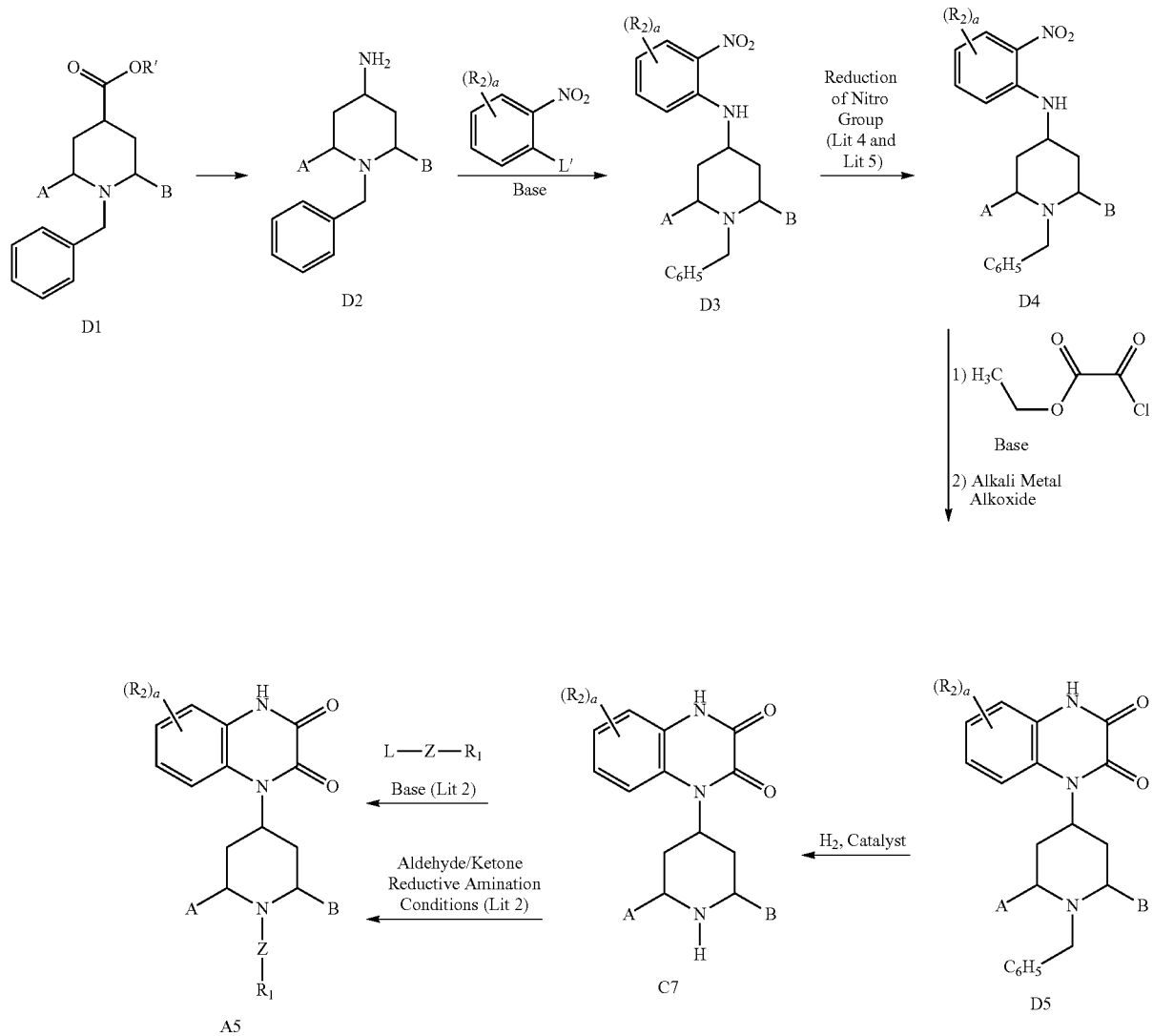

The compound of formula D1 is commercially available or can be prepared from compound C1 by methods known to the art. Compound D2 can be prepared from compound D1 in a similar manner to the preparation of compound C4 from compound C1 in Scheme C. Compound D2 can be reacted with a substituted or unsubstituted 2-halo-1-nitrobenzene (where the halo is fluoride or chloride) (similar to steps described in Scheme B) to provide compound D3. In the next step (similar to steps described in Scheme B), compound D3 can be converted to compound D4 by treatment with a hydrogenation catalyst such as Raney nickel in a suitable solvent such as ethanol under a hydrogen atmosphere, or by chemical means using a reducing agent such as Zn, Sn(II) chloride or Fe, or using sulfide or polysulfides by the Zinin Reduction as described in Scheme C. Thereafter (similar to steps described in Scheme A), compound D4 can be treated with ethyl 2-chloro-2-oxoacetate in the presence of a base such as triethylamine followed by treatment with an alkali metal alkoxide such as sodium ethoxide in a suitable solvent such as ethanol to provide compound D5. Compound D5 can be hydrogenolyzed using a noble metal catalyst, e.g., palladium on carbon, in a suitable solvent such as methanol or ethanol under a hydrogen atmosphere to provide compound C7. Compound A5 can be prepared by alkylation of compound C7 with an alkyl bromide or alkyl iodide or by reductive amination of compound C7 with an aldehyde or ketone (similar to steps described in Scheme A). Thereafter, compound A5 can be converted to compound A6 as described in Scheme A.

Scheme E

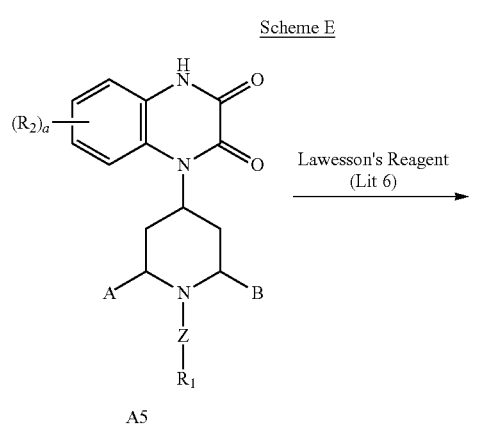

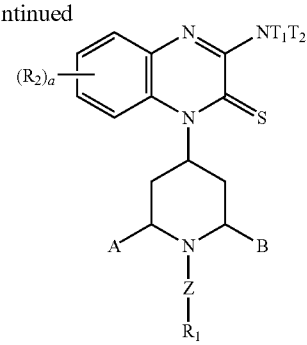

In Scheme E and the other schemes, "Lit 6" refers to the reference Perregaard et al., *Bull. Soc. Chim. Belg.*, 86: 679-691 (1977).

Compound E1, comprising a quinoxaline-2,3(1H,4H)-dithione, can be made by, e.g., reacting Compound A5 (i.e., comprising a quinoxaline-2,3(1H,4H)-dione) with Lawesson's reagent (i.e., 2,4-bis(4-methoxyphenyl)-1,3-dithia-2,4-diphosphetane-2,4-disulfide) according to the procedure described in reference "Lit 6." In one embodiment, Compound E1 can be made by reacting Compound A5 with Lawesson's reagent in a nonpolar solvent such as THF or toluene at a temperature of about 100° C. for about 2-3 hours, as shown above. Thereafter, compound E2 can be obtained from compound E1 in an analogous manner as described in Scheme A for obtaining compound A6 from compound A5 except that methyl iodide is used in place of thionyl chloride.

Scheme F

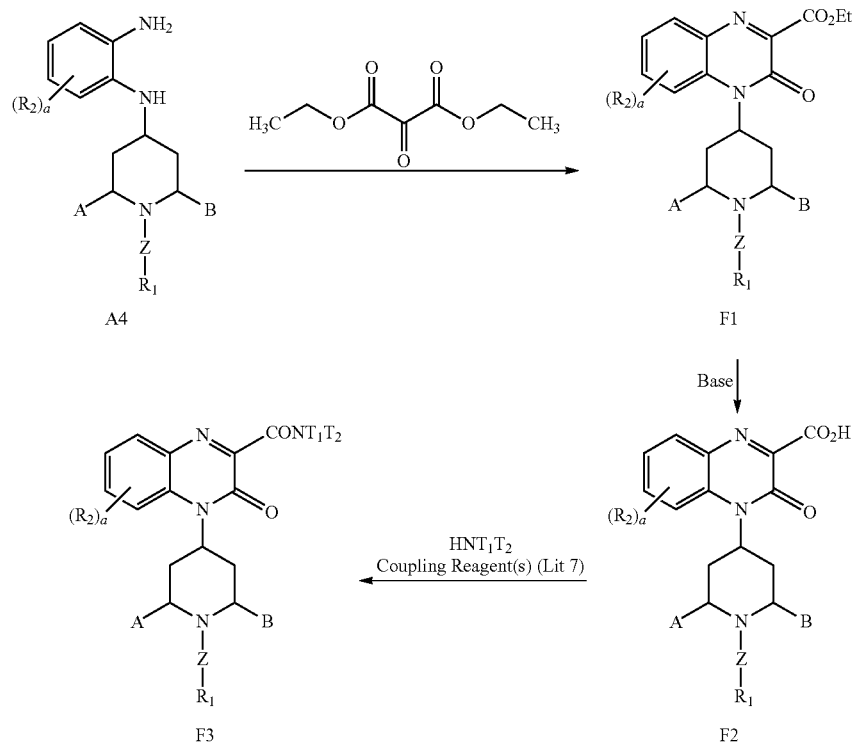

In Scheme F and the other schemes, "Lit 7" refers to the references *Biochem. Biophys. Res. Commun.* 63:99 (1975) and/or *Science* 211:586 (1981).

Compound A4 and diethyl 2-oxomalonate can be dissolved in a solvent with a high boiling point, such as toluene or xylene, and heated under reflux conditions with azeotropic removal of water to provide compound F1. Compound F1 can be hydrolyzed to the carboxylic acid F2 by treatment with a base, such as aqueous NaOH, in a solvent under appropriate conditions, such as methanol or ethanol at a temperature from about 0° C. to about 25° C. Upon completion of hydrolysis, the reaction mixture is neutralized, e.g., with dilute HCl, to provide compound F2. Compound F2 can be converted to amide derivative F3 by treatment with a coupling agent, such as N-(3,3-dimethylaminopropyl)-N'-ethylcarbodiimide and triethylamine, and the desired amine, e.g., $HNT_1T_2$ shown in the scheme, in a solvent, such as DMF, to provide compound F3, e.g., according to the procedure described in reference "Lit 7."

Scheme G

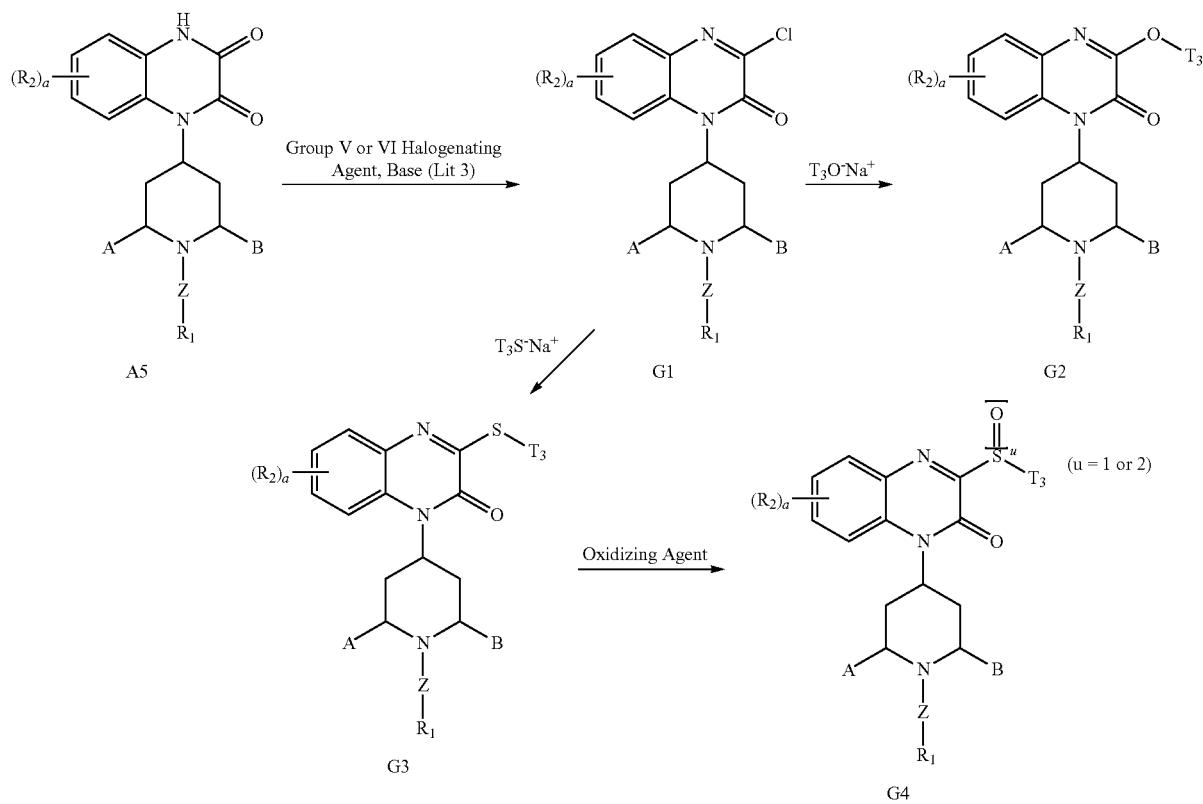

Compound G1 can be obtained by chlorinating compound A5, e.g., by adding a chlorinating agent, such as thionyl chloride, phosphorus oxychloride or phosphorus pentachloride, to a mixture of compound A5, DMF, and a base such as triethylamine in a solvent with a high boiling point, such as toluene or xylene, under reflux conditions such as is described in reference "Lit 3." Compound G1 can be converted to compound G2 by reacting the former with the desired alkoxide, e.g., a sodium alkoxide, in a solvent, such as tetrahydrofuran, DMF or an alcohol of the alkoxide, to provide compound G2. In a similar manner but with the desired thioalkoxide, e.g., a sodium thioalkoxide, compound G1 can be converted to compound G3, comprising a thioalkoxide, in a suitable solvent to provide compound G3. Compound G3 can be oxidized to the sulfoxide (u=1) or sulfone (u=2) of compound G4 by reacting compound G3 with an oxidizing agent, such as oxone, in a suitable solvent, e.g., as described in K. S. Webb, "A Mild, Inexpensive, and Practical Oxidation of Sulfides," Tetrahedron Let., 35(21): 3457-3460 (1994).

Scheme H

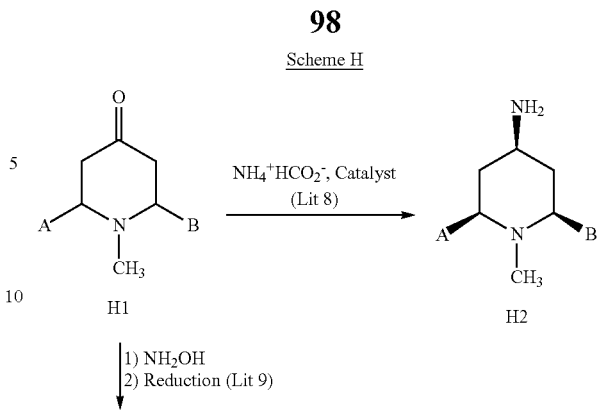

-continued

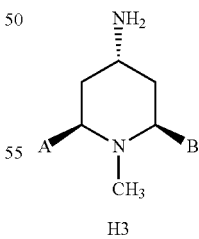

H3

In Scheme H and the other schemes, "Lit 8" refers to "A Modified Palladium Catalyzed Reductive Amination Procedure," Berdini et al., Tetrahedron, 58:5669-5674 (2002) and "Lit 9 refers to "Molecular Features Associated with Polyamine Modulation of NMDA Receptors," A. H. Lewin et al., J. Med. Chem. 41:988-995 (1998).

The compound of formula H1, wherein substituent groups A and B together form a bridge, e.g., a two carbon bridge, is commercially available or can be prepared by methods known to the art.

When substituent groups A and B together form a bridge, e.g., a two carbon bridge, compound H1 can be converted to compound H3, the "exo" isomer, by reduction using, e.g., sodium in propanol as described in reference "Lit 9."

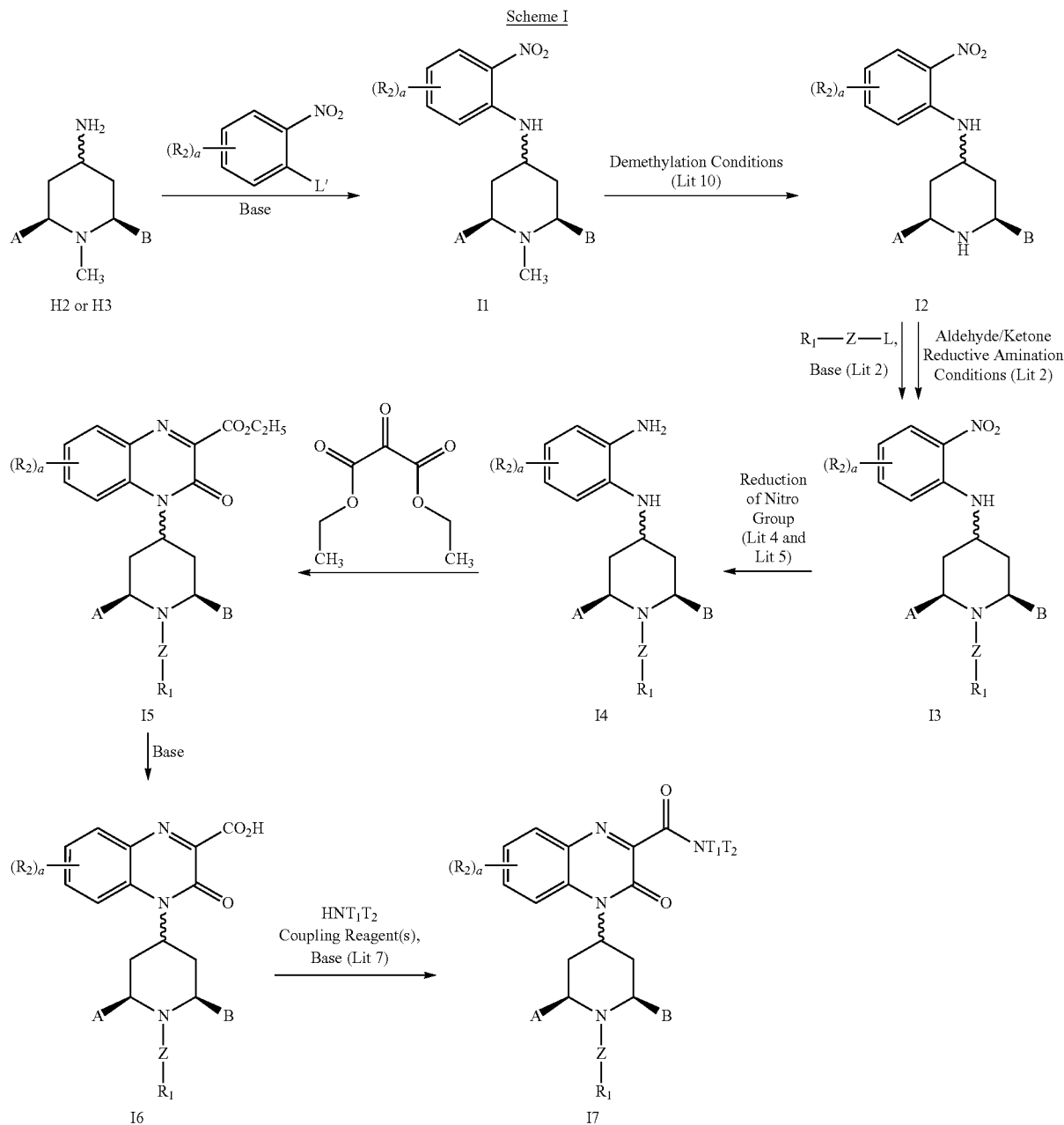

Scheme I

In Scheme I and the other schemes, "Lit 10" refers to the procedures described by R.A. Olofson et al. in *J. Org. Chem.*, 49:2081-2082 (1984) and to R.A. Olofson et al. in *Tetrahedron Let.*, 18:1571 (1977).

compound H2, the "endo" isomer, under reductive amination conditions using, e.g., ammonium formate and a noble metal catalyst, e.g., palladium on carbon, in a solvent such as ethanol or methanol as described in reference "Lit 8." Similarly, where substituent groups A and B together form a bridge, e.g., a two carbon bridge, compound H1 can be reacted with aqueous hydroxylamine in a solvent such as hexanes to form an intermediate hydroxylamine, which can be converted to its oxime by dehydration in a solvent with a high boiling point such as toluene, under Dean-stark conditions. The oxime intermediate can be converted to Substituted-Quinoxaline-Type Piperidine Compounds such as I6 and I7 where substituent groups A and B together form a bridge, e.g., a two carbon bridge, can be prepared as described in Scheme I. Compound H2 (the "endo" isomer) or H3 (the "exo" isomer) (where substituent groups A and B together form a bridge, e.g., a two carbon bridge) can be converted to compound I1 by reaction with a substituted or unsubstituted 2-halo-1-nitrobenzene (where the halo is fluoride or chloride) and a base such as potassium carbonate, in a suitable solvent such as DMF or acetonitrile at a temperature from about 20° C. to about 100° C. Compound I1 can be demethylated to give compound I2 using, e.g., 1-chloromethylchloroformate in a solvent such as 1,2-dichloroethane, followed by treatment with methanol as described in "Lit 10." Compound I2 can be converted to compound I3 (similar to steps described in reference "Lit 2" in Scheme A). Compound I3 can be converted to compound I4 by hydrogenation using a catalyst under a hydrogen atmosphere or by chemical means using a reducing agent (similar to steps described in references "Lit 4" and "Lit 5" in Scheme C). Compound I4 can be converted to compound I5 by reaction with diethyl 2-oxomalonate in a solvent with a high boiling point such as toluene or xylene under reflux conditions. Compound I5 can be converted to the carboxylic acid derivative I6 by hydrolysis using a base such as aqueous NaOH in a suitable solvent such as methanol or ethanol, followed by neutralization using an acid such as dilute HCl. Compound I6 can be converted to compound I7 by reaction with a coupling agent (similar to steps described in reference "Lit 7" in Scheme F).

Scheme K

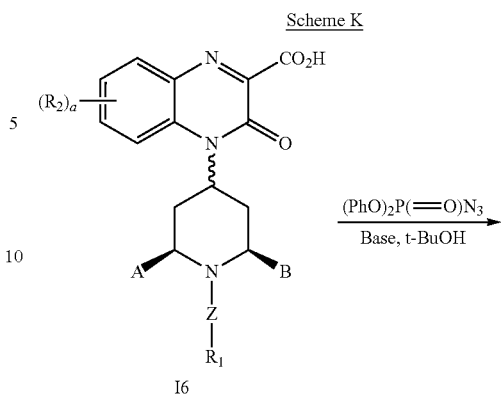

Scheme J

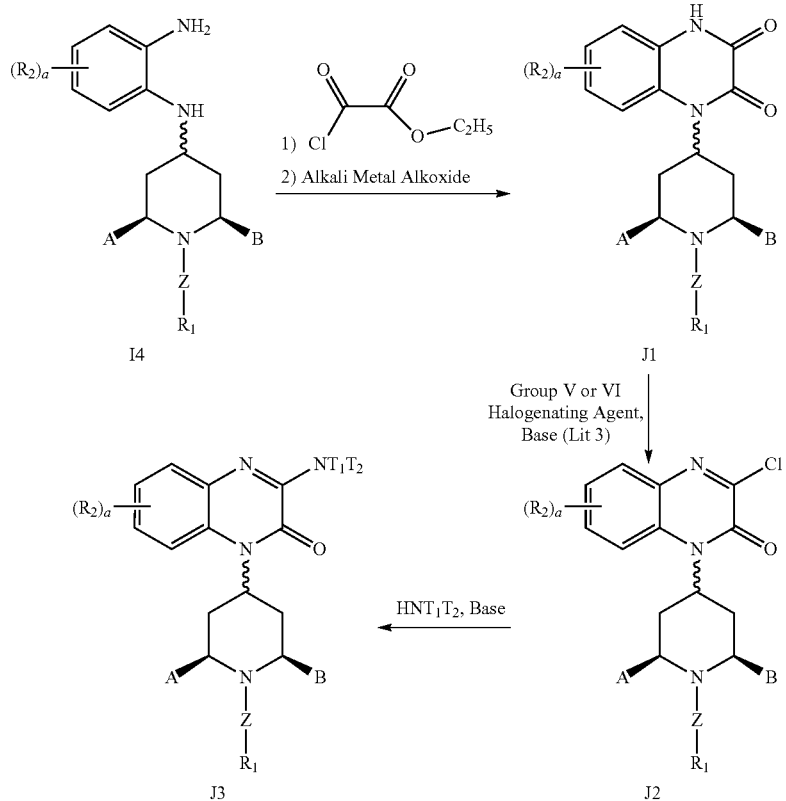

Substituted-Quinoxaline-Type Piperidine Compounds such as J3 where substituent groups A and B together form a bridge, e.g., a two carbon bridge, can be prepared as described in Scheme J. Compound I4 (where substituent groups A and B together form a bridge, e.g., a two carbon bridge, and Compound I4 may exist as either an "endo" isomer an "exo" isomer or a mixture of "endo/exo" isomers) can be converted to compound J1, as shown in Scheme J, by reaction with ethyl 2-chloro-2-oxoacetate and a base such as triethylamine in a suitable solvent such as dichloromethane, followed by reaction with an alkali metal alkoxide, using the procedures described in Scheme A. These "endo" and "exo" isomers can be conveniently separated by flash column chromatography. Compound J1 can be converted to compound J3, through compound J2 (similar to steps described previously in Scheme A).

-continued

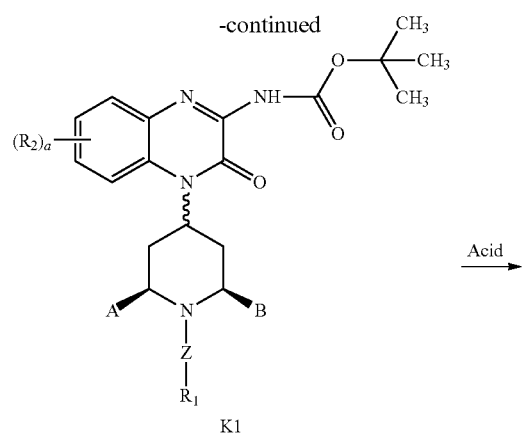

103

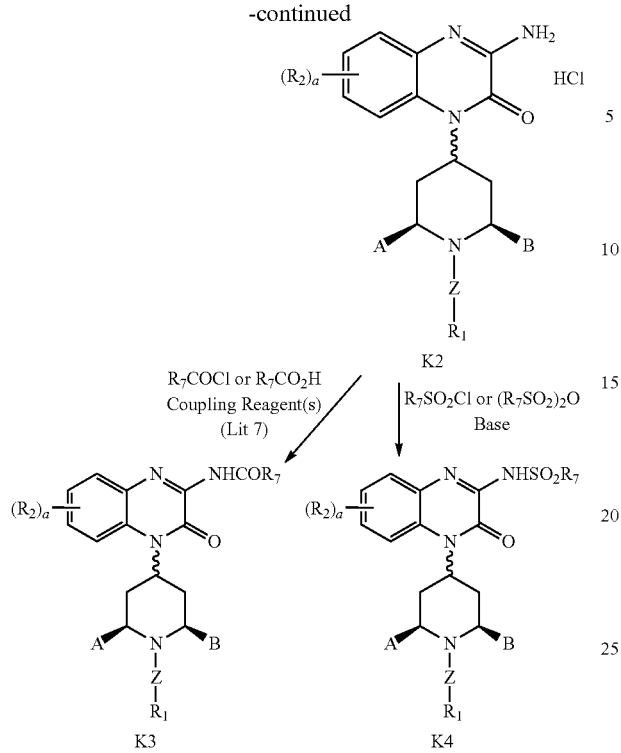

Substituted-Quinoxaline-Type Piperidine Compounds such as K2, K3 and K4 where substituent groups A and B together form a bridge, e.g., a two carbon bridge, can be prepared as described in Scheme K. Compound I6 (where substituent groups A and B together form a bridge, e.g., a two carbon bridge, and Compound I6 may exist as either an "endo" isomer an "exo" isomer or a mixture of "endo/exo" isomers) can be converted to compound K1, as shown in Scheme K, using diphenylphosporyl azide and t-butanol under Curtius Rearrangement Conditions (similar to steps described in Scheme C). The tert-butoxycarbonyl group in compound K1 can be removed using acid conditions such as HCl in a solvent such as dioxane or ether to give compound K2 as the hydrochloride salt. Compound K2 can be converted to compound K3 using an acid chloride $R_7COCl$ and a base such as triethylamine in a suitable solvent such as dichloromethane or DMF, or using a carboxylic acid $R_7COOH$, a coupling reagent such as N-(3,3-dimethylaminopropyl)-N'-ethylcarbodiimide, a base such as triethylamine in a suitable solvent such as DMF as described in the literature references in Scheme F. Compound K2 can be converted to compound K4 using an alkyl or aryl sulfonyl chloride such as methanesulfonyl chloride or sulfonic acid anhydride such as trifluoromethylsulfonic anhydride, a base such as triethylamine, in a suitable solvent such as dichloromethane.

Scheme L

104

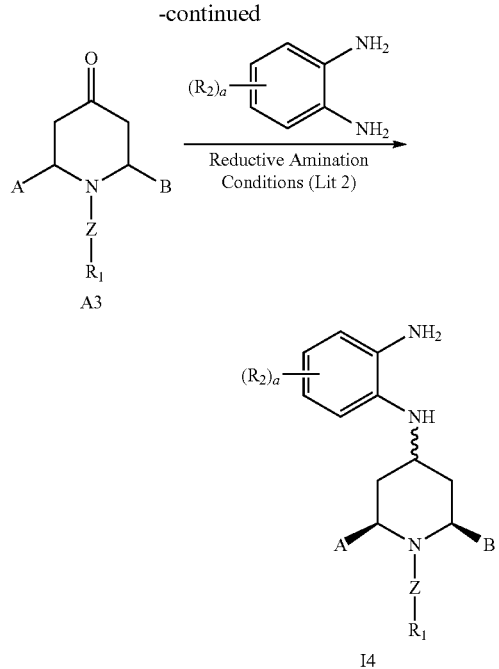

Compound I4 can be prepared, as shown in Scheme L, from compound A1 (similar to steps described in Scheme A). Where substituent groups A and B of compound I4 form a bridge, e.g., a two carbon bridge, the two isomers, "exo" and "endo," can be separated by chromatography and can be separately converted to compounds such as A5, A6, F2, F3, and the like as described earlier in Schemes A, B, and F.

Scheme M

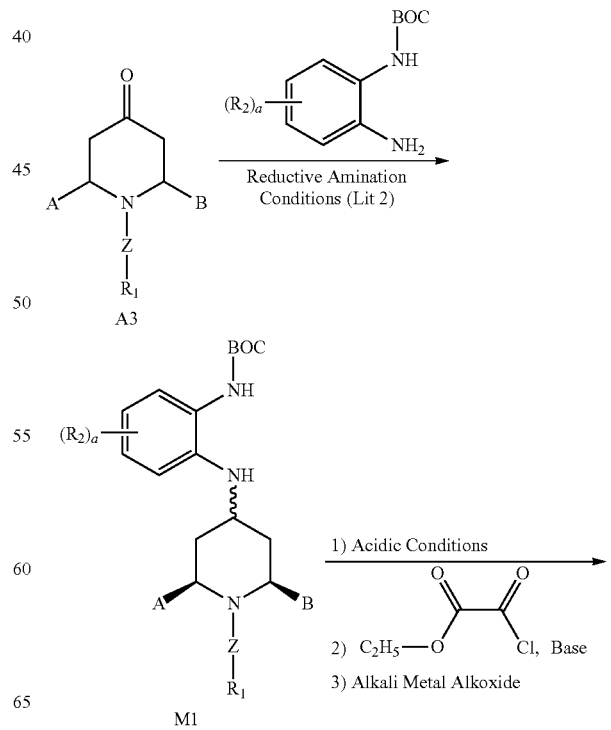

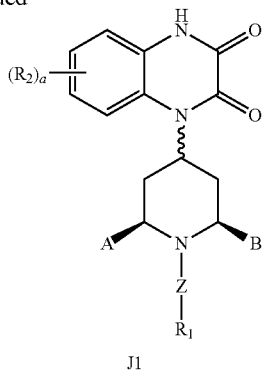

J1

As shown in Scheme M, compound A3 can be converted to compound M1 under reductive amination conditions using a BOC protected, substituted or unsubstituted 1,2-phenylenediamine and a reducing agent such as sodium triacetoxyborohydride or sodium cyanoborohydride in a suitable solvent such as dichloromethane or methanol respectively as described in reference "Lit 2." The BOC protecting group can be removed using acidic conditions, such as using HCl or 2,2,2-trifluoroacetic acid, to give an intermediate which can be converted to compound J1 in a two step procedure using ethyl 2-chloro-2-oxoacetate and a base such as triethylamine, followed by reaction with an alkali metal alkoxide such as sodium ethoxide in a suitable solvent such as ethanol. Where substituent groups A and B together form a bridge, e.g., a two carbon bridge, the "exo" and "endo" isomers which result can be conveniently separated using flash column chromatography.

Scheme N

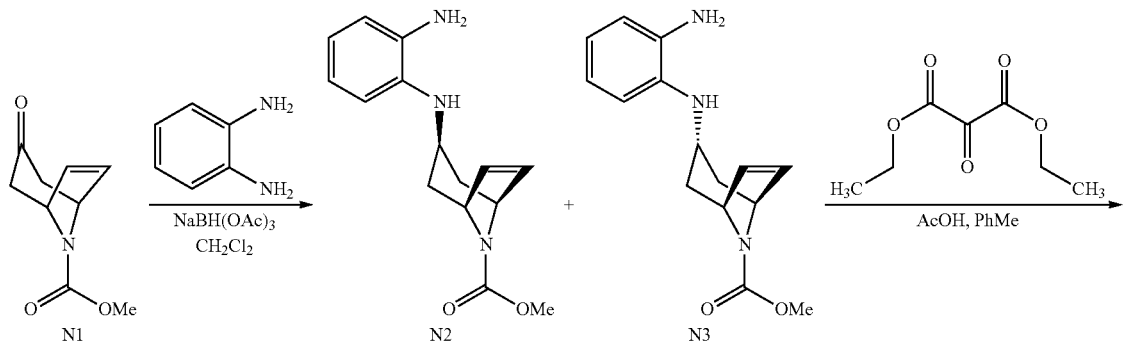

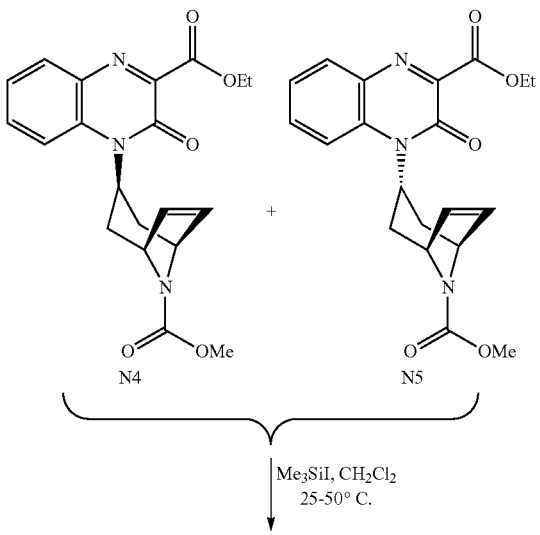

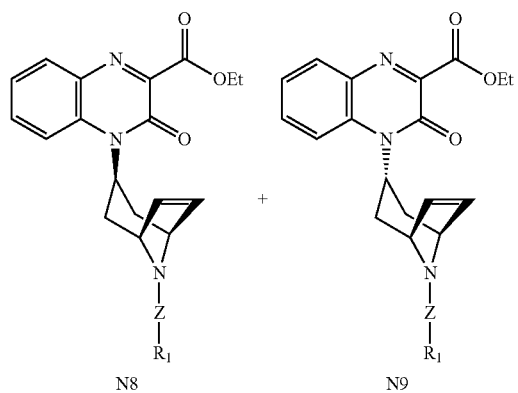

N8

N9

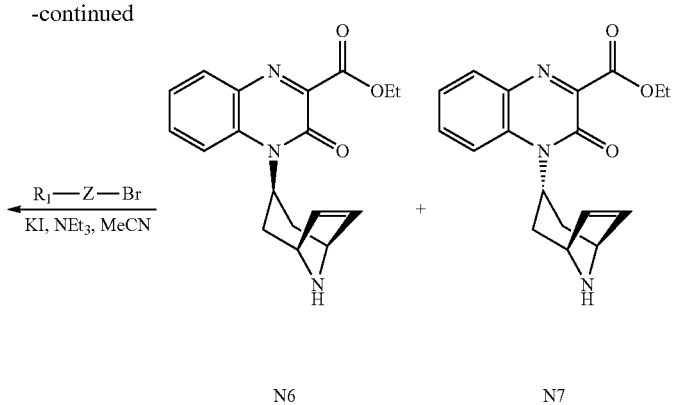

N6

N7

For example: Z = absent, R₁ = cyclooctenyl, cyclooctyl

Scheme N shows the conversion of the literature compound N1 to intermediates N8 and N9.

3-Oxo-8-aza-bicyclo[3.2.1]oct-6-ene-8-carboxylic acid methyl ester N1 can be prepared according to the literature procedure described in N. Cramer; S. Laschat; A. Baro; W. Frey; Syn. Lett., (2003), 14, 2175-2177.

This intermediate N1 can be reacted with 1,2-phenylenediamine under reductive amination conditions using sodium triacetoxyborohydride in dichloromethane to give the coupled products 3-(2-amino-phenylamino)-8-aza-bicyclo[3.2.1]oct-6-ene-8-carboxylic acid methyl esters N2 and N3 as a mixture of endo and exo isomers which can be taken to the next step without purification. Compounds N2 and N3 can be dissolved in toluene and acetic acid to which diethyl ketomalonate can be added and the mixture can be heated under reflux. Purification of the reaction mixture by column chromatography gives 4-(8-methoxycarbonyl-8-aza-bicyclo[3.2.1]oct-6-en-3-yl-3-oxo-3,4-dihydro-quinoxaline-2-carboxylic acid ethyl esters N4 and N5 as a mixture of endo and exo esters which can be purified by chromatography. The methyl carbamate group can be removed from N4 and N5 using iodo trimethylsilane in dichloromethane to give 4-(8-aza-bicyclo[3.2.1]oct-6-en-3-yl)-3-oxo-3,4-dihydroquinoxaline-2-carboxylic acid ethyl esters N6 and N7 as a mixture of exo and endo isomers. Intermediates N6 and N7 can be alkylated with various alkyl bromides and iodides such as 3-bromo-cyclooctene and a catalytic amount of potassium iodide and triethylamine in a solvent such as acetonitrile to give isomers N8 and N9 which can be separated by column chromatography. Finally hydrolysis of the ester group can be achieved using sodium hydroxide in aqueous ethanol to give the carboxylic acids N10 and N11 as shown in Scheme 0.

Scheme O

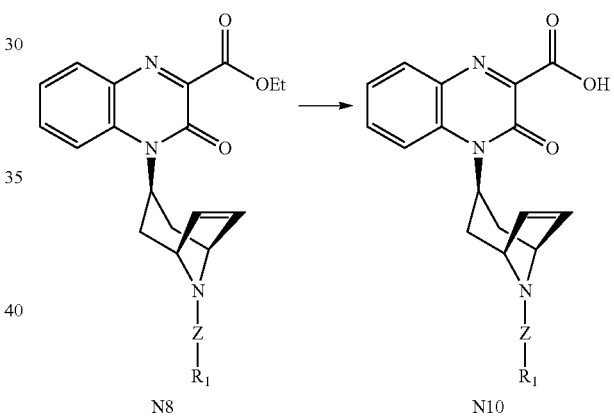

N8

N10

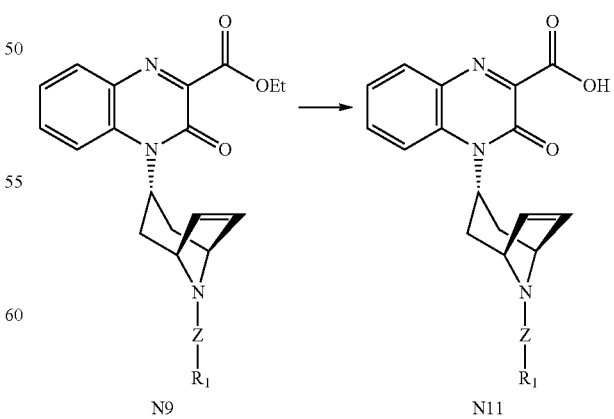

N9

N11 for example: Z = absent, R₁ = cyclooctenyl, cyclooctyl

4.5 Therapeutic Uses of the Substituted-Quinoxaline-Type Piperidine Compounds In accordance with the invention, the Substituted-Quinoxaline-Type Piperidine Compounds are administered to an animal in need of treatment or prevention of a Condition.

In one embodiment, an effective amount of a Substituted-Quinoxaline-Type Piperidine Compound can be used to treat or prevent any condition treatable or preventable by inhibiting the activity of the ORL-1 receptor. Examples of Conditions that are treatable or preventable by inhibiting the activity of the ORL-1 receptor include, but are not limited to, pain (CNS effect), memory disorders, obesity, constipation, depression, dementia, and Parkinsonism.

In another embodiment, an effective amount of a Substituted-Quinoxaline-Type Piperidine Compound can be used to treat or prevent any condition treatable or preventable by activating the ORL-1 receptor. Examples of Conditions that are treatable or preventable by activating the ORL-1 receptor include, but are not limited to, pain (PNS effect), anxiety, cough, diarrhea, blood pressure disorder (via vasodilation and via diuresis), epilepsy, anorexia/cachexia, urinary incontinence, and drug abuse.

The Substituted-Quinoxaline-Type Piperidine Compounds can be used to treat or prevent acute or chronic pain. Examples of pain that can be treated or prevented using a Substituted-Quinoxaline-Type Piperidine Compound include, but are not limited to, cancer pain, neuropathic pain, labor pain, myocardial infarction pain, pancreatic pain, colic pain, post-operative pain, headache pain, muscle pain, arthritic pain, and pain associated with a periodontal disease, including gingivitis and periodontitis.

The Substituted-Quinoxaline-Type Piperidine Compounds can also be used to treat or prevent pain associated with inflammation or with an inflammatory disease in an animal. Such pain can arise where there is an inflammation of the body tissue which can be a local inflammatory response or a systemic inflammation. For example, a Substituted-Quinoxaline-Type Piperidine Compound can be used to treat or prevent pain associated with inflammatory diseases including, but not limited to, organ transplant rejection; reoxygenation injury resulting from organ transplantation (see Grupp et al., *J. Mol, Cell Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory disease of the gum, including gingivitis and periodontitis; tuberculosis; leprosy; inflammatory diseases of the kidney, including uremic complications, glomerulonephritis and nephrosis; inflammatory disease of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microalbuminuria and progressive diabetic nephropathy), gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum), immune-complex vasculitis, and systemic lupus erythematosus (SLE); inflammatory disease of the heart, such as cardiomyopathy, ischemic heart disease hypercholesterolemia, and artherosclerosis; as well as various other diseases that can have significant inflammatory components, including preeclampsia, chronic liver failure, brain and spinal cord trauma, and cancer. A Substituted-Quinoxaline-Type Piperidine Compound can also be used to treat or prevent pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

The Substituted-Quinoxaline-Type Piperidine Compounds can also be used to treat or prevent pain associated with nerve injury (i.e., neuropathic pain). Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that chronic neuropathic pain patients suffer the abnormal pain sensations that can be described as spontaneous pain, continuous superficial burning and/or deep aching pain. The pain can be evoked by heat-, cold-, and mechano-hyperalgesia, or by heat-, cold-, or mechano-allodynia.

Chronic neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain can also be caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can cause nerve injury. Neuropathic pain includes but is not limited to pain caused by nerve injury such as, for example, the pain from which diabetics suffer.

The Substituted-Quinoxaline-Type Piperidine Compounds can be used to treat or prevent a migraine including, but not limited to, migraine without aura ("common migraine"), migraine with aura ("classic migraine"), migraine without headache, basilar migraine, familial hemiplegic migraine, migrainous infarction, and migraine with prolonged aura.

According to the invention, some of the Substituted-Quinoxaline-Type Piperidine Compounds are agonists at the ORL-1 receptor, some of the Substituted-Quinoxaline-Type Piperidine Compounds are partial agonists at the ORL-1 receptor, and some of the Substituted-Quinoxaline-Type Piperidine Compounds are antagonists at the ORL-1 receptor. In another embodiment, a Substituted-Quinoxaline-Type Piperidine Compound is an agonist at the ORL-1 receptor and an agonist at a μ, κ and/or δ opioid receptor, particularly at a μ opioid receptor. In another embodiment, a Substituted-Quinoxaline-Type Piperidine Compound is a partial agonist at the ORL-1 receptor and an agonist at a μ, κ and/or δ opioid receptor, particularly at a μ opioid receptor. In another embodiment, a Substituted-Quinoxaline-Type Piperidine Compound is an antagonist at the ORL-1 receptor and an agonist at a μ, κ and/or δ opioid receptor, particularly at a μ opioid receptor. In another embodiment, a Substituted-Quinoxaline-Type Piperidine Compound is an agonist at the ORL-1 receptor and an antagonist at a μ, κ and/or δ opioid receptor, particularly at a μ opioid receptor. In another embodiment, a Substituted-Quinoxaline-Type Piperidine Compound is a partial agonist at the ORL-1 receptor and an antagonist at a μ, κ and/or δ opioid receptor, particularly at a μ opioid receptor. In another embodiment, a Substituted-Quinoxaline-Type Piperidine Compound is an antagonist at the ORL-1 receptor and an antagonist at a μ, κ and/or δ opioid receptor, particularly at a μ opioid receptor.

The invention also provides methods for inhibiting ORL-1 receptor function in a cell, comprising contacting a cell capable of expressing the ORL-1 receptor with an amount of a Substituted-Quinoxaline-Type Piperidine Compound effective to inhibit ORL-1 receptor function in the cell. This method can be adapted for use in vitro as part of an assay to select compounds that can be useful for treating or preventing a Condition in an animal. Alternatively, this method can be adapted for use in vivo, (i.e., in an animal such as a human) by contacting a cell in the animal with an effective amount of a Substituted-Quinoxaline-Type Piperidine Compound. In one embodiment, the method is useful for treating or preventing pain in an animal in need of such treatment or prevention. In another embodiment, the method is useful for treating or preventing a memory disorder, obesity, constipation, depression, dementia, or Parkinsonism in an animal in need of such treatment or prevention.

The invention also relates to methods for activating ORL-1 receptor function in a cell, comprising contacting a cell capable of expressing the ORL-1 receptor with an amount of a Substituted-Quinoxaline-Type Piperidine Compound effective to activate ORL-1 receptor function in the cell. This method can be adapted for use in vitro as part of an assay to select compounds useful for treating or preventing, pain, anxiety, cough, diarrhea, high blood pressure, epilepsy, anorexia/cachexia, urinary incontinence, or drug abuse. Alternatively, the method can be adapted for use in vivo (i.e., in an animal such as a human), by contacting a cell in the animal with an effective amount of a Substituted-Quinoxaline-Type Piperidine Compound. In one embodiment the method is useful for treating or preventing pain in an animal in need of such treatment or prevention. In another embodiment, the method is useful for treating or preventing anxiety, cough, diarrhea, high blood pressure, epilepsy, anorexia/chachexia, urinary incontinence, or drug abuse in an animal in need of such treatment or prevention.

Examples of tissue comprising cells capable of expressing the ORL-1 receptor include but are not limited to brain, spinal cord, vas deferens, and gastrointestinal tract tissue. Methods for assaying cells that express the ORL-1 receptor are known in the art; for example, see Y. Shimohigashi et al., "Sensitivity of opioid receptor-like receptor ORL1 for chemical modification on nociceptin, a naturally occurring nociceptive peptide," *J. Biol. Chem.* 271(39):23642-23645 (1996); M. Narita et al., "Identification of the G-protein coupled ORL1 receptor in the mouse spinal cord by [$^{35}$S]-GTPγS binding and immunohistochemistry," *Brit. J. Pharmacol.* 128:1300-1306 (1999); G. Milligan, "Principles: Extending then utility of [$^{35}$S]GTPγS binding assays," *TIPS* 14:87-90 (2003): and S. Lazareno, "Measurement of agonist-stimulated [$^{35}$S]GTPγS binding to cell membranes," *Methods in Molecular Biology* Vol. 106:231245 (1999).

4.6 Therapeutic/Prophylactic Administration and Compositions of the Invention Due to their activity, the Substituted-Quinoxaline-Type Piperidine Compounds are advantageously useful in human and veterinary medicine. As described above, the Substituted-Quinoxaline-Type Piperidine Compounds are useful for treating or preventing a Condition in an animal in need thereof. The Substituted-Quinoxaline-Type Piperidine Compounds of the invention can be administered to any animal requiring modulation of the opioid and/or ORL-1 receptors.

When administered to an animal, a Substituted-Quinoxaline-Type Piperidine Compound can be administered as a component of a composition that comprises a pharmaceutically acceptable carrier or excipient. The invention compositions, which comprise a Substituted-Quinoxaline-Type Piperidine Compound, can be administered orally. A Substituted-Quinoxaline-Type Piperidine Compound can also be administered by any other convenient route, for example, by infusion or bolus injection, by absorption through epithelial or mucocutaneous linings (e.g., oral, rectal, and intestinal mucosa, etc.) and can be administered together with a second therapeutically active agent. Administration can be systemic or local. Various delivery systems are known, e.g., encapsulation in liposomes, microparticles, microcapsules, multiparticulates, capsules, etc., and can be used to administer a Substituted-Quinoxaline-Type Piperidine Compound.

Methods of administration include, but are not limited to, intradermal, intramuscular, intraperitoneal, parenteral, intravenous, subcutaneous, intranasal, epidural, oral, sublingual, intracerebral, intravaginal, transdermal, rectal, by inhalation, or topical, particularly to the ears, nose, eyes, or skin. The method of administration is left to the discretion of the practitioner. In most instances, administration will result in the release of a Substituted-Quinoxaline-Type Piperidine Compound into the bloodstream.

In specific embodiments, it can be desirable to administer a Substituted-Quinoxaline-Type Piperidine Compound locally. This can be achieved, for example and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce a Substituted-Quinoxaline-Type Piperidine Compound into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, a Substituted-Quinoxaline-Type Piperidine Compound can be formulated as a suppository, with traditional binders and excipients such as triglycerides.

When a Substituted-Quinoxaline-Type Piperidine Compound of the invention is incorporated for parenteral administration by injection (e.g., continuous infusion or bolus injection), the formulation for parenteral administration can be in the form of a suspension, solution, emulsion in an oily or aqueous vehicle, and such formulations can further comprise pharmaceutically necessary additives such as one or more stabilizing agents, suspending agents, dispersing agents, and the like. A Substituted-Quinoxaline-Type Piperidine Compound of the invention can also be in the form of a powder for reconstitution as an injectable formulation.

In another embodiment, a Substituted-Quinoxaline-Type Piperidine Compound can be delivered in a vesicle, in particular a liposome (see Langer, *Science* 249:1527-1533 (1990); and Treat et al., *Liposomes in the Therapy of Infectious Disease and Cancer* 317-327 and 353-365 (1989)).

In yet another embodiment, a Substituted-Quinoxaline-Type Piperidine Compound can be delivered in a controlled-release system or sustained-release system (see, e.g., Goodson, "Dental Applications" (pp. 115-138) in *Medical Applications of Controlled Release, Vol. 2, Applications and Evaluation*, R. S. Langer and D. L. Wise eds., CRC Press (1984)). Other controlled- or sustained-release systems discussed in the review by Langer, *Science* 249:1527-1533 (1990) can be used. In one embodiment, a pump can be used (Langer, *Science* 249:1527-1533 (1990); Sefton, *CRC Crit. Ref. Biomed. Eng.* 14:201 (1987); Buchwald et al., *Surgery* 88:507 (1980); and Saudek et al., *N Engl. J. Med.* 321:574 (1989)). In another embodiment, polymeric materials can be used (see *Medical Applications of Controlled Release* (Langer and Wise eds., 1974); *Controlled Drug Bioavailability, Drug Product Design and Performance* (Smolen and Ball eds., 1984); Langer and Peppas, *J. Macromol. Sci. Rev. Macromol. Chem.* 23:61 (1983); Levy et al., *Science* 228:190 (1985); During et al., *Ann. Neurol.* 25:351 (1989); and Howard et al., *J. Neurosurg.* 71:105 (1989)). In yet another embodiment, a controlled- or sustained-release system can be placed in proximity of a target of a Substituted-Quinoxaline-Type Piperidine Compound, e.g., the spinal column, brain, or gastrointestinal tract, thus requiring only a fraction of the systemic dose.

The invention compositions can optionally comprise a suitable amount of a pharmaceutically acceptable excipient so as to provide the form for proper administration to the animal. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when a Substituted-Quinoxaline-Type Piperidine Compound is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The invention compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, American Pharmaceutical Association (1986).

The invention compositions can take the form of solutions, suspensions, emulsions, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see, e.g., U.S. Pat. No. 5,698,155). Other examples of suitable pharmaceutical excipients are described in *Remington's Pharmaceutical Sciences* 1447-1676 (Alfonso R. Gennaro ed., 19th ed. 1995), incorporated herein by reference.

In one embodiment, the Substituted-Quinoxaline-Type Piperidine Compounds are formulated in accordance with routine procedures as a composition adapted for oral administration to human beings. A Substituted-Quinoxaline-Type Piperidine Compound to be orally delivered can be in the form of tablets, capsules, gelcaps, caplets, lozenges, aqueous or oily solutions, suspensions, granules, powders, emulsions, syrups, or elixirs, for example. When a Substituted-Quinoxaline-Type Piperidine Compound is incorporated into oral tablets, such tablets can be compressed, tablet triturates, enteric-coated, sugar-coated, film-coated, multiply compressed or multiply layered. Techniques and compositions for making solid oral dosage forms are described in *Pharmaceutical Dosage Forms: Tablets* (Lieberman, Lachman and Schwartz, eds., 2nd ed.) published by Marcel Dekker, Inc. Techniques and compositions for making tablets (compressed and molded), capsules (hard and soft gelatin) and pills are also described in *Remington's Pharmaceutical Sciences* 1553-1593 (Arthur Osol, ed., 16$^{th}$ ed., Mack Publishing, Easton, Pa. 1980).

Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and composition for making liquid oral dosage forms are described in *Pharmaceutical Dosage Forms: Disperse Systems*, (Lieberman, Rieger and Banker, eds.) published by Marcel Dekker, Inc.

When a Substituted-Quinoxaline-Type Piperidine Compound is to be injected parenterally, it can be, e.g., in the form of an isotonic sterile solution. Alternatively, when a Substituted-Quinoxaline-Type Piperidine Compound is to be inhaled, it can be formulated into a dry aerosol or can be formulated into an aqueous or partially aqueous solution.

An orally administered Substituted-Quinoxaline-Type Piperidine Compound can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the Substituted-Quinoxaline-Type Piperidine Compounds can be formulated for intravenous administration. Typically, compositions for intravenous administration comprise sterile isotonic aqueous buffer. Where necessary, the compositions can also include a solubilizing agent. A Substituted-Quinoxaline-Type Piperidine Compound for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Substituted-Quinoxaline-Type Piperidine Compound is to be administered by infusion, it can be dispensed, for example, with an infusion bottle containing sterile pharmaceutical grade water or saline. Where a Substituted-Quinoxaline-Type Piperidine Compound is administered by injection, an ampule of sterile water for injection or saline can be provided so that the ingredients can be mixed prior to administration.

A Substituted-Quinoxaline-Type Piperidine Compound can be administered by controlled-release or sustained-release means or by delivery devices that are known to those in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566, each of which is incorporated herein by reference. Such dosage forms can be used to provide controlled- or sustained-release of one or more active ingredients using, for example, hydropropylmethyl cellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known to those in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained-release counterparts. In one embodiment, a controlled- or sustained-release composition comprises a minimal amount of a Substituted-Quinoxaline-Type Piperidine Compound to treat or prevent the Condition or a symptom thereof in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the Substituted-Quinoxaline-Type Piperidine Compound, and can thus reduce the occurrence of adverse side effects.

Controlled- or sustained-release compositions can initially release an amount of a Substituted-Quinoxaline-Type Piperidine Compound that promptly produces the desired therapeutic or prophylactic effect, and gradually and continually release other amounts of the Substituted-Quinoxaline-Type Piperidine Compound to maintain this level of therapeutic or prophylactic effect over an extended period of time. To maintain a constant level of the Substituted-Quinoxaline-Type Piperidine Compound in the body, the Substituted-Quinoxaline-Type Piperidine Compound can be released from the dosage form at a rate that will replace the amount of Substituted-Quinoxaline-Type Piperidine Compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Substituted-Quinoxaline-Type Piperidine Compound that is effective for the treatment or prevention of a Condition can be determined by standard clinical techniques. In addition, in vitro and/or in vivo assays can optionally be employed to help identify optimal dosage ranges. The precise dose to be employed will also depend on, e.g., the route of administration and the seriousness of the Condition, and can be decided according to the judgment of a practitioner and/or each animal's circumstances. In other examples thereof, variations will necessarily occur depending upon the weight and physical condition (e.g., hepatic and renal function) of the animal being treated, the affliction to be treated, the severity of the symptoms, the frequency of the dosage interval, the presence of any deleterious side-effects, and the particular compound utilized, among other things.

Suitable effective dosage amounts, however, range from about 0.01 mg/kg of body weight to about 3000 mg/kg of body weight of the animal per day, although they are typically from about 0.01 mg/kg of body weight to about 2500 mg/kg of body weight of the animal per day or from about 0.01 mg/kg of body weight to about 1000 mg/kg of body weight of the animal per day. In one embodiment, the effective dosage amount is about 100 mg/kg of body weight of the animal per day or less. In another embodiment, the effective dosage amount ranges from about 0.01 mg/kg of body weight to about 100 mg/kg of body weight of the animal per day of a Substituted-Quinoxaline-Type Piperidine Compound, in another embodiment, about 0.02 mg/kg of body weight to about 50 mg/kg of body weight of the animal per day, and in another embodiment, about 0.025 mg/kg of body weight to about 20 mg/kg of body weight of the animal per day.

Administration can be as a single dose or as a divided dose. In one embodiment, an effective dosage amount is administered about every 24 hr until the Condition is abated. In another embodiment, an effective dosage amount is administered about every 12 hr until the Condition is abated. In another embodiment, an effective dosage amount is administered about every 8 hr until the Condition is abated. In another embodiment, an effective dosage amount is administered about every 6 hr until the Condition is abated. In another embodiment, an effective dosage amount is administered about every 4 hr until the Condition is abated. The effective dosage amounts described herein refer to total amounts administered; that is, if more than one Substituted-Quinoxaline-Type Piperidine Compound is administered, the effective dosage amounts correspond to the total amount administered.

Where a cell capable of expressing the ORL-1 receptor, the μ-opioid receptor, the κ-opioid receptor and/or the δ-opioid receptor is contacted with a Substituted-Quinoxaline-Type Piperidine Compound in vitro, the amount effective for inhibiting or activating that receptor function in a cell will typically range from about $10^{-12}$ mol/L to about $10^{-4}$ mol/L, in one embodiment, from about $10^{-12}$ mol/L to about $10^{-5}$ mol/L, in another embodiment, from about $10^{-12}$ mol/L to about $10^{-6}$ mol/L, and in another embodiment, from about $10^{-12}$ mol/L to about $10^{-9}$ mol/L of a solution or suspension of a pharmaceutically acceptable carrier or excipient. In one embodiment, the volume of solution or suspension comprising the Substituted-Quinoxaline-Type Piperidine Compound will be from about 0.01 μL to about 1 mL. In another embodiment, the volume of solution or suspension will be about 200 μL.

The Substituted-Quinoxaline-Type Piperidine Compounds will have a binding affinity ($K_i$) for the human ORL-1 receptor of about 1000 nM or less in one embodiment, or about 500 nM or less in another embodiment, about 100 nM or less in another embodiment, about 50 nM or less in another embodiment, or about 20 nM or less in another embodiment, or about 5 nM or less in another embodiment. The binding affinity $K_i$ can be measured in ways known to the art, e.g., by an assay utilizing membranes from recombinant HEK-293 cells expressing the ORL-1 receptor.

Typically, the Substituted-Quinoxaline-Type Piperidine Compounds will have a Ki (nM) of about 300 or less for binding to ORL-1 receptors. In one embodiment, the Substituted-Quinoxaline-Type Piperidine Compounds of the invention will have a Ki (nM) of about 100 or less. In another embodiment, the Substituted-Quinoxaline-Type Piperidine Compounds of the invention will have a Ki (nM) of about 35 or less. In another embodiment, the Substituted-Quinoxaline-Type. Piperidine Compounds of the invention will have a Ki (nM) of about 20 or less. In another embodiment, the Substituted-Quinoxaline-Type Piperidine Compounds of the invention will have a Ki (nM) of about 15 or less. In another embodiment, the Substituted-Quinoxaline-Type Piperidine Compounds of the invention will have a Ki (nM) of about 10 or less. In another embodiment, the Substituted-Quinoxaline-Type Piperidine Compounds of the invention will have a Ki (nM) of about 4 or less. In another embodiment, the Substituted-Quinoxaline-Type Piperidine Compounds of the invention will have a Ki (nM) of about 1 or less. In another embodiment, the Substituted-Quinoxaline-Type Piperidine Compounds of the invention will have a Ki (nM) of about 0.4 or less. In another embodiment, the Substituted-Quinoxaline-Type Piperidine Compounds of the invention will have a Ki (nM) of about 0.1 or less.

ORL-1 GTP $EC_{50}$ is the concentration of a compound providing 50% of the maximal response for the compound at an ORL-1 receptor. Substituted-Quinoxaline-Type Piperidine Compounds typically will have an ORL-1 GTP $EC_{50}$ (nM) of about 5000 or less to stimulate ORL-1 receptor function. In one embodiment, the Substituted-Quinoxaline-Type Piperidine Compounds of the invention will have an ORL-1 GTP $EC_{50}$ (nM) of about 1000 or less. In another embodiment, the Substituted-Quinoxaline-Type Piperidine Compounds of the invention will have an ORL-1 GTP $EC_{50}$ (nM) of about 100 or less. In another embodiment, the Substituted-Quinoxaline-Type Piperidine Compounds of the invention will have an ORL-1 GTP $EC_{50}$ (nM) of about 80 or less. In another embodiment, the Substituted-Quinoxaline-Type Piperidine Compounds of the invention will have an ORL-1 GTP $EC_{50}$ (nM) of about 50 or less. In another embodiment, the Substituted-Quinoxaline-Type Piperidine Compounds of the invention will have an ORL-1 GTP $EC_{50}$ (nM) of about 35 or less. In another embodiment, the Substituted-Quinoxaline-Type Piperidine Compounds of the invention will have an ORL-1 GTP $EC_{50}$ (nM) of about 15 or less. In another embodiment, the Substituted-Quinoxaline-Type Piperidine Compounds will have an ORL-1 GTP $EC_{50}$ (nM) of about 10 or less. In another embodiment, the Substituted-Quinoxaline-Type Piperidine Compounds will have an ORL-1 GTP $EC_{50}$ (nM) of about 4 or less. In another embodiment, the Substituted-Quinoxaline-Type Piperidine Compounds will have an ORL-1 GTP $EC_{50}$ (nM) of about 1 or less. In another embodiment, the Substituted-Quinoxaline-Type Piperidine Compounds will have an ORL-1 GTP $EC_{50}$ (nM) of about 0.4 or less. In another embodiment, the Substituted-Quinoxaline-Type Piperidine Compounds will have an ORL-1 GTP $EC_{50}$ (nM) of about 0.1 or less.

ORL-1 GTP Emax (%) is the maximal effect elicited by a compound relative to the effect elicited by nociceptin, a standard ORL-1 agonist. Typically, a Substituted-Quinoxaline-Type Piperidine Compound of the invention acting as an agonist will have an ORL-1 GTP Emax (%) of about 50% or greater. In one embodiment, agonist Substituted-Quinoxaline-Type Piperidine Compounds will have an ORL-1 GTP Emax (%) of about 75% or greater. In another embodiment, agonist Substituted-Quinoxaline-Type Piperidine Compounds will have an ORL-1 GTP Emax (%) of about 85% or greater. In another embodiment, agonist Substituted-Quinoxaline-Type Piperidine Compounds will have an ORL-1 GTP Emax (%) of about 95% or greater. In another embodiment, agonist Substituted-Quinoxaline-Type Piperidine Compounds will have an ORL-1 GTP Emax (%) of about 100% or greater. Typically, a Substituted-Quinoxaline-Type Piperidine Compound of the invention acting as a partial agonist will have an ORL-1 GTP Emax (%) of less than about 10%. In one embodiment, partial agonist Substituted-Quinoxaline-Type Piperidine Compounds will have an ORL-1 GTP Emax (%) of less than about 20%. In another embodiment, partial agonist Substituted-Quinoxaline-Type Piperidine Compounds will have an ORL-1 GTP Emax (%) of less than about 30%. In another embodiment, partial agonist Substituted-Quinoxaline-Type Piperidine Compounds will have an ORL-1 GTP Emax (%) of less than about 40%. In another embodiment, partial agonist Substituted-Quinoxaline-Type Piperidine Compounds will have an ORL-1 GTP Emax (%) of less than about 50%.

The Substituted-Quinoxaline-Type Piperidine Compounds will have a binding affinity (Ki) for the human g-opioid receptors of about 1000 nM or less in one embodiment, or about 500 nM or less in another embodiment, about 100 nM or less in another embodiment, about 50 nM or less in another embodiment, or about 20 nM or less in another embodiment, or about 5 nM or less in another embodiment.

Typically, the Substituted-Quinoxaline-Type Piperidine Compounds will have a Ki (nM) of about 3000 or less for binding to g-opioid receptors. In one embodiment, the Substituted-Quinoxaline-Type Piperidine Compounds of the invention will have a Ki (nM) of about 1000 or less. In another embodiment, the Substituted-Quinoxaline-Type Piperidine Compounds of the invention will have a Ki (nM) of about 650 or less. In another embodiment, the Substituted-Quinoxaline-Type Piperidine Compounds of the invention will have a Ki (nM) of about 525 or less. In another embodiment, the Substituted-Quinoxaline-Type Piperidine Compounds of the invention will have a Ki (nM) of about 250 or less. In another embodiment, the Substituted-Quinoxaline-Type Piperidine Compounds of the invention will have a Ki (nM) of about 100 or less. In another embodiment, the Substituted-Quinoxaline-Type Piperidine Compounds of the invention will have a Ki (nM) of about 10 or less. In another embodiment, the Substituted-Quinoxaline-Type Piperidine Compounds of the invention will have a Ki (nM) of about 1 or less.

$\mu$ GTP $EC_{50}$ is the concentration of a compound providing 50% of the maximal response for the compound at a $\mu$-opioid receptor. Substituted-Quinoxaline-Type Piperidine Compounds typically will have a $\mu$ GTP $EC_{50}$ (nM) of about 5000 or less to stimulate $\mu$-opioid receptor function. In one embodiment, the Substituted-Quinoxaline-Type Piperidine Compounds of the invention will have a g GTP $EC_{50}$ (nM) of about 4100 or less. In another embodiment, the Substituted-Quinoxaline-Type Piperidine Compounds of the invention will have a g GTP $EC_{50}$ (nM) of about 3100 or less. In another embodiment, the Substituted-Quinoxaline-Type Piperidine Compounds of the invention will have a $\mu$ GTP $EC_{50}$ (nM) of about 2000 or less. In another embodiment, the Substituted-Quinoxaline-Type Piperidine Compounds of the invention will have a $\mu$ GTP $EC_{50}$ (nM) of about 1000 or less. In another embodiment, the Substituted-Quinoxaline-Type Piperidine Compounds of the invention will have a $\mu$ GTP $EC_{50}$ (nM) of about 100 or less. In another embodiment, the Substituted-Quinoxaline-Type Piperidine Compounds will have a $\mu$ GTP $EC_{50}$ (nM) of about 10 or less. In another embodiment, the Substituted-Quinoxaline-Type Piperidine Compounds will have a $\mu$ GTP $EC_{50}$ (nM) of about 1 or less. In another embodiment, the Substituted-Quinoxaline-Type Piperidine Compounds will have a $\mu$ GTP $EC_{50}$ (nM) of about 0.4 or less.

$\mu$ GTP Emax (%) is the maximal effect elicited by a compound relative to the effect elicited by DAMGO, a standard $\mu$ agonist. Typically, the Substituted-Quinoxaline-Type Piperidine Compounds of the invention will have a $\mu$ GTP Emax (%) of about 10% or greater. In one embodiment, the Substituted-Quinoxaline-Type Piperidine Compounds will have a $\mu$ GTP Emax (%) of about 20% or greater. In another embodiment, the Substituted-Quinoxaline-Type Piperidine Compounds will have a $\mu$ GTP Emax (%) of about 50% or greater. In another embodiment, the Substituted-Quinoxaline-Type Piperidine Compounds will have a $\mu$ GTP Emax (%) of about 65% or greater. In another embodiment, the Substituted-Quinoxaline-Type Piperidine Compounds will have a $\mu$ GTP Emax (%) of about 75% or greater. In another embodiment, the Substituted-Quinoxaline-Type Piperidine Compounds will have a $\mu$ GTP Emax (%) of about 88% or greater.

Typically, the Substituted-Quinoxaline-Type Piperidine Compounds will have a Ki (nM) of about 20,000 or less for $\kappa$ receptors. In one embodiment, the Substituted-Quinoxaline-Type Piperidine Compounds will have substantially no activity. In another embodiment, the Substituted-Quinoxaline-Type Piperidine Compounds will have a Ki (nM) of about 10,000 or less. In another embodiment, the Substituted-Quinoxaline-Type Piperidine Compounds will have a Ki (nM) of about 5000 or less. In another embodiment, the Substituted-Quinoxaline-Type Piperidine Compounds will have a Ki (nM) of about 1000 or less. In another embodiment, the Substituted-Quinoxaline-Type Piperidine Compounds will have a Ki (nM) of about 500 or less. In another embodiment, the Substituted-Quinoxaline-Type Piperidine Compounds will have a Ki (nM) of about 300 or less. In another embodiment, the Substituted-Quinoxaline-Type Piperidine Compounds will have a Ki (nM) of about 100 or less. In another embodiment, the Substituted-Quinoxaline-Type Piperidine Compounds will have a Ki (nM) of about 50 or less. In another embodiment, the Substituted-Quinoxaline-Type Piperidine Compounds will have a Ki (nM) of about 20 or less. In another embodiment, the Substituted-Quinoxaline-Type Piperidine Compounds will have a Ki (nM) of about 15 or less.

$\kappa$ GTP $EC_{50}$ is the concentration of a compound providing 50% of the maximal response for the compound at a $\kappa$ receptor. Substituted-Quinoxaline-Type Piperidine Compounds typically will have a $\kappa$ GTP $EC_{50}$ (nM) of about 20,000 or less to stimulate $\kappa$ opioid receptor function. In one embodiment, the Substituted-Quinoxaline-Type Piperidine Compounds will have a $\kappa$ GTP $EC_{50}$ (nM) of about 10,000 or less. In another embodiment, the Substituted-Quinoxaline-Type Piperidine Compounds will have a $\kappa$ GTP $EC_{50}$ (nM) of about 5000 or less. In another embodiment, the Substituted-Quinoxaline-Type Piperidine Compounds will have a $\kappa$ GTP $EC_{50}$ (nM) of about 2000 or less. In another embodiment, the Substituted-Quinoxaline-Type Piperidine Compounds will have a $\kappa$ GTP $EC_{50}$ (nM) of about 1500 or less. In another embodiment, the Substituted-Quinoxaline-Type Piperidine Compounds will have a $\kappa$ GTP $EC_{50}$ (nM) of about 800 or less. In another embodiment, the Substituted-Quinoxaline-Type Piperidine Compounds will have a $\kappa$ GTP $EC_{50}$ (nM) of about 500 or less. In another embodiment, the Substituted-Quinoxaline-Type Piperidine Compounds will have a $\kappa$ GTP $EC_{50}$ (nM) of about 300 or less. In another embodiment, the Substituted-Quinoxaline-Type Piperidine Compounds will have a $\kappa$ GTP $EC_{50}$ (nM) of about 100 or less. In another embodiment, the Substituted-Quinoxaline-Type Piperidine Compounds will have a $\kappa$ GTP $EC_{50}$ (nM) of about 50 or less. In another embodiment, the Substituted-Quinoxaline-Type Piperidine Compounds will have a $\kappa$ GTP $EC_{50}$ (nM) of about 25 or less.

$\kappa$ GTP Emax (%) is the maximal effect elicited by a compound relative to the effect elicited by U69,593. Typically, the Substituted-Quinoxaline-Type Piperidine Compounds of the invention will have a $\kappa$ GTP Emax (%) of about 10% or greater. In one embodiment, the Substituted-Quinoxaline-Type Piperidine Compounds will have a $\kappa$ GTP Emax (%) of about 15% or greater. In another embodiment, the Substituted-Quinoxaline-Type Piperidine Compounds will have a $\kappa$ GTP Emax (%) of about 30% or greater. In another embodiment, the Substituted-Quinoxaline-Type Piperidine Compounds will have a $\kappa$ GTP Emax (%) of about 40% or greater. In another embodiment, the Substituted-Quinoxaline-Type Piperidine Compounds will have a $\kappa$ GTP Emax (%) of about 45% or greater. In another embodiment, the Substituted-Quinoxaline-Type Piperidine Compounds will have a $\kappa$ GTP Emax (%) of about 75% or greater. In another embodiment, the Substituted-Quinoxaline-Type Piperidine Compounds will have a $\kappa$ GTP Emax (%) of about 90% or greater.

Typically, the Substituted-Quinoxaline-Type Piperidine Compounds will have a Ki (nM) of about 20,000 or less for $\delta$ receptors. In one embodiment, the Substituted-Quinoxaline-Type Piperidine Compounds will have substantially no activity. In another embodiment, the Substituted-Quinoxaline-Type Piperidine Compounds will have a Ki (nM) of about 10,000 or less. In another embodiment, the Substituted-Quinoxaline-Type Piperidine Compounds will have a Ki (nM) of about 9000 or less. In another embodiment, the Substituted-Quinoxaline-Type Piperidine Compounds will have a Ki (nM) of about 7500 or less. In another embodiment, the Substituted-Quinoxaline-Type Piperidine Compounds will have a Ki (nM) of about 6500 or less. In another embodiment, the Substituted-Quinoxaline-Type Piperidine Compounds will have a Ki (nM) of about 5000 or less. In another embodiment, the Substituted-Quinoxaline-Type Piperidine Compounds will have a Ki (nM) of about 3000 or less. In another embodiment, the Substituted-Quinoxaline-Type Piperidine Compounds will have a Ki (nM) of about 2500 or less. In another embodiment, the Substituted-Quinoxaline-Type Piperidine Compounds will have a Ki (nM) of about 1000 or less. In another embodiment, the Substituted-Quinoxaline-Type Piperidine Compounds will have a Ki (nM) of about 500 or less. In another embodiment, the Substituted-Quinoxaline-Type Piperidine Compounds will have a Ki (nM) of about 350 or less. In another embodiment, the Substituted-Quinoxaline-Type Piperidine Compounds will have a Ki (nM) of about 250 or less. In another embodiment, the Substituted-Quinoxaline-Type Piperidine Compounds will have a Ki (nM) of about 100 or less.

δ GTP $EC_{50}$ is the concentration of a compound providing 50% of the maximal response for the compound at a δ receptor. Substituted-Quinoxaline-Type Piperidine Compounds typically will have a δ GTP $EC_{50}$ (nM) of about 20,000 or less to stimulate δ opioid receptor function. In one embodiment, the Substituted-Quinoxaline-Type Piperidine Compounds will have a δ GTP $EC_{50}$ (nM) of about 10,000 or less. In another embodiment, the Substituted-Quinoxaline-Type Piperidine Compounds will have a δ GTP $EC_{50}$ (nM) of about 1000 or less. In another embodiment, the Substituted-Quinoxaline-Type Piperidine Compounds will have a δ GTP $EC_{50}$ (nM) of about 100 or less. In another embodiment, the Substituted-Quinoxaline-Type Piperidine Compounds will have a δ GTP $EC_{50}$ (nM) of about 90 or less. In another embodiment, the Substituted-Quinoxaline-Type Piperidine Compounds will have a δ GTP $EC_{50}$ (nM) of about 50 or less. In another embodiment, the Substituted-Quinoxaline-Type Piperidine Compounds will have a δ GTP $EC_{50}$ (nM) of about 25 or less or less.

δ GTP Emax (%) is the maximal effect elicited by a compound relative to the effect elicited by met-enkephalin. Typically, the Substituted-Quinoxaline-Type Piperidine Compounds of the invention will have a δ GTP Emax (%) of about 10% or greater. In one embodiment, the Substituted-Quinoxaline-Type Piperidine Compounds will have a δ GTP Emax (%) of about 30% or greater. In another embodiment, the Substituted-Quinoxaline-Type Piperidine Compounds will have a δ GTP Emax (%) of about 50% or greater. In another embodiment, the Substituted-Quinoxaline-Type Piperidine Compounds will have a δ GTP Emax (%) of about 75% or greater. In another embodiment, the Substituted-Quinoxaline-Type Piperidine Compounds will have a δ GTP Emax (%) of about 90% or greater. In another embodiment, the Substituted-Quinoxaline-Type Piperidine Compounds will have a δ GTP Emax (%) of about 100% or greater.

The Substituted-Quinoxaline-Type Piperidine Compounds can be assayed in vitro or in vivo for the desired therapeutic or prophylactic activity prior to use in humans. Animal model systems can be used to demonstrate safety and efficacy.

The methods for treating or preventing a Condition in an animal in need thereof can further comprise co-administering to the animal being administered a Substituted-Quinoxaline-Type Piperidine Compound (i.e., a first therapeutic agent) a second therapeutic agent. In one embodiment, the second therapeutic agent is administered in an effective amount.

An effective amount of the second therapeutic agent will be known to those skilled the art depending on the agent. However, it is well within the skilled artisan's purview to determine the second therapeutic agent's optimal effective-amount range. A Substituted-Quinoxaline-Type Piperidine Compound and the second therapeutic agent combined can act either additively or synergistically to treat the same Condition, or they may act independently of each other such that the Substituted-Quinoxaline-Type Piperidine Compound treats or prevents a first Condition and the second therapeutic agent treats or prevents a second disorder, which can be the same as the first Condition or another disorder. In one embodiment of the invention, where a second therapeutic agent is administered to an animal for treatment of a Condition (e.g., pain), the minimal effective amount of the Substituted-Quinoxaline-Type Piperidine Compound will be less than its minimal effective amount would be where the second therapeutic agent is not administered. In this embodiment, the Substituted-Quinoxaline-Type Piperidine Compound and the second therapeutic agent can act synergistically to treat or prevent a Condition. In one embodiment, a Substituted-Quinoxaline-Type Piperidine Compound is administered concurrently with a second therapeutic agent as a single composition comprising an effective amount of a Substituted-Quinoxaline-Type Piperidine Compound and an effective amount of the second therapeutic agent. Alternatively, a composition comprising an effective amount of a Substituted-Quinoxaline-Type Piperidine Compound and a second composition comprising an effective amount of the second therapeutic agent are concurrently administered. In another embodiment, an effective amount of a Substituted-Quinoxaline-Type Piperidine Compound is administered prior or subsequent to administration of an effective amount of the second therapeutic agent. In this embodiment, the Substituted-Quinoxaline-Type Piperidine Compound is administered while the second therapeutic agent exerts its therapeutic effect, or the second therapeutic agent is administered while the Substituted-Quinoxaline-Type Piperidine Compound exerts its therapeutic effect for treating or preventing a Condition.

The second therapeutic agent can be, but is not limited to, an opioid agonist, a non-opioid analgesic, a non-steroidal anti-inflammatory agent, an antimigraine agent, a Cox-II inhibitor, a 5-lipoxygenase inhibitor, an anti-emetic, a β-adrenergic blocker, an anticonvulsant, an antidepressant, a $Ca^{2+}$-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for inhibiting vomiting, an agent for treating or preventing dyskinesia, an agent for treating or preventing depression, or any mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, or any mixture thereof.

In certain embodiments, the opioid agonist is selected from codeine, hydromorphone, hydrocodone, oxycodone, dihydrocodeine, dihydromorphine, morphine, tramadol, oxymorphone, pharmaceutically acceptable derivatives thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable derivative thereof, or any mixture thereof. Other suitable non-opioid analgesics include the following, non-limiting, chemical classes of analgesic, antipyretic, non-steroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable derivative thereof; or any mixture thereof. For a more detailed description of the NSAIDs, see Paul A. Insel, *Analgesic-Antipyretic and Anti-inflammatory Agents and Drugs Employed in the Treatment of Gout*, in *Goodman & Gilman's The Pharmacological Basis of Therapeutics* 617-57 (P. B. Molinhoff and R. W. Ruddon eds., 9th ed 1996), and G. R. Hanson, *Analgesic, Antipyretic and Anti-Inflammatory Drugs in Remington: The Science and Practice of Pharmacy Vol II* 1196-1221 (A. R. Gennaro ed. 19th ed. 1995), which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable derivative thereof, or any mixture thereof.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable derivative thereof, or any mixture thereof.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenyl-hydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, zonisamide, a pharmaceutically acceptable derivative thereof, or any mixture thereof.

Examples of useful $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, perhexiline, a pharmaceutically acceptable derivative thereof, or any mixture thereof.

Examples of useful therapeutic agents for treating or preventing UI include, but are not limited to, propantheline, imipramine, hyoscyamine, oxybutynin, dicyclomine, a pharmaceutically acceptable derivative thereof, or any mixture thereof.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; propanediol carbamates, such as meprobamate and tybamate; a pharmaceutically acceptable derivative thereof; or any mixture thereof.

Examples of useful therapeutic agents for treating or preventing diarrhea include, but are not limited to, diphenoxylate, loperamide, a pharmaceutically acceptable derivative thereof, or any mixture thereof.

Examples of useful therapeutic agents for treating or preventing epilepsy include, but are not limited to, carbamazepine, ethosuximide, gabapentin, lamotrigine, phenobarbital, phenytoin, primidone, valproic acid, trimethadione, benzodiazepines, γ vinyl GABA, acetazolamide, felbamate, a pharmaceutically acceptable derivative thereof, or any mixture thereof.

Examples of useful therapeutic agents for treating or preventing drug abuse include, but are not limited to, methadone, desipramine, amantadine, fluoxetine, buprenorphine, an opiate agonist, 3-phenoxypyridine, levomethadyl acetate hydrochloride, serotonin antagonists, a pharmaceutically acceptable derivative thereof, or any mixture thereof.

Examples of non-steroidal anti-inflammatory agents, 5-lipoxygenase inhibitors, anti-emetics, β-adrenergic blockers, antidepressants, and anti-cancer agents are known in the art and can be selected by those skilled in the art. Examples of useful therapeutic agents for treating or preventing memory disorder, obesity, constipation, cough, high blood pressure, anorexia/cachexia, an ulcer, IBD, IBS, addictive disorder, Parkinson's disease and parkinsonism, a stroke, a seizure, a pruritic condition, psychosis, Huntington's chorea, ALS, a cognitive disorder, a migraine, dyskinesia, depression, and/or treating, preventing or inhibiting vomiting include those that are known in the art and can be selected by those skilled in the art.

A composition of the invention is prepared by a method comprising admixing a Substituted-Quinoxaline-Type Piperidine Compound or a pharmaceutically acceptable derivative thereof with a pharmaceutically acceptable carrier or excipient. Admixing can be accomplished using methods known for admixing a compound (or derivative) and a pharmaceutically acceptable carrier or excipient. In one embodiment, the Substituted-Quinoxaline-Type Piperidine Compound is present in the composition in an effective amount.

4.7 Kits

The invention further provides kits that can simplify the handling and administration of a Substituted-Quinoxaline-Type Piperidine Compound to an animal.

A typical kit of the invention comprises a unit dosage form of a Substituted-Quinoxaline-Type Piperidine Compound. In one embodiment, the unit dosage form comprises a first container, which can be sterile, containing an effective amount of a Substituted-Quinoxaline-Type Piperidine Compound and a pharmaceutically acceptable carrier or excipient. The kit can further comprise a label or printed instructions instructing the use of the Substituted-Quinoxaline-Type Piperidine Compound to treat or prevent a Condition. The kit can further comprise a unit dosage form of a second therapeutic agent, for example, a second container containing an effective amount of the second therapeutic agent and a pharmaceutically acceptable carrier or excipient. In another embodiment, the kit comprises a container containing an effective amount of a Substituted-Quinoxaline-Type Piperidine Compound, an effective amount of a second therapeutic agent and a pharmaceutically acceptable carrier or excipient. Examples of second therapeutic agents include, but are not limited to, those listed above.

Kits of the invention can further comprise a device that is useful for administering the unit dosage forms. Examples of such a device include, but are not limited to, a syringe, a drip bag, a patch, an inhaler, and an enema bag.

The following examples are set forth to assist in understanding the invention and should not be construed as specifically limiting the invention described and claimed herein. Such variations of the invention, including the substitution of all equivalents now known or later developed, that would be within the purview of those skilled in the art, and changes in formulation or changes in experimental design, are to be considered to fall within the scope of the invention incorporated herein.

5. EXAMPLES

The following examples illustrate various aspects of the invention, and are not to be construed to limit the claims in any manner whatsoever.

5.1 Example 1

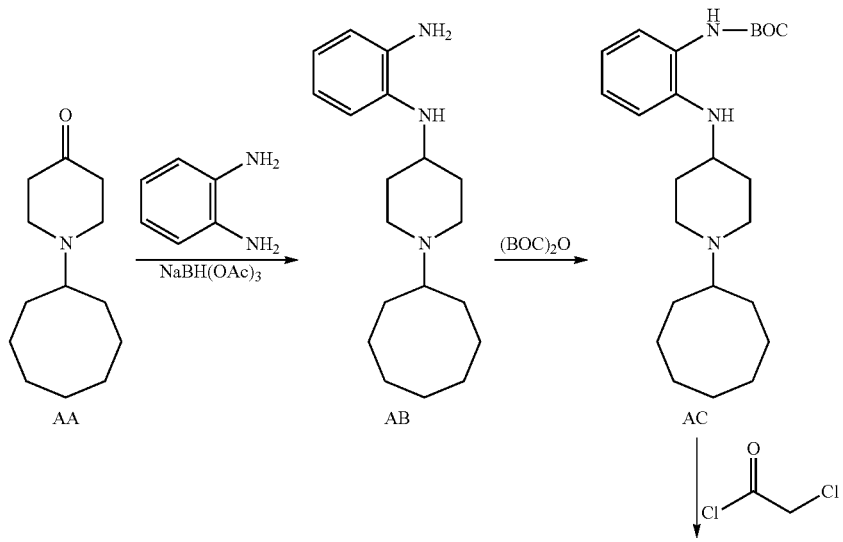

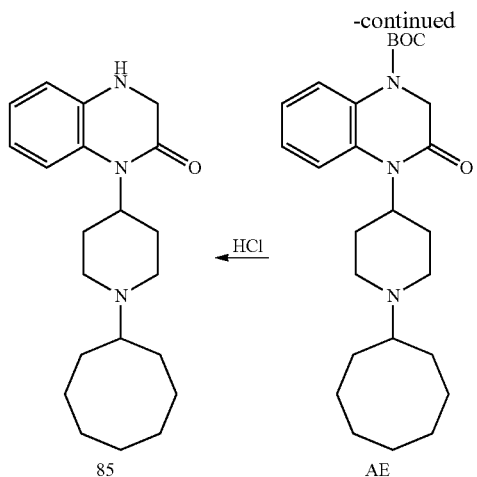
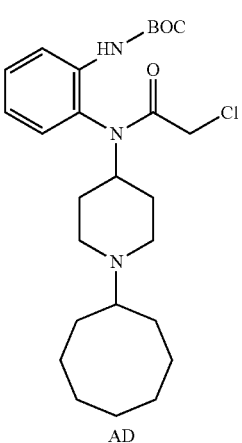

1-Cyclooctylpiperidin-4-one (compound of formula AA) was purchased from Vasudha Pharma Chem LTD (Hyderabad, Andhra Pradesh, India).

The compound of formula AA (10.00 g, 48.0 mmol) and 1,2-phenylenediamine (10.38 g, 96.0 mmol, Sigma-Aldrich, St. Louis, Mo.) were suspended in 200 mL of $CH_2Cl_2$. To this mixture, sodium triacetoxyborohydride ($NaBH(OAc)_3$, 30.42 g, 144.0 mmol, Acros Organics, Geel, Belgium) and acetic acid (10 mL) were added. The reaction mixture was stirred at a temperature of about 25° C. for 24 hrs after which the reaction mixture was extracted 10 times with about 200 mL of water each time. The organic portion was dried ($MgSO_4$), filtered, and concentrated to dryness under reduced pressure to provide 9.48 g of a compound of formula AB as a light orange oil (yield 65.6%).

The identity of the compound of formula AB, $N^1$-(1-cyclooctylpiperidin-4-yl)benzene-1,2-diamine, was confirmed using liquid chromatography/mass spectrometry (LC/MS).

Compound AB: LC/MS (95%, $t_r$=1.832 min): m/z=301.1 $[M+H]^+$ (Calc: 302.2).

To a suspension of 199 mg (0.66 mmol) of the compound of formula AB and excess $NaHCO_3$ in 10 mL of DCM at 0° C. was added di-tert-butyl dicarbonate ($(BOC)_2O$, 144 mg, 0.66 mmol, Sigma-Aldrich). After the addition, the reaction mixture was warmed to a temperature of about 25° C. and stirred for 2 hrs. The reaction mixture was then poured onto a silica gel column and eluted with 5%:95% MeOH:DCM to provide 247 mg of the compound of formula AC as light yellow solid (yield 93%).

The identity of the compound of formula AC, tert-butyl 2-(1-cyclooctylpiperidin-4-ylamino)phenylcarbamate, was confirmed using $^1$H NMR.

Compound AC: $^1$H NMR: $\delta_H$ (400 MHz, $CDCl_3$): 7.24 (bs, 1H), 6.98 (dt, 1H, J=1.5, 8 Hz), 6.67 (m, 2H), 6.12 (bs, 1H), 3.53 (bs, 1H), 3.13 (m, 1H), 2.71 (m, 2H), 2.56 (m, 1H), 2.27 (t, 2H, J=10 Hz), 1.95 (m, 2H), 1.70-1.35 (m, 15H), 1.43 (s, 9H).

To a suspension of 230 mg of the compound of formula AC and excess $NaHCO_3$ in DCM at 0° C. was added dropwise via a syringe 2-chloroacetyl chloride (0.047 mL, 0.57 mmol, Sigma-Aldrich). After addition, the reaction mixture was warmed to a temperature of about 25° C. and stirred for 30 min more. Thereafter, the reaction mixture was evaporated to dryness under reduced pressure to provide 273 mg of the compound of formula AD (yield >98%).

The identity of the compound of formula AD, tert-butyl 2-(2-chloro-N-(1-cyclooctylpiperidin-4-yl)acetamido)phenylcarbamate, was confirmed using mass spectrometry (MS).

Compound AD: MS: m/z=478 (M+1) (Calc: 477).

50 mg of the compound of formula AD was added to 3 mL of DMF at 0° C. To this mixture was added excess of NaH (3 equivalents, Sigma-Adrich). Thereafter, the reaction mixture was warmed to a temperature of about 25° C. and stirred for 10 min. After cooling to 0° C., the reaction mixture was quenched by the addition of ice water. The reaction mixture was diluted with EtOAc then washed twice with brine. The brine was extracted with EtOAc. The organic portions were combined, dried ($Na_2SO_4$), filtered, and concentrated under reduced pressure to provide a residue. The residue was chromatographed with a silica gel column eluted with EtOAc to provide the compound of formula AE (yield >98%).

The identity of the compound of formula AE, tert-butyl 4-(1-cyclooctylpiperidin-4-yl)-3-oxo-3,4-dihydroquinoxaline-1(2H)-carboxylate, was confirmed using $^1$H NMR.

Compound AE: $^1$H NMR: $\delta_H$ (400 MHz, $CDCl_3$): 7.63 (bs, 1H), 7.34 (dd, 1H, J=1.5, 8 Hz), 7.13 (dt, 1H, J=1.5, 8 Hz), 7.08 (dt, 1H, J=1.5, 8 Hz), 4.29 (s, 2H), 4.29 (m, 1H), 2.92 (bd, 2H, J=10 Hz), 2.66 (m, 1H), 2.54 (m, 2H), 2.36 (t, 2H, J=10 Hz), 1.80-1.43 (m, 16H), 1.54 (s, 9H).

The compound of formula AE was added to 4N HCl in 1,4-dioxane at a temperature of about 25° C. for 30 min then concentrated under reduced pressure to provide a residue. The residue was diluted with EtOAc and washed with saturated aqueous $NaHCO_3$ solution. The organic portion was dried ($Na_2SO_4$), filtered, and concentrated under reduced pressure to provide a residue. The residue was then chromatographed by preparative TLC (eluted with 15%:85% MeOH:DCM) to provide 31 mg of the Substituted-Quinoxaline-Type Piperidine Compound of formula 85 (yield 98%).

The identity of Substituted-Quinoxaline-Type Piperidine Compound 85, 1-(1-cyclooctylpiperidin-4-yl)-3,4-dihydroquinoxalin-2(1H)-one, was confirmed using $^1$H NMR and MS.

Substituted-Quinoxaline-Type Piperidine Compound 85: $^1$H NMR: $\delta_H$ (400 MHz, $CDCl_3$): 12.21 (bs, 0.5H), 7.78 (m, 1H), 6.99 (m, 1H), 6.87 (t, 1H, J=8 Hz), 6.66 (d, 1H, J=8

Hz), 5.03 (bs, 1H), 3.79 (s, 2H), 3.71 (s, 1H), 3.34 (m, 4H), 2.95 (m, 1H), 2.19 (m, 1H), 1.8-1.3 (m, 18H); MS: m/z=342 (M+1) (Calc: 341).

5.2 Example 2

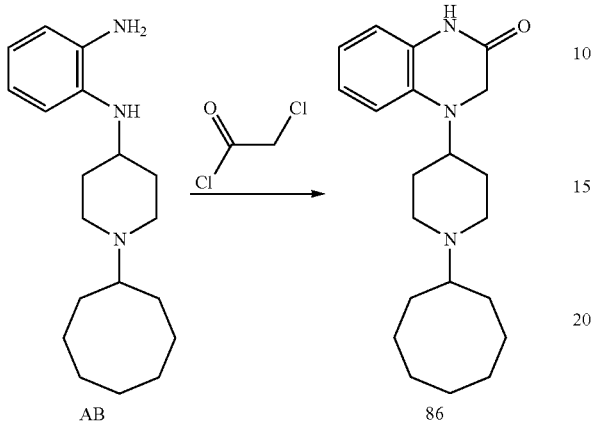

AB → 86

190 mg (0.63 mmol) of the compound of formula AB was mixed with 7 mL of DCM. NaHCO$_3$ (158 mg, 1.89 mmol) was added and the resulting suspension was stirred at 0° C. To the suspension was then added dropwise via a syringe 2-chloroacetyl chloride (0.051 mL, 0.63 mmol). After addition, the reaction mixture was warmed to a temperature of about 25° C. and stirred for 10 min. The reaction mixture was then evaporated to dryness under reduced pressure, acetonitrile was added, and the resulting suspension was heated at 80° C. for 48 hr. The suspension was poured onto a silica gel column and eluted with 5%:95% MeOH:DCM to provide 168 mg of Substituted-Quinoxaline-Type Piperidine Compound 86 as light yellow solid (yield 78%).

The identity of Substituted-Quinoxaline-Type Piperidine Compound 86, 4-(1-cyclooctylpiperidin-4-yl)-3,4-dihydro-quinoxalin-2(1H)-one, was confirmed using $^1$H NMR and MS.

Substituted-Quinoxaline-Type Piperidine Compound 86:
$^1$H NMR: $\delta_H$ (400 MHz, CDCl$_3$): 7.53 (bs, 1H), 6.93 (dt, 1H, J=1.5, 8 Hz), 6.69 (m, 2H), 3.71 (s, 2H), 3.43 (m, 1H), 2.88 (m, 2H), 2.61 (m, 1H), 2.31 (m, 2H), 1.80-1.38 (m, 18H); MS: m/z=342 (M+1) (Calc: 341).

5.3 Example 3

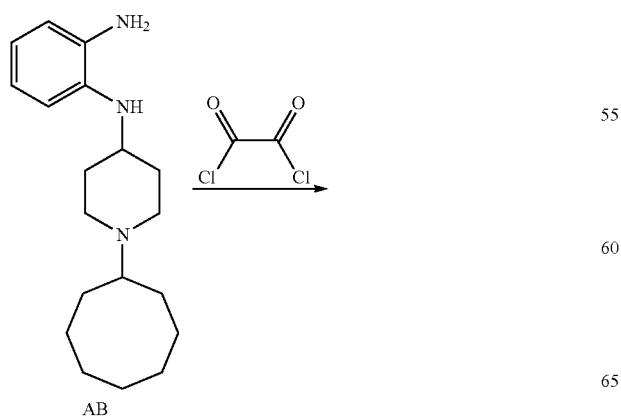

AB

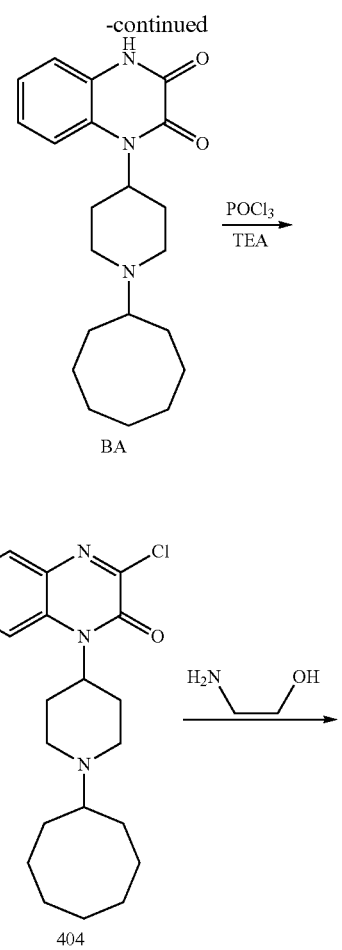

BA

404

3

The compound of formula AB (14.40 g, 47.84 mmol) was added to 100 mL of dry DCE. This mixture was added dropwise to a solution of oxalyl dichloride (8.37 g, 66.44 mmol, Sigma-Aldrich) in 200 mL of dry DCE. Under an argon atmosphere, the resulting mixture was magnetically stirred at a temperature of about 25° C. for 1 hr. The mixture was then warmed to 60° C. for 10 hrs. The mixture was then cooled to a temperature of about 25° C. and the solvent was removed under reduced pressure. The remaining material was added to 300 mL of MeOH and adsorbed onto silica gel to provide residues that were chromatographed with a silica gel column eluted with a gradient of from 100%:0% EtOAc: MeOH to 0%:100% EtOAc:MeOH. The product fractions were combined and concentrated to dryness under reduced pressure to provide 10.0 g of the compound of formula BA as a light orange solid (yield 58%).

The identity of the compound of formula BA, 1-(1-cyclooctylpiperidin-4-yl)quinoxaline-2,3(1H,4H)-dione, was confirmed using $^1$H NMR and LC/MS.

Compound BA: $^1$H NMR: $\delta_H$ (400 MHz, CD$_3$OD): 7.81 (1H, m), 7.31 (3H, m), 3.57 (3H, m), 3.43 (2H, m), 3.22 (2H, m), 2.17 (4H, m), 1.99 (4H, m), 1.78-1.46 (14H, m); LC/MS (100%, t$_r$=5.011 min): m/z=356.3 [M+H]$^+$ (Calc: 355.5).

TEA (2 mmol) and POCl$_3$ (5 mmol, Sigma-Aldrich) were added to a suspension of the compound of formula BA (784 mg, 2 mmol) in toluene (15 mL) and DMF (2 mL) at 25° C. The reaction mixture was warmed to 100° C. with stirring. A pale yellow solid formed after 30 min. Thereafter, the mixture was cooled to a temperature of about 25° C., filtered, washed twice with 1:5 EtOAc:Et$_2$O (10 mL for each wash), and dried under reduced pressure at 60° C. for 12 hr to provide 712 mg of Substituted-Quinoxaline-Type Piperidine Compound 404 as a colorless solid (yield 87%).

The identity of Substituted-Quinoxaline-Type Piperidine Compound 404, 3-chloro-1-(1-cyclooctylpiperidin-4-yl)quinoxalin-2(1H)-one, was confirmed using $^1$H NMR.

Substituted-Quinoxaline-Type Piperidine Compound 404: $^1$H NMR: $\delta_H$ (300 MHz, DMSO): 8.11 (1H, br), 7.79 (1H, d, J=8 Hz), 7.67 (1H, m), 7.44 (1H, t, J=8 Hz), 5.11 (1H, br), 3.45-3.30 (4H, m), 3.11 (2H, m), 1.96 (2H, m), 1.73 (2H, d, J=8 Hz), 1.76-1.42 (13H, m).

TEA (0.38 mmol) and 2-aminoethanol (0.57 mmol, Sigma-Aldrich) were added to a suspension of Substituted-Quinoxaline-Type Piperidine Compound 404 (80 mg, 0.19 mmol) in acetonitrile (3 mL) at 25° C. The resulting reaction mixture was stirred at 80° C. for 90 min. After cooling to about 25° C. and quenching with water (3 mL), a white precipitate formed. The precipitate was filtered, washed with water, and dried under reduced pressure at 60° C. for 12 hr to provide 55 mg of Substituted-Quinoxaline-Type Piperidine Compound 3 as light yellow solid (yield 73%).

The identity of Substituted-Quinoxaline-Type Piperidine Compound 3, 1-(1-cyclooctylpiperidin-4-yl)-3-(2-hydroxyethylamino)quinoxalin-2(1H)-one, was confirmed using $^1$H NMR and MS.

Substituted-Quinoxaline-Type Piperidine Compound 3: $^1$H NMR: $\delta_H$ (300 MHz, DMSO): 7.66 (1H, m), 7.44-7.32 (2H, m), 7.18 (2H, m), 4.82 (1H, t, J=5.4 Hz), 4.67 (1H, br), 3.58 (2H, q, J=5.7 Hz), 3.47 (2H, q, J=5.7 Hz), 2.86-2.68 (5H, m), 2.43-2.36 (2H, m), 1.72-1.41 (16H, m); MS: m/z=436.9 [M+H]$^+$ (Calc: 435.4).

5.4 Example 4

In a manner similar to Example 3, the following Substituted-Quinoxaline-Type Piperidine Compounds were prepared from Substituted-Quinoxaline-Type Piperidine Compound 404.

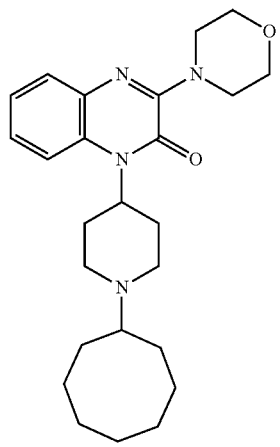

Substituted-Quinoxaline-Type Piperidine Compound 1 was prepared by using morpholine (Sigma-Aldrich) in place of 2-aminoethanol (yield 96%).

The identity of Substituted-Quinoxaline-Type Piperidine Compound 1, 1-1-yclooctylpiperidin-4-yl)-3-morpholinoquinoxalin-2(1H)-one, was confirmed using $^1$H NMR and LC/MS.

Substituted-Quinoxaline-Type Piperidine Compound 1: $^1$H NMR: $\delta_H$ (400 MHz, DMSO): 7.67 (1H, d, J=8 Hz), 7.45 (1H, d, J=8 Hz), 7.28 (2H, t, J=8 Hz), 7.21 (2H, t, J=8 Hz), 4.64 (1H, br), 3.77 (4H, m), 3.71 (4H, m), 2.84 (2H, m), 2.69-2.61 (3H, m), 2.39 (2H, m), 1.72-1.41 (17H, m); LC/MS: m/z=425.1 [M+H]$^+$ (Calc: 424.6).

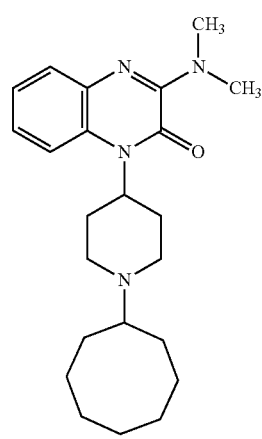

Substituted-Quinoxaline-Type Piperidine Compound 2 was prepared by using dimethylamine (Sigma-Aldrich) in place of 2-aminoethanol (yield 92%).

The identity of Substituted-Quinoxaline-Type Piperidine Compound 2, 1-(1-cyclooctylpiperidin-4-yl)-3-(dimethylamino)quinoxalin-2(1H)-one, was confirmed using $^1$H NMR and LC/MS.

Substituted-Quinoxaline-Type Piperidine Compound 2: $^1$H NMR: $\delta_H$ (400 MHz, DMSO): 7.60 (1H, d, J=8 Hz), 7.40 (1H, d, J=8 Hz), 7.20 (2H, m), 4.60 (1H, br), 3.22 (6H, s), 2.84 (2H, m), 2.69-2.62 (3H, m), 2.40 (2H, m), 1.72-1.41 (17H, m); LC/MS: m/z=383.1 [M+H]$^+$ (Calc: 382.5).

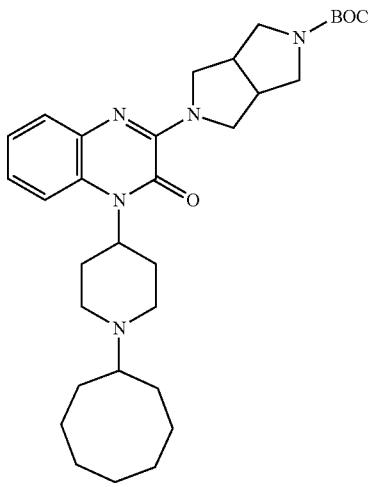

4

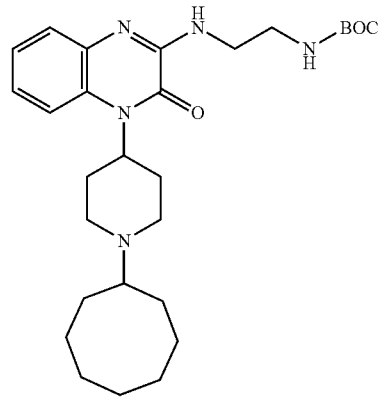

7

Substituted-Quinoxaline-Type Piperidine Compound 4 was prepared by using tert-butyl hexahydropyrrolo[3,4-c]pyrrole-2(1H)-carboxylate (Chembasics Pty. Ltd., Perth, Australia) in place of 2-aminoethanol (yield >98%).

The identity of Substituted-Quinoxaline-Type Piperidine Compound 4, tert-butyl 5-(4-(1-cyclooctylpiperidin-4-yl)-3-oxo-3,4-dihydroquinoxalin-2-yl)hexahydropyrrolo[3,4-c]pyrrole-2(1H)-carboxylate, was confirmed using $^1$H NMR and LC/MS.

Substituted-Quinoxaline-Type Piperidine Compound 4: $^1$H NMR: $\delta_H$ (400 MHz, DMSO): 7.61 (1H, d, J=4 Hz), 7.34 (1H, m), 7.22-7.18 (2H, m), 4.65 (1H, br), 4.01 (2H, m), 3.71 (1H, m), 3.44 (2H, m), 3.15 (3H, m), 2.92 (5H, m), 2.72 (3H, m), 1.78-1.40 (17H, m), 1.39 (9H, s); LC/MS: m/z=550.2 [M+H]$^+$ (Calc: 549.8).

(9H, m), 4.60 (2H, d, J=6 Hz), 3.41 (5H, m), 3.15 (2H, m), 2.10-1.47 (17H, m); LC/MS: m/z=445.1 [M+H]$^+$ (Calc: 444.6).

Substituted-Quinoxaline-Type Piperidine Compound 7 was prepared by using tert-butyl 2-aminoethylcarbamate (Sigma-Aldrich) in place of 2-aminoethanol (yield 90%).

The identity of Substituted-Quinoxaline-Type Piperidine Compound 7, tert-butyl 2-(4-(1-cyclooctylpiperidin-4-yl)-3-oxo-3,4-dihydroquinoxalin-2-ylamino)ethylcarbamate, was confirmed using $^1$H NMR and LC/MS.

Substituted-Quinoxaline-Type Piperidine Compound 7: $^1$H NMR: $\delta_H$ (400 MHz, DMSO): 8.00-7.5 (2H, br), 7.43 (1H, m), 7.22 (2H, m), 6.98 (1H, m), 4.98 (1H, br), 3.45 (7H, m), 3.21-3.09 (5H, m), 2.04-1.45 (15H, m), 1.37 (9H, s); LC/MS: m/z=498.1 [M+H]$^+$ (Calc: 497.7).

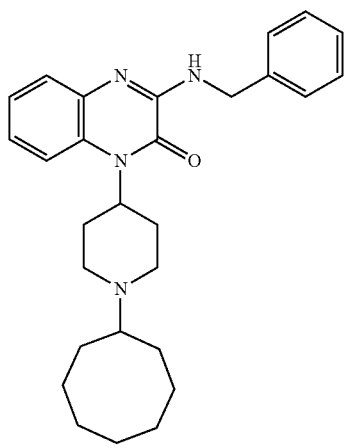

6

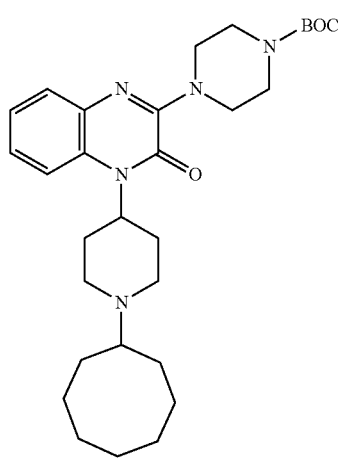

8

Substituted-Quinoxaline-Type Piperidine Compound 6 was prepared by using phenylmethanamine (Sigma-Aldrich) in place of 2-aminoethanol (yield >98%).

The identity of Substituted-Quinoxaline-Type Piperidine Compound 6, 3-(benzylamino)-1-(1-cyclooctylpiperidin-4-yl)quinoxalin-2(1H)-one, was confirmed using $^1$H NMR and LC/MS.

Substituted-Quinoxaline-Type Piperidine Compound 6: $^1$H NMR: $\delta_H$ (300 MHz, DMSO): 8.08 (1H, m), 7.40-7.19

Substituted-Quinoxaline-Type Piperidine Compound 8 was prepared by using tert-butyl piperazine-1-carboxylate (Sigma-Aldrich) in place of 2-aminoethanol (yield 86%).

The identity of Substituted-Quinoxaline-Type Piperidine Compound 8, tert-butyl 4-(4-(1-cyclooctylpiperidin-4-yl)-3-oxo-3,4-dihydroquinoxalin-2-yl)piperazine-1-carboxylate, was confirmed using $^1$H NMR and LC/MS.

Substituted-Quinoxaline-Type. Piperidine Compound 8: $^1$H NMR; $\delta_H$ (400 MHz, DMSO): 7.67 (1H, d, J=8 Hz), 7.45 (1H, d, J=8 Hz), 7.29 (1H, d, J=8 Hz), 7.21 (1H, d, J=8 Hz), 4.63 (1H, br), 3.75 (4H, s), 3.45 (4H, s), 2.84 (2H, m), 2.69-2.61 (3H, m), 2.39 (2H, t, J=8 Hz), 1.71-1.42 (17H, m), 1.42 (9H, s); LC/MS: m/z=524.1 [M+H]+ (Calc: 523.7).

7.31 (2H, s), 7.19 (2H, m), 5.23 (4H, br), 4.69 (1H, br), 2.87-2.28 (7H, m), 1.78-1.44 (16H, m); LC/MS: m/z=457 [M+H]+ (Calc: 456.6).

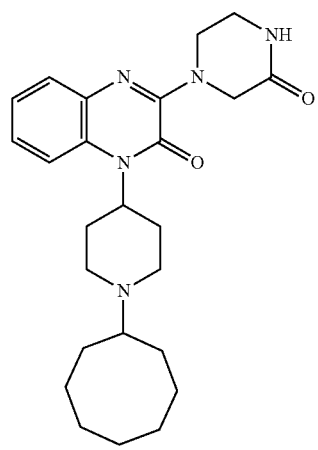

18

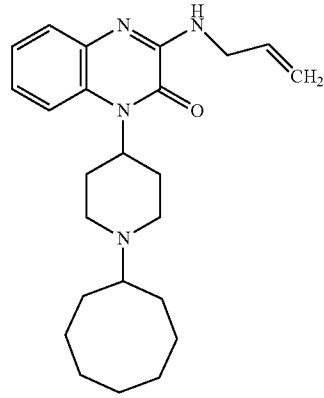

24

Substituted-Quinoxaline-Type Piperidine Compound 18 was prepared by using piperazin-2-one (Sigma-Aldrich) in place of 2-aminoethanol to provide a colorless solid (yield 86%).

The identity of Substituted-Quinoxaline-Type Piperidine Compound 18, 1-(1-cyclooctylpiperidin-4-yl)-3-(3-oxopiperazin-1-yl)quinoxalin-2(1H)-one, was confirmed using $^1$H NMR and LC/MS.

Substituted-Quinoxaline-Type Piperidine Compound 18: $^1$H NMR: $\delta_H$ (400 MHz, CDCl$_3$): 8.01 (1H, s), 7.83 (1H, m), 7.49 (1H, d, J=7.6 Hz), 7.28 (2H, m), 4.94 (1H, br), 4.31 (2H, s), 4.02 (2H, t, J=5.2 Hz), 3.41-3.58 (8H, m), 2.01-1.47 (17H, m); LC/MS: m/z=438 [M+H]+ (Calc: 437.6).

Substituted-Quinoxaline-Type Piperidine Compound 24 was prepared by using prop-2-en-1-amine (Sigma-Aldrich) in place of 2-aminoethanol to provide a colorless solid (yield 90%).

The identity of Substituted-Quinoxaline-Type Piperidine Compound 24, 3-(allylamino)-1-(1-cyclooctylpiperidin-4-yl)quinoxalin-2(1H)-one, was confirmed using $^1$H NMR and LC/MS.

Substituted-Quinoxaline-Type Piperidine Compound 24: $^1$H NMR: $\delta_H$ (300 MHz, DMSO): 7.65 (2H, m), 7.37 (1H, m), 7.18 (2H, m), 5.94 (1H, m), 5.14 (2H, m), 4.62 (1H, br), 4.01 (2H, t, J=5.4 Hz), 2.85-2.31 (7H, m), 1.73-1.42 (16H, m); LC/MS: m/z=395 [M+H]+ (Calc: 394.6).

19

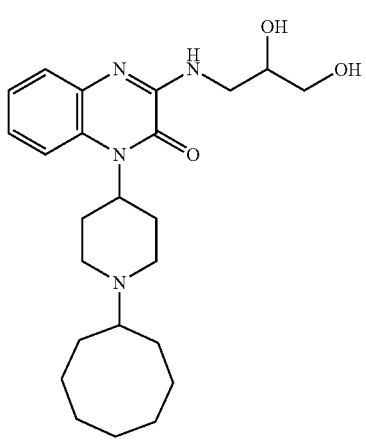

25

Substituted-Quinoxaline-Type Piperidine Compound 19 was prepared by using isoindoline (Sigma-Aldrich) in place of 2-aminoethanol to provide a colorless solid (yield 75%).

The identity of Substituted-Quinoxaline-Type Piperidine Compound 19, 1-(1-cyclooctylpiperidin-4-yl)-3-(isoindolin-2-yl)quinoxalin-2(1H)-one, was confirmed using $^1$H NMR and LC/MS.

Substituted-Quinoxaline-Type Piperidine Compound 19: $^1$H NMR: $\delta_H$ (300 MHz, DMSO): 7.62 (1H, s), 7.41 (3H, s), Substituted-Quinoxaline-Type Piperidine Compound 25 was prepared by using 3-aminopropane-1,2-diol (Sigma-Aldrich) in place of 2-aminoethanol to provide a colorless solid (yield 77%).

The identity of Substituted-Quinoxaline-Type Piperidine Compound 25, 1-(1-cyclooctylpiperidin-4-yl)-3-(2,3-dihydroxypropylamino)quinoxalin-2(1H)-one, was confirmed using $^1$H NMR and LC/MS.

Substituted-Quinoxaline-Type Piperidine Compound 25: $^1$H NMR: $\delta_H$ (300 MHz, DMSO): 7.70 (1H, m), 7.38 (1H, m), 7.31 (1H, m), 7.20 (2H, m), 5.02 (1H, d, J=5.1 Hz), 4.73

(1H, t, J=5.7 Hz), 4.72 (1H, br), 3.71 (1H, m), 3.57 (1H, m), 3.44-3.33 (3H, m), 3.00-2.36 (6H, m), 1.78-1.44 (17H, m); LC/MS: m/z=429 [M+H]$^+$ (Calc: 428.6).

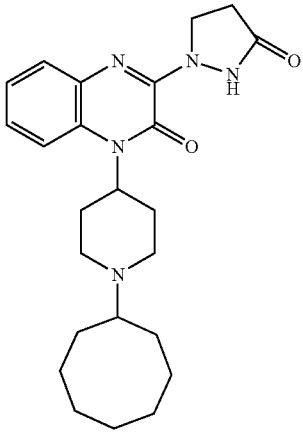

119

Substituted-Quinoxaline-Type Piperidine Compound 119 was prepared by using pyrazolidin-3-one hydrochloride (Sigma-Aldrich) in place of 2-aminoethanol to provide a white amorphous solid (yield 59%).

The identity of Substituted-Quinoxaline-Type Piperidine Compound 119, 1-(1-cyclooctylpiperidin-4-yl)-3-(3-oxopyrazolidin-1-yl)quinoxalin-2(1H)-one, was confirmed using $^1$H NMR and LC/MS.

Substituted-Quinoxaline-Type Piperidine Compound 119: $^1$H NMR: $\delta_H$ (300 MHz, CDCl$_3$): 7.64 (1H, br), 7.51 (1H, d, J=4 Hz), 7.25 (2H, m), 4.90 (1H, m), 4.44 (2H, d, J=8 Hz), 2.98 (2H, m), 2.80 (2H, d, J=8 Hz), 2.80 (1H, m), 2.70 (2H, m), 2.43 (2H, m), 1.75-1.40 (16H, m); LC/MS (100%, t$_r$=1.19 min): m/z=424.2 [M+H]$^+$ (Calc: 423.3).

5.5 Example 5

In a manner similar to Example 3, the following Substituted-Quinoxaline-Type Piperidine Compound was prepared from Substituted-Quinoxaline-Type Piperidine Compound 404.

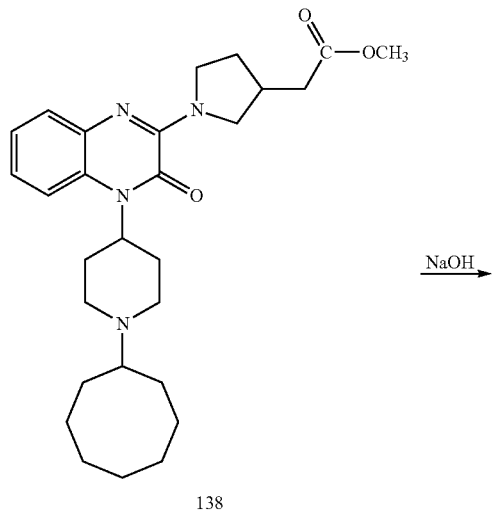

138

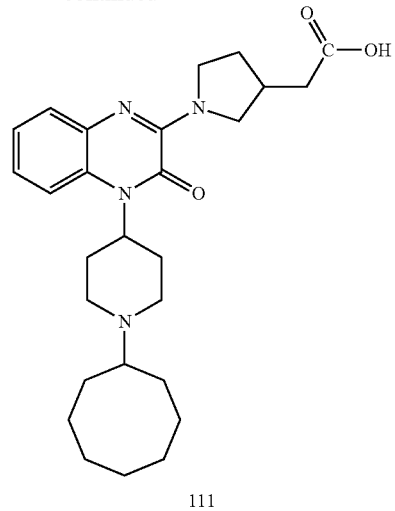

111

Substituted-Quinoxaline-Type Piperidine Compound 138 was prepared by using methyl 2-(pyrrolidin-3-yl)acetate in place of 2-aminoethanol (yield 98%).

The identity of Substituted-Quinoxaline-Type Piperidine Compound 138, methyl 2-(1-(4-(1-cyclooctylpiperidin-4-yl)-3-oxo-3,4-dihydroquinoxalin-2-yl)pyrrolidin-3-yl)acetate, was confirmed using $^1$H NMR and LC/MS.

Substituted-Quinoxaline-Type Piperidine Compound 138: $^1$H NMR: $\delta_H$ (400 MHz, CDCl$_3$): 7.53 (1H, br), 7.45 (1H, d, J=8 Hz), 7.13 (2H, m), 4.90 (1H, br), 4.12 (1H, br), 4.10 (1H, br), 3.85 (1H, br), 3.71 (3H; s), 3.55 (1H, br), 2.95 (2H, d, J=12 Hz), 2.79 (2H, m), 2.65 (2H, m), 2.55-2.36 (3H, m), 2.18 (1H, m), 1.90-1.40 (18H, m); LC/MS (99%, t$_r$=1.42 min): m/z=481.2 [M+H]$^+$ (Calc: 480.3).

To convert the ester to the acid, to a mixture of Substituted-Quinoxaline-Type Piperidine Compound 138 (115 mg, 0.239 mmol) and MeOH (4 mL) at a temperature of about 25° C. was added 2N aqueous NaOH (0.14 mL, 0.958 mmol). The resulting reaction mixture was warmed to a temperature of 50° C. and stirred for 2 h. After concentration under reduced pressure, the reaction mixture was diluted with water (5 mL) and extracted with EtOAc (5 mL). The aqueous portion was neutralized by adding 2N aqueous HCl at a temperature of 0° C. Thereafter, the mixture was extracted twice with EtOAc (10 mL for each extraction). The organic portions were combined, dried (MgSO$_4$), filtered, and concentrated under reduced pressure to provide 107 mg of Substituted-Quinoxaline-Type Piperidine Compound 111 as a white solid (yield 96%).

The identity of Substituted-Quinoxaline-Type Piperidine Compound 111, 2-(1-(4-(1-cyclooctylpiperidin-4-yl)-3-oxo-3,4-dihydroquinoxalin-2-yl)pyrrolidin-3-yl)acetic acid, was confirmed using $^1$H NMR and LC/MS.

Substituted-Quinoxaline-Type Piperidine Compound 111: $^1$H NMR: $\delta_H$ (400 MHz, CDCl$_3$): 7.61 (1H, m), 7.34 (1H, d, J=8 Hz), 7.14 (2H, m), 4.70 (1H, br), 4.40-3.40 (4H, m), 3.00 (2H, m), 2.80 (4H, m), 2.65 (2H, m), 2.40 (2H, m), 2.10 (1H, m), 1.85-1.40 (18H, m); LC/MS (100%, t$_r$=1.32 min): m/z=467.2 [M+H]$^+$ (Calc: 466.3).

Methyl 2-(pyrrolidin-3-yl)acetate was prepared as follows:

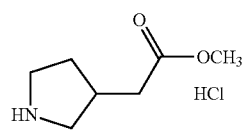

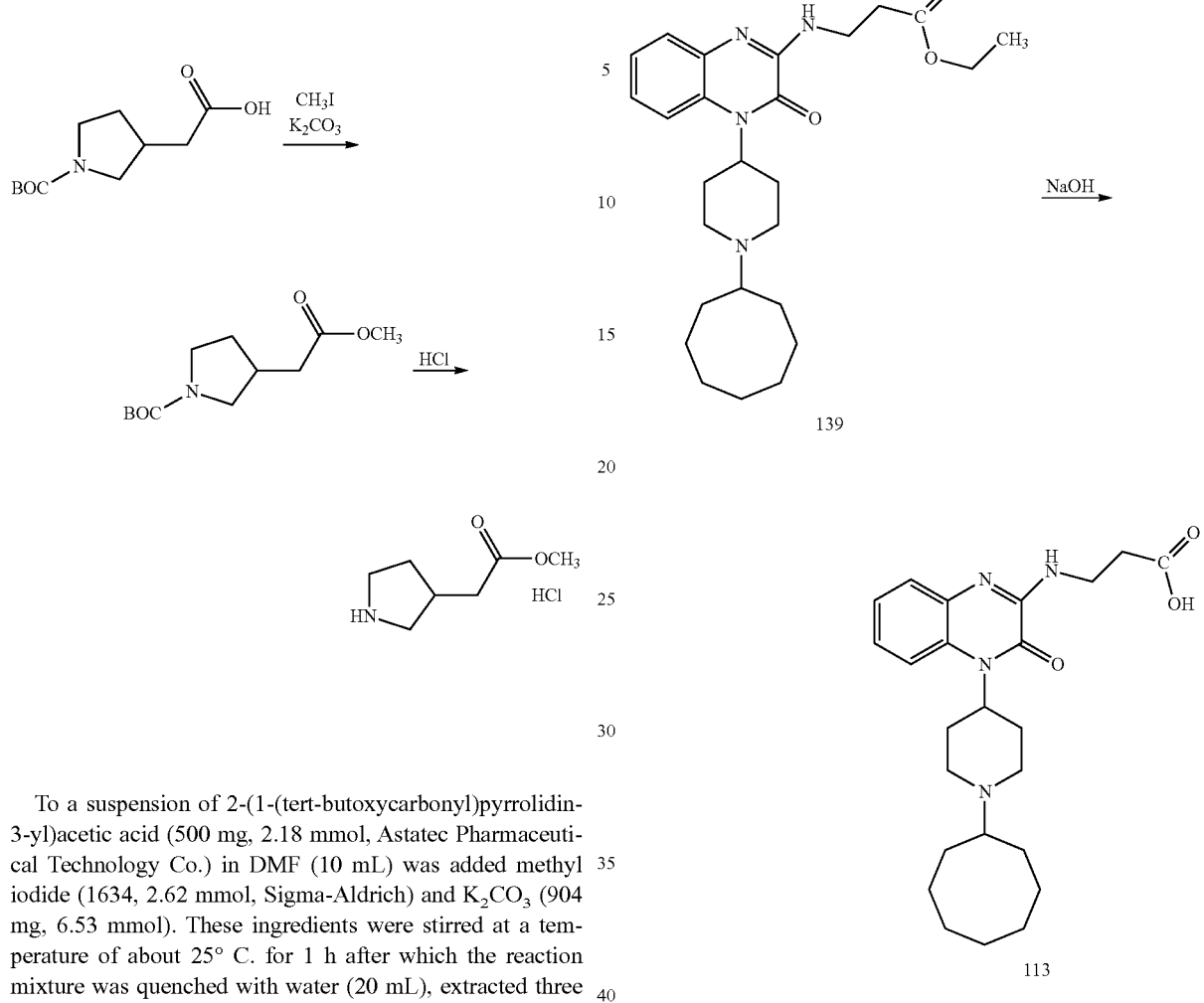

To a suspension of 2-(1-(tert-butoxycarbonyl)pyrrolidin-3-yl)acetic acid (500 mg, 2.18 mmol, Astatec Pharmaceutical Technology Co.) in DMF (10 mL) was added methyl iodide (1634, 2.62 mmol, Sigma-Aldrich) and $K_2CO_3$ (904 mg, 6.53 mmol). These ingredients were stirred at a temperature of about 25° C. for 1 h after which the reaction mixture was quenched with water (20 mL), extracted three times with EtOAc (20 mL for each extraction), washed twice with water (20 mL for each wash), washed with saturated aqueous NaCl (10 mL), dried ($MgSO_4$), and concentrated under reduced pressure to provide tert-butyl 3-(2-methoxy-2-oxoethyl)pyrrolidine-1-carboxylate as an oil. To a mixture of tert-butyl 3-(2-methoxy-2-oxoethyl)pyrrolidine-1-carboxylate (2.18 mmol) in dioxane (10 mL) at a temperature of about 25° C. was added 4N HCl in dioxane (10.8 mmol). Then the reaction mixture was stirred at 50° C. for 2 h. Thereafter, the mixture was concentrated under reduced pressure to provide 380 mg of the hydrochloride of methyl 2-(pyrrolidin-3-yl)acetate as a colorless oil (yield 96% for two steps), the identity of which was confirmed using $^1H$ NMR and LC/MS.

Methyl 2-(pyrrolidin-3-yl)acetate: $^1H$ NMR: $\delta_H$ (400 MHz, $CDCl_3$): 9.70 (2H, br), 3.70 (3H, s), 3.62 (1H, m), 3.47 (1H, m), 3.30 (1H, m), 3.00 (1H, m), 2.74 (1H, m), 2.54 (2H, d, J=8 Hz), 2.26 (1H, m), 1.73 (1H, m); LC/MS (100%, $t_r$=0.34 min): m/z=144.0 $[M+H]^+$ (Calc: 143.1).

In a manner similar to Example 3, the following Substituted-Quinoxaline-Type Piperidine Compounds were prepared from Substituted-Quinoxaline-Type Piperidine Compound 404 then converted from the ester to the acid in a manner similar to that described above.

Substituted-Quinoxaline-Type Piperidine Compound 139 was prepared by using ethyl 3-aminopropanoate (Sigma-Aldrich) in place of 2-aminoethanol (yield >98%).

The identity of Substituted-Quinoxaline-Type Piperidine Compound 139, ethyl 3-(4-(1-cyclooctylpiperidin-4-yl)-3-oxo-3,4-dihydroquinoxalin-2-ylamino)propanoate, was confirmed using NMR and LC/MS.

Substituted-Quinoxaline-Type Piperidine Compound 139: $^1H$ NMR: $\delta_H$ (400 MHz, $CDCl_3$): 7.60 (1H, br), 7.52 (1H, m), 7.19 (2H, m), 6.69 (1H, m), 5.00 (1H, br), 4.17 (2H, q, J=8 Hz), 3.82 (2H, q, J=8 Hz), 2.96 (2H, m), 2.80 (2H, m), 2.71 (2H, t, J=8 Hz), 2.50-2.35 (3H, m), 2.01 (2H, m), 1.80-1.40 (14H, m); LC/MS (95%, $t_r$=1.47 min): m/z=455.1 $[M+H]^+$ (Calc: 454.3).

The identity of Substituted-Quinoxaline-Type Piperidine Compound 113, 3-(4-(1-cyclooctylpiperidin-4-yl)-3-oxo-3,4-dihydroquinoxalin-2-ylamino)propanoic acid, was confirmed using $^1H$ NMR and LC/MS.

Substituted-Quinoxaline-Type Piperidine Compound 113: $^1H$ NMR: $\delta_H$ (400 MHz, $CDCl_3$): 7.68 (1H, m), 7.47 (1H, m), 7.41 (1H, m), 7.19 (1H, m), 5.00-4.30 (2H, m), 3.59 (2H, q, J=8 Hz), 3.50-3.10 (2H, m), 2.91 (2H, m), 2.71 (2H, m), 2.60 (2H, t, J=8 Hz), 2.50 (2H, m), 1.80-1.40 (16H, m); LC/MS (98%, $t_r$=1.34 min): m/z=427.2 $[M+H]^+$ (Calc: 426.3).

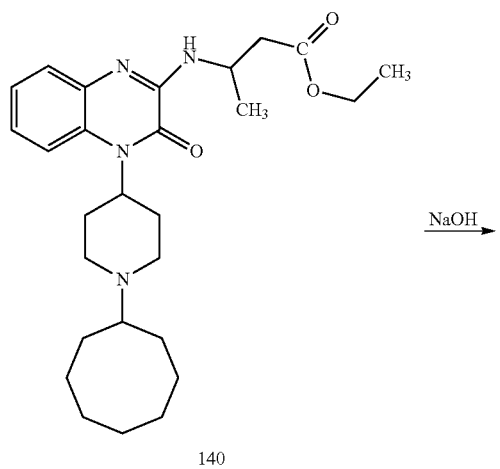

140

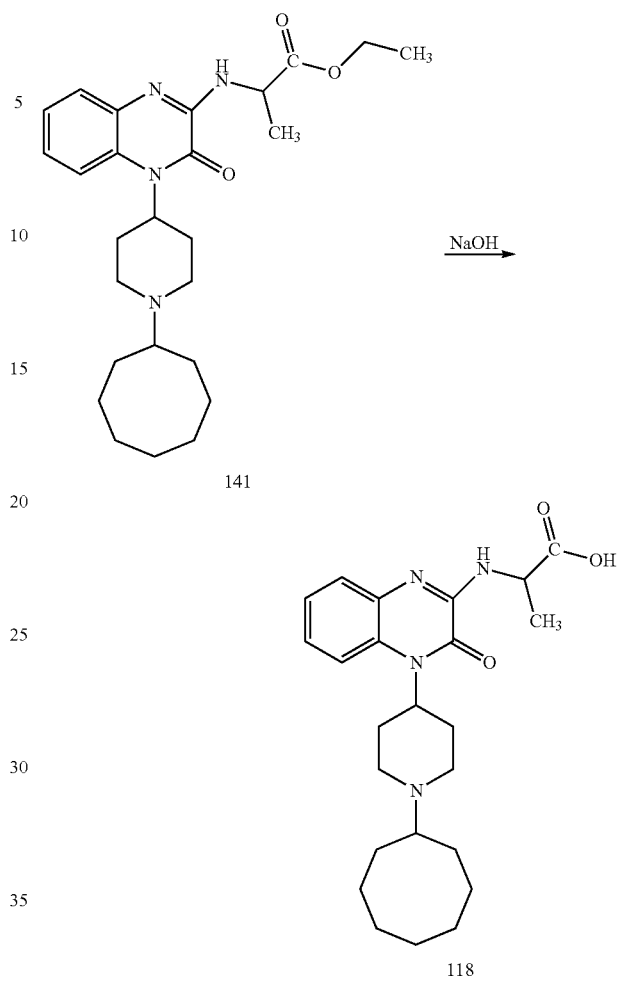

116

141

118

Substituted-Quinoxaline-Type Piperidine Compound 140 was prepared by using ethyl 3-aminobutanoate hydrochloride (Sigma-Aldrich) in place of 2-aminoethanol (yield 89%).

The identity of Substituted-Quinoxaline-Type Piperidine Compound 140, ethyl 3-(4-(1-cyclooctylpiperidin-4-yl)-3-oxo-3,4-dihydroquinoxalin-2-ylamino)butanoate, was confirmed using $^1$H NMR and LC/MS.

Substituted-Quinoxaline-Type Piperidine Compound 140: $^1$H NMR: $\delta_H$ (400 MHz, CDCl$_3$): 7.60 (1H, br), 7.52 (1H, m), 7.19 (2H, m), 6.57 (1H, d, J=8 Hz), 5.00 (1H, br), 4.60 (1H, m), 4.14 (2H, q, J=8 Hz), 3.20-2.30 (9H, m), 2.00-1.40 (16H, m), 1.37 (3H, d, J=8 Hz), 1.26 (3H, t, J=8 Hz); LC/MS (100%, t$_r$=1.52 min): m/z=469.2 [M+H]$^+$ (Calc: 468.3).

The identity of Substituted-Quinoxaline-Type Piperidine Compound 116, 3-(4-(1-cyclooctylpiperidin-4-yl)-3-oxo-3,4-dihydroquinoxalin-2-ylamino)butanoic acid, was confirmed using $^1$H NMR and LC/MS.

Substituted-Quinoxaline-Type Piperidine Compound 116: $^1$H NMR: $\delta_H$ (400 MHz, CDCl$_3$): 7.60 (1H, m), 7.40 (1H, m), 7.06 (2H, m), 5.70-5.00 (2H, m), 4.55 (1H, m), 3.40-3.20 (3H, m), 3.02 (2H, m), 2.80-2.60 (4H, m), 1.96 (2H, m), 1.80-1.38 (14H, m), 1.41 (3H, d, J=8 Hz); LC/MS (100%, t$_r$=1.47 min): m/z=441.2 [M+H]$^+$ (Calc: 440.3).

Substituted-Quinoxaline-Type Piperidine Compound 141 was prepared by using ethyl 2-aminopropanoate hydrochloride (Sigma-Aldrich) in place of 2-aminoethanol (yield 92%).

The identity of Substituted-Quinoxaline-Type Piperidine Compound 141, ethyl 2-(4-(1-cyclooctylpiperidin-4-yl)-3-oxo-3,4-dihydroquinoxalin-2-ylamino)propanoate, was confirmed using NMR and LC/MS.

Substituted-Quinoxaline-Type Piperidine Compound 141: $^1$H NMR: $\delta_H$ (400 MHz, CDCl$_3$): 7.60 (1H, br), 7.50 (1H, m), 7.19 (2H, m), 6.73 (1H, d, J=8 Hz), 4.75 (1H, m), 4.23 (2H, q, J=8 Hz), 2.97 (2H, m), 2.80 (2H, m), 2.67 (1H, m), 2.43 (2H, m), 1.85-1.40 (16H, m), 1.56 (3H, d, J=4 Hz), 1.29 (3H, t, J=8 Hz); LC/MS (100%, t$_r$=1.55 min): m/z=455.2 [M+H]$^+$ (Calc: 454.3).

The identity of Substituted-Quinoxaline-Type Piperidine Compound 118, 2-(4-(1-cyclooctylpiperidin-4-yl)-3-oxo-3,4-dihydroquinoxalin-2-ylamino)propanoic acid, was confirmed using $^1$H NMR and LC/MS.

Substituted-Quinoxaline-Type Piperidine Compound 118: $^1$H NMR: $\delta_H$ (400 MHz, DMSO): 7.77 (1H, m), 7.50 (1H, d, J=8 Hz), 7.39 (1H, m), 7.19 (2H, m), 4.80 (1H, br), 4.39 (1H, m), 3.20-2.85 (7H, m), 2.00-1.40 (16H, m), 1.44 (3H, d, J=8 Hz); LC/MS (100%, t$_r$=1.54 min): m/z=427.2 [M+H]$^+$ (Calc: 426.3).

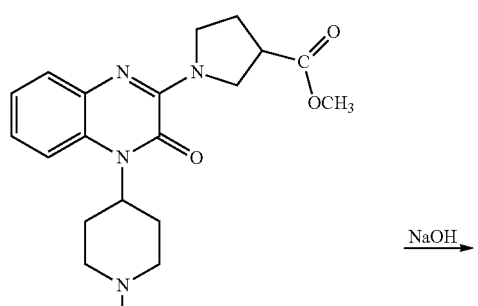

142

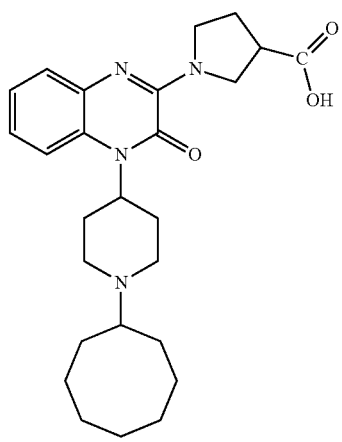

109

Substituted-Quinoxaline-Type Piperidine Compound 142 was prepared by using methyl pyrrolidine-3-carboxylate hydrochloride (Sigma-Aldrich) in place of 2-aminoethanol (yield 71%).

The identity of Substituted-Quinoxaline-Type Piperidine Compound 142, methyl 1-(4-(1-cyclooctylpiperidin-4-yl)-3-oxo-3,4-dihydroquinoxalin-2-yl)pyrrolidine-3-carboxylate, was confirmed using $^1$H NMR and LC/MS.

Substituted-Quinoxaline-Type Piperidine Compound 142: $^1$H NMR: $\delta_H$ (400 MHz, CDCl$_3$): 7.55 (1H, br), 7.50 (1H, d, J=8 Hz), 7.14 (2H, m), 4.90 (1H, br), 4.30-3.90 (4H, m), 3.72 (3H, s), 3.13 (1H, m), 2.95 (2H, m), 2.79 (2H, m), 2.67 (1H, m), 2.42 (2H, m), 2.23 (2H, m), 1.90-1.40 (18H, m); LC/MS (98%, t$_r$=1.46 min): m/z=467.1 [M+H]$^+$ (Calc: 466.3).

The identity of Substituted-Quinoxaline-Type Piperidine Compound 109, 1-(4-(1-cyclooctylpiperidin-4-yl)-3-oxo-3,4-dihydroquinoxalin-2-yl)pyrrolidine-3-carboxylic acid, was confirmed using $^1$H NMR and LC/MS.

Substituted-Quinoxaline-Type Piperidine Compound 109: $^1$H NMR: $\delta_H$ (400 MHz, DMSO): 7.76 (1H, br), 7.36 (1H, m), 7.16 (2H, m), 4.90 (1H, br), 4.20-3.70 (4H, m), 3.60-2.90 (8H, m), 2.20-1.90 (4H, m), 1.80-1.40 (14H, m); LC/MS (100%, t$_r$=1.38 min): m/z=453.3 [M+H]$^+$ (Calc: 452.3).

5.6 Example 6

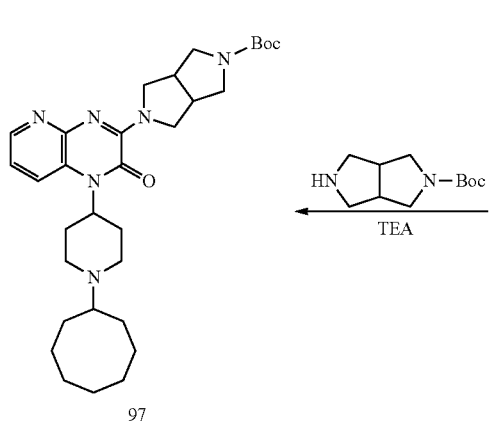

97

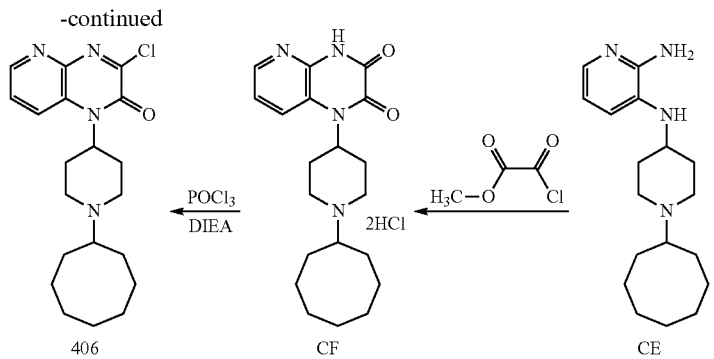

406  CF  CE

A mixture of the compound of formula CA (3-nitropyridin-2-amine, 1.39 g, 10 mmol, Sigma-Aldrich), (BOC)₂O (20 mmol), and DMAP (catalytic amount, Sigma-Aldrich) in THF (28 mL) was stirred at 90° C. for 1hr. After cooling to a temperature of about 25° C. and quenching with water (10 mL) the mixture was extracted three times with EtOAc, dried (MgSO₄), and concentrated under reduced pressure. At a temperature of about 25° C., the resulting yellow oil was mixed with MeOH (33 mL) then added to K₂CO₃ (30 mmol). The reaction mixture was stirred at 60° C. for 1 hr. After cooling to a temperature of about 25° C., 2N aqueous HCl (10 mL) was added and the pH was adjusted to be within the range of from about 7 to about 8. Thereafter, the mixture was extracted three times with EtOAc, dried (MgSO₄), and concentrated under reduced pressure. The resulting oil was chromatographed with a silica gel column eluted with a gradient of from 10%:90% EtOAc:n-hexane to 50%:50% EtOAc:n-hexane to provide the compound of formula CB as a yellow solid (yield 91%).

The identity of the compound of formula CB, tert-butyl 3-nitropyridin-2-ylcarbamate, was confirmed using $^1$H NMR.

Compound CB: $^1$H NMR: $\delta_H$ (300 MHz, CDCl₃): 9.59 (1H, s), 8.72 (1H, dd, J=4.5, 1.5 Hz), 8.5 (1H, dd, J=8.4, 1.5 Hz), 7.14 (1H, dd, J=8.4, 4.8 Hz), 1.56 (9H, s).

Under a hydrogen atmosphere, a mixture of the compound of formula CB (2.11 g, 9.07 mmol), 10% palladium on carbon (210 mg, Sigma-Aldrich), and MeOH (35 mL) was stirred at a temperature of about 25° C. for 16 hr. After the Pd/C was filtered off, the mixture was washed with EtOAc and MeOH, and the filtrate was concentrated under reduced pressure. The resulting solid was suspended with 3:2 n-hexane:diethyl ether which was filtered and washed with n-hexane to provide the compound of formula CC as a pale yellow solid (yield 87%).

The identity of the compound of formula CC, tert-butyl 3-aminopyridin-2-ylcarbamate, was confirmed using $^1$H NMR.

Compound CC: $^1$H NMR: $\delta_H$ (400 MHz, CDCl₃): 7.76 (1H, d, J=1.5 Hz), 7.10 (1H, dd, J=8.4, 1.5 Hz), 6.99 (1H, dd, J=8.4, 4.8 Hz), 1.52 (9H, s).

A mixture of the compound of formula CC (710 mg, 3.4 mmol), the compound of formula AA (5.1 mmol), NaBH(OAc)₃ (10.2 mmol) and AcOH (5.1 mmol) in CHCl₃ (18 mL) was stirred at a temperature of about 25° C. for 16 hr. After quenching with saturated NaHCO₃ solution, the mixture was extracted with CHCl₃, dried (MgSO₄), and concentrated under reduced pressure. The residue was chromatographed with an amino-silica gel column (Yamazen Corp. W091-01) eluted with a gradient of from 5%:95% EtOAc:n-hexane to 20%:80% EtOAc:n-hexane to 50%:50% EtOAc:n-hexane to provide the compound of formula CD as a colorless solid (yield 63%).

The identity of the compound of formula CD, tert-butyl 3-(1-cyclooctylpiperidin-4-ylamino)pyridin-2-ylcarbamate, was confirmed using $^1$H NMR.

Compound CD: $^1$H NMR: $\delta_H$ (400 MHz, DMSO-d₆): 8.59 (1H, s), 7.60 (1H, t, J=4 Hz), 7.01 (2H, d), 4.67 (1H, d, J=8 Hz), 3.25 (1H, m), 2.67 (2H, m), 2.35-2.30 (2H, m), 1.88-1.85 (2H, m), 1.69-1.60 (2H, m), 1.56-1.32 (25H, m).

To a suspension of the compound of formula CD (317 mg, 0.79 mmol) in EtOAc (5 mL) at a temperature of about 25° C. was added 4N HCl in EtOAc (7.9 mmol) which was stirred at about 25° C. for 1hr and then for 3 hr more at 50° C. After neutralization with 28% aqueous ammonia, the pH was adjusted to be within the range of from about 13 to about 14. Thereafter, the mixture was extracted three times with EtOAc, the organic portions were combined, dried (MgSO₄), and concentrated under reduced pressure to provide 237 mg of the compound of formula CE as a brown solid (yield >98%).

The identity of the compound of formula CE, N³-(1-cyclooctylpiperidin-4-yl)pyridine-2,3-diamine, was confirmed using $^1$H NMR.

Compound CE: $^1$H NMR: $\delta_H$(400 MHz, CDCl₃): 7.80 (1H, d, J=4 Hz), 7.66 (1H, s), 6.39 (1H, d, J=4 Hz), 4.12 (1H, m), 2.79 (1H, m), 2.68-2.61 (6H, m), 2.43 (2H, m), 1.92-1.48 (24H, m).

To a mixture of the compound of formula CE (168 mg, 0.79 mmol) in CH₂Cl₂ (10 mL) at 0° C. was added dropwise over 10 min methyl 2-chloro-2-oxoacetate (0.79 mmol, Sigma-Aldrich) in CH₂Cl₂ (3 mL). The resulting reaction mixture was stirred at 0° C. for 30 min. After quenching with saturated NaHCO₃ solution, the mixture was extracted three times with CHCl₃. Thereafter, the organic portions were combined, dried (MgSO$_4$), and concentrated under reduced pressure. At a temperature of about 25° C., the resulting oil was mixed with ethanol (4 mL) and the mixture was then added to sodium methoxide (1.09 mmol, Sigma-Aldrich). The reaction mixture was stirred at 70° C. for 1 hr. After concentration under reduced pressure, to the resulting oil was added water (0.5 mL) and 2N HCl (1 mL). The resulting precipitate was filtered, washed with 90%:10% water:MeOH, and dried under reduced pressure at 60° C. for 12 hr to provide the dihydrochloride of the compound of formula CF as a colorless solid.

The identity of the compound of formula CF, 1-(1-cyclooctylpiperidin-4-yl)pyrido[3,2-b]pyrazine-2,3(1H,4H)-dione, was confirmed using $^1$H NMR and LC/MS.

Compound CF: $^1$H NMR: $\delta_H$ (300 MHz, DMSO-d$_6$): 12.39 (1H, s), 9.8 (1H, br), 8.27 (1H, m), 8.14 (1H, d, J=4.5 Hz), 7.21 (1H, dd, J=4.5, 8.1 Hz), 4.91 (1H, m), 3.45-3.3 (6H, m), 2.99 (2H, m), 2.02 (2H, m), 1.99 (2H, m), 1.58-1.46 (11H, m); LC/MS: m/z=357 [M+H]$^+$ (Calc: 356.5).

Phosphoryl chloride (1.85 mmol, Sigma-Aldrich) was added to a suspension of the compound of formula CF (220 mg, 0.62 mmol) and DMA (1.85 mmol, Sigma-Aldrich) in toluene (6 mL) and DMF (1 mL) at 25° C. The resulting reaction mixture was stirred at 100° C. for 45 min. After cooling to a temperature of about 25° C. and quenching with water, the mixture was extracted three times with CHCl$_3$/water, dried (Na$_2$SO$_4$), and concentrated under reduced pressure to provide 187 mg of Substituted-Quinoxaline-Type Piperidine Compound 406 as a brown solid (yield 81%).

The identity of Substituted-Quinoxaline-Type Piperidine Compound 406, 3-chloro-1-(1-cyclooctylpiperidin-4-yl)pyrido[3,2-b]pyrazin-2(1H)-one, was confirmed using LC/MS.

Substituted-Quinoxaline-Type Piperidine Compound 406: LC/MS: m/z=375 [M+H]$^+$ (Calc: 374.2).

TEA (0.21 mmol) and tert-butyl hexahydropyrrolo[3,4-c]pyrrole-2(1H)-carboxylate (0.21 mmol) were added to a suspension of Substituted-Quinoxaline-Type Piperidine Compound 406 (80 mg, 0.21 mmol) in acetonitrile (3 mL) at 25° C. The resulting reaction mixture was stirred at 80° C. for 2 hr. After cooling to a temperature of about 25° C. and quenching with water (3 mL), the mixture was extracted three times with CHCl$_3$/water, dried (Na$_2$SO$_4$), and concentrated under reduced pressure to provide a yellow oil. The oil was chromatographed with a silica gel column eluted with a gradient of from 97%:3% CHCl$_3$:MeOH to 90%:10% CHCl$_3$:MeOH to provide 68 mg of Substituted-Quinoxaline-Type Piperidine Compound 97 as a yellow amorphous solid (yield 62%).

The identity of Substituted-Quinoxaline-Type Piperidine Compound 97, tert-butyl 5-(1-(1-cyclooctylpiperidin-4-yl)-2-oxo-1,2-dihydropyrido[3,2-b]pyrazin-3-yl)hexahydropyrrolo[3,4-c]pyrrole-2(1H)-carboxylate, was confirmed using $^1$H NMR.

Substituted-Quinoxaline-Type Piperidine Compound 97: $^1$H NMR: $\delta_H$ (400 MHz, CDCl$_3$): 8.33 (1H, d, J=4.8 Hz), 7.87 (1H, m), 7.04 (1H, m), 4.46 (1H, m), 4.20 (1H, m), 4.00 (1H, m), 3.82 (1H, m), 3.62 (2H, m), 3.30 (2H, m), 2.96 (4H, m), 2.66 (2H, m), 2.41 (2H, m), 1.75-1.44 (26H, m).

5.7 Example 7

To a suspension of Substituted-Quinoxaline-Type Piperidine Compound 4 (120 mg, 0.22 mmol) in 1,4-dioxane (4 mL) and MeOH (1 mL) was added 4N HCl in 1,4-dioxane (2 mL) at a temperature of about 25° C. The reaction mixture was stirred at 25° C. for 1 hr. The resulting precipitate was filtered, washed with diethyl ether (3 mL), and dried under reduced pressure at 70° C. to provide 123 mg of Substituted-Quinoxaline-Type Piperidine Compound 5 as a colorless solid (yield >98%).

The identity of Substituted-Quinoxaline-Type Piperidine Compound 5, 1-(1-cyclooctylpiperidin-4-yl)-3-(hexahydropyrrolo[3,4-c]pyrrol-2(1H)-yl)quinoxalin-2(1H)-one, was confirmed using $^1$H NMR and LC/MS.

Substituted-Quinoxaline-Type Piperidine Compound 5: $^1$H NMR: $\delta_H$ (400 MHz, DMSO): 9.67-9.54 (3H, br), 7.91 (1H, br), 7.53 (1H, s), 7.22 (2H, m), 5.03 (1H, br), 4.50-3.90 (12H, m), 3.41-3.00 (6H, m), 2.07 (2H, m), 1.89-1.43 (13H, m); LC/MS: m/z=450.1 [M+H]$^+$ (Calc: 449.6).

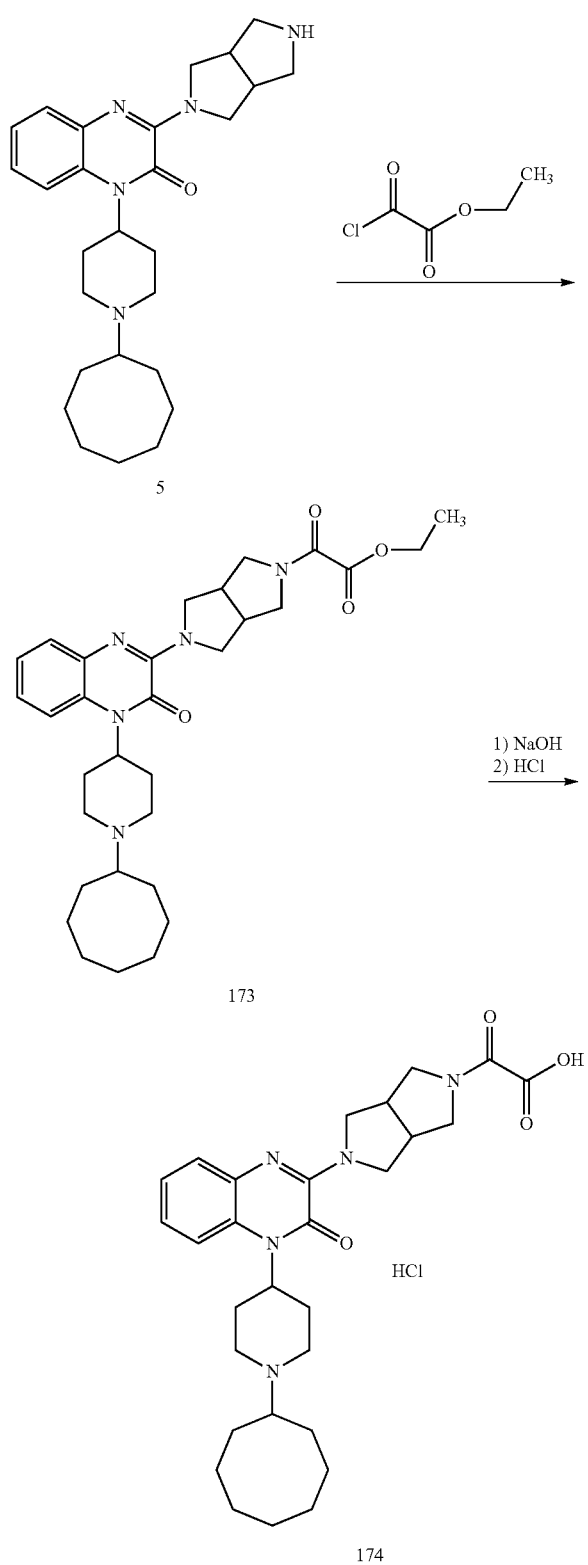

mixture was stirred for 2 h. The reaction mixture was diluted with water (5 mL) then extracted three times with CHCl₃ (10 mL for each extraction). The organic portions were combined, washed with saturated aqueous NaCl (10 mL), dried (MgSO₄), filtrated, and concentrated under reduced pressure. The residue was chromatographed with an amino-silica gel column (Yamazen Corp. W091-01) eluted with a gradient of from 10%:90% EtOAc:n-hexane to 50%:50% EtOAc: n-hexane to provide 89 mg of Substituted-Quinoxaline-Type Piperidine Compound 173 as a white amorphous solid (yield 47%).

The identity of Substituted-Quinoxaline-Type Piperidine Compound 173, ethyl 2-(5-(4-(1-cyclooctylpiperidin-4-yl)-3-oxo-3,4-dihydroquinoxalin-2-yl)hexahydropyrrolo[3,4-c]pyrrol-2(1H)-yl)-2-oxoacetate, was confirmed using $^1$H NMR and MS.

Substituted-Quinoxaline-Type Piperidine Compound 173: $^1$H NMR: $\delta_H$ (400 MHz, CDCl₃): 7.46 (1H, m), 7.32 (1H, m), 7.18 (2H, m), 5.20 (1H, br), 4.31 (2H, q, J=8.0 Hz), 4.20 (2H, m), 3.95-3.85 (4H, m), 3.70-3.50 (4H, m), 3.00 (2H, m), 2.40-1.90 (5H, m), 1.90-1.45 (18H, m), 1.39 (3H, t, J=8.0 Hz); MS: m/z=576 [M+H]⁺ (Calc: 575.3).

To a mixture of Substituted-Quinoxaline-Type Piperidine Compound 173 (85 mg, 0.148 mmol) in MeOH (4 mL) at a temperature of about 25° C. was added 2N aqueous NaOH (0.15 mL, 0.295 mmol). The reaction mixture was stirred for 2 h at a temperature of about 25° C. After concentration under reduced pressure, the mixture was diluted with water (5 mL) then extracted with EtOAc (5 mL). The aqueous portion was neutralized by adding a first treatment of 2N aqueous HCl at a temperature of 0° C. Thereafter, the mixture was extracted twice with CHCl₃ (10 mL for each extraction). The organic portions were combined, dried (MgSO₄), filtrated, and concentrated under reduced pressure to provide a white solid. To the solid was added water (2 mL) then a second treatment of 2N aqueous HCl (1 mL). Thereafter, the mixture was concentrated under reduced pressure to provide 77 mg of the hydrochloride of Substituted-Quinoxaline-Type Piperidine Compound 174 (yield 89%).

The identity of Substituted-Quinoxaline-Type Piperidine Compound 174,2454441-cyclooctylpiperidin-4-yl)-3-oxo-3,4-dihydroquinoxalin-2-yl)hexahydropyrrolo[3,4-c]pyrrol-2(1H)-yl)-2-oxoacetic acid, was confirmed using $^1$H NMR and LC/MS.

Substituted-Quinoxaline-Type Piperidine Compound 174: $^1$H NMR: $\delta_H$ (400 MHz, DMSO): 10.62 (0.9H, m), 9.84 (0.1H, m), 7.83 (0.9H, m), 7.72 (0.1H, m), 7.60 (1H, m), 7.28 (2H, m), 5.86 (1H, m), 4.40-4.00 (6H, m), 3.90-3.35 (4H, m), 3.10 (2H, m), 2.97 (1H, m), 2.60 (2H, m), 2.40-1.30 (20H, m); LC/MS (100%, t$_r$=1.45 min): m/z=548 [M+H]⁺ (Calc: 547.3).

5.8 Example 8

In a manner similar to the preparation of Substituted-Quinoxaline-Type Piperidine Compound 5 in Example 7, the following Substituted-Quinoxaline-Type Piperidine Compounds were prepared.

To a mixture of Substituted-Quinoxaline-Type Piperidine Compound 5 (180 mg, 0.328 mmol) and CH₂Cl₂ (4 mL) at 0° C. was added pyridine (934, 1.148 mmol) and ethyl 2-chloro-2-oxoacetate (92 µL, 0.820 mmol, Sigma-Aldrich). After heating to a temperature of about 25° C. the reaction

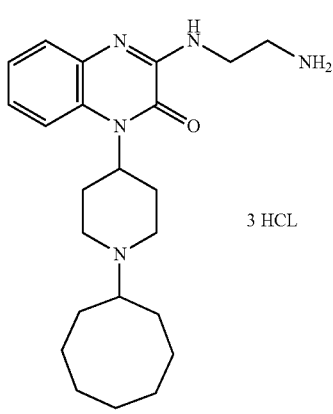

9

3 HCL

The trihydrochloride of Substituted-Quinoxaline-Type Piperidine Compound 9 was prepared by using Substituted-Quinoxaline-Type Piperidine Compound 7 in place of Substituted-Quinoxaline-Type Piperidine Compound 4 (yield 90%).

The identity of Substituted-Quinoxaline-Type Piperidine Compound 9, 3-(2-aminoethylamino)-1-(1-cyclooctylpiperidin-4-yl)quinoxalin-2(1H)-one, was confirmed using $^1$H NMR and LC/MS.

Substituted-Quinoxaline-Type Piperidine Compound 9: $^1$H NMR: $\delta_H$ (400 MHz, DMSO): 8.10-7.80 (4H, br), 7.50 (1H, s), 7.25 (2H, m), 5.00 (1H, br), 3.68 (2H, d, J=4 Hz), 3.43-3.39 (5H, m), 3.19-3.08 (4H, m), 2.06 (2H, s), 1.99-1.19 (15H, m); LC/MS: m/z=398.1 [M+H]$^+$ (Calc: 397.6).

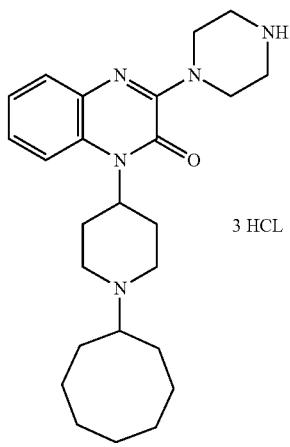

10

3 HCL

The trihydrochloride of Substituted-Quinoxaline-Type Piperidine Compound 10 was prepared by using Substituted-Quinoxaline-Type Piperidine Compound 8 in place of Substituted-Quinoxaline-Type Piperidine Compound 4 (yield 98%).

The identity of Substituted-Quinoxaline-Type Piperidine Compound 10, 1-(1-cyclooctylpiperidin-4-yl)-3-(piperazin-1-yl)quinoxalin-2(1H)-one, was confirmed using $^1$H NMR and LC/MS.

Substituted-Quinoxaline-Type Piperidine Compound 10: $^1$H NMR: $\delta_H$ (400 MHz, DMSO): 9.53 (1H, s), 7.53 (1H, d, J=4 Hz), 7.33-7.26 (2H, m), 5.39 (1H, br), 4.04 (4H, s), 3.42-3.35 (5H, m), 3.20 (4H, s), 1.99 (2H, s), 1.73-1.43 (15H, m); LC/MS: m/z=424.1 [M+H]$^+$ (Calc: 423.6).

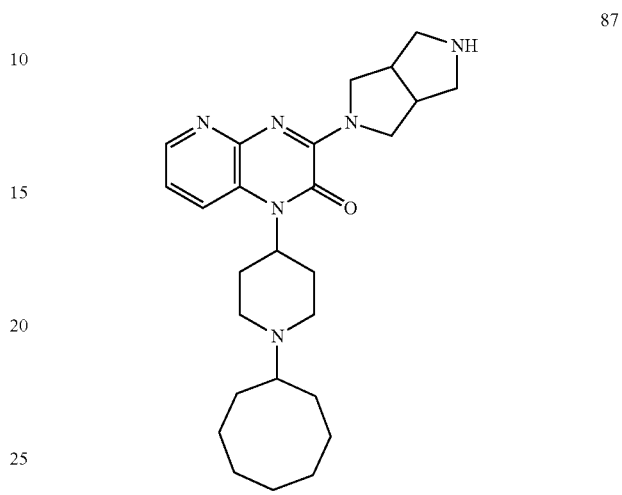

87

Substituted-Quinoxaline-Type Piperidine Compound 87 was prepared by using Substituted-Quinoxaline-Type Piperidine Compound 97 in place of Substituted-Quinoxaline-Type Piperidine Compound 4 (yield 82%).

The identity of Substituted-Quinoxaline-Type Piperidine Compound 87, 1-(1-cyclooctylpiperidin-4-yl)-3-(hexahydropyrrolo[3,4-c]pyrrol-2(1H)-yl)pyrido[3,2-b]pyrazin-2(1H)-one, was confirmed using $^1$H NMR and LC/MS.

Substituted-Quinoxaline-Type Piperidine Compound 87: $^1$H NMR: $\delta_H$ (400 MHz, DMSO): 10.0 (1H, m), 9.58 (1H, m), 8.89 (1H, br), 8.26 (1H, d, J=5.2 Hz), 7.44 (1H, m), 5.15 (1H, br), 4.42-4.36 (3H, m), 3.95-3.88 (3H, m), 3.56-3.02 (11H, m), 2.08-1.44 (16H, m); LC/MS: m/z=451 [M+H]$^+$ (Calc: 450.6).

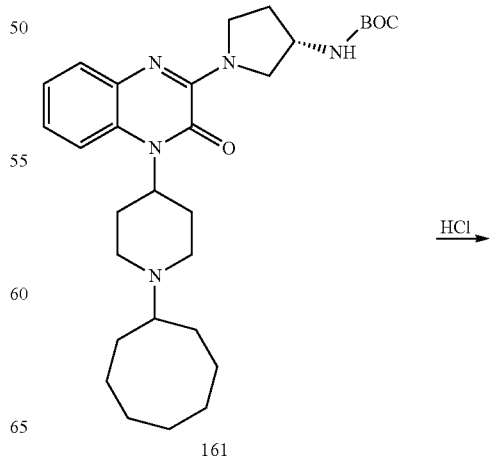

161

$\xrightarrow{\text{HCl}}$

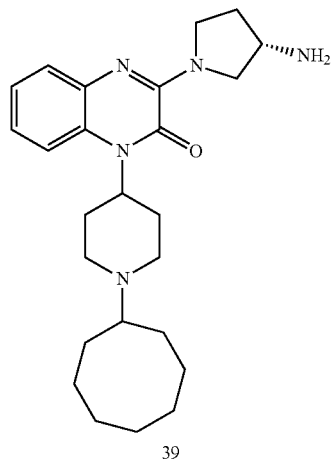

39

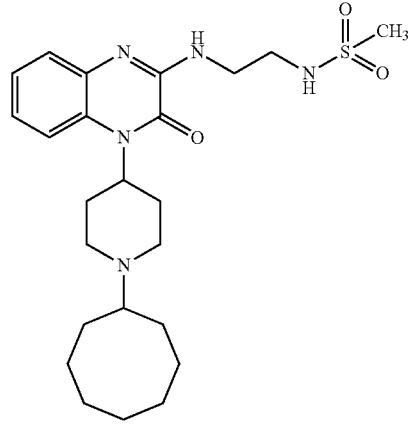

11

In a manner similar to Example 3, the hydrochloride of Substituted-Quinoxaline-Type Piperidine Compound 161, (S)-tert-butyl 1-(4-(1-cyclooctylpiperidin-4-yl)-3-oxo-3,4-dihydroquinoxalin-2-yl)pyrrolidin-3-ylcarbamate, was prepared from Substituted-Quinoxaline-Type Piperidine Compound 404 by using (S)-tert-butyl pyrrolidin-3-ylcarbamate (Sigma-Aldrich) in place of 2-aminoethanol. Thereafter, in a manner similar to the preparation of Substituted-Quinoxaline-Type Piperidine Compound 5 in Example 7, Substituted-Quinoxaline-Type Piperidine Compound 39 was prepared from Substituted-Quinoxaline-Type Piperidine Compound 161 (yield 98% for two steps).

The identity of Substituted-Quinoxaline-Type Piperidine Compound 39, (S)-3-(3-aminopyrrolidin-1-yl)-1-(1-cyclooctylpiperidin-4-yl)quinoxalin-2(1H)-one, was confirmed using $^1$H NMR and LC/MS.

Substituted-Quinoxaline-Type Piperidine Compound 39:
$^1$H NMR: $\delta_H$ (400 MHz, CD$_3$OD): 7.64 (1H, br), 7.41 (1H, br), 7.14 (2H, m), 4.08 (2H, m), 3.93 (1H, m), 3.72 (1H, m), 3.57 (1H, m), 3.02 (2H, d, J=12 Hz), 2.91 (2H, m), 2.77 (1H, m), 2.54 (2H, m), 2.14 (1H, m), 1.90-1.45 (18H, m); LC/MS (99%, t$_r$=0.58 min): m/z=424.3 [M+H]$^+$ (Calc: 423.3).

5.9 Example 9

TEA (0.316 mmol) and methansulfonyl chloride (0.087 mmol, Sigma-Aldrich) were added to a mixture of Substituted-Quinoxaline-Type Piperidine Compound 9 (40 mg, 0.079 mmol) in CH$_2$Cl$_2$ at 0° C. and the resulting reaction mixture was stirred for 3 hr. Thereafter, an additional portion of methansulfonyl chloride (0.174 mmol) was added and the reaction mixture was stirred at 50° C. for 7 hr. After cooling to a temperature of about 25° C., the mixture was extracted three times with CHCl$_3$/water, dried (MgSO$_4$), and concentrated under reduced pressure to provide a colorless oil. The oil was chromatographed with a silica gel column eluted with a gradient of from 95%:5% CHCl$_3$:MeOH to 90%:10% CHCl$_3$:MeOH to provide 27 mg of Substituted-Quinoxaline-Type Piperidine Compound 11 as a colorless solid (yield 73%).

The identity of Substituted-Quinoxaline-Type Piperidine Compound 11, N-(2-(4-(1-cyclooctylpiperidin-4-yl)-3-oxo-3,4-dihydroquinoxalin-2-ylamino)ethyl)methanesulfonamide, was confirmed using $^1$H NMR and LC/MS.

Substituted-Quinoxaline-Type Piperidine Compound 11:
$^1$H NMR: $\delta_H$(400 MHz, DMSO): 7.68 (1H, m), 7.57 (1H, m), 7.25-7.15 (2H, m), 3.53 (2H, t), 3.23 (2H, m), 2.93 (3H, s), 2.85-2.55 (4H, m), 2.45-2.30 (5H, m), 1.80-1.40 (14H, m); LC/MS (100%): m/z=476.7 [M+H]$^+$ (Calc: 476.1).

5.10 Example 10

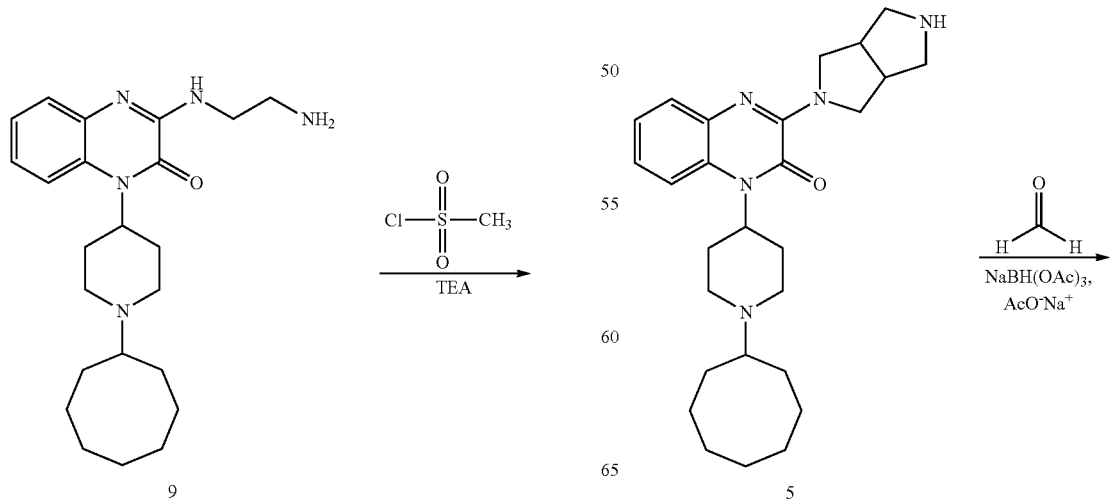

-continued

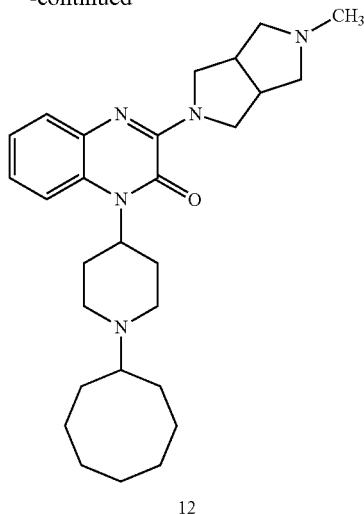

12

Substituted-Quinoxaline-Type Piperidine Compound 5 (100 mg, 0.18 mmmol), 39% formaldehyde (0.27 mmol, Sigma-Aldrich), NaBH(OAc)₃ (0.54 mmol), and sodium acetate (0.54 mmol, Sigma-Aldrich) were added to CHCl₃ (5 mL) and the resulting reaction mixture was stirred at 25° C. for 16 hr. After quenching with saturated NaHCO₃ solution, the mixture was extracted with CHCl₃/water. Thereafter, the organic portion was dried (MgSO₄) and concentrated under reduced pressure. The residue was chromatographed with an amino-silica gel column (Yamazen Corp. W091-01) eluted with a gradient of from 30%:70% EtOAc:n-hexane to 70%:30% EtOAc:n-hexane to provide Substituted-Quinoxaline-Type Piperidine Compound 12 as a colorless solid (yield 75%).

The identity of Substituted-Quinoxaline-Type Piperidine Compound 12, 1-(1-cyclooctylpiperidin-4-yl)-3-(5-methyl-hexahydropyrrolo[3,4-c]pyrrol-2(1H)-yl)quinoxalin-2(1H)-one, was confirmed using ¹H NMR and LC/MS.

Substituted-Quinoxaline-Type Piperidine Compound 12: ¹H NMR: $\delta_H$ (400 MHz, DMSO): 7.61 (1H, d, J=8 Hz), 7.36 (1H, t, J=4 Hz), 7.19-7.13 (2H, m), 4.66 (1H, br), 3.96 (3H, s), 3.78 (3H, m), 2.95-2.54 (10H, m), 2.22 (3H, s), 1.74-1.43 (17H, m); LC/MS: m/z=464.1 [M+H]⁺ (Calc: 463.7).

5.11 Example 11

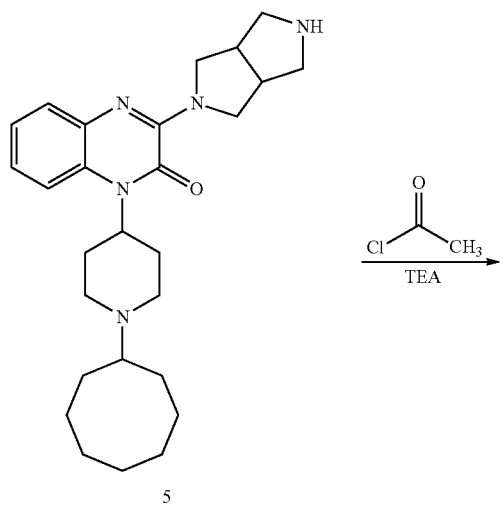

-continued

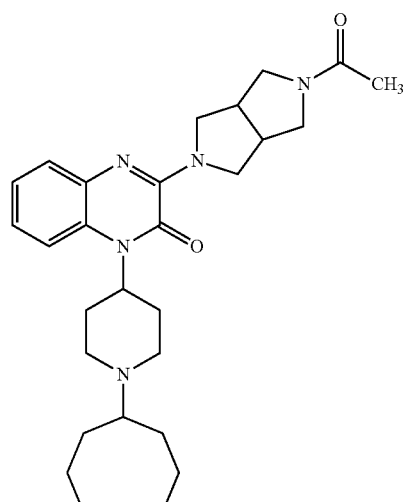

13

TEA (0.9 mmol) and acetyl chloride (0.27 mmol, Sigma-Aldrich) were added to a mixture of Substituted-Quinoxaline-Type Piperidine Compound 5 (100 mg, 0.18 mmol) in CH₂Cl₂ at 0° C. The resulting reaction mixture was stirred at 0° C. for 1 hr. After heating to a temperature of about 25° C., the mixture was extracted three times with CHCl₃/water, dried (MgSO₄), and concentrated under reduced pressure to provide a colorless oil. The oil was chromatographed with a silica gel column eluted with a gradient of from 97%:3% CHCl₃:MeOH to 90%:10% CHCl₃:MeOH to 85%:15% CHCl₃:MeOH to provide 64 mg of Substituted-Quinoxaline-Type Piperidine Compound 13 as a colorless solid (yield 73%).

The identity of Substituted-Quinoxaline-Type Piperidine Compound 13, 3-(5-acetylhexahydropyrrolo[3,4-c]pyrrol-2 (1H)-yl)-1-(1-cyclooctylpiperidin-4-yl)quinoxalin-2 (1H)-one, was confirmed using ¹H NMR and LC/MS.

Substituted-Quinoxaline-Type Piperidine Compound 13: ¹H NMR: $\delta_H$ (400 MHz, DMSO): 7.58 (1H, d, J=8 Hz), 7.35 (1H, t, J=4 Hz), 7.18-7.13 (2H, m), 4.61 (1H, br), 4.03 (1H, br), 3.68 (2H, dd, J=4 Hz), 3.54 (1H, dd, J=4 Hz), 3.40 (1H, m), 3.24 (1H, m), 2.99-2.40 (7H, m), 2.38 (2H, t, J=12 Hz), 1.93-1.43 (17H, m); LC/MS: m/z=492.1 [M+H]⁺ (Calc: 491.7).

5.12 Example 12
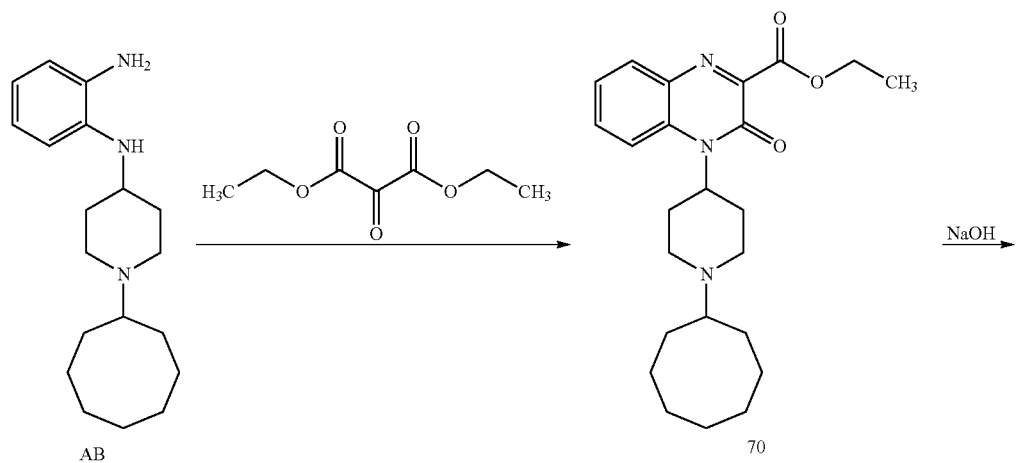 [SMILES: Nc1ccccc1NC1CCN(C2CCCCCCC2)CC1 ; CCOC(=O)C(=O)C(=O)OCC ; CCOC(=O)c1nc2ccccc2n(C2CCN(C3CCCCCCC3)CC2)c1=O ; "NaOH"]
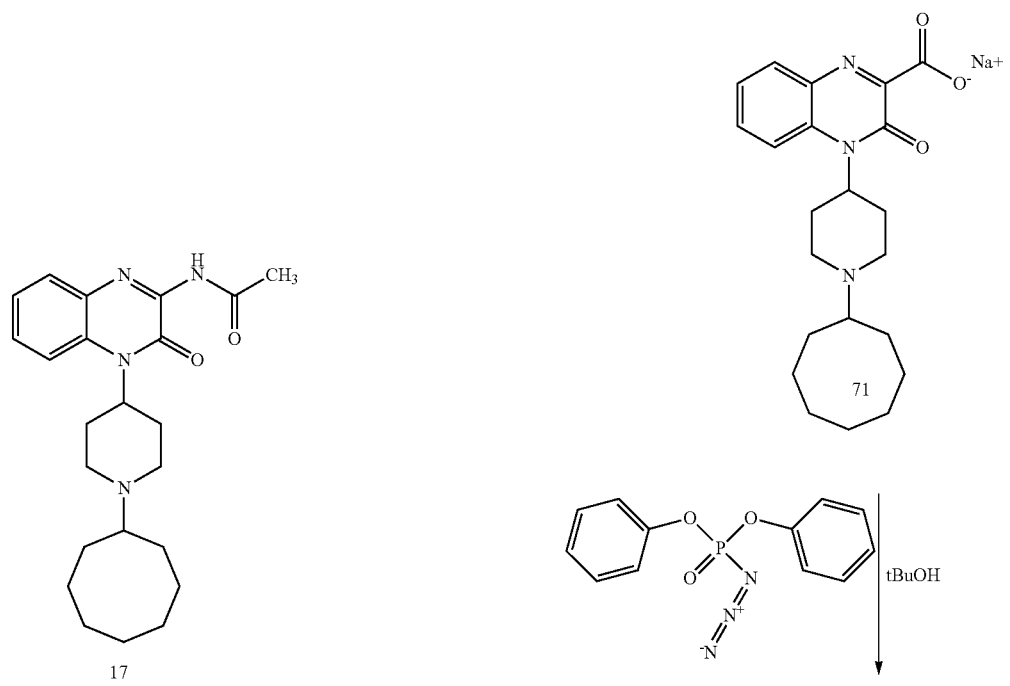

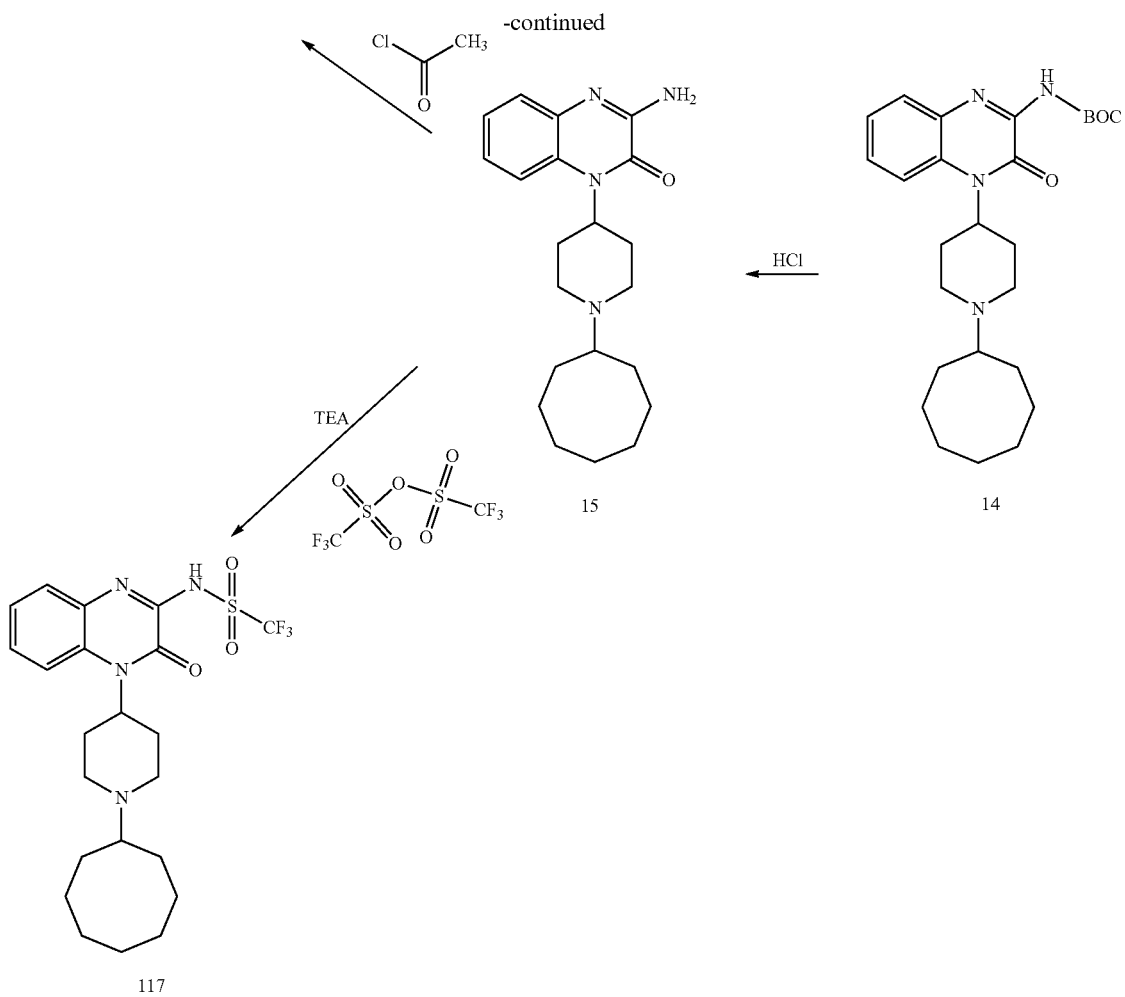

Diethyl 2-oxomalonate (5 mmol, Sigma-Aldrich) was added dropwise to a suspension of the compound of formula AB (1507 mg, 5 mmol) in toluene (15 mL) at 25° C. The resulting reaction mixture was stirred at 130° C. for 4 hr. After cooling to a temperature of about 25° C. and concentrating under reduced pressure, a red oil was obtained. The oil was chromatographed with a silica gel column eluted with a gradient of from 99%:1% CHCl$_3$:MeOH to 95%:5% CHCl$_3$:MeOH to provide a red amorphous solid. The solid was chromatographed with a silica gel column eluted with a gradient of from 95%:5% EtOAc:MeOH to 90%:10% EtOAc:MeOH to provide 1100 mg of Substituted-Quinoxaline-Type Piperidine Compound 70 as a colorless solid (yield 53%).

The identity of Substituted-Quinoxaline-Type Piperidine Compound 70, ethyl 4-(1-cyclooctylpiperidin-4-yl)-3-oxo-3,4-dihydroquinoxaline-2-carboxylate, was confirmed using $^1$H NMR and LC/MS.

Substituted-Quinoxaline-Type Piperidine Compound 70: $^1$H NMR: $\delta_H$ (300 MHz, DMSO): 7.95 (1H, d, J=8.7 Hz), 7.87 (1H, dd, J=7.8, 1.8 Hz), 7.31 (1H, t, J=7.2 Hz), 7.44 (1H, t, J=6.9 Hz), 4.78 (1H, br), 4.37 (2H, d, J=7.2 Hz), 2.85 (2H, m), 2.60-2.34 (5H, m), 1.70-1.42 (16H, m), 1.32 (3H, t, J=7.2 Hz); LC/MS: m/z=412 [M+H]$^+$ (Calc: 411.5).

2N NaOH (0.25 mmol) was added to a mixture of Substituted-Quinoxaline-Type Piperidine Compound 70 (104 mg, 0.25 mmol) in ethanol at 25° C. The resulting reaction mixture was stirred at 50° C. for 90 min. After concentration under reduced pressure, the resulting yellow solid was dried under reduced pressure at 80° C. for 12 hr to provide 100 mg of the sodium salt of Substituted-Quinoxaline-Type Piperidine Compound 71 as a yellow solid (yield >98%).

The identity of Substituted-Quinoxaline-Type Piperidine Compound 71, 4-(1-cyclooctylpiperidin-4-yl)-3-oxo-3,4-dihydroquinoxaline-2-carboxylate, was confirmed using $^1$H NMR and LC/MS.

Substituted-Quinoxaline-Type Piperidine Compound 71: $^1$H NMR: $\delta_H$ (300 MHz, DMSO): 7.76 (1H, d, J=8.4 Hz), 7.64 (1H, dd, J=7.8, 1.5 Hz), 7.48 (1H, t, J=8.4 Hz), 7.28 (1H, t, J=7.5 Hz), 4.67 (1H, br), 2.87-2.34 (7H, m), 1.71-1.42 (16H, m); LC/MS: m/z=384 [M+H]$^+$ (Calc: 383.5).

Diphenylphosphoryl azide ("DPPA", 1.2 mmol, Sigma-Aldrich) was added to a mixture of the sodium salt of Substituted-Quinoxaline-Type Piperidine Compound 71 (120 mg, 0.3 mmol) in tert-BuOH (i.e., 2-methylpropan-2-ol) at 25° C. Thereafter, the reaction mixture was warmed to a temperature of 100° C. and stirred for 3.5 h. After cooling to about 25° C. and quenching with saturated NaHCO$_3$ solution, the mixture was extracted three times with EtOAc/water, dried (MgSO$_4$), and concentrated under reduced pressure to provide an orange oil. The oil was chromatographed with a silica gel column eluted with a gradient of from 99%:1% CHCl$_3$:MeOH to 95%:5% CHCl$_3$:MeOH to provide 124 mg of Substituted-Quinoxaline-Type Piperidine Compound 14 as a pale yellow amorphous solid (yield 91%).

The identity of Substituted-Quinoxaline-Type Piperidine Compound 14, tert-butyl 4-(1-cyclooctylpiperidin-4-yl)-3-oxo-3,4-dihydroquinoxalin-2-ylcarbamate, was confirmed using $^1$H NMR and LC/MS.

Substituted-Quinoxaline-Type Piperidine Compound 14: $^1$H NMR: $\delta_H$ (300 MHz, DMSO): 8.84 (1H, s), 7.83 (1H, d, J=8.7 Hz), 7.60 (1H, d, J=7.8 Hz), 7.47 (1H, t, J=7.9 Hz), 7.34 (1H, t, J=7.2 Hz), 4.69 (1H, br), 2.83-2.42 (8H, m), 1.71-1.43 (24H, m); LC/MS: m/z=455.1 [M+H]$^+$ (Calc: 454.6).

Substituted-Quinoxaline-Type Piperidine Compound 15 was prepared from Substituted-Quinoxaline-Type Piperidine Compound 14 in a manner similar to the preparation of Substituted-Quinoxaline-Type Piperidine Compound 5 in Example 7 (yield 84%).

The identity of Substituted-Quinoxaline-Type Piperidine Compound 15, 3-amino-1-(1-cyclooctylpiperidin-4-yl)quinoxalin-2(1H)-one, was confirmed using $^1$H NMR and LC/MS.

Substituted-Quinoxaline-Type Piperidine Compound 15: $^1$H NMR: $\delta_H$ (400 MHz, DMSO): 7.65 (1H, d, J=8 Hz), 7.33 (1H, m), 7.19 (2H, m), 7.01 (2H, br), 4.72 (1H, br), 4.04 (4H, s), 2.85 (2H, d, J=12 Hz), 2.69-2.50 (3H, m), 2.40 (2H, m), 1.71-1.43 (16H, m); LC/MS: m/z=355.1 [M+H]$^+$ (Calc: 354.5).

Substituted-Quinoxaline-Type Piperidine Compound 17 was prepared from Substituted-Quinoxaline-Type Piperidine Compound 15 in a manner similar to Example 11 (yield 78%).

The identity of Substituted-Quinoxaline-Type Piperidine Compound 17, N-(4-(1-cyclooctylpiperidin-4-yl)-3-oxo-3,4-dihydroquinoxalin-2-yl)acetamide, was confirmed using $^1$H NMR and LC/MS.

Substituted-Quinoxaline-Type Piperidine Compound 17: $^1$H NMR: $\delta_H$ (300 MHz, DMSO): 9.65 (1H, s), 7.90 (1H, br), 7.63 (1H, d, J=6.3 Hz), 7.49 (1H, t, J=8.4 Hz), 7.35 (1H, t, J=7.5 Hz), 4.78 (1H, Br), 3.25-2.52 (6H, m), 2.37 (3H, s), 1.90-1.42 (17H, m); LC/MS: m/z=397 [M+H]$^+$ (Calc: 396.5).

At a temperature of 0° C., trifluoromethanesulfonic anhydride (41.44, 0.246 mmol, Sigma-Aldrich) and TEA (86.24, 0.615 mmol) were added to a mixture of Substituted-Quinoxaline-Type Piperidine Compound 15 (80 mg, 0.205 mmol) in $CH_2Cl_2$ (3 mL). After warming it to a temperature of about 25° C., the reaction mixture was stirred for 5.5 h. After cooling to 0° C., the mixture was quenched with saturated aqueous $NaHCO_3$ (5 mL) and extracted three times with $CHCl_3$ (5 mL for each extraction). The organic portions were combined, dried ($MgSO_4$), filtered, and concentrated under reduced pressure to provide a residue. The residue was triturated with MeOH, filtered, rinsed with MeOH, and collected to provide 36 mg of Substituted-Quinoxaline-Type Piperidine Compound 117 as a white solid (yield 36%).

The identity of Substituted-Quinoxaline-Type Piperidine Compound 117: N-(4-(1-cyclooctylpiperidin-4-yl)-3-oxo-3,4-dihydroquinoxalin-2-yl)-1,1,1-trifluoromethanesulfonamide, was confirmed using $^1$H NMR and LC/MS.

Substituted-Quinoxaline-Type Piperidine Compound 117: $^1$H NMR: $\delta_H$ (400 MHz, DMSO): 9.10 (1H, br), 7.68 (1H, d, J=8 Hz), 7.35 (1H, d, J=8 Hz), 7.24 (1H, t, J=8 Hz), 7.17 (1H, t, J=8 Hz), 4.90 (1H, m), 3.50-3.30 (3H, m), 3.10 (2H, m), 2.00-1.40 (18H, m); LC/MS: (100%, $t_r$=1.91 min): [M+H]$^+$ (Calc: 486.2).

5.13 Example 13

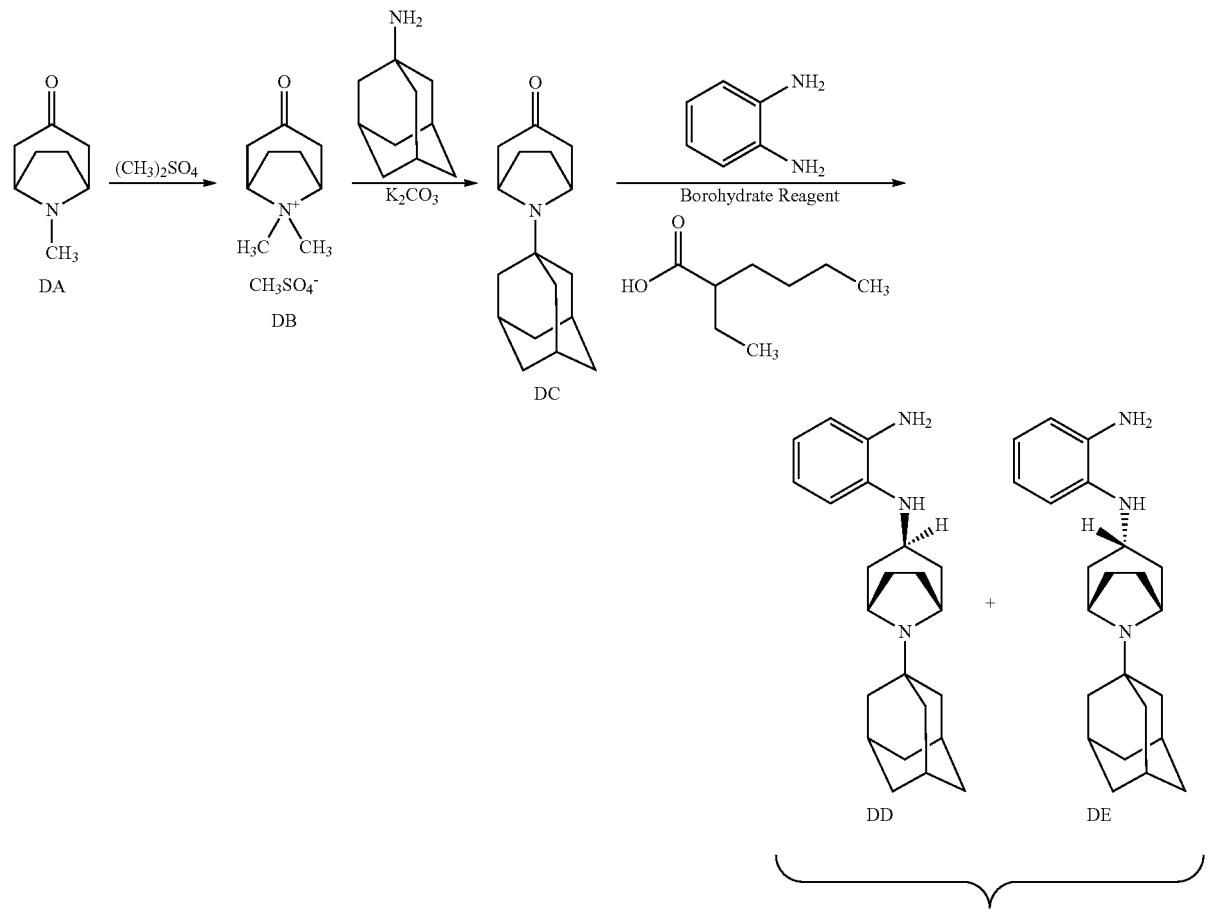

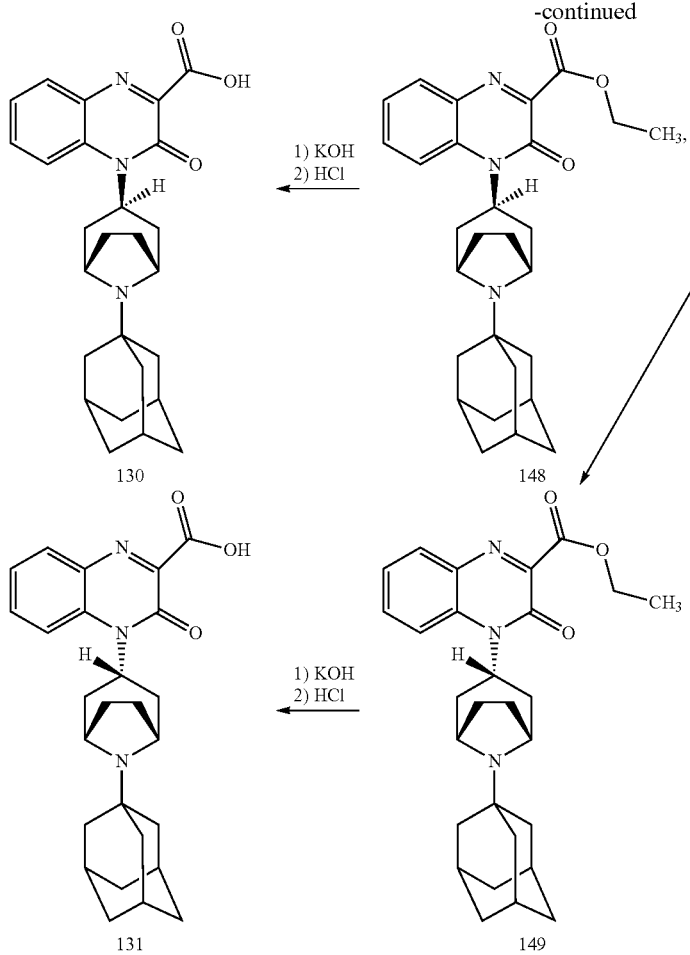

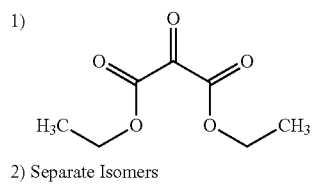

A mixture of the compound of formula DA (tropinone, 200 g, 1.438 mol, Sigma-Aldrich) and acetone (1 L) was cooled to 0° C. Dimethyl sulfate (143 mL, 1.5098 mol, Sigma-Aldrich) was added dropwise over 30 min and the resulting reaction mixture was stirred for 3 h, then filtered. The filter cake was dried under reduced pressure for 18 h to provide 380 g of a compound of formula DB as a white solid (yield >98%).

The identity of the compound of formula DB, tropinone dimethylsulfate salt, was confirmed using $^1$H NMR.

Compound DB: $^1$H NMR: $\delta_H$ (400 MHz, DMSO-$d_6$): 4.14 (2H, m), 3.40 (3H, s), 3.38 (3H, s), 3.32 (1H, m), 3.12 (1H, m), 2.55-2.40 (4H, m), 1.96 (2H, m).

A mixture of the compound of formula DB (40 g, 150.8 mmol) and water (70 mL) was added dropwise to a boiling mixture of 1-adamantylamine (22.8 g, 150.8 mmol, Sigma-Aldrich) in ethanol (250 mL) containing $K_2CO_3$ (2.1 g, 15 mmol). The reaction mixture was refluxed an additional 3 h then evaporated to dryness under reduced pressure to provide a residue. The residue was partitioned between EtOAc (500 mL) and 1M $K_2CO_3$ solution (500 mL). The organic phase was separated and the aqueous phase was extracted with EtOAc (500 mL). The organic portions were combined, dried ($MgSO_4$), and evaporated to dryness under reduced pressure to provide a brown oil. Flash chromatography of the oil with a silica gel column eluting with 3:10 hexanes: EtOAc provided 5.0 g of a compound of formula DC as a pale yellow solid (yield 13%).

The identity of the compound of formula DC, 8-adamantan-1-yl-8-aza-bicyclo[3.2.1]octan-3-one, was confirmed using $^1$H NMR.

Compound DC: $^1$H NMR: $\delta_H$ (400 MHz, CDCl$_3$): 3.96 (2H, m), 2.50 (2H, dd, J=16.0, 4.5 Hz), 2.27 (2H, dd, J=16, 1.7 Hz), 2.07 (2H, m), 1.78 (2H, m), 1.71-1.56 (15H, m).

Sodium tetrahydroborate (9.46 g, 250 mmol, Sigma-Aldrich) was suspended in dry $CH_2Cl_2$ (500 mL). 2-Ethylhexanoic acid (126.2 g, 875 mmol, Sigma-Aldrich) was added and the mixture stirred at a temperature of about 25° C. for 16 h. The resulting borohydrate reagent, believed to comprise sodium tris(2-ethylhexanoyloxy)hydroborate and assumed to have a molarity of 0.5M, was held for later use.

To a mixture of the compound of formula DC (5.2 g, 20.05 mmol), 1,2-phenylenediamine (4.34 g, 40.1 mmol), and $CH_2Cl_2$ (50 mL) was added 2-ethylhexanoic acid (5.2 mL, 20.05 mmol). Under a nitrogen atmosphere, the resulting mixture was cooled to 0° C. with stirring. The borohydride reagent (0.5M, 120.3 mL, 60.15 mmol), previously prepared as described above, was added and the reaction mixture was stirred for 18 h. The mixture was partitioned between EtOAc (400 mL) and 2M sodium carbonate (400 mL). The organic phase was separated, dried ($MgSO_4$), and evaporated to dryness under reduced pressure to provide a residue. Flash chromatography of the residue with a silica gel column eluting with 1:1 EtOAc:hexanes followed by eluting with 100:100:10:1 EtOAc:hexanes:MeOH:ammonia provided 5 g of the compounds of formula DD and DE as an approximately 2:1 mixture of endo:exo (DD:DE isomers (yield 71%).

The identity of the compound of formula DD:DE isomeric mixture, N-(8-adamantan-1-yl-8-aza-bicyclo[3.2.1]oct-3-yl)-benzene-1,2-diamine, was confirmed using $^1$H NMR.

Compounds DD:DE: $^1$H NMR: $\delta_H$ (400 MHz, CDCl$_3$): 6.82-6.50 (4H[isomer 1+2], m), 3.90-3.60 (3H[isomer 1+2], m), 2.55-1.96 (11H[isomer 1+2], m), 1.87-1.52 (15H[isomer 1+2], m).

The above DD:DE mixture (5.0 g, 14.22 mmol) and diethyl 2-oxomalonate (3.25 mL, 21.3 mmol, Sigma-Aldrich) were dissolved in dry toluene (100 mL). Powdered 4 Å molecular sieves (5 g) were added and the reaction mixture was refluxed for 7 h. The mixture was cooled then evaporated to dryness under reduced pressure to provide a residue. Flash chromatography of the residue with a silica gel column eluting with 3:1 hexanes:EtOAc provided two fractions—less polar fraction 1 and more polar fraction 2. Less polar fraction 1 was triturated with diethyl ether (25 mL) to provide 930 mg of a yellow solid. LC/MS showed this material to be a mixture of Substituted-Quinoxaline-Type Piperidine Compound 148, the endo isomer, and Substituted-Quinoxaline-Type Piperidine Compound 149, the exo isomer. More polar fraction 2 was also triturated with diethyl ether (50 mL) to provide 1.4 g of Substituted-Quinoxaline-Type Piperidine Compound 149 as a white solid.

The identity of Substituted-Quinoxaline-Type Piperidine Compound 149, exo-4-(8-adamantan-1-yl-8-aza-bicyclo[3.2.1]oct-3-yl)-3-oxo-3,4-dihydro-quinoxaline-2-carboxylic acid ethyl ester, was confirmed by nuclear Overhauser enhancement spectroscopy ("NOESY") NMR experiments and MS.

Substituted-Quinoxaline-Type Piperidine Compound 149: $^1$H NMR: $\delta_H$ (400 MHz, CDCl$_3$): 8.37 (1H, bm), 7.91 (1H, dd, J=8.10, 1.56 Hz), 7.59 (1H, dt, 7.24, 1.59 Hz), 7.34 (1H, dt, J=8.04, 0.84 Hz), 5.91 (1H, m), 4.51 (2H, q, J=7.1 Hz), 3.94 (2H, m), 2.61 (2H, dt, J=11.49, 8.30 Hz), 2.09 (3H, m), 1.85-1.55 (19H, m), 1.44 (3H, t, J=7.13 Hz); MS: m/z=462.3 [M+l]$^+$ (Calc.: 462.3).

Re-chromatography of Fraction 1 with a silica gel column eluting with 300:30:1:0.1 hexanes:EtOAc:MeOH:ammonia provided 440 mg of Substituted-Quinoxaline-Type Piperidine Compound 148 as a pale yellow solid.

The identity of Substituted-Quinoxaline-Type Piperidine Compound 148, endo-4-(8-adamantan-1-yl-8-aza-bicyclo[3.2.1]oct-3-yl)-3-oxo-3,4-dihydro-quinoxaline-2-carboxylic acid ethyl ester, was confirmed by NOESY NMR and MS.

Substituted-Quinoxaline-Type Piperidine Compound 148: $^1$H NMR: $\delta_H$ (400 MHz, CDCl$_3$): 7.92 (1H, dd, J=8.02, 1.49 Hz), 7.61 (1H, t, J=8.15 Hz), 7.52 (1H, d, J=8.15 Hz), 7.34 91H, dt, J=8.15, 1.49 Hz), 4.51 (2H, q, J=4.0 Hz), 3.87 (1H, m), 2.22 (2H, m), 2.05 (4H, m), 1.83 (4H, m), 1.72-1.53 (15H, m), 1.44 (3H, t, J=4.0 Hz); MS: m/z=462.3 [M+l]$^+$ (Calc.: 462.3).

To a mixture of Substituted-Quinoxaline-Type Piperidine Compound 148 (440 mg, 0.95 mmol) and tetrahydrofuran (10 mL) was added potassium hydroxide (220 mg, 3.8 mmol) in water (1 mL) and the reaction mixture was stirred at a temperature of about 25° C. for 3 h. TLC showed that the reaction was incomplete after this time so additional MeOH (5 mL) was added to form a homogeneous solution and the reaction mixture was stirred at about 25° C. for an additional 2 h. The reaction mixture was evaporated to dryness under reduced pressure to provide a residue. The residue was suspended in water (50 mL) and, using a pH meter, slowly acidified to pH 5.5 with 1M HCl. The mixture was filtered. The filter cake was washed with acetone (50 mL) and dried under reduced pressure at 70° C. for 18 h to provide 315 mg of a white solid (yield 78%). This solid (200 mg) was suspended in diethyl ether (5 mL) and 1M HCl (1 mL) was added. The resulting mixture was stirred at a temperature of about 25° C. for 1 h then filtered. The filter cake was dried under reduced pressure at 70° C. for 18 h to provide 208 mg of Substituted-Quinoxaline-Type Piperidine Compound 130 as a pale yellow solid.

The identity of Substituted-Quinoxaline-Type Piperidine Compound 130, endo-4-(8-adamantan-1-yl-8-aza-bicyclo[3.2.1]oct-3-yl)-3-oxo-3,4-dihydro-quinoxaline-2-carboxylic acid hydrochloride was confirmed using $^1$H NMR and MS.

Substituted-Quinoxaline-Type Piperidine Compound 130: $^1$H NMR: $\delta_H$ (500 MHz, CD$_3$OD+DCl): 8.16 (1H, d, J=8.61 Hz), 7.99 (1H, dd, J=6.87, 1.16 Hz), 7.82 (1H, dt, J=8.61, 1.16 Hz), 7.53 (1H, t, J=7.76 Hz), 6.15 (1H, m), 4.54 (2H, m), 2.96 (2H, m), 2.55 (2H, m), 2.37-2.25 (13H, m), 1.81-1.74 (6H, m); MS: m/z=434.5 [M+l]$^+$ (Calc.: 434.2).

Substituted-Quinoxaline-Type Piperidine Compound 149 (400 mg, 0.867 mmol) was dissolved in MeOH (10 mL) with minimal heating then the solution was quickly cooled to a temperature of about 25° C. Potassium hydroxide (300 mg, 5.35 mmol) in water (2 mL) was added and the reaction mixture was stirred at a temperature of about 25° C. for 18 h. The reaction mixture was evaporated to dryness under reduced pressure to provide a residue. The residue was suspended in water (30 mL) and, using a pH meter, slowly acidified to pH 5.5 with 1M HCl. The mixture was filtered. The filter cake was dried under reduced pressure at 50° C. for 18 h to provide 165 mg of a white solid. The solid was suspended in dry diethyl ether (5 mL) and 2M HCl in diethyl ether (1 mL) was added. The resulting mixture was stirred at a temperature of about 25° C. for 1 h then filtered. The filter cake was dried under reduced pressure at 50° C. for 18 h to provide 160 mg of Substituted-Quinoxaline-Type Piperidine Compound 131 as a pale yellow solid.

The identity of Substituted-Quinoxaline-Type Piperidine Compound 131, exo-4-(8-adamantan-1-yl-8-aza-bicyclo[3.2.1]oct-3-yl)-3-oxo-3,4-dihydro-quinoxaline-2-carboxylic acid, was confirmed using $^1$H NMR and MS.

Substituted-Quinoxaline-Type Piperidine Compound 131: $^1$H NMR: $\delta_H$ (400 MHz, (CD$_3$)$_2$SO): 14.07 (1H, bs), 8.17 (1H, m), 7.85 (1H, dd, J=7.6, 1.28 Hz), 7.69 (1H, t, J=8.28 Hz), 7.44 (1H, t, J=7.6 Hz), 5.29 (1H, bs), 4.54 (2H, s), 3.11 (2H, t, J=12.93 Hz), 2.28-2.04 (13H, m), 1.94 (2H, d, J=11.67 Hz), 1.62 (6H, s); MS: m/z=434.5 [M+l]$^+$ (Calc.: 434.5).

5.14 Example 14

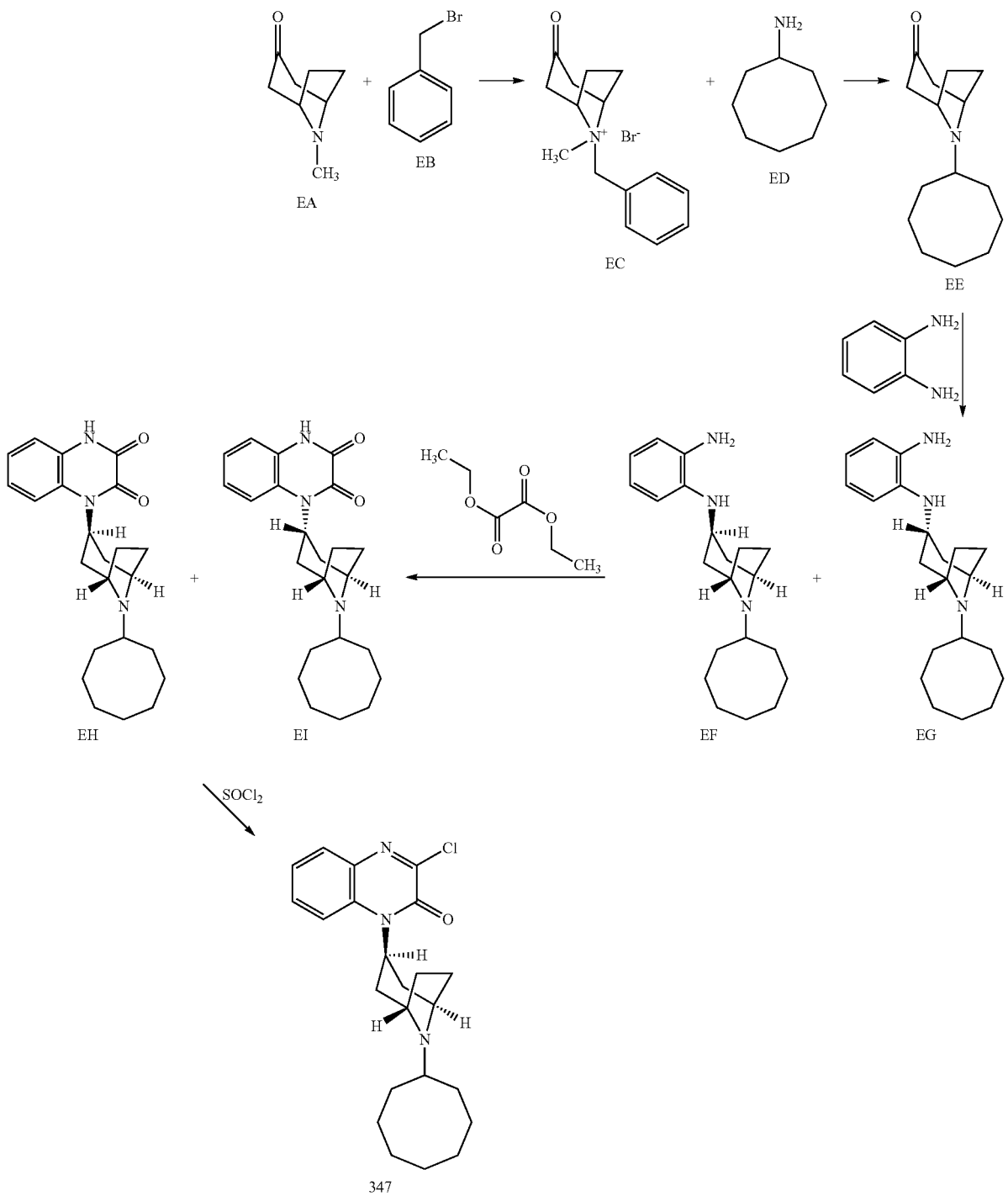

The compound of formula EB, (bromomethyl)benzene (6.5 g, 38 mmol, Sigma-Aldrich), was added to a mixture of the compound of formula EA, 8-methyl-8-azabicyclo[3.2.1]octan-3-one (5 g, 36 mmol, Sigma-Aldrich), in acetone (100 mL) over 30 min at a temperature of about 25° C. The resulting reaction mixture was stirred at a temperature of about 25° C. for 1 h then at 38° C. for 2 h. Thereafter, the mixture was cooled to a temperature of about 25° C., filtered, and washed twice with hexanes (10 mL for each wash) to provide 10 g of the compound of formula EC as white solid (yield 85%).

The compound of formula EC, 8-benzyl-8-methyl-3-oxo-8-azoniabicyclo[3.2.1]octane bromide (5 g, 16.1 mmol), was mixed with 40 mL of ethanol and 20 mL of water. Over 30 min, this mixture was added to a mixture of the compound of formula ED (cyclooctanamine, 2.0 g, 16 mmol, Sigma- Aldrich) and K₂CO₃ (0.2 g, 1.4 mmol) in ethanol (150 mL) at 70° C. After 3 h at 70° C., the reaction mixture was cooled to a temperature of about 25° C. and concentrated under reduced pressure. The residue was treated with water (50 mL) and extracted three times with CHCl₃ (100 mL for each extraction). The combined organic portions were washed with brine (50 mL) and concentrated under reduced pressure to provide 3.5 g of the compound of formula EE (yield 92%).

Sodium triacetoxyborohydride (50 mmol) was added to a mixture of the compound of formula EE, 8-cyclooctyl-8-azabicyclo[3.2.1]octan-3-one (3 g, 12.8 mmol), and 1,2-phenylenediamine (3 g, 27.8 mmol) in 100 mL of CH₂Cl₂ at a temperature of about 25° C. Thereafter, 3 mL of acetic acid was added. The resulting reaction mixture was stirred at a temperature of about 25° C. for about 16 h. Thereafter, MeOH (2 mL) and water (25 mL) were added and the mixture was neutralized with 28% aqueous ammonia to adjust the pH to about 8. The organic portion was separated, washed with brine (10 mL), concentrated under reduced pressure, and chromatographed with a silica gel column eluted with 10:1:1 EtOAc:MeOH:TEA to provide 2.8 g of a mixture of EF and EG as brown oil (yield 68%).

The identity of the compound of formula EF, N¹-((endo)-8-cyclooctyl-8-azabicyclo[3.2.1]octan-3-yl)benzene-1,2-diamine, was confirmed using TLC.

Compound EF: TLC (SiO₂) 100:7:1 EtOAc:MeOH:NH₄OH: Rf=0.6 with UV detection, Dragendorffs reagent.

The identity of the compound of formula EG, N¹-((exo)-8-cyclooctyl-8-azabicyclo[3.2.1]octan-3-yl)benzene-1,2-diamine, was confirmed using TLC.

Compound EG: TLC (SiO₂) 100:7:1 EtOAc:MeOH:NH₄OH: Rf=0.4 with UV detection, Dragendorffs reagent.

A mixture of the above brown oil (0.3 g, of the compounds of formula EF and EG) in 20 mL of diethyl oxalate (Sigma-Aldrich) was heated at 140° C. for 16 h. After cooling to a temperature of about 25° C., the reaction mixture was diluted with EtOAc, washed with 2N aqueous NaOH (30 mL), washed with brine (20 mL), concentrated under reduced pressure, and chromatographed with a silica gel column eluted with 5:5:0.5:0.5 EtOAc:hexane:MeOH:TEA to provide 60 mg and 20 mg of the two compounds of formula EH and EI, respectively, each as a white solid (yield 18% and 6%, respectively).

The identity of the compound of formula EH, 1-((endo)-8-cyclooctyl-8-azabicyclo[3.2.1]octan-3-yl)quinoxaline-2,3(1H,4H)-dione (i.e., the endo isomer), was confirmed using ¹H NMR, LC/MS and TLC.

Compound EH: ¹H NMR: $\delta_H$ (400 MHz, (CD₃OD+CDCl₃)): 7.51 (1H, d, J=7.9 Hz), 7.11-7.21 (m, 3H), 5.16-5.24 (m, 1H), 4.08 (br, 2H), 2.9 (br, 1H), 2.56-2.64 (m, 2H), 2.06-2.26 (m, 6H), 1.72-1.96 (m, 6H), 1.32-1.62 (m, 8H); LC/MS (100%, $t_r$=4.988 min): m/z=382.4 [M+H]⁺ (Calc: 381.5); TLC (SiO₂) 100:7:1 EtOAc:MeOH:NH₄OH: Rf=0.5 with UV detection, Dragendorffs reagent.

The identity of the compound of formula EI, 1-((exo)-8-cyclooctyl-8-azabicyclo[3.2.1]octan-3-yl)quinoxaline-2,3(1H,4H)-dione (i.e., the exo isomer), was confirmed using ¹H NMR, LC/MS and TLC.

Compound EI: ¹H NMR: $\delta_H$ (400 MHz, (CD₃OD+CDCl₃)): 7.62 (br, 1H), 7.21-7.24 (m, 3H), 4.95 (br, 1H), 3.75 (br, 2H), 3.36 (br, 1H), 2.91-2.98 (m, 2H), 2.06-2.16 (m, 2H), 1.42-1.96 (m, 18H); LC/MS (100%, $t_r$=4.718 min): m/z=382.2 [M+H]⁺ (Calc: 381.5); TLC (SiO₂) 100:7:1 EtOAc:MeOH:NH₄OH: Rf=0.45 with UV detection, Dragendorffs reagent.

The compound of formula EH (191 mg, 0.500 mmol) was suspended in thionyl chloride (0.8 mL, Sigma-Aldrich). A catalytic amount of DMF was added and the reaction mixture was refluxed for 30 min. Thereafter, the reaction mixture was cooled to 0° C. and diethyl ether (5 mL) was added. A precipitate formed. The precipitate was filtered and washed with diethyl ether to provide 196 mg of the hydrochloride of Substituted-Quinoxaline-Type Piperidine Compound 347 as a pale yellow solid (yield 90%). Thereafter, this hydrochloride was suspended in saturated aqueous NaHCO₃ and extracted with CHCl₃ to provide the free Substituted-Quinoxaline-Type Piperidine Compound 347, i.e., the endo isomer.

The identity of Substituted-Quinoxaline-Type Piperidine Compound 347, 3-chloro-1-((endo 8-cyclooctyl-8-azabicyclo[3.2.1]octan-3-yl)quinoxalin-2(1H)-one, was confirmed using ¹H NMR.

Substituted-Quinoxaline-Type Piperidine Compound 347: ¹H NMR: $\delta_H$ (400 MHz, CDCl₃): 7.80 (1H, d, J=8.1 Hz), 7.60-7.54 (2H, m), 7.37-7.33 (1H, m), 5.17 (1H, br s), 3.67 (2H, br s), 2.34-2.22 (5H, m), 2.04-1.98 (2H, m), 1.89-1.36 (16H, m).

5.15 Example 15

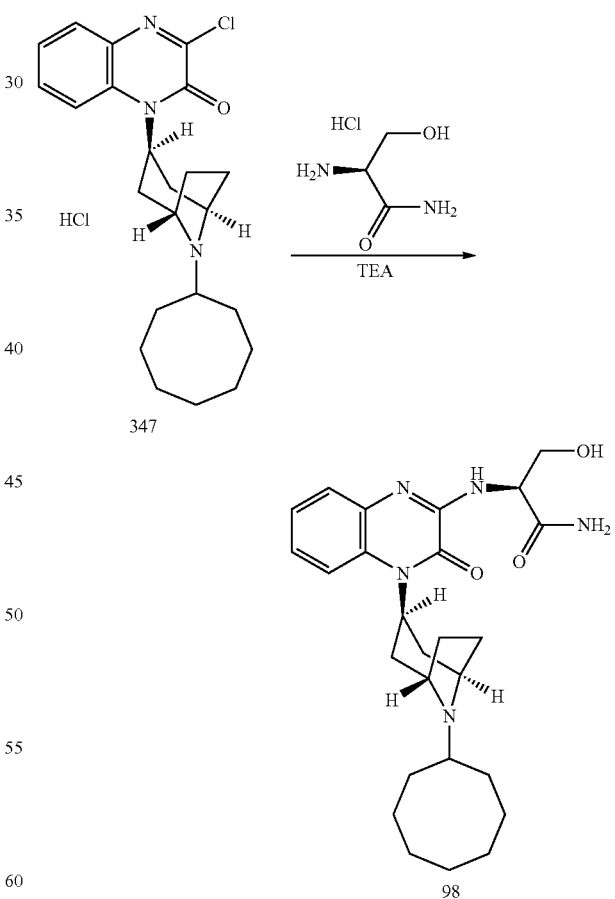

TEA (1.2 mmol) and serine amide hydrochloride (i.e., (S)-2-amino-3-hydroxypropanamide hydrochloride, 0.45 mmol, Sigma-Aldrich) were added to a mixture of the hydrochloride of Substituted-Quinoxaline-Type Piperidine Compound 347 (130 mg, 0.3 mmol) in N-methyl pyrrolidine (3 mL) at 25° C. The resulting reaction mixture was stirred at 80° C. for 3 hr. After cooling to a temperature of about 25° C. and quenching with water (3 mL), the mixture was extracted three times with EtOAc/water (50 mL for each extraction), washed three times with water (50 mL for each wash), dried (Na$_2$SO$_4$), and concentrated under reduced pressure to provide a yellow oil. The oil was chromatographed with a silica gel column eluted with a gradient of from 95:5:0.5 CHCl$_3$:MeOH:aqueous ammonia to 9:1:0.1 CHCl$_3$:MeOH:aqueous ammonia to provide 42 mg of Substituted-Quinoxaline-Type Piperidine Compound 98 as a pale yellow amorphous solid (yield 30%).

The identity of Substituted-Quinoxaline-Type Piperidine Compound 98, (2S)-2-(4-((endo)-8-cyclooctyl-8-azabicyclo[3.2.1]octan-3-yl)-3-oxo-3,4-dihydroquinoxalin-2-ylamino)-3-hydroxypropanamide, was confirmed using $^1$H NMR and LC/MS.

Substituted-Quinoxaline-Type Piperidine Compound 98: $^1$H NMR: $\delta_H$ (400 MHz, DMSO-d$_6$): 7.46-7.41 (3H, m), 7.28-7.15 (4H, m), 5.05 (1H, t, J=5.83 Hz), 4.45-4.41 (1H, m), 3.85-3.64 (4H, m), 2.38-1.41 (23H, m); LC/MS (98%, t$_r$=1.24 min): m/z=468.2 [M+H]$^+$ (Calc: 467.6).

5.16 Example 16

In a manner similar to Example 15, the following Substituted-Quinoxaline-Type Piperidine Compounds were prepared from Substituted-Quinoxaline-Type Piperidine Compound 347.

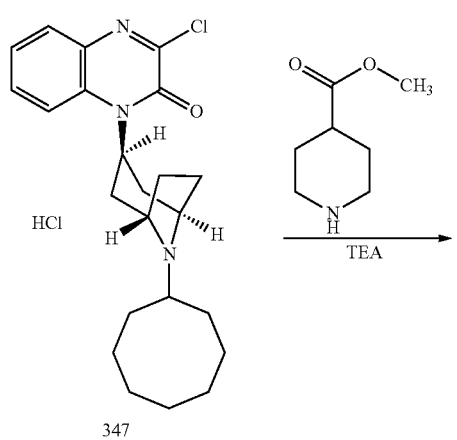

347

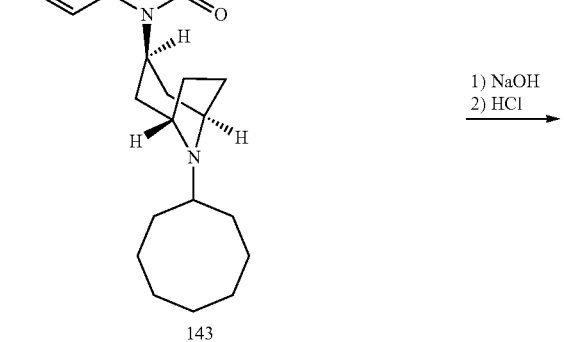

143

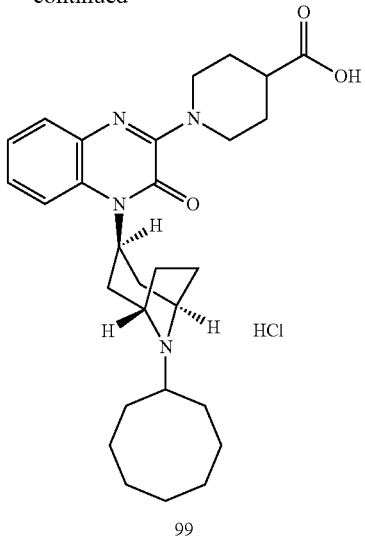

99

Substituted-Quinoxaline-Type Piperidine Compound 143 was prepared by using methyl piperidine-4-carboxylate (Sigma-Aldrich) in place of serine amide hydrochloride (yield 73%).

The identity of Substituted-Quinoxaline-Type Piperidine Compound 143, methyl 1-(4-((endo)-8-cyclooctyl-8-azabicyclo[3.2.1]octan-3-yl)-3-oxo-3,4-dihydroquinoxalin-2-yl)piperidine-4-carboxylate, was confirmed using $^1$H NMR.

Substituted-Quinoxaline-Type Piperidine Compound 143: $^1$H NMR: $\delta_H$ (400 MHz, DMSO-d$_6$): 7.45-7.18 (4H, m), 5.19 (1H, s), 4.57 (2H, d, J=13.18 Hz), 3.62 (5H, s), 3.04 (2H, t, J=11.15 Hz), 2.64 (1H, d, J=11.15 Hz), 2.36 (1H, s), 2.19 (2H, s), 2.02-1.40 (24H, m).

The hydrochloride of Substituted-Quinoxaline-Type Piperidine Compound 99 was prepared from Substituted-Quinoxaline-Type Piperidine Compound 143 in a manner similar to the preparation of Substituted-Quinoxaline-Type Piperidine Compound 174 in Example 7 (yield 70%).

The identity of Substituted-Quinoxaline-Type Piperidine Compound 99, 1-(4-((endo)-8-cyclooctyl-8-azabicyclo[3.2.1]octan-3-yl)-3-oxo-3,4-dihydroquinoxalin-2-yl)piperidine-4-carboxylic acid, was confirmed using $^1$H NMR and LC/MS.

Substituted-Quinoxaline-Type Piperidine Compound 99: $^1$H NMR: $\delta_H$ (400 MHz, DMSO-d$_6$): 10.50 (1H, s), 7.84 (1H, d, J=8.11 Hz), 7.50 (1H, dd, J=7.60, 1.52 Hz), 7.26 (2H, ddd, J=20.78, 12.67, 5.32 Hz), 5.83 (1H, t, J=9.38 Hz), 4.61 (2H, d, J=13.18 Hz), 4.21 (3H, s), 3.10 (2H, t, J=11.41 Hz), 2.93 (1H, s), 2.67-2.54 (3H, m), 1.88 (22H, m); LC/MS (100%, t$_r$=1.79 min): m/z=493.3 [M+H]$^+$ (Calc: 492.7).

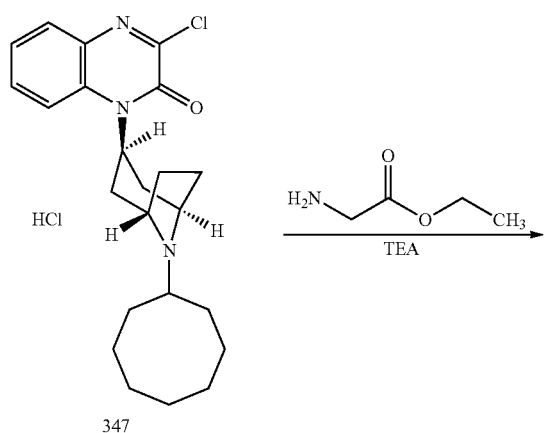

347

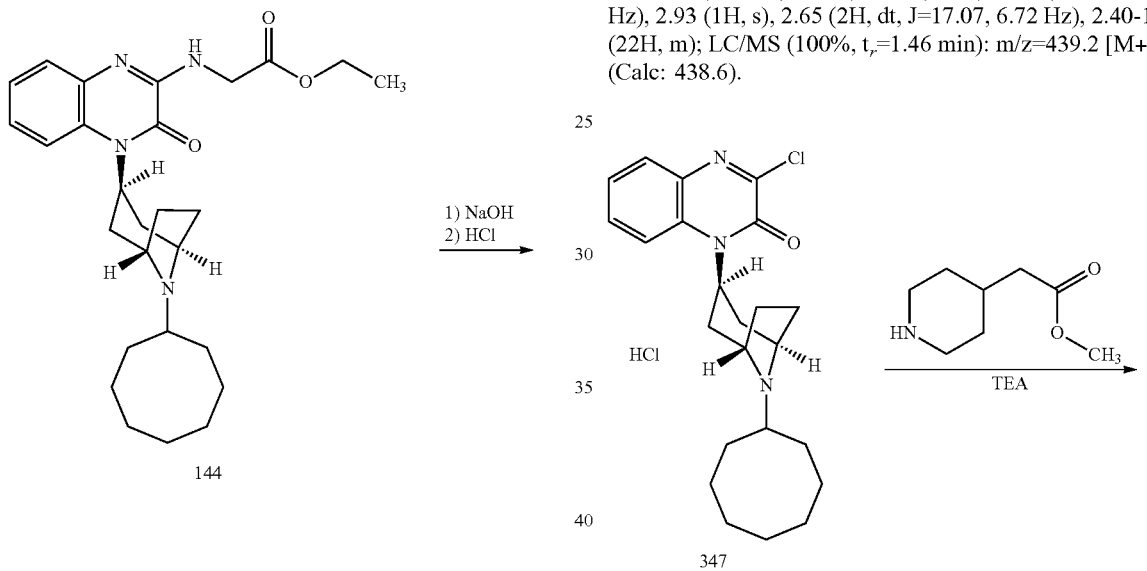

144

106 clo[3.2.1]octan-3-yl)-3-oxo-3,4-dihydroquinoxalin-2-ylamino)acetate, was confirmed using MS.

Substituted-Quinoxaline-Type Piperidine Compound 144: MS: m/z=467.3 [M+H]$^+$ (Calc: 466.6).

The hydrochloride of Substituted-Quinoxaline-Type Piperidine Compound 106 was prepared from Substituted-Quinoxaline-Type Piperidine Compound 144 in a manner similar to the preparation of Substituted-Quinoxaline-Type Piperidine Compound 174 in Example 7 (yield 88%).

The identity of Substituted-Quinoxaline-Type Piperidine Compound 106, 2-(4-((endo)-8-cyclooctyl-8-azabicyclo[3.2.1]octan-3-yl)-3-oxo-3,4-dihydroquinoxalin-2-ylamino)acetic acid, was confirmed using $^1$H NMR and LC/MS.

Substituted-Quinoxaline-Type Piperidine Compound 106: $^1$H NMR: $\delta_H$ (400 MHz, DMSO-d$_6$): 10.25 (0.9H, s), 9.43 (0.1H, s), 7.85-7.77 (2H, m), 7.41 (1H, dd, J=7.10, 2.03 Hz), 7.25 (2H, ddd, J=16.86, 9.25, 2.91 Hz), 5.81 (0.9H, t, J=9.38 Hz), 5.15 (0.1H, s), 4.21 (2H, s), 4.06 (2H, d, J=6.08 Hz), 2.93 (1H, s), 2.65 (2H, dt, J=17.07, 6.72 Hz), 2.40-1.39 (22H, m); LC/MS (100%, t$_r$=1.46 min): m/z=439.2 [M+H]$^+$ (Calc: 438.6).

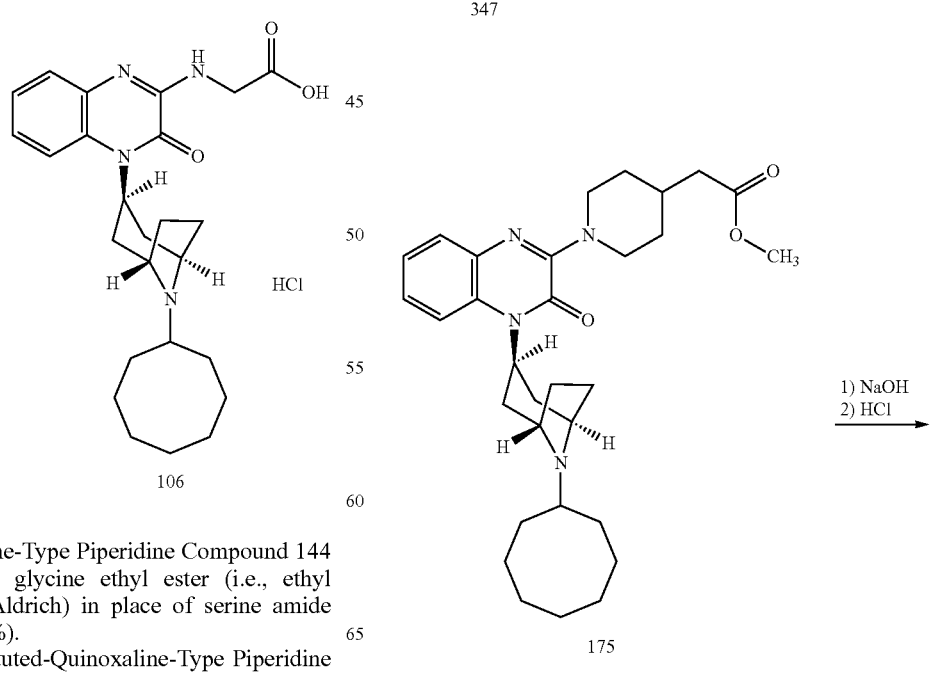

347

175

Substituted-Quinoxaline-Type Piperidine Compound 144 was prepared by using glycine ethyl ester (i.e., ethyl 2-aminoacetate, Sigma-Aldrich) in place of serine amide hydrochloride (yield 67%).

The identity of Substituted-Quinoxaline-Type Piperidine Compound 144, ethyl 2-(4-((endo)-8-cyclooctyl-8-azabicy-

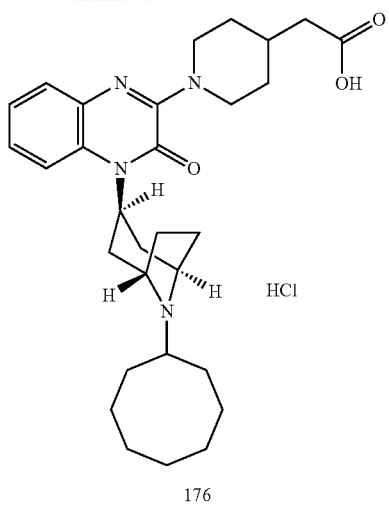

176

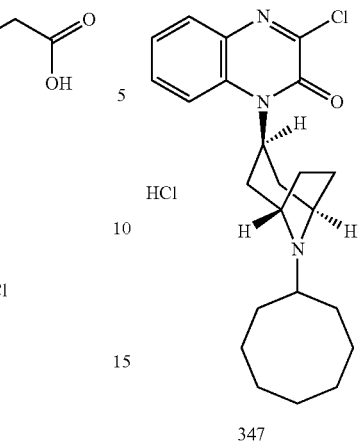

347

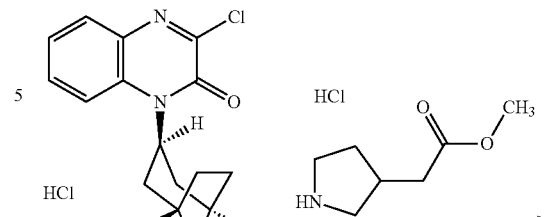

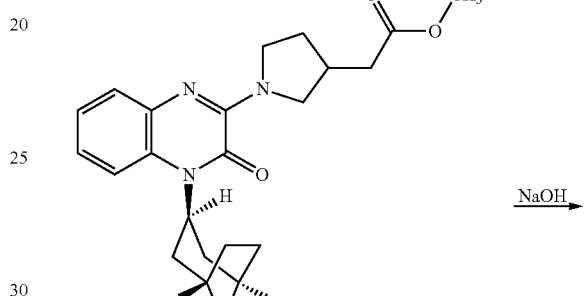

145

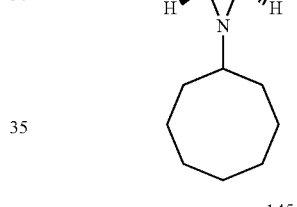

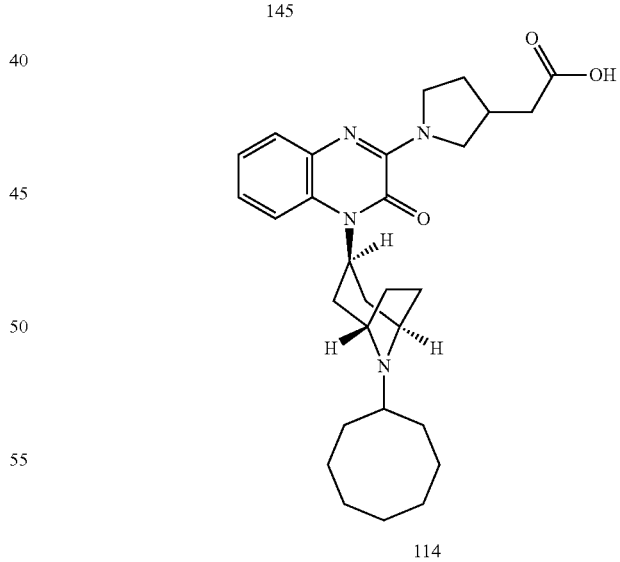

114

Substituted-Quinoxaline-Type Piperidine Compound 175 was prepared by using methyl 2-(piperidin-4-yl)acetate (Sigma-Aldrich) in place of serine amide hydrochloride (yield 89%).

The identity of Substituted-Quinoxaline-Type Piperidine Compound 175, methyl 2-(1-(4-((endo)-8-cyclooctyl-8-azabicyclo[3.2.1]octan-3-yl)-3-oxo-3,4-dihydroquinoxalin-2-yl)piperidin-4-yl)acetate, was confirmed using $^1$H NMR and LC/MS.

Substituted-Quinoxaline-Type Piperidine Compound 175: $^1$H NMR: $\delta_H$ (400 MHz, CDCl$_3$): 7.52 (1H, d, J=8.0 Hz), 7.37 (1H, d, J=8.0 Hz), 7.20 (2H, m), 5.20 (1H, br), 4.71 (2H, d, J=12.0 Hz), 3.69 (3H, s), 3.65 (2H, m), 2.90 (2H, t, J=12.0 Hz), 2.40-1.90 (7H, m), 1.90-1.35 (22H, m); LC/MS: m/z=521 [M+H]$^+$ (Calc: 520.3).

The hydrochloride of Substituted-Quinoxaline-Type Piperidine Compound 176 was prepared from Substituted-Quinoxaline-Type Piperidine Compound 175 in a manner similar to the preparation of Substituted-Quinoxaline-Type Piperidine Compound 174 in Example 7 (yield 76%).

The identity of Substituted-Quinoxaline-Type Piperidine Compound 176, 2-(1-(4-((endo)-8-cyclooctyl-8-azabicyclo[3.2.1]octan-3-yl)-3-oxo-3,4-dihydroquinoxalin-2-yl)piperidin-4-yl)acetic acid, was confirmed using $^1$H NMR and LC/MS.

Substituted-Quinoxaline-Type Piperidine Compound 176: $^1$H NMR: $\delta_H$ (400 MHz, DMSO-d$_6$): 12.1 (1H, m), 10.4 (0.9H, m), 9.52 (0.1H, m), 7.80 (1H, m), 7.43 (1H, m), 7.21 (2H, m), 5.80 (1H, m), 4.70 (2H, d, J=12.0 Hz), 4.20 (2H, m), 2.92 (2H, t, J=12.0 Hz), 2.60 (2H, m), 2.40-1.23 (27H, m); LC/MS (100%, t$_r$=1.84 min): m/z=507 [M+H]$^+$ (Calc: 506.3).

Substituted-Quinoxaline-Type Piperidine Compound 145 was prepared by using the hydrochloride of methyl 2-(pyrrolidin-3-yl)acetate in place of serine amide hydrochloride (yield 90%).

The identity of Substituted-Quinoxaline-Type Piperidine Compound 145, methyl 2-(1-(4-((endo)-8-cyclooctyl-8- azabicyclo[3.2.1]octan-3-yl)-3-oxo-3,4-dihydroquinoxalin-2-yl)pyrrolidin-3-yl)acetate, was confirmed using ¹H NMR.

Substituted-Quinoxaline-Type Piperidine Compound 145: ¹H NMR: δ$_H$ (400 MHz, DMSO-d$_6$): 7.31 (2H, dt, J=16.90, 6.84 Hz), 7.19-7.11 (2H, m), 5.12 (1H, br), 3.80 (6H, m), 3.62 (3H, s), 2.35 (1H, s), 2.22-1.38 (23H, m).

Substituted-Quinoxaline-Type Piperidine Compound 114 was prepared from Substituted-Quinoxaline-Type Piperidine Compound 145 in a manner similar to the preparation of Substituted-Quinoxaline-Type Piperidine Compound 111 in Example 5 (yield 71%).

The identity of Substituted-Quinoxaline-Type Piperidine Compound 114, 2-(1-(4-((endo)-8-cyclooctyl-8-azabicyclo[3.2.1]octan-3-yl)-3-oxo-3,4-dihydroquinoxalin-2-yl)pyrrolidin-3-yl)acetic acid, was confirmed using ¹H NMR and LC/MS.

Substituted-Quinoxaline-Type Piperidine Compound 114: ¹H NMR: δ$_H$ (400 MHz, DMSO-d$_6$): 7.32 (2H, td, J=10.01, 3.72 Hz), 7.19-7.10 (2H, m), 5.17 (1H, br), 4.22-3.03 (6H, br), 2.41 (4H, m), 2.25-1.37 (24 H, m); LC/MS (99%, t$_r$=1.39 min): m/z=493.3 [M+H]⁺ (Calc: 492.7).

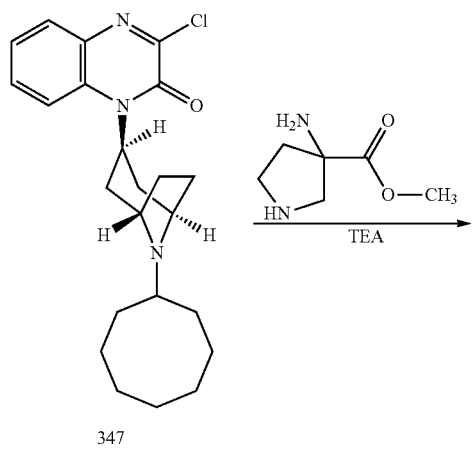

347

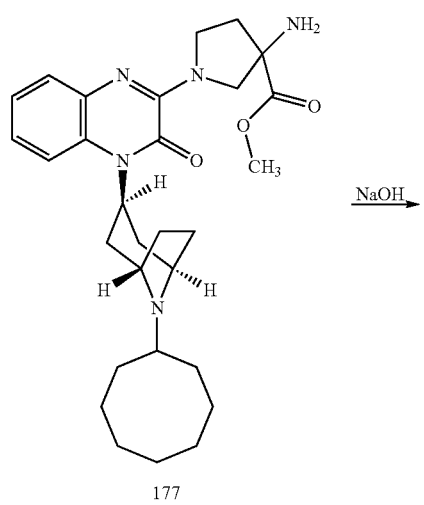

177

Substituted-Quinoxaline-Type Piperidine Compound 177 was prepared by using methyl 3-aminopyrrolidine-3-carboxylate (Sigma-Aldrich) in place of serine amide hydrochloride (yield 88%).

The identity of Substituted-Quinoxaline-Type Piperidine Compound 177, methyl 3-amino-1-(4-((endo)-8-cyclooctyl-8-azabicyclo[3.2.1]octan-3-yl)-3-oxo-3,4-dihydroquinoxalin-2-yl)pyrrolidine-3-carboxylate, was confirmed using ¹H NMR and LC/MS.

Substituted-Quinoxaline-Type Piperidine Compound 177: ¹H NMR: δ$_H$ (400 MHz, CDCl$_3$): 7.45 (1H, m), 7.30 (1H, m), 7.13 (2H, m), 5.20 (1H, br), 4.30-4.00 (4H, m), 3.77 (3H, s), 3.65 (2H, m), 2.50-2.00 (9H, m), 1.90-1.36 (16H, m); LC/MS: m/z=508 [M+H]⁺ (Calc: 507.3).

Substituted-Quinoxaline-Type Piperidine Compound 178 was prepared from Substituted-Quinoxaline-Type Piperidine Compound 177 in a manner similar to the preparation of Substituted-Quinoxaline-Type Piperidine Compound 111 in Example 5 (yield 72%).

The identity of Substituted-Quinoxaline-Type Piperidine Compound 178, 3-amino-1-(4-((endo)-8-cyclooctyl-8-azabicyclo[3.2.1]octan-3-yl)-3-oxo-3,4-dihydroquinoxalin-2-yl)pyrrolidine-3-carboxylic acid, was confirmed using ¹H NMR and LC/MS.

Substituted-Quinoxaline-Type Piperidine Compound 178: ¹H NMR: δ$_H$ (400 MHz, DMSO-d$_6$): 7.90 (2H, br), 7.36 (2H, m), 7.17 (2H, m), 5.20 (1H, m), 4.40-3.50 (6H, m), 2.50-1.30 (21H, m); LC/MS (100%, t$_r$=1.12 min): m/z=494 [M+H]⁺ (Calc: 493.3).

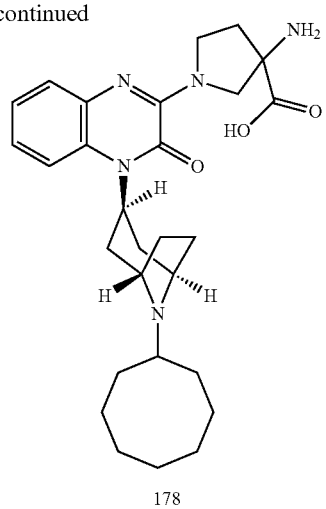

178

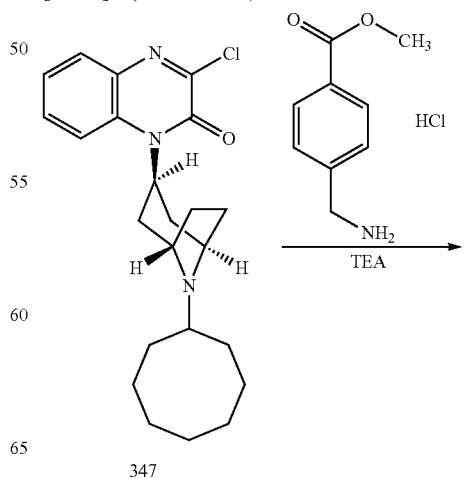

347

-continued

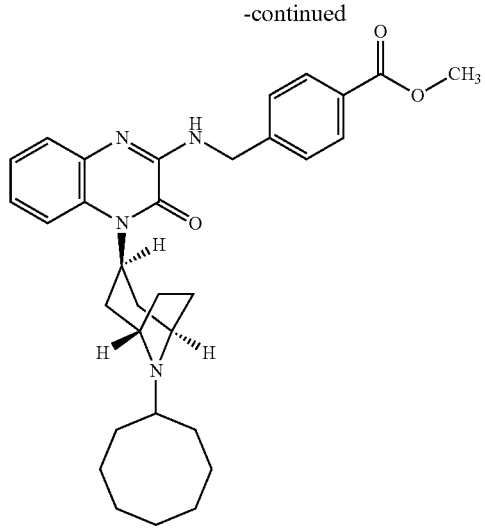

179

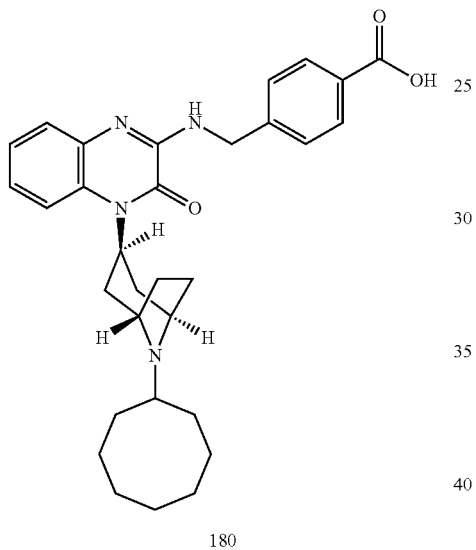

180

J=8.1 Hz), 7.39-7.45 (m, 1H), 7.20-7.27 (m, 2H), 5.76-5.80 (m, 1H), 4.71 (m, 2H), 4.18-4.26 (m, 2H), 2.95 (m, 1H), 2.60-2.67 (m, 2H), 1.39-2.38 (m, 20H); LC/MS: m/z=515 [M+H]$^+$ (Calc: 514).

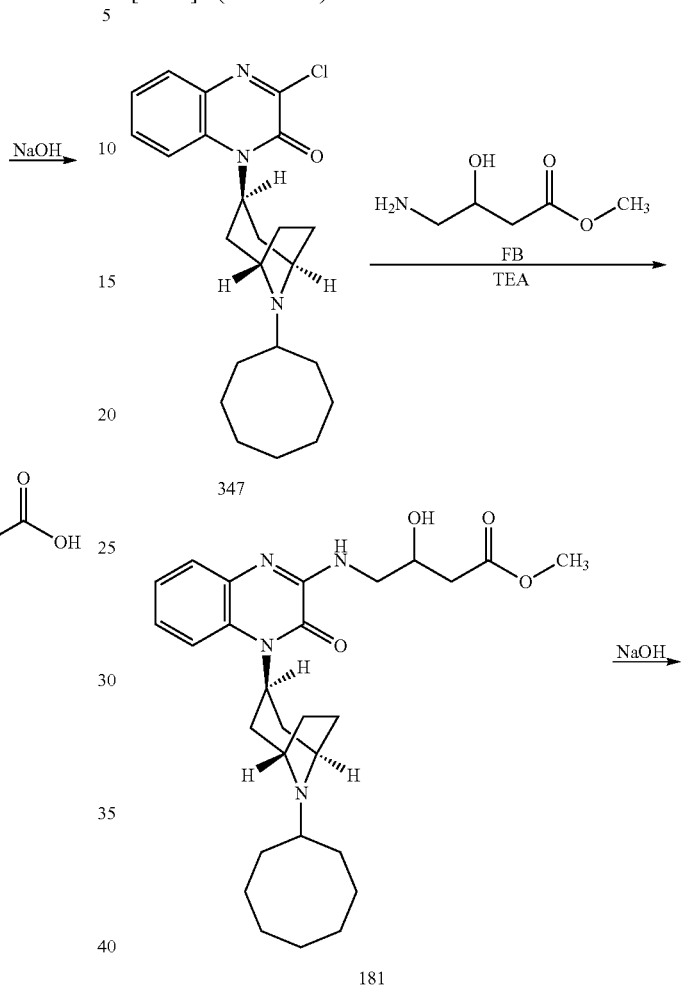

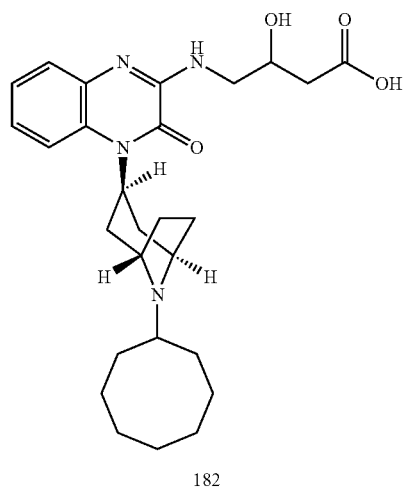

182

Substituted-Quinoxaline-Type Piperidine Compound 179 was prepared by using methyl 4-(aminomethyl)benzoate hydrochloride (Sigma-Aldrich) in place of serine amide hydrochloride (yield 36%).

The identity of Substituted-Quinoxaline-Type Piperidine Compound 179, methyl 4-((4-((endo)-8-cyclooctyl-8-azabicyclo[3.2.1]octan-3-yl)-3-oxo-3,4-dihydroquinoxalin-2-ylamino)methyl)benzoate, was confirmed using LC/MS.

Substituted-Quinoxaline-Type Piperidine Compound 179: LC/MS: m/z=529 [M+H]$^+$ (Calc: 528).

Substituted-Quinoxaline-Type Piperidine Compound 180 was prepared from Substituted-Quinoxaline-Type Piperidine Compound 179 in a manner similar to the preparation of Substituted-Quinoxaline-Type Piperidine Compound 111 in Example 5 (yield 28%).

The identity of Substituted-Quinoxaline-Type Piperidine Compound 180, 4-((4-((endo)-8-cyclooctyl-8-azabicyclo[3.2.1]octan-3-yl)-3-yl)-3-oxo-3,4-dihydroquinoxalin-2-ylamino)methyl)benzoic acid, was confirmed using $^1$H NMR and LC/MS.

Substituted-Quinoxaline-Type Piperidine Compound 180 $^1$H NMR: $\delta_H$(400 MHz, DMSO-d$_6$): 10.24 (br, 1H), 8.67 (br, 1H), 7.88 (d, 2H, J=8.1 Hz), 7.78-7.79 (m, 1H), 7.49 (d, 2H, Substituted-Quinoxaline-Type Piperidine Compound 181 was prepared by using methyl 4-amino-3-hydroxybutanoate (FB) in place of serine amide hydrochloride (yield 28%).

The identity of Substituted-Quinoxaline-Type Piperidine Compound 181, methyl 4-(4-((endo)-8-cyclooctyl-8-azabicyclo[3.2.1]octan-3-yl)-3-oxo-3,4-dihydroquinoxalin-2-ylamino)-3-hydroxybutanoate, was confirmed using LC/MS.

Substituted-Quinoxaline-Type Piperidine Compound 181: LC/MS: m/z=497 [M+H]$^+$ (Calc: 496).

Substituted-Quinoxaline-Type Piperidine Compound 182 was prepared from Substituted-Quinoxaline-Type Piperidine Compound 181 in a manner similar to the preparation of Substituted-Quinoxaline-Type Piperidine Compound 111 in Example 5 (yield 46%).

The identity of Substituted-Quinoxaline-Type Piperidine Compound 182, 4-(4-((endo)-8-cyclooctyl-8-azabicyclo[3.2.1]octan-3-yl)-3-oxo-3,4-dihydroquinoxalin-2-ylamino)-3-hydroxybutanoic acid, was confirmed using $^1$H NMR and LC/MS.

Substituted-Quinoxaline-Type Piperidine Compound 182: $^1$H NMR: δ$_H$ (400 MHz, DMSO-d$_6$): 7.31-7.40 (m, 2H), 7.16-7.24 (m, 2H), 4.01 (m, 1H), 3.63 (m, 2H), 3.29-3.41 (m, 2H), 1.39-2.37 (m, 25H); LC/MS: m/z=483 [M+H]$^+$ (Calc: 482).

The compound of formula FB was prepared as follows:

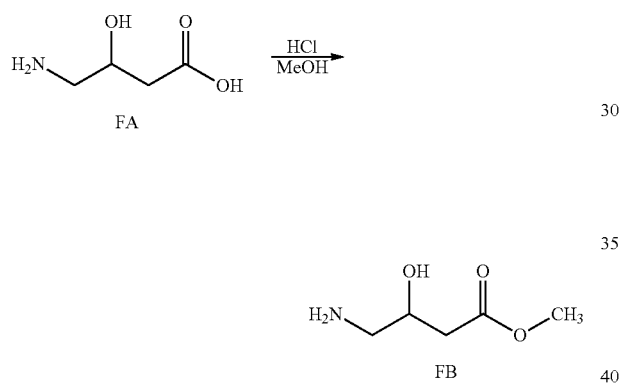

A mixture of 4-amino-3-hydroxybutanoic acid (FA, 1.00 g, 8.40 mmol, Sigma-Aldrich) and concentrated HCl (1 mL) in MeOH (20 mL) was refluxed for 19 hr. The mixture was concentrated under reduced pressure to provide 1.43 g of the compound of formula FB as a colorless oil (yield >98%).

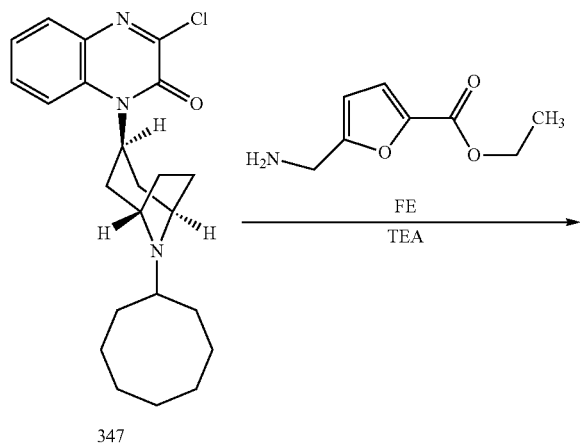

347

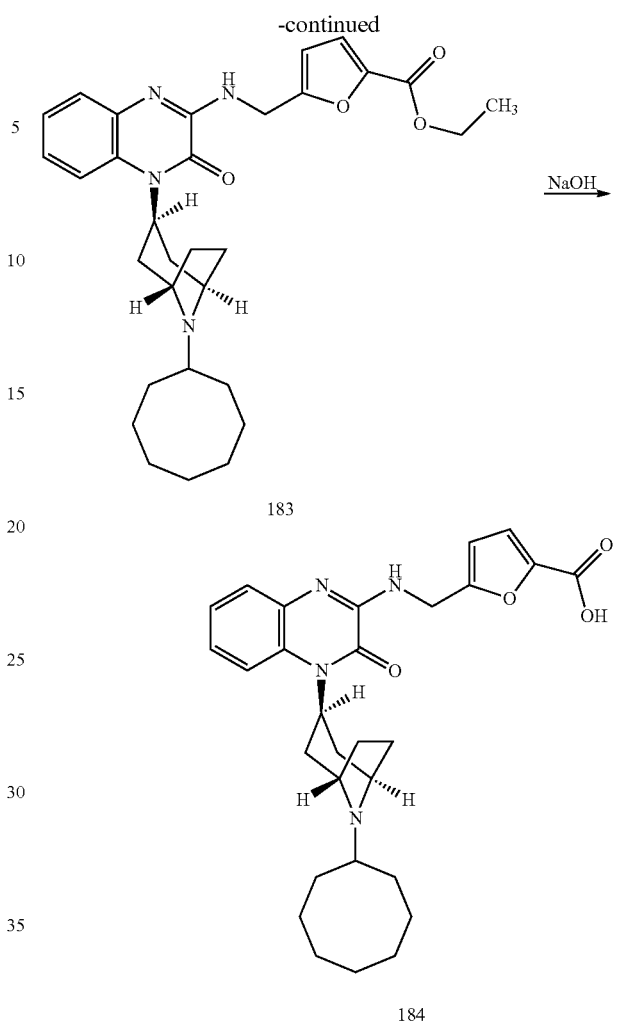

Substituted-Quinoxaline-Type Piperidine Compound 183 was prepared by using ethyl 5-(aminomethyl)furan-2-carboxylate (FE) in place of serine amide hydrochloride (yield 27%).

The identity of Substituted-Quinoxaline-Type Piperidine Compound 183, ethyl 5-((4-((endo)-8-cyclooctyl-8-azabicyclo[3.2.1]octan-3-yl)-3-oxo-3,4-dihydroquinoxalin-2-ylamino)methyl)furan-2-carboxylate, was confirmed using LC/MS.

Substituted-Quinoxaline-Type Piperidine Compound 183: LC/MS: m/z=533 [M+H]$^+$ (Calc: 532).

Substituted-Quinoxaline-Type Piperidine Compound 184 was prepared from Substituted-Quinoxaline-Type Piperidine Compound 183 in a manner similar to the preparation of Substituted-Quinoxaline-Type Piperidine Compound 111 in Example 5 (yield 37%).

The identity of Substituted-Quinoxaline-Type Piperidine Compound 184, 5-((4-((endo)-8-cyclooctyl-8-azabicyclo[3.2.1]octan-3-yl)-3-oxo-3,4-dihydroquinoxalin-2-ylamino)methyl)furan-2-carboxylic acid, was confirmed using $^1$H NMR and LC/MS.

Substituted-Quinoxaline-Type Piperidine Compound 184: $^1$H NMR: δ$_H$ (400 MHz, DMSO-d$_6$): 10.65 (br, 1H), 8.55 (br, 1H), 7.89-7.90 (m, 1H), 7.52-7.53 (m, 1H), 7.24-7.27 (m, 2H), 7.14-7.24 (m, 1H), 6.56 (s, 1H), 5.93-5.97 (m, 2H), 4.69 (m, 2H), 4.15-4.23 (m, 2H), 2.92 (m, 1H), 2.62-2.67 (m, 2H), 2.18-2.34 (m, 6H), 1.27-1.96 (m, 14H); LC/MS: m/z=505 [M+H]⁺ (Calc: 504).

The compound of formula FE was prepared as follows:

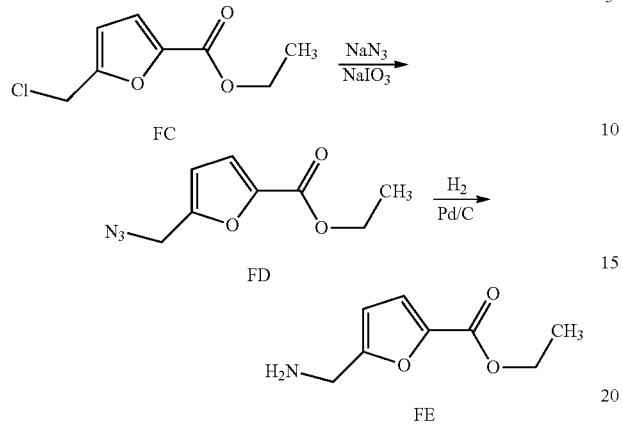

A mixture of ethyl 5-(chloromethyl)furan-2-carboxylate (EC, 1.00 g, 5.30 mmol, Sigma-Aldrich), sodium azide (379.1 mg, 5.83 mmol, Sigma-Aldrich), and sodium iodate (catalytic amount, Sigma-Aldrich) in DMF at a temperature of about 25° C. was stirred for 24 h. The reaction mixture was extracted with EtOAc/water. The organic portion was separated, washed with brine, dried (Na₂SO₄), filtered, and concentrated under reduced pressure to provide a residue. The residue was chromatographed with a silica gel column eluted with 1:10 EtOAc:hexane to provide 950 mg of the compound of formula FD as a pale yellow solid (yield 92%).

The identity of the compound of formula FD, ethyl 5-(azidomethyl)furan-2-carboxylate, was confirmed using ¹H NMR.

Compound FD: ¹H NMR: δ_H (400 MHz, CDCl₃): 7.14 (d, 1H, J=3.4 Hz), 6.47 (d, 1H, J=3.4 Hz), 4.39 (s, 2H), 4.37 (q, 2H, J=7.1 Hz), 1.38 (t, 3H, J=7.1 Hz).

Under a hydrogen atmosphere, a mixture of the compound of formula FD (952 mg, 4.88 mmol), 20% palladium on carbon (100 mg, Sigma-Aldrich), and MeOH (10 mL) was stirred at a temperature of about 25° C. for 3.5 hr. The Pd/C was filtered off, the mixture was washed with MeOH, and the filtrate was concentrated under reduced pressure to provide 843 mg of the compound of formula FE as a brown oil (yield >98%).

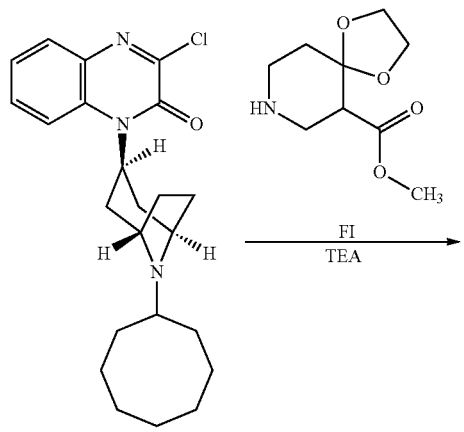

347

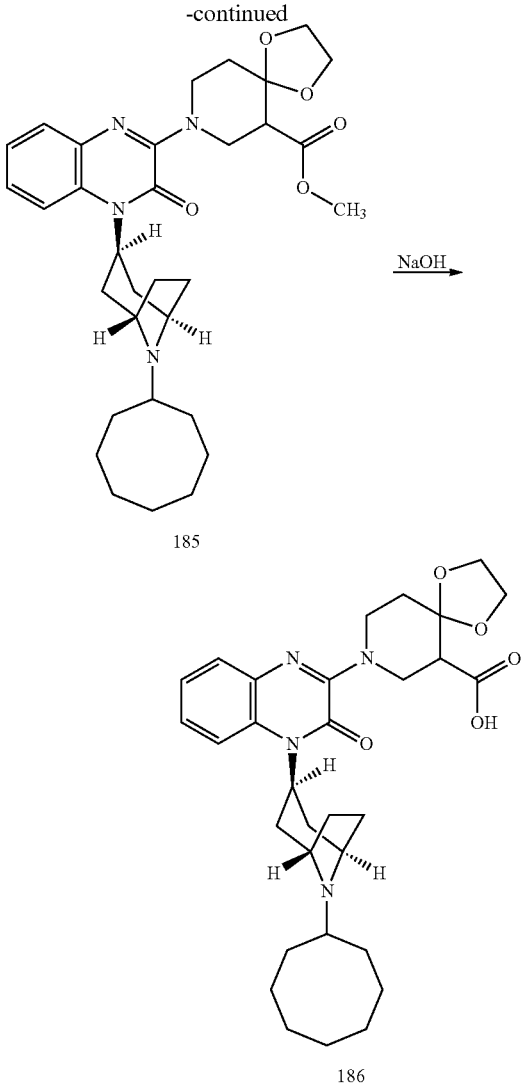

185

186

Substituted-Quinoxaline-Type Piperidine Compound 185 was prepared by using methyl 1,4-dioxa-8-azaspiro[4.5]decane-6-carboxylate (FI) in place of serine amide hydrochloride (yield 67%).

The identity of Substituted-Quinoxaline-Type Piperidine Compound 185, methyl 8-(4-((endo)-8-cyclooctyl-8-azabicyclo[3.2.1]octan-3-yl)-3-oxo-3,4-dihydroquinoxalin-2-yl)-1,4-dioxa-8-azaspiro[4.5]decane-6-carboxylate, was confirmed using LC/MS.

Substituted-Quinoxaline-Type Piperidine Compound 185: LC/MS: m/z=565 [M+H]⁺ (Calc: 564).

Substituted-Quinoxaline-Type Piperidine Compound 186 was prepared from Substituted-Quinoxaline-Type Piperidine Compound 185 in a manner similar to the preparation of Substituted-Quinoxaline-Type Piperidine Compound 111 in Example 5 (yield 27%).

The identity of Substituted-Quinoxaline-Type Piperidine Compound 186, 8-(4-((endo)-8-cyclooctyl-8-azabicyclo[3.2.1]octan-3-yl)-3-oxo-3,4-dihydroquinoxalin-2-yl)-1,4-dioxa-8-azaspiro[4.5]decane-6-carboxylic acid, was confirmed using ¹H NMR and LC/MS.

Substituted-Quinoxaline-Type Piperidine Compound 186: ¹H NMR: δ_H (400 MHz, DMSO-d₆): 12.25 (br, 1H), 7.37-7.43 (m, 2H), 7.28-7.35 (m, 1H), 7.19-7.21 (m, 1H), 5.05 (m, 1H), 4.30 (m, 1H), 4.09 (m, 1H), 3.92 (m, 4H), 3.61 (m, 2H), 2.68-2.73 (m, 1H), 1.40-2.45 (m, 25H); LC/MS: m/z=551 [M+H]+ (Calc: 550).

The compound of formula FI was prepared as follows:

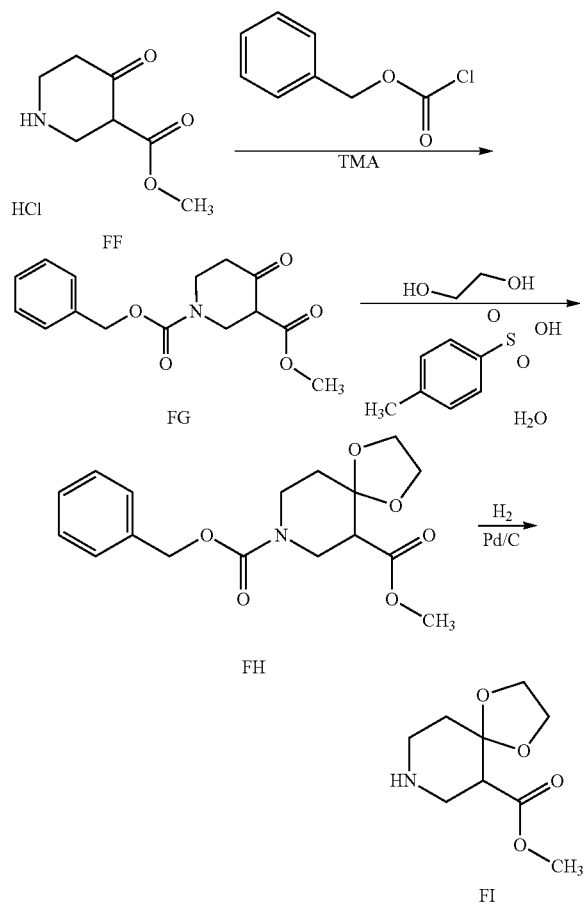

After cooling a mixture of the compound of formula FF (methyl 4-oxopiperidine-3-carboxylate hydrochloride, 5.00 g, 25.8 mmol, Sigma-Aldrich) and TMA (9.00 mL, 64.6 mmol, Sigma-Aldrich) in DCM (50 mL) to a temperature of 0° C., benzyl carbonochloridate (4.85 g, 28.4 mmol, Sigma-Aldrich) was added over a period of 10 min. After addition, the reaction mixture was stirred for 1hr at a temperature of 0° C., warmed to a temperature of about 25° C., and stirred for 1 hr more. Thereafter, the reaction mixture was extracted with DCM/water. The organic portion was separated, washed with 2N aqueous HCl, washed with saturated NaHCO₃, washed with brine, dried (MgSO₄), filtered, and concentrated under reduced pressure to provide 6.38 g of the compound of formula FG as a colorless oil (yield 85%).

The identity of the compound of formula FG, 1-benzyl 3-methyl 4-oxopiperidine-1,3-dicarboxylate, was confirmed using ¹H NMR.

Compound FG: ¹H NMR: $\delta_H$ (400 MHz, CDCl₃): 3.94-4.03 (m, 4H), 3.72 (s, 3H), 3.16-3.21 (m, 1H), 3.02-3.09 (m, 2H), 2.85-2.92 (m, 1H), 2.66-2.68 (m, 1H), 1.99-2.06 (m, 1H), 1.54-1.60 (m, 1H).

A reaction mixture of the compound of formula FG (6.38 g, 21.9 mmol), ethane-1,2-diol (3.66 mL, 65.7 mmol, Sigma-Aldrich), and 4-methylbenzenesulfonic acid monohydrate (200 mg, Sigma-Aldrich) in toluene (150 mL) was refluxed for 21 hr. The reaction mixture was extracted with diethyl ether:water. The organic portion was separated, washed with saturated NaHCO₃, washed with brine, dried (Na₂SO₄), filtered, and concentrated under reduced pressure to provide a residue. The residue was chromatographed with a silica gel column eluted with a gradient of from 0%:100% EtOAc:n-hexane to 50%:50% EtOAc:n-hexane to provide 2.48 g of the compound of formula FH as a colorless oil (yield 34%).

The identity of the compound of formula FH, 8-benzyl 6-methyl 1,4-dioxa-8-azaspiro[4.5]decane-6,8-dicarboxylate, was confirmed using LC/MS.

Compound FM LC/MS: m/z=336 [M+H]+ (Calc: 335), 358 [M+Na]+ (Calc: 357).

Under a hydrogen atmosphere, a mixture of the compound of formula FH (2.48 g, 7.40 mmol), 20% palladium on carbon (200 mg), and MeOH (50 mL) was stirred at a temperature of about 25° C. for 3 hr. The Pd/C was filtered off, the mixture was washed with MeOH, and the filtrate was concentrated under reduced pressure to provide 1.50 g of the compound of formula H as a pale yellow oil (yield >98%).

The identity of the compound of formula FI was confirmed using ¹H NMR.

Compound FI: ¹H NMR: $\delta_H$ (400 MHz, CDCl₃): 11.99 (s, 1H), 7.32-7.40 (m, 5H), 5.16 (s, 2H), 4.14 (m, 2H), 3.78 (s, 3H), 3.63-3.66 (m, 2H), 2.40 (m, 2H).

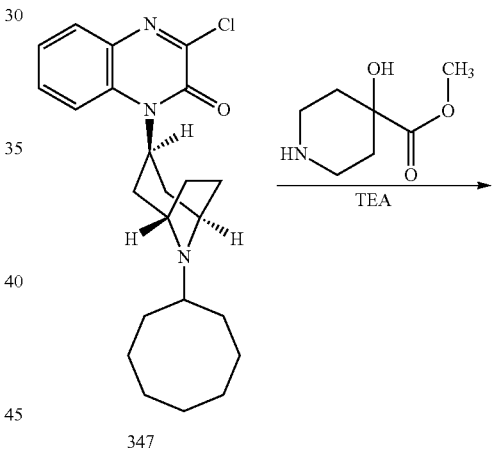

347

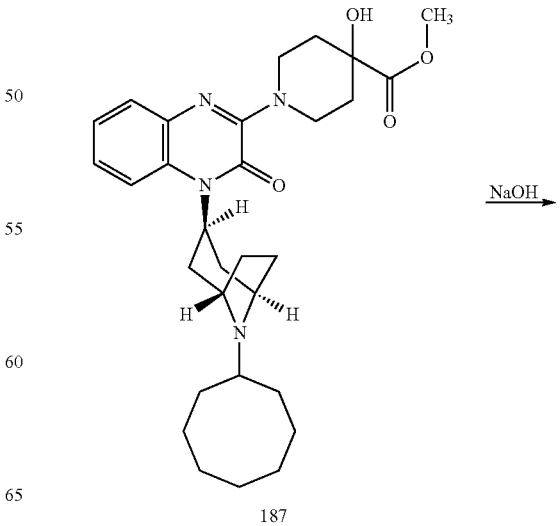

187

187

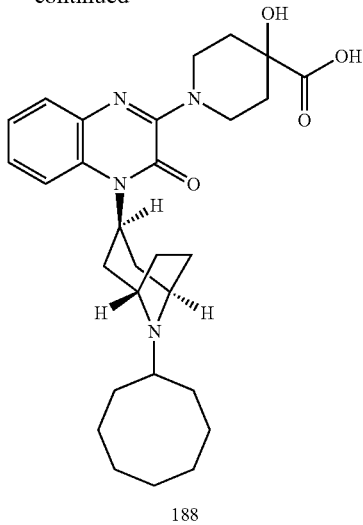

188

188

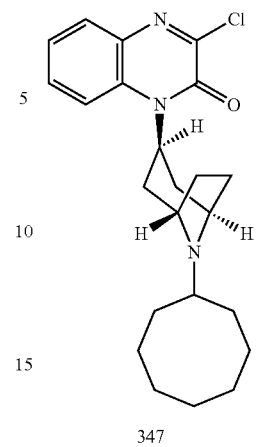 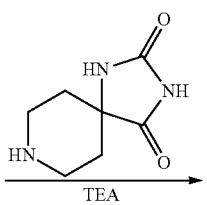

347

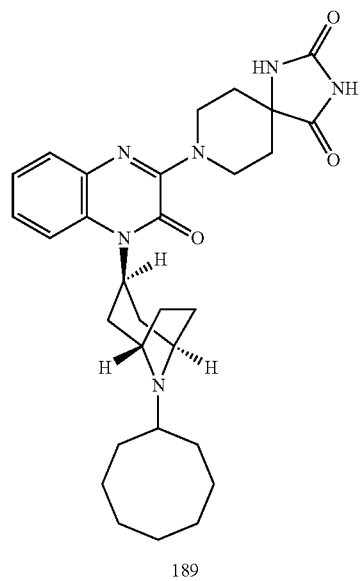

189

Substituted-Quinoxaline-Type Piperidine Compound 187 was prepared by using methyl 4-hydroxypiperidine-4-carboxylate (Sigma-Aldrich) in place of serine amide hydrochloride (yield 97%).

The identity of Substituted-Quinoxaline-Type Piperidine Compound 187, methyl 1-(4-((endo)-8-cyclooctyl-8-azabicyclo[3.2.1]octan-3-yl)-3-oxo-3,4-dihydroquinoxalin-2-yl)-4-hydroxypiperidine-4-carboxylate, was confirmed using $^1$H NMR and LC/MS.

Substituted-Quinoxaline-Type Piperidine Compound 187: $^1$H NMR: $\delta_H$ (400 MHz, DMSO-d$_6$): 7.43 (1H, d, J=8.0 Hz), 7.36 (1H, d, J=8.0 Hz), 7.29 (1H, t, J=8.0 Hz), 7.20 (1H, t, J=8.0 Hz), 5.56 (1H, s), 5.20 (1H, br), 4.42 (2H, d, J=13.18 Hz), 3.65 (3H, s), 3.65-3.60 (2H, m), 3.36 (2H, m), 2.36 (1H, m), 2.18 (2H, m), 2.02-1.30 (20H, m); LC/MS: m/z=523 [M+H]$^+$ (Calc: 522).

Substituted-Quinoxaline-Type Piperidine Compound 188 was prepared from Substituted-Quinoxaline-Type Piperidine Compound 187 in a manner similar to the preparation of Substituted-Quinoxaline-Type Piperidine Compound 111 in Example 5 (yield 84%).

The identity of Substituted-Quinoxaline-Type Piperidine Compound 188, 1-(4-((endo)-8-cyclooctyl-8-azabicyclo[3.2.1]octan-3-yl)-3-oxo-3,4-dihydroquinoxalin-2-yl)-4-hydroxypiperidine-4-carboxylic acid, was confirmed using $^1$H NMR and MS.

Substituted-Quinoxaline-Type Piperidine Compound 188: $^1$H NMR: $\delta_H$ (400 MHz, DMSO-d$_6$): 11.00-10.00 (1H, br) 7.74 (1H, d, J=8.0 Hz), 7.45 (1H, d, J=8.0 Hz), 7.26-7.22 (2H, m), 5.67 (1H, br), 5.90-5.10 (1H, br), 4.47 (2H, d, J=12.6 Hz), 4.18 (2H, s), 3.34 (2H, m), 2.92 (1H, m), 2.54 (2H, m), 2.25 (6H, m), 2.01-1.40 (18H, m); LC/MS (100%, t$_r$=1.53 min): m/z=509 [M+H]$^+$ (Calc: 508).

Substituted-Quinoxaline-Type Piperidine Compound 189 was prepared by using 1,3,8-triazaspiro[4.5]decane-2,4-dione (Sigma-Aldrich) in place of serine amide hydrochloride (yield 92%).

The identity of Substituted-Quinoxaline-Type Piperidine Compound 189, 8-(4-((endo)-8-cyclooctyl-8-azabicyclo[3.2.1]octan-3-yl)-3-oxo-3,4-dihydroquinoxalin-2-yl)-1,3,8-triazaspiro[4.5]decane-2,4-dione, was confirmed using $^1$H NMR and MS.

Substituted-Quinoxaline-Type Piperidine Compound 189: $^1$H NMR: $\delta_H$ (400 MHz, DMSO-d$_6$): 10.71 (1H, s), 8.63 (1H, s), 7.45 (1H, d, J=7.6 Hz), 7.37 (1H, m), 7.31 (1H, m), 7.21 (1H, m), 5.40-5.10 (1H, br), 4.49 (2H, s), 3.62 (2H, s), 3.38 (2H, m), 2.70 (1H, s), 2.36 (1H, m), 2.19 (2H, m), 2.10-1.30 (22H, m); LC/MS (100%, t$_r$=1.53 min): m/z=533 [M+H]$^+$ (Calc: 532).

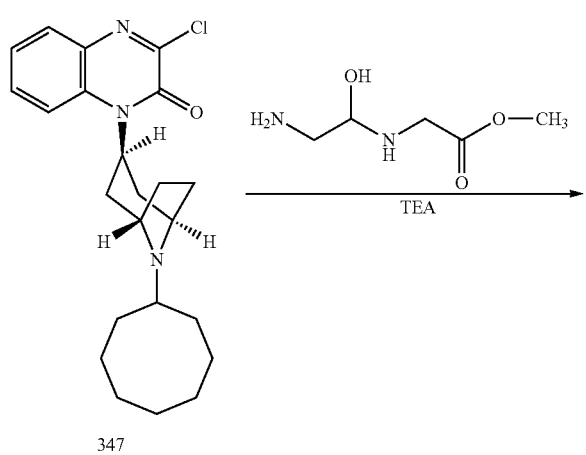

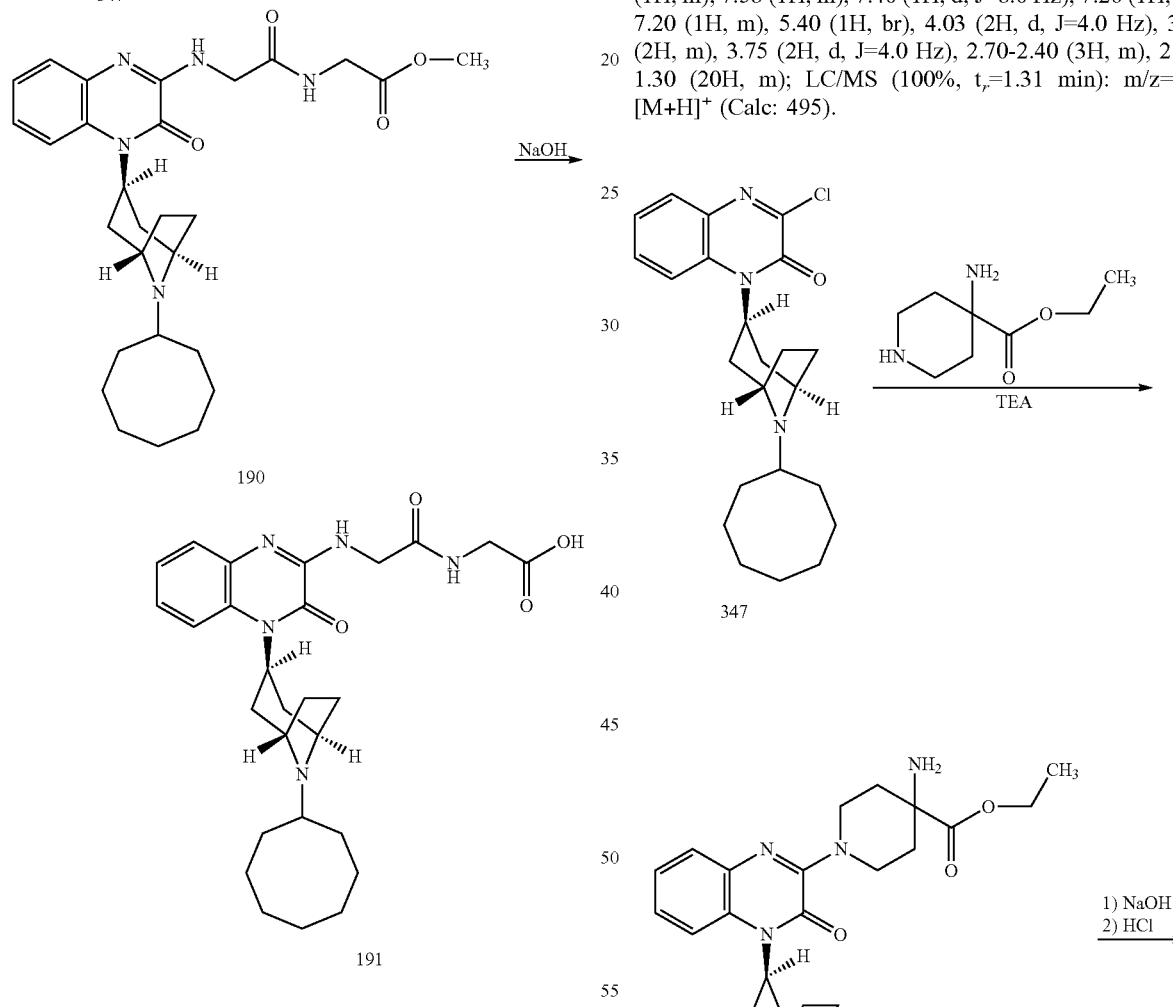

(1H, m), 7.39 (2H, m), 7.27 (1H, m), 7.21 (1H, m), 5.00 (1H, br), 4.02 (2H, d, J=8.0 Hz), 3.65 (2H, m), 3.63 (3H, s), 2.45-1.30 (19H, m); MS: m/z=510 [M+H]⁺ (Calc: 509).

Substituted-Quinoxaline-Type Piperidine Compound 191 was prepared from Substituted-Quinoxaline-Type Piperidine Compound 190 in a manner similar to the preparation of Substituted-Quinoxaline-Type Piperidine Compound 111 in Example 5 (yield 51%).

The identity of Substituted-Quinoxaline-Type Piperidine Compound 191, 2-(2-(4-((endo)-8-cyclooctyl-8-azabicyclo[3.2.1]octan-3-yl)-3-oxo-3,4-dihydroquinoxalin-2-ylamino)acetamido)acetic acid, was confirmed using ¹H NMR and LC/MS.

Substituted-Quinoxaline-Type Piperidine Compound 191: ¹H NMR: $\delta_H$ (400 MHz, DMSO-$d_6$): 8.21 (1H, m), 7.69 (1H, m), 7.58 (1H, m), 7.40 (1H, d, J=8.0 Hz), 7.26 (1H, m), 7.20 (1H, m), 5.40 (1H, br), 4.03 (2H, d, J=4.0 Hz), 3.96 (2H, m), 3.75 (2H, d, J=4.0 Hz), 2.70-2.40 (3H, m), 2.30-1.30 (20H, m); LC/MS (100%, $t_r$=1.31 min): m/z=496 [M+H]⁺ (Calc: 495).

Substituted-Quinoxaline-Type Piperidine Compound 190 was prepared by using methyl 2-(2-aminoacetamido)acetate (Sigma-Aldrich) in place of serine amide hydrochloride (yield 66%).

The identity of Substituted-Quinoxaline-Type Piperidine Compound 190, methyl 2-(2-(4-((endo)-8-cyclooctyl-8-azabicyclo[3.2.1]octan-3-yl)-3-oxo-3,4-dihydroquinoxalin-2-ylamino)acetamido)acetate, was confirmed using ¹H NMR and MS.

Substituted-Quinoxaline-Type Piperidine Compound 190: ¹H NMR: $\delta_H$ (400 MHz, DMSO-$d_6$): 8.35 (1H, m), 7.70

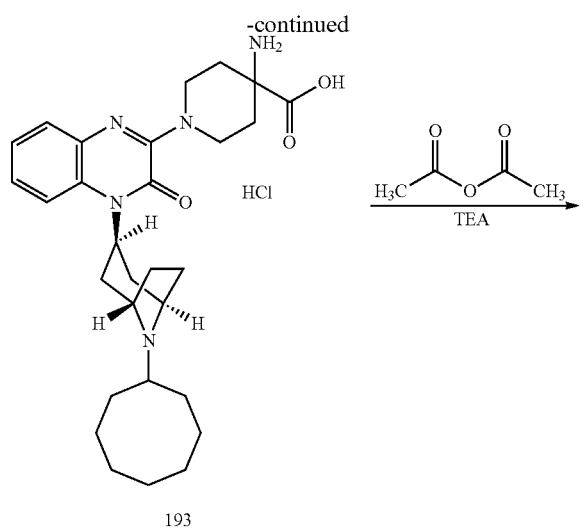

193

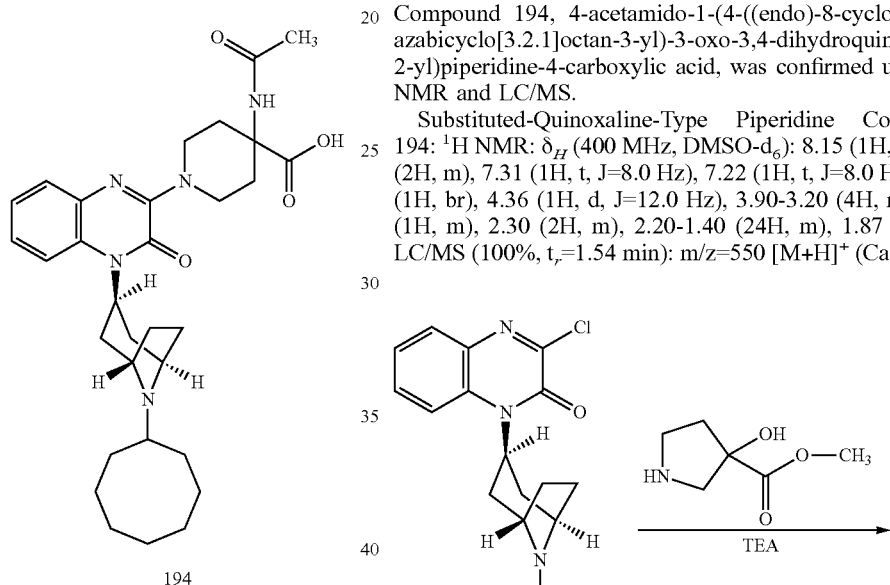

194

Substituted-Quinoxaline-Type Piperidine Compound 192 was prepared by using ethyl 4-aminopiperidine-4-carboxylate (Sigma-Aldrich) in place of serine amide hydrochloride (yield 92%).

The identity of Substituted-Quinoxaline-Type Piperidine Compound 192, ethyl 4-amino-1-(4-((endo)-8-cyclooctyl-8-azabicyclo[3.2.1]octan-3-yl)-3-oxo-3,4-dihydroquinoxalin-2-yl)piperidine-4-carboxylate, was confirmed using $^1$H NMR and MS.

Substituted-Quinoxaline-Type Piperidine Compound 192: $^1$H NMR: $\delta_H$ (400 MHz, DMSO-d$_6$): 7.43 (1H, d, J=8.0 Hz), 7.35 (1H, d, J=8.0 Hz), 7.28 (1H, t, J=8.0 Hz), 7.21 (1H, t, J=8.0 Hz), 5.20 (1H, br), 4.10 (4H, m), 3.62 (4H, m), 2.35 (1H, m), 2.20 (2H, m), 2.10-1.40 (24H, m), 1.20 (3H, t, J=8.0 Hz); MS: m/z=536 [M+H]$^+$ (Calc: 535).

The hydrochloride of Substituted-Quinoxaline-Type Piperidine Compound 193 was prepared from Substituted-Quinoxaline-Type Piperidine Compound 192 in a manner similar to the preparation of Substituted-Quinoxaline-Type Piperidine Compound 174 in Example 7 (yield 89%).

The identity of Substituted-Quinoxaline-Type Piperidine Compound 193, 4-amino-1-(4-((endo)-8-cyclooctyl-8-azabicyclo[3.2.1]octan-3-yl)-3-oxo-3,4-dihydroquinoxalin-2-yl)piperidine-4-carboxylic acid, was confirmed using $^1$H NMR and LC/MS.

Substituted-Quinoxaline-Type Piperidine Compound 193: $^1$H NMR: $\delta_H$ (400 MHz, DMSO-d$_6$): 10.75 (0.9H, m), 10.11 (0.1H, m), 8.82 (3H, s), 7.92 (0.9H, d, J=8.62 Hz), 7.79 (0.1H, d, J=8.0 Hz), 7.53 (1H, d, J=8.0 Hz), 7.30 (2H, m), 5.99-5.89 (0.9H, m), 5.10 (0.1H, m), 4.21-3.87 (8H, m), 2.92 (1H, s), 2.66-2.55 (2H, m), 2.36-1.23 (24H, m); LC/MS (98%, t$_r$=1.09 min): m/z=508 [M+H]$^+$ (Calc: 507).

To a mixture of Substituted-Quinoxaline-Type Piperidine Compound 193 (130 mg, 0.211 mmol) and CH$_2$Cl$_2$ (4 mL) at 0° C. was added acetic anhydride (23.7 mg, 0.232 mmol, Sigma-Aldrich) and TEA (131 µL, 0.948 mmol). The reaction mixture was stirred at 0° C. for 2 h. After concentration under reduced pressure, the reaction mixture was diluted with water (2 mL) to precipitate a white solid. The precipitate was filtered and rinsed with water to provide 38 mg of Substituted-Quinoxaline-Type Piperidine Compound 194 as a white solid (yield 33%).

The identity of Substituted-Quinoxaline-Type Piperidine Compound 194, 4-acetamido-1-(4-((endo)-8-cyclooctyl-8-azabicyclo[3.2.1]octan-3-yl)-3-oxo-3,4-dihydroquinoxalin-2-yl)piperidine-4-carboxylic acid, was confirmed using $^1$H NMR and LC/MS.

Substituted-Quinoxaline-Type Piperidine Compound 194: $^1$H NMR: $\delta_H$ (400 MHz, DMSO-d$_6$): 8.15 (1H, s), 7.45 (2H, m), 7.31 (1H, t, J=8.0 Hz), 7.22 (1H, t, J=8.0 Hz), 5.25 (1H, br), 4.36 (1H, d, J=12.0 Hz), 3.90-3.20 (4H, m), 2.50 (1H, m), 2.30 (2H, m), 2.20-1.40 (24H, m), 1.87 (3H, s); LC/MS (100%, t$_r$=1.54 min): m/z=550 [M+H]$^+$ (Calc: 549).

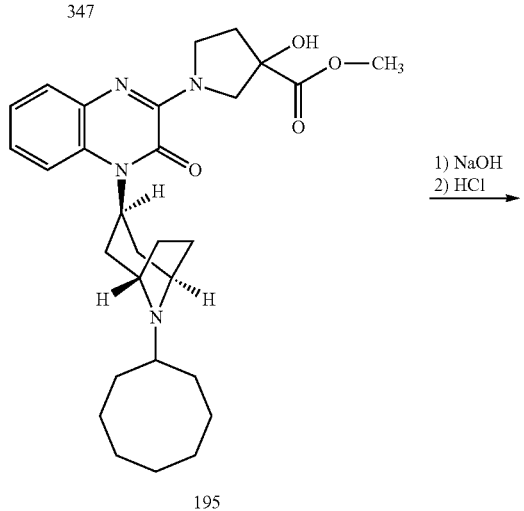

195

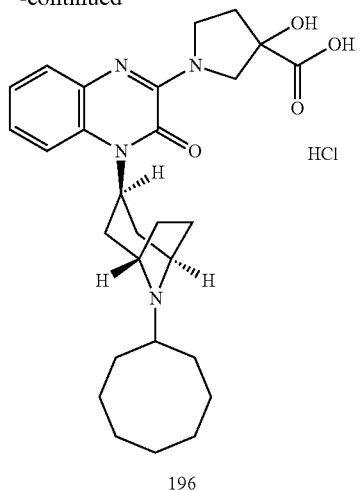

196

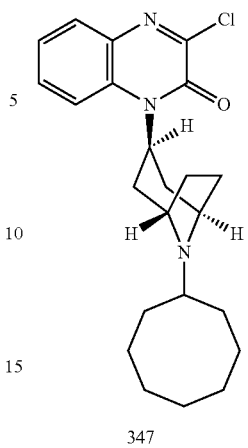

347

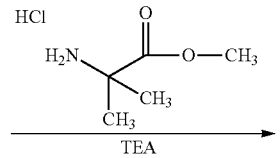

Substituted-Quinoxaline-Type Piperidine Compound 195 was prepared by using methyl 3-hydroxypyrrolidine-3-carboxylate (Sigma-Aldrich) in place of serine amide hydrochloride (yield 55%).

The identity of Substituted-Quinoxaline-Type Piperidine Compound 195, methyl 1-(4-((endo)-8-cyclooctyl-8-azabicyclo[3.2.1]octan-3-yl)-3-oxo-3,4-dihydroquinoxalin-2-yl)-3-hydroxypyrrolidine-3-carboxylate, was confirmed using $^1$H NMR and MS.

Substituted-Quinoxaline-Type Piperidine Compound 195: $^1$H NMR: $\delta_H$ (400 MHz, DMSO-d$_6$): 7.36 (1H, d, J=8.0 Hz), 7.31 (1H, d, J=8.0 Hz), 7.20 (1H, t, J=8.0 Hz), 7.15 (1H, t, J=8.0 Hz), 5.88 (1H, s), 5.10 (1H, br), 4.20 (2H, br), 3.72 (3H, s), 3.62 (2H, m), 3.35 (2H, m), 2.36 (1H, m), 2.30-1.40 (24H, m); MS: m/z=509 [M+H]$^+$ (Calc: 508).

The hydrochloride of Substituted-Quinoxaline-Type Piperidine Compound 196 was prepared from Substituted-Quinoxaline-Type Piperidine Compound 195 in a manner similar to the preparation of Substituted-Quinoxaline-Type Piperidine Compound 174 in Example 7 (yield 90%).

The identity of Substituted-Quinoxaline-Type Piperidine Compound 196, 1-(4-((endo)-8-cyclooctyl-8-azabicyclo[3.2.1]octan-3-yl)-3-oxo-3,4-dihydroquinoxalin-2-yl)-3-hydroxypyrrolidine-3-carboxylic acid, was confirmed using $^1$H NMR and LC/MS.

Substituted-Quinoxaline-Type Piperidine Compound 196: $^1$H NMR: $\delta_H$ (400 MHz, DMSO-d$_6$): 10.58 (0.9H, s), 9.80 (0.1H, s), 7.83 (0.9H, m), 7.74 (0.1H, m), 7.65 (1H, s), 7.25 (2H, m), 5.85 (0.9H, m), 5.05 (0.1H, m), 4.60-3.80 (6H, m), 2.98 (1H, m), 2.62 (2H, m), 2.40-1.30 (22H, m); LC/MS (100%, t$_r$=1.34 min): m/z=495 [M+H]$^+$ (Calc: 494.5).

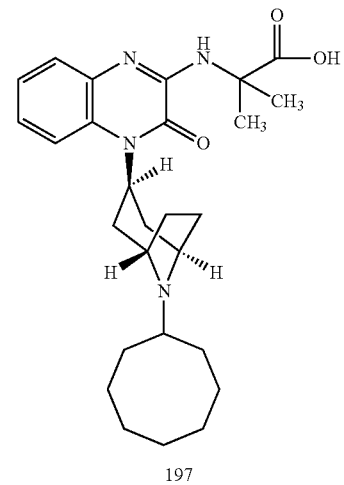

197

Substituted-Quinoxaline-Type Piperidine Compound 197 was prepared by using methyl 2-amino-2-methylpropanoate hydrochloride (Sigma-Aldrich) in place of serine amide hydrochloride (yield 30%).

The identity of Substituted-Quinoxaline-Type Piperidine Compound 197, 2-(4-((endo)-8-cyclooctyl-8-azabicyclo[3.2.1]octan-3-yl)-3-oxo-3,4-dihydroquinoxalin-2-ylamino)-2-methylpropanoic acid, was confirmed using $^1$H NMR and LC/MS.

Substituted-Quinoxaline-Type Piperidine Compound 197: $^1$H NMR: $\delta_H$ (400 MHz, DMSO-d$_6$): 7.58 (1H, br), 7.52 (1H, s), 7.35 (1H, d, J=8.0 Hz), 7.22 (2H, m), 5.40 (1H, br), 3.99 (2H, br), 2.65 (1H, m), 2.50 (2H, m), 2.40-1.40 (20H, m), 1.61 (6H, s); LC/MS (100%, t$_r$=1.81 min): m/z=467 [M+H]$^+$ (Calc: 466.5).

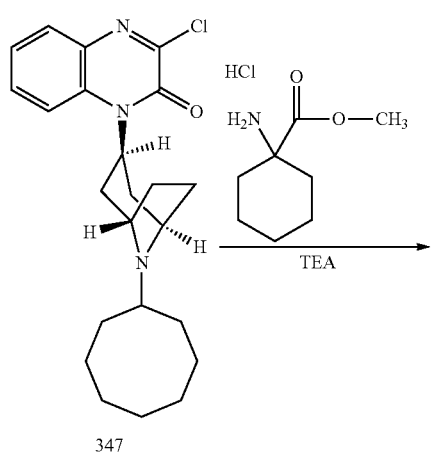

347

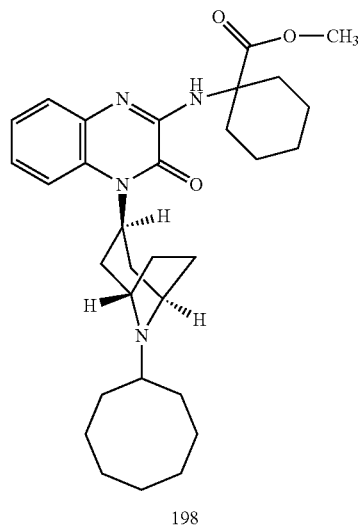

198

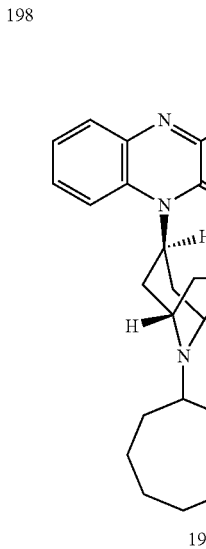

199

Substituted-Quinoxaline-Type Piperidine Compound 198 was prepared by using methyl 1-aminocyclohexanecarboxylate hydrochloride (Sigma-Aldrich) in place of serine amide hydrochloride (yield 35%).

The identity of Substituted-Quinoxaline-Type Piperidine Compound 198, methyl 1-(4-((endo)-8-cyclooctyl-8-azabicyclo[3.2.1]octan-3-yl)-3-oxo-3,4-dihydroquinoxalin-2-ylamino)cyclohexanecarboxylate, was confirmed using $^1$H NMR and MS.

Substituted-Quinoxaline-Type Piperidine Compound 198: $^1$H NMR: $\delta_H$ (400 MHz, DMSO-d$_6$): 7.40 (1H, d, J=8.0 Hz), 7.26 (2H, m), 7.20 (1H, m), 7.05 (1H, s), 5.00 (1H, br), 3.65 (2H, m), 3.56 (3H, s), 2.40-1.20 (33H, m); MS: m/z=521 [M+H]$^+$ (Calc: 520).

Substituted-Quinoxaline-Type Piperidine Compound 199 was prepared from Substituted-Quinoxaline-Type Piperidine Compound 198 in a manner similar to the preparation of Substituted-Quinoxaline-Type Piperidine Compound 111 in Example 5 (yield 81%).

The identity of Substituted-Quinoxaline-Type Piperidine Compound 199, 1-(4-((endo)-8-cyclooctyl-8-azabicyclo[3.2.1]octan-3-yl)-3-oxo-3,4-dihydroquinoxalin-2-ylamino)cyclohexanecarboxylic acid, was confirmed using $^1$H NMR and LC/MS.

Substituted-Quinoxaline-Type Piperidine Compound 199: $^1$H NMR: $\delta_H$(400 MHz, DMSO-d$_6$): 7.70 (1H, br), 7.30 (1H, d, J=8.0 Hz), 7.25 (1H, t, J=8.0 Hz), 7.21 (1H, t, J=8.0 Hz), 6.88 (1H, s), 5.60 (1H, br), 4.02 (2H, br), 2.80-1.30 (31H, m); LC/MS (100%, t$_r$=2.04 min): m/z=507 [M+H]$^+$ (Calc: 506.5).

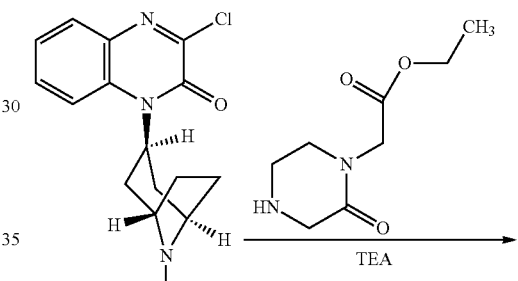

347

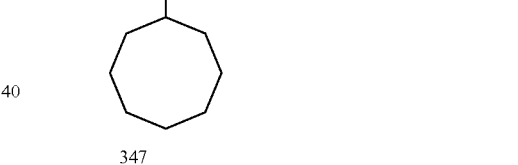

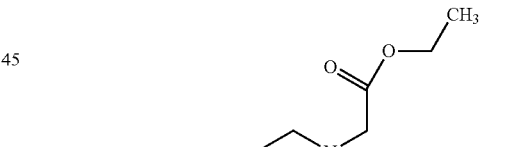

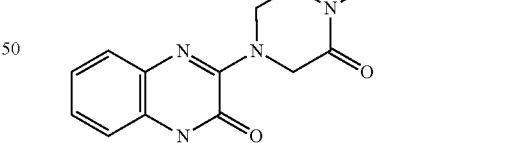

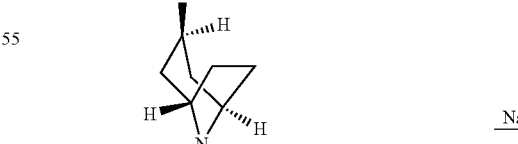

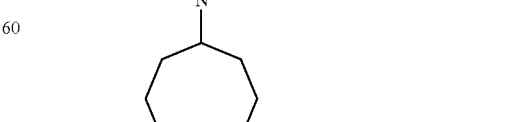

200

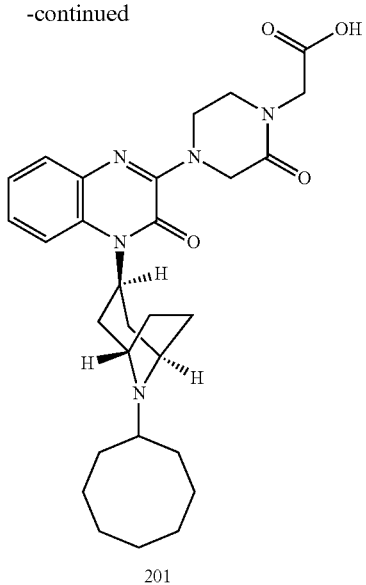

201

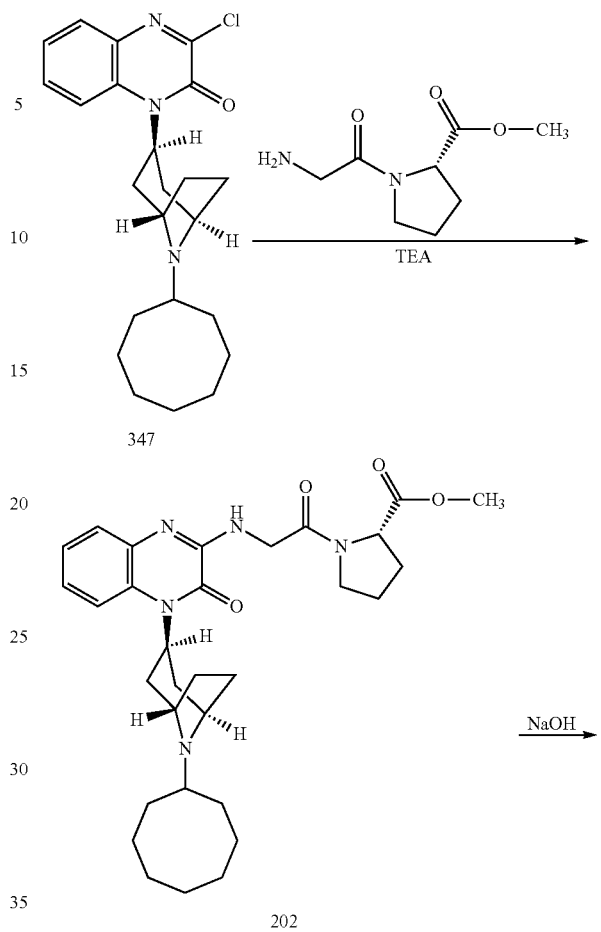

Substituted-Quinoxaline-Type Piperidine Compound 200 was prepared by using ethyl 2-(2-oxopiperazin-1-yl)acetate (Sigma-Aldrich) in place of serine amide hydrochloride (yield 89%).

The identity of Substituted-Quinoxaline-Type Piperidine Compound 200, ethyl 2-(4-(4-((endo)-8-cyclooctyl-8-azabicyclo[3.2.1]octan-3-yl)-3-oxo-3,4-dihydroquinoxalin-2-yl)-2-oxopiperazin-1-yl)acetate, was confirmed using $^1$H NMR and MS.

Substituted-Quinoxaline-Type Piperidine Compound 200: $^1$H NMR: $\delta_H$ (400 MHz, CDCl$_3$): 7.55 (1H, d, J=8.0 Hz), 7.41 (1H, d, J=8.0 Hz), 7.27 (1H, t, J=8.0 Hz), 7.21 (1H, t, J=8.0 Hz), 5.20 (1H, br), 4.59 (2H, s), 4.28 (2H, m), 4.20 (2H, m), 3.67 (2H, m), 3.60 (2H, m), 2.40-2.00 (7H, m), 1.90-1.40 (16H, m), 1.27 (3H, t, J=8.0 Hz); MS: m/z=550 [M+H]$^+$ (Calc: 549).

Substituted-Quinoxaline-Type Piperidine Compound 201 was prepared from Substituted-Quinoxaline-Type Piperidine Compound 200 in a manner similar to the preparation of Substituted-Quinoxaline-Type Piperidine Compound 111 in Example 5 (yield 94%).

The identity of Substituted-Quinoxaline-Type Piperidine Compound 201, 2-(4-(4-((endo)-8-cyclooctyl-8-azabicyclo[3.2.1]octan-3-yl)-3-oxo-3,4-dihydroquinoxalin-2-yl)-2-oxopiperazin-1-yl)acetic acid, was confirmed using $^1$H NMR and LC/MS.

Substituted-Quinoxaline-Type Piperidine Compound 201: $^1$H NMR: $\delta_H$ (400 MHz, DMSO-d$_6$): 7.54 (1H, m), 7.48 (1H, d, J=8.0 Hz), 7.34 (1H, t, J=8.0 Hz), 7.24 (1H, t, J=8.0 Hz), 5.40 (1H, m), 4.44 (2H, s), 4.13 (2H, m), 4.04 (2H, s), 3.85 (2H, m), 3.53 (2H, m), 2.67 (1H, m), 2.37 (2H, m), 2.20-1.35 (20H, m); LC/MS (100%, t$_r$=1.52 min): m/z=522 [M+H]$^+$ (Calc: 521.5).

Substituted-Quinoxaline-Type Piperidine Compound 202 was prepared by using (S)-methyl 1-(2-aminoacetyl)pyrrolidine-2-carboxylate (Sigma-Aldrich) in place of serine amide hydrochloride (yield 56%).

The identity of Substituted-Quinoxaline-Type Piperidine Compound 202, (S)-methyl 1-(2-(4-((endo)-8-cyclooctyl-8-azabicyclo[3.2.1]octan-3-yl)-3-oxo-3,4-dihydroquinoxalin-2-ylamino)acetyl)pyrrolidine-2-carboxylate, was confirmed using $^1$H NMR and MS.

Substituted-Quinoxaline-Type Piperidine Compound 202: $^1$H NMR: $\delta_H$ (400 MHz, CDCl$_3$): 7.51 (1H, d, J=8.0

Hz), 7.41 (1H, d, J=8.0 Hz), 7.20-7.05 (3H, m), 5.20 (1H, br), 4.57 (1H, m), 4.29 (2H, d, J=8.0 Hz), 3.73 (2H, s), 3.65 (2H, m), 2.84 (3H, s), 2.40-1.40 (27H, m); MS: m/z=550 [M+H]+ (Calc: 549).

Substituted-Quinoxaline-Type Piperidine Compound 203 was prepared from Substituted-Quinoxaline-Type Piperidine Compound 202 in a manner similar to the preparation of Substituted-Quinoxaline-Type Piperidine Compound 111 in Example 5 (yield 77%).

The identity of Substituted-Quinoxaline-Type Piperidine Compound 203, 1-(2-(4-((endo)-8-cyclooctyl-8-azabicyclo[3.2.1]octan-3-yl)-3-oxo-3,4-dihydroquinoxalin-2-ylamino)acetyl)pyrrolidine-2-carboxylic acid, was confirmed using $^1$H NMR and LC/MS.

Substituted-Quinoxaline-Type Piperidine Compound 203: $^1$H NMR: $\delta_H$ (400 MHz, DMSO-d$_6$): 7.69 (1H, br), 7.45 (2H, m), 7.23 (2H, m), 5.60 (1H, br), 4.68 (0.2H, m), 4.30-3.80 (4.8H, m), 3.65 (2H, m), 2.90-1.30 (27H, m); LC/MS (100%, t$_r$=1.56 min): m/z=536 [M+H]+ (Calc: 535.5).

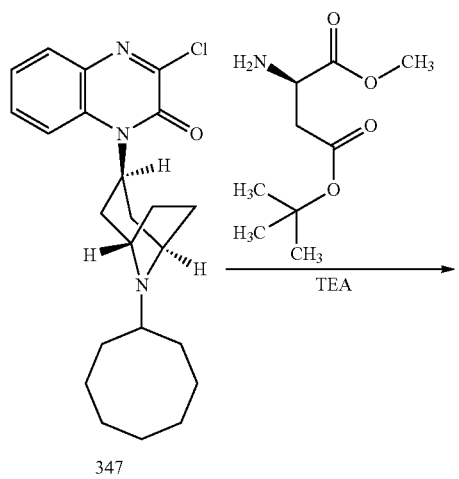

347

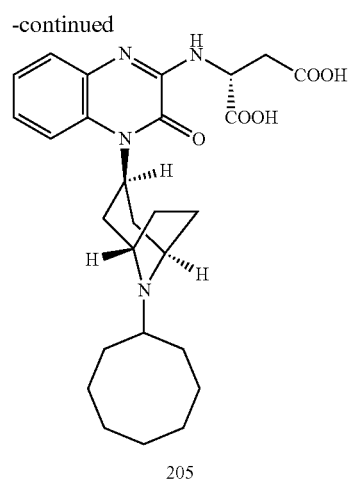

205

Substituted-Quinoxaline-Type Piperidine Compound 204 was prepared by using (R)-4-tert-butyl 1-methyl 2-aminosuccinate (Sigma-Aldrich) in place of serine amide hydrochloride (yield 28%).

The identity of Substituted-Quinoxaline-Type Piperidine Compound 204, (R)-4-tert-butyl 1-methyl 2-(4-((endo)-8-cyclooctyl-8-azabicyclo[3.2.1]octan-3-yl)-3-oxo-3,4-dihydroquinoxalin-2-ylamino)succinate, was confirmed using LC/MS.

Substituted-Quinoxaline-Type Piperidine Compound 204: LC/MS: m/z=567 [M+H]+ (Calc: 567).

Substituted-Quinoxaline-Type Piperidine Compound 205 was prepared from Substituted-Quinoxaline-Type Piperidine Compound 204 in a manner similar to the preparation of Substituted-Quinoxaline-Type Piperidine Compound 111 in Example 5 (yield 66%).

The identity of Substituted-Quinoxaline-Type Piperidine Compound 205, (R)-2-(4-((endo)-8-cyclooctyl-8-azabicyclo[3.2.1]octan-3-yl)-3-oxo-3,4-dihydroquinoxalin-2-ylamino)succinic acid was confirmed using $^1$H NMR and LC/MS.

Substituted-Quinoxaline-Type Piperidine Compound 205: $^1$H NMR: $\delta_H$ (400 MHz, DMSO-d$_6$): 1.35-2.37 (24H, m), 2.73 (1H, d, J=15.72 Hz), 3.62 (2H, s), 4.29 (1H, dd, J=10.65, 4.56 Hz), 5.11-5.42 (1H, m), 7.15-7.29 (2H, m), 7.36-7.44 (3H, m); LC/MS (98%, t$_r$=1.50 min): m/z=497 [M+H]+ (Calc: 497).

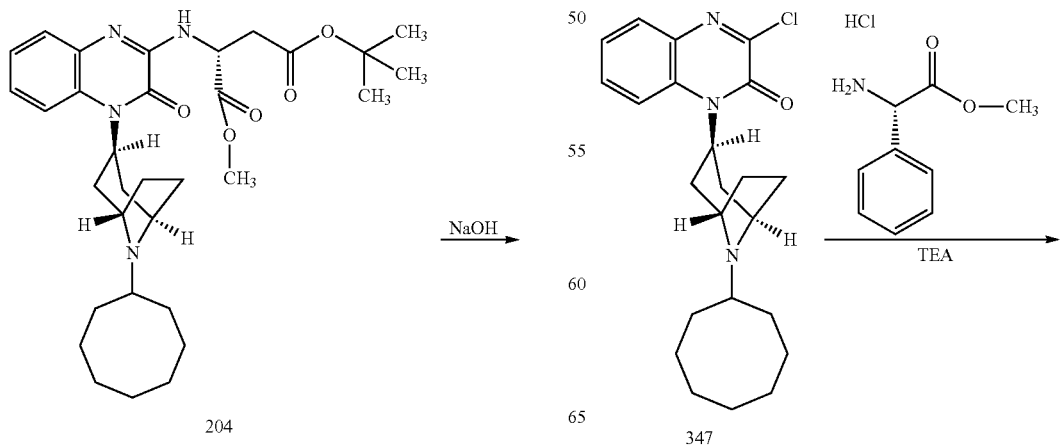

204        347

201

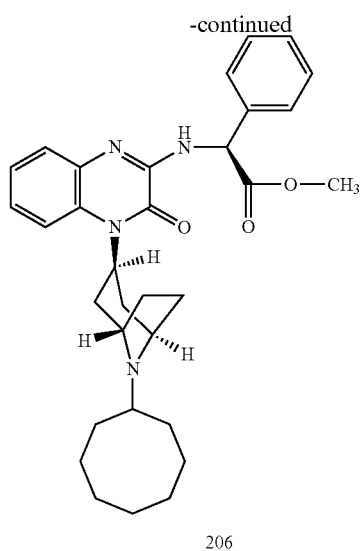

206

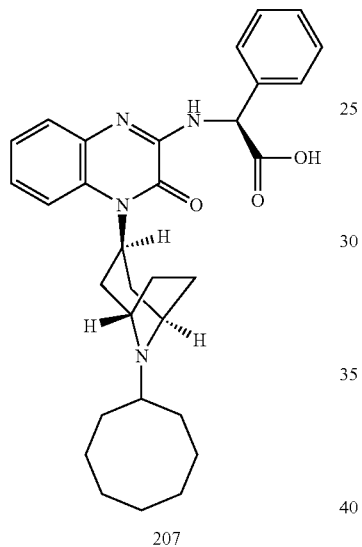

207

202

J=6.59, 2.03 Hz), 9.18 (0.1H, s), 9.94 (0.9H, s), 13.27 (1H, s); LC/MS (98%, $t_r$=2.05 min): m/z=515 [M+H]$^+$ (Calc: 515).

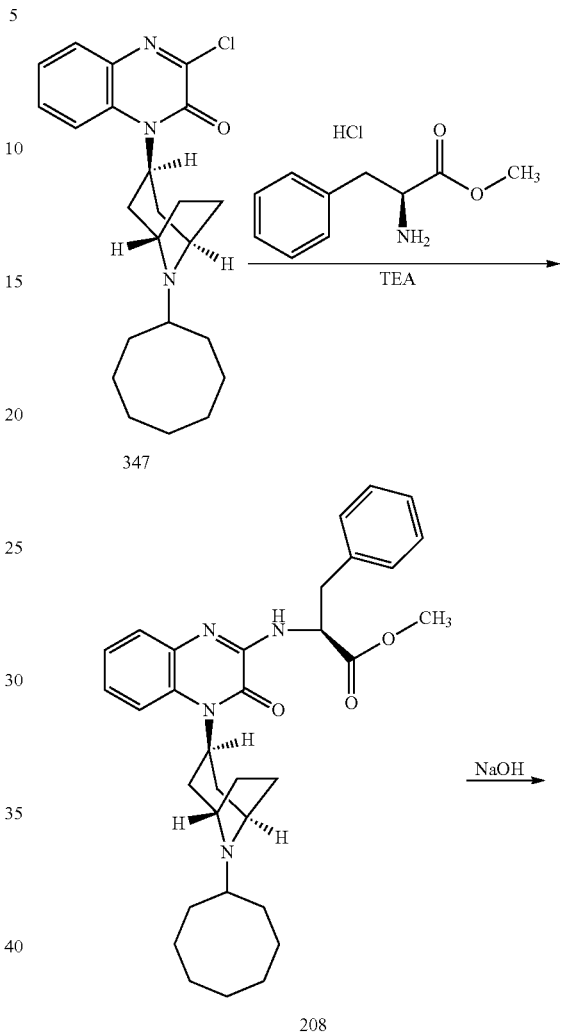

208

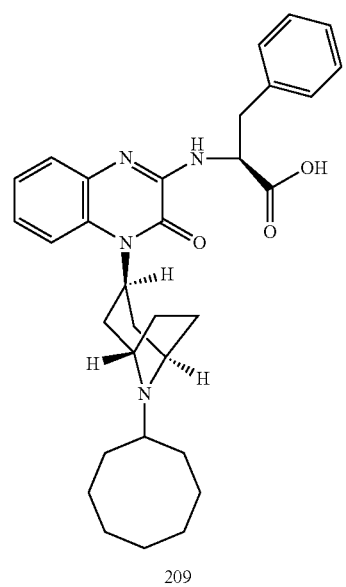

209

Substituted-Quinoxaline-Type Piperidine Compound 206 was prepared by using (9-methyl 2-amino-2-phenylacetate hydrochloride (Sigma-Aldrich) in place of serine amide hydrochloride (yield 54%).

The identity of Substituted-Quinoxaline-Type Piperidine Compound 206, (9-methyl 2-(4-((endo)-8-cyclooctyl-8-azabicyclo[3.2.1]octan-3-yl)-3-oxo-3,4-dihydroquinoxalin-2-ylamino)-2-phenylacetate, was confirmed using LC/MS.

Substituted-Quinoxaline-Type Piperidine Compound 206: LC/MS: m/z=529 [M+H]$^+$ (Calc: 529).

Substituted-Quinoxaline-Type Piperidine Compound 207 was prepared from Substituted-Quinoxaline-Type Piperidine Compound 206 in a manner similar to the preparation of Substituted-Quinoxaline-Type Piperidine Compound 111 in Example 5 (yield 15%).

The identity of Substituted-Quinoxaline-Type Piperidine Compound 207, (S)-2-(4-((endo)-8-cyclooctyl-8-azabicyclo[3.2.1]octan-3-yl)-3-oxo-3,4-dihydroquinoxalin-2-ylamino)-2-phenylacetic acid, was confirmed using $^1$H NMR and LC/MS.

Substituted-Quinoxaline-Type Piperidine Compound 207: $^1$H NMR: $\delta_H$(400 MHz, DMSO-d$_6$): 1.32-2.73 (22H, m), 2.94 (1H, s), 4.24 (2H, s), 5.14 (0.1H, s), 5.61 (1H, d, J=6.59 Hz), 5.69 (0.9H, s), 7.21-7.54 (9H, m), 7.73 (1H, dd, Substituted-Quinoxaline-Type Piperidine Compound 208 was prepared by using (S)-methyl 2-amino-3-phenylpropanoate hydrochloride (Sigma-Aldrich) in place of serine amide hydrochloride (yield 86%).

The identity of Substituted-Quinoxaline-Type Piperidine Compound 208, (S)-methyl 2-(4-((endo)-8-cyclooctyl-8-azabicyclo[3.2.1]octan-3-yl)-3-oxo-3,4-dihydroquinoxalin-2-ylamino)-3-phenylpropanoate, was confirmed using LC/MS.

Substituted-Quinoxaline-Type Piperidine Compound 208: LC/MS: m/z=542 [M+H]$^+$ (Calc: 543).

Substituted-Quinoxaline-Type Piperidine Compound 209 was prepared from Substituted-Quinoxaline-Type Piperidine Compound 208 in a manner similar to the preparation of Substituted-Quinoxaline-Type Piperidine Compound 111 in Example 5 (yield 33%).

The identity of Substituted-Quinoxaline-Type Piperidine Compound 209, (S)-2-(4-((endo)-8-cyclooctyl-8-azabicyclo[3.2.1]octan-3-yl)-3-oxo-3,4-dihydroquinoxalin-2-ylamino)-3-phenylpropanoic acid, was confirmed using $^1$H NMR and LC/MS.

Substituted-Quinoxaline-Type Piperidine Compound 209: $^1$H NMR: $\delta_H$ (400 MHz, DMSO-d$_6$): 1.32-2.40 (23H, m), 3.19-3.29 (2H, m), 3.75 (2H, s), 4.64 (1H, dd, J=12.17, 7.1 Hz), 5.23 (1H, br s), 7.26-7.12 (7H, m), 7.49-7.31 (3H, m); LC/MS (98%, t$_r$=2.04 min): m/z=529 [M+H]$^+$ (Calc: 529).

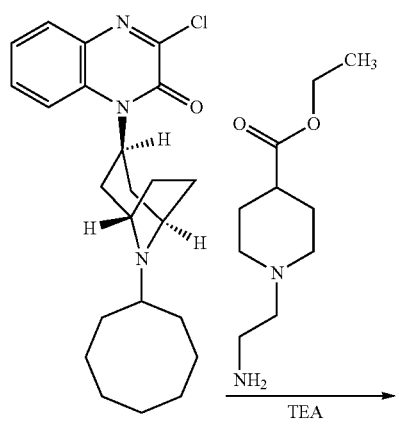

347

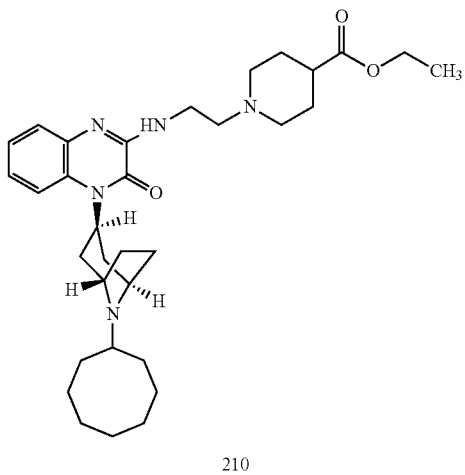

210

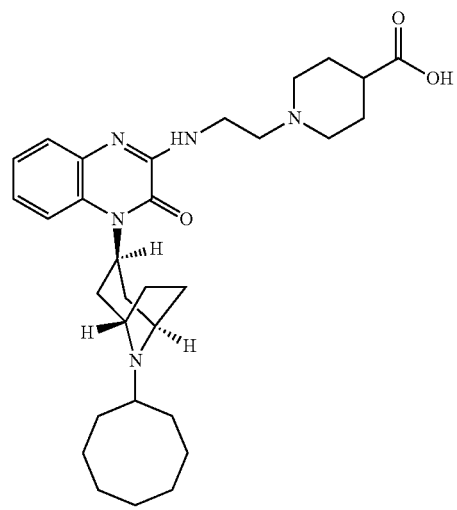

211

Substituted-Quinoxaline-Type Piperidine Compound 210 was prepared by using ethyl 1-(2-aminoethyl)piperidine-4-carboxylate (Sigma-Aldrich) in place of serine amide hydrochloride (yield 77%).

The identity of Substituted-Quinoxaline-Type Piperidine Compound 210, ethyl 14244-((endo)-8-cyclooctyl-8-azabicyclo[3.2.1]octan-3-yl)-3-oxo-3,4-dihydroquinoxalin-2-ylamino)ethyl)piperidine-4-carboxylate, was confirmed using $^1$H NMR and LC/MS.

Substituted-Quinoxaline-Type Piperidine Compound 210: $^1$H NMR: $\delta_H$ (400 MHz, CDCl$_3$): 1.26 (3H, t, J=7.1 Hz), 1.35-2.43 (30H, m), 2.61 (2H, t, J=6.08 Hz), 2.92 (2H, d, J=11.15 Hz), 3.59 (2H, q, J=5.75 Hz), 3.67 (2H, br s), 4.14 (2H, q, J=6.93 Hz), 5.18 (1H, br s), 6.71 (1H, br s), 7.15-7.22 (2H, m), 7.38-7.45 (1H, m), 7.49-7.55 (1H, m); LC/MS: m/z=564 [M+H]$^+$ (Calc: 564).

Substituted-Quinoxaline-Type Piperidine Compound 211 was prepared from Substituted-Quinoxaline-Type Piperidine Compound 210 in a manner similar to the preparation of Substituted-Quinoxaline-Type Piperidine Compound 111 in Example 5 (yield 79%).

The identity of Substituted-Quinoxaline-Type Piperidine Compound 211, 1-(2-(4-((endo)-8-cyclooctyl-8-azabicyclo[3.2.1]octan-3-yl)-3-oxo-3,4-dihydroquinoxalin-2-ylamino)ethyl)piperidine-4-carboxylic acid, was confirmed using $^1$H NMR and LC/MS.

Substituted-Quinoxaline-Type Piperidine Compound 211: $^1$H NMR: $\delta_H$ (400 MHz, DMSO-d$_6$): 1.32-2.56 (32H, m), 2.86 (2H, d, J=11.15 Hz), 3.46 (2H, d, J=5.58 Hz), 3.62 (2H, s), 5.03 (1H, br s), 7.15-7.25 (2H, m), 7.31-7.42 (3H, m), 12.16 (1H, br s); LC/MS (t$_r$=0.84 min): m/z=536 [M+H]$^+$ (Calc: 536).

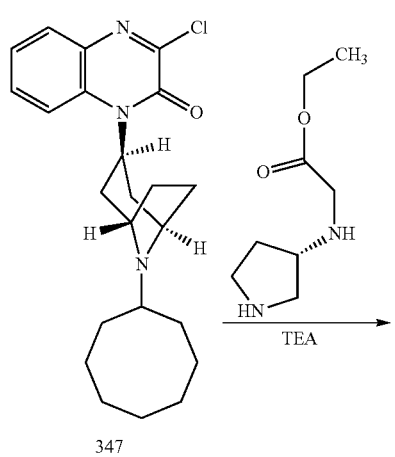

347

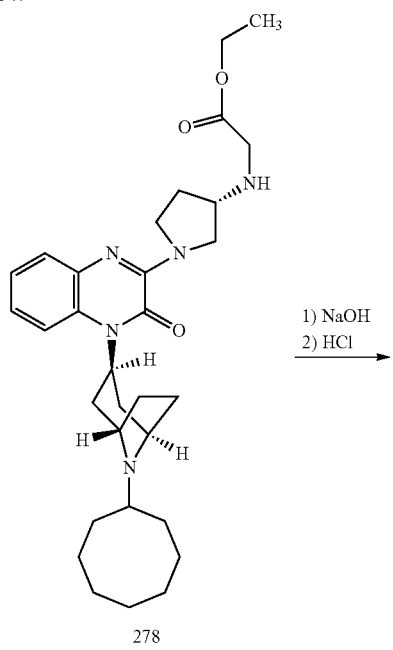

278

Substituted-Quinoxaline-Type Piperidine Compound 278 was prepared by using (S)-ethyl 2-(pyrrolidin-3-ylamino)acetate (Sigma-Aldrich) in place of serine amide hydrochloride (yield 80%).

The identity of Substituted-Quinoxaline-Type Piperidine Compound 278, ethyl 2-((S)-1-(4-((endo)-8-cyclooctyl-8-azabicyclo[3.2.1]octan-3-yl)-3-oxo-3,4-dihydroquinoxalin-2-yl)pyrrolidin-3-ylamino)acetate, was confirmed by $^1$H NMR and LC/MS.

Substituted-Quinoxaline-Type Piperidine Compound 278: $^1$H NMR: $\delta_H$ (CDCl$_3$): 7.44 (1H, m), 7.31 (1H, m), 7.13-7.12 (2H, m), 4.17 (2H, q, J=8.0 Hz), 4.15-3.60 (4H-1, m), 3.65 (2H, m), 3.43 (2H, s), 3.40 (1H, m), 2.38-2.00 (7H, m), 1.86-1.40 (18H, m), 1.26 (3H, t, J=8.0 Hz); LC/MS: m/z=536 [M+H]$^+$ (Calc: 535.7).

The hydrochloride of Substituted-Quinoxaline-Type Piperidine Compound 279 was prepared from Substituted-Quinoxaline-Type Piperidine Compound 278 in a manner similar to the preparation of Substituted-Quinoxaline-Type Piperidine Compound 174 in Example 7 (yield 47%).

The identity of Substituted-Quinoxaline-Type Piperidine Compound 279, 2-((S)-1-(4-((endo)-8-cyclooctyl-8-azabicyclo[3.2.1]octan-3-yl)-3-oxo-3,4-dihydroquinoxalin-2-yl)pyrrolidin-3-ylamino)acetic acid, was confirmed by $^1$H NMR and LC/MS.

Substituted-Quinoxaline-Type Piperidine Compound 279: $^1$H NMR: $\delta_H$ (DMSO-d$_6$): 10.78 (0.9H, d, J=7.6 Hz), 10.2 (0.1H, m), 9.71 (2H, s), 7.88 (0.9H, d, J=7.6 Hz), 7.75 (0.1H, m), 7.53 (1H, s), 7.23 (2H, m), 5.92 (1H, m), 4.22-3.91 (9H, m), 2.92 (1H, m), 2.65-2.60 (2H, m), 2.40-1.20 (22H, m); LC/MS (97%, t$_r$=1.16 min): m/z=508 [M+H]$^+$ (Calc: 507.6).

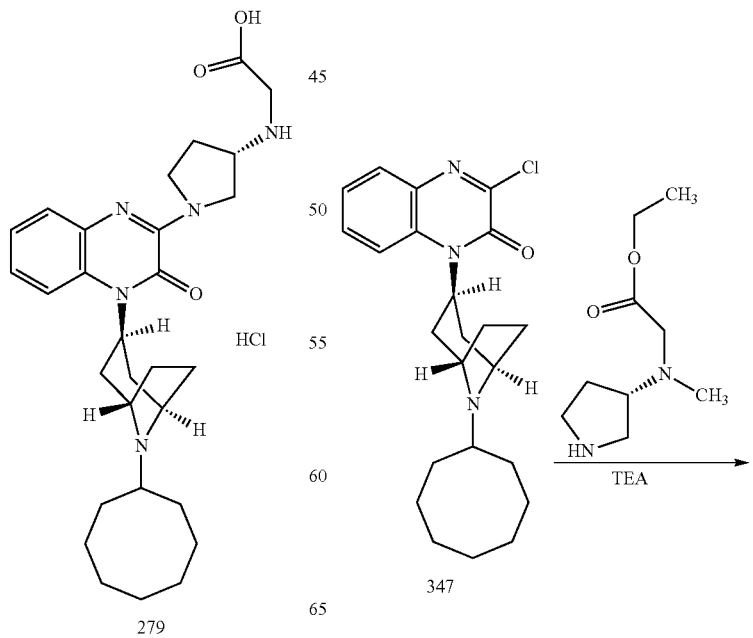

279

347

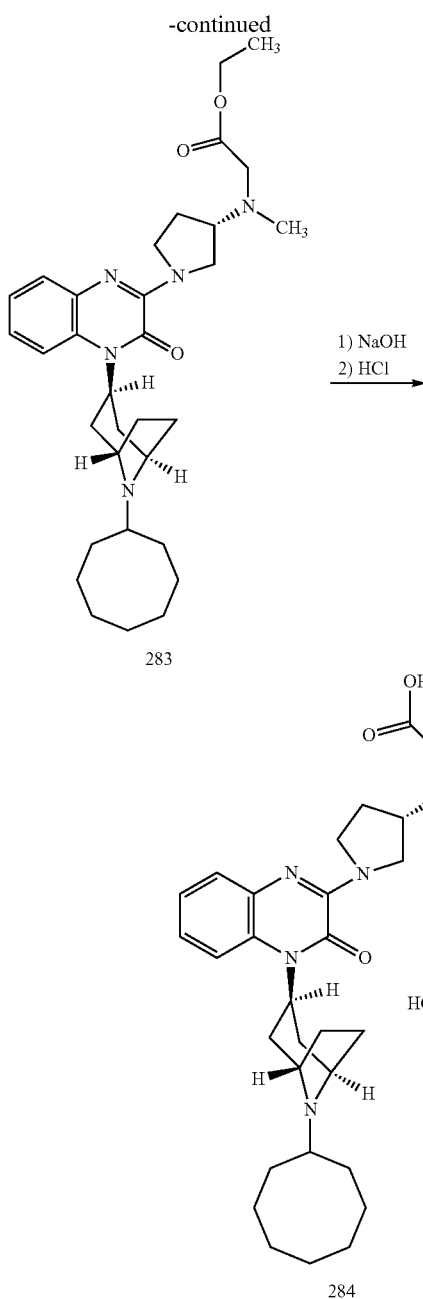

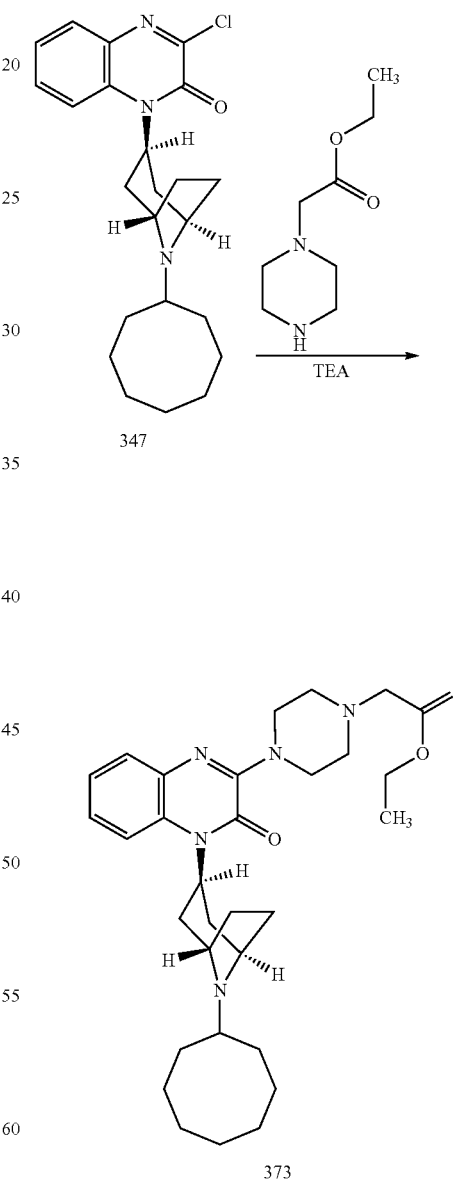

Substituted-Quinoxaline-Type Piperidine Compound 283 was prepared by using (S)-ethyl 2-(methyl(pyrrolidin-3-yl)amino)acetate (Sigma-Aldrich) in place of serine amide hydrochloride (yield 97%).

The identity of Substituted-Quinoxaline-Type Piperidine Compound 283, ethyl 2-(((S)-1-(4-((endo)-8-cyclooctyl-8-azabicyclo[3.2.1]octan-3-yl)-3-oxo-3,4-dihydroquinoxalin-2-yl)pyrrolidin-3-yl)(methyl)amino)acetate, was confirmed by $^1$H NMR and LC/MS.

Substituted-Quinoxaline-Type Piperidine Compound 283: $^1$H NMR: $\delta_H$ (CDCl$_3$): 7.44 (1H, m), 7.33 (1H, m), 7.13 (2H, m), 5.30 (1H, br), 4.20 (2H, q, J=8.0 Hz), 3.65 (2H, s), 3.39 (4H, m), 2.49 (3H, s), 2.40-1.40 (27H, m) 1.38 (3H, t, J=8.0 Hz); LC/MS: m/z=550 [M+H]$^+$ (Calc: 549.7).

The hydrochloride of Substituted-Quinoxaline-Type Piperidine Compound 284 was prepared from Substituted-Quinoxaline-Type Piperidine Compound 283 in a manner similar to the preparation of Substituted-Quinoxaline-Type Piperidine Compound 174 in Example 7 (yield 98%).

The identity of Substituted-Quinoxaline-Type Piperidine Compound 284, 2-(((S)-1-(4-((endo)-8-cyclooctyl-8-azabicyclo[3.2.1]octan-3-yl)-3-oxo-3,4-dihydroquinoxalin-2-yl)pyrrolidin-3-yl)(methyl)amino)acetic acid, was confirmed by $^1$H NMR and LC/MS.

Substituted-Quinoxaline-Type Piperidine Compound 284: $^1$H NMR: $\delta_H$ (DMSO-d$_6$): 11.00 (1H, br), 10.79 (0.9H, m), 10.2 (0.1H, m), 7.88 (0.9H, d, J=7.6 Hz), 7.70 (0.1H, m), 7.50 (1H, d, J=7.6 Hz), 7.22 (2H, m), 5.93 (1H, s), 4.40-3.60 (7H, m), 2.93 (3H, s), 2.70-1.40 (27H, m); LC/MS (99%, t$_r$=1.13 min); LC/MS: m/z=522 [M+H]$^+$ (Calc: 521.6).

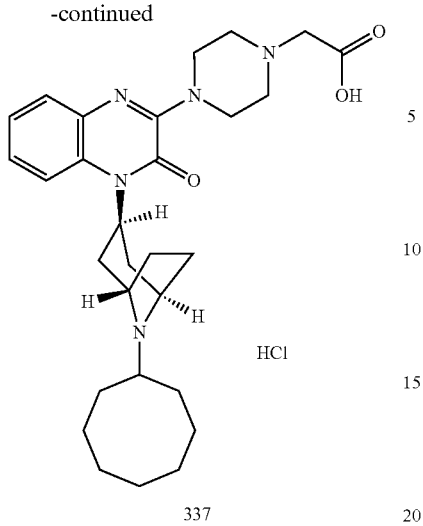

337

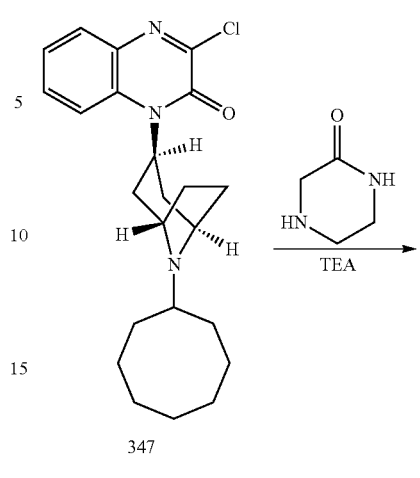

347

Substituted-Quinoxaline-Type Piperidine Compound 373 was prepared by using ethyl 2-(piperazin-1-yl)acetate (Sigma-Aldrich) in place of serine amide hydrochloride (yield 81%).

The identity of Substituted-Quinoxaline-Type Piperidine Compound 373, ethyl 24444-((endo)-8-cyclooctyl-8-azabicyclo[3.2.1]octan-3-yl)-3-oxo-3,4-dihydroquinoxalin-2-yl)piperazin-1-yl)acetate, was confirmed using $^1$H NMR and LC/MS.

Substituted-Quinoxaline-Type Piperidine Compound 373: $^1$H NMR: $\delta_H$ (DMSO-d$_6$): 1.19 (3H, t, J=7.6 Hz), 1.32-2.40 (23H, m), 2.64 (4H, t, J=4.56 Hz), 3.27 (2H, s), 3.62 (2H, br s), 3.79 (4H, br s), 4.09 (2H, q, J=7.1 Hz), 7.20 (1H, t, J=7.35 Hz), 7.31 (1H, t, J=7.1 Hz), 7.37 (1H, d, J=8.62 Hz), 7.45 (1H, d, J=4.56 Hz); LC/MS: m/z=536 [M+H]$^+$ (Calc: 536).

The hydrochloride of Substituted-Quinoxaline-Type Piperidine Compound 337 was prepared from Substituted-Quinoxaline-Type Piperidine Compound 373 in a manner similar to the preparation of Substituted-Quinoxaline-Type Piperidine Compound 174 in Example 7 (yield 70%).

The identity of Substituted-Quinoxaline-Type Piperidine Compound 337, 2-(4-(4-((endo)-8-cyclooctyl-8-azabicyclo[3.2.1]octan-3-yl)-3-oxo-3,4-dihydroquinoxalin-2-yl)piperazin-1-yl)acetic acid, was confirmed using $^1$H NMR and LC/MS.

Substituted-Quinoxaline-Type Piperidine Compound 337: $^1$H NMR: $\delta_H$ (400 MHz, DMSO-d$_6$): 1.31-2.35 (22H, m), 2.61 (2H, dd, J=20.78, 11.66 Hz), 2.93 (1H, s), 3.01 (4H, s), 3.59 (2H, s), 3.95 (4H, s), 4.21 (2H, s), 5.10 (0.1H, s), 5.83-5.96 (0.9H, m), 7.22-7.36 (2H, m), 7.48 (1H, dd, J=7.60, 1.52 Hz), 7.78 (0.1H, d, J=8.62 Hz), 7.90 (0.9H, d, J=8.11 Hz), 9.84 (0.1H, s), 10.64 (0.9H, s), 12.18 (1H, br s); LC/MS (t$_r$=1.10 min): m/z=508 [M+H]$^+$ (Calc: 508).

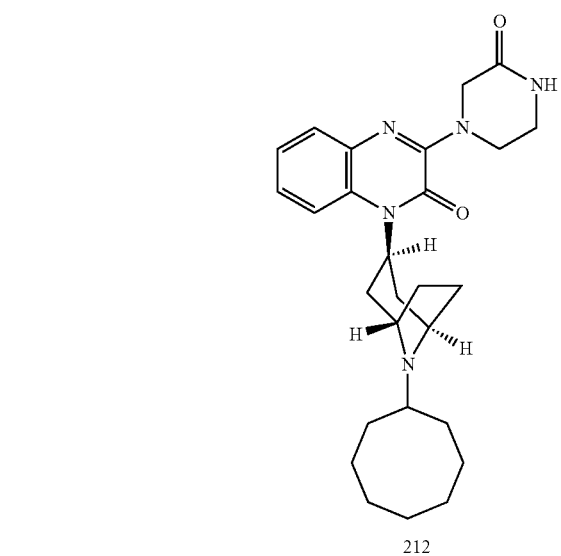

212

Substituted-Quinoxaline-Type Piperidine Compound 212 was prepared by using piperazin-2-one in place of serine amide hydrochloride (yield 99%).

The identity of Substituted-Quinoxaline-Type Piperidine Compound 212, 1-((endo)-8-cyclooctyl-8-azabicyclo[3.2.1]octan-3-yl)-3-(3-oxopiperazin-1-yl)quinoxalin-2(1H)-one, was confirmed using $^1$H NMR and LC/MS.

Substituted-Quinoxaline-Type Piperidine Compound 212: $^1$H NMR: $\delta_H$ (400 MHz, CDCl$_3$): 1.35-2.42 (23H, m), 3.57 (2H, s), 3.66 (2H, s), 4.17 (2H, s), 4.52 (2H, s), 5.19 (1H, br s), 6.53 (1H, br s), 7.18-7.32 (2H, m), 7.41 (1H, d, J=8.11 Hz), 7.56 (1H, d, J=8.11 Hz); LC/MS (t$_r$=1.66 min): m/z=464 [M+H]$^+$ (Calc: 464).

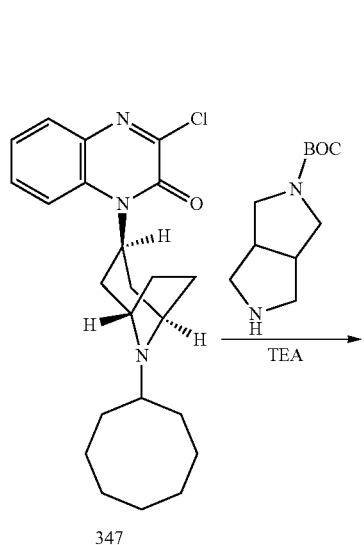
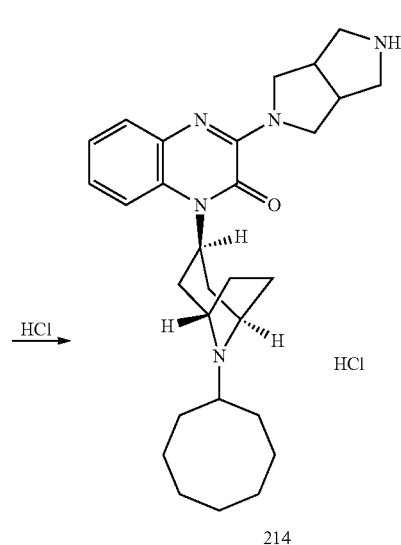
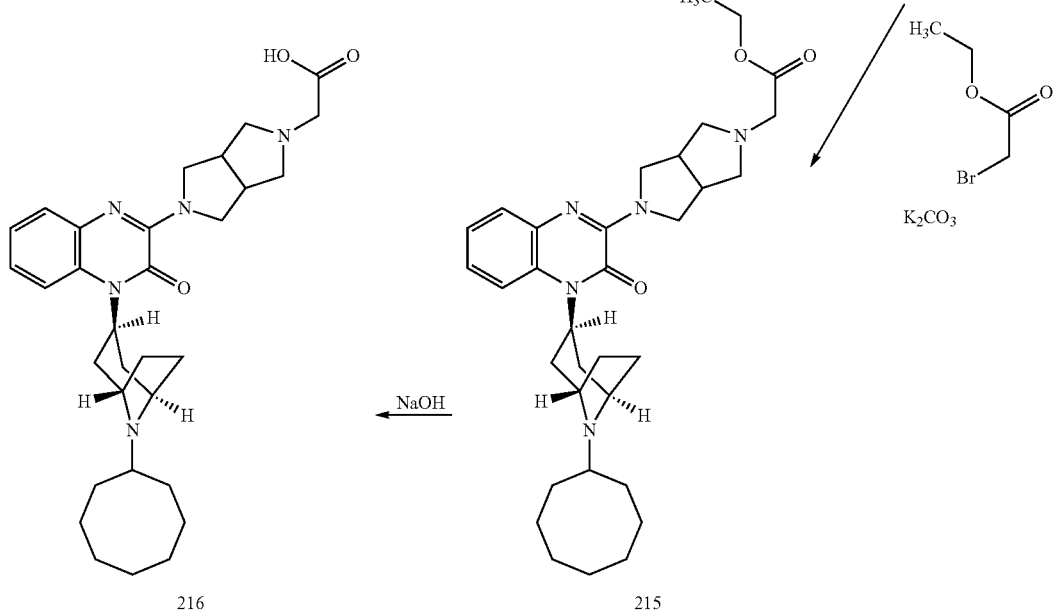

Substituted-Quinoxaline-Type Piperidine Compound 213 was prepared by using tert-butyl hexahydropyrrolo[3,4-c]pyrrole-2(1H)-carboxylate in place of serine amide hydrochloride (yield 98%).

The identity of Substituted-Quinoxaline-Type Piperidine Compound 213, tert-butyl 5-(4-((endo)-8-cyclooctyl-8-azabicyclo[3.2.1]octan-3-yl)-3-oxo-3,4-dihydroquinoxalin-2-yl)hexahydropyrrolo[3,4-c]pyrrole-2(1H)-carboxylate, was confirmed using $^1$H NMR and LC/MS.

Substituted-Quinoxaline-Type Piperidine Compound 213: $^1$H NMR: δ (400 MHz, DMSO) 7.34 (1H, d, J=8.0 Hz), 7.28 (1H, d, J=8.0 Hz), 7.18 (1H, t, J=8.0 Hz), 7.15 (1H, d, J=8.0 Hz), 5.10 (1H, br), 4.08 (2H, br), 3.80-3.50 (4H, m), 3.18 (2H, m), 2.80 (2H, m), 2.34 (1H, m), 2.16 (2H, m), 2.10-1.45 (22H, m), 1.39 (9H, s); LC/MS: m/z=576 [M+H]$^+$ (Calc: 575.3).

The hydrochloride of Substituted-Quinoxaline-Type Piperidine Compound 214 was prepared from Substituted-Quinoxaline-Type Piperidine Compound 213 in a manner similar to the preparation of Substituted-Quinoxaline-Type Piperidine Compound 5 in Example 7 (yield 99%).

The identity of Substituted-Quinoxaline-Type Piperidine Compound 214, 1-((endo)-8-cyclooctyl-8-azabicyclo[3.2.1]octan-3-yl)-3-(hexahydropyrrolo[3,4-c]pyrrol-2(1H)-yl)quinoxalin-2(1H)-one, was confirmed using $^1$H NMR and LC/MS.

Substituted-Quinoxaline-Type Piperidine Compound 214: $^1$H NMR: δ$_H$ (400 MHz, DMSO): 10.73 (1H, m), 9.69 (1H, m), 9.62 (1H, m), 7.88 (1H, d, J=8.0 Hz), 7.65 (1H, d, J=8.0 Hz), 7.28 (2H, m), 5.88 (1H, m), 4.22 (2H, m), 4.20-3.90 (4H, m), 3.45 (2H, m), 3.15 (4H, m), 2.90 (1H, m), 2.60 (2H, m), 2.40-1.30 (20H, m); LC/MS: m/z=476 [M+H]$^+$ (Calc: 475.3).

At a temperature of about 25° C., ethyl 2-bromoacetate (55 mg, 0.328 mmol, Sigma-Aldrich) and K$_2$CO$_3$ (151 mg, 1.094 mmol) were added to a mixture of Substituted-Quinoxaline-Type Piperidine Compound 214 (150 mg, 0.273 mmol) in DMF (4 mL). The resulting reaction mixture was stirred at about 25° C. for 3 h. The reaction mixture was diluted with water (5 mL) and extracted three times with EtOAc (10 mL for each extraction). The organic portions were combined, washed with saturated aqueous NaCl (10 mL), dried (MgSO$_4$), and concentrated under reduced pressure to provide a residue. The residue was chromatographed with a silica gel column eluted with a gradient of from 100%:0% CHCl$_3$:MeOH to 90%:10% CHCl$_3$:MeOH to provide 135 mg of Substituted-Quinoxaline-Type Piperidine Compound 215 as a white amorphous solid (yield 88%).

The identity of Substituted-Quinoxaline-Type Piperidine Compound 215, ethyl 2-(5-(4-((endo)-8-cyclooctyl-8-azabicyclo[3.2.1]octan-3-yl)-3-oxo-3,4-dihydroquinoxalin-2-yl)hexahydropyrrolo[3,4-c]pyrrol-2(1H)-yl)acetate, was confirmed using $^1$H NMR and LC/MS.

Substituted-Quinoxaline-Type Piperidine Compound 215: $^1$H NMR: δ$_H$ (400 MHz, DMSO): 10.40 (1H, m), 7.73 (1H, m), 7.39 (1H, d, J=8.0 Hz), 7.20 (2H, m), 5.70 (1H, m), 4.30-3.80 (8H, m), 3.20-2.80 (6H, m), 2.80-1.30 (23H, m); LC/MS: m/z=562 [M+H]$^+$ (Calc: 561.3).

Substituted-Quinoxaline-Type Piperidine Compound 216 was prepared from Substituted-Quinoxaline-Type Piperidine Compound 215 in a manner similar to the preparation of Substituted-Quinoxaline-Type Piperidine Compound 111 in Example 5 (yield 70%).

The identity of Substituted-Quinoxaline-Type Piperidine Compound 216, 2-(5-(4-((endo)-8-cyclooctyl-8-azabicyclo[3.2.1]octan-3-yl)-3-oxo-3,4-dihydroquinoxalin-2-yl)hexahydropyrrolo[3,4-c]pyrrol-2(1H)-yl)acetic acid, was confirmed using $^1$H NMR and LC/MS.

Substituted-Quinoxaline-Type Piperidine Compound 216: $^1$H NMR: δ$_H$ (400 MHz, DMSO): 10.40 (1H, m), 7.73 (1H, m), 7.39 (1H, d, J=8.0 Hz), 7.20 (2H, m), 5.70 (1H, m), 4.30-3.80 (8H, m), 3.20-2.80 (6H, m), 2.80-1.30 (23H, m); LC/MS (100%, t$_r$=1.20 min): m/z=534 [M+H]$^+$ (Calc: 533.5).

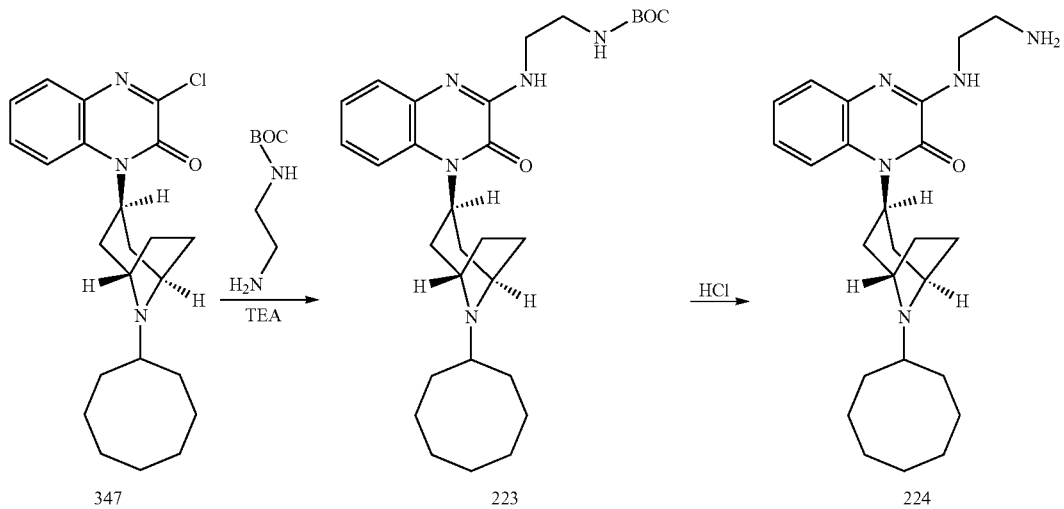

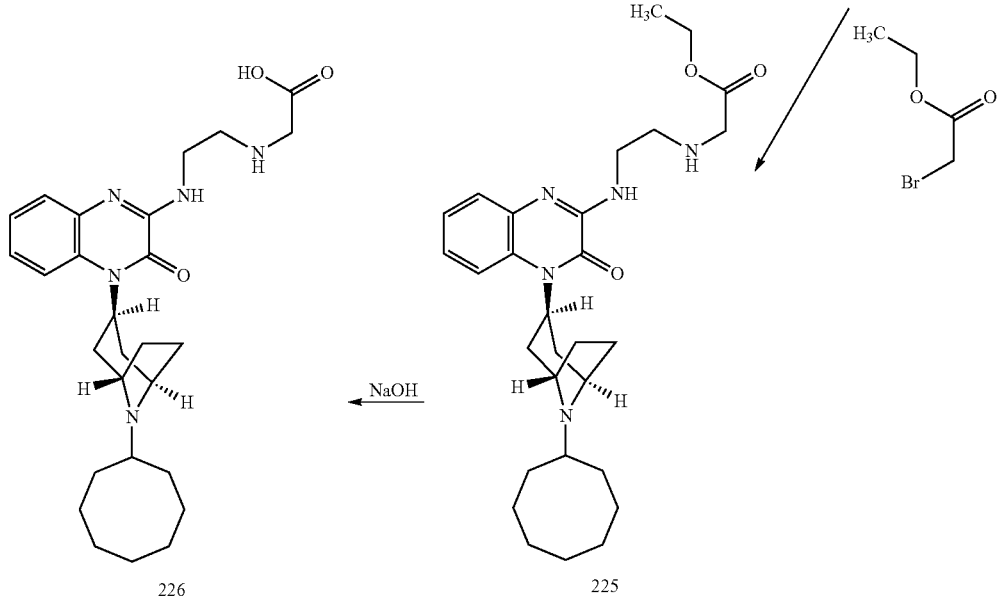

In a manner similar to the preparation of Substituted-Quinoxaline-Type Piperidine Compound 216, Substituted-Quinoxaline-Type Piperidine Compound 226 was prepared by using tert-butyl 2-aminoethylcarbamate in place of tert-butyl-hexahydropyrrolo[3,4-c]pyrrole-2(1H)-carboxylate (yield 17% for four steps).

The identity of Substituted-Quinoxaline-Type Piperidine Compound 223, tert-butyl 2-(4-((endo)-8-cyclooctyl-8-azabicyclo[3.2.1]octan-3-yl)-3-oxo-3,4-dihydroquinoxalin-2-ylamino)ethylcarbamate, was confirmed using $^1$H NMR and LC/MS.

Substituted-Quinoxaline-Type Piperidine Compound 223: $^1$H NMR: $\delta_H$(400 MHz, DMSO-d$_6$): 1.36-2.38 (32H, m), 3.18 (2H, q, J=5.91 Hz), 3.42 (2H, q, J=5.91 Hz), 3.63 (2H, br s), 5.06 (1H, br s), 6.91-6.94 (1H, m), 7.16-7.24 (2H, m), 7.38 (2H, t, J=6.08 Hz), 7.56 (1H, s); LC/MS: m/z=524 [M+H]$^+$ (Calc: 524).

The identity of Substituted-Quinoxaline-Type Piperidine Compound 224, 3-(2-aminoethylamino)-1-((endo)-8-cyclooctyl-8-azabicyclo[3.2.1]octan-3-yl)quinoxalin-2(1H)-one, was confirmed using $^1$H NMR and LC/MS.

Substituted-Quinoxaline-Type Piperidine Compound 224: $^1$H NMR: $\delta_H$ (400 MHz, DMSO-d$_6$): 1.41-2.37 (24H, m), 2.75 (2H, t, J=6.34 Hz), 3.36 (2H, t, J=6.08 Hz), 3.57 (2H, s), 3.62 (2H, br s), 5.08 (1H, br s), 7.17-7.21 (2H, m), 7.36-7.39 (2H, m), 7.50-7.52 (1H, m); LC/MS: m/z=424 [M+H]$^+$ (Calc: 424).

The identity of Substituted-Quinoxaline-Type Piperidine Compound 225, ethyl 2-(2-(4-((endo)-8-cyclooctyl-8-azabicyclo[3.2.1]octan-3-yl)-3-oxo-3,4-dihydroquinoxalin-2-ylamino)ethylamino)acetate, was confirmed using $^1$H NMR and LC/MS.

Substituted-Quinoxaline-Type Piperidine Compound 225: $^1$H NMR: $\delta_H$ (400 MHz, DMSO-d$_6$): 1.19 (3H, t, J=6.84 Hz), 1.98 (22H, dt, J=188.24, 72.62 Hz), 2.74 (2H, d, J=6.59 Hz), 2.77-2.78 (1H, m), 2.90 (2H, d, J=6.59 Hz), 3.37 (2H, d, J=6.59 Hz), 3.63 (2H, s), 4.04-4.11 (2H, m), 5.08 (1H, s), 7.16-7.25 (2H, m), 7.38 (2H, dd, J=12.67, 8.62 Hz), 7.49 (1H, d, J=5.07 Hz), 7.96 (1H, d, J=5.58 Hz); LC/MS: m/z=255.5 [M+2H]$^{2+}$ (Calc: 255.5).

The identity of Substituted-Quinoxaline-Type Piperidine Compound 226, 2-(2-(4-((endo)-8-cyclooctyl-8-azabicyclo[3.2.1]octan-3-yl)-3-oxo-3,4-dihydroquinoxalin-2-ylamino)ethylamino)acetic acid, was confirmed using $^1$H NMR and LC/MS.

Substituted-Quinoxaline-Type Piperidine Compound 226: $^1$H NMR: $\delta_H$ (400 MHz, DMSO-d$_6$): 1.98 (23H, dtt, J=301.97, 81.62, 34.22 Hz), 3.14 (2H, d, J=5.07 Hz), 3.43 (2H, s), 3.62 (2H, d, J=5.07 Hz), 4.17 (2H, s), 5.61 (1H, br s), 7.12 (1H, s), 7.20 (1H, d, J=7.6 Hz), 7.43 (1H, d, J=7.6 Hz), 7.57 (1H, s), 7.94 (1H, s), 10.72 (1H, brs); LC/MS (t$_r$=1.01 min): m/z=482 [M+H]$^+$ (Calc: 481.6).

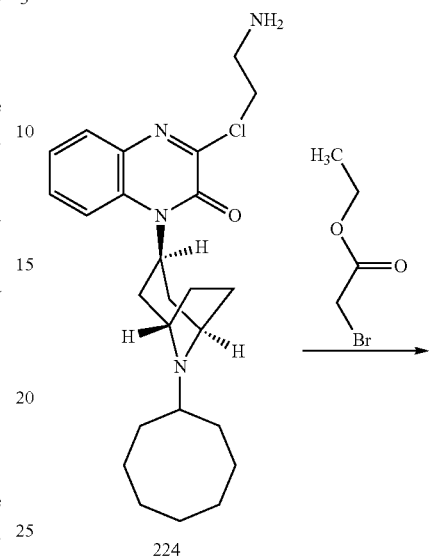

224

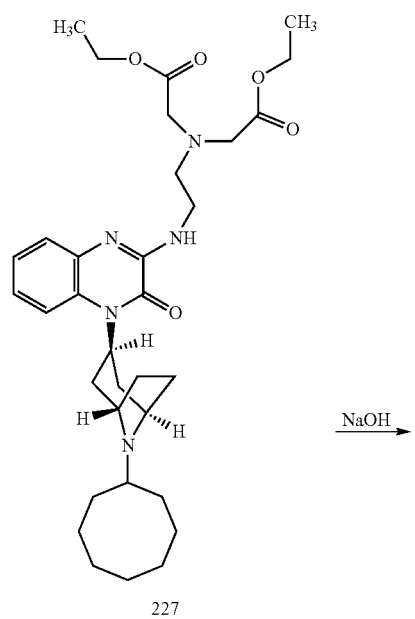

227

217
-continued

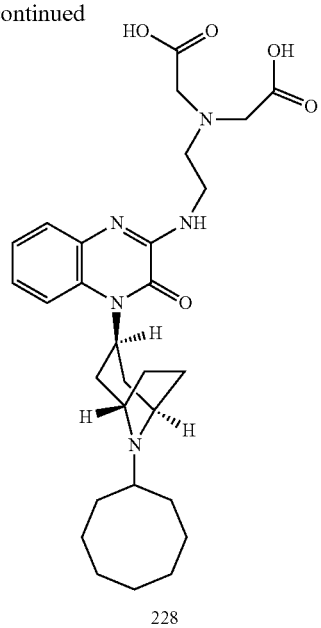

228

To a mixture of Substituted-Quinoxaline-Type Piperidine Compound 224 (38 mg, 0.090 mmol) and DMF (1 mL) at a temperature of about 25° C. was added a solution of ethyl 2-bromoacetate (0.187 mL, 0.188 mmol) in MeCN (1 mL). The resulting reaction mixture was stirred at about 25° C. for 2 h. The reaction mixture was diluted with water and extracted twice with EtOAc (20 mL for each extraction). The organic portions were combined, washed with brine, dried (MgSO$_4$), filtrated, and concentrated under reduced pressure to provide a residue. The residue was chromatographed with a silica gel column (Yamazen, S (amino)) eluted with a gradient of from 95%:5% hexanes:EtOAc to 75%:25% hexanes:EtOAc to provide 28.8 mg of Substituted-Quinoxaline-Type Piperidine Compound 227 as a yellow solid (yield 54%).

The identity of Substituted-Quinoxaline-Type Piperidine Compound 227, diethyl 2,2'-(2-(4-((endo)-8-cyclooctyl-8-azabicyclo[3.2.1]octan-3-yl)-3-oxo-3,4-dihydroquinoxalin-2-ylamino)ethylazanediyl)diacetate, was confirmed using $^1$H NMR and LC/MS.

Substituted-Quinoxaline-Type Piperidine Compound 227: $^1$H NMR: $\delta_H$ (400 MHz, DMSO-d$_6$): 1.17 (3H, t, J=7.1 Hz), 1.18 (3H, t, J=7.1 Hz), 1.31-2.42 (23H, m), 2.91 (2H, s), 3.42 (2H, s), 3.58 (4H, d, J=3.55 Hz), 3.64 (2H, s), 4.02-4.11 (4H, m), 5.05 (1H, br s), 7.15-7.26 (2H, m), 7.34-7.40 (2H, m), 7.42-7.48 (1H, m); LC/MS: m/z=298.5 [M+2H]$^{2+}$ (Calc: 298.5).

Substituted-Quinoxaline-Type Piperidine Compound 228 was prepared from Substituted-Quinoxaline-Type Piperidine Compound 227 in a manner similar to the preparation of Substituted-Quinoxaline-Type Piperidine Compound 111 in Example 5 (yield 56%).

The identity of Substituted-Quinoxaline-Type Piperidine Compound 228, 2,2'-(2-(4-((endo)-8-cyclooctyl-8-azabicyclo[3.2.1]octan-3-yl)-3-oxo-3,4-dihydroquinoxalin-2-ylamino)ethylazanediyl)diacetic acid, was confirmed using $^1$H NMR and LC/MS.

Substituted-Quinoxaline-Type Piperidine Compound 228: $^1$H NMR: $\delta_H$ (400 MHz, DMSO-d$_6$): 1.31-2.81 (22H, m), 2.88-2.98 (2H, m), 3.40-3.47 (2H, m), 3.51 (4H, s), 4.24 (2H, s), 5.11 (0.1H, s), 5.65 (0.9H, s), 7.19-7.26 (2H, m), 7.38-7.43 (1H, m), 7.58-7.64 (2H, m), 7.67-7.75 (2H, br m), 9.22 (0.1H, s), 9.95 (0.9H, s), 12.33 (1H, br s); LC/MS (t$_r$=1.36 min): m/z=540 [M+H]$^+$ (Calc: 540).

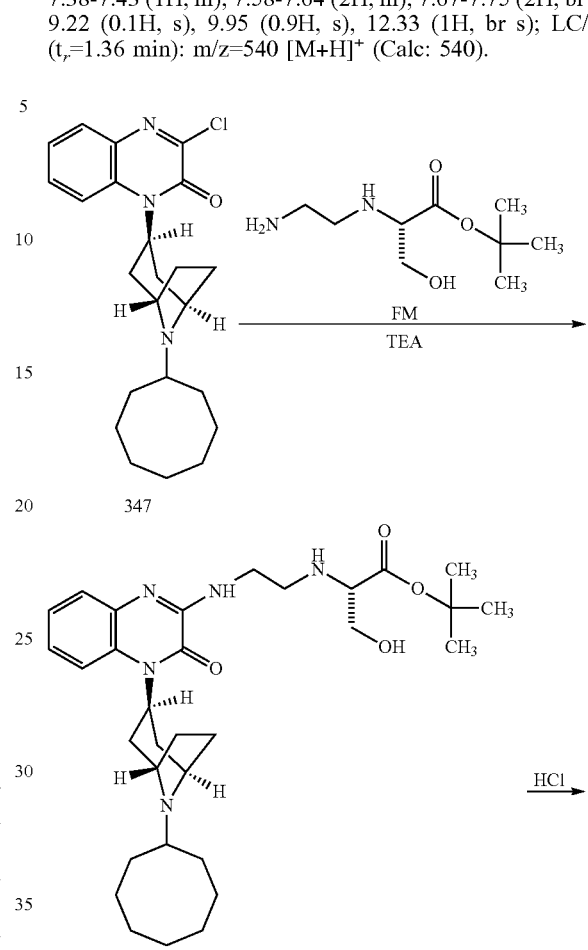

347

217

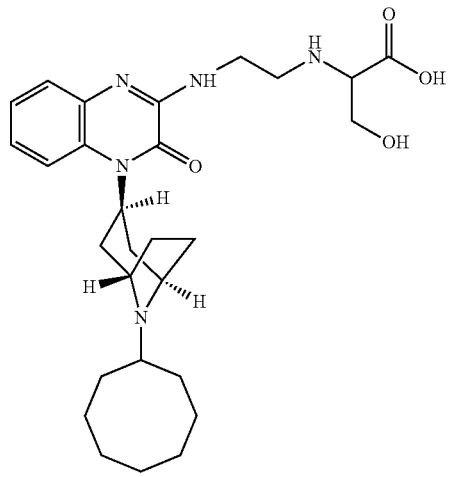

218

Substituted-Quinoxaline-Type Piperidine Compound 217 was prepared by using (S)-tert-butyl 2-(2-aminoethylamino)-3-hydroxypropanoate (FM) in place of serine amide hydrochloride (yield 99%).

The identity of Substituted-Quinoxaline-Type Piperidine Compound 217, (S)-tert-butyl 2-(2-(4-((endo)-8-cyclooctyl-8-azabicyclo[3.2.1]octan-3-yl)-3-oxo-3,4-dihydroquinoxalin-2-ylamino)ethylamino)-3-hydroxypropanoate, was confirmed using $^1$H NMR and LC/MS.

Substituted-Quinoxaline-Type Piperidine Compound 217: ¹H NMR: $\delta_H$ (CDCl$_3$): 1.36-2.42 (32H, m), 2.77-2.85 (1H, m), 2.93 (1H, br s), 3.02-3.10 (1H, m), 3.33 (1H, dd, J=6.59, 4.56 Hz), 3.52-3.58 (2H, m), 3.62-3.81 (4H, m), 5.15 (1H, br s), 6.64 (1H, br s), 7.17-7.23 (2H, m), 7.39-7.45 (1H, m), 7.50-7.56 (1H, m); LC/MS: m/z=568 [M+H]⁺ (Calc: 568).

Under a nitrogen atmosphere, to a mixture of Substituted-Quinoxaline-Type Piperidine Compound 217 (260 mg, 0.458 mmol) and dioxane (6 mL) at a temperature of about 25° C. was added 4N HCl in dioxane (2 mL, 8.00 mmol). The resulting reaction mixture was warmed to 50° C. and stirred for 4 h. The mixture was filtrated with a Hirsch funnel, washed with dioxane, dried under reduced pressure for 8 h at 85° C., then chromatographed by a reverse phase chromatography apparatus (Gilson Inc, Middletown Wis.). The collected fraction was dried under reduced pressure to provide 112 mg of Substituted-Quinoxaline-Type Piperidine Compound 218 (yield 48%).

The identity of Substituted-Quinoxaline-Type Piperidine Compound 218, 2-(2-(4-((endo)-8-cyclooctyl-8-azabicyclo[3.2.1]octan-3-yl)-3-oxo-3,4-dihydroquinoxalin-2-ylamino)ethylamino)-3-hydroxypropanoic acid, was confirmed using ¹H NMR and LC/MS.

Substituted-Quinoxaline-Type Piperidine Compound 218: ¹H NMR: $\delta_H$ (DMSO-d$_6$): 1.29-2.40 (21H, m), 2.53-2.73 (2H, m), 2.90 (1H, br s), 3.22 (3H, t, J=5.32 Hz), 3.62-3.75 (3H, m), 3.84 (2H, ddd, J=25.73, 11.79, 3.93 Hz), 4.16 (2H, d, J=24.33 Hz), 5.12 (0.1H, br s), 5.78 (0.9H, br s), 7.12-7.23 (2H, m), 7.44 (1H, d, J=7.1 Hz), 7.68-7.78 (1H, m), 8.00 (1H, t, J=5.58 Hz), 9.84 (0.1H, br s), 10.76 (0.9H, br s); LC/MS (t$_r$=1.09 min): m/z=512 [M+H]⁺ (Calc: 512).

The compound of formula FM was prepared as follows:

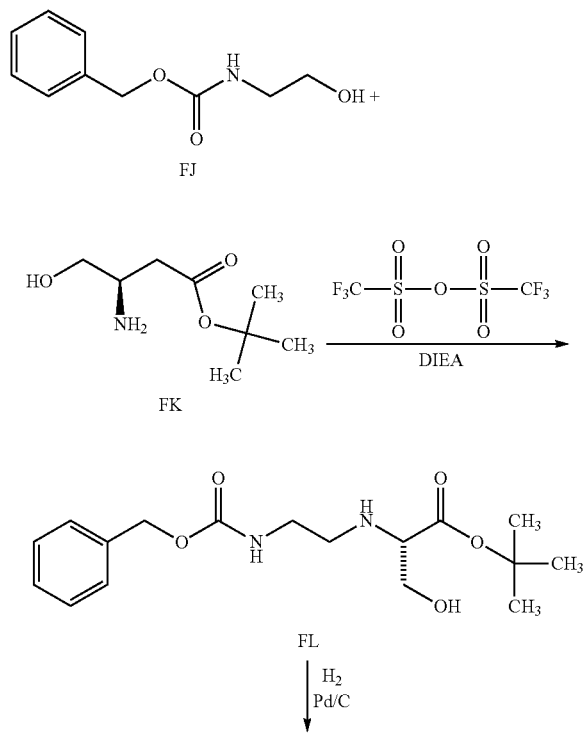

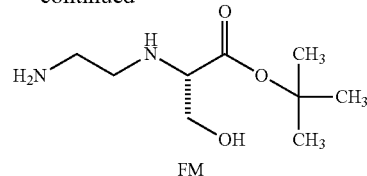

FM

Under a nitrogen atmosphere, to a mixture of benzyl 2-hydroxyethylcarbamate (FJ, 1000 mg, 5.12 mmol) and CH$_2$Cl$_2$ (13 mL) at a temperature of from −20° C. to −17° C. were added DIEA (2340 μL, 13.40 mmol) and trifluoromethanesulfonic anhydride (909 μL, 5.38 mmol). The resulting reaction mixture was stirred for 1 h at a temperature of −20° C. Thereafter, (R)-tert-butyl 3-amino-4-hydroxybutanoate (FK, 1239 mg, 7.68 mmol, Sigma-Aldrich) in CH$_2$Cl$_2$ (5 mL) was slowly added. The resulting reaction mixture was stirred for 4 h as its temperature warmed from −20° C. to −5° C. Thereafter, the reaction mixture was diluted with saturated aqueous NaHCO$_3$ then extracted 3 times with CHCl$_3$ (30 mL for each extraction). The organic portions were combined, washed with brine, dried (MgSO$_4$), filtered, and concentrated under reduced pressure. The residue was chromatographed with an amino-silica gel column (Yamazen Corp. W091-01) eluted with a gradient of from 20%:80% EtOAc:n-hexane to 80%:20% EtOAc:n-hexane to provide 921 mg of the compound of formula FL as a yellow oil (yield 53%).

The identity of the compound of formula FL, (S)-tert-butyl 2-(2-(benzyloxycarbonylamino)ethylamino)-3-hydroxypropanoate, was confirmed using ¹H NMR and LC/MS.

Compound FL: ¹H NMR: $\delta_H$ (400 MHz, CDCl$_3$): 1.46 (9H, s), 2.61-2.70 (1H, m), 2.82-2.91 (1H, m), 3.16-3.27 (2H, m), 3.30-3.42 (1H, m), 3.54 (1H, dd, J=10.90, 6.84 Hz), 3.74 (1H, dd, J=10.65, 4.56 Hz), 5.10 (2H, s), 5.21 (1H, br s), 7.31-7.37 (5H, m); LC/MS: m/z=339 [M+H]⁺ (Calc: 339).

Under a hydrogen atmosphere, a mixture of the compound of formula FL (906 mg, 2.68 mmol), 10% palladium on carbon, 50% wet (285 mg, 0.134 mmol), and MeOH (10 mL) was stirred at a temperature of about 25° C. for 3 h. The Pd/C was filtered off, the mixture was washed with MeOH, and the filtrate was concentrated under reduced pressure to provide 651 mg of the compound of formula FM as a pale yellow solid (yield >98%).

The identity of the compound of formula FM, (S)-tert-butyl 2-(2-aminoethylamino)-3-hydroxypropanoate, was confirmed using ¹H NMR and LC/MS.

Compound FM: ¹H NMR: $\delta_H$ (400 MHz, CDCl$_3$): 1.47 (9H, s), 2.55-2.64 (1H, m), 2.78-2.86 (3H, m), 3.27 (1H, dd, J=6.84, 4.31 Hz), 3.55 (1H, dd, J=10.65, 6.59 Hz), 3.77 (1H, dd, J=10.90, 4.31 Hz); LC/MS: m/z=205 [M+H]⁺ (Calc: 205).

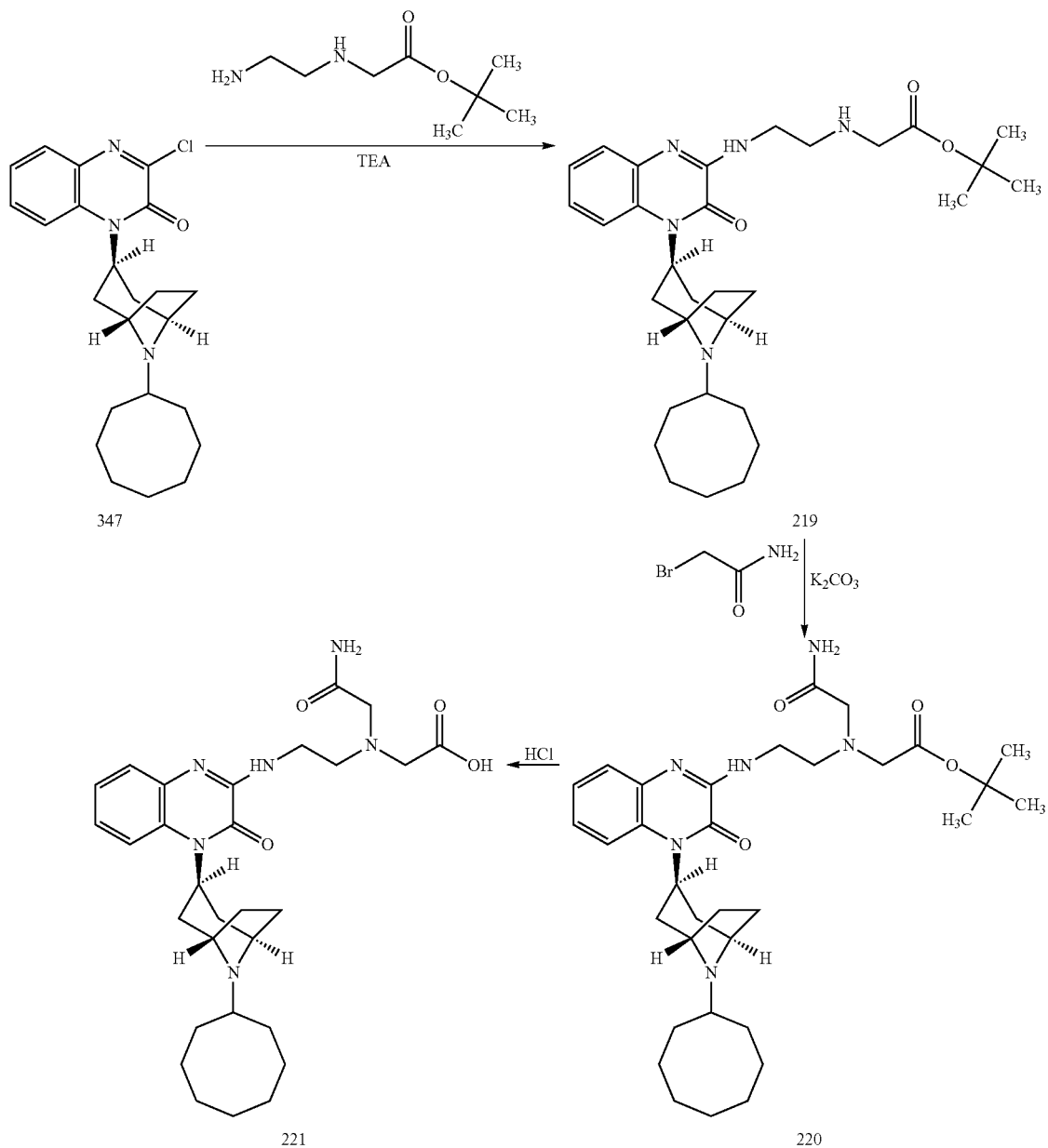

Substituted-Quinoxaline-Type Piperidine Compound 219 was prepared by using tert-butyl 2-(2-aminoethylamino)acetate (Sigma-Aldrich) in place of serine amide hydrochloride (yield 86%).

The identity of Substituted-Quinoxaline-Type Piperidine Compound 219, tert-butyl 2-(2-(4-((endo)-8-cyclooctyl-8-azabicyclo[3.2.1]octan-3-yl)-3-oxo-3,4-dihydroquinoxalin-2-ylamino)ethylamino)acetate, was confirmed using $^1$H NMR and LC/MS.

Substituted-Quinoxaline-Type Piperidine Compound 219: $^1$H NMR: $\delta_H$ (CDCl$_3$): 1.35-1.89 (2H, m), 1.98-2.03 (1H, m), 2.13-2.42 (4H, m), 2.91 (2H, t, J=5.83 Hz), 3.34 (2H, s), 3.61 (2H, q, J=5.91 Hz), 3.66 (2H, br s), 5.13 (1H, br s), 6.69 (1H, s), 7.16-7.22 (2H, m), 7.38-7.44 (1H, m), 7.49-7.55 (1H, m); LC/MS: m/z=538 [M+H]$^+$ (Calc: 538).

To a mixture of Substituted-Quinoxaline-Type Piperidine Compound 219 (305 mg, 0.567 mmol) and MeCN (5 mL) at a temperature of about 25° C. was added 2-bromoacetamide (86 mg, 0.624 mmol, Sigma-Aldrich) and K$_2$CO$_3$ (86 mg, 0.624 mmol). The resulting reaction mixture was warmed to 60° C. and stirred for 3 h. The reaction mixture was diluted with water and extracted twice with CHCl$_3$ (20 mL for each extraction). The organic portions were combined, washed with brine, dried (MgSO$_4$), filtrated, and concentrated under reduced pressure to provide a residue. The residue was chromatographed with a silica gel column (Yamazen, M (amino)) eluted with a gradient of from 60%:40% hexanes:EtOAc to 0%:100% hexanes:EtOAc to provide a fractions. The fractions were combined and concentrated under reduced pressure to provide a colorless amorphous solid which was chromatographed with a silica gel column (Yamazen, M (amino)) eluted with a gradient of from 99%:1% CHCl$_3$:(MeOH:NH$_3$=10:1) to 90%:10% CHCl$_3$:(MeOH:NH$_3$=10:1) to provide 252 mg of Substituted-Quinoxaline-Type Piperidine Compound 220 (yield 75%).

The identity of Substituted-Quinoxaline-Type Piperidine Compound 220, text-butyl 2-((2-amino-2-oxoethyl)(2-(4-((endo)-8-cyclooctyl-8-azabicyclo[3.2.1]octan-3-yl)-3-oxo-3,4-dihydroquinoxalin-2-ylamino)ethyl)amino)acetate, was confirmed using ¹H NMR and LC/MS.

Substituted-Quinoxaline-Type Piperidine Compound 220: ¹H NMR: $\delta_H$ (CDCl$_3$): 1.35-2.41 (32H, m), 2.96 (2H, t, J=4.82 Hz), 3.33 (2H, s), 3.38 (2H, s), 3.57-3.63 (2H, m), 3.66 (2H, br s), 5.18 (1H, br s), 5.40 (1H, br s), 6.65 (1H, br s), 7.17-7.23 (2H, m), 7.38-7.44 (1H, m), 7.47-7.53 (1H, m), 7.55 (1H, br s); LC/MS: m/z=595 [M+H]$^+$ (Calc: 595).

Substituted-Quinoxaline-Type Piperidine Compound 221 was prepared from Substituted-Quinoxaline-Type Piperidine Compound 220 in a manner similar to the preparation of Substituted-Quinoxaline-Type Piperidine Compound 218 (yield 96%).

The identity of Substituted-Quinoxaline-Type Piperidine Compound 221, 2-((2-amino-2-oxoethyl)(2-(4-((endo)-8-cyclooctyl-8-azabicyclo[3.2.1]octan-3-yl)-3-oxo-3,4-dihydroquinoxalin-2-ylamino)ethyl)amino)acetic acid, was confirmed using ¹H NMR and LC/MS.

Substituted-Quinoxaline-Type Piperidine Compound 221: ¹H NMR: $\delta_H$ (CD$_3$OD): 1.35-2.43 (20H, m), 2.61-2.74 (2H, m), 2.95-3.12 (3H, m), 3.34-3.71 (6H, m), 4.17 (2H, br s), 5.45 (1H, br s), 7.25-7.15 (2H, m), 7.46 (1H, d, J=7.6 Hz), 7.58 (1H, d, J=8.11 Hz); LC/MS (t$_r$=1.06 min): m/z=539 [M+H]$^+$ (Calc: 539).

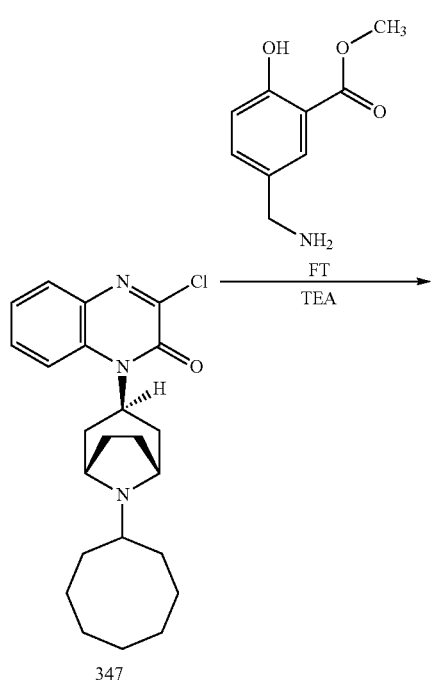

347

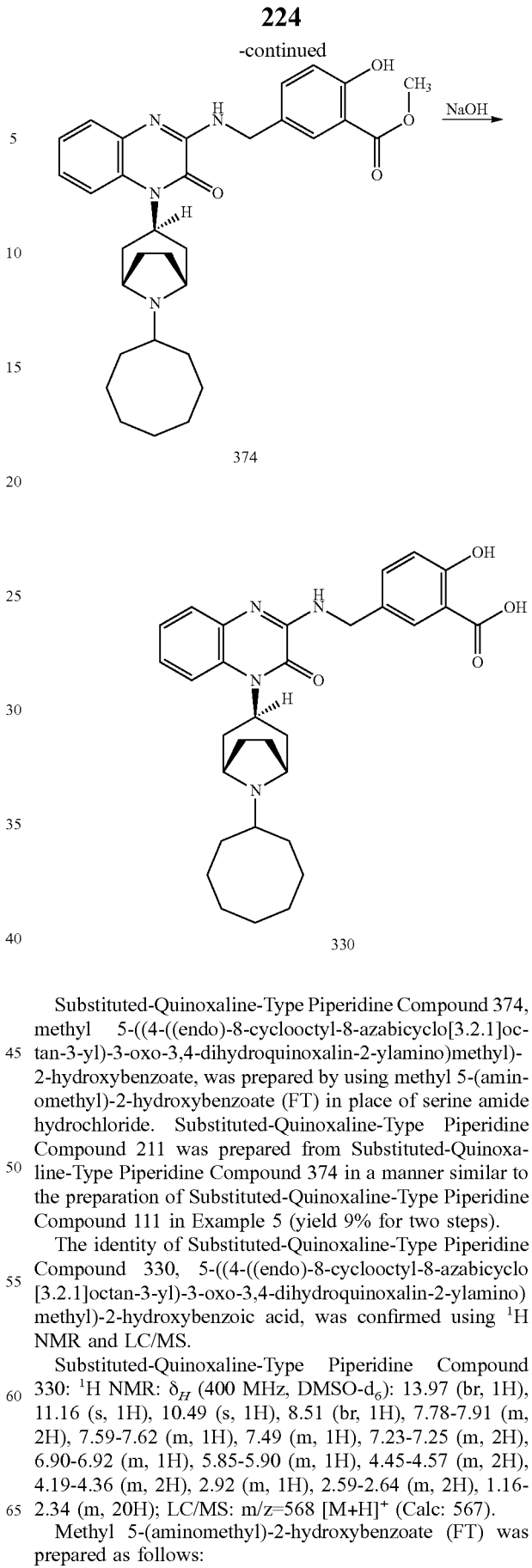

374

330

Substituted-Quinoxaline-Type Piperidine Compound 374, methyl 5-((4-((endo)-8-cyclooctyl-8-azabicyclo[3.2.1]octan-3-yl)-3-oxo-3,4-dihydroquinoxalin-2-ylamino)methyl)-2-hydroxybenzoate, was prepared by using methyl 5-(aminomethyl)-2-hydroxybenzoate (FT) in place of serine amide hydrochloride. Substituted-Quinoxaline-Type Piperidine Compound 211 was prepared from Substituted-Quinoxaline-Type Piperidine Compound 374 in a manner similar to the preparation of Substituted-Quinoxaline-Type Piperidine Compound 111 in Example 5 (yield 9% for two steps).

The identity of Substituted-Quinoxaline-Type Piperidine Compound 330, 5-((4-((endo)-8-cyclooctyl-8-azabicyclo[3.2.1]octan-3-yl)-3-oxo-3,4-dihydroquinoxalin-2-ylamino)methyl)-2-hydroxybenzoic acid, was confirmed using ¹H NMR and LC/MS.

Substituted-Quinoxaline-Type Piperidine Compound 330: ¹H NMR: $\delta_H$ (400 MHz, DMSO-d$_6$): 13.97 (br, 1H), 11.16 (s, 1H), 10.49 (s, 1H), 8.51 (br, 1H), 7.78-7.91 (m, 2H), 7.59-7.62 (m, 1H), 7.49 (m, 1H), 7.23-7.25 (m, 2H), 6.90-6.92 (m, 1H), 5.85-5.90 (m, 1H), 4.45-4.57 (m, 2H), 4.19-4.36 (m, 2H), 2.92 (m, 1H), 2.59-2.64 (m, 2H), 1.16-2.34 (m, 20H); LC/MS: m/z=568 [M+H]$^+$ (Calc: 567).

Methyl 5-(aminomethyl)-2-hydroxybenzoate (FT) was prepared as follows:

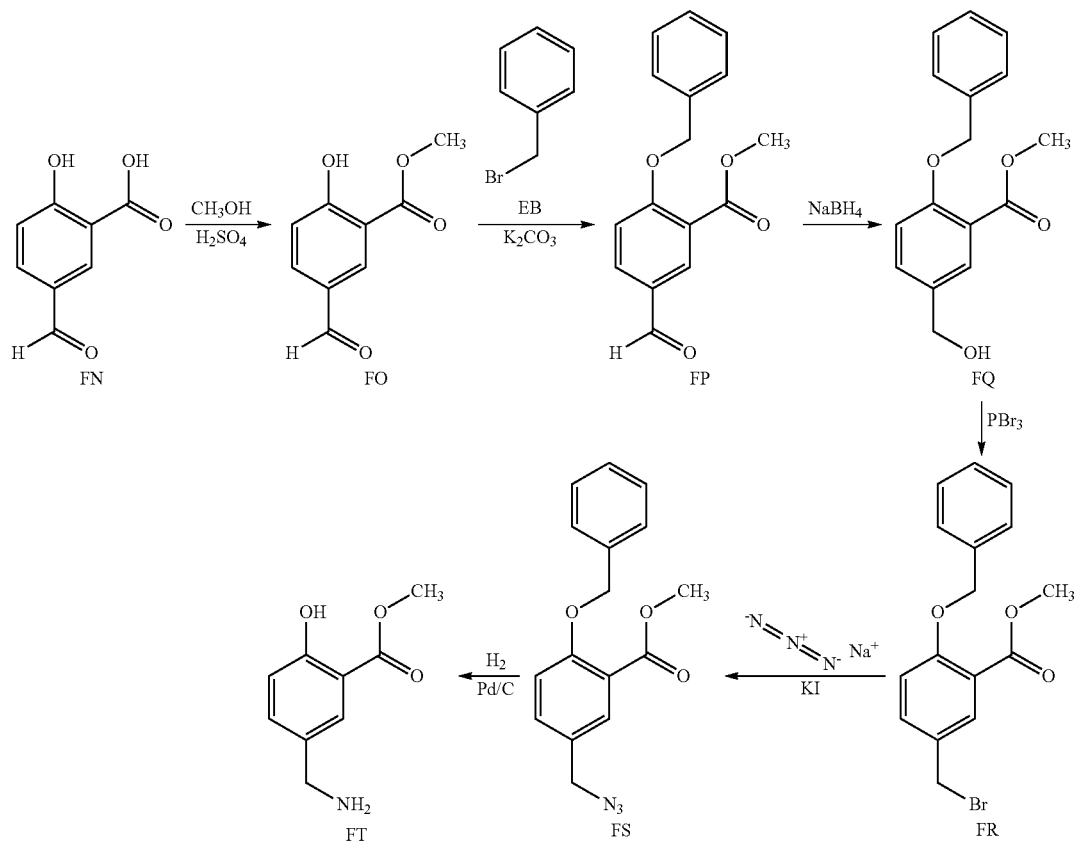

A reaction mixture of 5-formyl-2-hydroxybenzoic acid (FN, 5.00 g, 30.1 mmol, Sigma-Aldrich), concentrated $H_2SO_4$ (2.00 mL), and MeOH (50 mL) was stirred at reflux for 24 h. Thereafter, the mixture was concentrated under reduced pressure to provide 5.36 g of the compound of formula FO, methyl 5-formyl-2-hydroxybenzoate, as colorless oil (yield 99%). A reaction mixture of the compound of formula FO (5.36 g, 29.7 mmol), the compound of formula EB (3.89 mL, 32.8 mmol), $K_2CO_3$ (4.93 g, 35.7 mmol), and acetone (150 mL) was stirred at reflux for 22 h. Thereafter, the mixture was concentrated under reduced pressure to provide 4.92 g of the compound of formula FP, methyl 2-(benzyloxy)-5-formylbenzoate, as a white solid (yield 61%). A reaction mixture of the compound of formula FP (4.40 g, 16.3 mmol), sodium tetrahydroborate (738 mg, 19.5 mmol), and THF (50 mL) was stirred for 1 h at a temperature of 0° C., warmed to a temperature of about 25° C., and stirred for 1 h more. Thereafter, the reaction mixture was partitioned between EtOAc and water. The organic portion was separated, washed with saturated aqueous $NaHCO_3$, washed with brine, dried ($Na_2SO_4$), filtered, concentrated under reduced pressure, and chromatographed with a silica gel column eluted with a gradient of from 100%:0% hexane:EtOAc to 50%:50% hexane:EtOAc to provide 3.98 g of the compound of formula FQ, methyl 2-(benzyloxy)-5-(hydroxymethyl)benzoate, as a colorless oil (yield 90%).

A reaction mixture of the compound of formula FQ, (3.98 g, 14.6 mmol), phosphorus tribromide (687 mL, 7.31 mmol, Sigma-Aldrich), and diethyl ether (100 mL) was stirred for 1 h at a temperature of 0° C. Thereafter, the reaction mixture was partitioned between diethyl ether and water. The organic portion was separated, washed with saturated aqueous $NaHCO_3$, washed with brine, dried ($Na_2SO_4$), filtered, concentrated under reduced pressure to provide 4.90 g of the compound of formula FR, methyl 2-(benzyloxy)-5-(bromomethyl)benzoate, as a white solid (yield >99%). A reaction mixture of the compound of formula FR (4.90 g, 14.6 mmol), sodium azide (1.05 g, 16.1 mmol), potassium iodide (catalytic amount, Sigma-Aldrich), and DMF (100 mL) was stirred for 20 h at a temperature of about 25° C. Thereafter, the reaction mixture was partitioned between EtOAc and water. The organic portion was separated, washed with saturated aqueous $NaHCO_3$, washed with brine, dried ($Na_2SO_4$), filtered, concentrated under reduced pressure, and chromatographed with a silica gel column eluted with a gradient of from 100%:0% hexane:EtOAc to 50%:50% hexane:EtOAc to provide 2.82 g of the compound of formula FS, methyl 5-(azidomethyl)-2-(benzyloxy)benzoate, as a colorless oil (yield 65%). Under a hydrogen atmosphere, a mixture of the compound of formula FS (1.28 g, 4.30 mmol), 20% palladium on carbon by weight (120 mg), MeOH (5 mL), and EtOAc (10 mL) was stirred at a temperature of about 25° C. for 5 h. The Pd/C was filtered off with a CELITE pad, the mixture was washed with EtOAc, then concentrated under reduced pressure to provide a first residue. The first residue was suspended in MeOH, the insoluble solid filtered off, and the filtrate concentrated under reduced pressure to provide a second residue. The second residue was washed with EtOAc to provide 438 mg of the compound of formula FT as a brown solid (yield 56%).

227 228
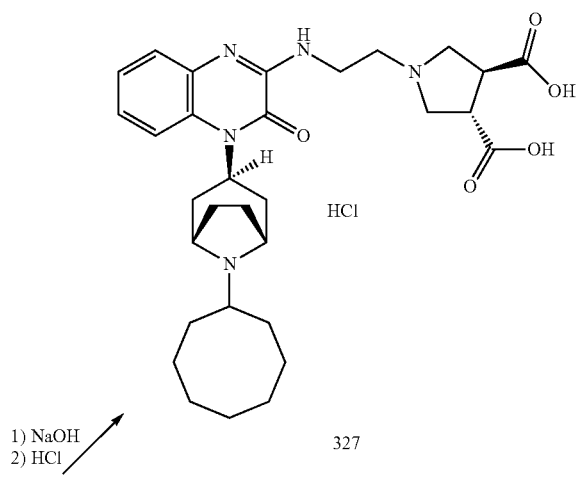
1) NaOH
2) HCl
327
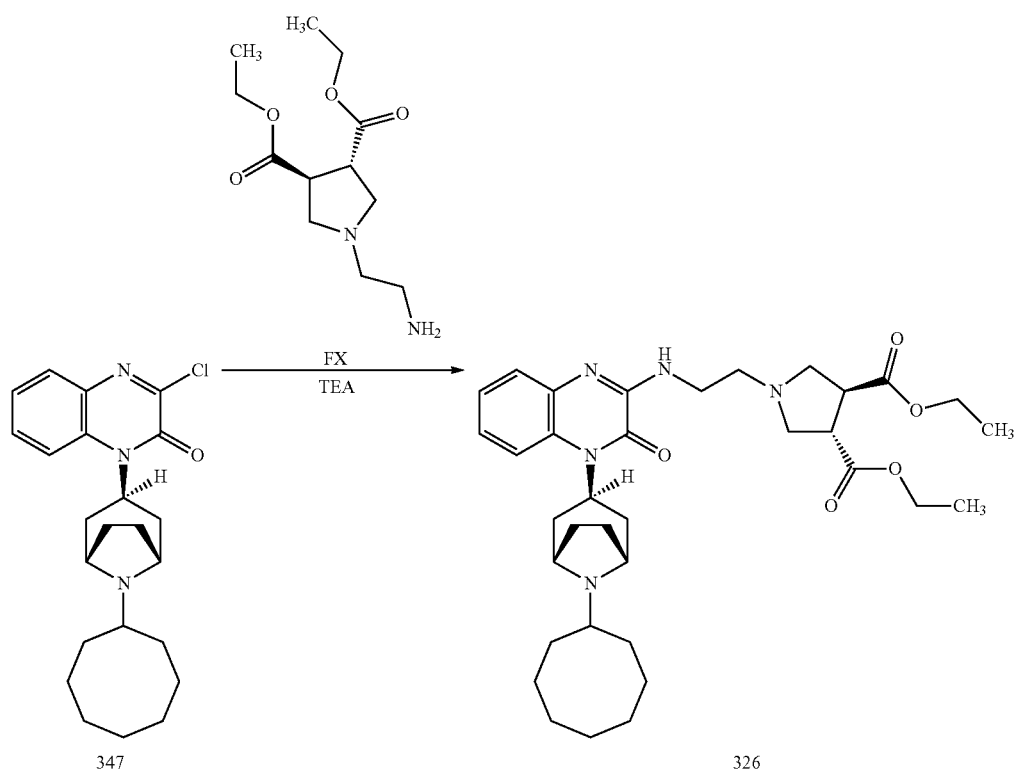
347  FX
TEA
326

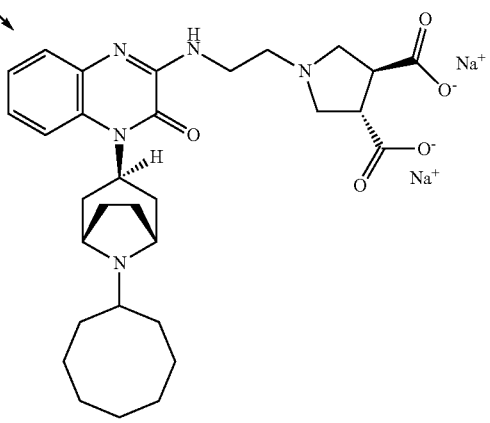

327

Substituted-Quinoxaline-Type Piperidine Compound 326 was prepared by using (3S,4S)-diethyl 1-(2-aminoethyl)pyrrolidine-3,4-dicarboxylate (FX) in place of serine amide hydrochloride (yield 75%).

The identity of Substituted-Quinoxaline-Type Piperidine Compound 326, (3S,4S)-diethyl 1-(2-(4-((endo)-8-cyclooctyl-8-azabicyclo[3.2.1]octan-3-yl)-3-oxo-3,4-dihydroquinoxalin-2-ylamino)ethyl)pyrrolidine-3,4-dicarboxylate, was confirmed using $^1$H NMR and LC/MS.

Substituted-Quinoxaline-Type Piperidine Compound 326: $^1$H NMR: $\delta_H$ (400 MHz, CD$_3$OD): 7.51 (m, 2H), 7.25 (m, 2H), 5.10 (s, br, 1H), 4.12 (dd, 4H), 3.7 (s, br, 2H), 3.60 (m, 1H), 3.42 (m, 2H), 2.89 (m, 2H), 2.75 (m, 2H), 2.55 (s, br, 1H), 2.38-1.35 (m, 22H), 1.25 (t, 6H); LC/MS: m/z=566 [M+H]$^+$ (Calc: 565).

The hydrochloride of Substituted-Quinoxaline-Type Piperidine Compound 327 was prepared from Substituted-Quinoxaline-Type Piperidine Compound 326 in a manner similar to the preparation of Substituted-Quinoxaline-Type Piperidine Compound 174 in Example 7 (yield 60%).

The identity of Substituted-Quinoxaline-Type Piperidine Compound 327, (3S,4S)-1-(2-(4-((endo)-8-cyclooctyl-8-azabicyclo[3.2.1]octan-3-yl)-3-oxo-3,4-dihydroquinoxalin-2-ylamino)ethyl)pyrrolidine-3,4-dicarboxylic acid, was confirmed using $^1$H NMR and LC/MS.

Substituted-Quinoxaline-Type Piperidine Compound 327: $^1$H NMR: $\delta_H$ (400 MHz, CD$_3$OD): 7.36-7.38 (m, 2H), 7.12-7.06 (m, 2H), 5.27-5.09 (s, br. 1H), 3.60 (s, br, 2H), 3.57-3.45 (m, 2H), 2.89 (t, J=8.8 Hz, 2H), 2.82-2.78 (m, 2H), 2.72-2.53 (m, 3H), 2.46-2.36 (s, br, 1H), 2.27-1.36 (m, 22H); LC/MS: m/z=566 [M+H]$^+$ (Calc: 565).

The sodium salt of Substituted-Quinoxaline-Type Piperidine Compound 327 was prepared as follows. To a mixture of Substituted-Quinoxaline-Type Piperidine Compound 326 (65 mg, 0.1 mmol) and 95% ethanol (3 mL) at a temperature of about 25° C. was added 2N aqueous NaOH (0.1 mL). The resulting reaction mixture was stirred at about 25° C. for 2 h after which a white precipitate formed. The precipitate was collected and dried under reduced pressure to provide 42.1 mg of the sodium salt of Substituted-Quinoxaline-Type Piperidine Compound 327 (yield 71%).

The compound of formula FX was prepared as follows:

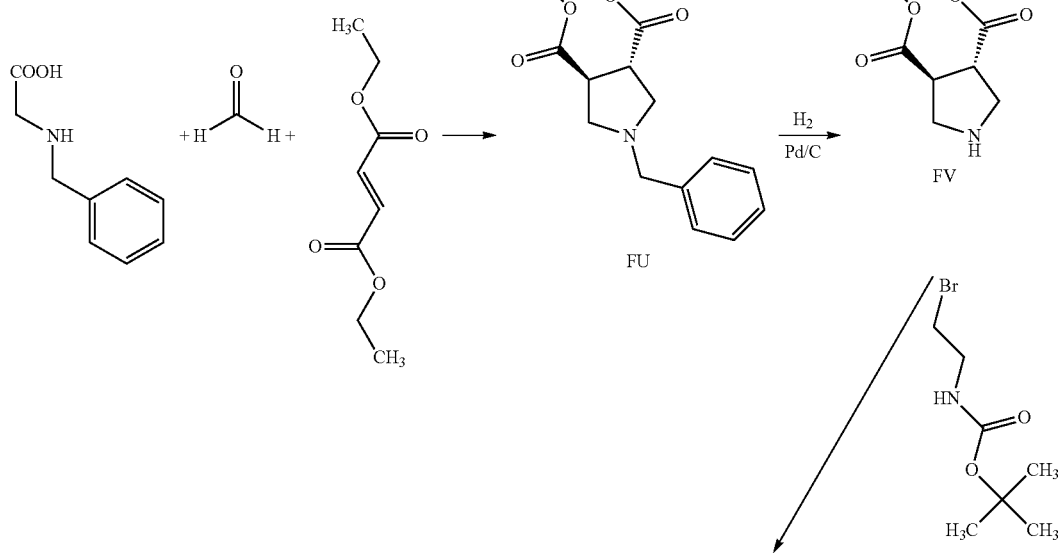

-continued

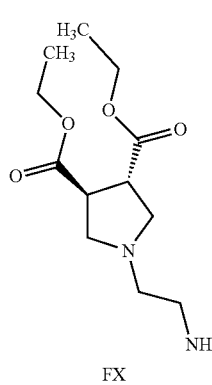

FX

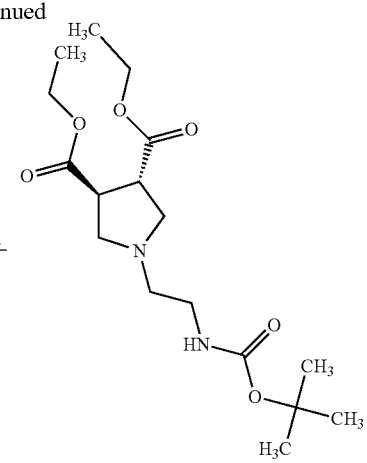

FW

To a mixture of diethyl fumarate (8.68 g, 50.4 mmol, Sigma-Aldrich) and toluene (800 mL) at 105° C. was added dropwise over 1 h a mixture of formaldehyde, in the form of paraformaldehyde, (10.2 g, 339 mmol (based on formaldehyde monomer molecular weight), Sigma-Aldrich) and 2-(benzylamino)acetic acid (12.2 g, 60.5 mmol, Sigma-Aldrich). The resulting reaction mixture was refluxed for 16 h in an apparatus comprising a Dean-Stark trap. After concentration under reduced pressure, the residue was dissolved in hexanes, filtered, and concentrated under reduced pressure to provide a brown oil. Flash chromatography of the oil with a silica gel column eluting with 1:5 EtOAc:hexanes provided 13.8 g of the compound of formula FU as a colorless oil (yield 74%).

The identity of the compound of formula FU, (3S,4S)-diethyl 1-benzylpyrrolidine-3,4-dicarboxylate, was confirmed using TLC and LC/MS.

Compound FU: TLC (SiO$_2$) 1:1 EtOAc:hexanes: Rf=0.8 with UV detection, Dragendorff's reagent; LC/MS: m/z=306 [M+H]$^+$ (Calc: 305).

Under a hydrogen atmosphere, a mixture of the compound of formula FU (4.08 g, 13.4 mmol), 10% palladium on carbon (4.7 g), and MeOH was stirred at a temperature of about 25° C. for 2 h. The Pd/C was filtered off with a CELITE pad and the filtrate was concentrated under reduced pressure to provide 2.89 g of the compound of formula FV as a pale yellow oil (yield >98%).

The identity of the compound of formula FV, (3S,4S)-diethyl pyrrolidine-3,4-dicarboxylate, was confirmed using TLC and LC/MS.

Compound FV: TLC (SiO$_2$) 1:3 EtOAc:hexanes: Rf=0.1 with UV detection, Dragendorff's reagent; LC/MS: m/z=216 [M+H]$^+$ (Calc: 215).

To a mixture of the compound of formula FV (2.4 g, 11.2 mmol) and dry DMF (150 mL) at a temperature of about 25° C. was added tert-butyl 2-bromoethylcarbamate (2.7 g, 12.3 mmol, Sigma-Aldrich) and TEA (22.4 mmol, 3.1 mL). The resulting reaction mixture was heated to 60° C. and stirred for 18 h at that temperature. Thereafter the solids were filtered off, the filtrate was washed with brine, and the aqueous phase was extracted three times with with EtOAc (100 mL for each extraction). The organic portions were combined, dried (MgSO$_4$), and concentrated under reduced pressure to provide an oil. Flash chromatography of the oil with a silica gel column eluting with 9:1 CH$_2$Cl$_2$:MeOH provided 2.59 g of the compound of formula FW as a pale yellow oil (yield 65%).

The identity of the compound of formula FW, (3S,4S)-diethyl 1-(2-(tert-butoxycarbonylamino)ethyl)pyrrolidine-3,4-dicarboxylate, was confirmed using TLC and LC/MS.

Compound FW: TLC (SiO$_2$) 5:1 EtOAc:hexanes: Rf=0.6 with UV detection, Dragendorff's reagent; LC/MS: m/z=359 [M+H]$^+$ (Calc: 358).

To a mixture of the compound of formula FW (1.5 g, 4.2 mmol) and EtOAc at 0° C. was added slowly 4N HCl in EtOAc (4.5 mL). After heating to a temperature of about 25° C. and stirring for 2 h, the reaction mixture became cloudy, indicating the formation of an HCl salt. After concentration under reduced pressure, the residue was washed with diethyl ether and the solids were filtered off and the dried under reduced pressure for 16 h to provide 1.08 g of the compound of formula FX as a white solid (yield 90%).

The identity of the compound of formula FX was confirmed using LC/MS.

Compound FX: LC/MS: m/z=259 [M+H]$^+$ (Calc: 258).

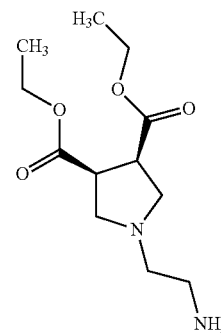

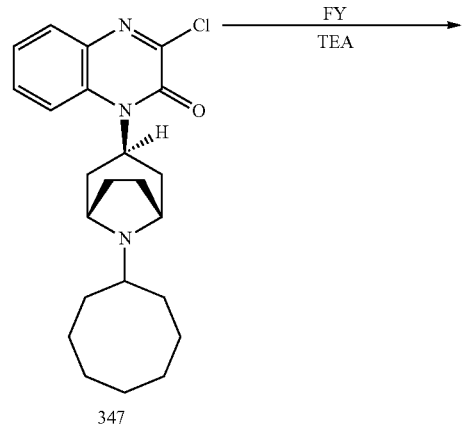

347

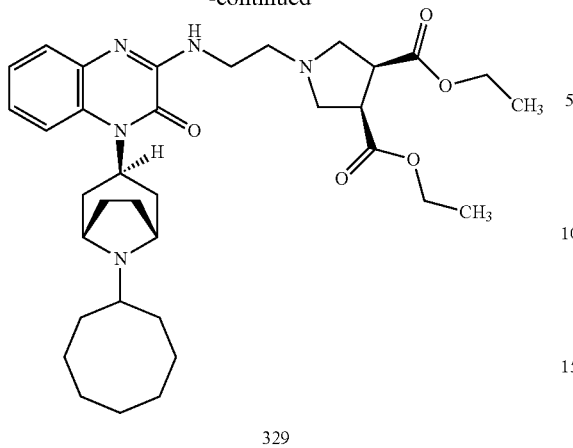

329

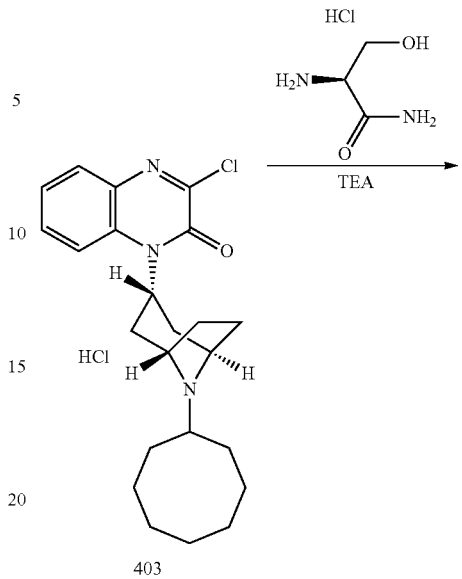

Substituted-Quinoxaline-Type Piperidine Compound 329 was prepared by using (3R,4S)-diethyl 1-(2-aminoethyl)pyrrolidine-3,4-dicarboxylate (FY) in place of serine amide hydrochloride (yield 86%).

The identity of Substituted-Quinoxaline-Type Piperidine Compound 329, (3R,4S)-diethyl 1-(2-(4-((endo)-8-cyclooctyl-8-azabicyclo[3.2.1]octan-3-yl)-3-oxo-3,4-dihydroquinoxalin-2-ylamino)ethyl)pyrrolidine-3,4-dicarboxylate, was confirmed using $^1$H NMR and LC/MS.

Substituted-Quinoxaline-Type Piperidine Compound 329: $^1$H NMR: $\delta_H$ (400 MHz, CD$_3$OD): 7.49-5.56 (m, 1H), 7.45-7.49 (s, br, 1H), 7.25-7.22 (m, 2H), 6.77-6.67 (s, br, 1H), 5.64-4.86 (s, br., 1H), 4.17-4.12 (dd, J=9.1, 8.2 Hz, 4H), 3.72 (s, br, 2H), 3.62-3.58 (dd, J=5.8, 11.5 Hz, 2H), 3.32-3.24 (m, 4H), 2.82-2.74 (m, 4H), 2.5-1.25 (m, 23H), 1.15 (t, J=7.1 Hz, 6H); LC/MS: m/z=566 [M+H]$^+$ (Calc: 565).

In a manner similar to the above preparation of the compound of formula FX, the compound of formula FY was prepared except that diethyl maleate (Sigma-Aldrich) was used in place of diethyl fumarate (yield 30% for four steps).

The identity of the compound of formula FY was confirmed using LC/MS.

Compound FY: LC/MS: m/z=259 [M+H]$^+$ (Calc: 258).

5.17 Example 17

In a manner similar to the preparation of Substituted-Quinoxaline-Type Piperidine Compound 347 from the compound of formula EH in Example 14, Substituted-Quinoxaline-Type Piperidine Compound 403, i.e., 3-chloro-1-((exo)-8-cyclooctyl-8-azabicyclo[3.2.1]octan-3-yl)quinoxalin-2(1H)-one or the exo isomer, was prepared from the compound of formula EI.

In a manner similar to Example 15, the following Substituted-Quinoxaline-Type Piperidine Compound was prepared from Substituted-Quinoxaline-Type Piperidine Compound 403 (yield 61%).

403

104

The identity of Substituted-Quinoxaline-Type Piperidine Compound 104, (2S)-2-(4-((exo)-8-cyclooctyl-8-azabicyclo[3.2.1]octan-3-yl)-3-oxo-3,4-dihydroquinoxalin-2-ylamino)-3-hydroxypropanamide, was confirmed using $^1$H NMR and LC/MS.

Substituted-Quinoxaline-Type Piperidine Compound 104: $^1$H NMR: $\delta_H$ (400 MHz, DMSO-d$_6$): 7.70 (1H, s), 7.49 (1H, s), 7.38 (1H, t, J=4.82 Hz), 7.19 (4H, m), 5.02 (2H, m), 4.47-4.43 (1H, m), 3.68 (4H, m), 2.81 (2H, m), 1.58 (21H, m); LC/MS (96%, t$_r$=1.14 min): m/z=468.2 [M+H]$^+$ (Calc: 467.6).

In a manner similar to the above preparation of Substituted-Quinoxaline-Type Piperidine Compound 104, the following Substituted-Quinoxaline-Type Piperidine Compound was prepared from Substituted-Quinoxaline-Type Piperidine Compound 403 except that (R)-3-amino-1,2-propanediol (Sigma-Aldrich) was used in place of serine amide hydrochloride (yield 70%).

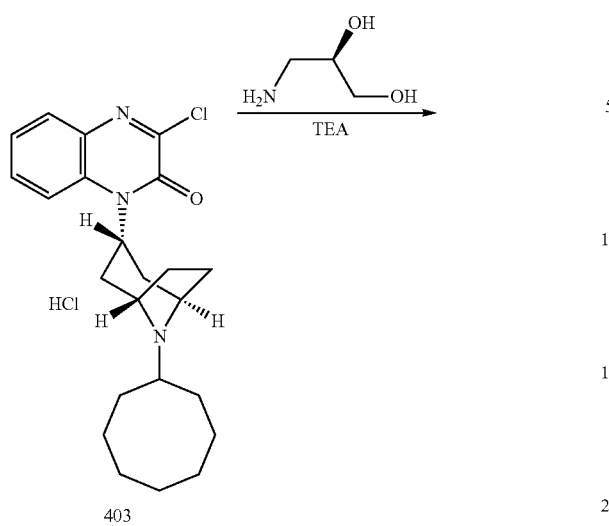

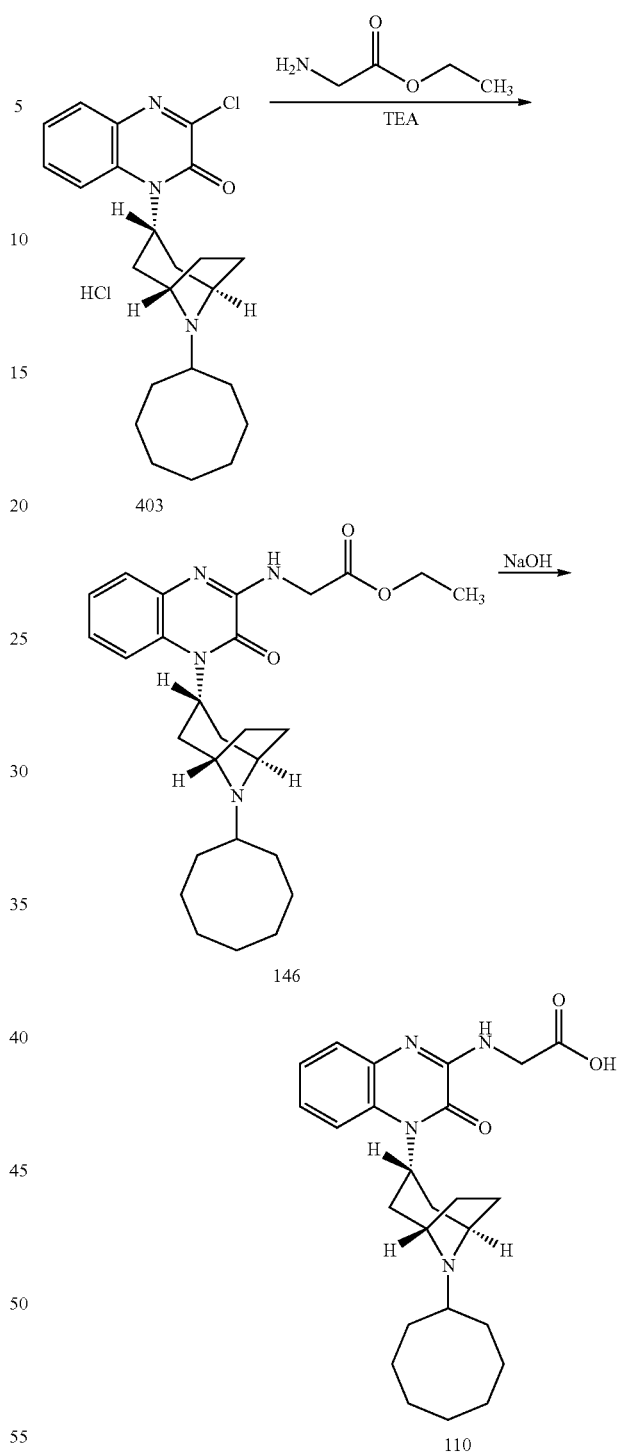

The identity of Substituted-Quinoxaline-Type Piperidine Compound 105, 1-((exo)-8-cyclooctyl-8-azabicyclo[3.2.1]octan-3-yl)-3-((R)-2,3-dihydroxypropylamino)quinoxalin-2(1H)-one, was confirmed using $^1$H NMR and LC/MS.

Substituted-Quinoxaline-Type Piperidine Compound 105: $^1$H NMR: $\delta_H$ (400 MHz, DMSO-d$_6$): 9.38 (0.1H, s), 7.69 (0.9H, s), 7.31 (4H, m), 5.00 (1.5H, d, J=5.07 Hz), 4.71 (1H, t, J=5.58 Hz), 4.28 (0.5H, s), 3.71 (1H, t, J=5.83 Hz), 3.55 (2H, t, J=6.59 Hz), 3.39 (3H, m), 2.80 (2H, br), 1.64 (23H, m); LC/MS (100%, t$_r$=1.14 min): m/z=455.2 [M+H]$^+$ (Calc: 454.6).

In a manner similar to the preparation of Substituted-Quinoxaline-Type Piperidine Compounds 144 and 106 in Example 16, the following Substituted-Quinoxaline-Type Piperidine Compounds were prepared from Substituted-Quinoxaline-Type Piperidine Compound 403.

The identity of Substituted-Quinoxaline-Type Piperidine Compound 146, ethyl 2-(4-((exo)-8-cyclooctyl-8-azabicyclo[3.2.1]octan-3-yl)-3-oxo-3,4-dihydroquinoxalin-2-ylamino)acetate, was confirmed using $^1$H NMR.

Substituted-Quinoxaline-Type Piperidine Compound 146: $^1$H NMR: $\delta_H$ (400 MHz, DMSO-d$_6$): 7.92 (1H, s), 7.68 (1H, s), 7.36 (1H, dd, J=7.60, 2.03 Hz), 7.21 (2H, q, J=7.94 Hz), 4.98 (1H, br), 4.15-4.08 (2H, m), 3.55 (2H, s), 2.80 (2H, s), 1.57 (23H, m).

The identity of Substituted-Quinoxaline-Type Piperidine Compound 110, 2-(4-((exo)-8-cyclooctyl-8-azabicyclo[3.2.1]octan-3-yl)-3-oxo-3,4-dihydroquinoxalin-2-ylamino)acetic acid, was confirmed using $^1$H NMR and LC/MS.

Substituted-Quinoxaline-Type Piperidine Compound 110: $^1$H NMR: $\delta_H$ (400 MHz, DMSO-d$_6$): 7.68 (1H, s), 7.53 (1H, t, J=5.32 Hz), 7.40-7.38 (1H, m), 7.23-7.17 (2H, m), 5.02 (1H, br), 3.85 (2H, d, J=5.07 Hz), 3.66 (2H, s), 2.82 (2H, s), 1.97-1.41 (21H, m); LC/MS (98%, t$_r$=1.38 min): m/z=439.2 [M+H]$^+$ (Calc: 438.6).

5.18 Example 18

In a manner similar to Example 15, the following Substituted-Quinoxaline-Type Piperidine Compounds were prepared from Substituted-Quinoxaline-Type Piperidine Compound 347.

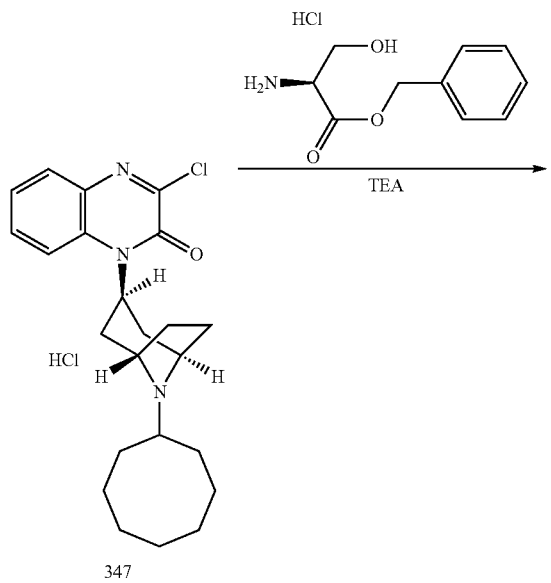

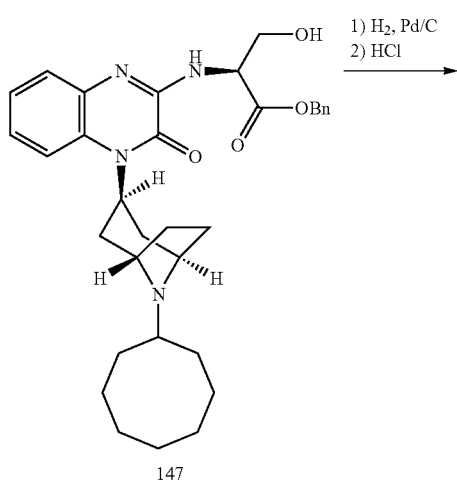

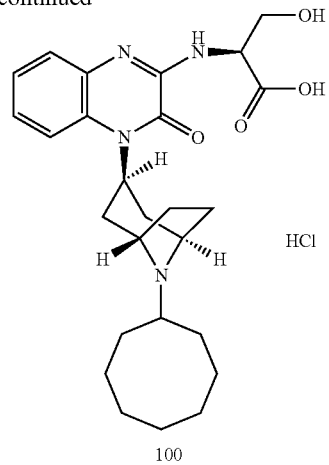

Substituted-Quinoxaline-Type Piperidine Compound 147 was prepared by using L-serine benzyl ester (i.e., (S)-benzyl 2-amino-3-hydroxypropanoate hydrochloride, Sigma-Aldrich) in place of serine amide hydrochloride (yield 93%).

The identity of Substituted-Quinoxaline-Type Piperidine Compound 147, (2S)-benzyl 2-(4-((endo)-8-cyclooctyl-8-azabicyclo[3.2.1]octan-3-yl)-3-oxo-3,4-dihydroquinoxalin-2-ylamino)-3-hydroxypropanoate, was confirmed using $^1$H NMR.

Substituted-Quinoxaline-Type Piperidine Compound 147: $^1$H NMR: $\delta_H$ (400 MHz, DMSO-d$_6$): 7.39-7.28 (9H, m), 4.68-4.64 (1H, m), 4.49 (2H, d, J=6.08 Hz), 4.04-3.87 (2H, m), 3.62 (2H, t, J=5.58 Hz), 2.37 (1H, s), 2.28-2.18 (2H, m), 2.03 (4H, d, J=34.47 Hz), 1.79-1.39 (17H, m).

Under a hydrogen atmosphere, a mixture of Substituted-Quinoxaline-Type Piperidine Compound 147 (176 mg, 0.32 mmol), 10% palladium on carbon (20 mg), and MeOH (5 mL) was stirred at a temperature of about 25° C. for 3 hr. After the Pd/C was filtered off, the mixture was washed with EtOAc and the filtrate was concentrated under reduced pressure. The resulting solid was chromatographed with a silica gel column eluted with a gradient of from 95:5:0.5 CHCl$_3$:MeOH:aqueous ammonia to 4:1:0.1 CHCl$_3$:MeOH:aqueous ammonia to provide Substituted-Quinoxaline-Type Piperidine Compound 100 as a colorless solid. Acidifying the solid with 2N aqueous HCl (2 mL) provided a white precipitate which was collected by filtration and washed twice with water (3 mL for each wash) to provide 67 mg of the hydrochloride of Substituted-Quinoxaline-Type Piperidine Compound 100 as a colorless solid (yield 45%).

The identity of Substituted-Quinoxaline-Type Piperidine Compound 100, (2S)-2-(4-((endo)-8-cyclooctyl-8-azabicyclo[3.2.1]octan-3-yl)-3-oxo-3,4-dihydroquinoxalin-2-ylamino)-3-hydroxypropanoic acid, was confirmed using $^1$H NMR and LC/MS.

Substituted-Quinoxaline-Type Piperidine Compound 100: $^1$H NMR: $\delta_H$ (400 MHz, DMSO-d$_6$): 10.48 (1H, s), 7.88 (1H, d, J=7.6 Hz), 7.41 (2H, m), 7.26 (2H, m), 5.91 (1H, t, J=9.38 Hz), 4.61-4.57 (1H, m), 4.21 (2H, s), 3.90 (2H, m), 2.94 (1H, s), 2.69 (2H, m), 2.40-1.38 (22H, m); LC/MS (98%, t$_r$=1.42 min): m/z=469.2 [M+H]$^+$ (Calc: 468.6).

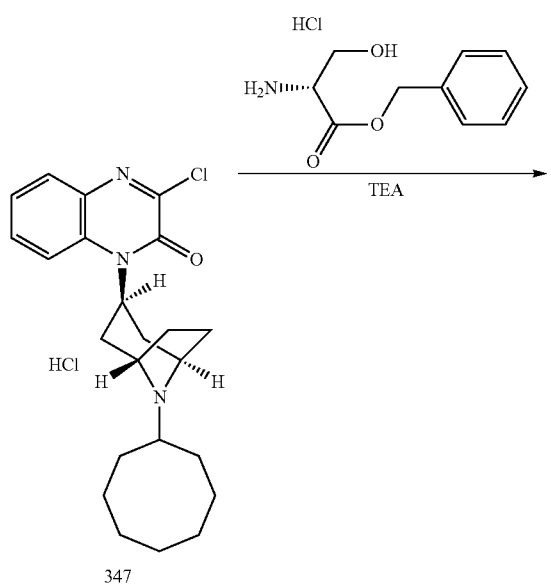

347

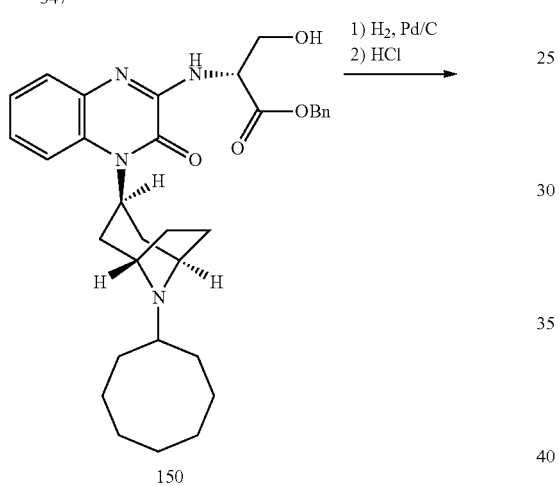

150

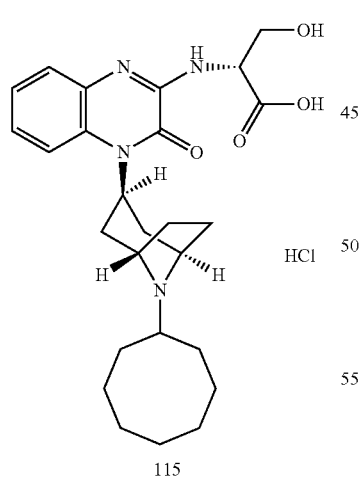

115

Substituted-Quinoxaline-Type Piperidine Compound 150 was prepared by using D-serine benzyl ester (i.e., (R)-benzyl 2-amino-3-hydroxypropanoate hydrochloride, Sigma-Aldrich) in place of serine amide hydrochloride (yield 62%).

The identity of Substituted-Quinoxaline-Type Piperidine Compound 150, (2R)-benzyl 2-(4-((endo)-8-cyclooctyl-8-azabicyclo[3.2.1]octan-3-yl)-3-oxo-3,4-dihydroquinoxalin-2-ylamino)-3-hydroxypropanoate, was confirmed using MS.

Substituted-Quinoxaline-Type Piperidine Compound 150: MS: m/z=559.3 [M+H]$^+$ (Calc: 558.3).

In a manner similar to the above preparation of the hydrochloride of Substituted-Quinoxaline-Type Piperidine Compound 100 from Substituted-Quinoxaline-Type Piperidine Compound 147, the hydrochloride of Substituted-Quinoxaline-Type Piperidine Compound 115 was prepared from Substituted-Quinoxaline-Type Piperidine Compound 150 (yield 93%).

The identity of Substituted-Quinoxaline-Type Piperidine Compound 115, (2R)-2-(4-((endo)-8-cyclooctyl-8-azabicyclo[3.2.1]octan-3-yl)-3-oxo-3,4-dihydroquinoxalin-2-ylamino)-3-hydroxypropanoic acid, was confirmed using $^1$H NMR and LC/MS.

Substituted-Quinoxaline-Type Piperidine Compound 115: $^1$H NMR: $\delta_H$ (400 MHz, DMSO-d$_6$): 10.60 (0.9H, d, J=5.07 Hz), 9.79 (0.1H, s), 7.92 (0.9H, d, J=7.6 Hz), 7.81 (0.1H, d, J=8.11 Hz), 7.49-7.45 (2H, m), 7.28-7.23 (2H, m), 6.00-5.91 (0.9H, m), 5.16 (0.1H, s), 4.65-4.62 (1H, m), 4.20 (2H, s), 3.94-3.90 (2H, m), 2.94 (1H, s), 2.78-2.61 (2H, m), 2.28 (6H, m), 2.02-1.37 (14H, m); LC/MS (100%, t$_r$=1.39 min): m/z=469.2 [M+H]$^+$ (Calc: 468.6)

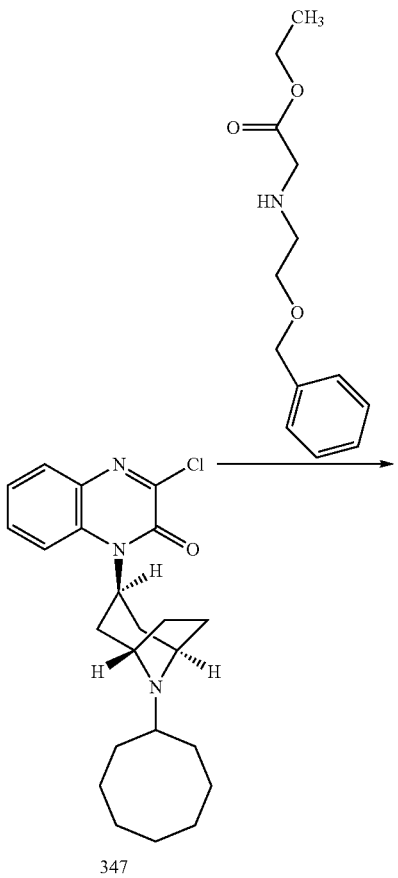

347

-continued

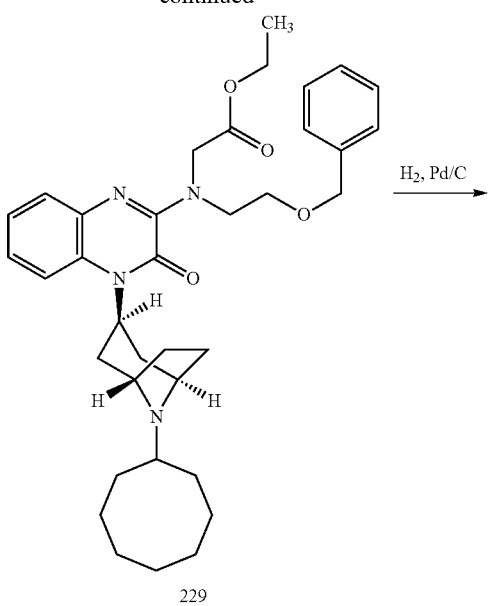

229

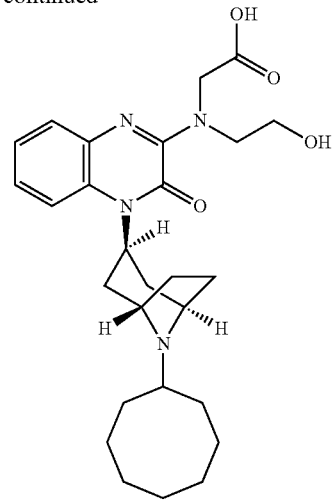

231

Substituted-Quinoxaline-Type Piperidine Compound 229 was prepared by using ethyl 2-(2-(benzyloxy)ethylamino)acetate (Sigma-Aldrich) in place of serine amide hydrochloride (yield 76%).

The identity of Substituted-Quinoxaline-Type Piperidine Compound 229, ethyl 2-((2-(benzyloxy)ethyl)(4-((endo)-8-cyclooctyl-8-azabicyclo[3.2.1]octan-3-yl)-3-oxo-3,4-dihydroquinoxalin-2-yl)amino)acetate, was confirmed using $^1$H NMR and LC/MS.

Substituted-Quinoxaline-Type Piperidine Compound 229: $^1$H NMR: $\delta_H$ (400 MHz, CDCl$_3$): 7.43 (1H, d, J=8.0 Hz), 7.35-7.20 (6H, m), 7.18 (2H, m), 5.20 (1H, m), 4.60 (2H, m), 4.51 (2H, s), 4.14 (1H, q, H=8.0 Hz), 4.06 (2H, m), 3.86 (2H, m), 3.63 (2H, m), 2.36 (1H, m), 2.25 (2H, m), 2.10-1.90 (4H, m), 1.90-1.40 (16H, m), 1.25 (3H, t, J=8.0 Hz); LC/MS: m/z=601 [M+H]$^+$ (Calc: 600.3).

Substituted-Quinoxaline-Type Piperidine Compound 230 was prepared from Substituted-Quinoxaline-Type Piperidine Compound 229 in a manner similar to that described above except that the acid treatment was omitted (yield 48%).

The identity of Substituted-Quinoxaline-Type Piperidine Compound 230, ethyl 2-((4-((endo)-8-cyclooctyl-8-azabicyclo[3.2.1]octan-3-yl)-3-oxo-3,4-dihydroquinoxalin-2-yl)(2-hydroxyethyl)amino)acetate, was confirmed using $^1$H NMR and LC/MS.

Substituted-Quinoxaline-Type Piperidine Compound 230: $^1$H NMR: $\delta_H$ (400 MHz, CDCl$_3$): 7.45 (1H, d, J=8.0 Hz), 7.35 (1H, d, J=8.0 Hz), 7.20 (1H, m), 7.15 (1H, m), 5.15 (1H, br), 4.39 (2H, m), 4.25 (2H, q, J=8.0 Hz), 4.02 (2H, m), 3.89 (2H, m), 3.64 (2H, m), 2.40-1.30 (23H, m), 1.31 (3H, t, J=8.0 Hz); LC/MS: m/z=511 [M+H]$^+$ (Calc: 510.3).

Substituted-Quinoxaline-Type Piperidine Compound 231 was prepared from Substituted-Quinoxaline-Type Piperidine Compound 230 in a manner similar to the preparation of Substituted-Quinoxaline-Type Piperidine Compound 111 in Example 5 (yield 62%).

The identity of Substituted-Quinoxaline-Type Piperidine Compound 231, 2-((4-((endo)-8-cyclooctyl-8-azabicyclo[3.2.1]octan-3-yl)-3-oxo-3,4-dihydroquinoxalin-2-yl)(2-hydroxyethyl)amino)acetic acid, was confirmed using $^1$H NMR and LC/MS.

Substituted-Quinoxaline-Type Piperidine Compound 231: $^1$H NMR: $\delta_H$ (400 MHz, DMSO-d$_6$): 7.35 (2H, m), 7.24 (1H, t, J=8.0 Hz), 7.16 (1H, t, J=8.0 Hz), 5.20 (1H, br), 4.48

(2H, m), 3.82 (2H, m), 3.72 (2H, m), 3.66 (2H, m), 2.60-1.30 (23H, m); LC/MS (100%, $t_r$=1.47 min): m/z=483 [M+H]$^+$ (Calc: 482.3).

5.19 Example 19

In a manner similar to Example 17 except that L-serine benzyl ester hydrochloride was used, the following Substituted-Quinoxaline-Type Piperidine Compound was prepared from Substituted-Quinoxaline-Type Piperidine Compound 403 (yield 50%).

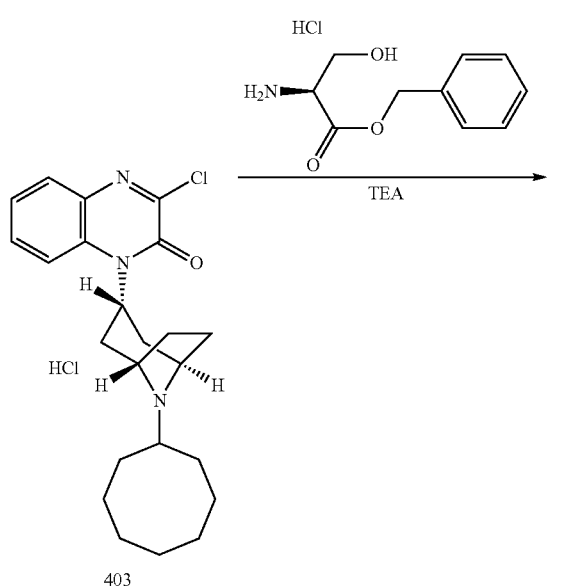

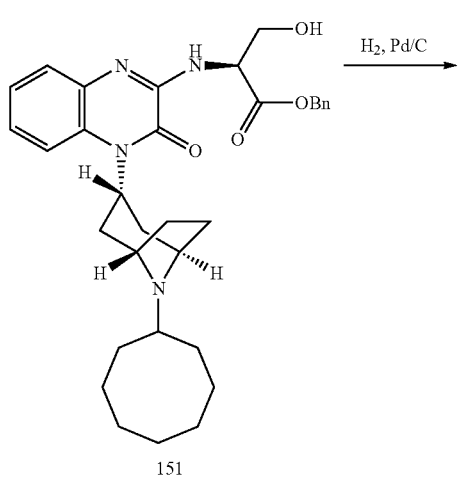

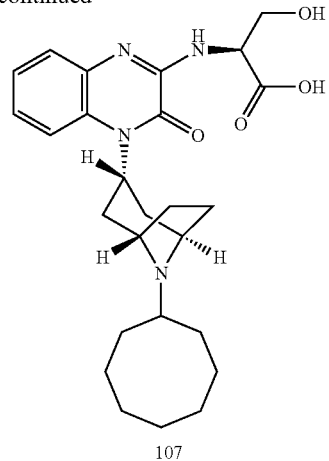

The identity of Substituted-Quinoxaline-Type Piperidine Compound 151, (2S)-benzyl 2-(4-((exo)-8-cyclooctyl-8-azabicyclo[3.2.1]octan-3-yl)-3-oxo-3,4-dihydroquinoxalin-2-ylamino)-3-hydroxypropanoate, was confirmed using MS.

Substituted-Quinoxaline-Type Piperidine Compound 151: MS: m/z=559.3 [M+H]$^+$ (Calc: 558.7).

In a manner similar to Example 18 except that the acidification was omitted, Substituted-Quinoxaline-Type Piperidine Compound 107 was prepared from the compound of formula 151 (yield 63%).

The identity of Substituted-Quinoxaline-Type Piperidine Compound 107, (2S)-2-(4-((exo)-8-cyclooctyl-8-azabicyclo[3.2.1]octan-3-yl)-3-oxo-3,4-dihydroquinoxalin-2-ylamino)-3-hydroxypropanoic acid, was confirmed using $^1$H NMR and LC/MS.

Substituted-Quinoxaline-Type Piperidine Compound 107: $^1$H NMR: $\delta_H$ (400 MHz, DMSO-d$_6$): 7.75 (1H, s), 7.40 (1H, dd, J=7.10, 2.03 Hz), 7.26 (3H, m), 4.99 (1H, s), 4.45 (1H, t, J=3.8 Hz), 3.86 (41-1, m), 2.91 (2H, s), 1.79 (21H, m); LC/MS (100%, $t_r$=1.33 min): m/z=469.2 [M+H]$^+$ (Calc: 468.6).

5.20 Example 20

In a manner similar to Example 15, Substituted-Quinoxaline-Type Piperidine Compound 152 was prepared from Substituted-Quinoxaline-Type Piperidine Compound 347.

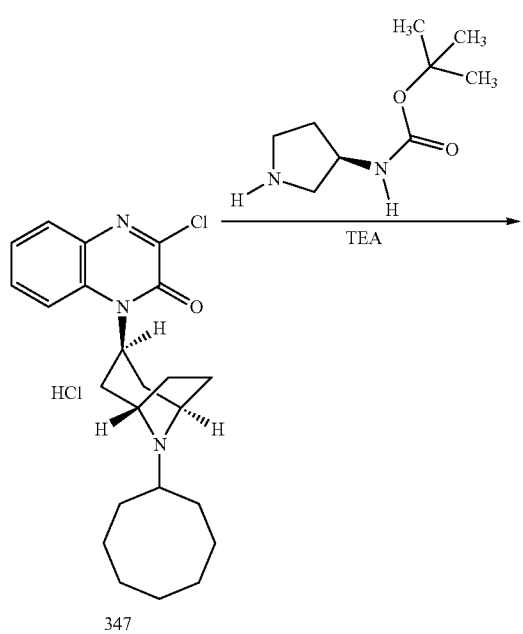

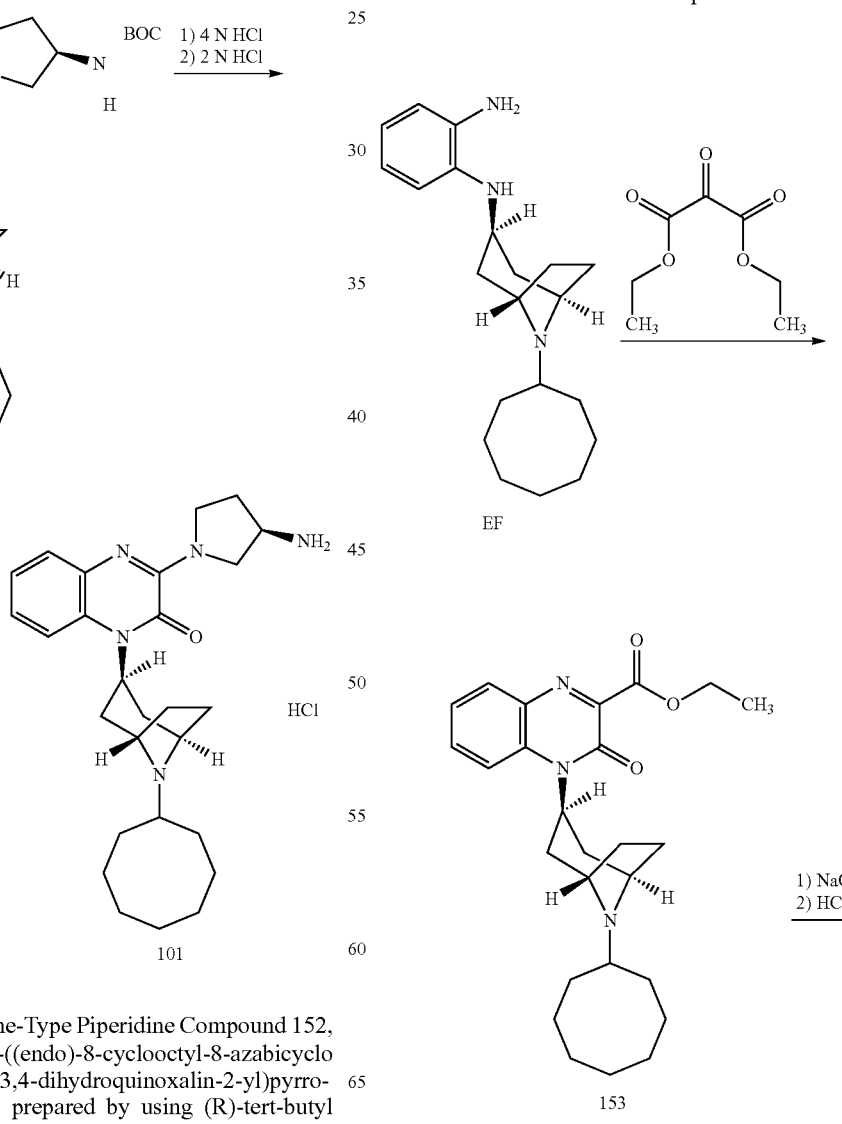

Substituted-Quinoxaline-Type Piperidine Compound 152, i.e., tert-butyl (3R)-1-(4-((endo)-8-cyclooctyl-8-azabicyclo[3.2.1]octan-3-yl)-3-oxo-3,4-dihydroquinoxalin-2-yl)pyrrolidin-3-ylcarbamate, was prepared by using (R)-tert-butyl pyrrolidin-3-ylcarbamate (Sigma-Aldrich) in place of serine amide hydrochloride. In a manner similar to the preparation of Substituted-Quinoxaline-Type Piperidine Compound 5 in Example 7, the free Substituted-Quinoxaline-Type Piperidine Compound 101 was prepared from Substituted-Quinoxaline-Type Piperidine Compound 152. Thereafter, the hydrochloride of Substituted-Quinoxaline-Type Piperidine Compound 101 was prepared in a manner similar to the preparation of Substituted-Quinoxaline-Type Piperidine Compound 174 in Example 7 (overall yield 84%).

The identity of Substituted-Quinoxaline-Type Piperidine Compound 101, 3-((R)-3-aminopyrrolidin-1-yl)-1-((endo)-8-cyclooctyl-8-azabicyclo[3.2.1]octan-3-yl)quinoxalin-2(1H)-one, was confirmed using $^1$H NMR and LC/MS.

Substituted-Quinoxaline-Type Piperidine Compound 101: $^1$H NMR: $\delta_H$ (400 MHz, DMSO-d$_6$): 10.67 (1H, s), 8.40 (3H, s), 7.85 (1H, d, J=9.12 Hz), 7.49 (1H, d, J=6.08 Hz), 7.22 (2H, td, J=8.49, 5.24 Hz), 5.89 (1H, t, J=9.38 Hz), 4.22-3.86 (9H, m), 2.92 (1H, s), 2.61 (2H, m), 2.27-1.37 (22H, m); LC/MS (98%, t$_r$=0.78 min): m/z=450.2 [M+H]$^+$ (Calc: 449.6).

5.21 Example 21

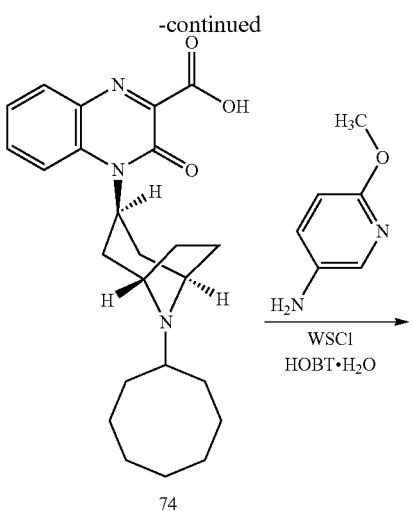

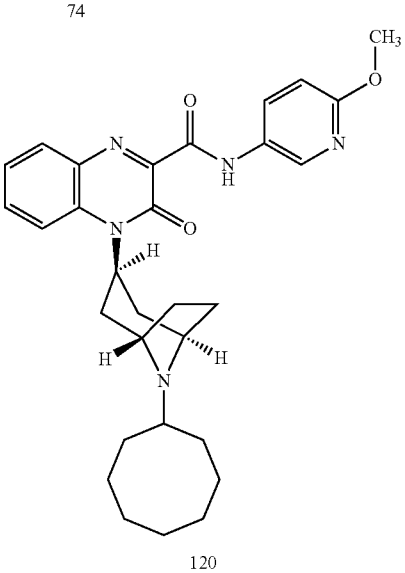

In a manner similar to the preparation of Substituted-Quinoxaline-Type Piperidine Compound 70 from the compound of formula AB in Example 12, Substituted-Quinoxaline-Type Piperidine Compound 153 was prepared from diethyl 2-oxomalonate and the compound of formula EF (yield 40%).

The identity of Substituted-Quinoxaline-Type Piperidine Compound 153, ethyl 4-((endo)-8-cyclooctyl-8-azabicyclo[3.2.1]octan-3-yl)-3-oxo-3,4-dihydroquinoxaline-2-carboxylate, was confirmed using $^1$H NMR.

Substituted-Quinoxaline-Type Piperidine Compound 153: $^1$H NMR: $\delta_H$ (300 MHz, CDCl$_3$): 7.91 (1H, d, J=8.1 Hz), 7.63-7.55 (2H, m), 7.34 (1H, t, J=7.4 Hz), 5.21 (1H, br s), 4.50 (2H, q, J=7.1 Hz), 3.66 (2H, br s), 2.43-2.15 (5H, m), 2.07-1.93 (2H, m), 1.88-1.35 (20H, m).

Substituted-Quinoxaline-Type Piperidine Compound 74 was prepared from Substituted-Quinoxaline-Type Piperidine Compound 153 in a manner similar to the preparation of Substituted-Quinoxaline-Type Piperidine Compound 111 in Example 5 (yield 63%).

The identity of Substituted-Quinoxaline-Type Piperidine Compound 74, 4-((endo)-8-cyclooctyl-8-azabicyclo[3.2.1]octan-3-yl)-3-oxo-3,4-dihydroquinoxaline-2-carboxylic acid, was confirmed using $^1$H NMR and LC/MS.

Substituted-Quinoxaline-Type Piperidine Compound 74: $^1$H NMR: $\delta_H$ (400 MHz, DMSO-d$_6$): 10.38 (1H, br s), 8.06 (1H, d, J=8.6 Hz), 7.89 (1H, d, J=7.6 Hz), 7.76 (1H, t, J=7.6 Hz), 7.47 (1H, t, J=7.6 Hz), 6.00-5.91 (1H, m), 4.24 (2H, br s), 2.99-2.89 (1H, m), 2.67-2.59 (2H, m), 2.38-1.38 (20H, m); LC/MS (99%, t$_r$=1.02 min): m/z=410.2 [M+H]$^+$ (Calc: 409).

At a temperature of about 25° C., a reaction mixture of Substituted-Quinoxaline-Type Piperidine Compound 74 (150 mg, 0.37 mmol), 6-methoxypyridin-3-amine (0.55 mmol, Sigma-Aldrich), WSCI (0.74 mmol), and HOBT.H$_2$O (0.74 mmol, Sigma-Aldrich) in DMF (4 mL) was stirred for 4 hr. The mixture was quenched with saturated aqueous NaHCO$_3$, extracted three times with EtOAc/water (40 mL for each extraction), washed twice with water (20 mL for each wash), dried (MgSO$_4$), and concentrated under reduced pressure to provide a yellow solid. The solid was triturated with 4:1:0.5 Et$_2$O:n-hexane:EtOAc (20 mL), sonicated, and filtrated to provide a yellow solid. The solid was dried under reduced pressure at 70° C. for 12 hr to provide 133 mg of Substituted-Quinoxaline-Type Piperidine Compound 120 (yield 70%).

The identity of Substituted-Quinoxaline-Type Piperidine Compound 120, 4-((endo)-8-cyclooctyl-8-azabicyclo[3.2.1]octan-3-yl)-N-(6-methoxypyridin-3-yl)-3-oxo-3,4-dihydro-quinoxaline-2-carboxamide, was confirmed using $^1$H NMR and LC/MS.

Substituted-Quinoxaline-Type Piperidine Compound 120: $^1$H NMR: $\delta_H$(400 MHz, DMSO-d$_6$): 10.82 (1H, s), 8.47 (1H, d, J=2.53 Hz), 8.02 (1H, dd, J=8.87, 2.79 Hz), 7.92 (1H, d, J=8.11 Hz), 7.77 (1H, d, J=7.1 Hz), 7.65 (1H, d, J=8.62 Hz), 7.46 (1H, t, J=7.6 Hz), 6.88 (1H, d, J=8.62 Hz), 5.29 (1H, s), 3.85 (3H, s), 3.65 (2H, s), 2.30-1.37 (23H, m); LC/MS (100%, t$_r$=1.73 min): m/z=516.2 [M+H]$^+$ (Calc: 515.7).

5.22 Example 22

In a manner similar to Example 21, the following Substituted-Quinoxaline-Type Piperidine Compounds ("endo" isomers) were prepared from Substituted-Quinoxaline-Type Piperidine Compound 74.

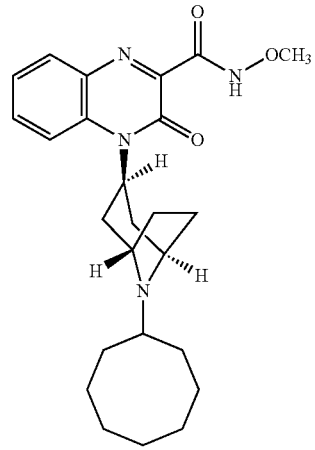

Substituted-Quinoxaline-Type Piperidine Compound 121 was prepared by using O-methylhydroxylamine (Sigma-Aldrich) in place of 4-methoxyaniline (yield 54%).

The identity of Substituted-Quinoxaline-Type Piperidine Compound 121, 4-((endo)-8-cyclooctyl-8-azabicyclo[3.2.1]

octan-3-yl)-N-hydroxy-3-oxo-3,4-dihydroquinoxaline-2-carboxamide, was confirmed using $^1$H NMR and LC/MS.

Substituted-Quinoxaline-Type Piperidine Compound 121: $^1$H NMR: $\delta_H$ (400 MHz, DMSO-d$_6$): 11.71 (1H, s), 7.89 (1H, d, J=7.6 Hz), 7.77 (1H, s), 7.44 (1H, s), 5.26 (0.81I, s), 4.23 (0.21I, s), 3.74 (3H, s), 3.58 (2H, m), 2.39-1.39 (23H, m); LC/MS (98%, t$_r$=1.20 min): m/z=439.2 [M+H]$^+$ (Calc: 438.6).

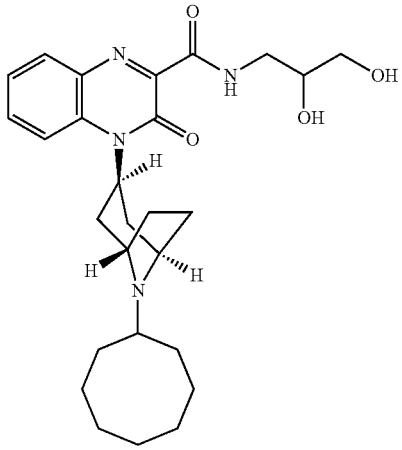

125

Substituted-Quinoxaline-Type Piperidine Compound 125 was prepared by using 3-amino-1,2-propanediol (Sigma-Aldrich) in place of 4-methoxyaniline (yield 16%).

The identity of Substituted-Quinoxaline-Type Piperidine Compound 125, 4-((endo)-8-cyclooctyl-8-azabicyclo[3.2.1]octan-3-yl)-N-(2,3-dihydroxypropyl)-3-oxo-3,4-dihydro-quinoxaline-2-carboxamide, was confirmed using $^1$H NMR and LC/MS.

Substituted-Quinoxaline-Type Piperidine Compound 125: $^1$H NMR: $\delta_H$ (400 MHz, DMSO-d$_6$): 10.09 (1H, s), 8.17 (1H, d, J=8.11 Hz), 7.67 (2H, m), 7.43 (1H, t, J=7.6 Hz), 5.30 (1H, br), 3.93 (1H, t, J=4.82 Hz), 3.69 (6H, m), 2.37-1.22 (25H, m); LC/MS (96%, t$_r$=1.00 min): m/z=483.2 [M+H]$^+$ (Calc: 482.6).

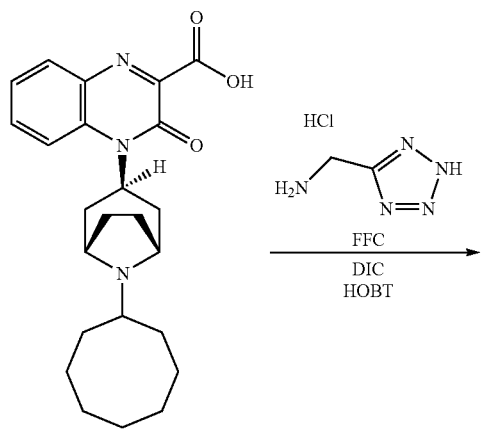

74

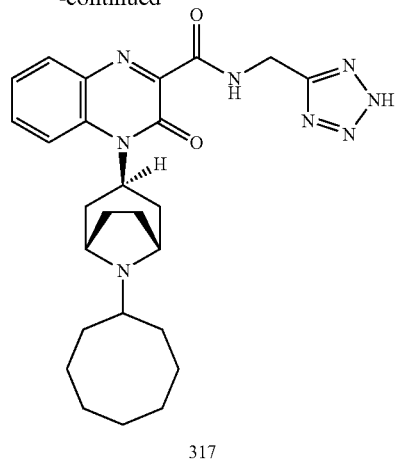

317

Substituted-Quinoxaline-Type Piperidine Compound 317 was prepared by using (2H-tetrazol-5-yl)methanamine hydrochloride (FFC) in place of 4-methoxyaniline and DIC in place of WSCI (yield 29%).

The identity of Substituted-Quinoxaline-Type Piperidine Compound 317, N-((2H-tetrazol-5-yl)methyl)-4-((endo)-8-cyclooctyl-8-azabicyclo[3.2.1]octan-3-yl)-3-oxo-3,4-dihydroquinoxaline-2-carboxamide, was confirmed using $^1$H NMR and LC/MS.

Substituted-Quinoxaline-Type Piperidine Compound 317: $^1$H NMR: $\delta_H$ (400 MHz, CD$_3$OD): 8.06 (d, 1H, J=7.9 Hz), 7.83-7.84 (m, 2H), 7.52-7.56 (m, 1H) 5.57-5.59 (m, 1H), 5.01 (s, 2H), 4.38 (m, 2H), 3.15 (m, 1H) 2.77-2.80 (m, 2H), 1.47-2.54 (m, 20H); LC/MS: m/z=491 [M+H]$^+$ (Calc: 490).

(2H-tetrazol-5-yl)methanamine hydrochloride (FFC) was prepared as follows:

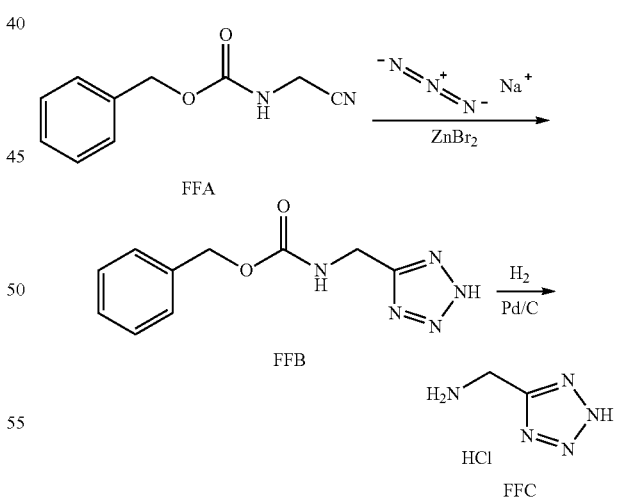

A mixture of benzyl cyanomethylcarbamate (FFA, 2.00 g, 10.5 mmol, Sigma-Aldrich), sodium azide (1.37 g, 21.0 mmol), zinc bromide (1.18 g, 5.26 mmol, Sigma-Aldrich), 2-propanol (15 mL), and water (30 mL) at a temperature of about 25° C. was stirred for 15 h. To the reaction mixture was added 2N aqueous HCl (7 mL). The mixture was partitioned between EtOAc and water, the organic portion was separated, washed with brine, dried (Na$_2$SO$_4$), filtered, and concentrated under reduced pressure to provide 1.51 g of the compound of formula FFB as a white solid (yield 61%).

The identity of the compound of formula FFB, benzyl (2H-tetrazol-5-yl)methylcarbamate, was confirmed using LC/MS.

Compound FFB: LC/MS: m/z=234 [M+H]$^+$ (Calc: 233).

Under a hydrogen atmosphere, a mixture of the compound of formula FFC (754 mg, 3.23 mmol), 20% palladium on carbon (50 mg), and MeOH (8 mL) was stirred at a temperature of about 25° C. for 1 h. The Pd/C was filtered off with a CELITE pad, the mixture was washed with MeOH, then concentrated under reduced pressure to provide 438 mg of the compound of formula FFC as a yellow oil (yield >98%).

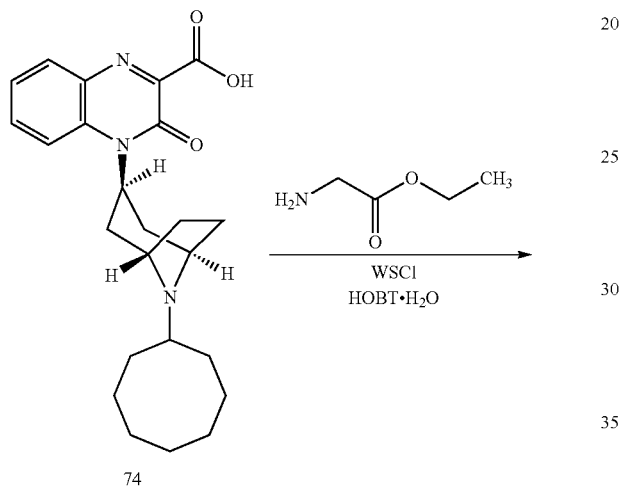

74

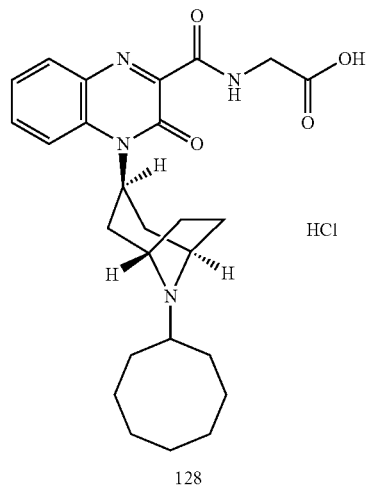

128

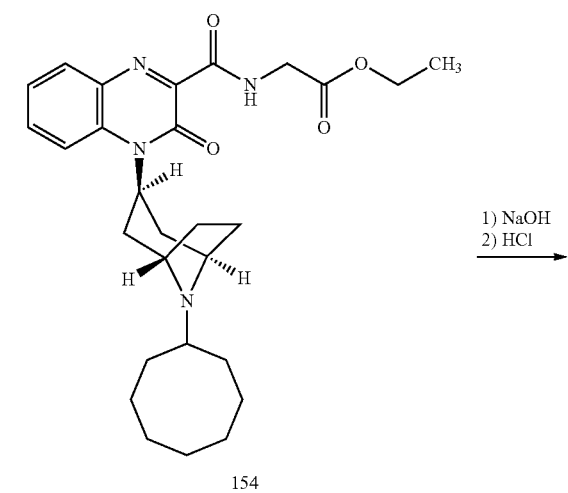

154

Substituted-Quinoxaline-Type Piperidine Compound 154 was prepared by using glycine ethyl ester in place of 4-methoxyaniline (yield 96%).

The identity of Substituted-Quinoxaline-Type Piperidine Compound 154, ethyl 2-(4-((endo)-8-cyclooctyl-8-azabicyclo[3.2.1]octan-3-yl)-3-oxo-3,4-dihydroquinoxaline-2-carboxamido)acetate, was confirmed using $^1$H NMR.

Substituted-Quinoxaline-Type Piperidine Compound 154: $^1$H NMR: $\delta_H$ (400 MHz, DMSO-d$_6$): 9.25 (1H, m), 7.90 (1H, t, J=4.06 Hz), 7.76 (1H, t, J=7.1 Hz), 7.62 (1H, d, J=8.62 Hz), 7.44 (1H, t, J=7.6 Hz), 5.23 (1H, br), 4.13 (4.2H, m), 3.65 (2H, s), 2.37-1.45 (23H, m), 1.23 (3H, t, J=7.1 Hz).

The hydrochloride of Substituted-Quinoxaline-Type Piperidine Compound 128 was prepared from Substituted-Quinoxaline-Type Piperidine Compound 154 in a manner similar to the preparation of Substituted-Quinoxaline-Type Piperidine Compound 174 in Example 7 (yield 30%).

The identity of Substituted-Quinoxaline-Type Piperidine Compound 128, 2-(4-((endo)-8-cyclooctyl-8-azabicyclo[3.2.1]octan-3-yl)-3-oxo-3,4-dihydroquinoxaline-2-carboxamido)acetic acid, was confirmed using $^1$H NMR and LC/MS.

Substituted-Quinoxaline-Type Piperidine Compound 128: $^1$H NMR: $\delta_H$ (400 MHz, DMSO-d$_6$): 12.78-12.74 (1H, m), 10.33 (0.9H, br), 9.38 (0.1H, s), 9.10 (1H, t, J=5.58 Hz), 8.04 (1H, d, J=8.11 Hz), 7.92 (1H, dd, J=7.86, 1.27 Hz), 7.76 (1H, t, J=7.35 Hz), 7.47 (1H, t, J=7.6 Hz), 5.93 (0.9H, t, J=9.12 Hz), 5.20 (0.1H, s), 4.25 (2H, s), 4.03 (2H, d, J=5.58 Hz), 2.94 (1H, s), 2.61 (2H, m), 2.35-1.37 (20H, m); LC/MS (96%, t$_r$=1.18 min): m/z=467.3 [M+H]$^+$ (Calc: 466.6).

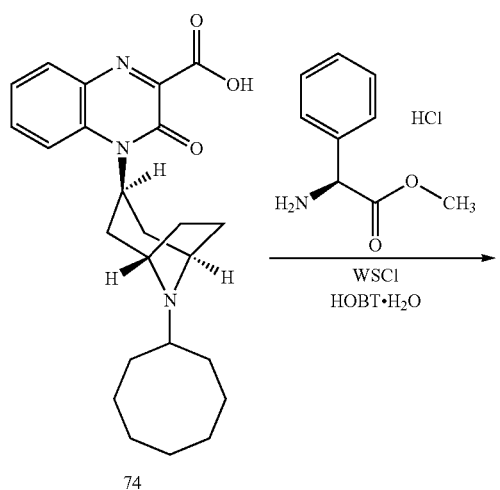

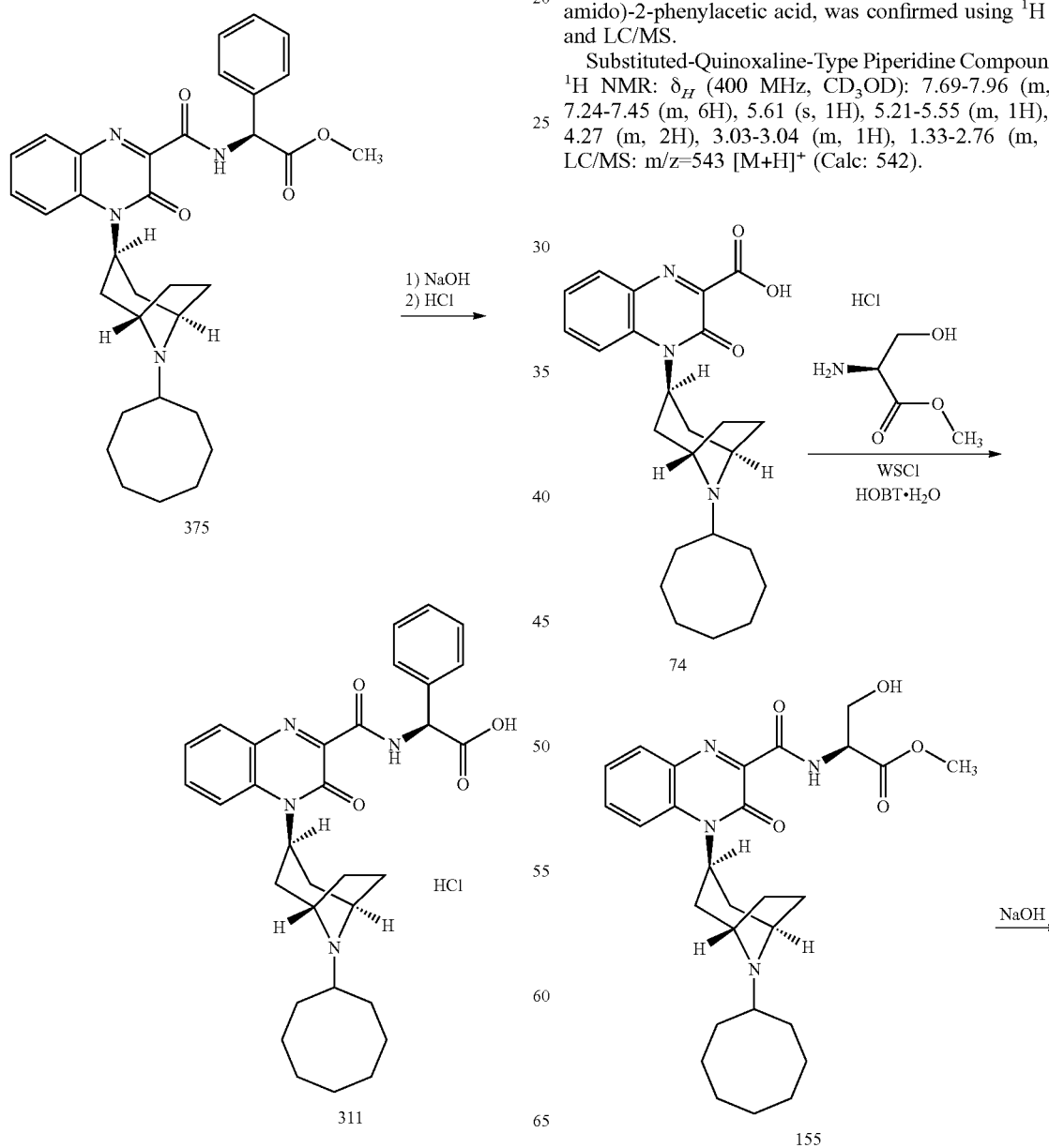

Substituted-Quinoxaline-Type Piperidine Compound 375 was prepared by using (S)-(+)-methyl 2-amino-2-phenylacetate hydrochloride in place of 4-methoxyaniline (yield 49%).

The identity of Substituted-Quinoxaline-Type Piperidine Compound 375, (S)-methyl 2-(4-((endo)-8-cyclooctyl-8-azabicyclo[3.2.1]octan-3-yl)-3-oxo-3,4-dihydroquinoxaline-2-carboxamido)-2-phenylacetate, was confirmed using LC/MS.

Substituted-Quinoxaline-Type Piperidine Compound 375: LC/MS: m/z=557 [M+H]$^+$ (Calc: 556).

The hydrochloride of Substituted-Quinoxaline-Type Piperidine Compound 311 was prepared from Substituted-Quinoxaline-Type Piperidine Compound 375 in a manner similar to the preparation of Substituted-Quinoxaline-Type Piperidine Compound 174 in Example 7 (yield 30%).

The identity of Substituted-Quinoxaline-Type Piperidine Compound 311, (S)-2-(4-((endo)-8-cyclooctyl-8-azabicyclo[3.2.1]octan-3-yl)-3-oxo-3,4-dihydroquinoxaline-2-carboxamido)-2-phenylacetic acid, was confirmed using $^1$H NMR and LC/MS.

Substituted-Quinoxaline-Type Piperidine Compound 311: $^1$H NMR: $\delta_H$ (400 MHz, CD$_3$OD): 7.69-7.96 (m, 3H), 7.24-7.45 (m, 6H), 5.61 (s, 1H), 5.21-5.55 (m, 1H), 4.19-4.27 (m, 2H), 3.03-3.04 (m, 1H), 1.33-2.76 (m, 22H); LC/MS: m/z=543 [M+H]$^+$ (Calc: 542).

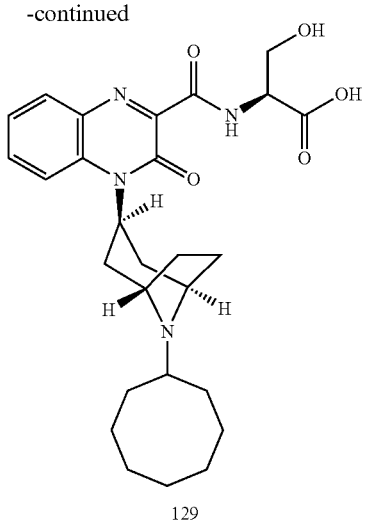

129

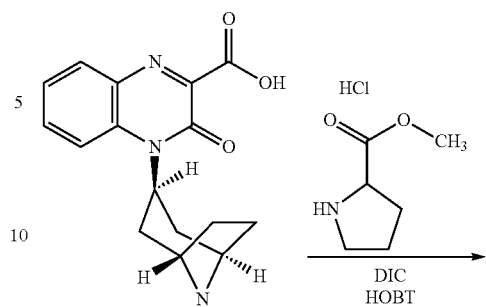

74

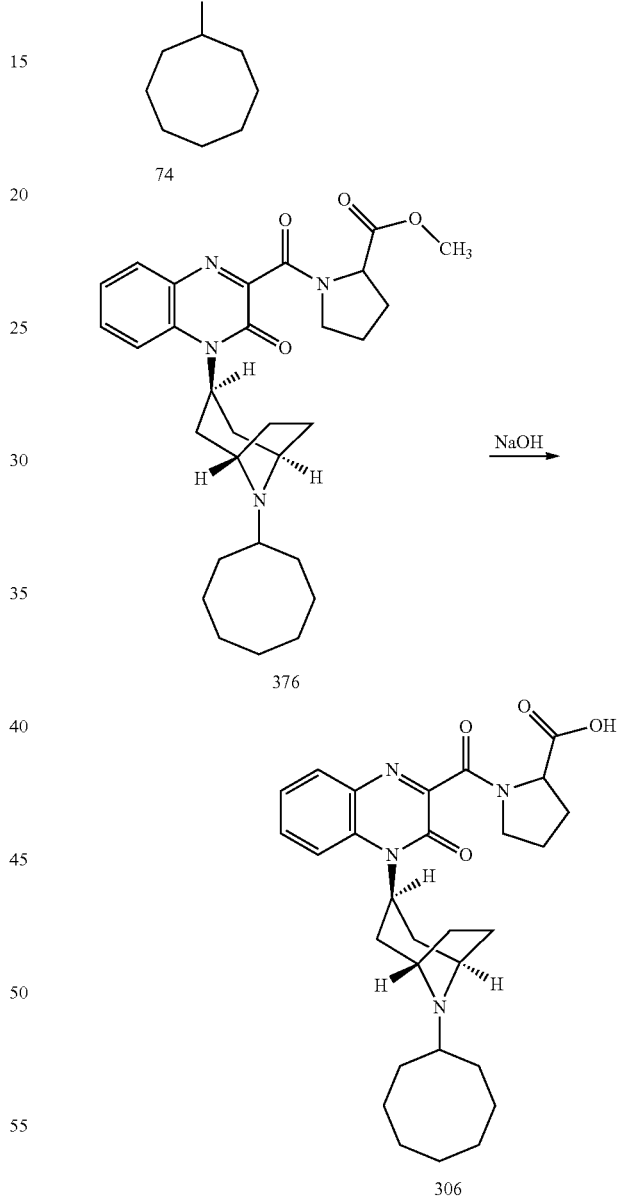

376

306

Substituted-Quinoxaline-Type Piperidine Compound 155 was prepared by using L-serine methyl ester hydrochloride (i.e., (S)-methyl 2-amino-3-hydroxypropanoate hydrochloride, Sigma-Aldrich) in place of 4-methoxyaniline (yield >98%).

The identity of Substituted-Quinoxaline-Type Piperidine Compound 155, (2S)-methyl 2-(4-((endo)-8-cyclooctyl-8-azabicyclo[3.2.1]octan-3-yl)-3-oxo-3,4-dihydroquinoxaline-2-carboxamido)-3-hydroxypropanoate, was confirmed using $^1$H NMR.

Substituted-Quinoxaline-Type Piperidine Compound 155: $^1$H NMR: $\delta_H$ (400 MHz, DMSO-d$_6$): 9.44 (1H, m), 7.92 (1H, d, J=8.11 Hz), 7.77 (1H, t, J=7.35 Hz), 7.62 (1H, d, J=8.62 Hz), 7.45 (1H, t, J=7.6 Hz), 5.22 (1H, br), 5.21 (1H, t, J=5.58 Hz), 4.61-4.56 (1H, m), 3.86-3.81 (1H, m), 3.70 (6H, m), 1.89 (23H, m).

Substituted-Quinoxaline-Type Piperidine Compound 129 was prepared from Substituted-Quinoxaline-Type Piperidine Compound 155 in a manner similar to the preparation of Substituted-Quinoxaline-Type Piperidine Compound 111 in Example 5 (yield 78%).

The identity of Substituted-Quinoxaline-Type Piperidine Compound 129, (2S)-2-(4-((endo)-8-cyclooctyl-8-azabicyclo[3.2.1]octan-3-yl)-3-oxo-3,4-dihydroquinoxaline-2-carboxamido)-3-hydroxypropanoic acid, was confirmed using $^1$H NMR and LC/MS.

Substituted-Quinoxaline-Type Piperidine Compound 129: $^1$H NMR: $\delta_H$ (400 MHz, DMSO-d$_6$): 9.30 (1H, s), 7.92 (1H, dd, J=7.86, 1.27 Hz), 7.72 (2H, m), 7.44 (1H, t, J=7.86 Hz), 5.36 (1H, br), 4.44-4.40 (1.1H, m), 3.77 (4H, m), 2.34 (2H, m), 2.08 (4H, m), 1.91-1.40 (17H, m); LC/MS (98%, t$_r$=1.15 min): m/z=497.2 [M+H]$^+$ (Calc: 496.6).

Substituted-Quinoxaline-Type Piperidine Compound 376 was prepared by using methyl pyrrolidine-2-carboxylate hydrochloride (Bachem Americas, Inc., Torrance, Calif.) in place of 4-methoxyaniline and DIC in place of WSCI (yield 29%).

The identity of Substituted-Quinoxaline-Type Piperidine Compound 376, methyl 1-(4-((endo)-8-cyclooctyl-8-azabicyclo[3.2.1]octan-3-yl)-3-oxo-3,4-dihydroquinoxaline-2-carbonyl)pyrrolidine-2-carboxylate, was confirmed using LC/MS.

Substituted-Quinoxaline-Type Piperidine Compound 376: LC/MS: m/z=521 [M+H]$^+$ (Calc: 520).

Substituted-Quinoxaline-Type Piperidine Compound 306 was prepared from Substituted-Quinoxaline-Type Piperidine Compound 376 in a manner similar to the preparation of Substituted-Quinoxaline-Type Piperidine Compound 111 in Example 5 (yield 40%).

The identity of Substituted-Quinoxaline-Type Piperidine Compound 306, 1-(4-((endo)-8-cyclooctyl-8-azabicyclo[3.2.1]octan-3-yl)-3-oxo-3,4-dihydroquinoxaline-2-carbonyl)pyrrolidine-2-carboxylic acid, was confirmed using $^1$H NMR and LC/MS.

Substituted-Quinoxaline-Type Piperidine Compound 306: $^1$H NMR: $\delta_H$ (400 MHz, CD$_3$OD): 7.39-7.90 (m, 4H), 5.28-5.50 (m, 1H), 4.35-4.42 (m, 1H), 3.54-3.79 (m, 5H), 1.45-2.35 (m, 24H); LC/MS: m/z=507 [M+H]$^+$ (Calc: 506).

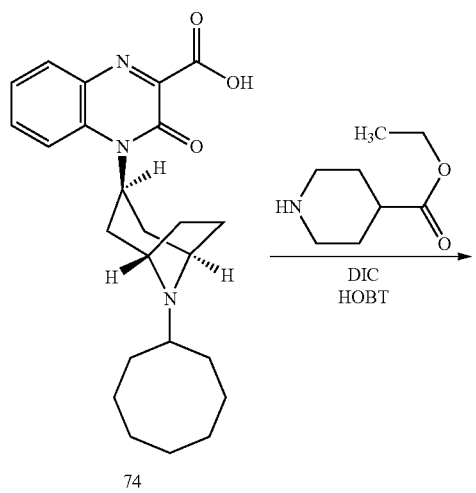

74

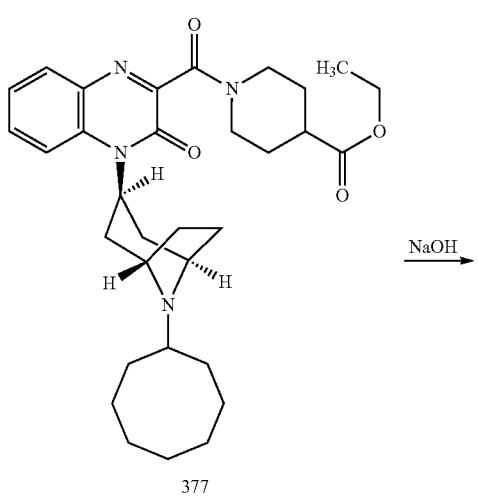

377

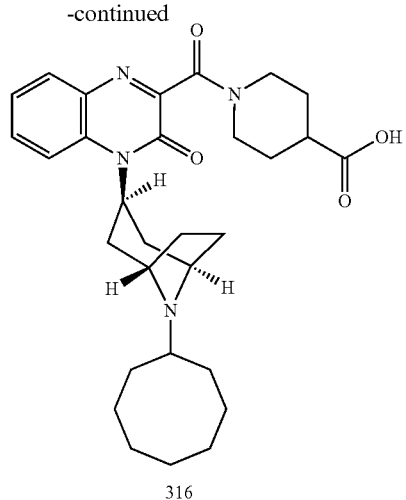

316

Substituted-Quinoxaline-Type Piperidine Compound 377 was prepared by using ethyl piperidine-4-carboxylate (Sigma-Aldrich) in place of 4-methoxyaniline and DIC in place of WSCI (yield 29%).

The identity of Substituted-Quinoxaline-Type Piperidine Compound an ethyl 1-(4-((endo)-8-cyclooctyl-8-azabicyclo[3.2.1]octan-3-yl)-3-oxo-3,4-dihydroquinoxaline-2-carbonyl)piperidine-4-carboxylate, was confirmed using LC/MS.

Substituted-Quinoxaline-Type Piperidine Compound 377: LC/MS: m/z=549 [M+H]$^+$ (Calc: 548).

Substituted-Quinoxaline-Type Piperidine Compound 316 was prepared from Substituted-Quinoxaline-Type Piperidine Compound 377 in a manner similar to the preparation of Substituted-Quinoxaline-Type Piperidine Compound 111 in Example 5 (yield 23%).

The identity of Substituted-Quinoxaline-Type Piperidine Compound 316, 1-(4-((endo)-8-cyclooctyl-8-azabicyclo[3.2.1]octan-3-yl)-3-oxo-3,4-dihydroquinoxaline-2-carbonyl)piperidine-4-carboxylic acid, was confirmed using $^1$H NMR and LC/MS.

Substituted-Quinoxaline-Type Piperidine Compound 316: $^1$H NMR: $\delta_H$ (400 MHz, CD$_3$OD): 7.91 (dd, 1H, J=1.2 Hz, 7.9 Hz), 7.79-7.87 (m, 1H), 7.75-7.77 (m, 1H), 7.48-7.51 (m, 1H), 5.59-5.63 (m, 08H), 5.30 (m, 0.2H), 4.52 (m, 1H), 4.49 (m, 2H), 3.67-3.70 (m, 1H), 3.14-3.32 (m, 3H), 1.46-2.84 (m, 27H); LC/MS: m/z=521 [M+H]$^+$ (Calc: 520).

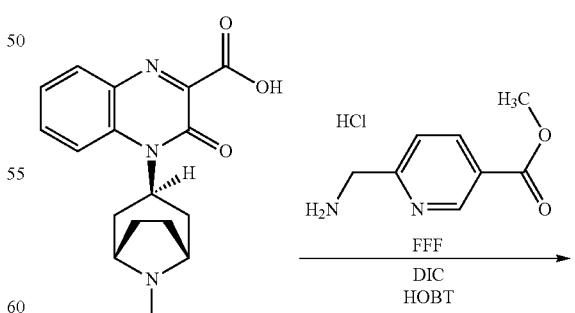

74

259

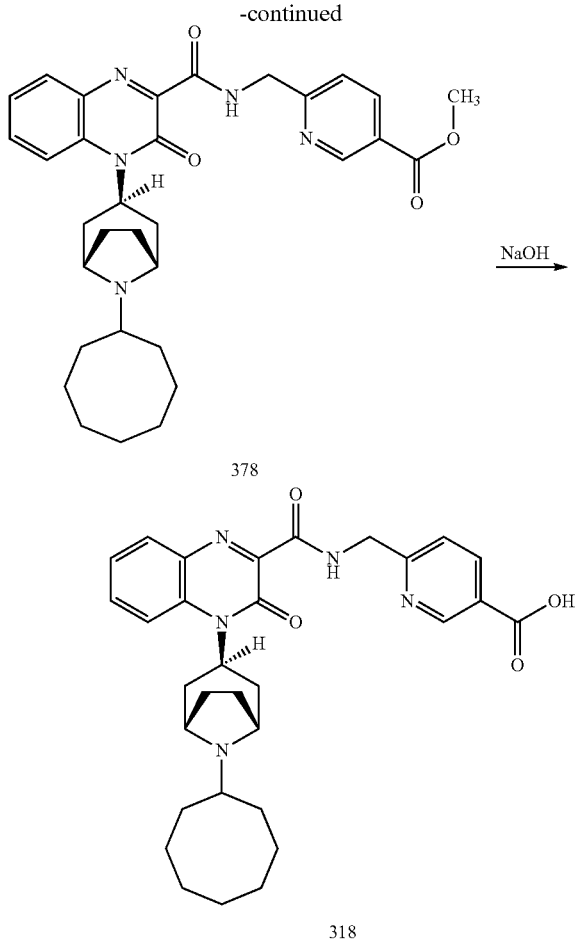

Substituted-Quinoxaline-Type Piperidine Compound 378 was prepared by using methyl 6-(aminomethyl)nicotinate hydrochloride (FFF) in place of 4-methoxyaniline and DIC in place of WSCI (yield 39%).

The identity of Substituted-Quinoxaline-Type Piperidine Compound 378, methyl 6-((4-((endo)-8-cyclooctyl-8-azabicyclo[3.2.1]octan-3-yl)-3-oxo-3,4-dihydroquinoxaline-2-carboxamido)methyl)nicotinate, was confirmed using LC/MS.

Substituted-Quinoxaline-Type Piperidine Compound 378: LC/MS: m/z=558 [M+H]$^+$ (Calc: 557).

Substituted-Quinoxaline-Type Piperidine Compound 318 was prepared from Substituted-Quinoxaline-Type Piperidine Compound 378 in a manner similar to the preparation of Substituted-Quinoxaline-Type Piperidine Compound 111 in Example 5 (yield 32%).

The identity of Substituted-Quinoxaline-Type Piperidine Compound 318, 6-((4-((endo)-8-cyclooctyl-8-azabicyclo[3.2.1]octan-3-yl)-3-oxo-3,4-dihydroquinoxaline-2-carboxamido)methyl)nicotinic acid, was confirmed using $^1$H NMR and LC/MS.

Substituted-Quinoxaline-Type Piperidine Compound 318: $^1$H NMR: $\delta_H$ (400 MHz, DMSO-d$_6$): 9.43-9.46 (m, 1H), 9.03 (d, 1H, J=1.1 Hz), 8.27 (dd, 1H, J=1.9 Hz, 8.1 Hz), 7.89 (d, 1H, J=7.7 Hz), 7.67-7.75 (m, 2H), 7.59 (d, 1H, J=8.1 Hz), 7.42-7.46 (m, 1H), 5.21-5.42 (m, 1H), 4.65 (d, 2H, J=5.7 Hz), 3.65-3.76 (m, 2H), 1.42-2.35 (m, 23H); LC/MS: m/z=544 [M+H]$^+$ (Calc: 543).

260

Methyl 6-(aminomethyl)nicotinate hydrochloride (FFF) was prepared as follows:

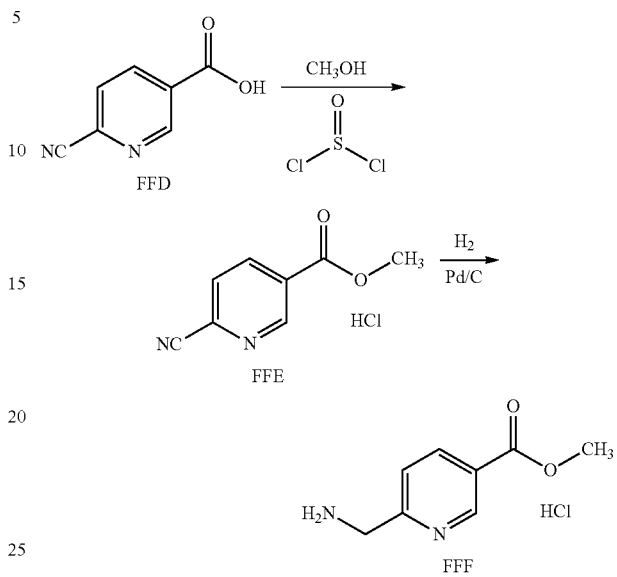

To a mixture of 6-cyanonicotinic acid (FFD, 1.00 g, 6.75 mmol, Sigma-Aldrich) and DMF (4 drops) in CHCl$_3$ (20 mL) at a temperature of about 25° C. was added thionyl chloride (1.08 mL, 14.85 mmol). The reaction mixture was refluxed for 2 h, then concentrated under reduced pressure to provide a residue. The residue was dissolved in MeOH (20 mL), stirred at a temperature of about 25° C. for 2 h, then concentrated under reduced pressure to provide 1.34 g of the compound of formula FFE, methyl 6-cyanonicotinate hydrochloride, as a pale yellow solid (yield >98%). Under a hydrogen atmosphere, a mixture of the compound of formula FFE (1.34 g, 6.75 mmol), 20% palladium on carbon (650 mg), and MeOH (20 mL) was stirred at a temperature of about 25° C. for 16 h. The Pd/C was filtered off with a CELITE pad, the mixture was washed with MeOH, then recrystalized from EtOAc/MeOH/hexane to provide 488.2 mg of the compound of formula FFF as a purple solid (yield 36%).

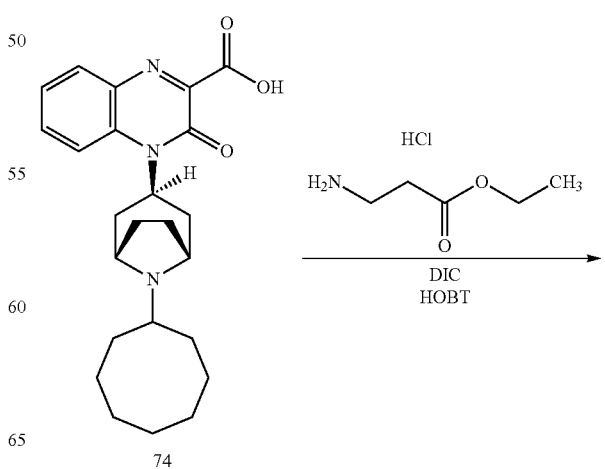

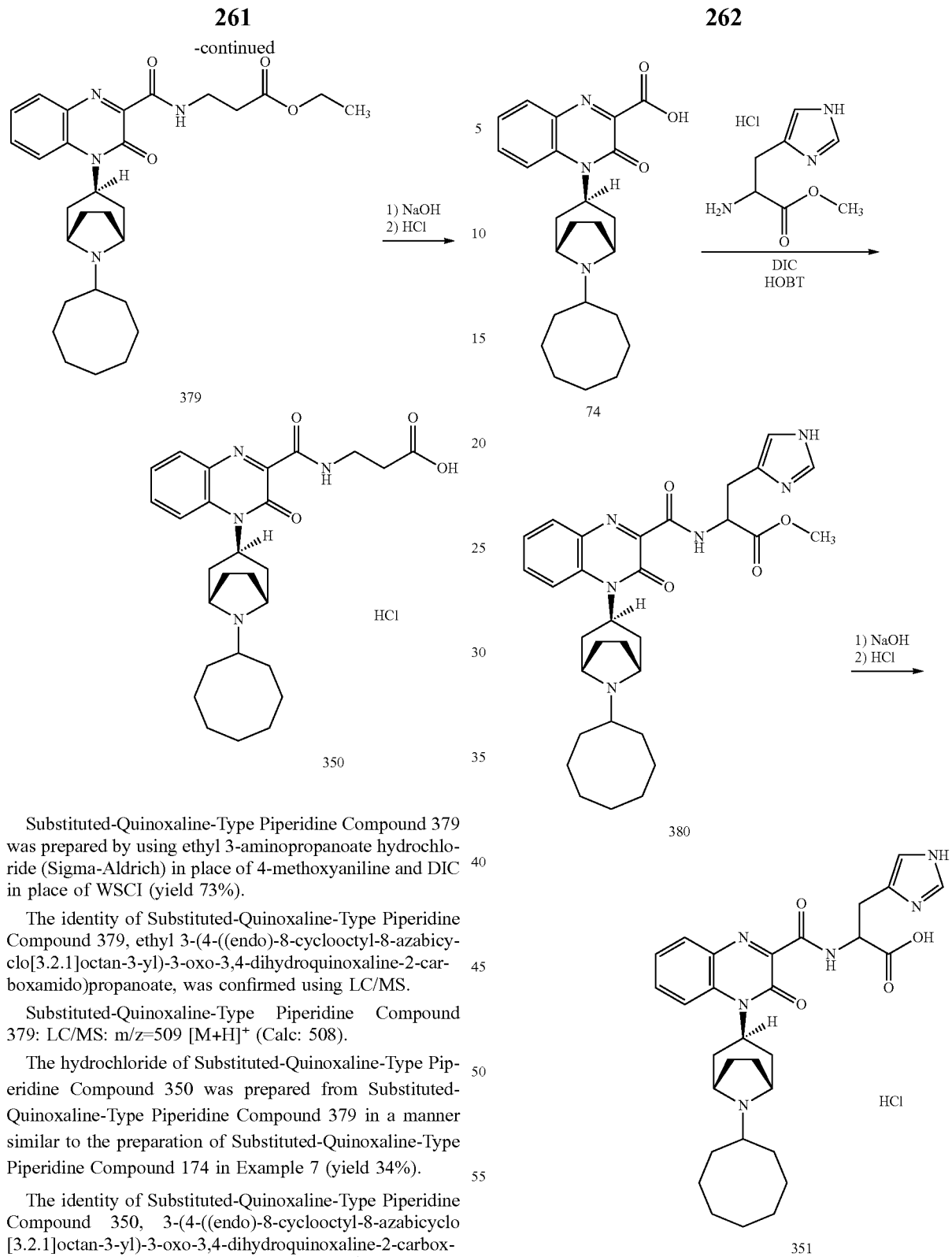

Substituted-Quinoxaline-Type Piperidine Compound 379 was prepared by using ethyl 3-aminopropanoate hydrochloride (Sigma-Aldrich) in place of 4-methoxyaniline and DIC in place of WSCI (yield 73%).

The identity of Substituted-Quinoxaline-Type Piperidine Compound 379, ethyl 3-(4-((endo)-8-cyclooctyl-8-azabicyclo[3.2.1]octan-3-yl)-3-oxo-3,4-dihydroquinoxaline-2-carboxamido)propanoate, was confirmed using LC/MS.

Substituted-Quinoxaline-Type Piperidine Compound 379: LC/MS: m/z=509 [M+H]$^+$ (Calc: 508).

The hydrochloride of Substituted-Quinoxaline-Type Piperidine Compound 350 was prepared from Substituted-Quinoxaline-Type Piperidine Compound 379 in a manner similar to the preparation of Substituted-Quinoxaline-Type Piperidine Compound 174 in Example 7 (yield 34%).

The identity of Substituted-Quinoxaline-Type Piperidine Compound 350, 3-(4-((endo)-8-cyclooctyl-8-azabicyclo[3.2.1]octan-3-yl)-3-oxo-3,4-dihydroquinoxaline-2-carboxamido)propanoic acid, was confirmed using $^1$H NMR and LC/MS.

Substituted-Quinoxaline-Type Piperidine Compound 350: $^1$H NMR: $\delta_H$ (400 MHz, CD$_3$OD): 7.92-7.94 (m, 1H), 7.67-7.74 (m, 2H), 7.38-7.42 (m, 1H), 5.50 (m, 1H), 4.25 (m, 2H), 3.63 (t, 2H, J=6.5 Hz), 3.02-3.04 (m, 1H), 2.63-2.68 (m, 2H), 2.59 (t, 2H, J=6.5 Hz), 2.28-2.57 (m, 6H), 1.35-1.86 (14H, m); LC/MS: m/z=481 [M+H]$^+$ (Calc: 480).

Substituted-Quinoxaline-Type Piperidine Compound 380 was prepared by using methyl 2-amino-3-(1H-imidazol-4-yl)propanoate hydrochloride (Sigma-Aldrich) in place of 4-methoxyaniline and DIC in place of WSCI (yield 29%).

The identity of Substituted-Quinoxaline-Type Piperidine Compound 380, methyl 2-(4-((endo)-8-cyclooctyl-8-azabicyclo[3.2.1]octan-3-yl)-3-oxo-3,4-dihydroquinoxaline-2-carboxamido)-3-(1H-imidazol-4-yl)propanoate, was confirmed using LC/MS.

Substituted-Quinoxaline-Type Piperidine Compound 380: LC/MS: m/z=561 [M+H]+ (Calc: 560).

The hydrochloride of Substituted-Quinoxaline-Type Piperidine Compound 351 was prepared from Substituted-Quinoxaline-Type Piperidine Compound 380 in a manner similar to the preparation of Substituted-Quinoxaline-Type Piperidine Compound 174 in Example 7 (yield 34%).

The identity of Substituted-Quinoxaline-Type Piperidine Compound 351, 2-(4-((endo)-8-cyclooctyl-8-azabicyclo[3.2.1]octan-3-yl)-3-oxo-3,4-dihydroquinoxaline-2-carboxamido)-3-(1H-imidazol-4-yl)propanoic acid, was confirmed using $^1$H NMR and LC/MS.

Substituted-Quinoxaline-Type Piperidine Compound 351: $^1$H NMR: $\delta_H$ (400 MHz, CD$_3$OD): 8.87 (s, 1H), 8.02 (m, 2H), 7.80-7.84 (m, 1H), 7.52 (m, 1H), 7.47 (s, 1H), 5.80 (m, 1H), 5.09 (m, 1H), 4.36 (m, 2H), 3.52-3.55 (m, 1H), 3.13 (m, 1H), 1.45-2.80 (m, 21H); LC/MS: m/z=547 [M+H]+ (Calc: 546).

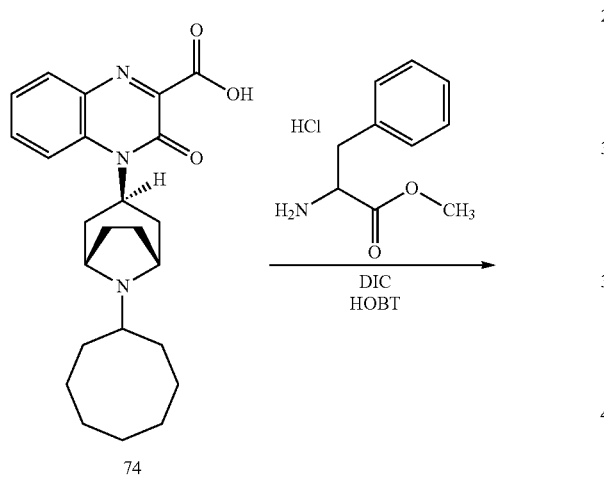

74

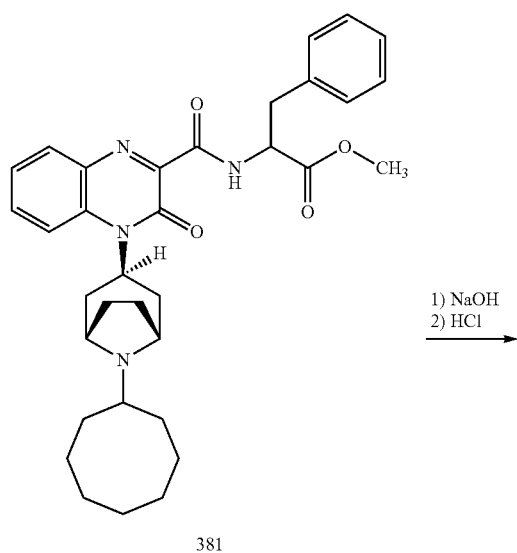

381

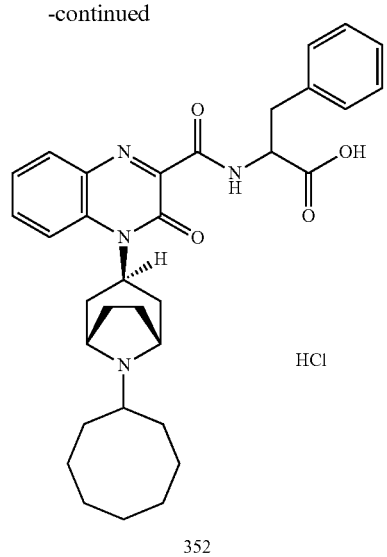

352

Substituted-Quinoxaline-Type Piperidine Compound 381 was prepared by using methyl 2-amino-3-phenylpropanoate hydrochloride (Sigma-Aldrich) in place of 4-methoxyaniline and DIC in place of WSCI (yield 53%).

The identity of Substituted-Quinoxaline-Type Piperidine Compound 381, methyl 2-(4-((endo)-8-cyclooctyl-8-azabicyclo[3.2.1]octan-3-yl)-3-oxo-3,4-dihydroquinoxaline-2-carboxamido)-3-phenylpropanoate, was confirmed using LC/MS.

Substituted-Quinoxaline-Type Piperidine Compound 381: LC/MS: m/z=571 [M+H]+ (Calc: 570).

The hydrochloride of Substituted-Quinoxaline-Type Piperidine Compound 352 was prepared from Substituted-Quinoxaline-Type Piperidine Compound 381 in a manner similar to the preparation of Substituted-Quinoxaline-Type Piperidine Compound 174 in Example 7 (yield 15%).

The identity of Substituted-Quinoxaline-Type Piperidine Compound 352, 2-(4-((endo)-8-cyclooctyl-8-azabicyclo[3.2.1]octan-3-yl)-3-oxo-3,4-dihydroquinoxaline-2-carboxamido)-3-phenylpropanoic acid, was confirmed using $^1$H NMR and LC/MS.

Substituted-Quinoxaline-Type Piperidine Compound 352: $^1$H NMR: $\delta_H$ (400 MHz, CD$_3$OD): 7.95-7.97 (m, 2H), 7.67-7.73 (m, 2H), 7.40-7.43 (m, 1H), 7.14-7.24 (m, 5H), 5.45 (m, 1H), 4.85-4.91 (m, 1H), 4.08-4.27 (m, 2H), 3.02-3.04 (m, 1H), 1.35-2.70 (22H, m); LC/MS: m/z=556 [M+H]+ (Calc: 557).

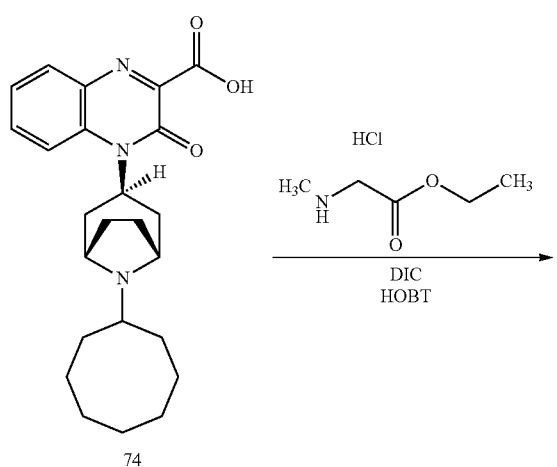

74

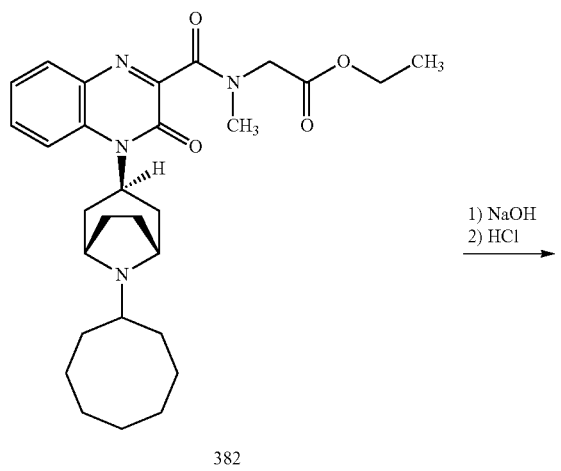

382

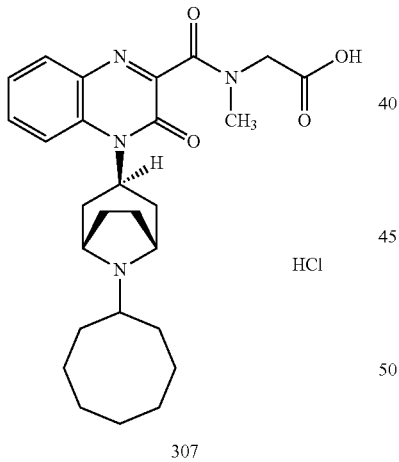

307

Substituted-Quinoxaline-Type Piperidine Compound 382 was prepared by using ethyl 2-(methylamino)acetate hydrochloride (Sigma-Aldrich) in place of 4-methoxyaniline and DIC in place of WSCI (yield 74%).

The identity of Substituted-Quinoxaline-Type Piperidine Compound 382, ethyl 2-(4-((endo)-8-cyclooctyl-8-azabicyclo[3.2.1]octan-3-yl)-N-methyl-3-oxo-3,4-dihydroquinoxaline-2-carboxamido)acetate, was confirmed using LC/MS.

Substituted-Quinoxaline-Type Piperidine Compound 382: LC/MS: m/z=509 [M+H]$^+$ (Calc: 508).

The hydrochloride of Substituted-Quinoxaline-Type Piperidine Compound 307 was prepared from Substituted-Quinoxaline-Type Piperidine Compound 382 in a manner similar to the preparation of Substituted-Quinoxaline-Type Piperidine Compound 174 in Example 7 (yield 23%).

The identity of Substituted-Quinoxaline-Type Piperidine Compound 307, 2-(4-((endo)-8-cyclooctyl-8-azabicyclo[3.2.1]octan-3-yl)-N-methyl-3-oxo-3,4-dihydroquinoxaline-2-carboxamido)acetic acid, was confirmed using $^1$H NMR and LC/MS.

Substituted-Quinoxaline-Type Piperidine Compound 307: $^1$H NMR: δ$_H$ (400 MHz, CD$_3$OD): 7.78-7.96 (m, 3H), 7.46-7.52 (m, 1H), 5.29-5.64 (m, 1H), 4.18-7.90 (m, 4H), 3.11 (s, 3H), 1.46-2.88 (m, 21H); LC/MS: m/z=481 [M+H]$^+$ (Calc: 480).

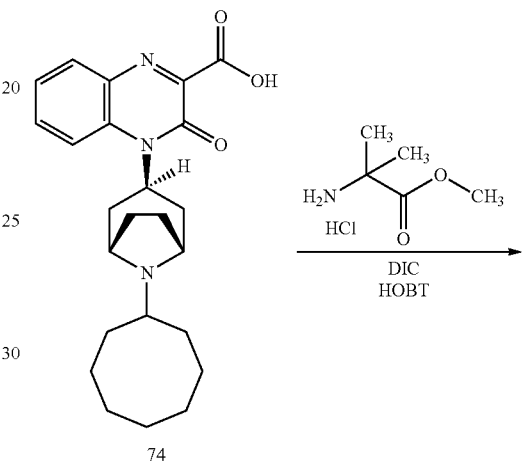

74

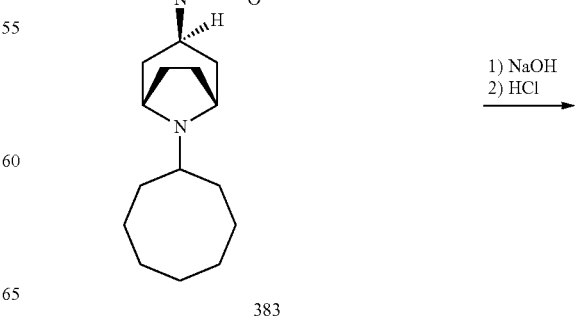

383

267

-continued

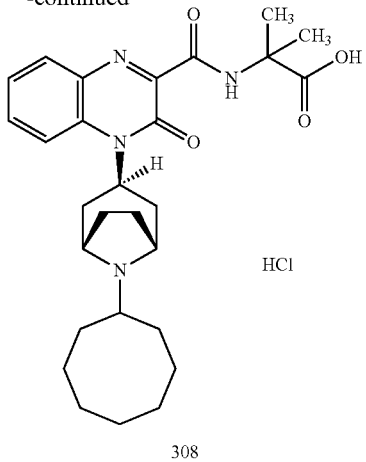

308

Substituted-Quinoxaline-Type Piperidine Compound 383 was prepared by using methyl 2-amino-2-methylpropanoate hydrochloride (Sigma-Aldrich) in place of 4-methoxyaniline and DIC in place of WSCI (yield 49%).

The identity of Substituted-Quinoxaline-Type Piperidine Compound 383, methyl 2-(4-((endo)-8-cyclooctyl-8-azabicyclo[3.2.1]octan-3-yl)-3-oxo-3,4-dihydroquinoxaline-2-carboxamido)-2-methylpropanoate, was confirmed using LC/MS.

Substituted-Quinoxaline-Type Piperidine Compound 383: LC/MS: m/z=509 [M+H]$^+$ (Calc: 508).

The hydrochloride of Substituted-Quinoxaline-Type Piperidine Compound 308 was prepared from Substituted-Quinoxaline-Type Piperidine Compound 383 in a manner similar to the preparation of Substituted-Quinoxaline-Type Piperidine Compound 174 in Example 7 (yield 16%).

The identity of Substituted-Quinoxaline-Type Piperidine Compound 308, 2-(4-((endo)-8-cyclooctyl-8-azabicyclo[3.2.1]octan-3-yl)-3-oxo-3,4-dihydroquinoxaline-2-carboxamido)-2-methylpropanoic acid, was confirmed using $^1$H NMR and LC/MS.

Substituted-Quinoxaline-Type Piperidine Compound 308: $^1$H NMR: δ$_H$ (400 MHz, CD$_3$OD): 8.06-8.13 (m, 1H), 7.81-7.95 (m, 2H), 7.51-7.55 (m, 1H), 5.33-5.66 (m, 1H), 4.38 (m, 2H), 3.14-3.16 (m, 1H), 1.55-2.83 (m, 22H); LC/MS: m/z=495 [M+H]$^+$ (Calc: 494).

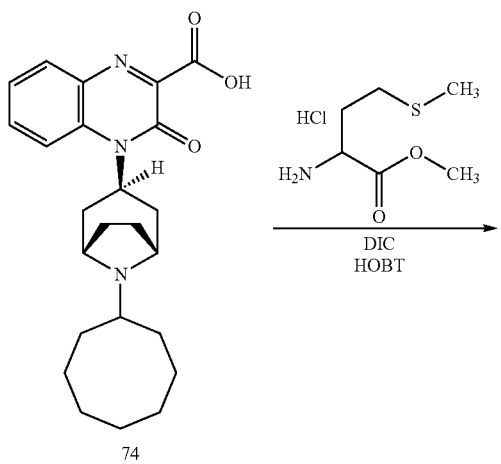

74

268

-continued

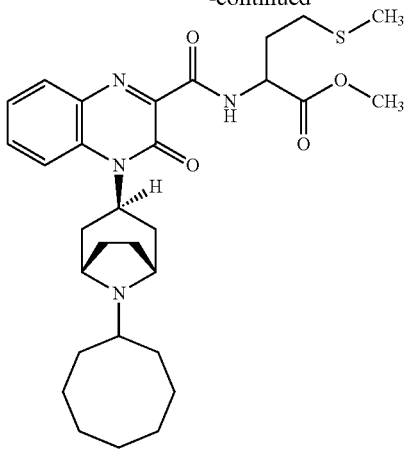

384

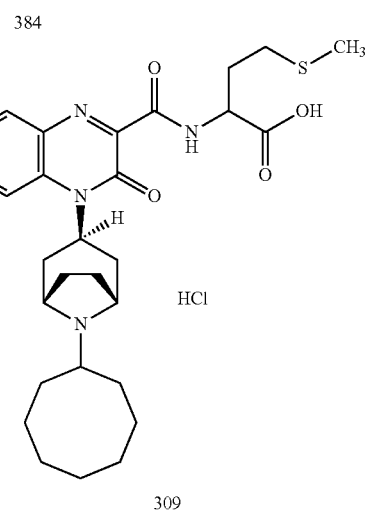

309

Substituted-Quinoxaline-Type Piperidine Compound 384 was prepared by using methyl 2-amino-4-(methylthio)butanoate hydrochloride (Sigma-Aldrich) in place of 4-methoxyaniline and DIC in place of WSCI (yield 44%).

The identity of Substituted-Quinoxaline-Type Piperidine Compound 384, methyl 2-(4-((endo)-8-cyclooctyl-8-azabicyclo[3.2.1]octan-3-yl)-3-oxo-3,4-dihydroquinoxaline-2-carboxamido)-4-(methylthio)butanoate, was confirmed using LC/MS.

Substituted-Quinoxaline-Type Piperidine Compound 384: LC/MS: m/z=555 [M+H]$^+$ (Calc: 554).

The hydrochloride of Substituted-Quinoxaline-Type Piperidine Compound 309 was prepared from Substituted-Quinoxaline-Type Piperidine Compound 384 in a manner similar to the preparation of Substituted-Quinoxaline-Type Piperidine Compound 174 in Example 7 (yield 9%).

The identity of Substituted-Quinoxaline-Type Piperidine Compound 309, 2-(4-((endo)-8-cyclooctyl-8-azabicyclo[3.2.1]octan-3-yl)-3-oxo-3,4-dihydroquinoxaline-2-carboxamido)-4-(methylthio)butanoic acid, was confirmed using $^1$H NMR and LC/MS.

Substituted-Quinoxaline-Type Piperidine Compound 309: $^1$H NMR: δ$_H$ (400 MHz, CD$_3$OD): 7.71-7.96 (m, 3H), 7.43 (m, 1H), 5.21-5.50 (m, 1H), 4.20-4.27 (m, 2H), 3.03-3.04 (m, 1H), 1.53-2.66 (m, 27H); LC/MS: m/z=541 [M+H]$^+$ (Calc: 540).

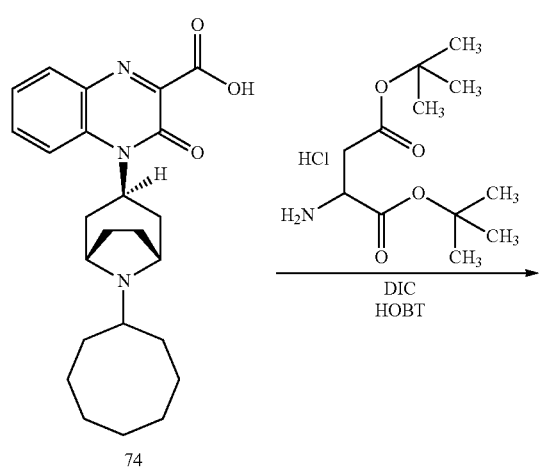

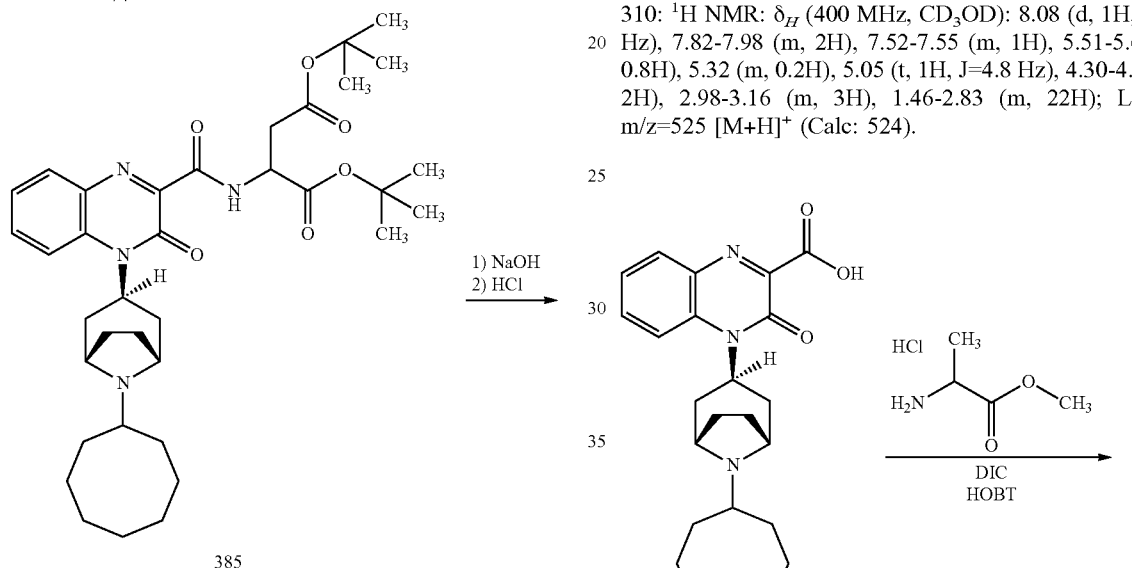

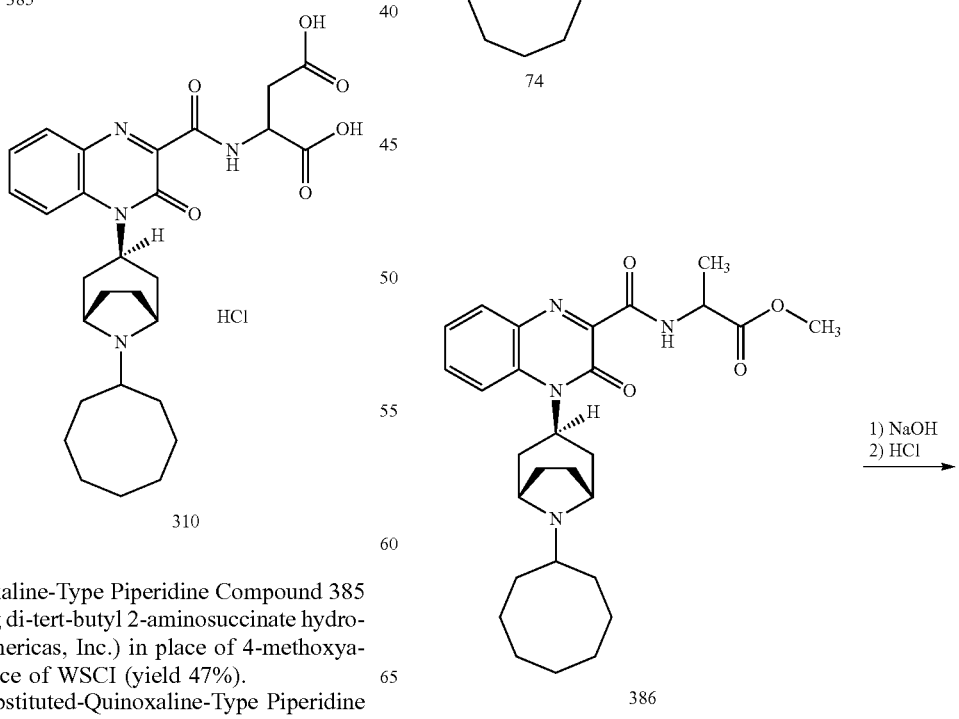

Substituted-Quinoxaline-Type Piperidine Compound 385 was prepared by using di-tert-butyl 2-aminosuccinate hydrochloride (Bachem Americas, Inc.) in place of 4-methoxyaniline and DIC in place of WSCI (yield 47%).

The identity of Substituted-Quinoxaline-Type Piperidine Compound 385, di-tert-butyl 2-(4-((endo)-8-cyclooctyl-8-azabicyclo[3.2.1]octan-3-yl)-3-oxo-3,4-dihydroquinoxaline-2-carboxamido)succinate, was confirmed using LC/MS.

Substituted-Quinoxaline-Type Piperidine Compound 385: LC/MS: m/z=637 [M+H]$^+$ (Calc: 636).

The hydrochloride of Substituted-Quinoxaline-Type Piperidine Compound 310 was prepared from Substituted-Quinoxaline-Type Piperidine Compound 385 in a manner similar to the preparation of Substituted-Quinoxaline-Type Piperidine Compound 174 in Example 7 (yield 14%).

The identity of Substituted-Quinoxaline-Type Piperidine Compound 310, 2-(4-((endo)-8-cyclooctyl-8-azabicyclo[3.2.1]octan-3-yl)-3-oxo-3,4-dihydroquinoxaline-2-carboxamido)succinic acid, was confirmed using $^1$H NMR and LC/MS.

Substituted-Quinoxaline-Type Piperidine Compound 310: $^1$H NMR: $\delta_H$ (400 MHz, CD$_3$OD): 8.08 (d, 1H, J=7.9 Hz), 7.82-7.98 (m, 2H), 7.52-7.55 (m, 1H), 5.51-5.64 (m, 0.8H), 5.32 (m, 0.2H), 5.05 (t, 1H, J=4.8 Hz), 4.30-4.38 (m, 2H), 2.98-3.16 (m, 3H), 1.46-2.83 (m, 22H); LC/MS: m/z=525 [M+H]$^+$ (Calc: 524).

-continued

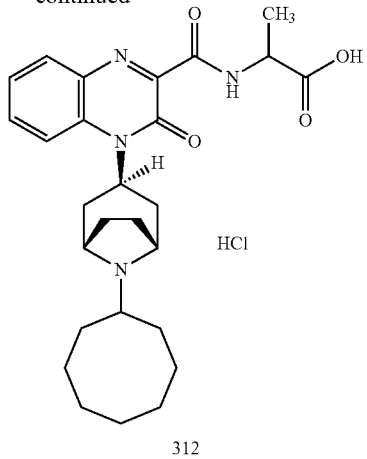

312

Substituted-Quinoxaline-Type Piperidine Compound 386 was prepared by using methyl 2-aminopropanoate hydrochloride (Sigma-Aldrich) in place of 4-methoxyaniline and DIC in place of WSCI (yield 38%).

The identity of Substituted-Quinoxaline-Type Piperidine Compound 386, methyl 2-(4-((endo)-8-cyclooctyl-8-azabicyclo[3.2.1]octan-3-yl)-3-oxo-3,4-dihydroquinoxaline-2-carboxamido)propanoate, was confirmed using LC/MS.

Substituted-Quinoxaline-Type Piperidine Compound 386: LC/MS: m/z=495 [M+H]$^+$ (Calc: 494).

The hydrochloride of Substituted-Quinoxaline-Type Piperidine Compound 312 was prepared from Substituted-Quinoxaline-Type Piperidine Compound 386 in a manner similar to the preparation of Substituted-Quinoxaline-Type Piperidine Compound 174 in Example 7 (yield 14%).

The identity of Substituted-Quinoxaline-Type Piperidine Compound 312, 2-(4-((endo)-8-cyclooctyl-8-azabicyclo[3.2.1]octan-3-yl)-3-oxo-3,4-dihydroquinoxaline-2-carboxamido)propanoic acid, was confirmed using $^1$H NMR and LC/MS.

Substituted-Quinoxaline-Type Piperidine Compound 312: $^1$H NMR: $\delta_H$ (400 MHz, CD$_3$OD): 8.08-8.10 (m, 1H), 7.78-7.98 (m, 2H), 7.53-7.56 (m, 1H), 5.31-5.53 (m, 1H), 4.71-4.74 (m, 1H), 4.13-4.39 (m, 2H), 3.14-3.23 (m, 1H), 1.31-2.81 (m, 25H); LC/MS: m/z=481 [M+H]$^+$ (Calc: 480).

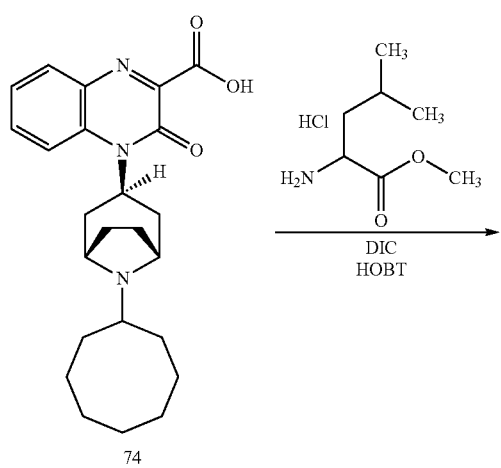

74

-continued

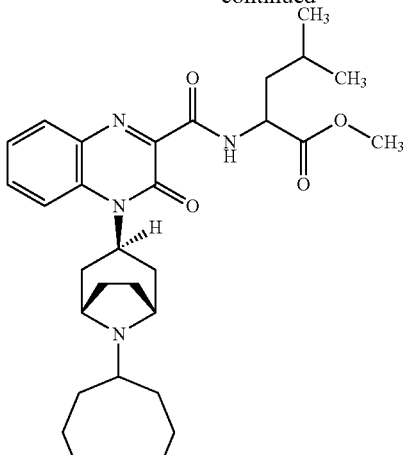

387

1) NaOH
2) HCl

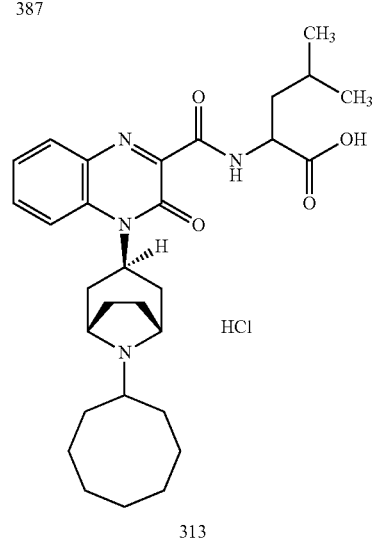

313

Substituted-Quinoxaline-Type Piperidine Compound 387 was prepared by using methyl 2-amino-4-methylpentanoate hydrochloride (Sigma-Aldrich) in place of 4-methoxyaniline and DIC in place of WSCI (yield 90%).

The identity of Substituted-Quinoxaline-Type Piperidine Compound 387, methyl 2-(4-((endo)-8-cyclooctyl-8-azabicyclo[3.2.1]octan-3-yl)-3-oxo-3,4-dihydroquinoxaline-2-carboxamido)-4-methylpentanoate, was confirmed using LC/MS.

Substituted-Quinoxaline-Type Piperidine Compound 387: LC/MS: m/z=537 [M+H]$^+$ (Calc: 536).

The hydrochloride of Substituted-Quinoxaline-Type Piperidine Compound 313 was prepared from Substituted-Quinoxaline-Type Piperidine Compound 387 in a manner similar to the preparation of Substituted-Quinoxaline-Type Piperidine Compound 174 in Example 7 (yield 9%).

The identity of Substituted-Quinoxaline-Type Piperidine Compound 313, 2-(4-((endo)-8-cyclooctyl-8-azabicyclo[3.2.1]octan-3-yl)-3-oxo-3,4-dihydroquinoxaline-2-carboxamido)-4-methylpentanoic acid, was confirmed using $^1$H NMR and LC/MS.

Substituted-Quinoxaline-Type Piperidine Compound 313: $^1$H NMR: $\delta_H$ (400 MHz, CD$_3$OD): 7.69-8.08 (m, 3H), 7.40-7.43 (m, 1H), 5.21-5.53 (m, 1H), 4.64-4.67 (m, 1H), 4.20-4.27 (m, 2H), 3.03-3.04 (m, 1H), 1.34-2.71 (m, 25H), 0.92 (d, 6H, J=5.8 Hz); LC/MS: m/z=523 [M+H]+ (Calc: 522).

Substituted-Quinoxaline-Type Piperidine Compound 388: LC/MS: m/z=557 [M+H]+ (Calc: 556).

The hydrochloride of Substituted-Quinoxaline-Type Piperidine Compound 314 was prepared from Substituted-Quinoxaline-Type Piperidine Compound 388 in a manner similar to the preparation of Substituted-Quinoxaline-Type Piperidine Compound 174 in Example 7 (yield 73%).

The identity of Substituted-Quinoxaline-Type Piperidine Compound 314, 4#4-((endo)-8-cyclooctyl-8-azabicyclo[3.2.1]octan-3-yl)-3-oxo-3,4-dihydroquinoxaline-2-carboxamido)methyl)benzoic acid, was confirmed using $^1$H NMR and LC/MS.

Substituted-Quinoxaline-Type Piperidine Compound 314: $^1$H NMR: $\delta_H$ (400 MHz, CD$_3$OD): 8.02-8.06 (m, 3H), 7.79-7.89 (m, 2H), 7.50-7.58 (m, 3H), 5.63-5.67 (m, 0.8H), 5.32 (m, 0.2H), 4.77 (s, 2H), 4.36 (m, 2H), 3.14-3.16 (m, 1H), 1.30-2.82 (m, 22H); LC/MS: m/z=543 [M+H]+ (Calc: 542).

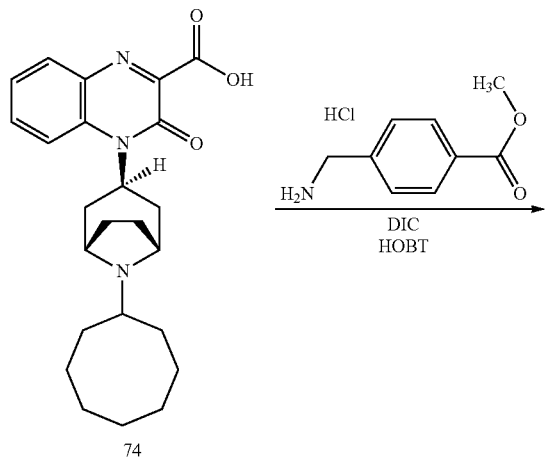

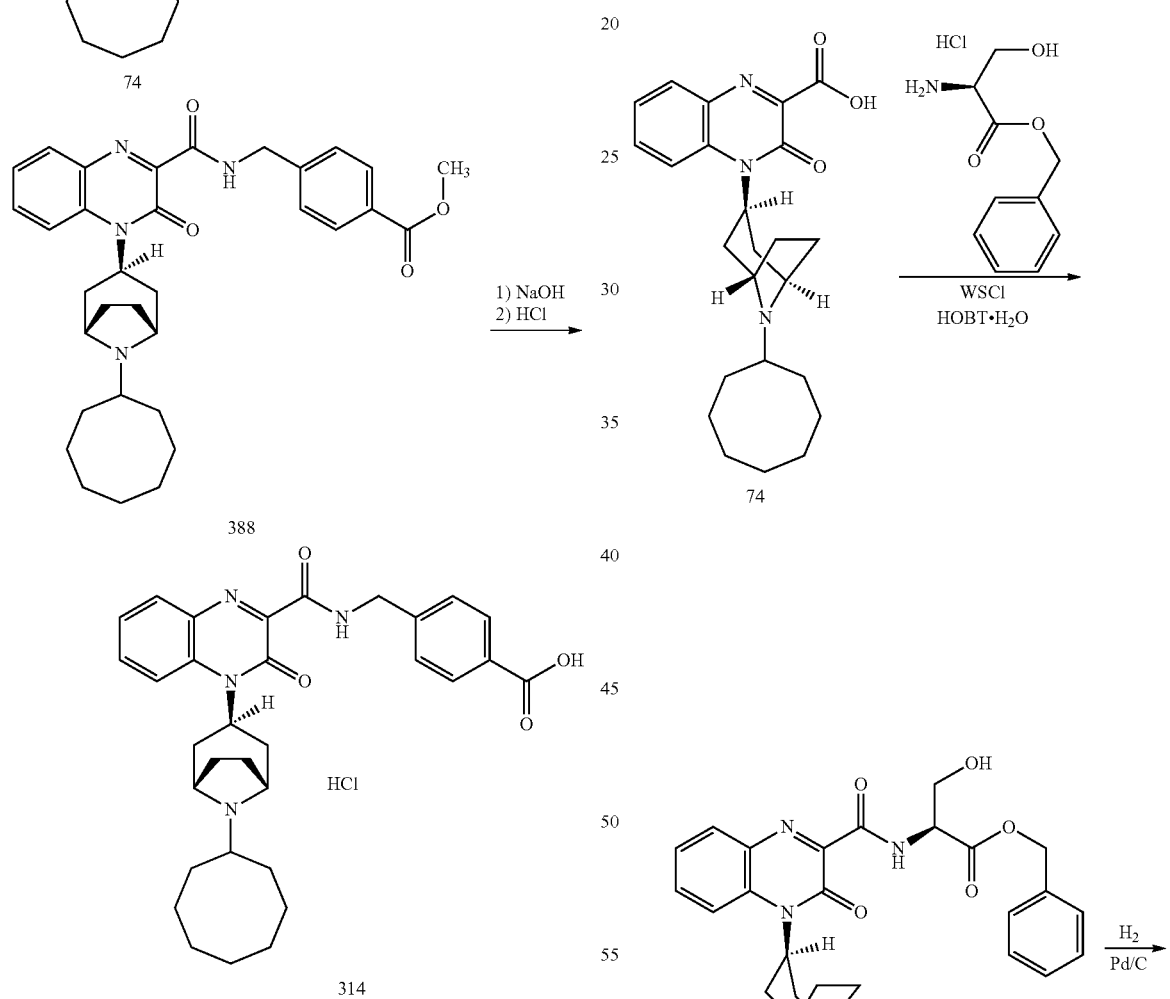

Substituted-Quinoxaline-Type Piperidine Compound 388 was prepared by using methyl 4-(aminomethyl)benzoate hydrochloride (Sigma-Aldrich) in place of 4-methoxyaniline and DIC in place of WSCI (yield 47%).

The identity of Substituted-Quinoxaline-Type Piperidine Compound 388, methyl 4-((4-((endo)-8-cyclooctyl-8-azabicyclo[3.2.1]octan-3-yl)-3-oxo-3,4-dihydroquinoxaline-2-carboxamido)methyl)benzoate, was confirmed using LC/MS.

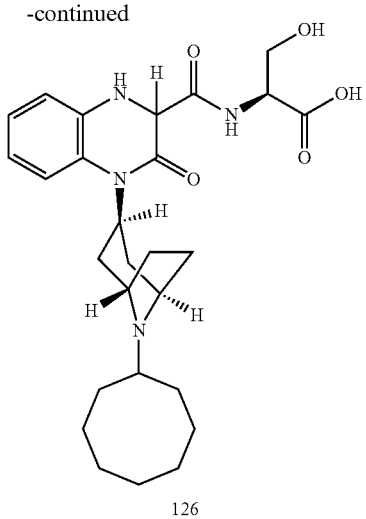

126

Substituted-Quinoxaline-Type Piperidine Compound 156 was prepared by using L-serine benzyl ester in place of 4-methoxyaniline and DIC in place of WSCI (yield 95%).

The identity of Substituted-Quinoxaline-Type Piperidine Compound 156, (2S)-benzyl 2-(4-((endo)-8-cyclooctyl-8-azabicyclo[3.2.1]octan-3-yl)-3-oxo-3,4-dihydroquinoxaline-2-carboxamido)-3-hydroxypropanoate, was confirmed using $^1$H NMR.

Substituted-Quinoxaline-Type Piperidine Compound 156: $^1$H NMR: $\delta_H$ (400 MHz, DMSO-d$_6$): 9.47 (1H, m), 7.90 (1H, m), 7.66 (1H, m), 7.61 (1H, m), 7.47-7.33 (8H, m), 5.26 (2H, t, J=4.2 Hz), 5.20 (2H, s), 3.89-3.64 (5H, s), 2.44-1.43 (22H, m).

Substituted-Quinoxaline-Type Piperidine Compound 126 was prepared from Substituted-Quinoxaline-Type Piperidine Compound 156 in a manner similar to the final step of Example 18 except that the acidification was omitted (yield 84%).

The identity of Substituted-Quinoxaline-Type Piperidine Compound 126, (2S)-2-(4-((endo)-8-cyclooctyl-8-azabicyclo[3.2.1]octan-3-yl)-3-oxo-1,2,3,4-tetrahydroquinoxaline-2-carboxamido)-3-hydroxypropanoic acid, was confirmed using $^1$H NMR and LC/MS.

Substituted-Quinoxaline-Type Piperidine Compound 126: $^1$H NMR: $\delta_H$ (400 MHz, DMSO-d$_6$): 7.94 (1H, t, J=8.36 Hz), 7.02 (1H, t, J=7.6 Hz), 6.84 (2H, t, J=6.34 Hz), 6.72 (1H, td, J=8.36, 3.72 Hz), 6.50 (1H, d, J=15.21 Hz), 4.83 (1H, s), 4.44 (1H, dd, J=6.84, 1.77 Hz), 4.08 (1H, dq, J=16.22, 4.06 Hz), 3.92 (2H, s), 3.69-3.61 (1H, m), 3.47 (1H, m), 2.71 (1H, s), 2.42 (1H, m), 2.18-1.39 (22H, m); LC/MS (100%, t$_r$=1.27 min): m/z=499.2 [M+H]$^+$ (Calc 498.6).

5.23 Example 23

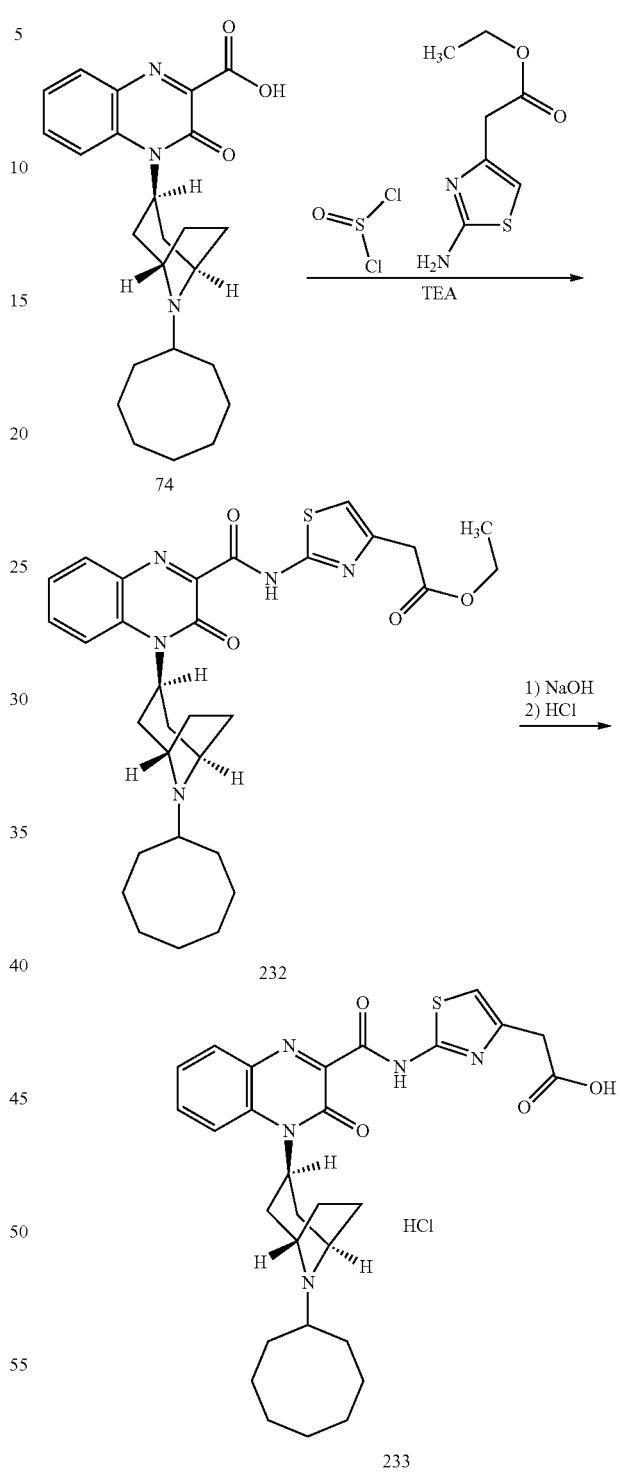

Thionyl chloride (214 μL, 0.293 mmol) was added to a mixture of Substituted-Quinoxaline-Type Piperidine Compound 74 (120 mg, 293 mmol), a catalytic amount of DMF (5 drops), and CHCl$_3$ (2 mL) at a temperature of about 25° C. The reaction mixture was refluxed for 2 h then concentrated under reduced pressure to provide a residue. Ethyl 2-(2-aminothiazol-4-yl)acetate (71.0 mg, 0.381 mmol, Sigma-Aldrich) was added to a mixture of the residue and CHCl₃ (2 mL). The reaction mixture was stirred at a temperature of about 25° C. for 21 h, 100 μL of TEA was added, and the reaction mixture was stirred at a temperature of about 25° C. for 24 h more. The mixture was partitioned between DCM and water. The organic portion was separated, washed with brine, dried (MgSO₄), filtered, and concentrated under reduced pressure to provide a residue. The residue was then chromatographed by preparative TLC (eluted with 10%:90% MeOH:DCM) to provide 84.5 mg of Substituted-Quinoxaline-Type Piperidine Compound 232 as a pale yellow solid (yield 49.9%).

The identity of Substituted-Quinoxaline-Type Piperidine Compound 232, ethyl 24244-((endo)-8-cyclooctyl-8-azabi-cyclo[3.2.1]octan-3-yl)-3-oxo-3,4-dihydroquinoxaline-2-carboxamido)thiazol-4-yl)acetate, was confirmed using LC/MS.

Substituted-Quinoxaline-Type Piperidine Compound 232: LC/MS: m/z=578 [M+H]⁺ (Calc: 577).

The hydrochloride of Substituted-Quinoxaline-Type Piperidine Compound 233 was prepared from Substituted-Quinoxaline-Type Piperidine Compound 232 in a manner similar to the preparation of Substituted-Quinoxaline-Type Piperidine Compound 174 in Example 7 (yield 37%).

The identity of Substituted-Quinoxaline-Type Piperidine Compound 233, 2-(2-(4-((endo)-8-cyclooctyl-8-azabicyclo[3.2.1]octan-3-yl)-3-oxo-3,4-dihydroquinoxaline-2-carboxamido)thiazol-4-yl)acetic acid, was confirmed using ¹H NMR and LC/MS.

Substituted-Quinoxaline-Type Piperidine Compound 233: ¹H NMR: δ$_H$ (400 MHz, DMSO-d₆): 12.64-12.87 (1H, br), 12.44 (1H, br), 10.43 (1H, br), 8.13 (1H, m), 7.97 (1H, dd, J=1.0, 7.9 Hz), 7.80-7.84 (1H, m), 7.50-7.53 (1H, m), 7.13 (1H, s), 6.02 (1H, m), 4.26 (2H, m), 3.66 (2H, s), 2.94 (2H, m), 2.60-2.67 (2H, m), 1.39-2.41 (20H, m); LC/MS: m/z=550 [M+H]⁺ (Calc: 549).

5.24 Example 24

In a manner similar to Example 21, the following Substituted-Quinoxaline-Type Piperidine Compounds ("exo" isomers) were prepared from the compound of formula EG.

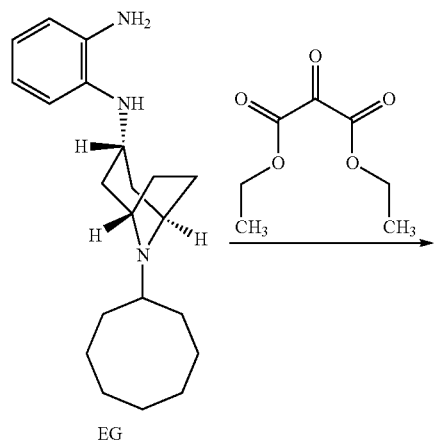

EG

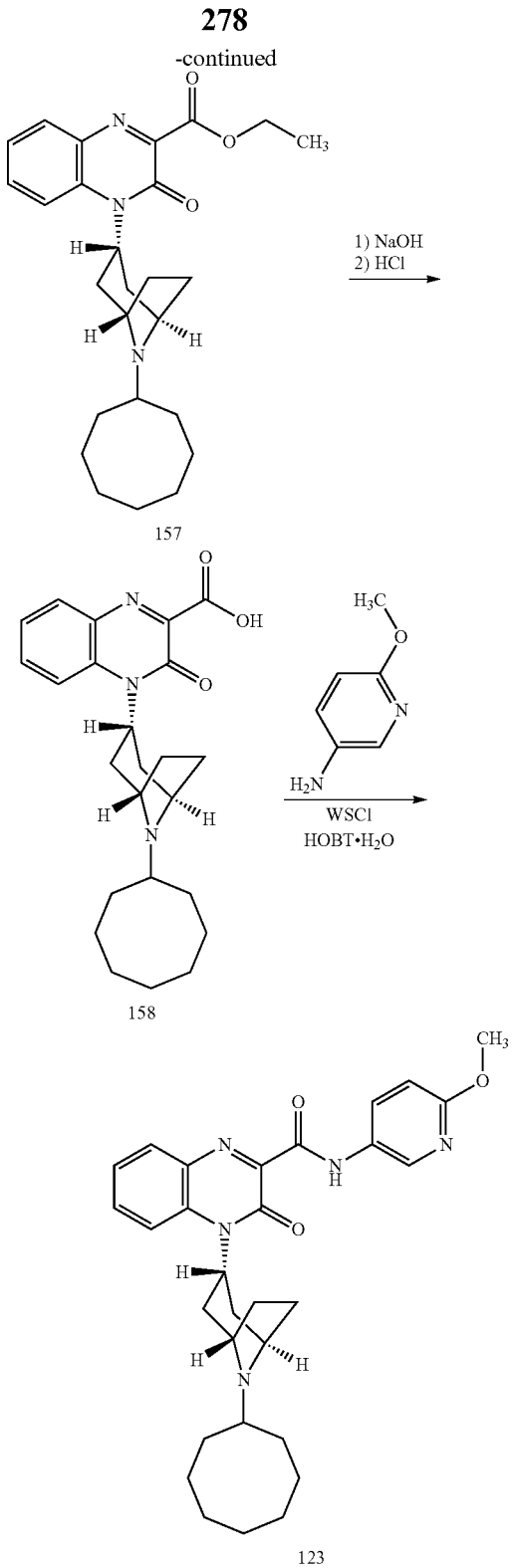

Substituted-Quinoxaline-Type Piperidine Compound 123 was prepared from Substituted-Quinoxaline-Type Piperidine Compound 158 (4-((exo)-8-cyclooctyl-8-azabicyclo[3.2.1]octan-3-yl)-3-oxo-3,4-dihydroquinoxaline-2-carboxylic acid) (yield 82%), which was prepared from Substituted-Quinoxaline-Type Piperidine Compound 157 (ethyl 4-((exo)-8-cyclooctyl-8-azabicyclo[3.2.1]octan-3-yl)-3-oxo-3,4-dihydroquinoxaline-2-carboxylate), which was prepared from the compound of formula EG.

The identity of Substituted-Quinoxaline-Type Piperidine Compound 123, 4-((exo)-8-cyclooctyl-8-azabicyclo[3.2.1]octan-3-yl)-N-(6-methoxypyridin-3-yl)-3-oxo-3,4-dihydroquinoxaline-2-carboxamide, was confirmed using $^1$H NMR and LC/MS.

Substituted-Quinoxaline-Type Piperidine Compound 123: $^1$H NMR: $\delta_H$ (400 MHz, DMSO-d$_6$): 10.84 (1H, s), 8.45 (1H, d, J=2.53 Hz), 7.98 (3H, dt, J=21.46, 8.24 Hz), 7.76 (1H, s), 7.50 (1H, d, J=7.6 Hz), 6.89 (1H, d, J=9.12 Hz), 5.15 (1H, br), 4.29 (2H, br), 3.85 (3H, s), 2.85 (2H, br), 2.33-1.48 (21H, m); LC/MS (99%, t$_r$=1.63 min): m/z=516.3 [M+H]$^+$ (Calc: 515.7).

5.25 Example 25

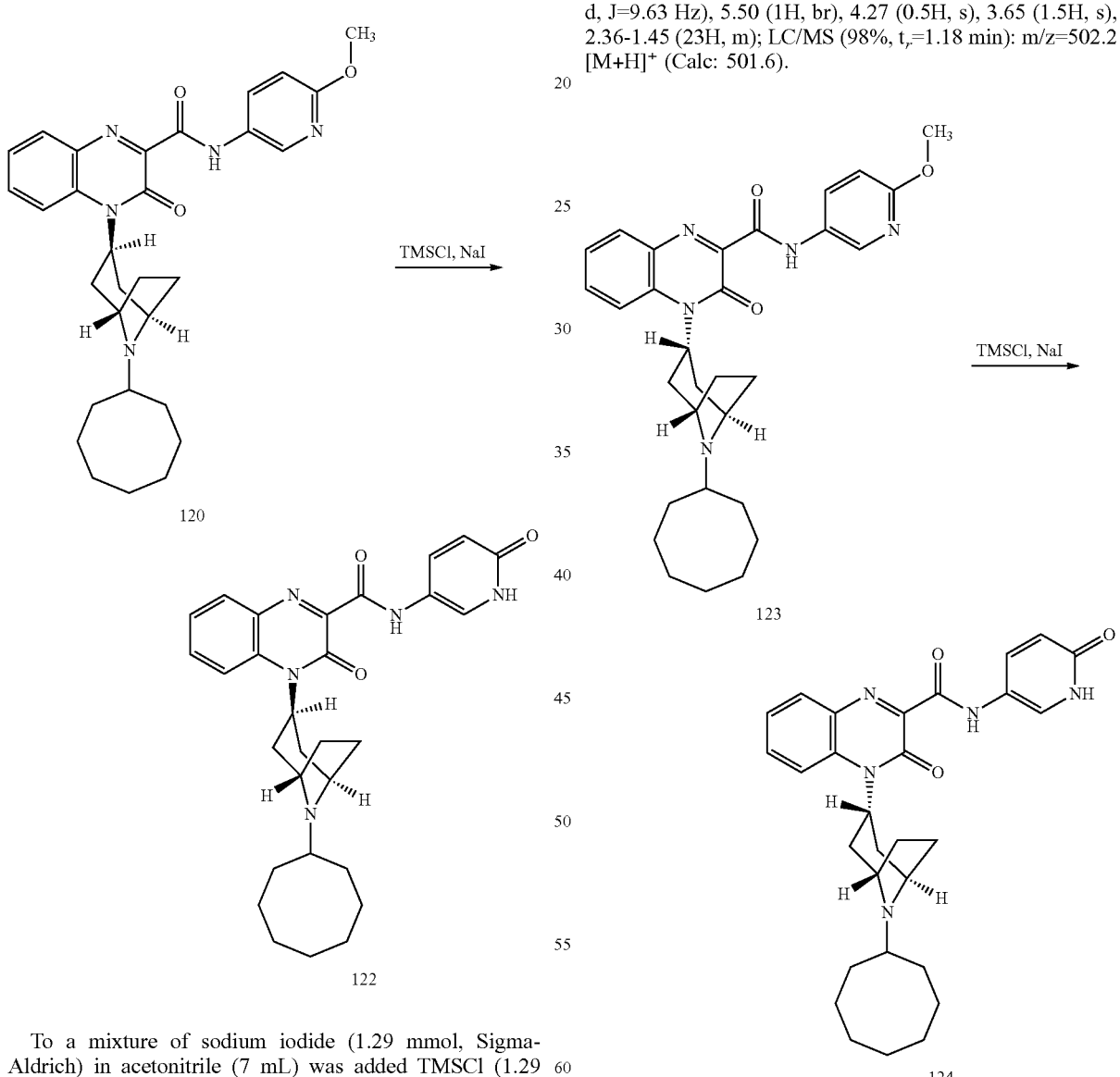

To a mixture of sodium iodide (1.29 mmol, Sigma-Aldrich) in acetonitrile (7 mL) was added TMSCl (1.29 mmol, Sigma-Aldrich) and the mixture was stirred at a temperature of about 25° C. for 30 min. Thereafter, to the mixture was added Substituted-Quinoxaline-Type Piperidine Compound 120 (133 mg, 0.26 mmol) in acetonitrile (3 mL). The resulting reaction mixture was heated with stirring at 80° C. for 2.5 h. After cooling to a temperature of about 25° C., the reaction mixture was extracted three times with EtOAc/water (30 mL for each extraction). The organic portions were combined, washed with saturated aqueous Na$_2$SO$_3$ solution (10 mL), brine (10 mL), dried (MgSO$_4$), and concentrated under reduced pressure to provide a yellow solid. The solid was chromatographed with a silica gel column eluted with a gradient of from 97%:3% CHCl$_3$:MeOH to 85%:15% CHCl$_3$:MeOH to provide 38 mg of Substituted-Quinoxaline-Type Piperidine Compound 122 as a yellow solid (yield 30%).

The identity of Substituted-Quinoxaline-Type Piperidine Compound 122, 4-((endo)-8-cyclooctyl-8-azabicyclo[3.2.1]octan-3-yl)-3-oxo-N-(6-oxo-1,6-dihydropyridin-3-yl)-3,4-dihydroquinoxaline-2-carboxamide, was confirmed using $^1$H NMR and LC/MS.

Substituted-Quinoxaline-Type Piperidine Compound 122: $^1$H NMR: $\delta_H$ (400 MHz, DMSO-d$_6$): 11.44 (0.9H, s), 10.59 (1H, s), 9.73 (0.1H, s), 8.02-7.46 (6H, m), 6.41 (1H, d, J=9.63 Hz), 5.50 (1H, br), 4.27 (0.5H, s), 3.65 (1.5H, s), 2.36-1.45 (23H, m); LC/MS (98%, t$_r$=1.18 min): m/z=502.2 [M+H]$^+$ (Calc: 501.6).

In a manner similar to the above preparation of Substituted-Quinoxaline-Type Piperidine Compound 122, Substituted-Quinoxaline-Type Piperidine Compound 124 was prepared from Substituted-Quinoxaline-Type Piperidine Compound 123 (yield 53%).

The identity of Substituted-Quinoxaline-Type Piperidine Compound 124, 4-((exo)-8-cyclooctyl-8-azabicyclo[3.2.1]octan-3-yl)-3-oxo-N-(6-oxo-1,6-dihydropyridin-3-yl)-3,4-dihydroquinoxaline-2-carboxamide, was confirmed using $^1$H NMR and LC/MS.

Substituted-Quinoxaline-Type Piperidine Compound 124: $^1$H NMR: $\delta_H$ (400 MHz, DMSO-d$_6$): 11.45 (1H, s), 10.61 (1H, s), 7.96 (3H, m), 7.75 (1H, s), 7.50 (2H, m), 6.42 (1H, d, J=9.63 Hz), 5.13 (1H, br), 4.27 (0.5H, br), 3.59 (1.5H, br), 2.72 (2H, m), 2.00-1.47 (21H, m); LC/MS (96%, t$_r$=1.02 min): m/z=502.2 [M+H]$^+$ (Calc: 501.6).

5.26 Example 26 octan-3-yl)-N-hydroxy-3-oxo-3,4-dihydroquinoxaline-2-carboxamide, was confirmed using $^1$H NMR and LC/MS.

Substituted-Quinoxaline-Type Piperidine Compound 127: $^1$H NMR: $\delta_H$ (400 MHz, CD$_3$OD): 8.02 (1H, d, J=8.11 Hz), 7.78 (2H, t, J=6.59 Hz), 7.51-7.47 (1H, m), 5.44 (1H, s), 4.13 (2H, s), 2.95 (1H, s), 2.66-2.58 (2H, m), 2.33 (6H, m), 2.02-1.47 (15H, m); LC/MS (100%, t$_r$=1.05 min): m/z=425.2 [M+H]$^+$ (Calc: 424.5).

5.27 Example 27

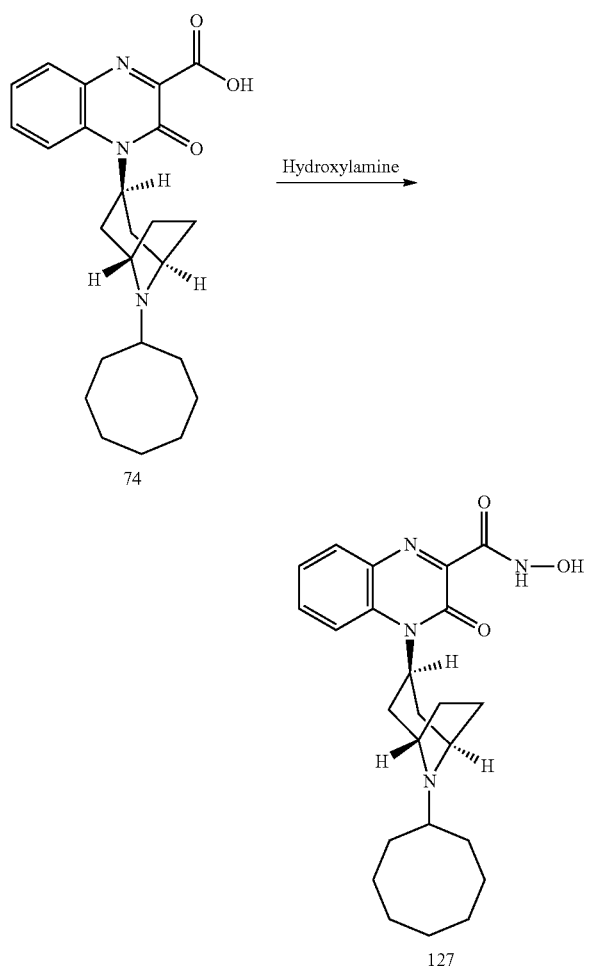

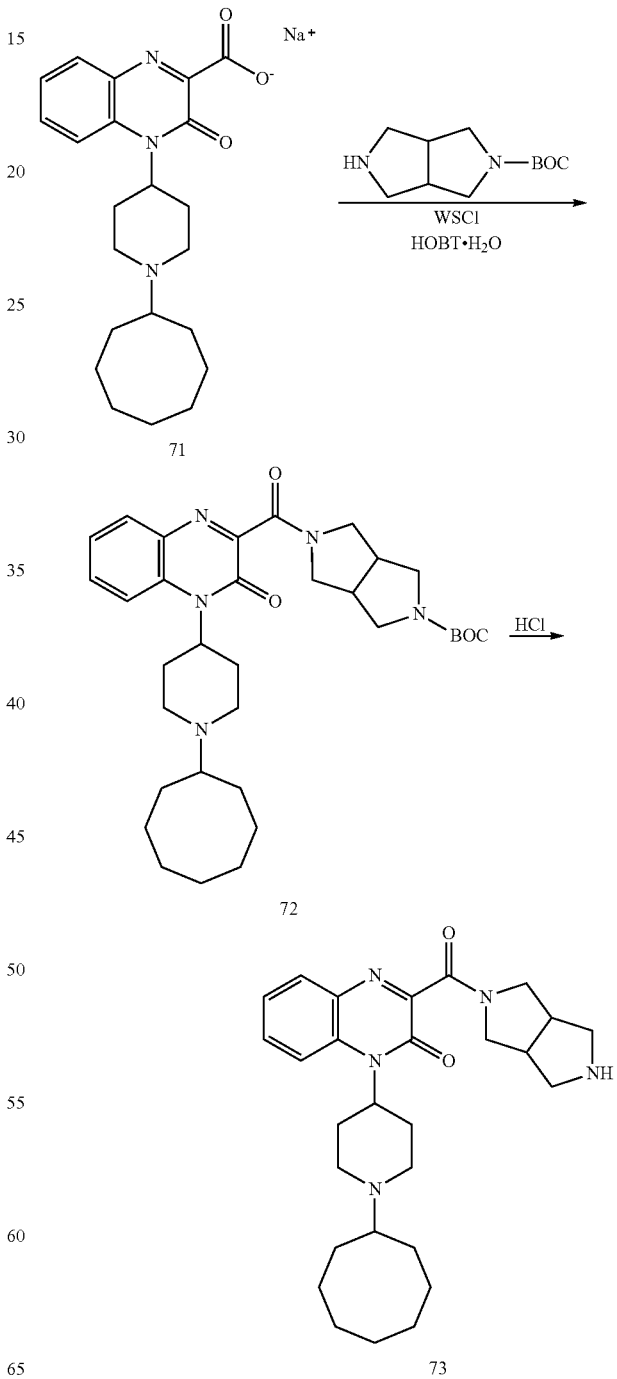

To a mixture of Substituted-Quinoxaline-Type Piperidine Compound 74 (100 mg, 0.23 mmol) in ethanol (3 mL) was added dropwise at a temperature of about 25° C. a 50% aqueous solution of hydroxylamine (1 mL, Sigma-Aldrich). The resulting reaction mixture was stirred at a temperature of about 25° C. for 4 h. A yellow precipitate formed. Diethyl ether (20 mL) was added to the precipitate which was then collected by filtration, washed twice with diethyl ether (5 mL for each wash), and dried under reduced pressure a temperature of about 25° C. for 12 hr to provide 49 mg of Substituted-Quinoxaline-Type Piperidine Compound 127 as a pale yellow solid (yield 51%).

The identity of Substituted-Quinoxaline-Type Piperidine Compound 127, 4-((endo)-8-cyclooctyl-8-azabicyclo[3.2.1]

In a manner similar to the preparation of Substituted-Quinoxaline-Type Piperidine Compound 120 from Substituted-Quinoxaline-Type Piperidine Compound 74 in Example 21, Substituted-Quinoxaline-Type Piperidine Compound 72 was prepared from Substituted-Quinoxaline-Type Piperidine Compound 71 (yield 70%).

The identity of Substituted-Quinoxaline-Type Piperidine Compound 72, tert-butyl 5-(4-(1-cyclooctylpiperidin-4-yl)-3-oxo-3,4-dihydroquinoxaline-2-carbonyl)hexahydropyrrolo[3,4-c]pyrrole-2(1H)-carboxylate, was confirmed using $^1$H NMR and LC/MS.

Substituted-Quinoxaline-Type Piperidine Compound 72: $^1$H NMR: $\delta_H$ (400 MHz, DMSO-$d_6$): 7.93 (1H, d, J=8 Hz), 7.84 (1H, d, J=8 Hz), 7.68 (1H, t, J=8 Hz), 7.42 (1H, t, J=8 Hz), 4.75 (1H, br), 3.69 (1H, s), 3.55-2.42 (16H, m), 1.71-1.40 (16H, m), 1.39 (9H, s); LC/MS: m/z=578.2 [M+H]$^+$ (Calc: 577.8).

Substituted-Quinoxaline-Type Piperidine Compound 73 was prepared from Substituted-Quinoxaline-Type Piperidine Compound 72 in a manner similar to the preparation of Substituted-Quinoxaline-Type Piperidine Compound 5 in Example 7 (yield 72%).

The identity of Substituted-Quinoxaline-Type Piperidine Compound 73, 1-(1-cyclooctylpiperidin-4-yl)-3-(octahydropyrrolo[3,4-c]pyrrole-2-carbonyl)quinoxalin-2(1H)-one, was confirmed using $^1$H NMR and LC/MS.

Substituted-Quinoxaline-Type Piperidine Compound 73: $^1$H NMR: $\delta_H$ (400 MHz, DMSO): 7.93 (1H, d, J=8 Hz), 7.83 (1H, d, J=4 Hz), 7.68 (1H, t, J=4 Hz), 7.42 (1H, t, J=8 Hz), 4.72 (1H, br), 3.70 (1H, m), 3.48 (1H, m), 3.38 (1H, m), 3.09 (1H, m), 2.92-2.38 (13H, m), 1.73-1.43 (17H, m); LC/MS: m/z=478.1 [M+H]$^+$ (Calc: 477.6).

5.28 Example 28

To a mixture of cyclooctanone (GA, 17 g, 135 mmol, Sigma-Aldrich) in ethanol (200 mL) and water (200 mL) were added KCN (17.5 g, 269 mmol, Sigma-Aldrich) followed by ammonium carbonate ([NH$_4$]$_2$CO$_3$, 51.8 g, 539 mmol, Sigma-Aldrich). The resulting reaction mixture was stirred at 80° C. for 6 h. The reaction mixture was evaporated to dryness under reduced pressure to provide a white solid precipitate which was filtered, collected, and dried for 16 h to provide 15.9 g of the compound of formula GB, 1,3-diazaspiro[4.7]dodecane-2,4-dione (yield 73%).

A mixture of the compound of formula GB (15.9 g, 81 mmol) in 2N NaOH was refluxed for 96 hr. The reaction mixture was neutralized by the addition of 2N HCl to provide a white solid precipitate which was filtered and collected to provide the compound of formula GC, 1-aminocyclooctanecarboxylic acid. The compound of formula GC was dissolved with hot phenylmethanol (i.e., phenylmethanol) then concentrated HCl was added. The resulting reaction mixture was refluxed for 16 hr. After neutralizing the reaction mixture with 2N NaOH, the resulting mixture was extracted three times with 4:1 CHCl$_3$:MeOH. The organic portions were combined, washed with water, washed with brine, dried (MgSO$_4$), filtered, and concentrated under reduced pressure to provide 920 mg of the compound of formula GD, benzyl 1-aminocyclooctanecarboxylate (yield 6% for two steps).

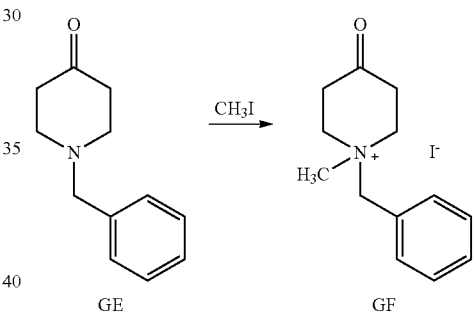

The compound of formula GF was prepared in a manner similar to the preparation of the compound of formula DB in Example 13 except 1-benzylpiperidin-4-one (GE, Sigma-Aldrich) was used in place of tropinone and methyl iodide was used in place of dimethyl sulfate.

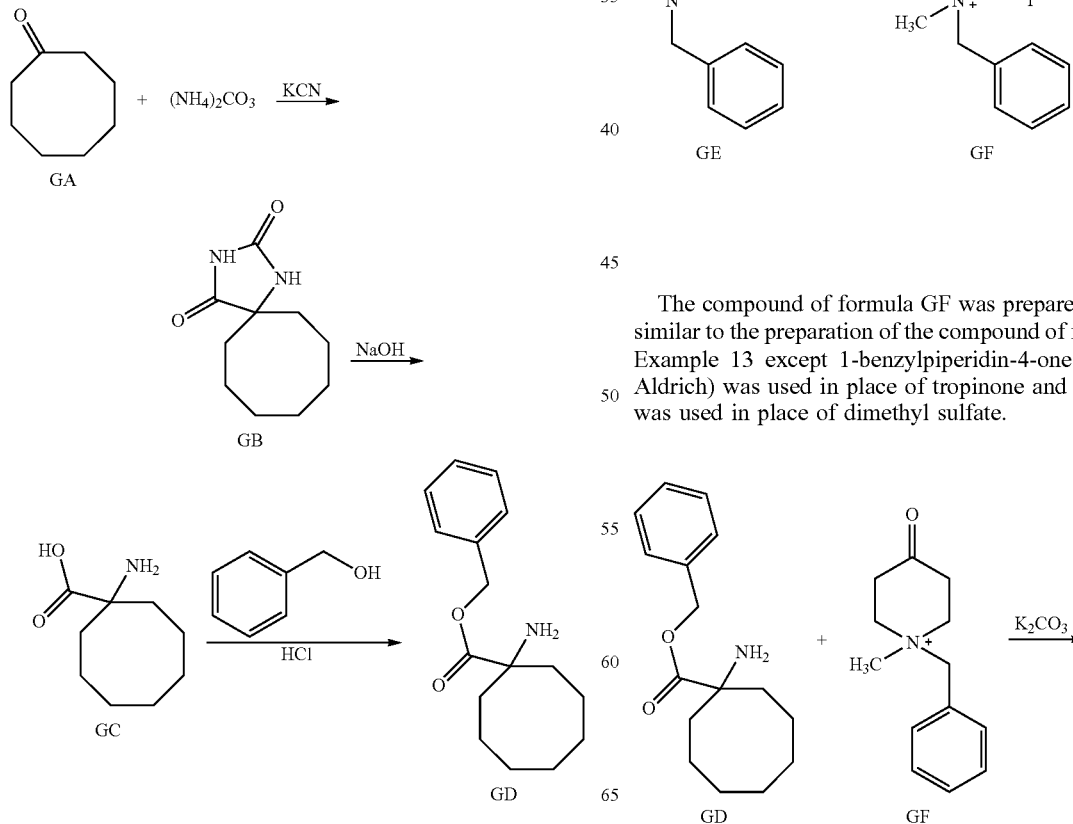

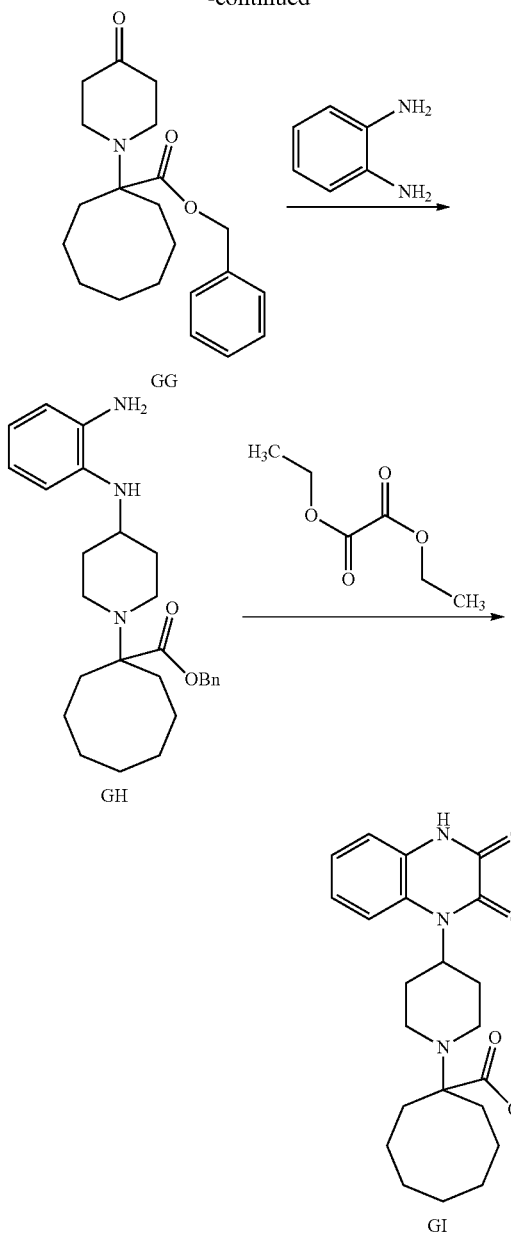

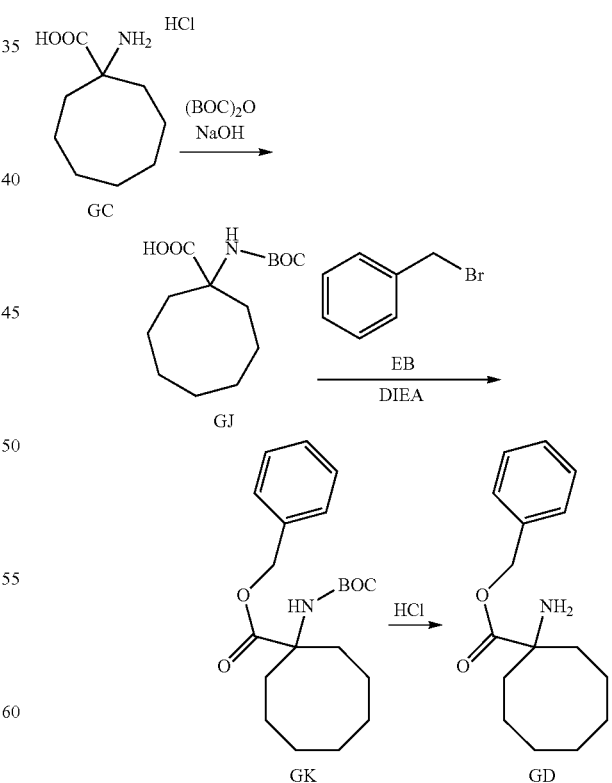

acetic acid was added. The resulting mixture was stirred at a temperature of about 25° C. for about 16 h. MeOH (2 mL) and water (25 mL) were added and the mixture was neutralized with 28% aqueous ammonia to adjust the pH to about 8. The organic portion was separated, washed with brine (10 mL), concentrated under reduced pressure, and chromatographed with a silica gel column eluted with 10:1:1 EtOAc:MeOH:TEA to provide the compound of formula GH, benzyl 1-(4-(2-aminophenylamino)piperidin-1-yl)cyclooctanecarboxylate.

A mixture of the compound of formula GH in 20 mL of diethyl oxalate (Sigma-Aldrich) was heated at 140° C. for 16 h. After cooling to a temperature of about 25° C., the reaction mixture was diluted with EtOAc, washed with 2N aqueous NaOH (30 mL), washed with brine (20 mL), concentrated under reduced pressure, and chromatographed with a silica gel column eluted with 5:5:0.5:0.5 EtOAc: hexane:MeOH:TEA to provide the compound of formula GI.

The identity of the compound of formula GI, benzyl 1-(4-(2,3-dioxo-3,4-dihydroquinoxalin-1(2H)-yl)piperidin-1-yl)cyclooctanecarboxylate, was confirmed using $^1$H NMR and LC/MS.

Compound GI: $^1$H NMR: $\delta_H$ (300 MHz, DMSO-d$_6$): 11.51 (1H, s), 7.47 (1H, d, J=8.1 Hz), 7.41-7.33 (5H, m), 7.24-7.17 (3H, m), 5.17 (2H, s), 4.58 (1H, br), 3.24 (2H, d, J=11.1 Hz), 2.76 (2H, d, J=9.3 Hz), 2.33 (2H, t, J=10.8 Hz), 2.01-1.47 (16H, m); LC/MS (100%, t$_r$=1.87 min): m/z=490.2 [M+H]$^+$ (Calc: 489.3).

Alternatively, the compound of formula GD was prepared by the following route.

At a temperature of 90° C., a mixture of the compound of formula GF (10 mmol), MeOH (6 mL) and water (20 mL) was added dropwise to a mixture of the compound of formula GD (10 mmol), K$_2$CO$_3$ (1 mmol), MeOH (10 mL) and water (4 mL) over 20 min. The resulting reaction mixture was stirred at 90° C. for 48 hr. After concentration under reduced pressure, the mixture was extracted three times with a mixture of EtOAc and water. The organic portions were combined, dried (MgSO$_4$), and concentrated under reduced pressure to provide a yellow oil. The resulting oil was chromatographed with a silica gel column eluted with a gradient of from 10%:90% EtOAc:n-hexane to 50%:50% EtOAc:n-hexane to provide the compound of formula GG, benzyl 1-(4-oxopiperidin-1-yl)cyclooctanecarboxylate.

Sodium triacetoxyborohydride (50 mmol) was added to a mixture of the compound of formula GG (12.8 mmol), and 1,2-phenylenediamine (3 g, 27.8 mmol) in 100 mL of CH$_2$Cl$_2$ at a temperature of about 25° C. Thereafter, 3 mL of To a mixture of the hydrochloride of the compound of formula GC (414 mg, 2.00 mmol), aqueous 1N NaOH (4 mL, 4.00 mmol), and dioxane (4 mL) at a temperature of about 25° C. was added (BOC)₂O (0.51 mL, 2.2 mmol). After the addition, the reaction mixture was stirred for 18 h at a temperature of about 25° C. The mixture was quenched by pouring it into aqueous 1N HCl and extracted with CHCl₃. The organic portion was dried (Na₂SO₄) and concentrated under reduced pressure to provide a white solid. The solid was triturated with iso-propyl ether and collected to provide 221 mg of the compound of formula GJ as a colorless solid (yield 41%).

The identity of the compound of formula GJ, 1-(tert-butoxycarbonylamino)cyclooctanecarboxylic acid, was confirmed using $^1$H NMR.

Compound GJ: $^1$H NMR: $\delta_H$ (400 MHz, DMSO-d₆): 12.01 (1H, s), 6.90 (1H, s), 1.89-1.45 (14H, m), 1.35 (9H, s).

To a mixture of the compound of formula GJ (215 mg, 0.792 mmol) in DMF (1 mL) at a temperature of about 25° C. was added the compound of formula EB (0.103 mmol, 0.871 mmol) and DIEA (0.166 mL, 0.950 mmol). After the addition, the reaction mixture was stirred for 20 h at a temperature of about 25° C. The mixture was quenched by pouring it into water. A white precipitate formed. The precipitate was collected, washed with dilute aqueous NaHCO₃, and washed with water to provide 240 mg of the compound of formula GK as a white solid (yield 84%).

The identity of the compound of formula GK, benzyl 1-(tert-butoxycarbonylamino)cyclooctanecarboxylate, was confirmed using $^1$H NMR.

Compound GK: $^1$H NMR: $\delta_H$ (400 MHz, CDCl₃): 7.37-7.34 (5H, m), 5.16 (2H, s), 4.69 (1H, s), 2.08-2.04 (4H, m), 1.57 (10H, d, J=8.06 Hz), 1.43 (9H, s).

The compound of formula GD was prepared from the compound of formula GK in a manner similar to the preparation of Substituted-Quinoxaline-Type Piperidine Compound 5 in Example 7 (yield >98%).

The identity of the compound of formula GD was confirmed using $^1$H NMR.

Compound GD: $^1$H NMR: $\delta_H$ (400 MHz, CDCl₃): 7.40-7.34 (5H, m), 5.21 (2H, s), 2.06-1.71 (14H, m).

Alternatively, the compound of formula GI was prepared by the following route.

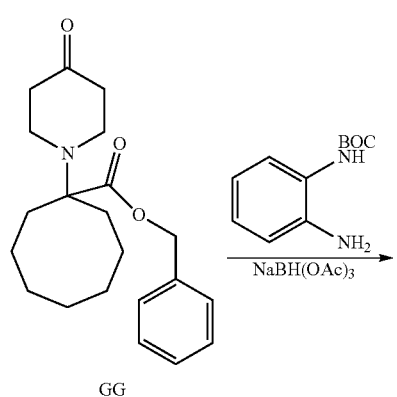

GG

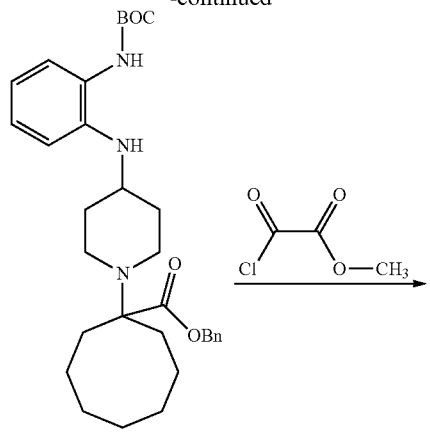

GL

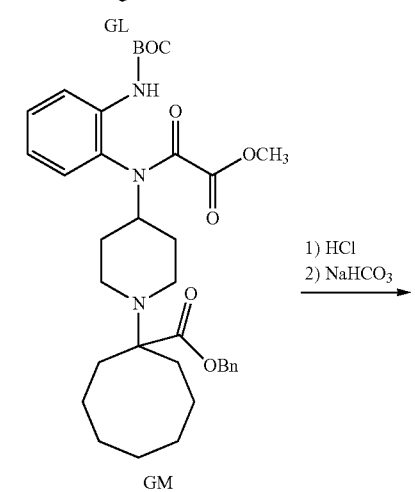

GM

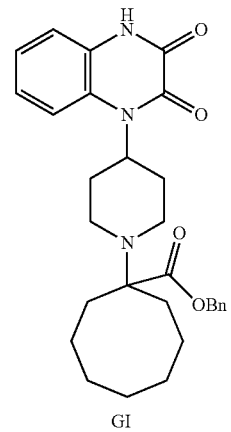

GI

The compound of formula GG was prepared from the compounds of formula GD and GF in a manner similar to that described above (yield 38%).

The identity of the compound of formula GG was confirmed using $^1$H NMR.

Compound GG: $^1$H NMR: $\delta_H$ (400 MHz, CDCl₃): 7.38-7.36 (5H, m), 5.14 (2H, s), 2.92 (4H, t, J=5.62 Hz), 2.39 (4H, t, J=5.79 Hz), 2.00-1.59 (14H, m).

The compound of formula GL was prepared from the compound of formula GG in a manner similar to the preparation of the compound of formula AB in Example 1 except tert-butyl 2-aminophenylcarbamate (Sigma-Aldrich) was used in place of 1,2-phenylenediamine (yield 95%).

The identity of the compound of formula GL, benzyl 1-(4-(2-(tert-butoxycarbonylamino)phenylamino)piperidin-1-yl)cyclooctanecarboxylate, was confirmed using $^1$H NMR.

Compound GL: $^1$H NMR: $\delta_H$ (400 MHz, CDCl$_3$): 7.46-7.37 (5H, m), 7.07 (2H, dd, J=12.51, 6.13 Hz), 6.78-6.71 (2H, m), 6.10 (1H, s), 5.16 (3H, s), 3.58 (1H, dd, J=9.65, 4.95 Hz), 3.19-2.90 (4H, m), 2.41-1.34 (18H, m), 2.41 (9H, s).

The compound of formula GM was prepared from the compound of formula GL and methyl 2-chloro-2-oxoacetate in a manner similar to the preparation of the compound of formula CF in Example 6 (yield >98%).

The identity of the compound of formula GM, benzyl 1-(4-(N-(2-(tert-butoxycarbonylamino)phenyl)-2-methoxy-2-oxoacetamido)piperidin-1-yl)cyclooctanecarboxylate, was confirmed using $^1$H NMR.

Compound GM: $^1$H NMR: $\delta_H$ (400 MHz, CDCl$_3$): 7.98 (1H, d, J=5.1 Hz), 7.42-7.32 (5H, m), 7.06-7.04 (2H, m), 6.68 (1H, s), 5.10 (2H, s), 4.35 (1H, m), 3.49 (3H, s), 3.02 (2H, t, J=10.8 Hz), 2.90 (1H, t, J=6.0 Hz), 2.35 (1H, t, J=6.0 Hz), 2.24 (2H, t, J=12.0 Hz), 1.87-1.78 (6H, m), 1.51-1.27 (19H, m).

To the compound of formula GM (553 mg, 0.89 mmol) was added 4N HCl in EtOAc (5.5 mL) at 0° C. Thereafter, the reaction mixture was stirred for 30 min at a temperature of about 25° C. A white precipitate formed. Saturated aqueous NaHCO$_3$ (pH>8) was added and the reaction mixture was stirred for 30 min at a temperature of about 25° C. Thereafter, the mixture was extracted twice with CHCl$_3$ (50 mL for each extraction). The organic portions were combined, washed with water, dried (MgSO$_4$), and concentrated under reduced pressure to provide a colorless amorphous solid. The solid was recrystallized from a mixture of diethyl ether and iso-propyl ether to provide 333 mg of the compound of formula GI as a white powder (yield 76%).

5.29 Example 29

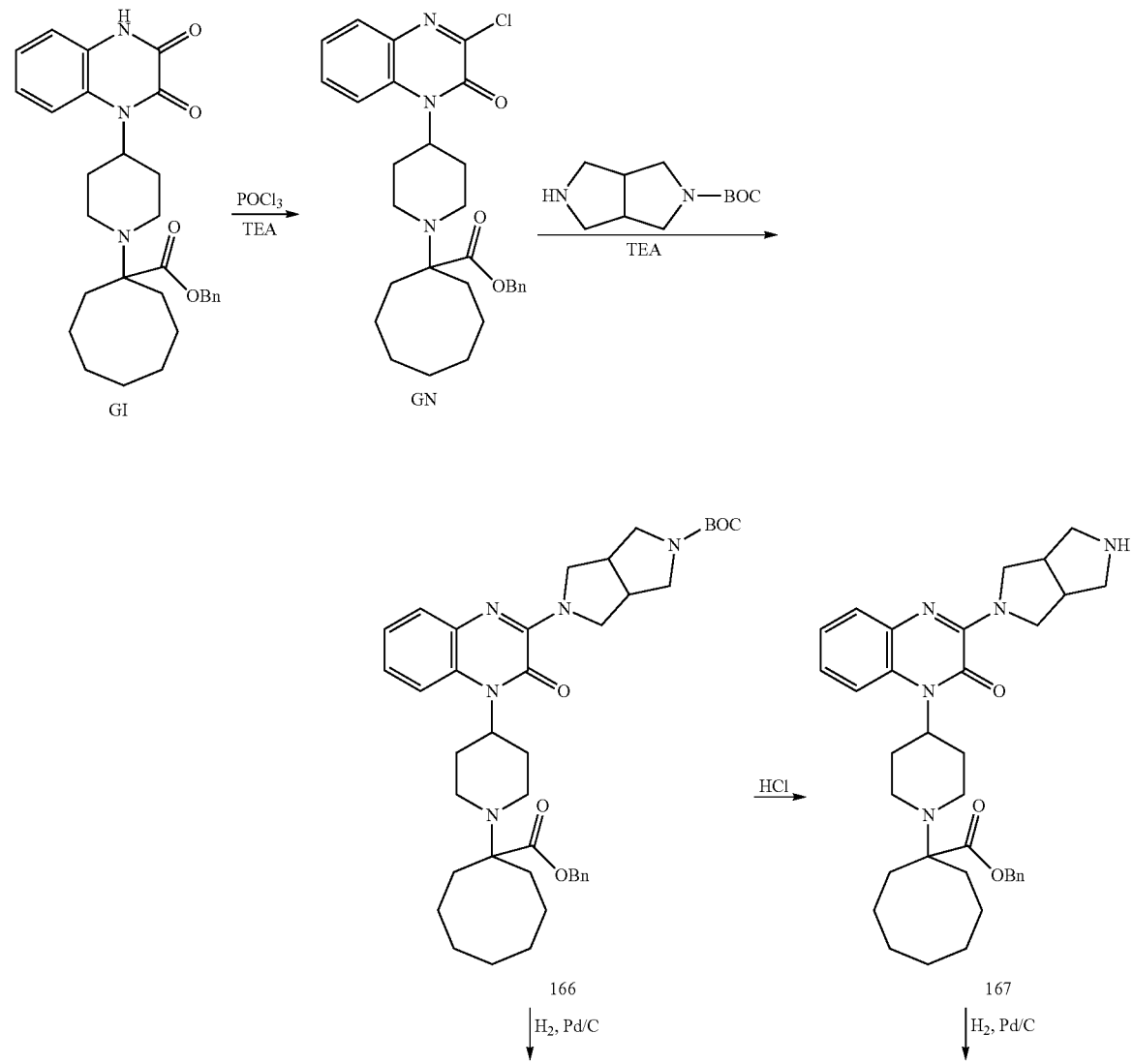

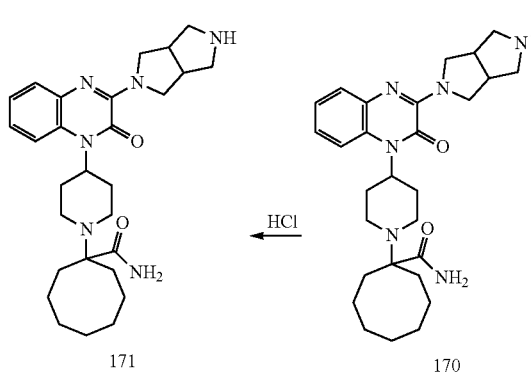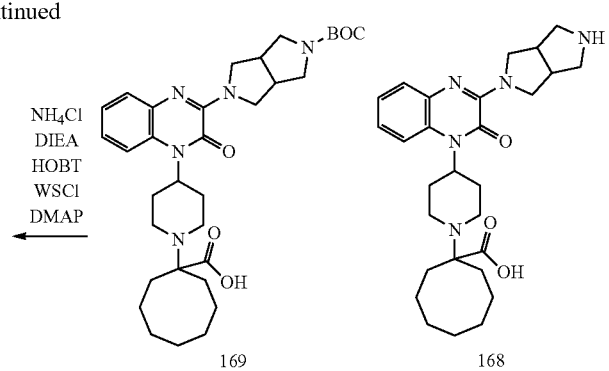

In a manner similar to Example 3, the compound of formula GN was prepared from the compound of formula GI (yield 92%) then Substituted-Quinoxaline-Type Piperidine Compound 166 was prepared from tert-butyl hexahydropyrrolo[3,4-c]pyrrole-2(1H)-carboxylate and the compound of formula GN (yield >98%).

The identity of the compound of formula GN, benzyl 1-(4-(3-chloro-2-oxo-3,4-dihydroquinoxalin-1(2H)-yl)piperidin-1-yl)cyclooctanecarboxylate, was confirmed using $^1$H NMR.

Compound GN: $^1$H NMR: $\delta_H$ (300 MHz, CDCl$_3$): 7.81 (1H, d, J=8.1 Hz), 7.59-7.56 (2H, m), 7.39-7.35 (6H, m), 5.16 (2H, s), 4.83 (1H, br), 3.49 (3H, s), 3.25 (2H, d, J=11.7 Hz), 2.91 (2H, m), 2.34 (2H, t, J=6.0 Hz), 2.00-1.47 (16H, m).

The identity of Substituted-Quinoxaline-Type Piperidine Compound 166, tert-butyl 5-(4-(1-(1-(benzyloxycarbonyl)cyclooctyl)piperidin-4-yl)-3-oxo-3,4-dihydroquinoxalin-1(2H)-yl)hexahydropyrrolo[3,4-c]pyrrole-2(1H)-carboxylate, was confirmed using $^1$H NMR.

Substituted-Quinoxaline-Type Piperidine Compound 166: $^1$H NMR: $\delta_H$ (300 MHz, DMSO-d$_6$): 7.51-7.38 (7H, m), 7.18-7.15 (2H, m), 5.16 (2H, s), 4.45 (1H, br), 4.00 (2H, br), 3.71 (2H, br), 3.50 (2H, br), 3.24 (2H, d, J=11.1 Hz), 2.76 (2H, d, J=9.3 Hz), 2.33 (2H, t, J=10.8 Hz), 2.01-1.47 (16H, m).

In a manner similar to the preparation of Substituted-Quinoxaline-Type Piperidine Compound 5 in Example 7, Substituted-Quinoxaline-Type Piperidine Compound 167, benzyl 1-(4-(3-(hexahydropyrrolo[3,4-c]pyrrol-2(1H)-yl)-2-oxo-3,4-dihydroquinoxalin-1(2H)-yl)piperidin-1-yl)cyclooctanecarboxylate, was prepared from Substituted-Quinoxaline-Type Piperidine Compound 166 (yield 90%) then, in a manner similar to the removal of the benzyl group in Example 18, Substituted-Quinoxaline-Type Piperidine Compound 168 was prepared from Substituted-Quinoxaline-Type Piperidine Compound 167 (yield 27%).

The identity of Substituted-Quinoxaline-Type Piperidine Compound 168, 1-(4-(3-(hexahydropyrrolo[3,4-c]pyrrol-2(1H)-yl)-2-oxo-3,4-dihydroquinoxalin-1(2H)-yl)piperidin-1-yl)cyclooctanecarboxylic acid, was confirmed using $^1$H NMR and LC/MS.

Substituted-Quinoxaline-Type Piperidine Compound 168: $^1$H NMR: $\delta_H$ (300 MHz, DCl/D$_2$O): 7.53 (2H, d, J=8.1 Hz), 7.34 (1H, t, J=8.1 Hz), 7.23 (1H, t, J=8.1 Hz), 4.38 (5H, br), 3.57 (4H, d, J=5.7 Hz), 3.35-3.22 (6H, m), 3.07-2.99 (2H, m), 2.23-2.00 (6H, m), 1.54 (6H, br), 1.24 (4H, br); LC/MS (100%, t$_r$=0.83 min): m/z=494.2 [M+H]$^+$ (Calc. 493.3).

In a manner similar to the removal of the benzyl group in Example 18, Substituted-Quinoxaline-Type Piperidine Compound 169 was prepared from Substituted-Quinoxaline-Type Piperidine Compound 166 (yield 81%).

The identity of Substituted-Quinoxaline-Type Piperidine Compound 169, 14443-(5-(tert-butoxycarbonyl)hexahydropyrrolo[3,4-c]pyrrol-2(1H)-yl)-2-oxo-3,4-dihydroquinoxalin-1(2H)-yl)piperidin-1-yl)cyclooctanecarboxylic acid, was confirmed using $^1$H NMR.

Substituted-Quinoxaline-Type Piperidine Compound 169: $^1$H NMR: $\delta_H$ (300 MHz, CD$_3$OD): 7.55-7.48 (2H, m), 7.23-7.19 (2H, m), 4.16 (2H, br), 3.90 (2H, br), 3.68-3.62 (4H, m), 3.30-3.22 (4H, m), 2.98 (2H, br), 2.24-2.00 (6H, m), 1.74-1.47 (21H, m).

At a temperature of about 25° C., a reaction mixture of Substituted-Quinoxaline-Type Piperidine Compound 169 (150 mg, 0.25 mmol, 1 eq), NH$_4$Cl (16 mg, 0.30 mmol, 1.2 eq), DIEA (51 µL, 0.30 mmol, 1.2 eq), HOBT (38 mg, 0.28 mmol, 1.1 eq, Acros Organics), WSCI (54 mg, 0.28 mmol, 1.1 eq, Sigma-Aldrich), and DMAP (5.6 mg, 0.05 mmol, 0.2 eq) in DMF (3 mL) was stirred for 48 hr. Thereafter, the mixture was poured into water (20 mL) and extracted twice with CHCl$_3$ (30 mL for each extraction). The organic portions were combined, washed with saturated aqueous NaHCO$_3$, washed with water, dried (MgSO$_4$), and concentrated under reduced pressure to provide a pale yellow amorphous solid.

The solid was chromatographed with a silica gel column eluted with a gradient of from 100%:0% CHCl$_3$:MeOH to 97%:3% CHCl$_3$:MeOH to provide 40 mg of Substituted-Quinoxaline-Type Piperidine Compound 170 as a colorless amorphous solid (yield 27%).

The identity of Substituted-Quinoxaline-Type Piperidine Compound 170, tert-butyl 5-(4-(1-(1-carbamoylcyclooctyl)piperidin-4-yl)-3-oxo-3,4-dihydroquinoxalin-1(2H)-yl)hexahydropyrrolo[3,4-c]pyrrole-2(1H)-carboxylate, was confirmed using $^1$H NMR.

Substituted-Quinoxaline-Type Piperidine Compound 170: $^1$H NMR: $\delta_H$ (300 MHz, DMSO-d$_6$): 7.71 (1H, br), 7.35-7.32 (1H, m), 7.16-7.12 (2H, m), 6.96 (1H, m), 3.99 (2H, br), 3.73 (1H, br), 3.50 (2H, br), 3.18-3.15 (2H, m), 2.99-2.89 (2H, m), 2.68-2.65 (2H, m), 2.38-2.31 (2H, m), 1.96-1.39 (28H, m).

In a manner similar to the preparation of Substituted-Quinoxaline-Type Piperidine Compound 5 in Example 7, Substituted-Quinoxaline-Type Piperidine Compound 171 was prepared from Substituted-Quinoxaline-Type Piperidine Compound 170 (yield 41%).

The identity of Substituted-Quinoxaline-Type Piperidine Compound 171, 1-(4-(3-(hexahydropyrrolo[3,4-c]pyrrol-2

(1H)-yl)-2-oxo-3,4-dihydroquinoxalin-1(2H)-yl)piperidin-1-yl)cyclooctanecarboxamide, was confirmed using $^1$H NMR and LC/MS.

Substituted-Quinoxaline-Type Piperidine Compound 171: $^1$H NMR: $\delta_H$ (300 MHz, DMSO-$d_6$): 7.70 (1H, br), 7.36-7.33 (1H, m), 7.16-7.13 (3H, m), 6.96 (1H, s), 4.65 (1H, br), 3.99 (2H, br), 3.50 (2H, br), 3.02-2.96 (4H, m), 2.80-2.66 (6H, m), 2.34 (2H, t, J=11.4 Hz), 2.00-1.95 (2H, m), 1.83-1.78 (2H, m), 1.62-1.39 (12H, m); LC/MS (100%, $t_r$=0.78 min): m/z=493.2 [M+H]$^+$ (Calc: 492.7).

5.30 Example 30

The identity of the compound of formula BE, 1-adamantan-1-yl-piperidin-4-one, was confirmed using $^1$H NMR.

Compound HB: $^1$H NMR: $\delta_H$ (300 MHz, CDCl$_3$): 2.96 (4H, s), 2.46 (4H, s), 2.14 (3H, s), 1.79-1.62 (14H, m).

The compound of formula HC was prepared in a manner similar to the preparation of the compound of formula AB in Example 1 except tert-butyl 2-aminophenylcarbamate was used in place of 1,2-phenylenediamine (yield 60%).

The identity of the compound of formula HC, [2-(1-adamantan-1-yl-piperidin-4-yl-amino)-phenyl]-carbamic acid tert-butyl ester, was confirmed using $^1$H NMR and LC/MS.

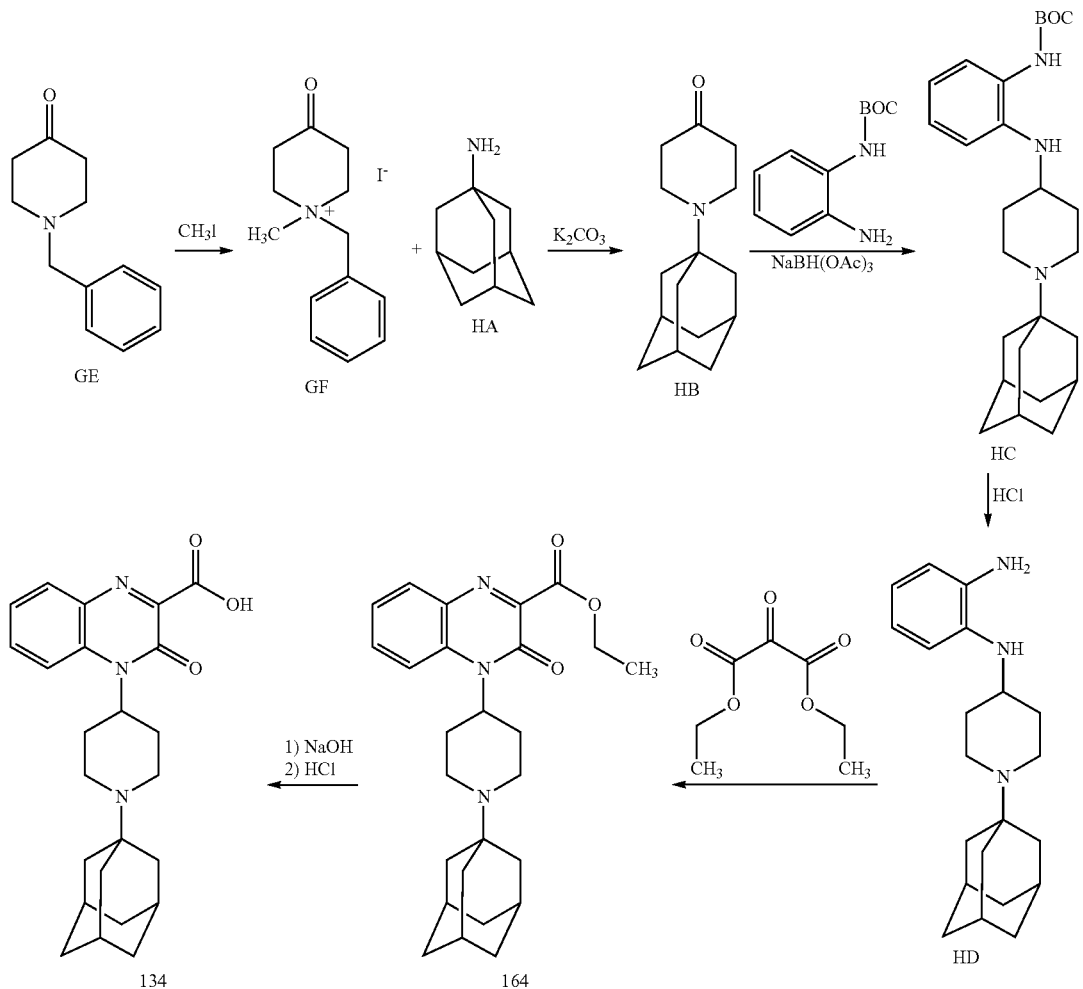

At a temperature of about 25° C., K$_2$CO$_3$ (228 mg, 1.65 mmol, 0.1 eq) was added to a mixture of the compound of formula HA (1-adamantylamine, 5.02 g, 33.2 mmol), ethanol (12 mL), and water (12 mL). Then, a mixture of the compound of formula GF (5.47 g, 16.5 mmol), ethanol (13 mL), and water (13 mL) was added. The resulting reaction mixture was refluxed for 3 h. Thereafter, the mixture was poured into water and extracted with EtOAc. The organic portion was dried (Na$_2$SO$_4$) then concentrated under reduced pressure to provide a residue. The residue was chromatographed with a silica gel column eluted with 97%:3% CHCl$_3$:MeOH to provide 1.97 g of the compound of formula HB as a colorless solid (yield 51%).

Compound HC: $^1$H NMR: $\delta_H$ (400 MHz, DMSO-$d_6$): 8.32 (1H, s), 7.13 (1H, d, J=7.6 Hz), 6.96-6.92 (1H, m), 6.62 (1H, d, J=7.6 Hz), 6.54-6.50 (1H, m), 4.52 (1H, d, J=7.1 Hz), 3.18 (1H, dd, J=7.35, 3.30 Hz), 2.99 (2H, d, J=11.15 Hz), 2.25 (2H, t, J=10.14 Hz), 2.03 (3H, s), 1.91 (2H, d, J=11.66 Hz), 1.65-1.54 (12H, m), 1.43 (9H, s), 1.30 (2H, q, J=9.97 Hz); LC/MS: m/z=426 [M+H]$^+$ (Calc: 425.3).

In a manner similar to the preparation of Substituted-Quinoxaline-Type Piperidine Compound 5 in Example 7, the compound of formula HD was prepared from the compound of formula HC (yield >98%).

The identity of the compound of formula HD, N-(1-adamantan-1-yl-piperidin-4-yl)benzene-1,2-diamine, was confirmed using $^1$H NMR and LC/MS.

Compound HD: $^1$H NMR: $\delta_H$ (400 MHz, DMSO-d$_6$): 6.54-6.35 (4H, m), 4.45 (2H, s), 4.05 (1H, d, J=7.6 Hz), 3.10 (3H, m), 2.20 (2H, s), 2.04 (3H, s), 1.93 (2H, d, J=10.65 Hz), 1.60 (12H, m), 1.31 (2H, br); LC/MS: m/z=325.8 [M+H]$^+$ (Calc: 325.3).

In a manner similar to the preparation of Substituted-Quinoxaline-Type Piperidine Compound 120 from Substituted-Quinoxaline-Type Piperidine Compound 74 in Example 21, Substituted-Quinoxaline-Type Piperidine Compound 164 was prepared from the compound of formula HD (yield 20%).

The identity of Substituted-Quinoxaline-Type Piperidine Compound 164, 4-(1-adamantan-1-yl)-piperidin-4-yl)-3-oxo-3,4-dihydro-quinoxaline-2-carboxylic acid ethyl ester, was confirmed using $^1$H NMR and LC/MS.

Substituted-Quinoxaline-Type Piperidine Compound 164: $^1$H NMR: $\delta_H$ (400 MHz, DMSO-d$_6$): 7.90 (2H, m), 7.76-7.71 (1H, m), 7.44 (1H, t, J=7.6 Hz), 4.73 (1H, br), 4.37 (2H, q, J=7.1 Hz), 3.25 (2H, m), 2.59 (2H, m), 2.28 (2H, t, J=10.9 Hz), 2.06 (3H, s), 1.69-1.57 (14H, m), 1.32 (3H, t, J=7.1 Hz); LC/MS: m/z=435.9 [M+H]$^+$ (Calc: 435.3).

Substituted-Quinoxaline-Type Piperidine Compound 134 was prepared from Substituted-Quinoxaline-Type Piperidine Compound 164 in a manner similar to the preparation of Substituted-Quinoxaline-Type Piperidine Compound 111 in Example 5 (yield 91%).

The identity of Substituted-Quinoxaline-Type Piperidine Compound 134, 4-(1-adamantan-1-yl-piperidin-4-yl)-3-oxo-3,4-dihydro-quinoxalin-2-carboxylic acid, was confirmed using $^1$H NMR and LC/MS.

Substituted-Quinoxaline-Type Piperidine Compound 134: $^1$H NMR: $\delta_H$ (400 MHz, DMSO-d$_6$): 8.11 (1H, br), 7.70 (1H, dd, J=8.11, 1.52 Hz), 7.51 (1H, t, J=7.35 Hz), 7.32 (1H, t, J=7.6 Hz), 5.15 (1H, br), 3.67 (2H, s), 3.19-3.02 (6H, m), 2.17 (3H, s), 1.92 (7H, m), 1.65 (6H, s); LC/MS (100%, t$_r$=1.33 min): m/z=408.3 [M+H]$^+$ (Calc: 407.5).

5.31 Example 31

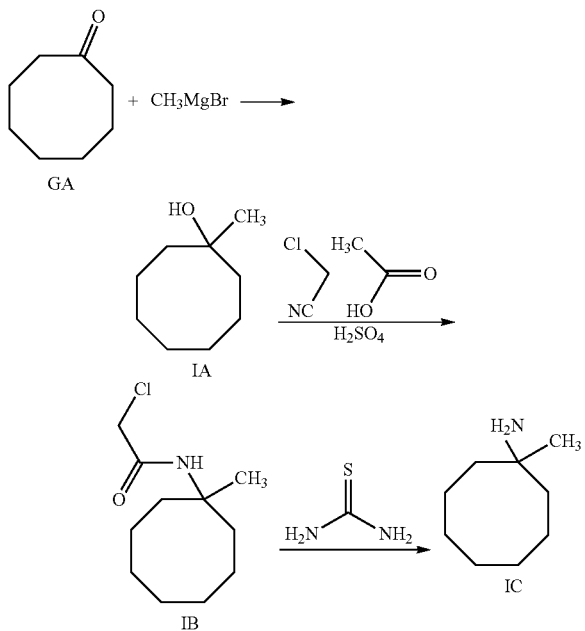

Under a nitrogen atmosphere, to a mixture of the compound of formula GA (28 g, 222 mmol) and Et$_2$O (500 mL) at a temperature of −40° C. was added methylmagnesium bromide (89 mL, 266 mmol, Sigma-Aldrich). The resulting reaction mixture was stirred for 4 h as its temperature warmed from -40° C. to 0° C. then stirred an additional 1.5 h as its temperature warmed from 0° C. to about 25° C. Thereafter, saturated aqueous NH$_4$Cl was added, the mixture was neutralized with 2N aqueous HCl to adjust the pH into the range between 5-6, and the mixture was extracted 3 times with Et$_2$O (400 mL for each extraction). The organic portions were combined, dried (Na$_2$SO$_4$), filtered, and concentrated under reduced pressure to provide the compound of formula IA, 1-methylcyclooctanol, as a colorless oil. Acetic acid (29.3 mL, 512 mmol) was added to a mixture of the compound of formula IA (26 g, 183 mmol) and 2-chloroacetonitrile (23.20 mL, 365 mmol, Sigma-Aldrich) and the resulting reaction mixture was cooled to a temperature in the range of from 0° C. to 3° C. H$_2$SO$_4$ (29.2 mL, 548 mmol) was added dropwise over 1 h such that the temperature was kept below 10° C. Thereafter, the reaction mixture was warmed to a temperature of about 25° C. and stirred for 1.5 hrs. After quencing with ice-water (400 mL), the mixture was neutralized with a 30% NaOH aqueous solution to adjust the pH into the range between 7-8; a white precipitate formed. The precipitate was collected by filtration, washed twice with water (100 mL for each wash), and dried under reduced pressure at 60° C. for 6 h to provide 27 g of the compound of formula IB (yield 56%).

The identity of the compound of formula IB, 2-chloro-N-(1-methylcyclooctyl)acetamide, was confirmed using $^1$H NMR.

Compound IB: $^1$H NMR: $\delta_H$ (400 MHz, CDCl$_3$): 6.28 (1H, s), 3.95 (2H, s), 2.05-2.00 (2H, m), 1.72 (2H, td, J=10.01, 4.06 Hz), 1.57 (11.2H, m), 1.41 (3H, s).

Under a nitrogen atmosphere, to a mixture of the compound of formula IB (27 g, 124 mmol) and ethanol (240 mL) at a temperature of about 25° C. was added thiourea (11.30 g, 148 mmol, Sigma-Aldrich) and acetic acid (45 mL) The resulting reaction mixture was warmed to 110° C. and stirred for 7 h. After cooling the mixture to a temperature of about 25° C. and quencing with water (700 mL), the white precipitate that formed was filtered off. The filtrate was neutralized with a 30% NaOH aqueous solution, its pH was adjusted to pH14, it was washed twice with n-hexane:H$_2$O (400 mL for each wash), dried (Na$_2$SO$_4$), and concentrated under reduced pressure to provide 17 g of the compound of formula IC as a pale yellow oil (yield 97%).

The identity of the compound of formula IC, 1-methylcyclooctanamine, was confirmed using $^1$H NMR.

Compound IC: $^1$H NMR: $\delta_H$ (300 MHz, CDCl$_3$): 1.58-1.47 (14H, m), 1.26-1.21 (2H, m), 1.07 (3H, s).

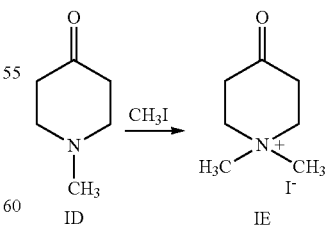

The compound of formula IE was prepared in a manner similar to the preparation of the compound of formula DB in Example 13 except 1-methylpiperidin-4-one (ID), Sigma-Aldrich) was used in place of tropinone and methyl iodide was used in place of dimethyl sulfate.

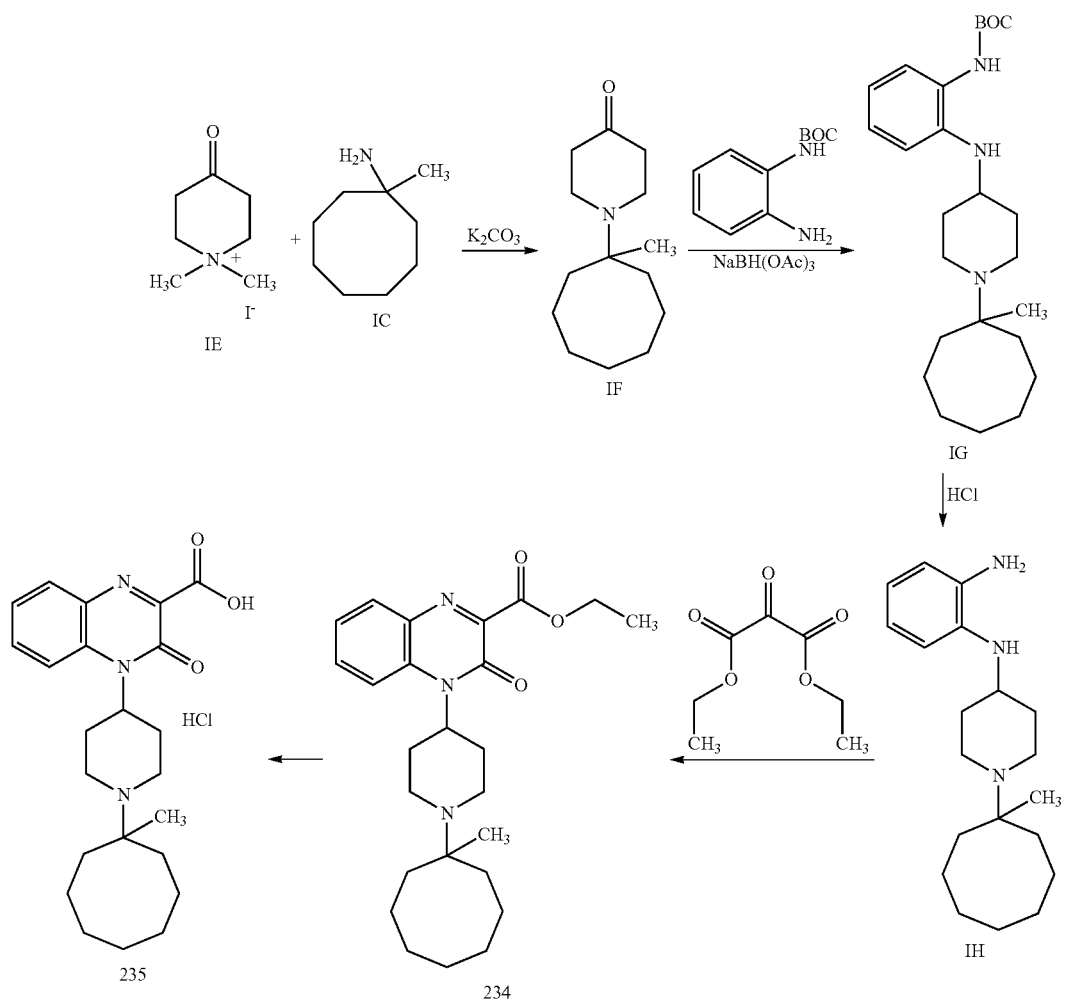

In a manner similar to Example 30, Substituted-Quinoxaline-Type Piperidine Compound 234 was prepared except that the compound of formula IE was used in place of the compound of formula GF and the compound of formula IC was used in place of the compound of formula HA.

The identity of Substituted-Quinoxaline-Type Piperidine Compound 234, ethyl 4-(1-(1-methylcyclooctyl)piperidin-4-yl)-3-oxo-3,4-dihydroquinoxaline-2-carboxylate, was confirmed using $^1$H NMR and LC/MS.

Substituted-Quinoxaline-Type Piperidine Compound 234: $^1$H NMR: $\delta_H$ (400 MHz, CDCl$_3$): 7.93 (1H, dd, J=8.11, 1.01 Hz), 7.76 (1H, d, J=4.56 Hz), 7.61 (1H, dd, J=11.66, 4.06 Hz), 7.36 (1H, t, J=7.6 Hz), 4.90 (1H, br), 4.50 (2H, q, J=7.1 Hz), 3.15 (2H, d, J=11.66 Hz), 2.78 (2H, dd, J=5.07, 3.55 Hz), 2.23 (2H, t, J=11.41 Hz), 1.86-1.24 (20H, m), 0.84 (3H, d, J=10.65 Hz); LC/MS: m/z=426 [M+H]$^+$ (Calc: 425).

At a temperature of about 25° C., to a mixture of Substituted-Quinoxaline-Type Piperidine Compound 234 (188 mg, 0.442 mmol) and ethanol (8 mL) was added 2N aqueous NaOH (0.663 mL, 1.325 mmol) and the reaction mixture was stirred for 45 min. Thereafter, the mixture was concentrated under reduced pressure to provide a residue. The residue was diluted with water, neutralized with 2N aqueous HCl (0.663 mL), and extracted with CHCl$_3$:H$_2$O to provide an emulsion that was concentrated under reduced pressure to provide a second residue. The second residue was diluted with CHCl$_3$, dried (MgSO$_4$), and concentrated under reduced pressure to provide a pale yellow solid. The solid was washed with 1:1 EtOAc:Et$_2$O, filtrated, and dried under reduced pressure at 70° C. for 12 h to provide a third residue. The third residue was diluted with 2N aqueous HCl (2 mL), heated, sonicated, and concentrated under reduced pressure to provide an oil. The oil was dried under reduced pressure at 70° C. for 12 h to provide the hydrochloride of Substituted-Quinoxaline-Type Piperidine Compound 235 as a yellow amorphous solid.

The identity of Substituted-Quinoxaline-Type Piperidine Compound 235, 4-(1-(1-methylcyclooctyl)piperidin-4-yl)-3-oxo-3,4-dihydroquinoxaline-2-carboxylic acid, was confirmed using $^1$H NMR and LC/MS.

Substituted-Quinoxaline-Type Piperidine Compound 235: $^1$H NMR: $\delta_H$ (400 MHz, DMSO-d$_6$): 8.28 (1H, br), 7.84 (1H, s), 7.65 (1H, s), 7.44 (1H, s), 5.32 (1H, s), 3.63 (4H, d, J=2.53 Hz), 2.14-1.36 (21H, m); LC/MS (100%, t$_r$=1.40 min): m/z=398 [M+H]$^+$ (Calc: 397).

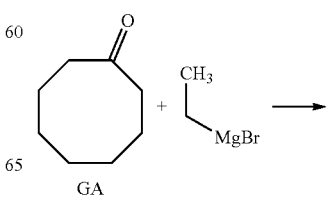

-continued

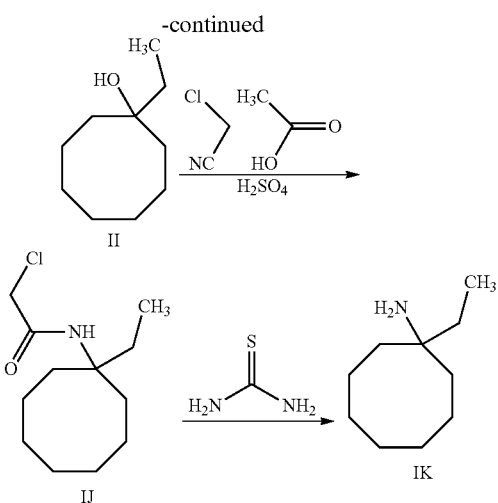

In a manner similar to that described above, the compound of formula IK was prepared from the compound of formula GA except that ethylmagnesium bromide (Sigma-Aldrich) was used in place of methylmagnesium bromide (yield 20%).

The identity of the compound of formula IK, 1-ethylcyclooctanamine, was confirmed using $^1$H NMR.

Compound IK: $^1$H NMR: $\delta_H$ (400 MHz, CDCl$_3$): 1.63-1.34 (16H, m), 1.10 (2H, s), 0.86 (3H, t, J=7.6 Hz).

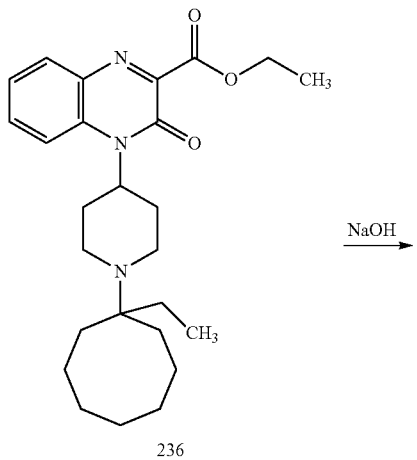

236

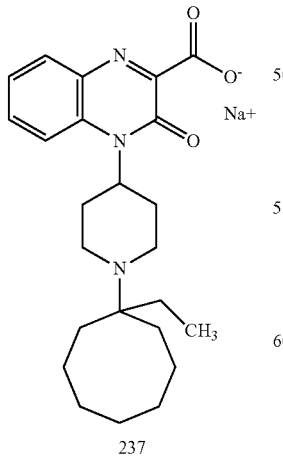

237

In a manner similar to that described above, Substituted-Quinoxaline-Type Piperidine Compound 236 was prepared from the compound of formula IE except that the compound of formula IK was used in place of the compound of formula IC.

The identity of Substituted-Quinoxaline-Type Piperidine Compound 236, ethyl 4-(1-(1-ethylcyclooctyl)piperidin-4-yl)-3-oxo-3,4-dihydroquinoxaline-2-carboxylate, was confirmed using $^1$H NMR and LC/MS.

Substituted-Quinoxaline-Type Piperidine Compound 236: $^1$H NMR: $\delta_H$ (400 MHz, CDCl$_3$): 7.93 (1H, d, J=8.11 Hz), 7.76 (1H, d, J=1.01 Hz), 7.61 (1H, dd, J=7.86, 6.84 Hz), 7.35 (1H, t, J=7.6 Hz), 4.94 (1H, br), 4.50 (2H, ddd, J=14.19, 7.10, 1.52 Hz), 3.15 (2H, d, J=10.65 Hz), 2.71 (2H, br), 2.34 (2H, t, J=11.41 Hz), 1.83-1.39 (18H, m), 0.86 (3H, t, J=7.35 Hz); LC/MS: m/z=440 [M+H]$^+$ (Calc: 439).

2N aqueous NaOH (0.114 mL, 0.227 mmol) was added to a mixture of Substituted-Quinoxaline-Type Piperidine Compound 236 (100 mg, 0.227 mmol) and ethanol (2 mL) at 25° C. The resulting reaction mixture was stirred at a temperature of about 25° C. for 2 h. After concentration under reduced pressure, the resulting solid was triturated with Et$_2$O, filtered, and dried under reduced pressure at 80° C. to provide 98 mg of the sodium salt of Substituted-Quinoxaline-Type Piperidine Compound 237 as a pale yellow solid (yield >98%).

The identity of Substituted-Quinoxaline-Type Piperidine Compound 237, 4-(1-(1-ethylcyclooctyl)piperidin-4-yl)-3-oxo-3,4-dihydroquinoxaline-2-carboxylate, was confirmed using $^1$H NMR and LC/MS.

Substituted-Quinoxaline-Type Piperidine Compound 237: $^1$H NMR: $\delta_H$ (400 MHz, CD$_3$OD): 7.82 (2H, dd, J=28.13, 7.86 Hz), 7.58 (1H, dd, J=8.36, 7.35 Hz), 7.34 (1H, t, J=7.6 Hz), 3.19 (2H, d, J=10.65 Hz), 2.80 (2H, d, J=10.65 Hz), 2.40 (2H, t, J=11.41 Hz), 1.89-1.46 (18H, m), 0.89 (3H, t, J=7.35 Hz); LC/MS (100%, t$_r$=1.57 min): m/z=411 [M+H]$^+$ (Calc: 410).

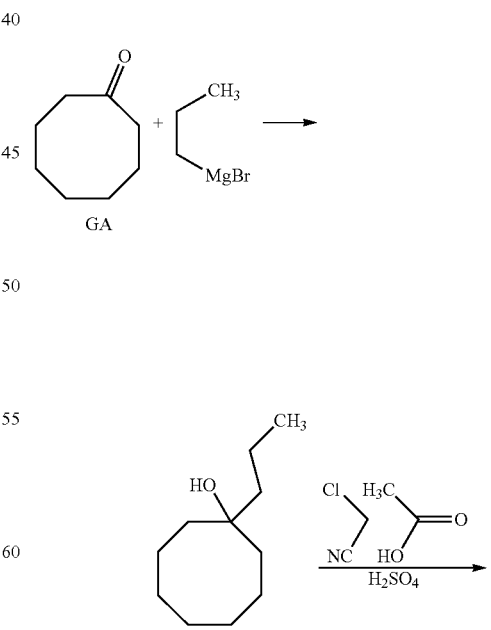

-continued

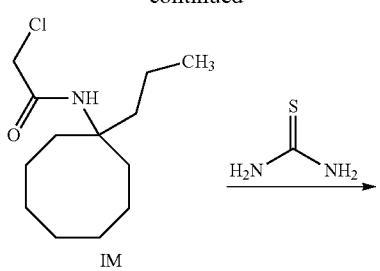

IM

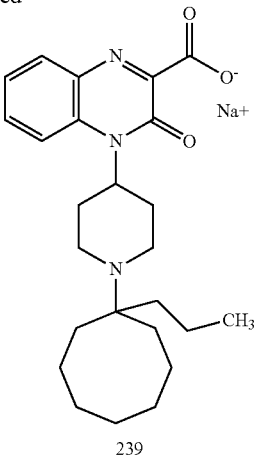

239

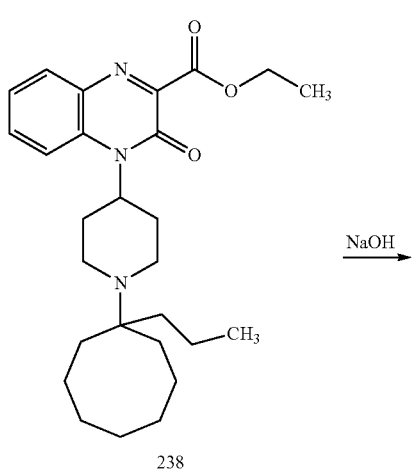

IN

In a manner similar to that described above, the compound of formula IN was prepared from the compound of formula GA except that propylmagnesium bromide (Sigma-Aldrich) was used in place of methylmagnesium bromide (yield 26%).

The identity of the compound of formula IN, 1-propylcyclooctanamine, was confirmed using $^1$H NMR.

Compound IN: $^1$H NMR: $\delta_H$ (400 MHz, CDCl$_3$): 1.63-1.19 (20H, m), 0.92 (3H, t, J=5.83 Hz).

In a manner similar to that described above, Substituted-Quinoxaline-Type Piperidine Compound 238 was prepared from the compound of formula IE except that the compound of formula IN was used in place of the compound of formula IC.

The identity of Substituted-Quinoxaline-Type Piperidine Compound 238, ethyl 3-oxo-4-(1-(1-propylcyclooctyl)piperidin-4-yl)-3,4-dihydroquinoxaline-2-carboxylate, was confirmed using $^1$H NMR and LC/MS.

Substituted-Quinoxaline-Type Piperidine Compound 238: $^1$H NMR: $\delta_H$ (400 MHz, CDCl$_3$): 7.93 (1H, d, J=7.6 Hz), 7.75 (1H, dd, J=3.80, 1.77 Hz), 7.63-7.59 (1H, m), 7.35 (1H, t, J=7.6 Hz), 4.93 (1H, br), 4.53-4.48 (2H, m), 3.54 (1H, br), 3.14 (2H, d, J=11.15 Hz), 2.73 (2H, ddd, J=18.38, 11.03, 3.93 Hz), 2.33 (2H, t, J=11.41 Hz), 1.80-1.24 (20H, m), 0.91 (3H, d, J=12.67 Hz); LC/MS: m/z=454 [M+H]$^+$ (Calc: 453).

In a manner similar to that described above, the sodium salt of Substituted-Quinoxaline-Type Piperidine Compound 239 was prepared from Substituted-Quinoxaline-Type Piperidine Compound 238 (yield 88%).

The identity of Substituted-Quinoxaline-Type Piperidine Compound 239, 3-oxo-4-(1-(1-propylcyclooctyl)piperidin-4-yl)-3,4-dihydroquinoxaline-2-carboxylate, was confirmed using $^1$H NMR and LC/MS.

Substituted-Quinoxaline-Type Piperidine Compound 239: $^1$H NMR: $\delta_H$ (400 MHz, CD$_3$OD): 7.86-7.77 (2H, m), 7.60-7.56 (1H, m), 7.34 (1H, t, J=7.6 Hz), 3.18 (2H, d, J=11.15 Hz), 2.79 (2H, d, J=9.63 Hz), 2.39 (2H, t, J=11.41 Hz), 1.90-1.29 (20H, m), 0.91 (3H, t, J=5.83 Hz); LC/MS (96%, t$_r$=1.82 min): m/z=425 [M+H]$^+$ (Calc: 424).

5.32 Example 32

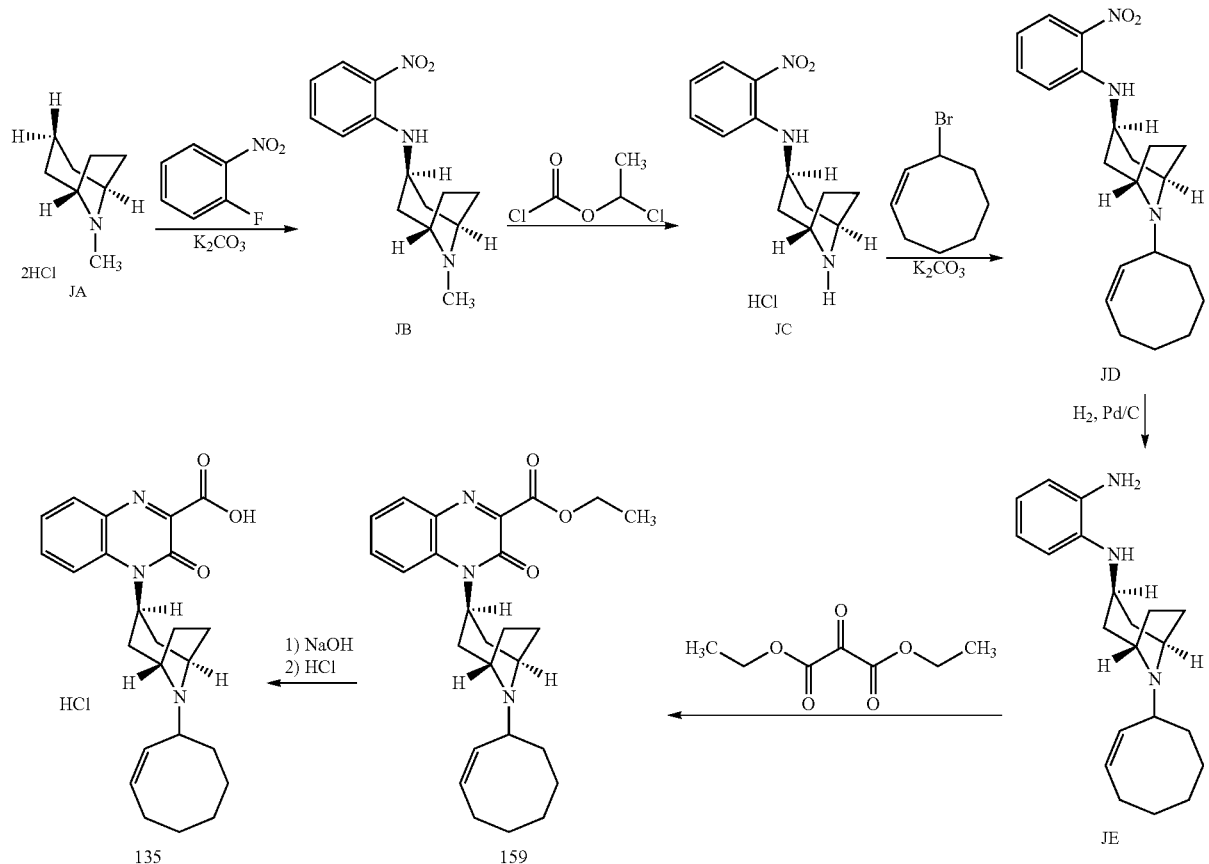

The compound of formula JA, (endo)-8-methyl-8-azabicyclo[3.2.1]octan-3-amine, was prepared by a method known to those in the art, e.g., M. Allegretti et al., *Tetrahedron Let.*, 58:5669-5674 (2002). $K_2CO_3$ (9.12 g, 66 mmol) was added to a mixture of the dihydrochloride of the compound of formula JA (4.69 g, 22 mmol) and 1-fluoro-2-nitrobenzene (3.10 g, 22 mmol, Sigma-Aldrich) in THF (30 mL) and water (10 mL). The resulting reaction mixture was refluxed for 15 h. After cooling to a temperature of about 25° C. and quenching with water (50 mL), the mixture was extracted twice with $CHCl_3$. The organic portions were combined, dried ($MgSO_4$), and concentrated under reduced pressure to provide a residue. The residue was chromatographed with an amino-silica gel column eluted with a gradient of from 30%:70% EtOAc:n-hexane to 100%:0% EtOAc:n-hexane to provide 5.5 g of the compound of formula JB as an orange solid (yield 93%).

The identity of the compound of formula JB, (endo)-8-methyl-N-(2-nitrophenyl)-8-azabicyclo[3.2.1]octan-3-amine, was confirmed using $^1H$ NMR.

Compound JB: $^1H$ NMR: $\delta_H$ (300 MHz, $CDCl_3$): 8.68 (1H, d, J=6.1 Hz), 8.18 (1H, d, J=8.6 Hz), 7.41 (1H, dd, J=8.4, 7.4 Hz), 6.73 (1H, d, J=8.6 Hz), 6.61 (1H, dd, J=8.4, 7.4 Hz), 3.81 (1H, q, J=6.8 Hz), 3.19 (2H, s), 2.30-2.27 (5H, m), 2.15-2.10 (2H, m), 1.96-1.94 (2H, m), 1.81 (2H, d, J=14.7 Hz).

After cooling a mixture of the compound of formula JB (5.49 g, 20.4 mmol) and $CHCl_3$ (55 mL) to a temperature of 0° C., 1-chloroethyl chloroformate (3.3 mL, 30.6 mmol, Sigma-Aldrich) was added and the reaction mixture was refluxed for 2.5 h. After cooling to a temperature of about 25° C., the mixture was concentrated under reduced pressure to provide a residue. The residue was mixed with MeOH (55 mL) to form a second reaction mixture which was refluxed for 5 h. After cooling to a temperature of about 25° C., the mixture was diluted with EtOAc (100 mL) and cooled further to 0° C. where a precipitate formed. The precipitate was filtered, washed with EtOAc, and dried at 45° C. under reduced pressure to provide 4.66 g of the hydrochloride of the compound of formula JC as a yellow solid (yield 81%).

The identity of the compound of formula JC, (endo)-N-(2-nitrophenyl)-8-azabicyclo[3.2.1]octan-3-amine, was confirmed using $^1H$ NMR.

Compound JC: $^1H$ NMR: $\delta_H$ (300 MHz, DMSO-$d_6$): 9.22 (2H, br s), 8.39 (1H, d, J=6.6 Hz), 8.11 (1H, dd, J=8.6, 1.5 Hz), 7.60-7.55 (1H, m), 7.02 (1H, d, J=8.6 Hz), 6.75 (1H, t, J=7.9 Hz), 4.08-3.98 (3H, m), 2.52-2.49 (4H, m), 2.47-2.40 (2H, m), 2.17-2.08 (4H, m), 2.01 (2H, d, J=15.7 Hz).

A reaction mixture of the compound of formula JC (3.41 g, 12.0 mmol), (Z)-3-bromocyclooct-1-ene (3.40 g, 18.0 mmol, Sigma-Aldrich), $K_2CO_3$ (4.98 g, 36.0 mmol), and acetonitrile (120 mL) was refluxed for 4.5 h. After cooling to a temperature of about 25° C. and quenching with water (100 mL), the mixture was extracted twice with $CHCl_3$. The organic portions were combined, dried ($MgSO_4$), and concentrated under reduced pressure to provide a residue. The residue was recrystallized from EtOAc:n-hexane to provide 3.85 g of the compound of formula JD as an orange solid (yield 97%).

The identity of the compound of formula JD, (endo)-8-((Z)-cyclooct-2-enyl)-N-(2-nitrophenyl)-8-azabicyclo[3.2.1]octan-3-amine, was confirmed using $^1$H NMR.

Compound JD: $^1$H NMR: $\delta_H$ (300 MHz, CDCl$_3$): 8.73 (1H, d, J=6.6 Hz), 8.19 (1H, dd, J=8.6, 1.5 Hz), 7.42-7.39 (1H, m), 6.73 (1H, d, J=8.6 Hz), 6.61 (1H, t, J=7.6 Hz), 5.77 (1H, dd, J=18.8, 8.1 Hz), 5.38 (1H, t, J=9.4 Hz), 3.87 (1H, q, J=6.6 Hz), 3.57-3.41 (3H, m), 2.33-1.26 (18H, m).

Under a hydrogen atmosphere, a mixture of the compound of formula JD (13.8 g, 38.8 mmol), 10% palladium on carbon (50 mg, 0.047 mmol), MeOH (10 mL), and EtOAc (10 mL) was stirred at a temperature of about 25° C. for 5 h. After the Pd/C was filtered off through cellulose powder, the mixture was washed with MeOH (50 mL) and concentrated under reduced pressure to provide the compound of formula JE, $N^1$-((endo)-8-((Z)-cyclooct-2-enyl)-8-azabicyclo[3.2.1]octan-3-yl)benzene-1,2-diamine, as a brown solid. In a manner similar to the preparation of Substituted-Quinoxaline-Type Piperidine Compound 70 from the compound of formula AB in Example 12, Substituted-Quinoxaline-Type Piperidine Compound 159 was prepared from diethyl 2-oxomalonate and the compound of formula JE (yield 20% for two steps).

The identity of Substituted-Quinoxaline-Type Piperidine Compound 159, ethyl 4-((endo)-8-((Z)-cyclooct-2-enyl)-8-azabicyclo[3.2.1]octan-3-yl)-3-oxo-3,4-dihydroquinoxaline-2-carboxylate, was confirmed using $^1$H NMR and LC/MS.

Substituted-Quinoxaline-Type Piperidine Compound 159: $^1$H NMR: $\delta_H$ (300 MHz, CDCl$_3$): 7.88 (1H, dd, J=8.11, 1.52 Hz), 7.79-7.75 (1H, m), 7.66 (1H, d, J=9.12 Hz), 7.44 (1H, t, J=7.86 Hz), 5.72 (1H, dd, J=18.25, 8.11 Hz), 5.38 (2H, t, J=9.63 Hz), 4.41-4.34 (2H, m), 3.71 (1H, t, J=7.6 Hz), 3.51 (1H, t, J=7.86 Hz), 3.19 (1H, dd, J=15.97, 8.36 Hz), 2.30-2.22 (2H, m), 2.13-1.55 (14H, m), 1.39-1.18 (8H, m); LC/MS: m/z=435.9 [M+H]$^+$ (Calc: 435.3).

The hydrochloride of Substituted-Quinoxaline-Type Piperidine Compound 135 was prepared from Substituted-Quinoxaline-Type Piperidine Compound 159 in a manner similar to the preparation of Substituted-Quinoxaline-Type Piperidine Compound 174 in Example 7 (yield 73%).

The identity of Substituted-Quinoxaline-Type Piperidine Compound 135, 4-((endo)-8-((Z)-cyclooct-2-enyl)-8-azabicyclo[3.2.1]octan-3-yl)-3-oxo-3,4-dihydroquinoxaline-2-carboxylic acid, was confirmed using $^1$H NMR and LC/MS.

Substituted-Quinoxaline-Type Piperidine Compound 135: $^1$H NMR: $\delta_H$ (400 MHz, DMSO-d$_6$): 11.05 (1H, s), 8.09 (1H, d, J=8.11 Hz), 7.90 (1H, dd, J=7.86, 1.27 Hz), 7.76 (1H, t, J=7.35 Hz), 7.47 (1H, t, J=7.6 Hz), 6.05 (2H, dt, J=23.66, 7.98 Hz), 5.85 (1H, t, J=9.63 Hz), 4.37 (1H, t, J=7.1 Hz), 4.01 (1H, s), 3.85 (1H, s), 2.63 (2H, dd, J=21.54, 9.38 Hz), 2.36-1.91 (9H, m), 1.72 (3H, m), 1.31 (3H, m); LC/MS (98%, t$_r$=1.31 min): m/z=408.2 [M+H]$^+$ (Calc: 407.5).

Alternatively, Substituted-Quinoxaline-Type Piperidine Compound 159 was prepared by the following route.

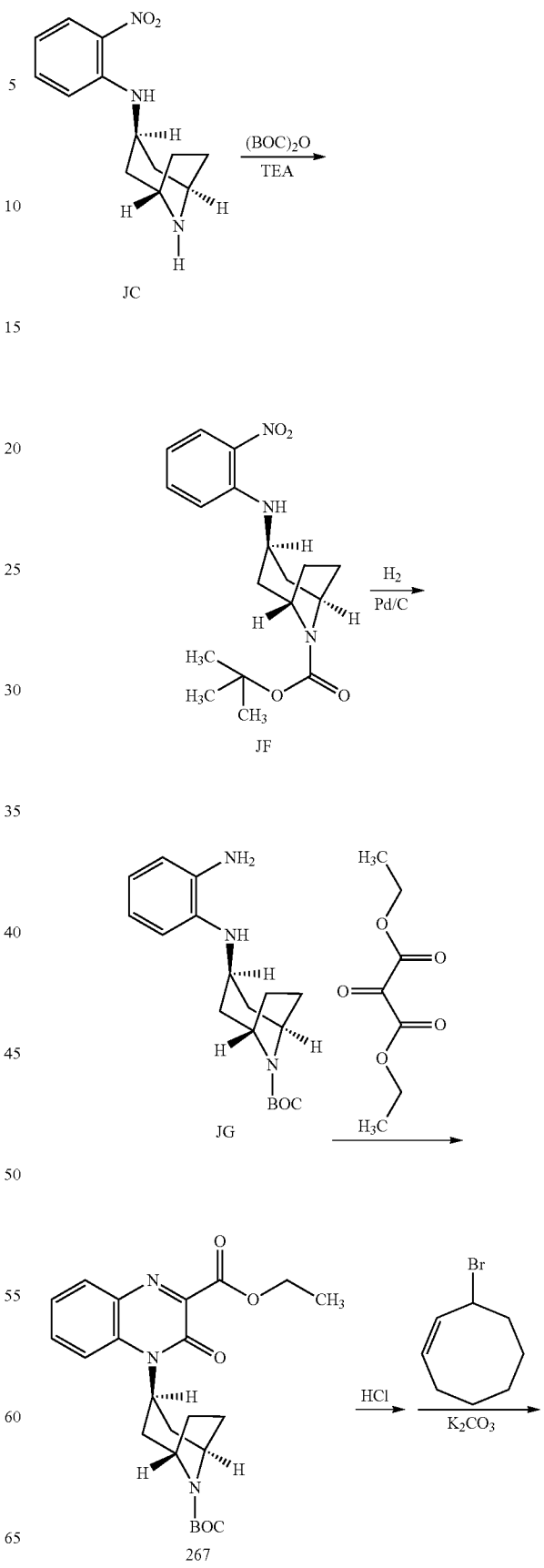

267

-continued

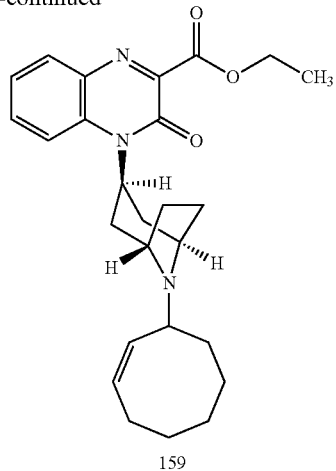

159

To a mixture of the compound of formula JC (2012 mg, 7.09 mmol) and CH$_2$Cl$_2$ (20 mL) at 0° C. was added TEA (2.95 mL, 21.3 mmol) and di-tert-butyl dicarbonate (1.81 μL, 7.80 mmol). The resulting reaction mixture was stirred at 0° C. for 2 h then concentrated under reduced pressure, diluted with water (20 mL), and extracted three times with EtOAc (20 mL for each extraction). The organic portions were combined, washed with saturated aqueous NaHCO$_3$ (10 mL), washed with saturated aqueous NaCl (10 mL), dried (MgSO$_4$), and concentrated under reduced pressure to provide an oil. The oil was chromatographed with a silica gel column eluted with 2:1 hexanes:EtOAc to provide 2421 mg of the compound of formula JF as a yellow amorphous solid (yield 98%).

The identity of the compound of formula JF, (endo)-tert-butyl 3-(2-nitrophenylamino)-8-azabicyclo[3.2.1]octane-8-carboxylate, was confirmed using $^1$H NMR and LC/MS.

Compound JF: $^1$H NMR: δ$_H$ (400 MHz, DMSO): 8.60 (1H, d, J=8.0 Hz), 8.10 (1H, d, J=8.0 Hz), 7.55 (1H, t, J=8.0 Hz), 6.96 (1H, d, J=8.0 Hz), 6.71 (1H, t, J=8.0 Hz), 4.12 (2H, m), 4.03 (1H, m), 2.20 (2H, m), 2.06-1.90 (4H, m), 1.80 (2H, m), 1.43 (9H, s); LC/MS (100%, t$_r$=2.99 min): m/z=348 [M+H]$^+$ (Calc: 347.2).

In a manner similar to the preparation of the compound of formula CC in Example 6, the compound of formula JG was prepared except that the compound of formula JF was used in place of the compound of formula CB (yield 85%).

The identity of the compound of formula JG, (endo)-tert-butyl 3-(2-aminophenylamino)-8-azabicyclo[3.2.1]octane-8-carboxylate, was confirmed using $^1$H NMR and LC/MS.

Compound JG: $^1$H NMR: δ$_H$ (400 MHz, DMSO): 6.58 (1H, d, J=8.0 Hz), 6.50 (2H, m), 6.34 (1H, d, J=8.0 Hz), 4.49 (2H, s), 4.25 (1H, s), 4.03 (2H, m), 3.59 (1H, m), 2.13 (2H, d, J=8.0 Hz), 2.04 (2H, m), 1.90-1.70 (4H, m), 1.42 (9H, s); LC/MS (100%, t$_r$=1.91 min): m/z=318 [M+H]$^+$ (Calc: 317.2).

In a manner similar to the preparation of Substituted-Quinoxaline-Type Piperidine Compound 70 from the compound of formula AB in Example 12, Substituted-Quinoxaline-Type Piperidine Compound 267 was prepared from diethyl 2-oxomalonate and the compound of formula JG (yield 92%).

The identity of Substituted-Quinoxaline-Type Piperidine Compound 267, ethyl 4-((endo)-8-(tert-butoxycarbonyl)-8-azabicyclo[3.2.1]octan-3-yl)-3-oxo-3,4-dihydroquinoxaline-2-carboxylate, was confirmed using $^1$H NMR and LC/MS.

Substituted-Quinoxaline-Type Piperidine Compound 267: $^1$H NMR: δ$_H$ (400 MHz, DMSO): 7.90 (1H, d, J=8.0 Hz), 7.77 (1H, t, J=8.0 Hz), 7.57 (1H, J=8.0 Hz), 7.46 (1H, t, J=8.0 Hz), 4.36 (2H, q, J=8.0 Hz), 4.27 (2H, m), 2.37 (2H, m), 2.18 (2H, m), 2.02 (2H, m), 1.89 (2H, m), 1.48 (9H, s), 1.33 (3H, t, J=8.0 Hz); LC/MS (100%, t$_r$=2.48 min): m/z=428 [M+H]$^+$ (Calc: 427.2).

In a manner similar to the preparation of Substituted-Quinoxaline-Type Piperidine Compound 5 in Example 7, Substituted-Quinoxaline-Type Piperidine Compound 267 was treated with 4N HCl in dioxane to remove the BOC group; after concentration under reduced pressure, the resulting solid was reacted with (Z)-3-bromocyclooct-1-ene in a manner similar to the preparation of the compound of formula JD described above to provide Substituted-Quinoxaline-Type Piperidine Compound 159 (yield 68% for two steps).

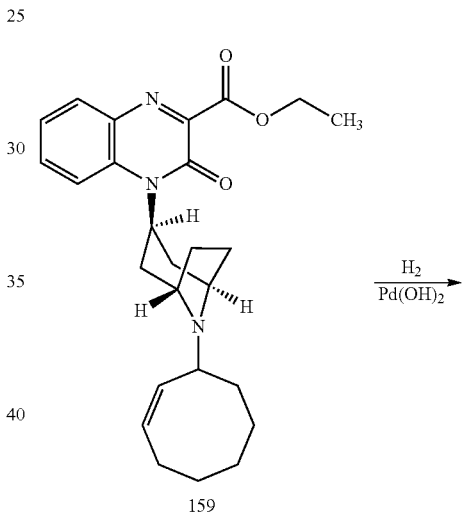

159

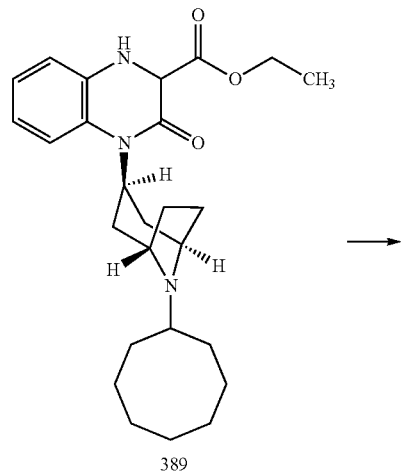

389

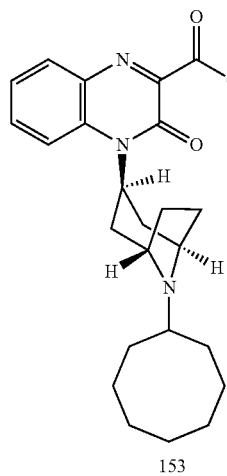

153

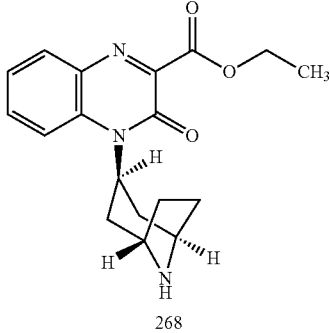

268

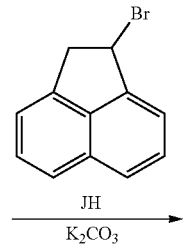

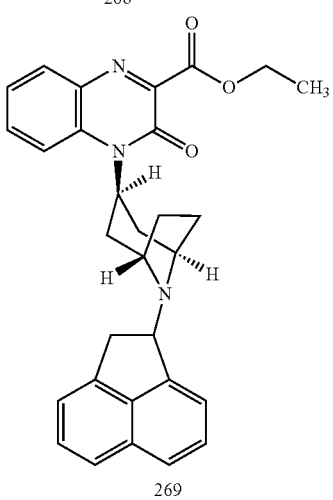

269

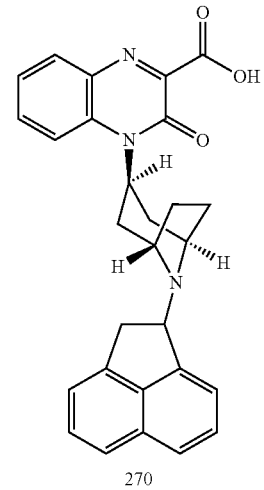

270

Under a hydrogen atmosphere at a pressure of 4 Kgf/cm², a mixture of Substituted-Quinoxaline-Type Piperidine Compound 159 (124 mg, 0.285 mmol), 20% Pd(OH)$_2$ (24 mg, Sigma-Aldrich), and MeOH (12 mL) was stirred at 50° C. for 8 h. After the Pd(OH)$_2$ was filtered off, the filtrate was washed with EtOAc and concentrated under reduced pressure to provide Substituted-Quinoxaline-Type Piperidine Compound 389, ethyl 4-((endo)-8-cyclooctyl-8-azabicyclo[3.2.1]octan-3-yl)-3-oxo-1,2,3,4-tetrahydroquinoxaline-2-carboxylate.

A mixture of the above Substituted-Quinoxaline-Type Piperidine Compound 389 and xylene (4 mL) was stirred at 130° C. for 5 days. After concentration under reduced pressure, the residue was chromatographed with a silica gel column eluted with 10:1 CHCl$_3$:MeOH to provide 113 mg of Substituted-Quinoxaline-Type Piperidine Compound 153 as a yellow solid (yield 91% for two steps).

The identity of Substituted-Quinoxaline-Type Piperidine Compound 153 was confirmed using $^1$H NMR and LC/MS.

Substituted-Quinoxaline-Type Piperidine Compound 153: $^1$H NMR: $\delta_H$ (400 MHz, DMSO): 7.88 (1H, d, J=8.0 Hz), 7.77 (1H, t, J=8.0 Hz), 7.63 (1H, d, J=8.0 Hz), 7.44 (1H, t, J=8.0 Hz), 5.20 (1H, br), 4.37 (2H, q, J=8.0 Hz), 3.63 (2H, m), 2.36 (1H, m), 2.26 (2H, m), 2.06 (2H, m), 1.99 (2H, m), 1.85-1.20 (16H, m), 1.32 (3H, t, J=8.0 Hz); LC/MS (100%, t$_r$=1.63 min): m/z=438 [M+H]$^+$ (Calc: 437.3).

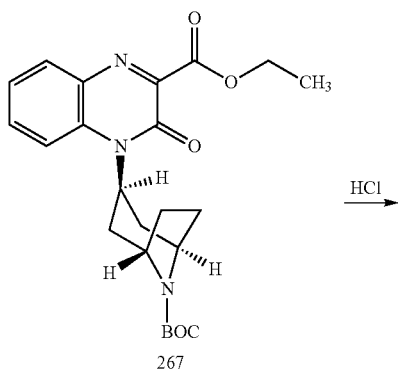

267

In a manner similar to the preparation of Substituted-Quinoxaline-Type Piperidine Compound 5 in Example 7, Substituted-Quinoxaline-Type Piperidine Compound 268 was prepared by treating Substituted-Quinoxaline-Type Piperidine Compound 267 with 4N HCl in dioxane to remove the BOC group (yield >98%).

The identity of Substituted-Quinoxaline-Type Piperidine Compound 268, ethyl 4-((endo)-8-azabicyclo[3.2.1]octan-3-yl)-3-oxo-3,4-dihydroquinoxaline-2-carboxylate, was confirmed using LC/MS.

Substituted-Quinoxaline-Type Piperidine Compound 268: LC/MS: m/z=328 [M+H]$^+$ (Calc: 327).

In a manner similar to the preparation of the compound of formula JD described above, Substituted-Quinoxaline-Type Piperidine Compound 269 was prepared except that the compound of formula JH was used in place of (Z)-3-bromocyclooct-1-ene (yield 39%).

The identity of Substituted-Quinoxaline-Type Piperidine Compound 269, ethyl 4-((endo)-8-(1,2-dihydroacenaphthylen-1-yl)-8-azabicyclo[3.2.1]octan-3-yl)-3-oxo-3,4-dihydroquinoxaline-2-carboxylate, was confirmed using $^1$H NMR and LC/MS.

Substituted-Quinoxaline-Type Piperidine Compound 269: $^1$H NMR: $\delta_H$ (400 MHz, CDCl$_3$): 7.90 (1H, d, J=7.6 Hz), 7.68 (2H, dd, J=27.37, 8.11 Hz), 7.58-7.47 (5H, m), 7.32 (2H, dd, J=11.91, 6.84 Hz), 4.54-4.47 (3H, m), 4.08 (1H, br), 3.64-3.51 (2H, m), 3.27 (1H, d, J=16.73 Hz), 2.33-1.98 (9H, m), 1.58 (3H, s), 1.44 (3H, t, J=7.1 Hz); LC/MS: m/z=480 [M+H]$^+$ (Calc: 479).

Substituted-Quinoxaline-Type Piperidine Compound 270 was prepared from Substituted-Quinoxaline-Type Piperidine Compound 269 in a manner similar to the preparation of Substituted-Quinoxaline-Type Piperidine Compound 111 in Example 5 (yield 84%).

The identity of Substituted-Quinoxaline-Type Piperidine Compound 270, 4-((endo)-8-(1,2-dihydroacenaphthylen-1-yl)-8-azabicyclo[3.2.1]octan-3-yl)-3-oxo-3,4-dihydroquinoxaline-2-carboxylic acid, was confirmed using $^1$H NMR and LC/MS.

Substituted-Quinoxaline-Type Piperidine Compound 270: $^1$H NMR: $\delta_H$ (400 MHz, DMSO-d$_6$): 7.83-7.52 (8H, m), 7.42-7.37 (2H, m), 5.18 (1H, s), 4.73 (1H, brz), 4.21 (1H, br), 3.84-3.82 (1H, m), 3.65 (2H, br), 2.33-1.99 (8H, m); LC/MS (100%, t$_r$=1.45 min): m/z=452 [M+H]$^+$ (Calc: 451).

The compound of formula JH was prepared as follows:

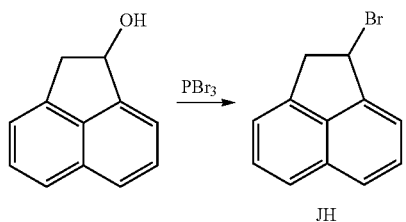

Under a nitrogen atmosphere and at a temperature of about 25° C., a 1M solution of tribromophosphine in CH$_2$Cl$_2$ (2.350 mL, 2.350 mmol, Sigma-Aldrich) was added to a suspension of 1,2-dihydroacenaphthylen-1-ol (1000 mg, 5.88 mmol, Sigma-Aldrich) in diethyl ether (8 mL). The resulting reaction mixture was stirred at a temperature of about 25° C. for 30 min; a yellow precipitate formed. After quenching with saturated aqueous NaHCO$_3$, the pH was adjusted to be within the range of from about 7 to about 8. Thereafter, the mixture was extracted twice with EtOAc:water (70 mL for each extraction), dried (MgSO$_4$), concentrated under reduced pressure, and dried to provide 1350 mg of the compound of formula JH, 1-bromo-1,2-dihydroacenaphthylene, as a pale yellow solid (yield 99%).

5.33 Example 33

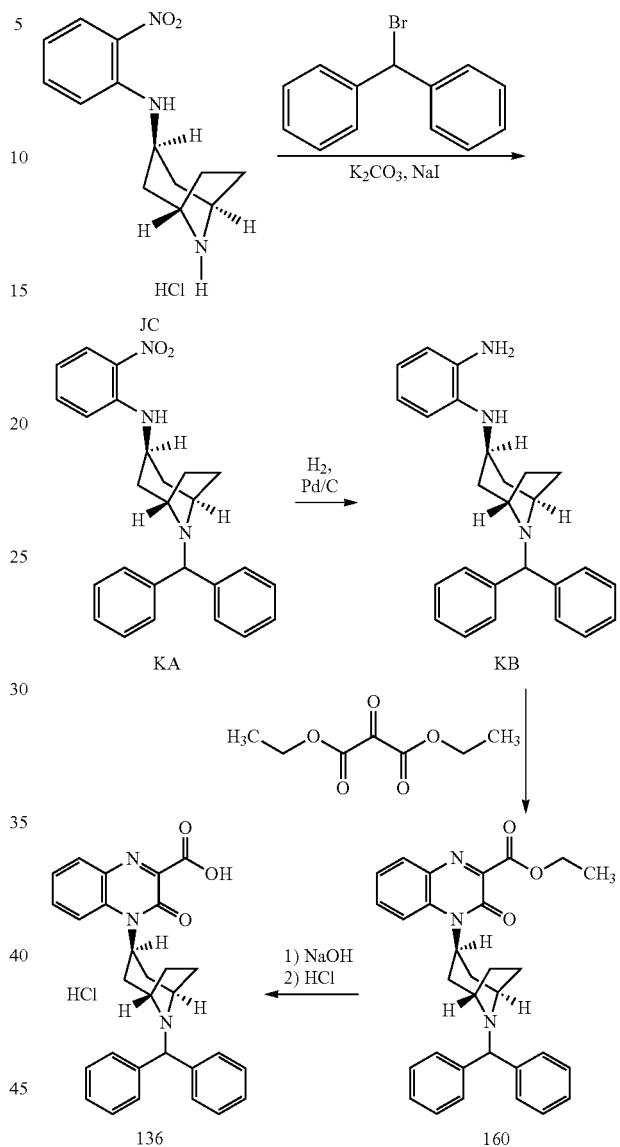

Under a nitrogen atmosphere at a temperature of about 25° C., K$_2$CO$_3$ (1218 mg, 8.81 mmol), sodium iodide (52.8 mg, 0.352 mmol), and (bromomethylene)dibenzene (523 mg, 2.115 mmol, Sigma-Aldrich) were added to a mixture of the compound of formula JC (500 mg, 1.762 mmol) and acetonitrile (10 mL). The resulting reaction mixture was heated with stirring at 90° C. for 1 h. The reaction mixture was diluted with water (5 mL), extracted twice with CHCl$_3$ (50 mL for each extraction), washed with brine, dried (MgSO$_4$), and concentrated under reduced pressure to provide a yellow oil. The oil was chromatographed with an amino-silica gel column eluted with a gradient of from 0%:100% EtOAc:n-hexane to 20%:80% EtOAc:n-hexane to provide 464 mg of the compound of formula KA as an orange solid (yield 64%).

The identity of the compound of formula KA, (endo)-8-benzhydryl-N-(2-nitrophenyl)-8-azabicyclo[3.2.1]octan-3-amine, was confirmed using $^1$H NMR and LC/MS.

Compound KA: $^1$H NMR: $\delta_H$ (300 MHz, DMSO-$d_6$): 8.58 (1H, d, J=7.1 Hz), 8.07 (1H, dd, J=8.62, 1.52 Hz), 7.54 (5H, dd, J=9.89, 4.31 Hz), 7.29 (4H, t, J=7.6 Hz), 7.17 (2H, t, J=7.35 Hz), 6.93 (1H, d, J=8.62 Hz), 6.70-6.65 (1H, m), 4.62 (1H, s), 4.02 (1H, dd, J=6.84, 4.82 Hz), 3.07 (2H, s), 2.25 (2H, m), 2.10 (2H, m), 1.83 (2H, dd, J=14.70, 6.59 Hz), 1.65 (2H, d, J=13.69 Hz); LC/MS: m/z=413.8 [M+H]$^+$ (Calc: 413.2).

In a manner similar to the preparation of Substituted-Quinoxaline-Type Piperidine Compound 135 from the compound of formula KD in Example 32, the compound of formula KB was prepared from the compound of formula KA (yield 90%), Substituted-Quinoxaline-Type Piperidine Compound 160 was prepared from the compound of formula KB and diethyl 2-oxomalonate (yield 49%), and the hydrochloride of Substituted-Quinoxaline-Type Piperidine Compound 136 was prepared from Substituted-Quinoxaline-Type Piperidine Compound 160 (yield 70%).

The identity of the compound of formula KB, N$^1$-((endo)-8-benzhydryl-8-azabicyclo[3.2.1]octan-3-yl)benzene-1,2-diamine, was confirmed using $^1$H NMR and LC/MS.

Compound KB: $^1$H NMR: $\delta_H$ (300 MHz, DMSO-$d_6$): 7.52 (2H, d, J=7.6 Hz), 7.30-7.14 (8H, m), 6.58-6.29 (4H, m), 4.44 (1H, s), 4.12 (1H, s), 3.58 (1H, m), 2.99 (1H, s), 2.14-1.91 (5H, m), 1.65 (3H, m); LC/MS: m/z=383.9 [M+H]$^+$ (Calc: 383.2).

The identity of Substituted-Quinoxaline-Type Piperidine Compound 160, ethyl 4-((endo)-8-benzhydryl-8-azabicyclo [3.2.1]octan-3-yl)-3-oxo-3,4-dihydroquinoxaline-2-carboxylate, was confirmed using $^1$H NMR and LC/MS.

Substituted-Quinoxaline-Type Piperidine Compound 160: $^1$H NMR: $\delta_H$ (400 MHz, DMSO-$d_6$): 7.91-7.16 (14H, m), 4.47 (1H, s), 4.36 (2H, q, J=6.9 Hz), 2.52 (1H, m), 2.33-1.99 (6H, m), 1.75 (2H, m), 1.33 (3H, t, J=6.9 Hz); LC/MS: m/z=494.0 [M+H]$^+$ (Calc: 493.2).

The identity of Substituted-Quinoxaline-Type Piperidine Compound 136, 4-((endo)-8-benzhydryl-8-azabicyclo [3.2.1]octan-3-yl)-3-oxo-3,4-dihydroquinoxaline-2-carboxylic acid, was confirmed using $^1$H NMR and LC/MS.

Substituted-Quinoxaline-Type Piperidine Compound 136: $^1$H NMR: $\delta_H$ (400 MHz, DMSO-$d_6$): 14.02 (0.7H, br), 10.95 (0.3H, br), 8.15-7.19 (14H, m), 6.19 (0.3H, br), 5.42 (0.711, br), 4.47 (0.4H, s), 3.77 (0.6H, s), 2.69 (1H, m), 2.39-2.10 (6H, m), 1.77 (1H, s); LC/MS (96%, $t_r$=2.25 min): m/z=466.2 [M+H]$^+$ (Calc: 465.5).

5.34 Example 34

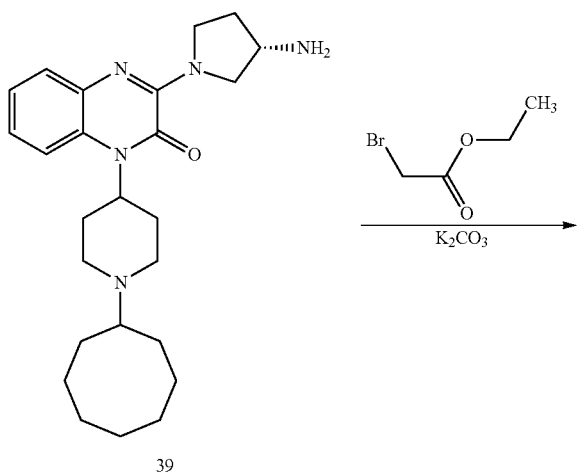

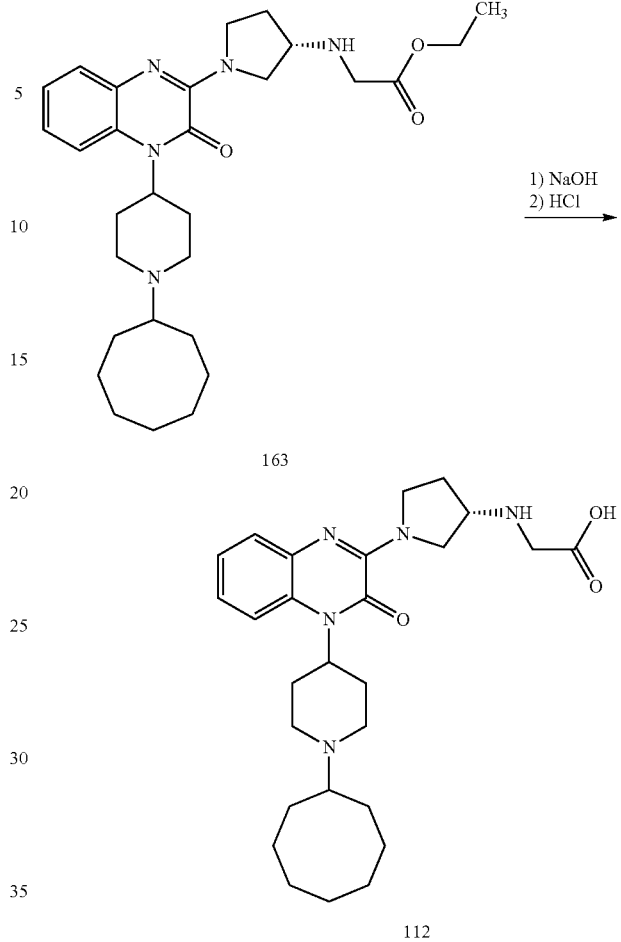

At a temperature of 0° C., ethyl 2-bromoacetate (20.2 µL, 0.182 mmol) and K$_2$CO$_3$ (25.2 mg, 0.182 mmol) were added to a mixture of Substituted-Quinoxaline-Type Piperidine Compound 39 (70 mg, 0.165 mmol) in THF (3 mL). The resulting reaction mixture was stirred at 0° C. for 2 h. After warming it to 50° C., the reaction mixture was stirred at 50° C. for 2 h. After cooling to about 25° C., the mixture was diluted with water (10 mL) and extracted twice with EtOAc (10 mL for each extraction). The organic portions were combined, washed with brine (10 mL), dried (MgSO$_4$), and concentrated under reduced pressure to provide a residue. The residue was chromatographed with a silica gel column eluted with 10:1 CHCl$_3$:MeOH to provide 53 mg of Substituted-Quinoxaline-Type Piperidine Compound 163 as a white solid (yield 63%).

The identity of Substituted-Quinoxaline-Type Piperidine Compound 163, (S)-ethyl 2-(1-(4-(1-cyclooctylpiperidin-4-yl)-3-oxo-3,4-dihydroquinoxalin-2-yl)pyrrolidin-3-ylamino)acetate, was confirmed using $^1$H NMR and LC/MS.

Substituted-Quinoxaline-Type Piperidine Compound 163: $^1$H NMR: $\delta_H$ (400 MHz, CDCl$_3$): 7.55 (1H, m), 7.45 (1H, d, J=8 Hz), 7.10 (2H, m), 4.95 (1H, br), 4.20 (2H, q, J=8 Hz), 4.30-3.90 (3H, m), 3.82 (1H, m), 3.46 (2H, s), 3.43 (1H, m), 2.98 (2H, m), 2.79 (2H, m), 2.68 (1H, m), 2.44 (2H, m), 2.10 (1H, m), 2.00-1.40 (18H, m), 1.60 (3H, t, J=8 Hz); LC/MS (98%, $t_r$=1.08 min): m/z=510.2 [M+H]$^+$ (Calc: 509.3).

Substituted-Quinoxaline-Type Piperidine Compound 112 was prepared from Substituted-Quinoxaline-Type Piperidine Compound 163 in a manner similar to the preparation of Substituted-Quinoxaline-Type Piperidine Compound 111 in Example 5 (yield 96%).

The identity of Substituted-Quinoxaline-Type Piperidine Compound 112, (S)-2-(1-(4-(1-cyclooctylpiperidin-4-yl)-3-oxo-3,4-dihydroquinoxalin-2-yl)pyrrolidin-3-ylamino)acetic acid, was confirmed using $^1$H NMR and LC/MS.

Substituted-Quinoxaline-Type Piperidine Compound 112: $^1$H NMR: $\delta_H$ (400 MHz, DMSO-$d_6$): 7.97 (1H, br), 7.36 (1H, d, J=8 Hz), 7.17 (2H, m), 5.00 (1H, br), 4.30-3.10 (9H, m), 2.20 (2H, m), 2.10 (3H, m), 1.92 (2H, d, J=4 Hz), 1.90-1.40 (16H, m); LC/MS (100%, $t_r$=1.07 min): m/z=482.2 [M+H]$^+$ (Calc: 481.3).

5.35 Example 35 prepared except that the compound of formula LB was used in place of the compound of formula EC. Thereafter, Substituted-Quinoxaline-Type Piperidine Compound 240 was prepared from diethyl 2-oxomalonate in a manner similar to Example 12 except that the compound of formula LD was used in place of the compound of formula AB (overall yield 7%).

The identity of Substituted-Quinoxaline-Type Piperidine Compound 240, ethyl 4-((endo)-9-cyclooctyl-9-azabicyclo[3.3.1]nonan-3-yl)-3-oxo-3,4-dihydroquinoxaline-2-carboxylate, was confirmed using $^1$H NMR, LC/MS and LC.

Substituted-Quinoxaline-Type Piperidine Compound 240: $^1$H NMR: $\delta_H$ (400 MHz, CDCl$_3$): 7.92 (d, 1H, J=8.2 Hz), 7.58-7.66 (m, 2H), 7.36 (dd, 1H, J=8.1, 8.2 Hz), 5.16 (br, 1H), 4.52 (t, 2H, J=7.0 Hz), 3.48-3.53 (m, 2H), 3.02-3.06 (m, 1H), 2.72-2.74 (m, 2H), 2.38-2.44 (m, 1H), 1.98-

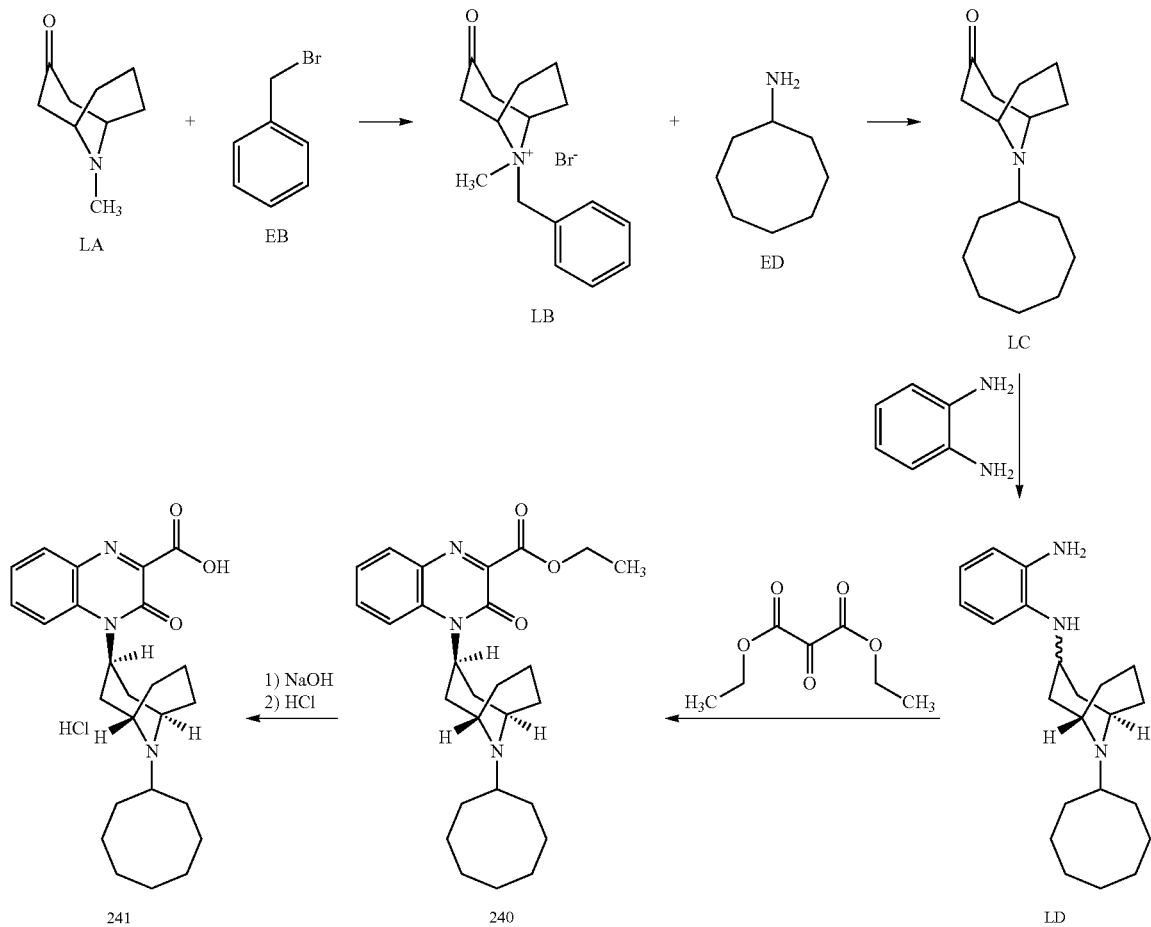

2.04 (m, 2H), 1.4-1.8 (m, 25H), 1.12-1.15 (m, 2H); LC/MS (98.7%, $t_r$=7.534 min): m/z=452.7 [M+H]$^+$ (Calc: 451.6); LC (SiO$_2$) 1:2 then 3:1 Et$_2$O:hexanes: Rf=0.5 with UV detection, Dragendorffs reagent.

In a manner similar to Example 7, the hydrochloride of Substituted-Quinoxaline-Type Piperidine Compound 241 was prepared from Substituted-Quinoxaline-Type Piperidine Compound 240 (yield 40%).

The identity of Substituted-Quinoxaline-Type Piperidine Compound 241, 4-((endo)-9-cyclooctyl-9-azabicyclo[3.3.1]nonan-3-yl)-3-oxo-3,4-dihydroquinoxaline-2-carboxylic acid, was confirmed using $^1$H NMR and LC/MS.

A mixture of the compound of formula LA (10.00 g, 65.4 mmol, Trans World Chemicals, Inc., Rockville, Md.) and the compound of formula EB (11.17 g, 65.4 mmol) was refluxed in acetone (150 mL) for 3 h, cooled, filtered, washed twice with diethyl ether (30 mL for each wash), washed twice with hexanes (30 mL for each wash), and dried under reduced pressure to provide 10 g of the compound of formula LB, 9-methyl-9-benzyl-9-azabicyclo[3.3.1]nonan-3-one bromide, as white solid (yield 47%).

In a manner similar to Example 14, the endo:exo isomeric mixture of the compound of formula LD, N$^1$-(9-cyclooctyl-9-azabicyclo[3.3.1]nonan-3-yl)benzene-1,2-diamine, was Substituted-Quinoxaline-Type Piperidine Compound 241: $^1$H NMR: $\delta_H$ (400 MHz, 1:3 CDCl$_3$:CD$_3$OD): 8.45 (d, 1H, J=8.8 Hz), 8.02 (dd, 1H, J=1.5, 8.1 Hz), 7.82-7.86 (m, 1H), 7.5 (dd, 1H, 7.5, 7.9 Hz), 5.96-6.04 (m, 1H), 4.16-4.22 (m, 2H), 3.80-3.86 (m, 1H), 3.04-3.08 (m, 2H), 2.78-2.84 (m, 1H), 2.48-2.54 (m, 2H), 1.6-2.2 (m, 24H); LC/MS (98.7%, t$_r$=5.612 min): m/z=424.6 [M+H]$^+$.

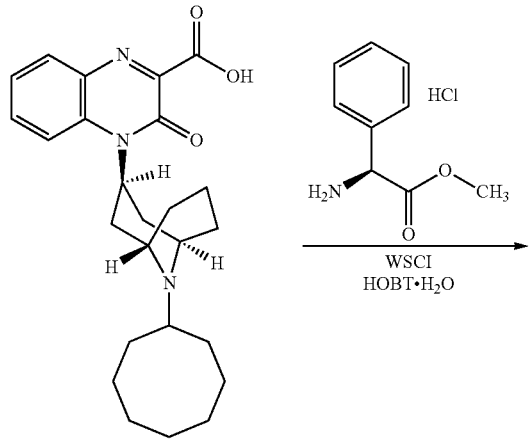

241

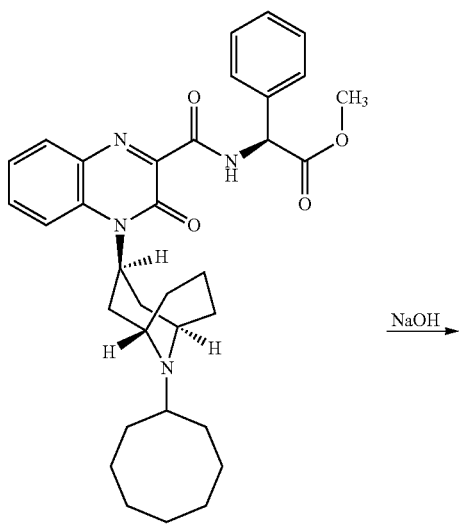

402

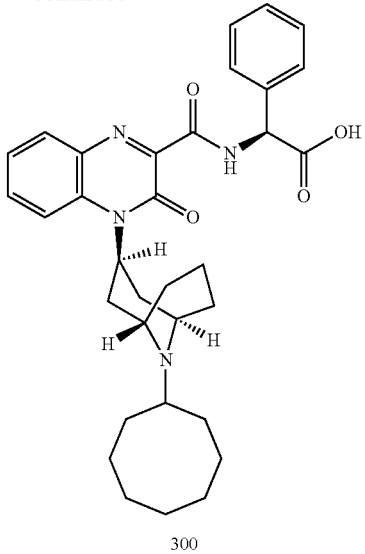

300

In a manner similar to Example 21, Substituted-Quinoxaline-Type Piperidine Compound 402 was prepared by using Substituted-Quinoxaline-Type Piperidine Compound 241 in place of Substituted-Quinoxaline-Type Piperidine Compound 74 and (S)-(+)-methyl 2-amino-2-phenylacetate hydrochloride in place of 4-methoxyaniline (yield 60%).

The identity of Substituted-Quinoxaline-Type Piperidine Compound 402, (5)-methyl 2-(4-((endo)-9-cyclooctyl-9-azabicyclo[3.3.1]nonan-3-yl)-3-oxo-3,4-dihydroquinoxaline-2-carboxamido)-2-phenylacetate, was confirmed using LC/MS.

Substituted-Quinoxaline-Type Piperidine Compound 402: LC/MS: m/z=571 [M+H]$^+$ (Calc: 570).

Substituted-Quinoxaline-Type Piperidine Compound 300 was prepared from Substituted-Quinoxaline-Type Piperidine Compound 402 in a manner similar to the preparation of Substituted-Quinoxaline-Type Piperidine Compound 111 in Example 5 (yield 81%).

The identity of Substituted-Quinoxaline-Type Piperidine Compound 300, (S)-2-(4-((endo)-9-cyclooctyl-9-azabicyclo[3.3.1]nonan-3-yl)-3-oxo-3,4-dihydroquinoxaline-2-carboxamido)-2-phenylacetic acid, was confirmed using $^1$H NMR and LC/MS.

Substituted-Quinoxaline-Type Piperidine Compound 300: $^1$H NMR: $\delta_H$ (400 MHz, DMSO-d$_6$): 9.56 (d, 1H, J=7.0 Hz), 8.35 (s, 1H), 7.89 (d, 1H, J=7.8 Hz), 7.70-7.74 (m, 1H), 7.31-7.51 (m, 7H), 5.84 (s, 1H), 5.52 (d, 1H, J=7.0 Hz) 4.02 (s, 2H), 1.29-3.58 (m, 25H); LC/MS: m/z=557 [M+H]$^+$ (Calc: 556).

5.36 Example 36

In a manner similar to Example 35, the following Substituted-Quinoxaline-Type Piperidine Compounds were prepared from the compound of formula LB.

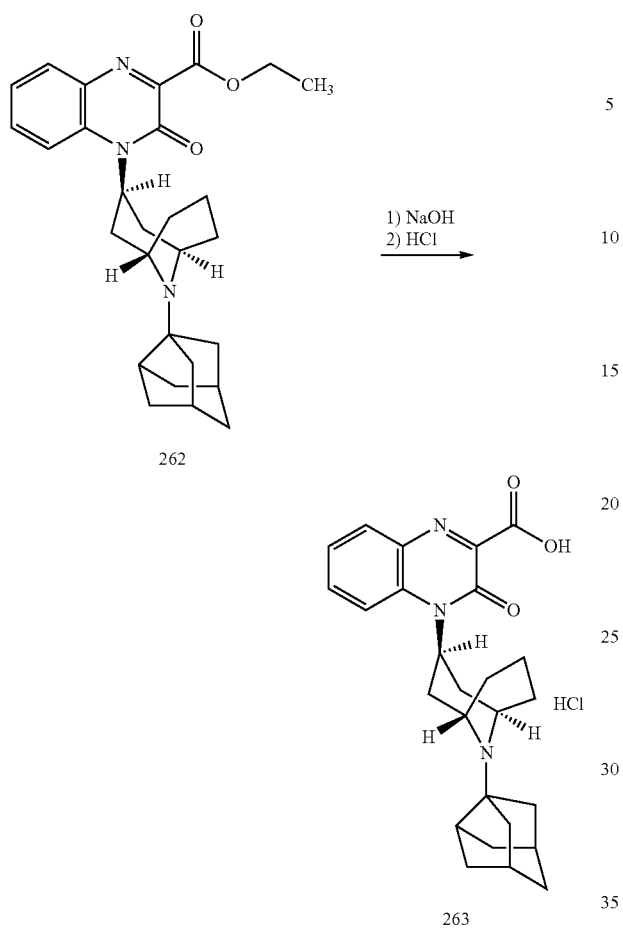

262

263

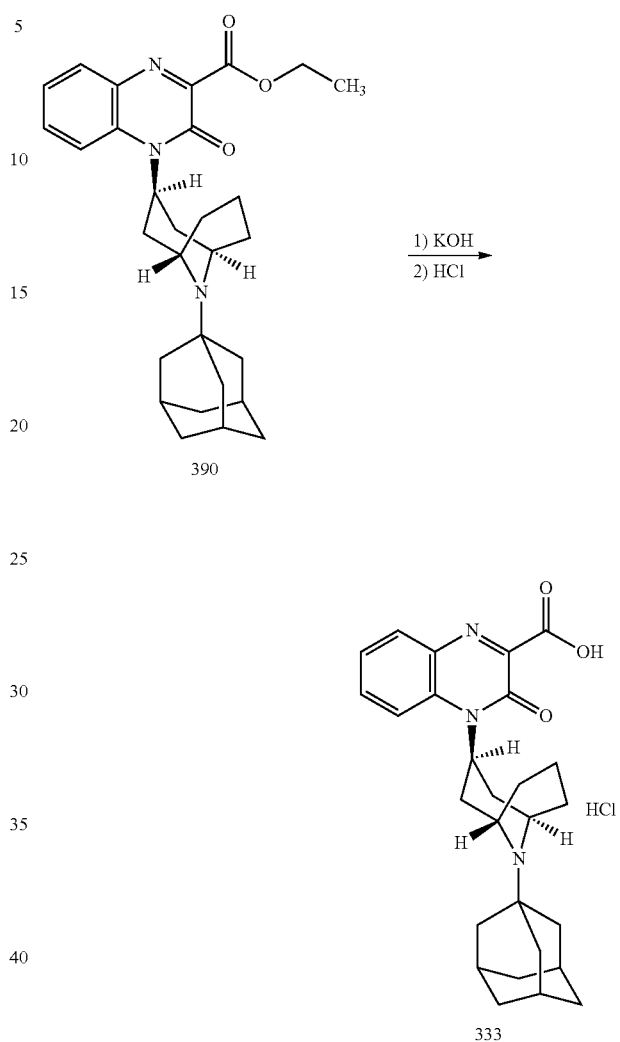

390

333

Substituted-Quinoxaline-Type Piperidine Compound 262 (yield 19% for three steps) and the hydrochloride of Substituted-Quinoxaline-Type Piperidine Compound 263 (yield 90%) were prepared by using 3-noradamantamine hydrochloride (Sigma-Aldrich) in place of the compound of formula ED.

The identity of Substituted-Quinoxaline-Type Piperidine Compound 262, endo-4-(9-(hexahydro-2,5-methano-pentalen-3a-yl)-9-aza-bicyclo[3.3.1]non-3-yl)-3-oxo-3,4-dihydro-quinoxaline-2-carboxylic acid ethyl ester, was confirmed using $^1$H NMR and LC/MS.

Substituted-Quinoxaline-Type Piperidine Compound 262: $^1$H NMR: $\delta_H$ (400 MHz, CDCl$_3$): 7.93 (1H, d, J=8 Hz), 7.63 (1H, t, J=8 Hz), 7.55 (1H, bs), 7.36 (1H, t, J=8 Hz), 4.52 (2H, q, J=8.5 Hz), 3.55 (2H, m), 2.73-2.38 (3H, m), 2.32 (2H, s), 2.22 (1H, t, J=8 Hz), 2.03-1.50 (18H, m), 1.46 (3H, t, J=8 Hz). 1.36 (2H, m); LC/MS: m/z=462.6 [M+H]$^+$.

The identity of Substituted-Quinoxaline-Type Piperidine Compound 263, 4-(9-(hexahydro-2,5-methano-pentalen-3a-yl)-9-aza-bicyclo[3.3.1]non-3-yl)-3-oxo-3,4-dihydro-quinoxaline-2-carboxylic acid, was confirmed using $^1$H NMR and LC/MS.

Substituted-Quinoxaline-Type Piperidine Compound 263: $^1$H NMR: $\delta_H$ (600 MHz, (CD$_3$)$_2$SO): 14.05 (1H, bs), 7.91 (1H, bd), 7.80 (1H, bt), 7.69 (1H, bs), 7.48 (1H, bt), 4.85 (1H, bs), 3.55 (2H, m), 2.50-2.20 (6H, m), 2.12-1.52 (15H, m), 1.36 (2H, m); LC/MS (100%): m/z=434.2 [M+H]$^+$.

In a manner similar to Example 35, the following Substituted-Quinoxaline-Type Piperidine Compounds were prepared from the compound of formula LB except that KOH replaced NaOH in the de-esterification step.

Substituted-Quinoxaline-Type Piperidine Compound 390 and the hydrochloride of Substituted-Quinoxaline-Type Piperidine Compound 333 were prepared by using 1-adamantylamine in place of the compound of formula ED.

The identity of Substituted-Quinoxaline-Type Piperidine Compound 390, endo-4-(9-adamantan-1-yl)-9-aza-bicyclo[3.3.1]non-3-yl)-3-oxo-3,4-dihydro-quinoxaline-2-carboxylic acid ethyl ester, was confirmed using LC/MS.

Substituted-Quinoxaline-Type Piperidine Compound 390: LC/MS (96.1%, t$_r$=2.374 min): m/z=476.6 [M+H]$^+$ (Calc: 475.6).

The identity of Substituted-Quinoxaline-Type Piperidine Compound 333, endo-4-(9-adamantan-1-yl)-9-aza-bicyclo[3.3.1]non-3-yl)-3-oxo-3,4-dihydro-quinoxaline-2-carboxylic acid, was confirmed using $^1$H NMR and LC/MS.

Substituted-Quinoxaline-Type Piperidine Compound 333: $^1$H NMR: $\delta_H$ (400 MHz, CDCl$_3$): 14.19 (1H, s), 9.21 (1H, m), 8.98 (1H, s), 8.21 (1H, m), 7.99 (1H, m), 7.59 (1H, m), 7.01 (1H, m), 4.31 (2H, s), 3.06 (1H, m), 2.79 (4H, m), 2.57 (6H, s), 2.31 (5H, m), 1.81 (9H, m); LC/MS (100%, t$_r$=5.604 min): m/z=448.5 [M+H]$^+$ (Calc: 447.6).

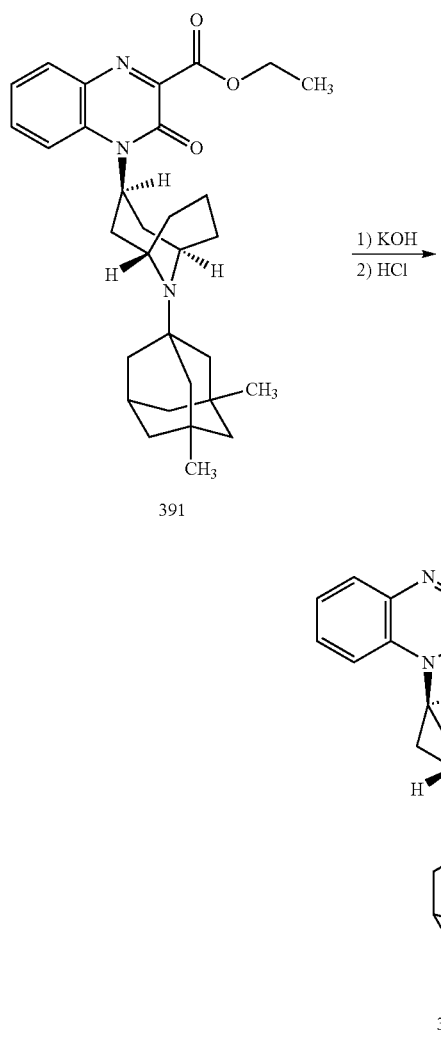

391

334

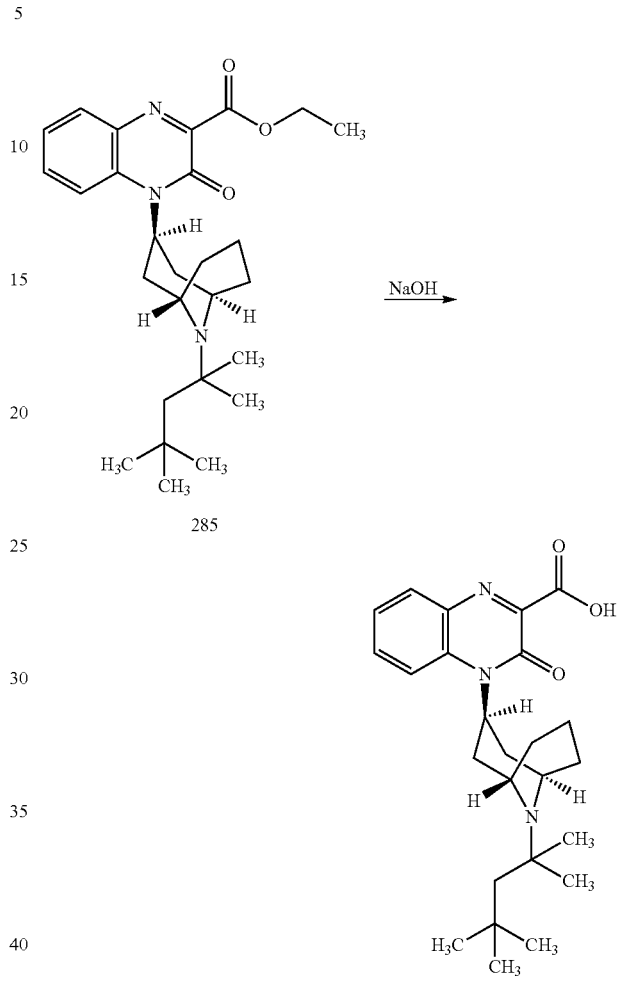

285

286

Substituted-Quinoxaline-Type Piperidine Compound 391 (yield 9.1% for three steps) and the hydrochloride of Substituted-Quinoxaline-Type Piperidine Compound 333 (yield 38%) were prepared by using the hydrochloride of memantine (Sigma-Aldrich) in place of the compound of formula ED.

The identity of Substituted-Quinoxaline-Type Piperidine Compound 391, endo-4-[9-(3,5-dimethyl-adamantan-1-yl)-9-aza-bicyclo[3.3.1]non-3-yl]-3-oxo-3,4-dihydro-quinoxaline-2-carboxylic acid ethyl ester, was confirmed using LC/MS.

Substituted-Quinoxaline-Type Piperidine Compound 391: LC/MS (92.7%, $t_r$=2.453 min): m/z=504.2 [M+H]$^+$ (Calc: 503.7).

The identity of Substituted-Quinoxaline-Type Piperidine Compound 334, endo-4-[9-(3,5-dimethyl-adamantan-1-yl)-9-aza-bicyclo[3.3.1]non-3-yl]-3-oxo-3,4-dihydro-quinoxaline-2-carboxylic acid, was confirmed using $^1$H NMR and LC/MS.

Substituted-Quinoxaline-Type Piperidine Compound 334: $^1$H NMR: $\delta_H$ (400 MHz, CDCl$_3$): 14.09 (1H, s), 9.20 (1H, m), 9.08 (1H, s), 8.21 (1H, m), 8.00 (1H, m), 7.59 (1H, m), 7.01 (1H, m), 4.28 (2H, s), 3.17 (1H, m), 2.78 (4H, m), 2.39 (3H, s), 2.28 (2H, m), 2.20 (4H, s), 1.80 (3H, m), 1.60 (1H, s), 1.51 (2H, m), 1.18-1.45 (5H, m), 0.98 (3H, s); LC/MS (100%, $t_r$=7.12 min): m/z=476.5 [M+H]$^+$ (Calc: 475.6).

In a manner similar to Example 35, the following Substituted-Quinoxaline-Type Piperidine Compounds were prepared from the compound of formula LB except that the final HCl treatment was omitted.

Substituted-Quinoxaline-Type Piperidine Compounds 285 (yield 0.42% for three steps) and 286 (yield 92%) were prepared by using 2,4,4-trimethylpentan-2-amine (Sigma-Aldrich) in place of the compound of formula ED.

The identity of Substituted-Quinoxaline-Type Piperidine Compound 285, ethyl 3-oxo-4-((endo)-9-(2,4,4-trimethylpentan-2-yl)-9-azabicyclo[3.3.1]nonan-3-yl)-3,4-dihydroquinoxaline-2-carboxylate, was confirmed using $^1$H NMR and LC/MS.

Substituted-Quinoxaline-Type Piperidine Compound 285: $^1$H NMR: $\delta_H$ (CDCl$_3$): 7.92 (1H, d, J=7.6 Hz), 7.60 (2H, m), 7.35 (1H, t, J=7.6 Hz), 4.80 (1H, m), 4.51 (2H, q, J=7.2 Hz), 3.71 (2H, m), 2.58 (3H, m), 1.94 (2H, m), 1.70 (3H, m), 1.57 (3H, s), 1.45 (3H, t, J=7.2 Hz), 1.32 (2H, m), 1.31 (6H, s), 1.04 (9H, s); LC/MS: m/z=454 [M+H]$^+$ (Calc: 453.6).

The identity of Substituted-Quinoxaline-Type Piperidine Compound 286, 3-oxo-4-((endo)-9-(2,4,4-trimethylpentan-2-yl)-9-azabicyclo[3.3.1]nonan-3-yl)-3,4-dihydroquinoxaline-2-carboxylic acid, was confirmed using $^1$H NMR and LC/MS.

Substituted-Quinoxaline-Type Piperidine Compound 286: $^1$H NMR: $\delta_H$ (DMSO-d$_6$): 7.87 (1H, d, J=7.6 Hz), 7.74

(1H, t, J=7.6 Hz), 7.62 (1H, br), 7.44 (1H, t, J=7.6 Hz), 4.80 (1H, br), 3.68 (2H, m), 2.40 (3H, m), 1.95 (2H, m), 1.65 (3H, m), 1.55 (2H, s), 1.27 (6H, s), 1.25 (2H, m), 1.05 (9H, s); LC/MS (98%, $t_r$=2.09 min): m/z=426 [M+H]$^+$ (Calc: 425.6).

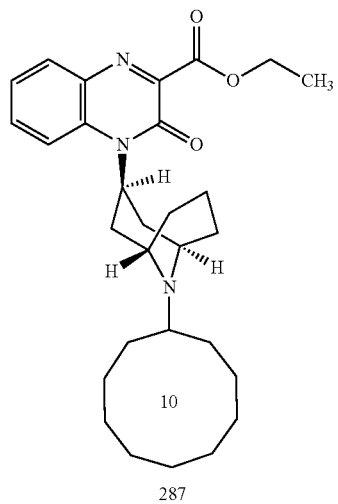

287

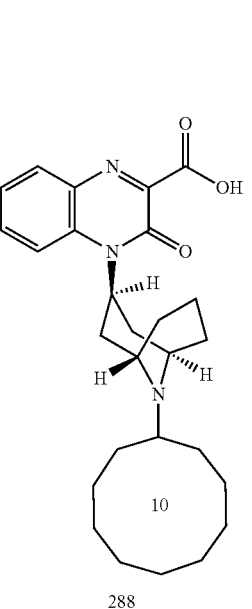

288

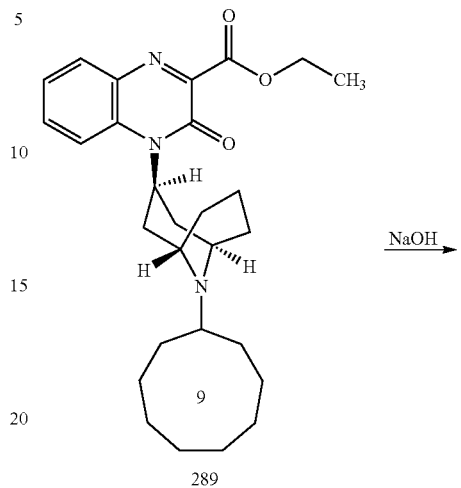

289

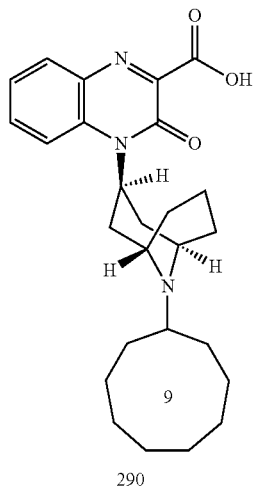

290 m), 2.60 (2H, m), 2.20 (4H, m), 1.90-1.40 (18H, m); LC/MS (100%, $t_r$=1.87 min): m/z=452 [M+H]$^+$ (Calc: 454.6).

Substituted-Quinoxaline-Type Piperidine Compounds 287 and 288 were prepared by using cyclodecanamine (Sigma-Aldrich) in place of the compound of formula ED.

The identity of Substituted-Quinoxaline-Type Piperidine Compound 287, ethyl 4-((endo)-9-cyclodecyl-9-azabicyclo[3.3.1]nonan-3-yl)-3-oxo-3,4-dihydroquinoxaline-2-carboxylate, was confirmed using $^1$H NMR and LC/MS.

Substituted-Quinoxaline-Type Piperidine Compound 287: $^1$H NMR: δ$_H$ (CDCl$_3$): 7.93 (1H, d, J=8.0 Hz), 7.66-7.52 (2H, m), 7.36 (1H, m), 5.11 (1H, br), 4.51 (2H, q, J=7.2 Hz), 3.51 (2H, d, J=11.15 Hz), 3.05 (1H, m), 2.71 (2H, m), 2.39 (1H, m), 2.01 (2H, m), 1.82-1.40 (29H, m), 1.15 (2H, m); LC/MS: m/z=480 [M+H]$^+$ (Calc: 479.6).

The identity of Substituted-Quinoxaline-Type Piperidine Compound 288, 4-((endo)-9-cyclodecyl-9-azabicyclo[3.3.1]nonan-3-yl)-3-oxo-3,4-dihydroquinoxaline-2-carboxylic acid, was confirmed using $^1$H NMR and LC/MS.

Substituted-Quinoxaline-Type Piperidine Compound 288: $^1$H NMR: δ$_H$ (CDCl$_3$, DCl): 8.70 (0.2H, m), 8.17 (0.8H, m), 7.93 (1H, m), 7.69 (1H, m), 7.29 (1H, m), 6.10 (1H, br), 4.18 (2H, m), 3.60 (2H, br), 3.05 (2H, m), 2.89 (1H, Substituted-Quinoxaline-Type Piperidine Compounds 289 and 290 were prepared by using cyclononanamine (Sigma-Aldrich) in place of the compound of formula ED.

The identity of Substituted-Quinoxaline-Type Piperidine Compound 289, ethyl 4-((endo)-9-cyclononyl-9-azabicyclo[3.3.1]nonan-3-yl)-3-oxo-3,4-dihydroquinoxaline-2-carboxylate, was confirmed using $^1$H NMR and LC/MS.

Substituted-Quinoxaline-Type Piperidine Compound 289: $^1$H NMR: δ$_H$ (CDCl$_3$): 7.93 (1H, d, J=8.11 Hz), 7.63 (2H, m), 7.36 (1H, t, J=8.11 Hz), 5.18 (1H, br), 4.51 (2H, q, J=7.1 Hz), 3.51 (2H, d, J=10.65 Hz), 3.04 (1H, m), 2.73 (2H, m), 2.40 (1H, m), 2.00 (2H, m), 1.82-1.43 (22H, m), 1.14 (2H, m); LC/MS: m/z=466 [M+H]$^+$ (Calc: 465.6).

The identity of Substituted-Quinoxaline-Type Piperidine Compound 290, 4-((endo)-9-cyclononyl-9-azabicyclo[3.3.1]nonan-3-yl)-3-oxo-3,4-dihydroquinoxaline-2-carboxylic acid, was confirmed using $^1$H NMR and LC/MS.

Substituted-Quinoxaline-Type Piperidine Compound 290: $^1$H NMR: δ$_H$ (CDCl$_3$): 8.11 (1H, m), 7.87 (1H, d, J=8.11 Hz), 7.57 (1H, m), 7.25 (1H, m), 6.03 (1H, br), 4.16 (2H, s), 3.69 (1H, s), 3.08-2.89 (3H, m), 2.57 (2H, m), 2.23-1.38 (21H, m); LC/MS (100%, $t_r$=1.67 min): m/z=438 [M+H]$^+$ (Calc: 437.6).

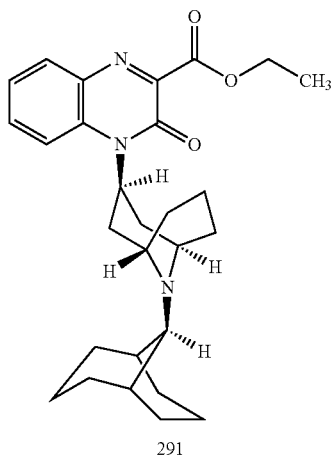

291

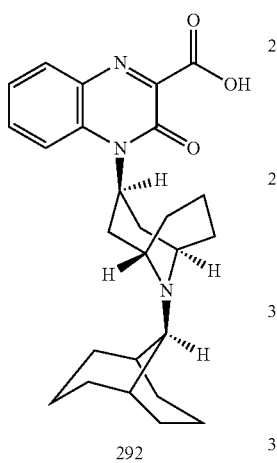

292

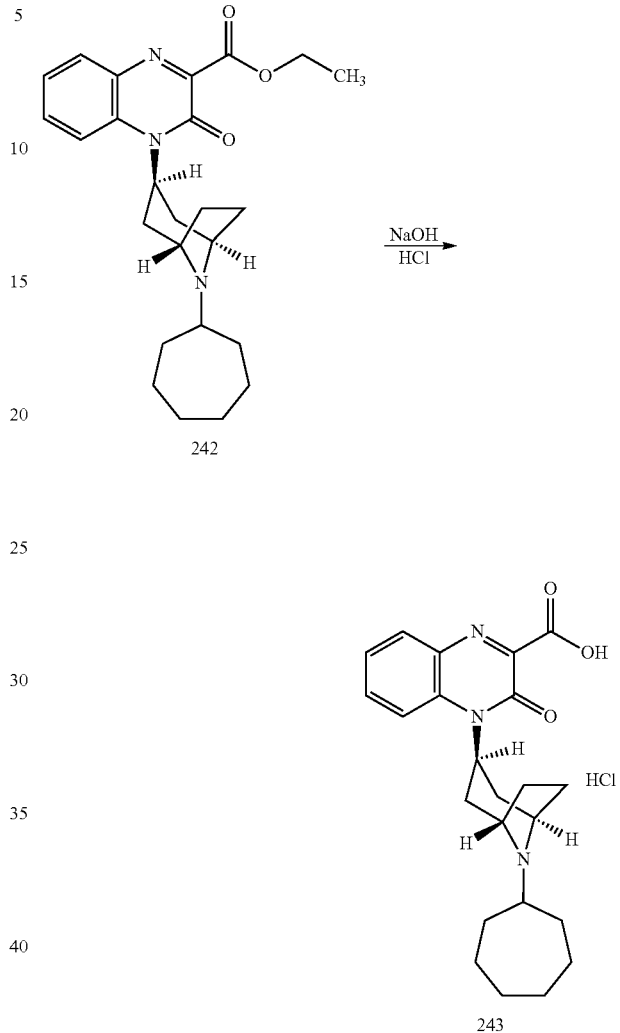

pared except that the compound of formula EC was used in place of the compound of formula LB.

Substituted-Quinoxaline-Type Piperidine Compounds 291 and 292 were prepared by using exo)-bicyclo[3.3.1]nonan-9-amine (Sigma-Aldrich) in place of the compound of formula ED.

The identity of Substituted-Quinoxaline-Type Piperidine Compound 291, ethyl 4-((endo)-9-((exo)-bicyclo[3.3.1]nonan-9-yl)-9-azabicyclo[3.3.1]nonan-3-yl)-3-oxo-3,4-dihydroquinoxaline-2-carboxylate, was confirmed using $^1$H NMR and LC/MS.

Substituted-Quinoxaline-Type Piperidine Compound 291: $^1$H NMR: $\delta_H$ (CDCl$_3$): 7.93 (1H, d, J=8.11 Hz), m), 7.36 (1.1H, t, J=7.35 Hz), 5.28 (1H, m), 4.51 (2H, q, J=7.1 Hz), 3.55 (2H, m), 2.81 (3H, m), 2.36 (1H, m), 2.09-1.41 (22H, m), 1.07 (2H, d, J=12.67 Hz); LC/MS: m/z=464 [M+H]$^+$ (Calc: 463.6).

The identity of Substituted-Quinoxaline-Type Piperidine Compound 292, 4-((endo)-9-((exo)-bicyclo[3.3.1]nonan-9-yl)-9-azabicyclo[3.3.1]nonan-3-yl)-3-oxo-3,4-dihydroquinoxaline-2-carboxylic acid, was confirmed using $^1$H NMR and LC/MS.

Substituted-Quinoxaline-Type Piperidine Compound 292: $^1$H NMR: $\delta_H$ (CDCl$_3$): 8.26 (1H, d, J=8.11 Hz), 7.81 (1H, t, J=7.6 Hz), 7.70 (1H, m), 7.55 (1H, m), 5.40 (1H, m), 3.61 (2H, d, J=10.14 Hz), 2.85 (1H, s), 2.81 (2H, m), 2.35 (1H, m), 2.13-1.46 (19H, m), 1.12 (2H, m); LC/MS (100%, t$_r$=1.67 min): m/z=436 [M+H]$^+$ (Calc: 435.6).

5.37 Example 37

In a manner similar to Example 35, the following Substituted-Quinoxaline-Type Piperidine Compounds were prepared except that the compound of formula EC was used in place of the compound of formula LB.

Substituted-Quinoxaline-Type Piperidine Compound 242, ethyl 4-((endo)-8-cycloheptyl-8-azabicyclo[3.2.1]octan-3-yl)-3-oxo-3,4-dihydroquinoxaline-2-carboxylate, and the hydrochloride of Substituted-Quinoxaline-Type Piperidine Compound 243 were prepared by using cycloheptanamine (Sigma-Aldrich) in place of the compound of formula ED.

The identity of Substituted-Quinoxaline-Type Piperidine Compound 243, 4-((endo)-8-cycloheptyl-8-azabicyclo[3.2.1]octan-3-yl)-3-oxo-3,4-dihydroquinoxaline-2-carboxylic acid, was confirmed using $^1$H NMR and LC/MS.

Substituted-Quinoxaline-Type Piperidine Compound 243: $^1$H NMR: $\delta_H$ (400 MHz, 1:3 CDCl$_3$:CD$_3$OD): 8.01-8.04 (m, 1H), 7.94-7.96 (m, 1H), 7.82-7.86 (m, 1H), 7.51-7.55 (m, 1H), 5.7-5.8 (m, 1H), 4.26-4.38 (m, 2H), 3.02-3.12 (m, 1H), 2.72-2.85 (m, 2H), 2.20-2.64 (m, 8H), 1.60-1.92 (m, 10H); LC/MS (100%, t$_r$=4.981 min): m/z=396.6 [M+H]$^+$.

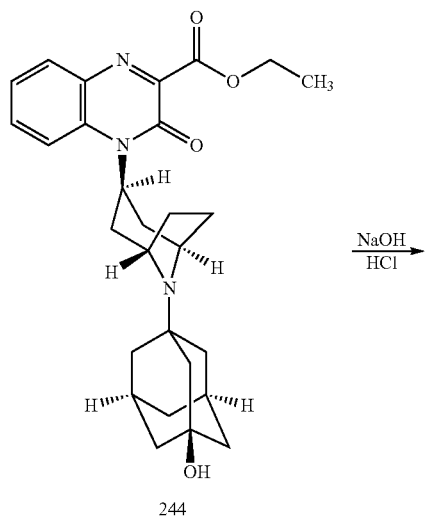

244

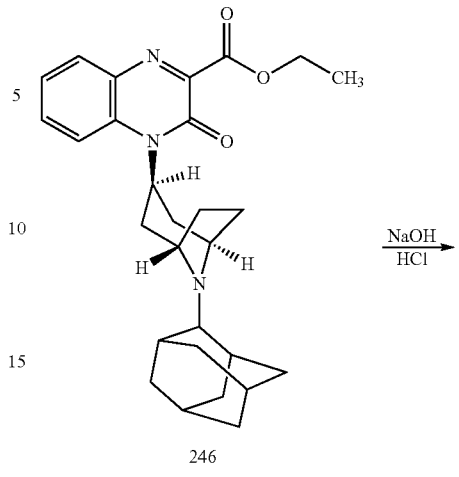

246

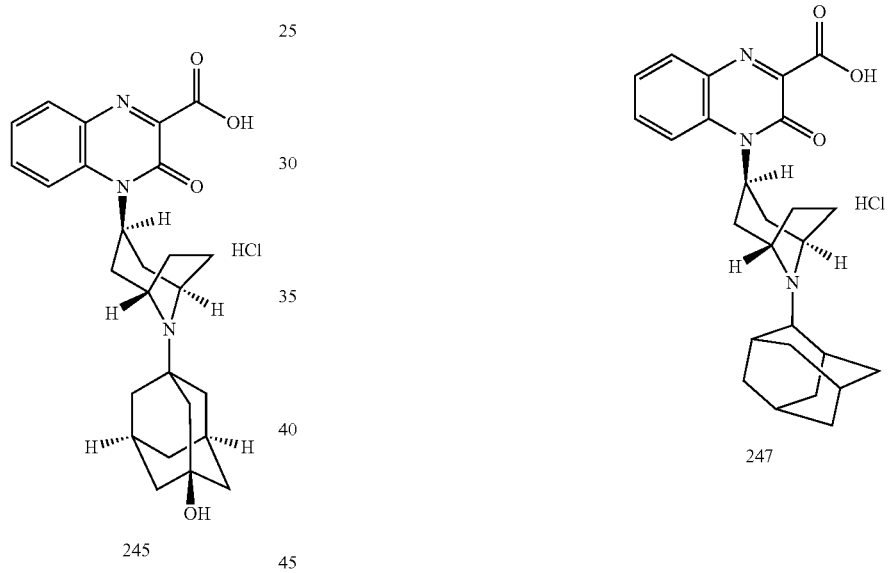

245

247

Substituted-Quinoxaline-Type Piperidine Compound 244, endo-4-[8-(3-hydroxy-adamantan-1-yl)-8-aza-bicyclo[3.2.1]oct-3-yl]-3-oxo-3,4-dihydro-quinoxaline-2-carboxylic acid ethyl ester, and the hydrochloride of Substituted-Quinoxaline-Type Piperidine Compound 245 were prepared by using 3-amino-adamantan-1-ol (Sigma-Aldrich) in place of the compound of formula ED.

The identity of Substituted-Quinoxaline-Type Piperidine Compound 245, endo-4-[8-(3-hydroxy-adamantan-1-yl)-8-aza-bicyclo[3.2.1]oct-3-yl]-3-oxo-3,4-dihydro-quinoxaline-2-carboxylic acid, was confirmed using $^1$H NMR and LC/MS.

Substituted-Quinoxaline-Type Piperidine Compound 245: $^1$H NMR: $\delta_H$ (400 MHz, 1:3 CDCl$_3$:CD$_3$OD): 8.1 (d, 1H, J=8.8 Hz), 8.02 (dd, 1H, J=1.2, 7.8 Hz), 7.83 (ddd, 1H, J=1.5, 7.2, 8.3 Hz), 7.51-7.55 (m, 1H), 6.04-6.18 (m, 1H), 4.48-4.52 (m, 2H), 2.94-3.02 (m, 2H), 2.60-3.64 (m, 2H), 2.32-2.68 (m, 6H), 2.08-2.24 (m, 6H), 1.6-1.8 (m, 6H); LC/MS (100%, t$_r$=4.338 min): m/z=450.6 [M+H]$^+$.

Substituted-Quinoxaline-Type Piperidine Compound 246, endo-4-(8-adamantan-2-yl-8-aza-bicyclo[3.2.1]oct-3-yl)-3-oxo-3,4-dihydro-quinoxaline-2-carboxylic acid ethyl ester (yield 35%), and the hydrochloride of Substituted-Quinoxaline-Type Piperidine Compound and 247 (yield 58%) were prepared by using 2-amino-adamantane (Sigma-Aldrich) in place of the compound of formula ED.

The identity of Substituted-Quinoxaline-Type Piperidine Compound 247, endo-4-(8-adamantan-2-yl-8-aza-bicyclo[3.2.1]oct-3-yl)-3-oxo-3,4-dihydro-quinoxaline-2-carboxylic acid, was confirmed using $^1$H NMR and LC/MS.

Substituted-Quinoxaline-Type Piperidine Compound 247: $^1$H NMR: $\delta_H$ (400 MHz, 1:3 CDCl$_3$:CD$_3$OD): 8.1 (d, 1H, J=8.7 Hz), 8.03 (d, 1H, J=8.1 Hz), 7.82-7.86 (m, 1H), 7.51-7.55 (m, 1H), 6.14-6.21 (m, 1H), 4.28-4.42 (m, 2H), 3.18-3.26 (m, 1H), 2.97-3.04 (m, 2H), 2.58-2.64 (m, 4H), 2.28-2.44 (m, 6H), 1.6-2.2 (m, 10H); LC/MS (97.9%, t$_r$=5.362 min): m/z=434.5 [M+H]$^+$.

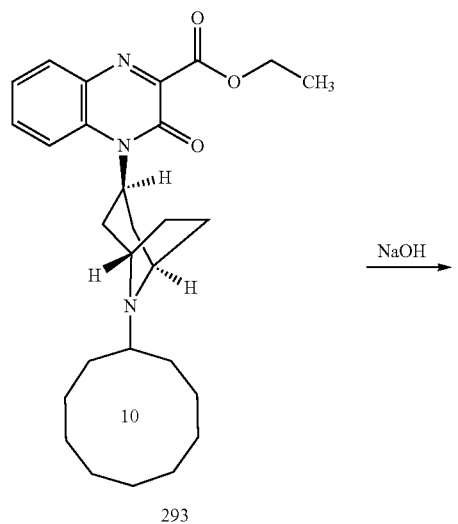

293

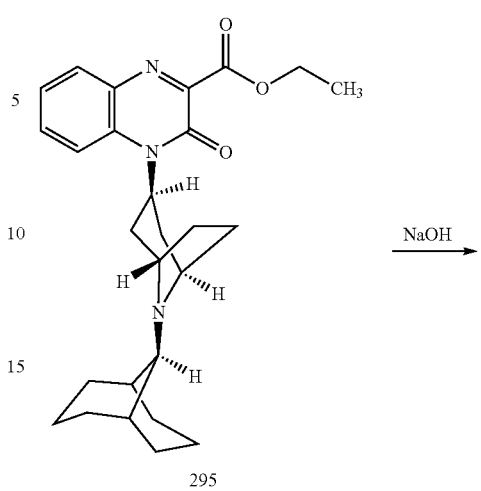

295

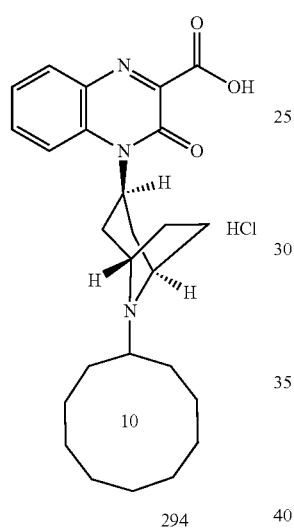

294

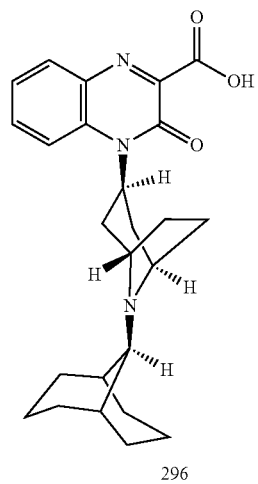

296

Substituted-Quinoxaline-Type Piperidine Compounds 293 and 294 were prepared by using cyclodecanamine in place of the compound of formula ED and omitting the final HCl treatment.

The identity of Substituted-Quinoxaline-Type Piperidine Compound 293, ethyl 4-((endo)-8-cyclodecyl-8-azabicyclo[3.2.1]octan-3-yl)-3-oxo-3,4-dihydroquinoxaline-2-carboxylate, was confirmed using $^1$H NMR and LC/MS.

Substituted-Quinoxaline-Type Piperidine Compound 293: $^1$H NMR: $\delta_H$ (CDCl$_3$): 7.91 (1H, m), 7.64-7.54 (2H, m), 7.34 (1H, m), 5.20 (1H, br), 4.49 (2H, q, J=7.1 Hz), 3.68 (2H, s), 2.45-2.20 (5H, m), 2.02 (2H, m), 1.81 (2H, m), 1.72-1.42 (22H, m); LC/MS: m/z=466 [M+H]$^+$ (Calc: 465.6).

The identity of Substituted-Quinoxaline-Type Piperidine Compound 294, 4-((endo)-8-cyclodecyl-8-azabicyclo[3.2.1]octan-3-yl)-3-oxo-3,4-dihydroquinoxaline-2-carboxylic acid, was confirmed using $^1$H NMR and LC/MS.

Substituted-Quinoxaline-Type Piperidine Compound 294: $^1$H NMR: $\delta_H$ (CDCl$_3$): 7.88 (2H, m), 7.42 (1H, m), 7.24 (1H, m), 5.80 (1H, m), 4.13 (2H, m), 3.10 (1H, m), 2.85 (1H, m), 2.60-1.40 (24H, m); LC/MS (99%, t$_r$=1.76 min): m/z=438 [M+H]$^+$ (Calc: 437.6).

Substituted-Quinoxaline-Type Piperidine Compounds 295 and 296 were prepared by using (exo)-bicyclo[3.3.1]nonan-9-amine in place of the compound of formula ED and omitting the final HCl treatment.

The identity of Substituted-Quinoxaline-Type Piperidine Compound 295, ethyl 4-((endo)-8-((exo)-bicyclo[3.3.1]nonan-9-yl)-8-azabicyclo[3.2.1]octan-3-yl)-3-oxo-3,4-dihydroquinoxaline-2-carboxylate, was confirmed using $^1$H NMR and LC/MS.

Substituted-Quinoxaline-Type Piperidine Compound 295: $^1$H NMR: $\delta_H$ (CDCl$_3$): 7.92 (1H, d, J=8.11 Hz), 7.62 (1H, t, J=7.86 Hz), 7.52 (1H, d, J=8.62 Hz), 7.35 (1.1H, t, J=7.6 Hz), 5.20 (1H, br), 4.49 (2H, q, J=7.1 Hz), 3.68 (2H, s), 2.45-2.20 (5H, m), 2.02 (2H, m), 1.81 (2H, m), 1.72-1.42 (24H, m); LC/MS: m/z=450 [M+H]$^+$ (Calc: 449.6).

The identity of Substituted-Quinoxaline-Type Piperidine Compound 296, 4-((endo)-8-((exo)-bicyclo[3.3.1]nonan-9-yl)-8-azabicyclo[3.2.1]octan-3-yl)-3-oxo-3,4-dihydroquinoxaline-2-carboxylic acid, was confirmed using $^1$H NMR and LC/MS.

Substituted-Quinoxaline-Type Piperidine Compound 296: $^1$H NMR: $\delta_H$ (CDCl$_3$): 8.42 (1H, m), 8.21 (1H, m), 7.92 (1H, m), 7.58 (1H, m), 6.60 (1H, m), 4.27 (2H, m), 3.10 (3H, m), 2.60-1.30 (22H, m); LC/MS (100%, t$_r$=1.54 min): m/z=424 [M+H]$^+$ (Calc: 423.6).

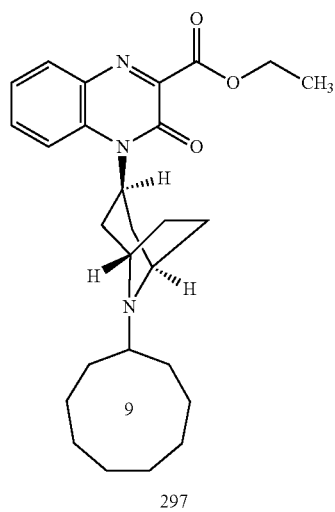

297

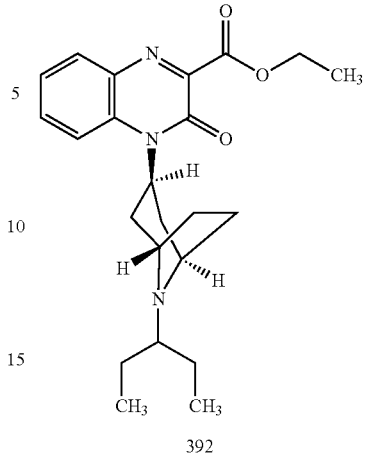

392

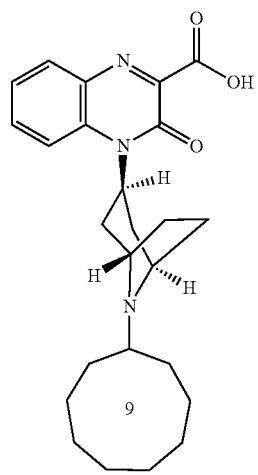

298

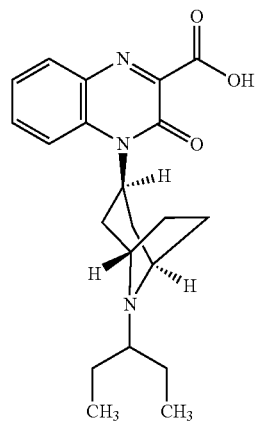

365

Substituted-Quinoxaline-Type Piperidine Compounds 297 and 298 were prepared by using cyclononanamine in place of the compound of formula ED and omitting the final HCl treatment.

The identity of Substituted-Quinoxaline-Type Piperidine Compound 297, ethyl 4-((endo)-8-cyclononyl-8-azabicyclo[3.2.1]octan-3-yl)-3-oxo-3,4-dihydroquinoxaline-2-carboxylate, was confirmed using $^1$H NMR and LC/MS.

Substituted-Quinoxaline-Type Piperidine Compound 297: $^1$H NMR: $\delta_H$ (CDCl$_3$): 7.92 (1H, d, J=8.0 Hz), 7.62 (1H, t, J=8.0 Hz), 7.52 (1H, d, J=8.0 Hz), 7.35 (1H, t, J=8.0 Hz), 5.40 (1H, br), 4.50 (2H, q, J=7.1 Hz), 3.68 (2H, s), 2.28-1.40 (26H, m); LC/MS: m/z=450 [M+H]$^+$ (Calc: 449.6).

The identity of Substituted-Quinoxaline-Type Piperidine Compound 298, 4-((endo)-8-cyclononyl-8-azabicyclo[3.2.1]octan-3-yl)-3-oxo-3,4-dihydroquinoxaline-2-carboxylic acid, was confirmed using $^1$H NMR and LC/MS.

Substituted-Quinoxaline-Type Piperidine Compound 298: $^1$H NMR: $\delta_H$ (CDCl$_3$): 8.23 (1H, d, J=8.11 Hz), 7.74 (2H, m), 7.53 (1H, t, J=7.6 Hz), 5.60 (1H, br), 3.75 (2H, s), 3.49 (1H, s), 2.40-1.47 (22H, m); LC/MS (100%, t$_r$=1.40 min): m/z=422 [M+H]$^+$ (Calc: 421.6).

Substituted-Quinoxaline-Type Piperidine Compounds 392 and 365 were prepared by using pentan-3-amine (Sigma-Aldrich) in place of the compound of formula ED and omitting the final HCl treatment.

The identity of Substituted-Quinoxaline-Type Piperidine Compound 392, ethyl 3-oxo-4-((endo)-8-(pentan-3-yl)-8-azabicyclo[3.2.1]octan-3-yl)-3,4-dihydroquinoxaline-2-carboxylate, was confirmed using $^1$H NMR.

Substituted-Quinoxaline-Type Piperidine Compound 392: $^1$H NMR: $\delta_H$ (CDCl$_3$): 0.95 (t, J=7.39 Hz, 6H), 1.40-1.60 (m, 7H), 1.85 (m, 2H), 2.05 (m, 2H), 2.15-2.38 (m, 5H), 3.67 (m, 2H), 4.54 (q, J=7.11 Hz, 2H), 5.30 (br, 1H), 7.38 (t, J=8.0 Hz, 1H), 7.57 (d, J=8.0 Hz, 1H), 7.68 (t, J=8.0 Hz, 1H), 7.96 (d, J=8.0 Hz, 1H).

The identity of Substituted-Quinoxaline-Type Piperidine Compound 365, 3-oxo-4-((endo)-8-(pentan-3-yl)-8-azabicyclo[3.2.1]octan-3-yl)-3,4-dihydroquinoxaline-2-carboxylic acid, was confirmed using $^1$H NMR and LC/MS.

Substituted-Quinoxaline-Type Piperidine Compound 365: $^1$H NMR: $\delta_H$ (DMSO-d$_6$): 0.96 (t, J=7.4 Hz, 6H), 1.86 (m, 4H), 2.16-2.27 (m, 6H), 2.66 (m, 2H), 2.84 (m, 1H), 4.20 (m, 2H), 6.14 (m, 1H), 7.44 (t, J=8.0 Hz, 1H), 7.73 (t, J=8.0 Hz, 1H), 7.87 (d, J=8.0 Hz, 1H), 8.11 (d, J=8.0 Hz, 1H); LC/MS (99%, t$_r$=0.81 min): m/z=370 [M+H]$^+$ (Calc: 369.6).

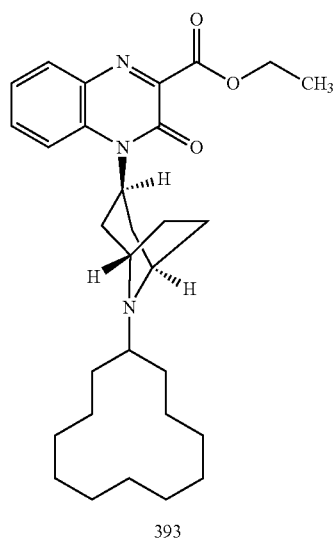

393

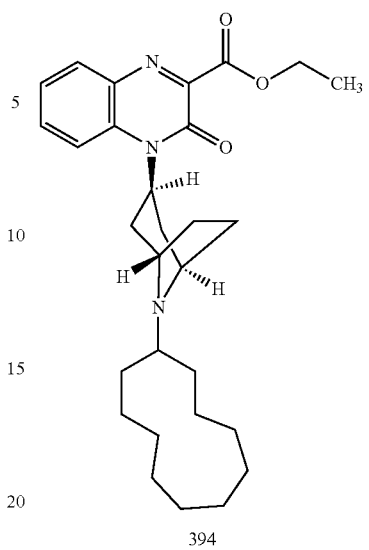

394

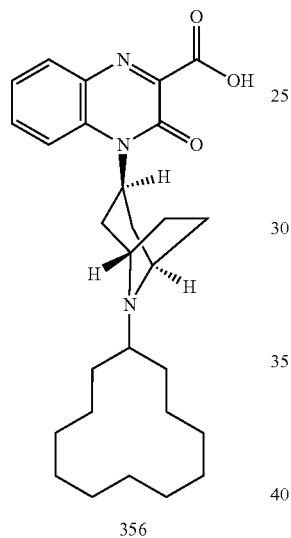

356

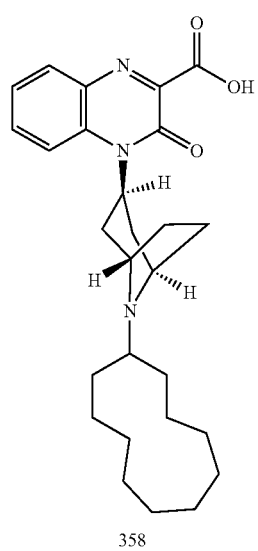

358

Substituted-Quinoxaline-Type Piperidine Compounds 393 and 356 were prepared by using cyclododecanamine (Sigma-Aldrich) in place of the compound of formula ED and omitting the final HCl treatment.

The identity of Substituted-Quinoxaline-Type Piperidine Compound 393, ethyl 4-((endo)-8-cyclododecyl-8-azabicyclo[3.2.1]octan-3-yl)-3-oxo-3,4-dihydroquinoxaline-2-carboxylate, was confirmed using $^1$H NMR and LC/MS.

Substituted-Quinoxaline-Type Piperidine Compound 393: $^1$H NMR: $\delta_H$ (CDCl$_3$): 1.35 (m, 25H), 1.82 (m, 2H), 2.02 (m, 2H), 2.26 (m, 5H), 3.68 (m, 2H), 4.49 (q, J=7.1 Hz, 2H), 5.20 (br, 1H), 7.34 (t, J=7.6 Hz, 1H), 7.54 (d, J=7.6 Hz, 1H), 7.62 (t, J=7.6 Hz, 1H), 7.91 (d, J=7.6 Hz, 1H); LC/MS: m/z=494 [M+H]$^+$ (Calc: 493.6).

The identity of Substituted-Quinoxaline-Type Piperidine Compound 356, 4-((endo)-8-cyclododecyl-8-azabicyclo[3.2.1]octan-3-yl)-3-oxo-3,4-dihydroquinoxaline-2-carboxylic acid, was confirmed using $^1$H NMR and LC/MS.

Substituted-Quinoxaline-Type Piperidine Compound 356: $^1$H NMR: $\delta_H$ (CDCl$_3$): 1.42 (m, 16H), 1.60-2.60 (m, 12H), 2.72 (s, 1H), 3.06 (m, 2H), 4.16 (s, 2H), 6.00 (br, 1H), 7.32 (t, J=7.35 Hz, 1H), 7.60 (m, 1H), 7.93 (d, J=8.11 Hz, 1H). 8.10 (m, 1H); LC/MS (100%, t$_r$=2.20 min): m/z=466 [M+H]$^+$ (Calc: 465.6).

Substituted-Quinoxaline-Type Piperidine Compounds 394 and 358 were prepared by using cycloundecanamine (Sigma-Aldrich) in place of the compound of formula ED and omitting the final HCl treatment.

The identity of Substituted-Quinoxaline-Type Piperidine Compound 394, ethyl 4-((endo)-8-cycloundecyl-8-azabicyclo[3.2.1]octan-3-yl)-3-oxo-3,4-dihydroquinoxaline-2-carboxylate, was confirmed using $^1$H NMR and LC/MS.

Substituted-Quinoxaline-Type Piperidine Compound 394: $^1$H NMR: $\delta_H$ (CDCl$_3$): 1.30-1.70 (m, 24H), 1.83 (m, 2H), 2.00 (m, 2H), 2.25 (m, 5H), 3.66 (m, 2H), 4.50 (d, J=7.14 Hz, 2H), 5.20 (br, 1H), 7.36 (t, J=7.6 Hz, 1H), 7.56 (d, J=7.6 Hz, 1H), 7.60 (t, J=7.6 Hz, 1H), 7.91 (d, J=7.6 Hz, 1H); LC/MS: m/z=480 [M+H]$^+$ (Calc: 479.6).

The identity of Substituted-Quinoxaline-Type Piperidine Compound 358, 4-((endo)-8-cycloundecyl-8-azabicyclo[3.2.1]octan-3-yl)-3-oxo-3,4-dihydroquinoxaline-2-carboxylic acid, was confirmed using $^1$H NMR and LC/MS.

Substituted-Quinoxaline-Type Piperidine Compound 358: $^1$H NMR: $\delta_H$ (CDCl$_3$): 1.30-1.60 (m, 14H), 1.75 (m, 2H), 2.13 (m, 6H), 2.39 (m, 4H), 2.61 (m, 1H), 3.04 (m, 2H), 4.12 (m, 2H), 5.83 (m, 1H), 7.25 (m, 1H), 7.44 (m, 1H), 7.85-7.94 (m, 21-1); LC/MS (99%, t$_r$=2.06 min): m/z=452 [M+H]$^+$ (Calc: 451.6).

5.38 Example 38

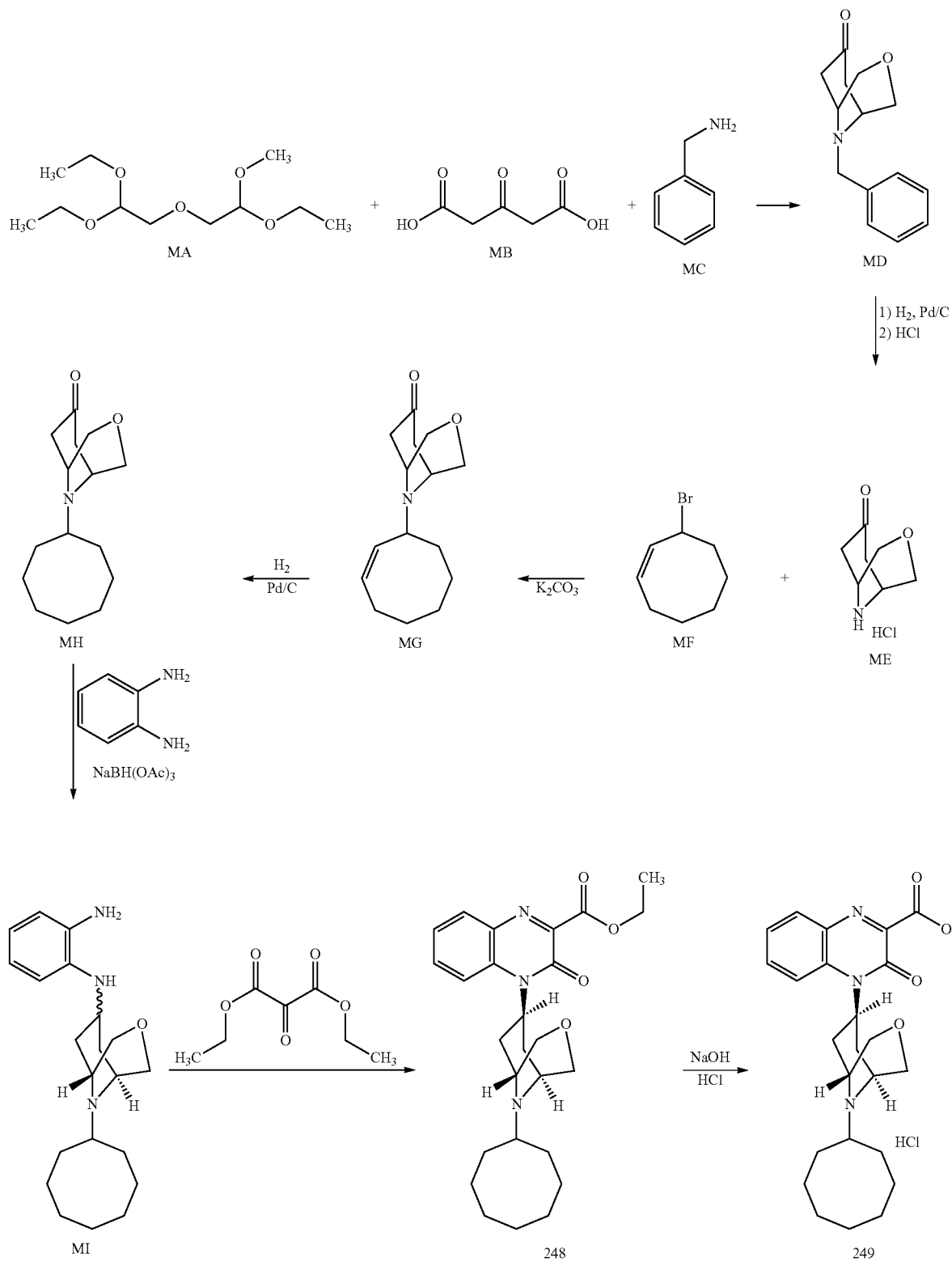

The compound of formula MA, 2-(2,2-diethoxyethoxy)-1,1-diethoxyethane, was prepared according the procedure described in C. L. Zirkle et al., *J. Org. Chem.* 26:395 (1961). A mixture of the compound of formula MA (25 g, 0.14 mmol), AcOH (7 mL), and water (25 mL) was warmed to 100° C. and stirred for 2 h. After cooling to about 25° C., the resulting colorless solution was added to 350 mL of a buffer solution containing 36 g of $Na_2HPO_4.7 H_2O$ and 25 g citric acid. Under an argon atmosphere, 400 mL of water and the compounds of formula MB (3-oxopentanedioic acid, 40 g, 0.27 mol, Sigma-Aldrich) and MC (phenylmethanamine, 27 g, 0.25 mol) were added. After holding the reaction mixture at 26-28° C. for 24 h, it was saturated with NaCl, neutralized with about 50 g of NaOH to a pH of about 11, and extracted four times with DCM (250 mL for each extraction). The organic portions were combined and concentrated under reduced pressure to provide a brown oil which was diluted with acetone (200 mL), concentrated under reduced pressure, and dried to provide about 7 g of the compound of formula MD, 9-benzyl-3-oxa-9-azabicyclo[3.3.1]nonan-7-one, as white solid. In a manner similar to Example 18, the benzyl group of the compound of formula MD was removed to provide 3.8 g of the hydrochloride of the compound of formula ME, 3-oxa-9-azabicyclo[3.3.1]nonan-7-one, as a white solid.

In a manner similar to Example 32, the compound of formula MG, 9-((Z)-cyclooct-2-enyl)-3-oxa-9-azabicyclo[3.3.1]nonan-7-one, was prepared from the compound of formula MF except that the compound of formula ME was used in place of the compound of formula JC (yield 90%). Under a hydrogen atmosphere, a mixture of the compound of formula MG, 5% palladium on carbon (1.0 g, Sigma-Aldrich), and EtOH (20 mL) was stirred at a temperature of about 25° C. for 4 h. After the Pd/C was filtered off, the filtrate was concentrated under reduced pressure to provide the compound of formula MH, 9-cyclooctyl-3-oxa-9-azabicyclo[3.3.1]nonan-7-one.

Substituted-Quinoxaline-Type Piperidine Compound 248: $^1$H NMR: $\delta_H$ (400 MHz, CDCl$_3$): 8.30 (br, 1H), 7.95 (dd, 11-1, J=1.5, 8.1 Hz), 7.64 (ddd, 1H, J=1.5, 7.2, 8.2 Hz), 7.35 (ddd, 1H, J=1.1, 7.1, 8.3 Hz), 6.05 (br, 1H), 4.52 (t, 2H, J=7.2 Hz), 3.80-3.83 (m, 2H), 3.66-3.71 (m, 2H), 3.30-3.34 (m, 2H), 3.04-3.08 (m, 1H), 2.20-2.24 (m, 2H), 1.4-1.8 (m, 19H); LC/MS (100%, t$_r$=6.056 min): m/z=454.6 [M+H]$^+$ (Calc: 453.6).

The hydrochloride of Substituted-Quinoxaline-Type Piperidine Compound 249 was prepared from Substituted-Quinoxaline-Type Piperidine Compound 248 in a manner similar to the preparation of Substituted-Quinoxaline-Type Piperidine Compound 174 in Example 7 (yield 78%).

The identity of Substituted-Quinoxaline-Type Piperidine Compound 249, 4-((endo)-9-cyclooctyl-3-oxa-9-azabicyclo[3.3.1]nonan-7-yl)-3-oxo-3,4-dihydroquinoxaline-2-carboxylic acid, was confirmed using $^1$H NMR and LC/MS.

Substituted-Quinoxaline-Type Piperidine Compound 249: $^1$H NMR: $\delta_H$ (400 MHz, 1:3 CDCl$_3$:CD$_3$OD): 8.25-8.42 (m, 1H), 8.02-8.06 (m, 1H), 7.83-7.86 (m, 1H), 7.53 (dd, 1H, J=7.4, 7.9 Hz), 6.24 (br, 1H), 3.80-4.32 (m, 7H), 3.20-3.26 (m, 1H), 2.60-3.78 (m, 3H), 1.60-2.24 (m, 14H); LC/MS (99.1%, t$_r$=2.067 min): m/z=426.5 [M+H]$^+$.

5.39 Example 39

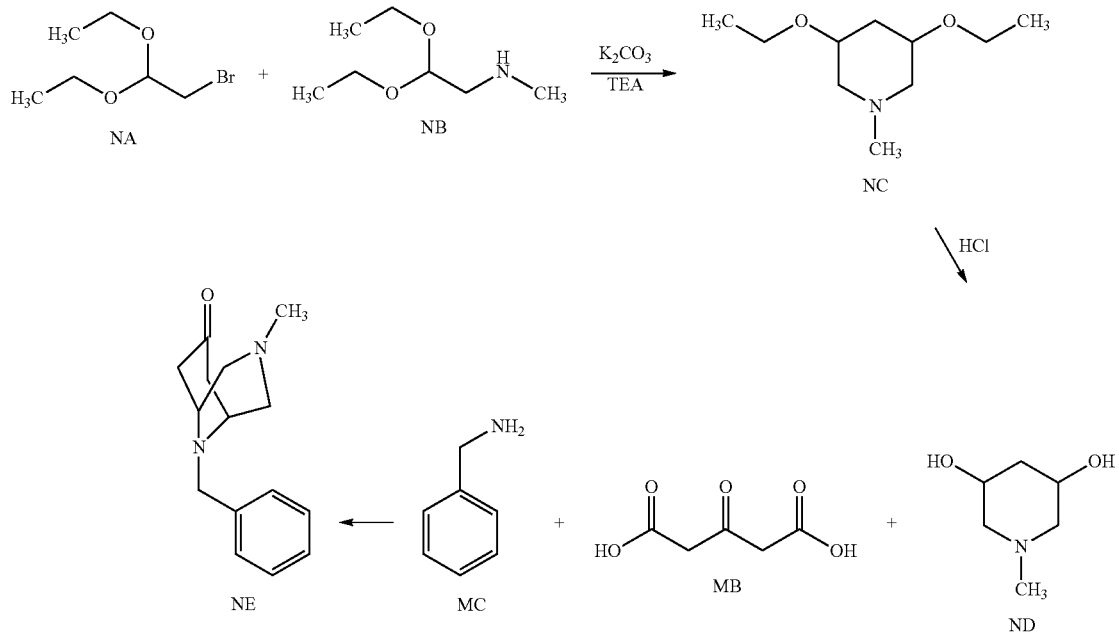

In a manner similar to Example 1, a mixture of the endo and exo isomers of the compound of formula MI, N$^1$-9-cyclooctyl-3-oxa-9-azabicyclo[3.3.1]nonan-7-yl)benzene-1,2-diamine, was prepared except that the compound of formula MH was used in place of the compound of formula AA. Substituted-Quinoxaline-Type Piperidine Compound 248 was prepared from diethyl 2-oxomalonate in a manner similar to Example 12 except that the compound of formula MI was used in place of the compound of formula AB (yield 15% from MH).

The identity of Substituted-Quinoxaline-Type Piperidine Compound 248, ethyl 4-((endo)-9-cyclooctyl-3-oxa-9-azabicyclo[3.3.1]nonan-7-yl)-3-oxo-3,4-dihydroquinoxaline-2-carboxylate, was confirmed using $^1$H NMR and LC/MS.

A reaction mixture of 2-bromo-1,1-diethoxyethane (NA, 25 g, Sigma-Aldrich), 2,2-diethoxy-N-methylethanamine (NB, 1.0 eq, Sigma-Aldrich), TEA (1.0 eq), and K$_2$CO$_3$ (1.0 eq) in CH$_3$CN (200 mL) was warmed to 60° C. and stirred for 20 h. After cooling to about 25° C., the reaction mixture was diluted with water, extracted with Et$_2$O, concentrated under reduced pressure, and distilled (at 56-60° C. and 0.5 mmHg) to provide 30 g of the compound of formula NC, 3,5-diethoxy-1-methylpiperidine, as a colorless oil (yield 87%). The compound of formula NC was treated with 1N HCl (150 mL) at a temperature of 100° C. for 2 h to provide the compound of formula ND, 1-methylpiperidine-3,5-diol. Thereafter, the compound of formula NE, 9-benzyl-3-methyl-3,9-diazabicyclo[3.3.1]nonan-7-one, was prepared in a manner similar to the preparation of the compound of formula MD in Example 38 except that the compound of formula ND was used in place of the compound of formula MA.

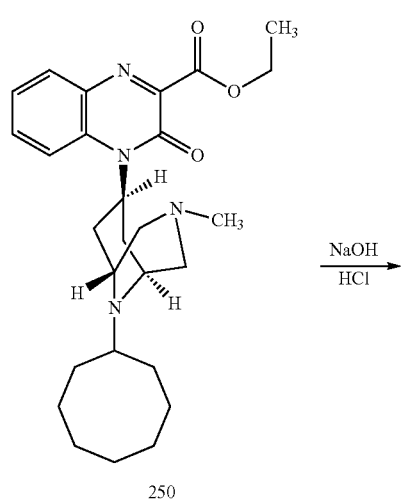

250

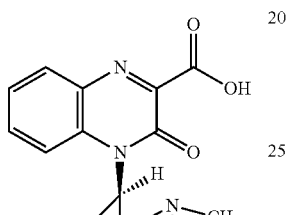

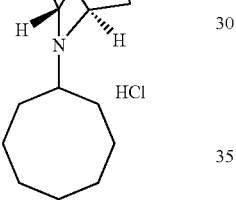

251

In a manner similar to Example 38, Substituted-Quinoxaline-Type Piperidine Compound 250, ethyl 4-((endo)-9-cyclooctyl-3-methyl-3,9-diazabicyclo[3.3.1]nonan-7-yl)-3-oxo-3,4-dihydroquinoxaline-2-carboxylate, was prepared except that the compound of formula NE was used in place of the compound of formula MD.

The hydrochloride of Substituted-Quinoxaline-Type Piperidine Compound 251 was prepared from Substituted-Quinoxaline-Type Piperidine Compound 250 in a manner similar to the preparation of Substituted-Quinoxaline-Type Piperidine Compound 174 in Example 7 (yield 36%).

The identity of Substituted-Quinoxaline-Type Piperidine Compound 251, 4-((endo)-9-cyclooctyl-3-methyl-3,9-diazabicyclo[3.3.1]nonan-7-yl)-3-oxo-3,4-dihydroquinoxaline-2-carboxylic acid, was confirmed using $^1$H NMR and LC/MS.

Substituted-Quinoxaline-Type Piperidine Compound 251: $^1$H NMR: $\delta_H$ (400 MHz, 1:3 CDCl$_3$:CD$_3$OD): 8.08-8.11 (m, 1H), 7.86-7.93 (m, 2H), 7.59-7.63 (m, 1H), 5.64 (br, 1H), 4.08 (br, 2H), 3.44-3.60 (m, 4H), 3.16 (s, 3H, Nme), 2.66-2.78 (m, 3H), 1.6-2.24 (m, 16H); LC/MS (99.1%, t$_r$=4.586 min): m/z=439.2 [M+H]$^+$ (Calc: 438.6).

5.40 Example 40

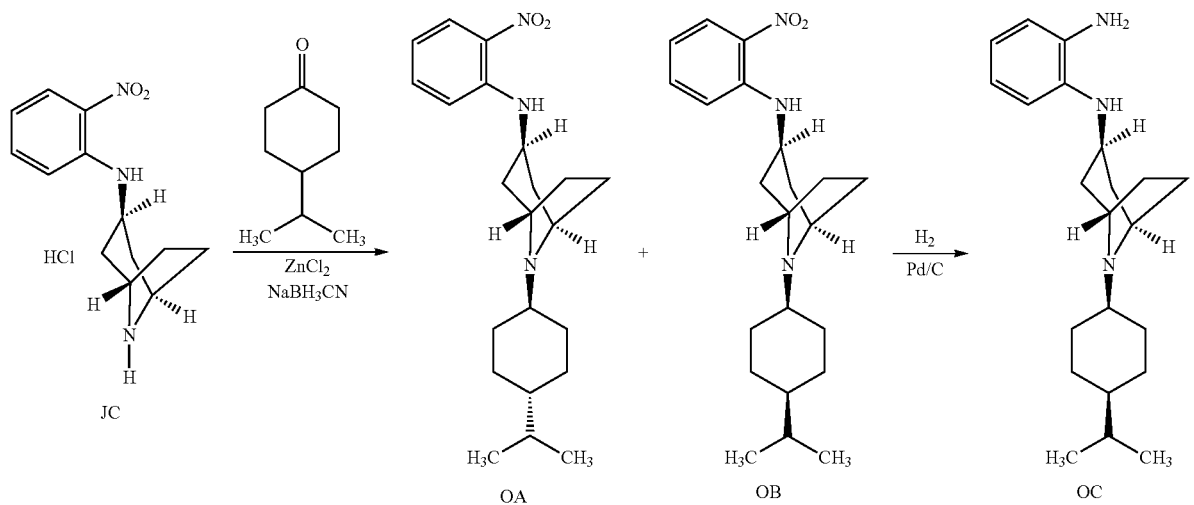

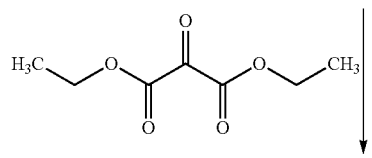

-continued

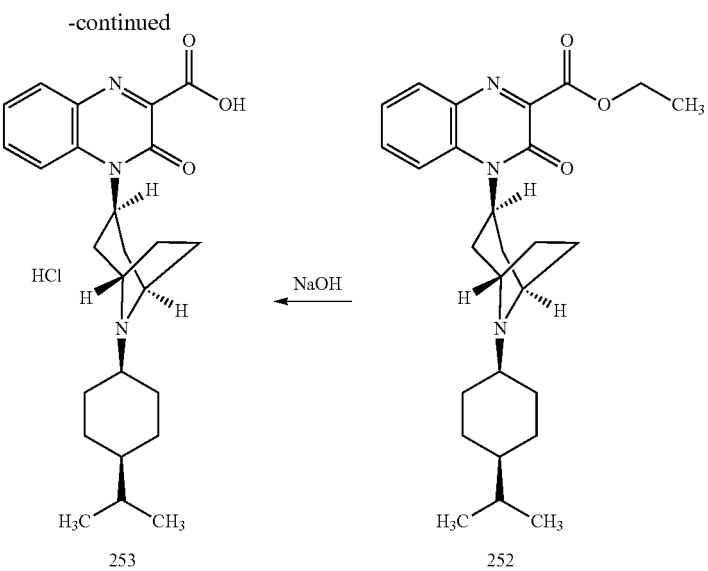

At a temperature of about 25° C., a 28% aqueous ammonia solution was added to a mixture of the compound of formula JC (1.0 g, 3.52 mmol) and CHCl₃ (30 mL) and the reaction mixture was stirred for 10 min. The mixture was extracted three times with CHCl₃:H₂O (30 mL for each extraction), dried (MgSO₄), and concentrated under reduced pressure to provide a yellow oil. Under a nitrogen atmosphere, to a mixture of the resulting oil and MeOH (300 mL) at a temperature of about 25° C. was added 4-isopropylcyclohexanone (0.593 g, 4.23 mmol, Sigma-Aldrich), NaBH₃CN (1.107 g, 17.62 mmol, Sigma-Aldrich) and zinc chloride (4.804 g, 35.2 mmol, Sigma-Aldrich). The resulting reaction mixture was stirred at a temperature of about 25° C. for 72 h. Thereafter, the mixture was concentrated under reduced pressure, neutralized with 28% aqueous ammonia to adjust the pH to about 14, and extracted twice with CHCl₃: H₂O (100 mL for each extraction). The organic portions were combined, dried (MgSO₄), and concentrated under reduced pressure to provide a yellow oil. The oil was chromatographed with an amino-silica gel column (Yamazen Corp. W091-01) eluted with a gradient of from 5%:95% EtOAc:n-hexane to 15%:85% EtOAc:n-hexane to 50%:50% EtOAc:n-hexane to provide 320 mg of the compound of formula OA (yield 24%) and 989 mg of the compound of formula OB (yield 75%), each as a yellow solid.

The identity of the compound of formula OA, (endo)-8-((trans)-4-isopropylcyclohexyl)-N-(2-nitrophenyl)-8-azabicyclo[3.2.1]octan-3-amine, was confirmed using ¹H NMR and LC/MS.

Compound OA: ¹H NMR: δ$_H$(400 MHz, CDCl₃): 8.73 (1H, d, J=6.08 Hz), 8.18 (1H, t, J=4.31 Hz), 7.40 (1H, dd, J=8.36, 7.35 Hz), 6.71 (1H, d, J=9.12 Hz), 6.61 (1H, dd, J=8.36, 7.35 Hz), 3.86 (1H, q, J=6.59 Hz), 3.56 (2H, s), 2.27 (3H, dd, J=8.36, 4.31 Hz), 2.02-1.94 (6.3H, m), 1.70 (6H, m), 1.44-1.40 (1H, m), 1.07 (5H, m), 0.85 (6H, dd, J=11.66, 7.10 Hz); LC/MS: m/z=372 [M+H]⁺ (Calc: 371).

The identity of the compound of formula OB, (endo)-8-((cis)-4-isopropylcyclohexyl)-N-(2-nitrophenyl)-8-azabicyclo[3.2.1]octan-3-amine, was confirmed using ¹H NMR and LC/MS.

Compound OB: ¹H NMR: δ$_H$(400 MHz, CDCl₃): 8.74 (1H, d, J=6.08 Hz), 8.18 (1H, d, J=8.62 Hz), 7.40 (1H, dd, J=8.11, 7.10 Hz), 6.72 (1H, d, J=8.62 Hz), 6.60 (1H, dd, J=8.36, 7.35 Hz), 3.85 (1H, q, J=6.42 Hz), 3.47 (2H, s), 2.52 (1H, s), 2.25 (2H, m), 1.95 (5H, m), 1.75-1.02 (17.6H, m), 0.87 (7H, dd, J=5.58, 4.56 Hz); LC/MS: m/z=372 [M+H]⁺ (Calc: 371).

In a manner similar to the preparation of the compound of formula CC in Example 6, the compound of formula OC was prepared except that the compound of formula OB was used in place of the compound of formula CB (yield 98%).

The identity of the compound of formula OC, N¹-((endo)-8-((cis)-4-isopropylcyclohexyl)-8-azabicyclo[3.2.1]octan-3-yl)benzene-1,2-diamine, was confirmed using LC/MS.

Compound OC: LC/MS: m/z=342 [M+H]⁺ (Calc: 341).

In a manner similar to the preparation of Substituted-Quinoxaline-Type Piperidine Compound 70 in Example 12, Substituted-Quinoxaline-Type Piperidine Compound 252 was prepared except that the compound of formula OC was used in place of the compound of formula AB (yield 19%).

The identity of Substituted-Quinoxaline-Type Piperidine Compound 252, ethyl 4-((endo)-8-((cis)-4-isopropylcyclohexyl)-8-azabicyclo[3.2.1]octan-3-yl)-3-oxo-3,4-dihydroquinoxaline-2-carboxylate, was confirmed using ¹H NMR and LC/MS.

Substituted-Quinoxaline-Type Piperidine Compound 252: ¹H NMR: δ$_H$ (400 MHz, DMSO-d₆): 7.89 (1H, d, J=8.11 Hz), 7.73 (1H, t, J=7.86 Hz), 7.58 (1H, d, J=8.62 Hz), 7.44 (1H, t, J=7.6 Hz), 5.20 (1H, br), 4.37 (2H, q, J=7.1 Hz), 3.61 (2H, br), 2.34-1.16 (30H, m), 0.92 (7H, d, J=6.59 Hz); LC/MS: m/z=452 [M+H]⁺ (Calc: 451).

The hydrochloride of Substituted-Quinoxaline-Type Piperidine Compound 253 was prepared from Substituted-Quinoxaline-Type Piperidine Compound 252 in a manner similar to the preparation of Substituted-Quinoxaline-Type Piperidine Compound 174 in Example 7 (yield 64%).

The identity of Substituted-Quinoxaline-Type Piperidine Compound 253, 4-((endo)-8-((cis)-4-isopropylcyclohexyl)-8-azabicyclo[3.2.1]octan-3-yl)-3-oxo-3,4-dihydroquinoxaline-2-carboxylic acid, was confirmed using ¹H NMR and LC/MS.

Substituted-Quinoxaline-Type Piperidine Compound 253: ¹H NMR: δ$_H$ (400 MHz, DMSO-d₆): 10.30 (0.8H, s), 9.73 (0.2H, s), 8.12 (1H, d, J=8.62 Hz), 7.89 (1H, d, J=7.6 Hz), 7.75 (1H, t, J=7.86 Hz), 7.47 (1H, t, J=7.35 Hz), 6.00 (0.8H, t, J=9.63 Hz), 5.24 (0.2H, s), 4.22 (2H, m), 2.91 (1H, m), 2.65 (2H, m), 2.34-2.09 (6H, m), 1.90-1.60 (8H, m), 1.37-1.14 (3H, m), 0.90 (6H, d, J=6.08 Hz); LC/MS (100%, t$_r$=1.66 min): m/z=424 [M+H]$^+$ (Calc: 423).

In a manner similar to the above preparation of Substituted-Quinoxaline-Type Piperidine Compounds 252 and 253, the following Substituted-Quinoxaline-Type Piperidine Compounds were prepared except that the compound of formula OA was used in place of from the compound of formula OB.

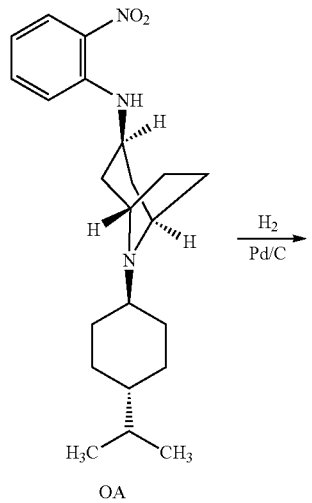

OA

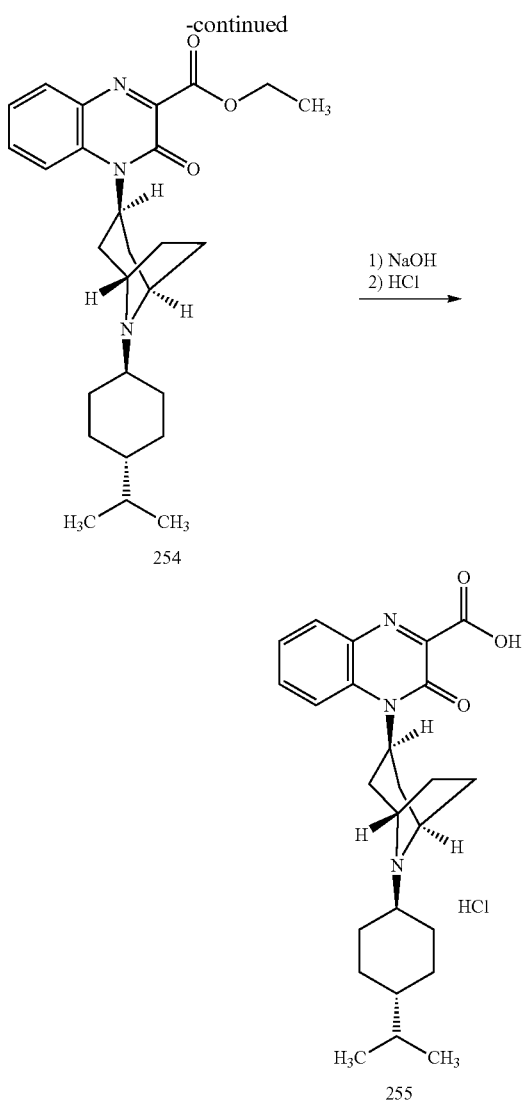

254

255

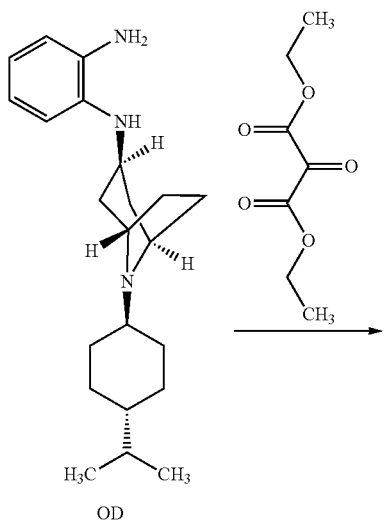

OD

The identity of Substituted-Quinoxaline-Type Piperidine Compound 254, ethyl 4-((endo)-8-((trans)-4-isopropylcyclohexyl)-8-azabicyclo[3.2.1]octan-3-yl)-3-oxo-3,4-dihydroquinoxaline-2-carboxylate, was confirmed using $^1$H NMR and LC/MS.

Substituted-Quinoxaline-Type Piperidine Compound 254: $^1$H NMR: δ$_H$ (400 MHz, DMSO-d$_6$): 7.88 (1H, d, J=7.6 Hz), 7.77 (1H, t, J=7.1 Hz), 7.65 (1H, d, J=6.59 Hz), 7.44 (1H, t, J=7.35 Hz), 5.17 (1H, br), 4.36 (2H, t, J=7.1 Hz), 3.69 (2H, d, J=16.22 Hz), 2.23 (2H, q, J=9.97 Hz), 2.02-1.71 (14H, m), 1.41-1.30 (5H, m), 1.08-0.84 (15H, m); LC/MS: m/z=452 [M+H]$^+$ (Calc: 451).

The identity of Substituted-Quinoxaline-Type Piperidine Compound 255, 4-((endo)-8-((trans)-4-isopropylcyclohexyl)-8-azabicyclo[3.2.1]octan-3-yl)-3-oxo-3,4-dihydroquinoxaline-2-carboxylic acid, was confirmed using $^1$H NMR and LC/MS.

Substituted-Quinoxaline-Type Piperidine Compound 255: $^1$H NMR: δ$_H$ (400 MHz, DMSO-d$_6$): 10.22 (0.8H, s), 9.72 (0.2H, s), 8.09 (1H, d, J=8.62 Hz), 7.89 (1H, d, J=8.11 Hz), 7.76 (1H, t, J=7.86 Hz), 7.47 (1H, t, J=7.6 Hz), 5.97 (0.8H, t, J=9.38 Hz), 5.23 (0.2H, s), 4.31 (1.5H, s), 4.13 (0.5H, s), 2.83 (1H, s), 2.63-2.55 (2H, m), 2.24 (8H, tt, J=30.92, 8.28 Hz), 1.95-1.22 (7H, m), 1.04 (3H, s), 0.86 (6H, d, J=6.59 Hz); LC/MS (98%, t$_r$=1.77 min): m/z=424 [M+H]$^+$ (Calc: 423).

In a manner similar to the above preparation of Substituted-Quinoxaline-Type Piperidine Compounds 252 and 253, the following Substituted-Quinoxaline-Type Piperidine Compounds were prepared except that 4-tert-butylcyclohexanone (Sigma-Aldrich) was used in place of 4-isopropylcyclohexanone and titanium(IV) iso-propoxide (Sigma-Aldrich) was used in place of zinc chloride.

J=8.11 Hz), 7.69 (1H, t, J=7.6 Hz), 7.54 (1H, d, J=8.62 Hz), 7.44 (1H, t, J=7.6 Hz), 5.22 (1H, s), 4.37 (2H, q, J=7.1 Hz), 3.62 (2H, s), 2.36 (1H, s), 2.19 (4H, m), 1.93 (4H, m), 1.62 (4H, m), 1.36 (8H, m), 1.09 (1H, m), 0.94 (9H, d, J=19.77 Hz); LC/MS: m/z=466 [M+H]$^+$ (Calc: 465).

The identity of Substituted-Quinoxaline-Type Piperidine Compound 257, 4-((endo)-8-((cis)-4-tert-butylcyclohexyl)-8-azabicyclo[3.2.1]octan-3-yl)-3-oxo-3,4-dihydroquinoxaline-2-carboxylic acid, was confirmed using $^1$H NMR and LC/MS.

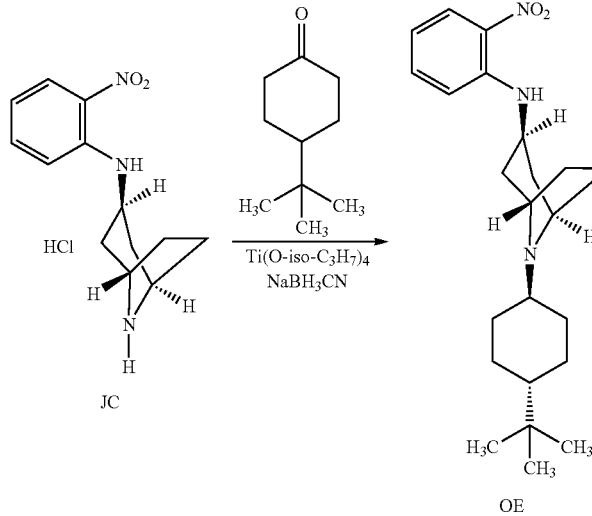

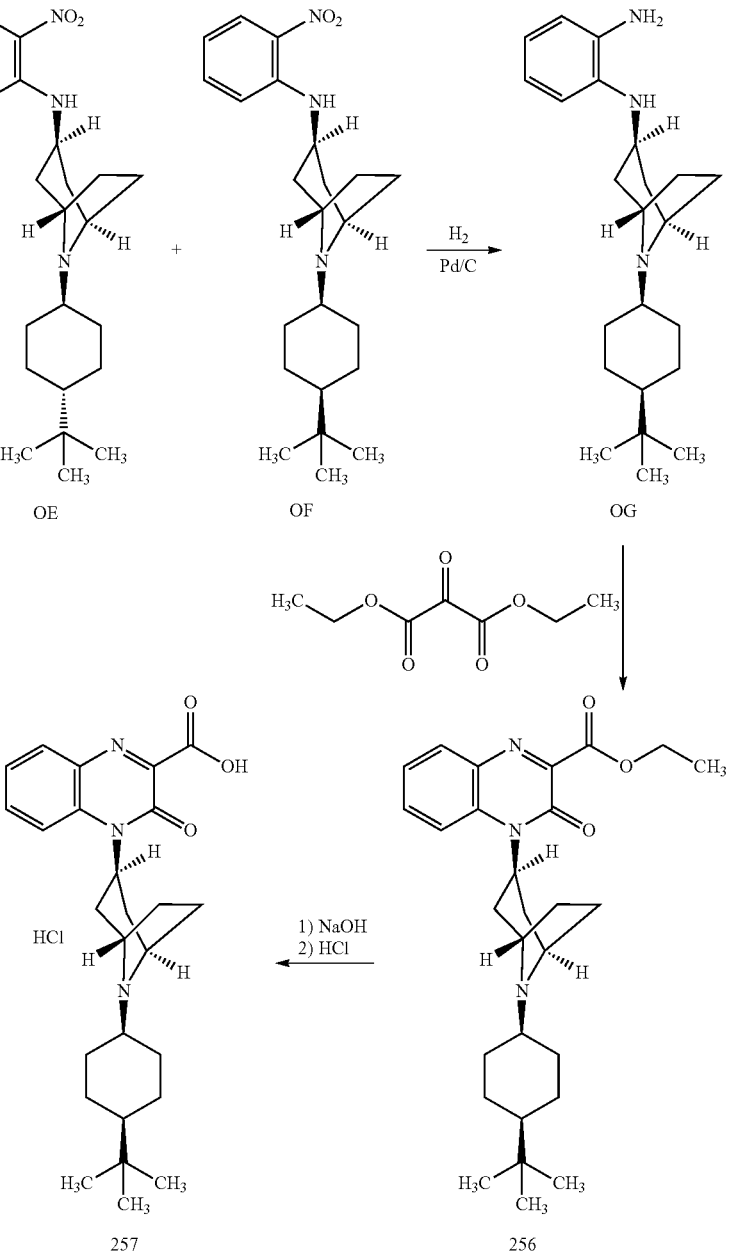

The identity of Substituted-Quinoxaline-Type Piperidine Compound 256, ethyl 4-((endo)-8-((cis)-4-tert-butylcyclohexyl)-8-azabicyclo[3.2.1]octan-3-yl)-3-oxo-3,4-dihydroquinoxaline-2-carboxylate, was confirmed using $^1$H NMR and LC/MS.

Substituted-Quinoxaline-Type Piperidine Compound 256: $^1$H NMR: δ$_H$ (400 MHz, DMSO-d$_6$): 7.89 (1H, d, Substituted-Quinoxaline-Type Piperidine Compound 257: $^1$H NMR: δ$_H$ (400 MHz, DMSO-d$_6$): 10.06 (0.7H, br), 8.85 (0.311, s), 8.13 (1H, d, J=9.12 Hz), 7.89 (1H, d, J=8.11 Hz), 7.75 (1H, t, J=7.35 Hz), 7.47 (1H, t, J=7.1 Hz), 6.17 (0.7H, br), 5.26 (0.3H, s), 4.22 (2H, s), 3.63 (0.3H, br), 3.04 (0.7H, br), 2.69 (2H, dd, J=20.53, 11.41 Hz), 2.41-1.50

(15H, m), 1.17 (1H, m), 0.90-0.82 (9H, m); LC/MS (100%, $t_r$=1.87 min): m/z=438 [M+H]$^+$ (Calc: 437).

In a manner similar to the above preparation of Substituted-Quinoxaline-Type Piperidine Compounds 256 and 257, the following Substituted-Quinoxaline-Type Piperidine Compounds were prepared except that the compound of formula OE was used in place of from the compound of formula OF.

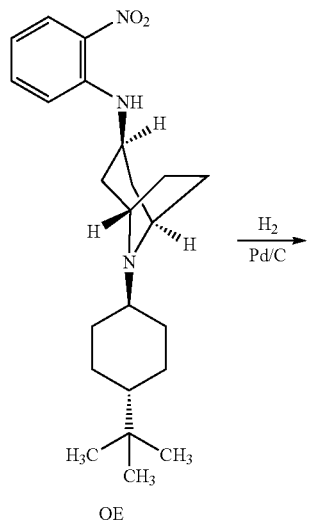

OE

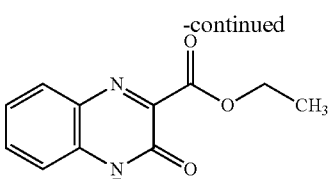

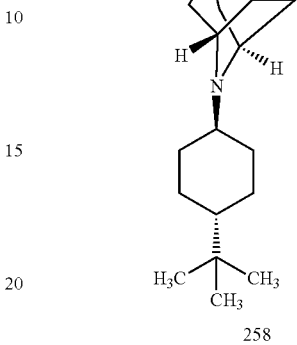

258

259

The identity of Substituted-Quinoxaline-Type Piperidine Compound 258, ethyl 4-((endo)-8-((trans)-4-tert-butylcyclohexyl)-8-azabicyclo[3.2.1]octan-3-yl)-3-oxo-3,4-dihydroquinoxaline-2-carboxylate, was confirmed using $^1$H NMR and LC/MS.

Substituted-Quinoxaline-Type Piperidine Compound 258: $^1$H NMR: $\delta_H$ (400 MHz, DMSO-d$_6$): 7.88 (1H, d, J=7.6 Hz), 7.76 (1H, d, J=8.11 Hz), 7.66 (1H, s), 7.44 (1H, m), 4.37 (2H, q, J=6.93 Hz), 3.69 (2H, m), 2.23 (2H, d, J=12.17 Hz), 1.87 (15H, m), 1.32 (3H, m), 1.02 (6H, m), 0.84 (9H, s); LC/MS: m/z=466 [M+H]$^+$ (Calc: 465).

The identity of Substituted-Quinoxaline-Type Piperidine Compound 259, 4-((endo)-8-((trans)-4-tert-butylcyclohexyl)-8-azabicyclo[3.2.1]octan-3-yl)-3-oxo-3,4-dihydroquinoxaline-2-carboxylic acid, was confirmed using $^1$H NMR and LC/MS.

Substituted-Quinoxaline-Type Piperidine Compound 259: $^1$H NMR: $\delta_H$ (400 MHz, DMSO-d$_6$): 10.22 (0.8H, s), 9.69 (0.2H, s), 8.09 (1H, d, J=8.11 Hz), 7.89 (1H, d, J=8.11 Hz), 7.76 (1H, t, J=7.1 Hz), 7.47 (1H, t, J=7.35 Hz), 5.96 (0.8H, dd, J=13.18, 5.58 Hz), 5.24 (0.2H, s), 4.23 (2H, m), 2.85 (1H, br), 2.58 (2H, br), 2.25 (7H, m), 1.95-1.56 (4H, m), 1.27 (1H, m), 1.11-0.86 (12H, m); LC/MS (100%, $t_r$=1.92 min): m/z=438 [M+H]$^+$ (Calc: 437).

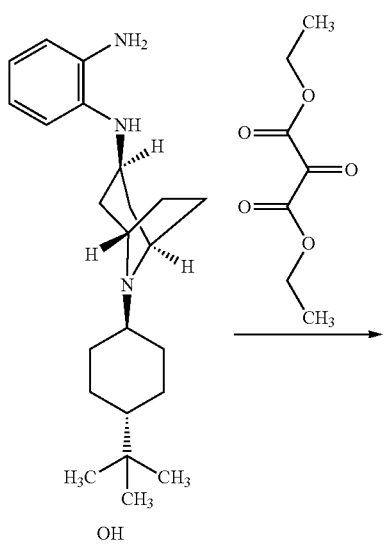

5.41 Example 41

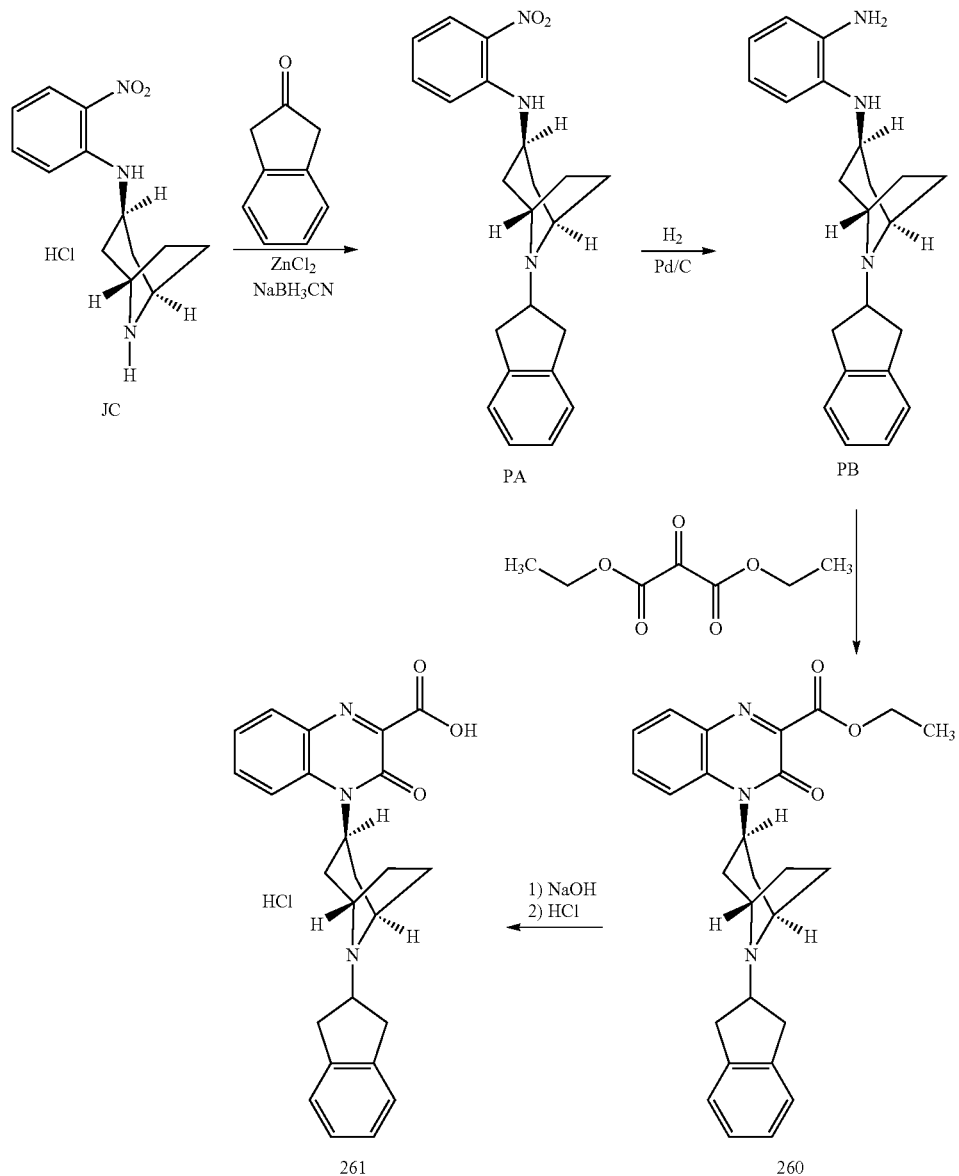

Substituted-Quinoxaline-Type Piperidine Compound 260 was prepared in a manner similar to the preparation of Substituted-Quinoxaline-Type Piperidine Compound 252 in Example 40 except that 1H-inden-2(3H)-one (Sigma-Aldrich) was used in place of 4-iso-propylcyclohexanone (yield 23%).

The identity of Substituted-Quinoxaline-Type Piperidine Compound 260, ethyl 4-((endo)-8-(2,3-dihydro-1H-inden-2-yl)-8-azabicyclo[3.2.1]octan-3-yl)-3-oxo-3,4-dihydroquinoxaline-2-carboxylate, was confirmed using $^1$H NMR and LC/MS.

Substituted-Quinoxaline-Type Piperidine Compound 260: $^1$H NMR: $\delta_H$ (400 MHz, DMSO-$d_6$): 7.88 (1H, d, J=7.6 Hz), 7.74 (2H, d, J=7.1 Hz), 7.44 (1H, t, J=7.6 Hz), 7.15 (4H, dt, J=25.52, 4.31 Hz), 5.23 (1H, br), 4.38 (2H, q, J=7.1 Hz), 3.59 (2H, s), 3.25-3.07 (3H, m), 2.78 (2H, m), 2.33 (2H, dd, J=21.54, 8.87 Hz), 2.05 (4H, dd, J=28.39, 16.73 Hz), 1.76 (2H, d, J=7.1 Hz), 1.32 (3H, t, J=6.84 Hz); LC/MS: m/z=444 [M+H]$^+$ (Calc: 443).

The hydrochloride of Substituted-Quinoxaline-Type Piperidine Compound 261 was prepared from Substituted-Quinoxaline-Type Piperidine Compound 260 in a manner similar to the preparation of Substituted-Quinoxaline-Type Piperidine Compound 174 in Example 7 (yield >98%).

The identity of Substituted-Quinoxaline-Type Piperidine Compound 261, 4-((endo)-8-(2,3-dihydro-1H-inden-2-yl)-8-azabicyclo[3.2.1]octan-3-yl)-3-oxo-3,4-dihydroquinoxaline-2-carboxylic acid, was confirmed using $^1$H NMR and LC/MS.

Substituted-Quinoxaline-Type Piperidine Compound 261: $^1$H NMR: $\delta_H$ (400 MHz, DMSO-$d_6$): 11.42 (0.7H, s), 10.78 (0.2H, s), 8.09 (1H, d, J=8.11 Hz), 7.90 (1H, d, J=7.6 Hz), 7.76 (1H, t, J=7.1 Hz), 7.47 (1H, t, J=7.6 Hz), 7.25 (4H, d, J=13.18 Hz), 6.04-6.00 (0.8H, m), 5.32 (0.2H, s), 4.11 (3H, m), 3.58 (2H, m), 2.76-2.68 (2H, m), 2.55-2.20 (11H, m); LC/MS (100%, t$_r$=1.2 min): m/z=416 [M+H]$^+$ (Calc: 415).

5.42 Example 42

The identity of the compound of formula QB, 9-((exo)-bicyclo[3.3.1]nonan-3-yl)-9-azabicyclo[3.3.1]nonan-3-one, was confirmed using $^1$H NMR and LC/MS.

Compound QB: $^1$H NMR: δ$_H$ (400 MHz, CDCl$_3$): 1.40-1.70 (m, 12H), 1.75-1.90 (m, 2H), 1.90-2.10 (m, 4H), 2.20 (d, J=0.20 Hz, 2H), 2.60 (m, 2H), 3.35 (m, 1H), 3.66 (m, 2H); LC/MS: m/z=262.1 [M+1]$^+$ (Calc: 261).

Under a nitrogen atmosphere, to a solution of the compound of formula QB (1020 mg, 3.90 mmol) in CH$_2$Cl$_2$ (15

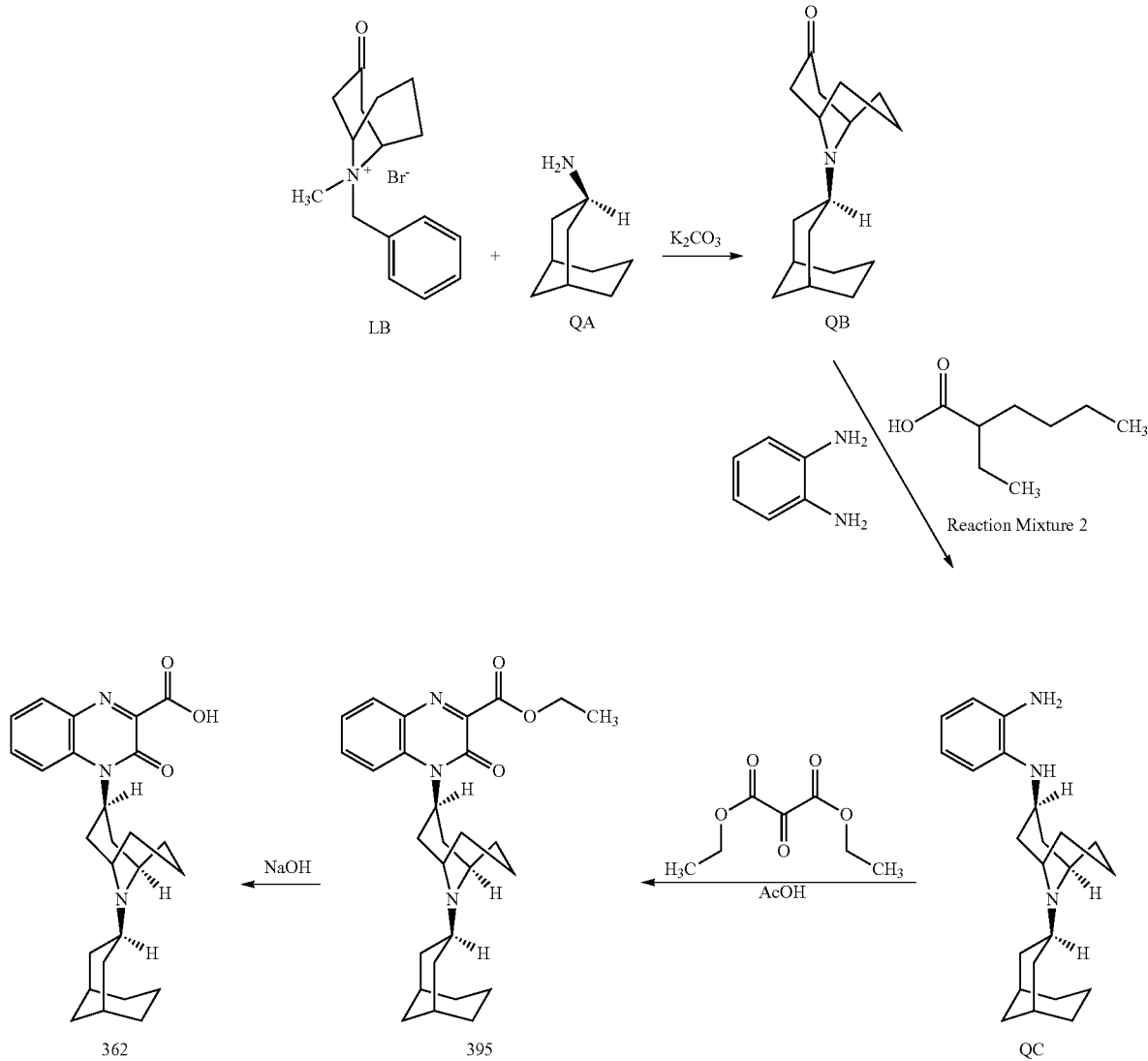

To a solution of the compound of formula QA ((exo)-bicyclo[3.3.1]nonan-3-amine, 10.44 mmol) in EtOH (3.1 mL) and water (0.7 mL), K$_2$CO$_3$ (144 mg, 1.04 mmol), at a temperature of about 25° C. was added a mixture of the compound of formula LB (4060 mg, 12.53 mmol) in EtOH (29 mL), and water (18 mL). After the addition, the resulting reaction mixture was warmed to a temperature of 90° C. and stirred for 5 h. Thereafter, the reaction mixture was cooled to a temperature of about 0° C. to provide a white precipitate. The precipitate was filtrated, washed twice with water (8 mL for each wash), and dried to provide 1580 mg of the compound of formula QB as a white solid (yield 57.9%).

mL) at a temperature of about 25° C. was added 1,2-phenylenediamine (1266 mg, 11.71 mmol) and 2-ethyl-hexanoic acid (0.938 mL, 5.85 mmol). The mixture was stirred at a temperature of about 25° C. for 30 min to provide reaction mixture 1.

Under a nitrogen atmosphere, to a solution of sodium tetrahydroborate (590 mg, 15.61 mmol) in CH$_2$Cl$_2$ (10 mL) at a temperature of about 25° C. was added 2-ethylhexanoic acid (8.75 mL, 54.6 mmol). The mixture was stirred at a temperature of about 25° C. for 30 min to provide reaction mixture 2.

Under a nitrogen atmosphere, to reaction mixture 1 at 0° C. was added reaction mixture 2 dropwise over a 15 min period. After the addition, the resulting reaction mixture was warmed to a temperature of about 25° C. and stirred for 30 min. Thereafter, the reaction mixture was warmed to a temperature of 60° C. and stirred for 16 h. After cooling the reaction mixture to a temperature of about 25° C., saturated aqueous NaHCO$_3$ (20 mL) was added, the mixture stirred for 10 min, then extracted twice with 1M aqueous K$_2$CO$_3$/EtOAc (200 mL for each extraction). The organic portions were combined, dried (Na$_2$SO$_4$), and concentrated under reduced pressure to provide a brown solid. The solid was chromatographed with an amino-silica gel column (Yamazen Corp. W091-01) eluted with a gradient of from 0%:100% EtOAc:n-hexane to 30%:70% EtOAc:n-hexane to provide 815 mg of the compound of formula Q as a colorless solid (yield 59%).

The identity of the compound of formula QC, N$^1$-((endo)-9-((exo)-bicyclo[3.3.1]nonan-3-yl)-9-azabicyclo[3.3.1]nonan-3-yl)benzene-1,2-diamine, was confirmed using $^1$H NMR and LC/MS.

Compound QC: $^1$H NMR: δ$_H$ (400 MHz, CDCl$_3$): 1.02-1.83 (m, 17H), 2.01 (m, 5H), 2.40-2.48 (m, 2H), 3.06-3.45 (m, 6H), 3.76 (br, 1H), 6.61-6.82 (m, 4H); LC/MS: m/z=354.1 [M+H]$^+$ (Calc: 353).

Under a nitrogen atmosphere, to a solution of the compound of formula QC (815 mg, 2.305 mmol) in toluene (16 mL) at a temperature of about 25° C. was added diethyl 2-oxomalonate (0.407 mL, 2.54 mmol) and AcOH (0.145 mL, 2.54 mmol). After the addition, the resulting reaction mixture was warmed to a temperature of 130° C. and stirred for 1 h. Thereafter, the reaction mixture was cooled to a temperature of about 25° C. and concentrated under reduced pressure to provide a sticky oil. The oil was diluted with saturated aqueous NaHCO$_3$, extracted twice with CHCl$_3$/water (100 mL for each extraction), dried (Na$_2$SO$_4$), and concentrated under reduced pressure to provide an orange solid. The solid was chromatographed with an amino-silica gel column (Yamazen Corp. W091-01) eluted with a gradient of from 0%:100% EtOAc:n-hexane to 20%:80% EtOAc:n-hexane to provide 560 mg of Substituted-Quinoxaline-Type Piperidine Compound 395 as a colorless solid (yield 52%).

Alternatively, compound 395 can be prepared as follows:

Under a nitrogen atmosphere, to a solution of the compound of formula QC (11.04 g, 31.2 mmol) in toluene (202 mL) at a temperature of about 25° C. was added diethyl 2-ketomalonate (6.02 mL, 37.5 mmol) and AcOH (2.143 mL, 37.5 mmol). After the addition, the resulting reaction mixture was warmed to a temperature of 130° C. and stirred for 1 h. Thereafter, the reaction mixture was cooled to a temperature of about 25° C. and concentrated under reduced pressure to provide a sticky oil. The oil was diluted with saturated aqueous NaHCO$_3$, extracted twice with CHCl$_3$ (600 mL for each extraction), dried (Na$_2$SO$_4$), and concentrated under reduced pressure to provide an orange solid. The resulting orange solid was sonicated by n-hexane/Et$_2$O (4/1), collected by filtration and dried under reduced pressure at 65° C. for 8 hr to give 1-(exo-9-bicyclo[3.3.1]-endo-9-aza-bicyclo[3.3.1]non-3-yl)-2-oxo-1,2-dihydro-quinoxaline-3-carboxylic acid ethyl ester 395 as a pale yellow solid. The remaining filtrate was purified by column chromatography (silica-gel; CHCl$_3$/MeOH=100/0~95/5) to give further 395 as a pale yellow solid. (Combined Yield; 9.83 g, 67%).

The identity of Substituted-Quinoxaline-Type Piperidine Compound 395, ethyl 4-((endo)-9-((exo)-bicyclo[3.3.1]nonan-3-yl)-9-azabicyclo[3.3.1]nonan-3-yl)-3-oxo-3,4-dihydroquinoxaline-2-carboxylate, was confirmed using $^1$H NMR and LC/MS.

Substituted-Quinoxaline-Type Piperidine Compound 395: $^1$H NMR: δ$_H$ (400 MHz, CDCl$_3$): 1.04-1.11 (m, 2H), 1.35-1.86 (m, 17H), 1.92-2.02 (m, 6H), 2.37-2.47 (m, 1H), 2.67-2.79 (m, 1H), 3.46-3.56 (m, 3H), 4.51 (q, J=7.07 Hz, 2H), 5.20 (m, 1H), 7.34-7.37 (m, 1H), 7.63 (t, J=6.57 Hz, 2H), 7.92 (d, J=8.08 Hz, 1H); LC/MS: m/z=464.2 [M+H]$^+$ (Calc: 463).

To a suspension of Substituted-Quinoxaline-Type Piperidine Compound 395 (561 mg, 1.21 mmol) in ethanol (15 mL) at a temperature of about 25° C. was added 2N aqueous NaOH (1.812 mL, 3.62 mmol). The resulting reaction mixture was stirred at a temperature of about 25° C. for 1 h. Thereafter, the reaction mixture was concentrated under reduced pressure to provide a residue. The residue was diluted with water (10 mL) to form a colorless solution, neutralized with 2N aqueous HCl (2.3 mL), and sonicated to provide a white precipitate. The precipitate was collected by filtration, washed with water, and dried for 5 h under reduced pressure at 75° C. to provide 396 mg of Substituted-Quinoxaline-Type Piperidine Compound 362 as a colorless solid (yield 75%).

The identity of Substituted-Quinoxaline-Type Piperidine Compound 362, 4-((endo)-9-((exo)-bicyclo[3.3.1]nonan-3-yl)-9-azabicyclo[3.3.1]nonan-3-yl)-3-oxo-3,4-dihydroquinoxaline-2-carboxylic acid, was confirmed using $^1$H NMR and LC/MS.

Substituted-Quinoxaline-Type Piperidine Compound 362: $^1$H NMR: δ$_H$ (400 MHz, CDCl$_3$): 0.83 (dq, J=8.72, 2.78 Hz, 1H), 1.22 (s, 1H), 1.38 (br, 1H), 1.54 (d, J=12.63 Hz, 1H), 1.69 (s, 6H), 1.87 (m, 4H), 2.05 (t, J=13.89 Hz, 2H), 2.22 (s, 2H), 2.51 (dd, J=19.71, 11.12 Hz, 2H), 2.70 (m, 3H), 2.98 (t, J=12.38 Hz, 2H), 4.11-4.22 (m, 3H), 6.65 (br, 1H), 7.51-7.62 (m, 4H), 7.93 (t, J=7.83 Hz, 1H), 8.16 (d, J=8.08 Hz, 1H), 8.96 (dd, J=7.83, 6.32 Hz, 1H), 10.89 (s, 1H); LC/MS (100%, t$_r$=1.55 min): m/z=436.2 [M+H]$^+$ (Calc: 436).

Alternatively the compound QC and Substituted-Quinoxaline-Type Piperidine Compound 362 can be synthesized via an different route, which is shown below:

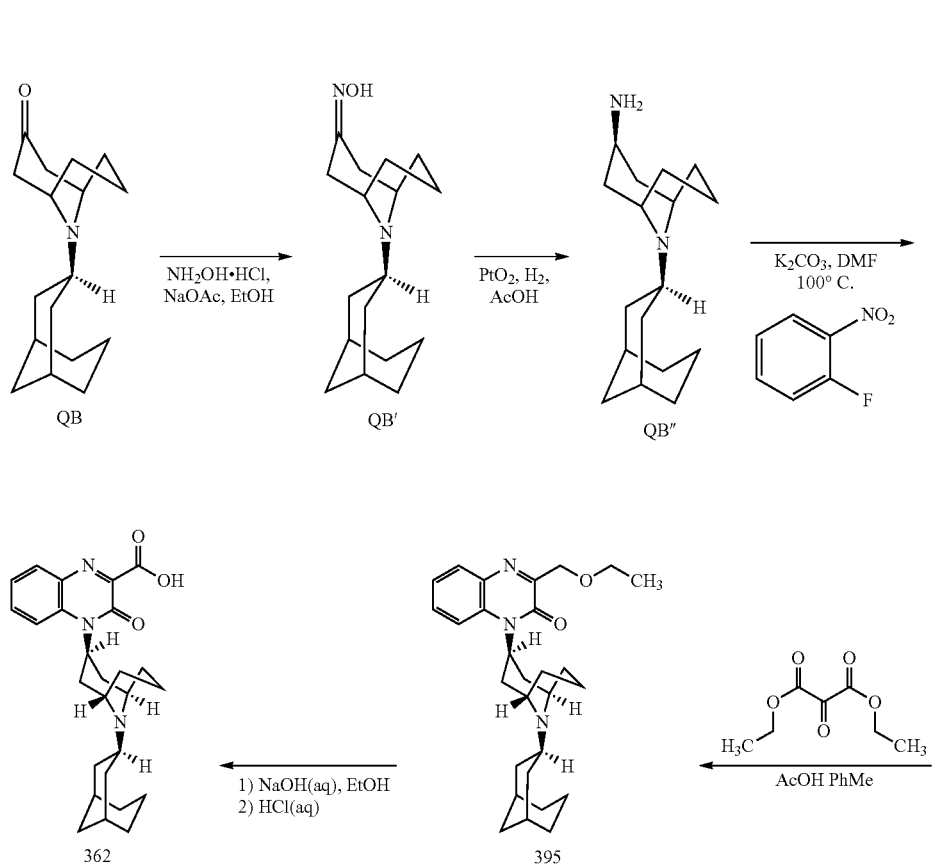

Compound QB' was prepared as follows:

Under a nitrogen atmosphere, to a suspension of the compound of formula QB (10.77 g, 41.2 mmol) in ethanol (215 mL) at a temperature of about 25° C. was added hydroxylamine hydrochloride (4.29 g, 61.8 mmol) and sodium acetate (5.07 g, 61.8 mmol). After the addition, the mixture was stirred at this temperature for 1.5 hr. After quenching with water (50 mL), the mixture was separated by CHCl$_3$/saturated NaHCO$_3$ (200 mL for each extraction). The organic portions were combined, dried over Na$_2$SO$_4$, and concentrated to under reduced pressure to give 9-bicyclo [3.3.1]non-3-yl-9-aza-bicyclo[3.3.1]nonan-3-one oxime (QB') as a pale yellow solid which was used in the next reaction without further purification (Yield; 11.39 g, 100%).

The identity of the compound of formula QB', 9-bicyclo [3.3.1]non-3-yl-9-aza-bicyclo[3.3.1]nonan-3-one oxime, was confirmed by LC/MS.

Compound QB': LC/MS: m/z=277.45 [M+H]$^+$ (Calc: 276.42).

Compound QB" was prepared as follows:

To a solution of QB', (11.39 g, 41.2 mmol) in AcOH (203 mL) at a temperature of about 25'C was added platinum(IV) oxide (1.871 g, 8.24 mmol). The mixture was stirred at a temperature of about 25° C. for 24 hr under a hydrogen atmosphere at 5 atm pressure. After filtration and washing with AcOEt (100 mL), the filtrate was concentrated under reduced pressure to give a sticky yellow oil. To this oil water was added, and the resulting mixture was neutralized by 28% aqueous ammonia solution to give a white gel like precipitate. The mixture was extracted twice using CHCl$_3$/MeOH/H$_2$O (700 mL for each extraction). The combined organic phases were dried over MgSO$_4$ and concentrated in vacuo to give the desired product, 9-exo-bicyclo[3.3.1]non-3-yl-9-endo-aza-bicyclo[3.3.1]non-3-ylamine QB" only in the endo-form, as a colorless solid, which was used in the next reaction without purification. (Yield; 9.07 g, 84%).

The identity of the compound of formula QB", 9-exo-bicyclo[3.3.1]non-3-yl-9-endo-aza-bicyclo[3.3.1]non-3-ylamine, was confirmed using $^1$H NMR and LC/MS.

Compound QB": $^1$H-NMR (400 MHz, DMSO-d$_6$) δ: 0.92-0.99 (m, 4H), 1.23-1.65 (m, 16H), 1.98 (m, 7H), 3.12 (s, 1H), 3.28 (s, 2H); LC/MS: m/z=263.15 [M+H]$^+$ (Calc: 262.43).

Compound QB'" was prepared as follows:

Under a nitrogen atmosphere, to a solution of QB" (9.07 g, 34.6 mmol) in DMF (136 mL) at a temperature of about 25° C. was added potassium carbonate (7.16 g, 51.8 mmol) and 1-fluoro-2-nitrobenzene (3.65 mL, 34.6 mmol). The mixture was stirred at 100° C. for 2 hr. The reaction mixture was cooled and quenched with ice-water (100 mL) and saturated NaHCO$_3$ (10 mL) to give a yellow precipitate which was collected by filtration. The precipitate was subsequently washed twice with water (50 mL each), dried under reduced pressure at 70° C. for 8 hr to give the desired product (9-bicyclo[3.3.1]non-3-yl-9-aza-bicyclo[3.3.1]non-3-yl-(2-nitro-phenyl)-amine OB'" as a yellow solid (Yield; 11.98 g, 90%).

The identity of the compound of formula OB'", (9-bicyclo [3.3.1]non-3-yl-9-aza-bicyclo[3.3.1]non-3-yl-(2-nitro-phenyl)-amine, was confirmed using $^1$H NMR and LC/MS.

Compound QB'": $^1$H-NMR (400 MHz, CDCl$_3$) δ: 0.85-2.02 (m, 26H), 2.45 (m, 2H), 3.49 (m, 3H), 4.03 (t, J=3.79

Hz, 1H), 6.58 (t, J=7.58 Hz, 1H), 6.93 (d, J=8.08 Hz, 1H), 7.40 (t, J=7.33 Hz, 1H), 8.09 (dd, J=48.50, 7.58 Hz, 2H); LC/MS: m/z=384.2 [M+H]⁺ (Calc: 383.53).

Compound QC was prepared as follows:

Under a hydrogen atmosphere, to a suspension of QB''' (11.98 g, 31.2 mmol) in MeOH (240 mL) at a temperature of about 25° C. was added 10% Pd—C (1.330 g, 1.249 mmol), and the mixture was stirred at this temperature for 1.5 h. After the addition of CHCl₃ (150 mL), the mixture was filtrated, washed with CHCl₃ and concentrated in vacuo to give N-(9-bicyclo[3.3.1]non-3-yl-9-aza-bicyclo[3.3.1]non-3-yl)benzene-1,2-diamine (QC) as a pale green solid which was very pure by NMR and therefore used in the next step without purification (Yield; 11.04 g, 100%).

The identity of the compound of formula QC, N-(9-bicyclo[3.3.1]non-3-yl-9-aza-bicyclo[3.3.1]non-3-yl)benzene-1,2-diamine, was confirmed using ¹H NMR and LC/MS.

Compound QC: ¹H-NMR (400 MHz, CDCl₃) δ: 1.02-1.83 (m, 17H), 2.01 (m, 5H), 2.40-2.48 (m, 2H), 3.06-3.45 (m, 6H), 3.76 (br, 1H), 6.61-6.82 (m, 4H); LC/MS: m/z=354.14 [M+H]⁺ (Calc: 353).

The compound of formula QA was prepared as follows:

on carbon (570 mg, 0.536 mmol), and MeOH (150 mL) was stirred at a temperature of about 25° C. for 4 h. After the Pd/C was filtered off, the mixture was concentrated under reduced pressure to provide a colorless oil. The oil was chromatographed with a silica gel column eluted with a gradient of from 3%:97% EtOAc:n-hexane to 20%:80% EtOAc:n-hexane to provide 3500 mg of the compound of formula QF as a colorless solid (yield 66%).

The identity of the compound of formula QF, bicyclo [3.3.1]nonane-3-carbonitrile, was confirmed using ¹H NMR.

Compound at: ¹H NMR: δ$_H$ (400 MHz, CDCl₃): 1.22 (m, 1H), 1.38-1.59 (m, 8H), 1.72-1.82 (m, 1H), 2.04-2.08 (m, 2H), 2.20-2.28 (m, 2H), 2.60-2.69 (m, 1H).

Under a nitrogen atmosphere, to a solution of the compound of formula QF (2530 mg, 16.95 mmol) in 2-methoxyethanol (26.9 mL, 339 mmol) at a temperature of about 25° C. was added KOH (4280 mg, 76 mmol). After the addition, the resulting reaction mixture was warmed to a temperature of 120° C. and stirred for 16 h. Thereafter, the reaction mixture was cooled to a temperature of about 25° C., 2N aqueous HCl was added to adjust the pH within the range of from about 3 to about 4, and a pale brown precipitate formed. The precipitate was collected by filtration, washed

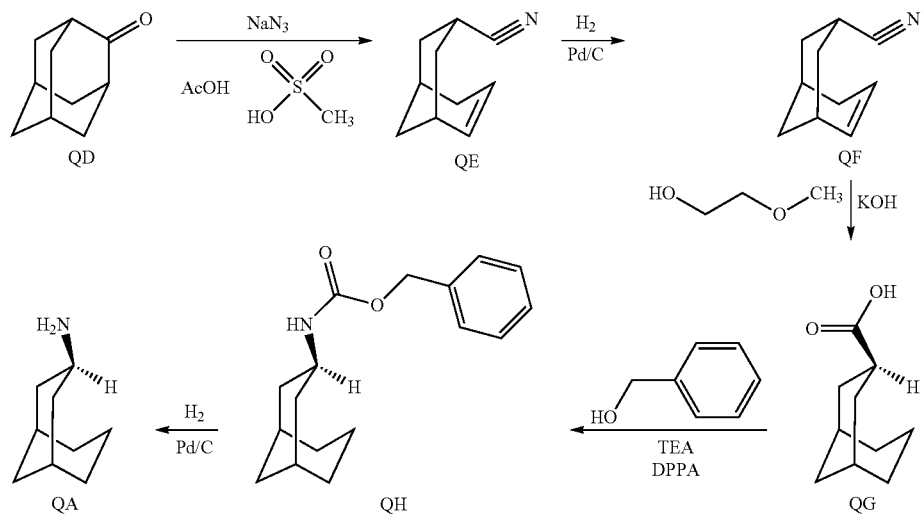

Under a nitrogen atmosphere, to a solution of the compound of formula QD (adamantane-2-one, 60 g, 399 mmol, Sigma-Aldrich) in AcOH (251 mL, 4394 mmol) and methanesulfonic acid (182.00 mL, 2803 mmol, Sigma-Aldrich) at a temperature of 20° C. was added sodium azide (29.9 g, 459 mmol) portionwise over 45 min. After the addition, the resulting reaction mixture was stirred for 30 min at a temperature of from 20° C. to 25° C. Thereafter, ice water (1 L) was poured into the reaction mixture to provide a white precipitate that was collected by filtration, washed with water (400 mL), and dried for 4 h under reduced pressure at 60° C. to provide 40.78 g of the compound of formula QE as a colorless solid (yield 69%).

The identity of the compound of formula QE, bicyclo [3.3.1]non-6-ene-3-carbonitrile, was confirmed using ¹H NMR.

Compound QE: ¹H NMR: δ$_H$ (400 MHz, CDCl₃): 1.53 (d, J=12.67 Hz, 1H), 1.72-2.05 (m, 5H), 2.23 (dt, J=17.91, 8.11 Hz, 2H), 2.41-2.50 (m, 2H), 2.96 (dd, J=9.63, 4.06 Hz, 1H), 5.85-5.95 (m, 2H).

Under a hydrogen atmosphere, a mixture of the compound of formula QE (5260 mg, 35.7 mmol), 10% palladium with water, and dried for 3 h under reduced pressure at 70° C. to provide a pale brown solid, which ¹H NMR showed to be a 1:9 mixture of endo:exo isomers.

Under a nitrogen atmosphere, to a solution of the above endo:exo isomer mixture in 2-methoxyethanol (73.5 mL, 932 mmol) at a temperature of about 25° C. was added KOH (4756 mg, 85 mmol). After the addition, the resulting reaction mixture was warmed to a temperature of 120° C. and stirred for 16 h. Thereafter, the reaction mixture was cooled to a temperature of about 25° C., 2N aqueous HCl was added to adjust the pH within the range of from about 3 to about 4, and a pale brown precipitate formed. The precipitate was collected by filtration, washed with water, and dried for 3 h under reduced pressure at 70° C. to provide 2187 mg of the compound of formula QG as a pale brown solid, with a melting point of 126-128° C. and present only as the exo isomer (yield 77%).

The identity of the compound of formula QG, (exo)-bicyclo[3.3.1]nonane-3-carboxylic acid, was confirmed using ¹H NMR.

Compound QG: ¹H NMR: δ$_H$ (400 MHz, CDCl₃): 1.52-1.85 (m, 10H), 1.96 (t, J=6.59 Hz, 4H), 3.10-3.19 (m, 1H).

Under a nitrogen atmosphere, to a solution of the compound of formula QG (2680 mg, 15.93 mmol) in toluene (25 mL) at a temperature of about 25° C. was added TEA (2.65 mL, 19.12 mmol) and DPPA (4.51 mL, 19.12 mmol). After the addition, the resulting reaction mixture was warmed to a temperature of 70° C. and stirred for 1 h. Thereafter, the reaction mixture was cooled to a temperature of about 25° C. and concentrated under reduced pressure to provide a pale yellow oil, which was dried under reduced pressure at a temperature of about 25° C. To the oil was added phenylmethanol (4.77 mL, 45.9 mmol, Sigma-Aldrich). After the addition, the resulting reaction mixture was warmed to a temperature of 90° C. and stirred for 1.5 h. Thereafter, the reaction mixture was cooled to a temperature of about 25° C. and chromatographed with a silica gel column eluted with a gradient of from 2%:98% EtOAc:n-hexane to 10%:90% EtOAc:n-hexane to provide 4270 mg of the compound of formula OH as a colorless solid (yield 98%).

The identity of the compound of formula QH, benzyl (exo)-bicyclo[3.3.1]nonan-3-ylcarbamate, was confirmed using $^1$H NMR and LC/MS.

Compound QH: $^1$H NMR: $\delta_H$ (400 MHz, CDCl$_3$): 1.32 (td, J=12.25, 3.71 Hz, 2H), 1.44-1.80 (m, 8H), 1.97-2.09 (m, 4H), 4.28-4.46 (m, 2H), 5.08 (s, 2H), 7.26-7.35 (m, 5H); LC/MS: m/z=274:2 [M+H]$^+$ (Calc: 273).

Under a hydrogen atmosphere, a mixture of the compound of formula QH (4456 mg, 16.30 mmol), 10% palladium on carbon (694 mg, 0.652 mmol), and EtOH (50 mL) was stirred at a temperature of about 25° C. for 3 h. After filtering off the Pd/C and washing with EtOH, the mixture was concentrated under reduced pressure to a volume of 20 mL. The ethanol solution contained 2270 mg (16.30 mmol) of the compound of formula QA.

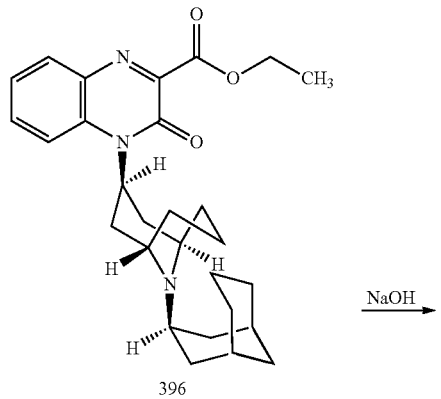

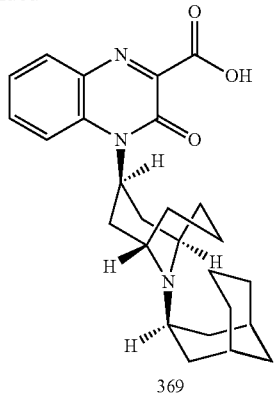

In a manner similar to that described above, Substituted-Quinoxaline-Type Piperidine Compounds 396 (yield 8% for three steps) and 369 (yield 91%) were prepared from the compound of formula LB by using (endo)-bicyclo[3.3.1]nonan-3-amine (QI) in place of the compound of formula QA.

The identity of Substituted-Quinoxaline-Type Piperidine Compound 396, ethyl 4-((endo)-9-((endo)-bicyclo[3.3.1]nonan-3-yl)-9-azabicyclo[3.3.1]nonan-3-yl)-3-oxo-3,4-dihydroquinoxaline-2-carboxylate, was confirmed using $^1$H NMR and LC/MS.

Substituted-Quinoxaline-Type Piperidine Compound 396: $^1$H NMR: $\delta_H$ (400 MHz, CDCl$_3$): 0.98-1.12 (m, 5H), 1.26 (s, 1H), 1.43 (m, 7H), 1.57 (m, 1H), 1.75-1.85 (m, 5H), 2.10 (m, 5H), 2.40-2.45 (m, 1H), 2.72 (br, 2H), 3.00-3.07 (m, 1H), 3.53 (d, J=10.11 Hz, 2H), 4.51 (q, J=7.07 Hz, 2H), 5.20 (br, 1H), 7.36 (t, J=3.54 Hz, 1H), 7.65 (s, 2H), 7.93 (d, J=8.08 Hz, 1H); LC/MS: m/z=464.1 [M+H]$^+$ (Calc: 463).

The identity of Substituted-Quinoxaline-Type Piperidine Compound 369, 4-((endo)-9-((endo)-bicyclo[3.3.1]nonan-3-yl)-9-azabicyclo[3.3.1]nonan-3-yl)-3-oxo-3,4-dihydroquinoxaline-2-carboxylic acid, was confirmed using $^1$H NMR and LC/MS.

Substituted-Quinoxaline-Type Piperidine Compound 369: $^1$H NMR: $\delta_H$ (400 MHz, CDCl$_3$): 0.84-0.89 (m, 1H), 1.27 (m, 4H), 1.40-1.52 (m, 2H), 1.66 (m, 5H), 1.85 (m, 1H), 2.11 (m, 2H), 2.28 (s, 4H), 2.50 (m, 2H), 2.76 (m, 1H), 3.00 (t, J=12.63 Hz, 2H), 3.69-3.74 (m, 1H), 4.16 (d, J=10.11 Hz, 2H), 6.78 (s, 1H), 7.56 (t, J=7.58 Hz, 1H), 7.93 (t, J=7.83 Hz, 1H), 8.19 (d, J=8.08 Hz, 1H), 9.07 (t, J=7.58 Hz, 1H), 11.08 (s, 1H); LC/MS (100%, t$_r$=1.55 min): m/z=436.2 [M+H]$^+$ (Calc: 436).

The compound of formula QI was prepared as follows:

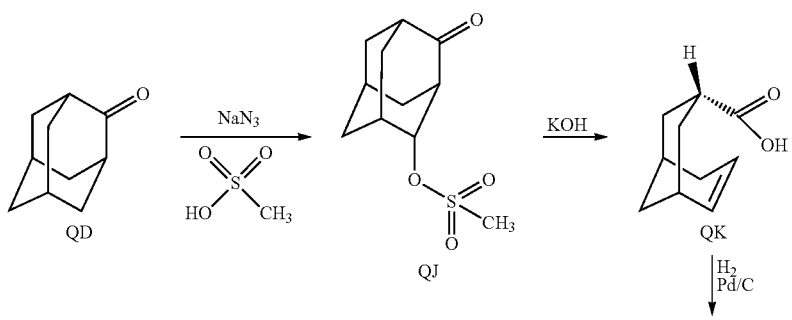

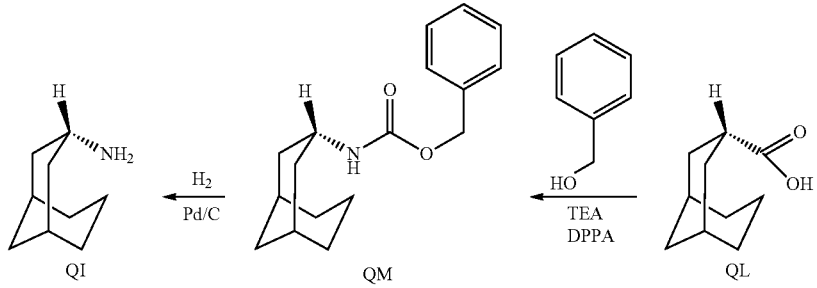

Under a nitrogen atmosphere, to a solution of the compound of formula QD (6.0 g, 39.9 mmol) in methanesulfonic acid (33.7 mL, 519 mmol) at a temperature of 20° C. was added sodium azide (2.726 g, 41.9 mmol) portionwise over 2.5 h. After the addition, the resulting reaction mixture was stirred for 3 days at 20° C. Thereafter, ice water (300 mL) was poured into the reaction mixture to provide a white precipitate that was collected by filtration, washed with water, and dried for 6 h under reduced pressure at 40° C. to provide 5.63 g of the compound of formula QJ as a colorless solid with a melting point of 69-72° C. (yield 58%).

The identity of the compound of formula QJ, methanesulfonic acid 4-oxo-adamantan-2-yl ester, was confirmed using $^1$H NMR.

Compound QJ: $^1$H NMR: $\delta_H$ (400 MHz, CDCl$_3$): 1.75-2.12 (m, 9H), 2.31 (m, 1H), 2.41-2.50 (m, 2H), 2.58 (s, 1H), 2.88 (s, 1H), 3.05 (d, J=6.59 Hz, 3H), 4.80 (t, J=3.55 Hz, 1H).

To a solution of the compound of formula QJ (5.63 g, 23.04 mmol) in EtOH (100 mL) at a temperature of about 25° C. was added a KOH (8.469 g, 151 mmol) in water (67 mL) solution. After the addition, the resulting reaction mixture was warmed to a temperature of 110° C. and stirred for 12 h. Thereafter, the reaction mixture was cooled to a temperature of about 25° C., 10% aqueous HCl was added to adjust the pH within the range of from about 3 to about 4, and a colorless precipitate formed. The precipitate was collected by filtration, washed with water, concentrated under reduce pressure, and dried for 8 h under reduced pressure at 50° C. to provide 3.61 g of the compound of formula as a colorless solid with a melting point of 189-192° C. (yield 94%).

The identity of the compound of formula QK, (endo)-bicyclo[3.3.1]non-6-ene-3-carboxylic acid, was confirmed using $^1$H NMR.

Compound QK: $^1$H NMR: $\delta_H$ (400 MHz, CDCl$_3$): 1.64 (m, 4H), 2.07-2.42 (m, 6H), 2.58 (t, J=6.32 Hz, 1H), 5.57-5.68 (m, 2H).

In a manner similar to the preparation of the compound of formula QF above, the compound of formula QL was prepared from the compound of formula OK (yield 99%).

The identity of the compound of formula QL, (endo)-bicyclo[3.3.1]nonane-3-carboxylic acid, was confirmed using $^1$H NMR.

Compound QL: $^1$H NMR: $\delta_H$ (400 MHz, CDCl$_3$): 1.17 (d, J=13.18 Hz, 1H), 1.37-1.82 (m, 10H), 2.12 (m, 4H), 2.51-2.60 (m, 1H).

In a manner similar to the preparation of the compound of formula QH above, the compound of formula QM was prepared from the compound of formula QL (yield 90%).

The identity of the compound of formula QM, benzyl (endo)-bicyclo[3.3.1]nonan-3-ylcarbamate, was confirmed using $^1$H NMR and LC/MS.

Compound QM: $^1$H NMR: $\delta_H$ (400 MHz, CDCl$_3$): 1.31 (m, 2H), 1.44-1.76 (m, 9H), 2.04 (s, 2H), 2.09 (s, 2H), 4.31-4.40 (m, 2H), 5.08 (s, 2H), 7.28-7.39 (m, 5H); LC/MS: m/z=274.2 [M+H]$^+$ (Calc: 273).

Under a hydrogen atmosphere, a mixture of the compound of formula QM (4.11 g, 15.03 mmol), 10% palladium on carbon (0.64 g, 0.601 mmol), and EtOH (45 mL) was stirred at a temperature of about 25° C. for 3 h. After filtering off the Pd/C and washing with EtOH, the mixture was concentrated under reduced pressure to a volume of 10 mL. The ethanol solution contained 2.093 g (15.03 mmol) of the compound of formula QI.

Alternatively the compound of formula QA can be prepared by the two further synthetic routes shown below:

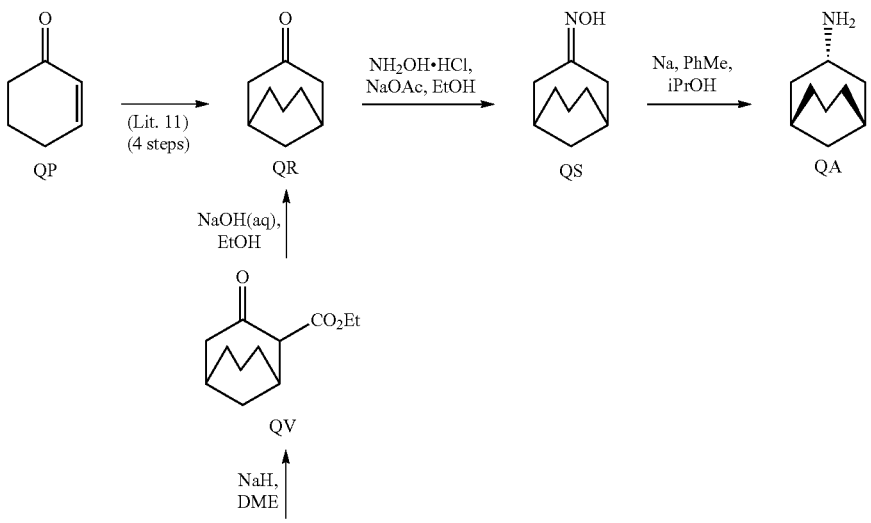

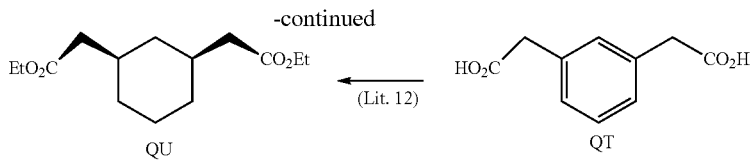

(Lit. 12)

The compound of formula QR can be prepared according to a literature procedure described in "Improved synthetic methods for bicyclo[3.3.1]nonan-3-one". Momose et al., *Chemical and Pharmaceutical Bulletin* 26(1):288-295 (1978) (Lit. 11) starting from cyclohexen-2-one, QP. The compound of formula QR can also be prepared starting from cis-cyclohexane-1,3-diacetic acid diethyl ester, as described in H. K. Hall, *J. Org. Chem.* 28:3213-3214 (1963) (Lit. 12).

The compound of formula QU can be prepared as follows (Lit. 12):

Concentrated sulfuric acid (2 mL) was added at a temperature of about 25° C. to a solution of phenyl-1,3-diacetic acid (QT, 50 g, 0.26 mol, TCI US) in ethanol (500 mL). The resulting mixture was heated under reflux for 24 h. After cooling to a temperature of about 25° C., the mixture was concentrated to about 200 mL under reduced pressure, and diluted with toluene (400 mL). The toluene solution was washed with water (100 mL), and brine (100 mL) and concentrated to dryness in vacuo to give intermediate phenyl-1,3-diacetic acid diethyl ester as a colorless oil (63 g, 98%).

The identity of the intermediate phenyl-1,3-diacetic acid diethyl ester was confirmed using $^1$H NMR.

Intermediate phenyl-1,3-diacetic acid diethyl ester: $^1$H NMR (CDCl$_3$, 400 MHz): 7.26-7.3 (m, 1H), 7.18-7.21 (m, 3H), 4.15 (q, J=7.1 Hz, 4H), 3.6 (s, 4H), 1.25 (t, J=7.2 Hz, 6H).

A mixture of phenyl-1,3-diacetic acid diethyl ester (63 g, 0.25 mol) and platinum dioxide (2 g, 0.09 mol) in acetic acid (250 mL) was degassed and stirred under an hydrogen atmosphere at 30° C. for 15 h. The reaction mixture was flushed with argon, and diluted with water (40 mL). Subsequently, the catalyst was removed by filtration and the solution was concentrated to about 200 mL. The resulting mixture was then diluted with toluene (400 mL). The mixture was washed with water twice (100 mL each), NaHCO$_3$ (100 mL each) and brine (100 mL). The solvent was removed under reduced pressure to give crude cis-cyclohexane-1,3-diacetic acid diethyl ester QU as a colorless oil (Lit. 12).

The identity of the compound of formula QU was confirmed using $^1$H NMR.

Compound QU: $^1$H NMR (CDCl$_3$, 400 MHz): 4.15 (q, J=7.2 Hz, 4H), 2.17 (d, J=7.0 Hz, 4H), 1.4-1.9 (m, 7H), 1.25 (t, J=7.1 Hz, 6H), 0.83-0.92 (m, 2H), 0.71 (dd, J=11.8, 11.9 Hz).

The compound of formula QV can be prepared as follows:

Cis-cyclohexane-1,3-diacetic acid diethyl ester QU was dissolved in dry DME (300 mL). To this solution, sodium hydride (15 g) was added and the suspension stirred at 94° C. for 16 h. After cooling, the reaction mixture was slowly poured into ice-water (500 mL) and extracted four times with EtOAc (200 mL each). The combined organic layer was washed with brine, and concentrated to give 3-oxo-bicyclo[3.3.1]nonane-2-carboxylic acid ethyl ester QV which was used without purification in the next step.

Alternative preparation of bicyclo[3.3.1]nonan-3-one (QR):

Compound QV from the previous reaction was dissolved in ethanol (150 mL). To this solution, sodium hydroxide (30 g, 750 mmol) in water (150 mL) was added and the mixture heated to 70° C. for 8 h. The reaction mixture was concentrated in vacuo, diluted with brine (150 mL) and extracted three times with ether (150 mL each). The combined organic extracts were concentrated to dryness in vacuo to give bicyclo[3.3.1]nonan-3-one QR as a white solid (Yield: 18 g, 51% from 1,3-phenyl-diacetic acid).

The identity of the compound of formula QR was confirmed using $^1$H NMR.

Compound QR: $^1$H-NMR (CDCl$_3$) δ: 2.52-1.31 (m, 6H), 1.82 (m, 2H), 1.70-1.56 (m, 5H), 1.54-1.32 (m, 2H).

Preparation of bicyclo[3.3.1]nonan-3-one oxime (QS):

Under a nitrogen atmosphere, to a solution of QR (975 mg, 7.05 mmol) in ethanol (40 mL) at a temperature of about 25° C. was added sodium acetate (1,157 mg, 14.11 mmol) and hydroxylamine hydrochloride (980 mg, 14.11 mmol). The mixture was stirred at a temperature of about 25° C. for 2 hr. The reaction mixture was diluted with saturated NaHCO$_3$, then extracted thrice with EtOAc (30 mL each). The organic layers were combined and washed with saturated NaCl. The combined organic layers were dried over MgSO$_4$ and evaporated in vacuo to give QS (800 mg, 76%) as a yellow solid. The oxime was used for the next reaction without purification.

The identity of the compound of formula QS was confirmed using $^1$H NMR.

Compound QS: $^1$H-NMR (CDCl$_3$) δ: 1.40 (m, 1H), 1.50-1.80 (m, 8H), 1.99-2.17 (m, 3H), 2.40 (d, J=8.0 Hz, 2H), 3.20 (d, J=16.0 Hz, 1H).

Alternative preparation of bicyclo[3.3.1]non-3-ylamine (QA) (Ref: *J. Med. Chem.* 49:1781-1791 (2006)):

Under a nitrogen atmosphere, to a refluxing suspension of sodium (2.401 g, 104 mmol) in toluene (20 mL) at a temperature of about 115° C. was added dropwise over 30 min bicyclo[3.3.1]nonan-3-one oxime (QS, 1.60 g, 10.44 mmol) in 2-propanol (8 mL). The mixture was stirred at reflux for 2 hr. After addition of the oxime solution is completed, 2-propanol (3 mL) was added dropwise. The reaction mixture was heated to reflux until all of the Na was consumed followed by cooling to a temperature of about 25° C. The reaction mixture was then quenched by the addition of H$_2$O (20 mL). The organic layer was separated, and washed twice with 1N HCl (30 mL each). The acidic solution was made alkaline by the addition of 2N NaOH (50 mL), and extracted thrice with Et$_2$O (50 mL each). The organic layers were combined and washed with saturated NaCl (50 mL). The organic layer was dried over Na$_2$SO$_4$, filtered and concentrated in vacuo to give of bicyclo[3.3.1]non-3-ylamine QA. This compound was used in the next step without purification in 2-propanol solution.

The identity of the compound of formula QA was confirmed using $^1$H NMR.

Compound QA: $^1$H-NMR (CDCl$_3$) δ: 1.20-1.70 (m, 10H), 1.90 (m, 4H), 3.38 (m, 1H).

5.43 Example 43

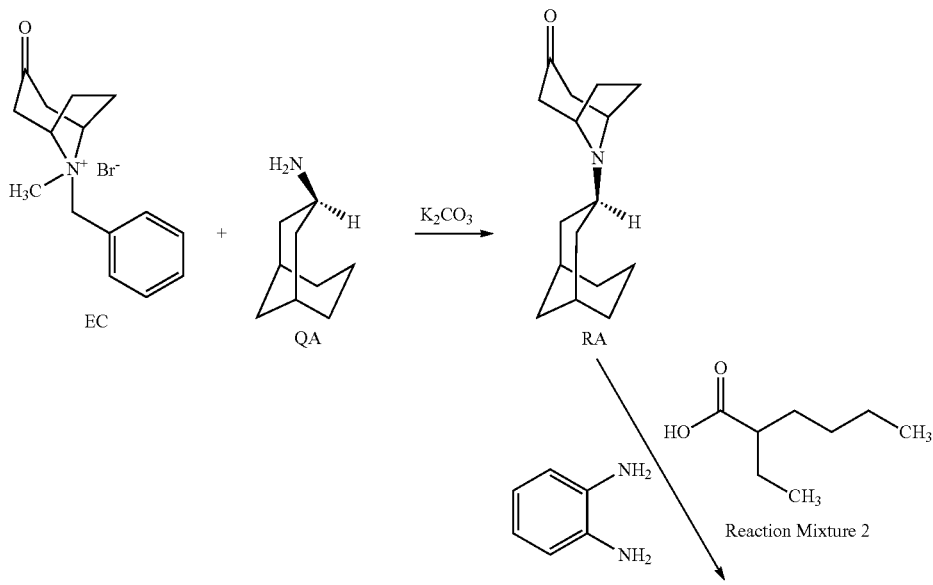

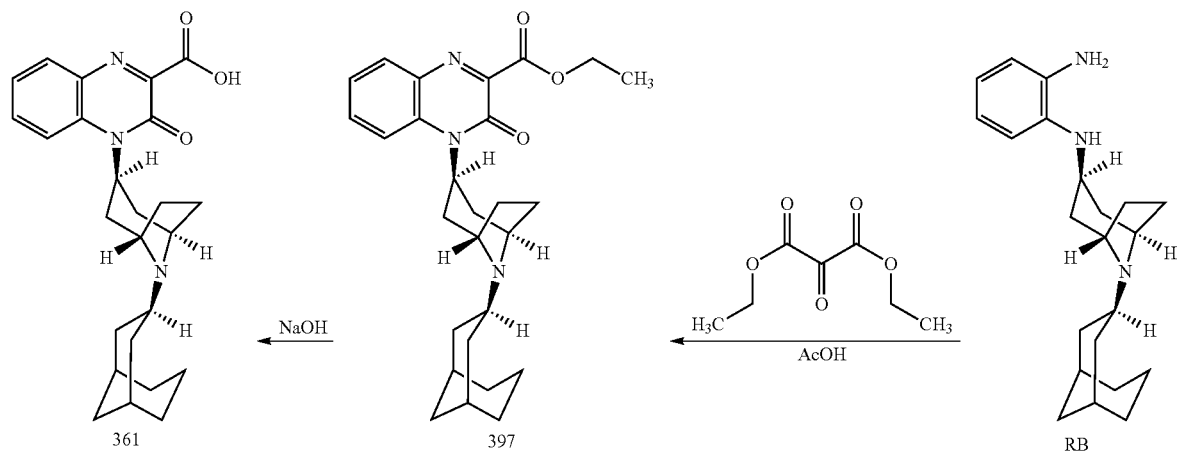

To a mixture of the compound of formula QA (2270 mg, 16.30 mmol), K₂CO₃ (225.3 mg, 1.63 mmol), EtOH (20 mL), and water (5 mL) at a temperature of about 25° C. was added dropwise a mixture of the compound of formula EC (5058 mg, 16.30 mmol), EtOH (20 mL), and water (27 mL). After the addition, the resulting reaction mixture was warmed to a temperature of 90° C. and stirred for 4 h. Thereafter, the reaction mixture was cooled to a temperature of about 25° C., diluted with saturated aqueous NaHCO₃, then extracted twice with EtOAc/water (100 mL for each extraction). The organic portions were combined, dried (Na₂SO₄), and concentrated under reduced pressure to provide an oil. The oil was chromatographed with a silica gel column eluted with a gradient of from 20%:80% EtOAc:n-hexane to 80%:20% EtOAc:n-hexane to provide 2030 mg of the compound of formula RA as a colorless solid (yield 50%).

The identity of the compound of formula RA, 8-((exo)-bicyclo[3.3.1]nonan-3-yl)-8-azabicyclo[3.2.1]octan-3-one, was confirmed using $^1$H NMR and LC/MS.

Compound RA: $^1$H NMR: $\delta_H$ (400 MHz, CDCl₃): 1.79 (m, 12H), 2.26 (m, 8H), 2.87 (d, J=13.64 Hz, 2H), 3.52 (td, J=11.12, 5.56 Hz, 1H), 3.99 (s, 2H); LC/MS: m/z=248.5 [M+H]⁺ (Calc: 247).

Under a nitrogen atmosphere, to a solution of the compound of formula RA (2029 mg, 8.20 mmol) in CH₂Cl₂ (25 mL) at a temperature of about 25° C. was added 1,2-phenylenediamine (2661 mg, 24.61 mmol) and 2-ethylhexanoic acid (1.971 mL, 12.30 mmol). The mixture was stirred at a temperature of about 25° C. for 30 min to provide reaction mixture 1.

Under a nitrogen atmosphere, to a solution of sodium tetrahydroborate (1241 mg, 32.8 mmol) in CH$_2$Cl$_2$ (17 mL) at a temperature of about 25° C. was added 2-ethylhexanoic acid (18.40 mL, 115 mmol). The mixture was stirred at a temperature of about 25° C. for 30 min to provide reaction mixture 2.

Under a nitrogen atmosphere, to reaction mixture 1 at 0° C. was added reaction mixture 2 dropwise over a 15 min period. After the addition, the resulting reaction mixture was warmed to a temperature of about 25° C. and stirred for 30 min. Thereafter, the reaction mixture was warmed to a temperature of 60° C. and stirred for 16 h. After cooling the reaction mixture to a temperature of about 25° C., saturated aqueous NaHCO$_3$ (20 mL) was added, the mixture stirred for 10 min, then extracted twice with 1M aqueous K$_2$CO$_3$/EtOAc (150 mL for each extraction). The organic portions were combined, dried (Na$_2$SO$_4$), and concentrated under reduced pressure to provide a yellow oil. The oil was chromatographed with a silica gel column eluted with a gradient of from 97%:3% CHCl$_3$:(10% NH$_3$ in MeOH) to 80%:20% CHCl$_3$:(10% NH$_3$ in MeOH) to provide 874 mg of the compound of formula RB as a pale yellow amorphous solid (yield 31%).

The identity of the compound of formula RB, -((endo)-8-((exo)-bicyclo[3.3.1]nonan-3-yl)-8-azabicyclo[3.2.1]octan-3-yl)benzene-1,2-diamine, was confirmed using $^1$H NMR and LC/MS.

Compound RB: $^1$H NMR: $\delta_H$ (400 MHz, CDCl$_3$): 0.91 (m, 3H), 1.26-2.10 (m, 20H), 2.35 (m, 2H), 3.28-3.33 (m, 1H), 3.69 (m, 3H), 6.57 (d, J=7.58 Hz, 1H), 6.75 (m, 3H); LC/MS: m/z=340.6 [M+H]$^+$ (Calc: 339).

Under a nitrogen atmosphere, to a solution of the compound of formula RB (870 mg, 2.56 mmol) in xylene (15 mL) at a temperature of about 25° C. was added diethyl 2-oxomalonate (0.494 mL, 3.07 mmol) and AcOH (0.176 mL, 3.07 mmol). After the addition, the resulting reaction mixture was warmed to a temperature of 130° C. and stirred for 1 h. Thereafter, the reaction mixture was cooled to a temperature of about 25° C., diluted with saturated aqueous NaHCO$_3$, extracted twice with EtOAc (100 mL for each extraction), dried (Na$_2$SO$_4$), and concentrated under reduced pressure to provide an orange oil. The oil was chromatographed with an amino-silica gel column (Yamazen Corp. W091-01) eluted with a gradient of from 5%:95% EtOAc:n-hexane to 30%:70% EtOAc:n-hexane to provide a pale yellow solid. The solid was triturated with 1:4 Et$_2$O:n-hexane and dried under reduced pressure at 70° C. to provide 343 mg of Substituted-Quinoxaline-Type Piperidine Compound 397 as a colorless solid (yield 30%).

The identity of Substituted-Quinoxaline-Type Piperidine Compound 397, ethyl 4-((endo)-8-((exo)-bicyclo[3.3.1]nonan-3-yl)-8-azabicyclo[3.2.1]octan-3-yl)-3-oxo-3,4-dihydroquinoxaline-2-carboxylate, was confirmed using $^1$H NMR and LC/MS.

Substituted-Quinoxaline-Type Piperidine Compound 397: $^1$H NMR: $\delta_H$ (400 MHz, CDCl$_3$): 0.83-0.88 (m, 1H), 126 (dd, J=33.09, 17.94 Hz, 3H), 1.51 (m, 11H), 1.91 (m, 8H), 2.20 (s, 3H), 2.79 (dt, J=11.62, 3.66 Hz, 1H), 3.70 (s, 2H), 4.50 (q, J=7.07 Hz, 2H), 5.20 (br, 1H), 7.34 (t, J=7.07 Hz, 1H), 7.61 (q, J=7.92 Hz, 2H), 7.91 (d, J=7.58 Hz, 1H); LC/MS: m/z=450.1 [M+H]$^+$ (Calc: 449).

To a solution of Substituted-Quinoxaline-Type Piperidine Compound 397 (343 mg, 0.763 mmol) in ethanol (10 mL) at a temperature of about 25° C. was added 2N aqueous NaOH (1.144 mL, 2.289 mmol). The resulting reaction mixture was stirred at a temperature of about 25° C. for 1 h. Thereafter, the reaction mixture was concentrated under reduced pressure to provide a residue. The residue was diluted with water (2 mL) to form a pale yellow solution, neutralized with 2N aqueous HCl (1.144 mL), and sonicated to provide a white precipitate. The precipitate was collected by filtration, washed with water, and dried for 8 h under reduced pressure at 75° C. to provide 312 mg of Substituted-Quinoxaline-Type Piperidine Compound 361 as a colorless solid (yield 97%).

The identity of Substituted-Quinoxaline-Type Piperidine Compound 361, 4-((endo)-8-((exo)-bicyclo[3.3.1]nonan-3-yl)-8-azabicyclo[3.2.1]octan-3-yl)-3-oxo-3,4-dihydroquinoxaline-2-carboxylic acid, was confirmed using $^1$H NMR and LC/MS.

Substituted-Quinoxaline-Type Piperidine Compound 361: $^1$H NMR: $\delta_H$ (400 MHz, CDCl$_3$): 0.86 (m, 2H), 1.64 (m, 6H), 1.89 (m, 1H), 2.03 (dq, J=9.09, 2.44 Hz, 2H), 2.42 (m, 9H), 3.01 (m, 2H), 3.49 (s, 1H), 4.26 (d, J=1.01 Hz, 2H), 6.55 (s, 1H), 7.55 (t, J=7.33 Hz, 1H), 7.92 (dd, J=9.85, 5.81 Hz, 1H), 8.18 (d, J=7.58 Hz, 1H), 8.40 (d, J=8.59 Hz, 1H), 11.41 (s, 1H); LC/MS (100%, t$_r$=1.38 min): m/z=422.5 [M+H]$^+$ (Calc: 421.5).

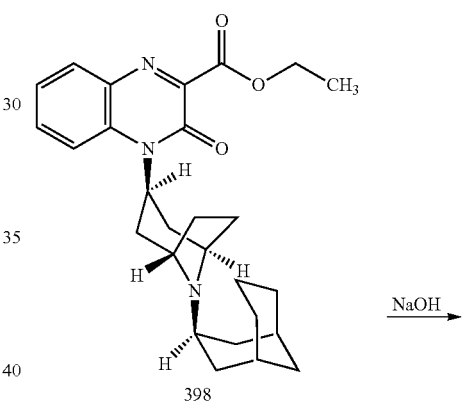

398

NaOH

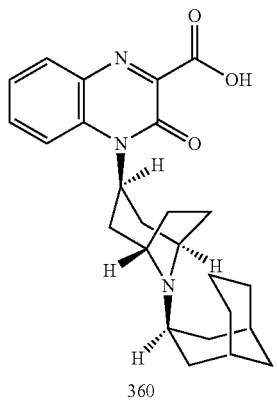

360

In a manner similar to that described above, Substituted-Quinoxaline-Type Piperidine Compounds 398 (yield 4% for three steps) and 360 (yield 87%) were prepared from the compound of formula EC by using the compound of formula QI in place of the compound of formula QA.

The identity of Substituted-Quinoxaline-Type Piperidine Compound 398, ethyl 4-((endo)-8-((endo)-bicyclo[3.3.1]nonan-3-yl)-8-azabicyclo[3.2.1]octan-3-yl)-3-oxo-3,4-dihydroquinoxaline-2-carboxylate, was confirmed using $^1$H NMR and LC/MS.

Substituted-Quinoxaline-Type Piperidine Compound 398: $^1$H NMR: $\delta_H$ (400 MHz, CDCl$_3$): 0.86 (dq, J=10.11, 2.69 Hz, 1H), 1.07 (m, 3H), 1.21-1.45 (m, 10H), 1.65-2.37 (m, 15H), 3.67 (t, J=2.53 Hz, 2H), 4.50 (q, J=7.07 Hz, 2H), 5.18 (br, 1H), 7.35 (t, J=7.33 Hz, 1H), 7.60 (t, J=9.60 Hz, 2H), 7.91 (d, J=8.08 Hz, 1H); LC/MS: m/z=450.2 [M+H]$^+$ (Calc: 449).

The identity of Substituted-Quinoxaline-Type Piperidine Compound 360, 4-((endo)-8-((endo)-bicyclo[3.3.1]nonan-3-yl)-8-azabicyclo[3.2.1]octan-3-yl)-3-oxo-3,4-dihydroquinoxaline-2-carboxylic acid, was confirmed using $^1$H NMR and LC/MS.

Substituted-Quinoxaline-Type Piperidine Compound 360: $^1$H NMR: $\delta_H$ (400 MHz, CDCl$_3$): 0.84-0.88 (m, 4H), 1.38-1.46 (m, 1H), 1.54-1.65 (m, 3H), 2.27 (m, 6H), 2.46 (dt, J=12.80, 4.93 Hz, 3H), 2.95 (br, 3H), 4.25 (s, 2H), 6.61 (s, 1H), 7.51 (d, J=8.08 Hz, 1H), 7.88 (dd, J=9.60, 5.05 Hz, 1H), 8.14 (d, J=8.59 Hz, 1H), 8.44 (d, J=4.04 Hz, 1H), 11.55 (s, 1H); LC/MS (100%, $t_r$=1.48 min): m/z=422.2 [M+H]$^+$ (Calc: 421.5).

Alternatively the compound RB and compound 361 can be synthesized via an alternative route, which is shown below:

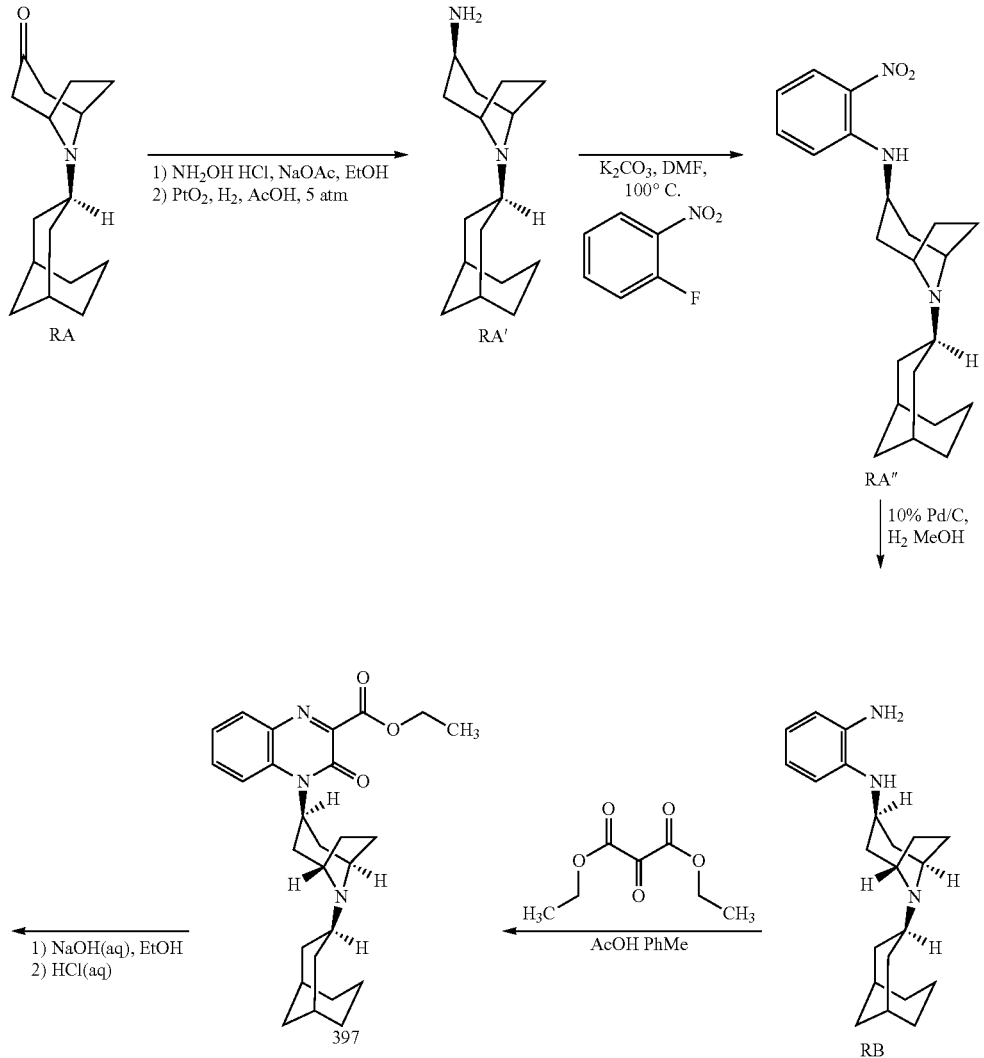

In an alternative procedure, the intermediate (RA) can be converted to the oxime using hydroxylamine hydrochloride and sodium acetate in ethanol, and the oxime reduced to 8-exo bicyclo[3.3.1]non-3-yl-8-endo-aza-bicyclo[3.2.1]oct-3-ylamine (RA') by hydrogenation using platinum oxide in acetic acid under 5 atmospheres of hydrogen. Intermediate (RA') can be reacted with 2-fluoro nitrobenzene and potassium carbonate in DMF to give 8-exo-bicyclo[3.3.1]non-3-yl-8-endo-aza-bicyclo[3.2.1]oct-3-yl)-(2-nitro-phenyl)-amine (RA"). Finally reduction of the nitro group using 10% palladium on charcoal can give N-(exo-8-bicyclo[3.3.1]non-3-yl-8-endo-aza-bicyclo[3.2.1]oct-3-yl)benzene-1,2-diamine (RB).

5.44 Example 44

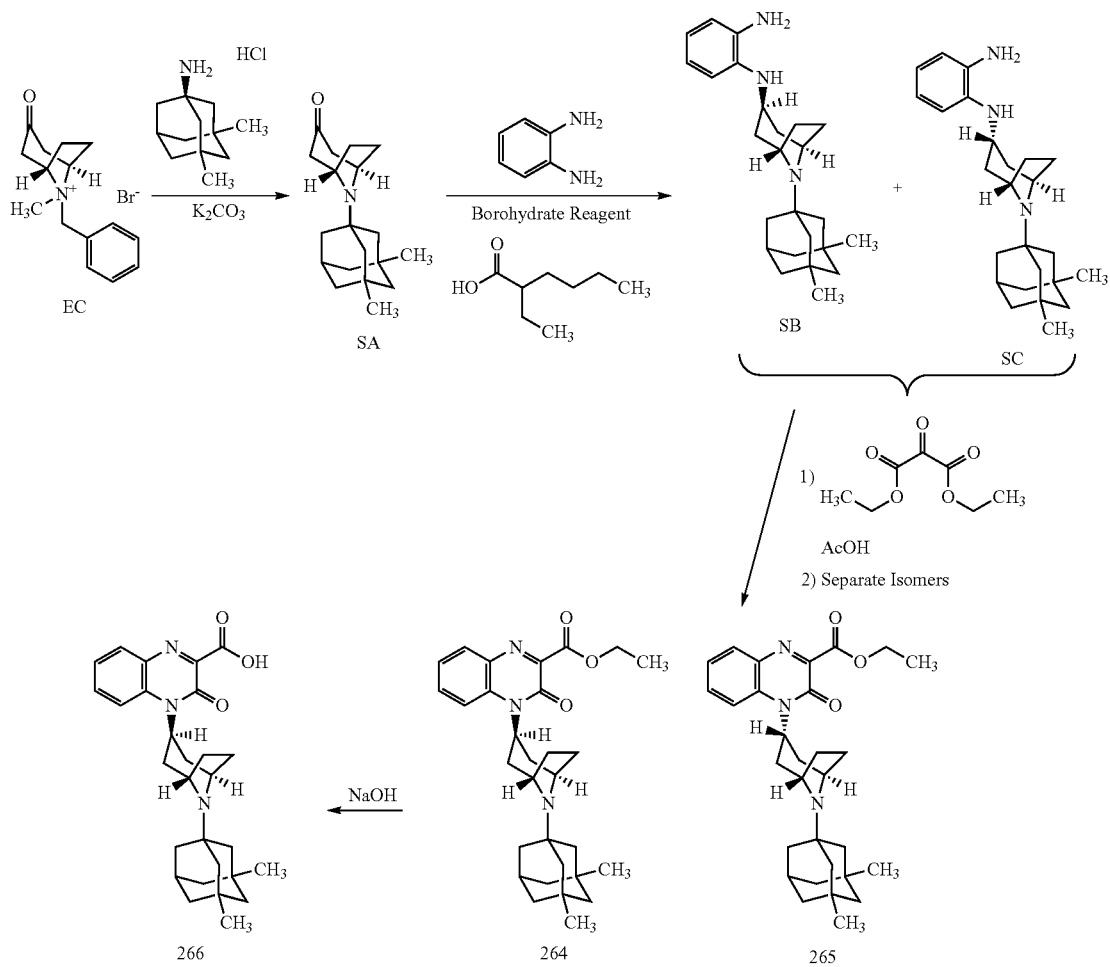

266      264      265

In a manner similar to the preparation of the compound of formula DC in Example 13, the compound of formula SA was prepared except that the compound of formula EC was used in place of the compound of formula DB and memantine hydrochloride (i.e., the hydrochloride of 1-amine-3,5-dimethyl-adamantane, Sigma-Aldrich) was used in place of 1-adamantylamine (yield 5%).

The identity of the compound of formula SA, 8-(3,5-dimethyl-adamantan-1-yl)-8-aza-bicyclo[3.2.1]octan-3-one, was confirmed using $^1$H NMR.

Compound SA: $^1$H NMR: $\delta_H$ (400 MHz, CDCl$_3$): 3.95 (2H, m), 2.52 (2H, dd, J=16.7, 6.7 Hz), 2.28 (2H, dd, J=16.7, 3.3 Hz), 2.12 (1H, m), 1.80 (2H, m), 1.67-1.51 (9H, m), 1.37-1.23 (8H, m), 1.10 (2H, m), 0.86 (6H, s).

In a manner similar to the preparation of the compounds of formula DD and DE in Example 13, the compounds of formula SB and SC were prepared except that the compound of formula SA was Used in place of the compound of formula DC (yield 85% of 1:1 SB:SC).

The identity of the compound of formula SB:SC endo:exo isomeric mixture, N-[8-3,5-dimethyl-adamantan-1-yl)-8-aza-bicyclo[3.2.1]oct-3-yl]-benzene-1,2-diamine, was confirmed using $^1$H NMR.

Compounds SB:SC: $^1$H NMR: $\delta_H$ (400 MHz, CDCl$_3$): 6.84-6.55 (4H, m), 3.90 (1H, m, isomer 1 (SD)), 3.80 (1H, m, isomer 2 (SC)), 3.69 (1H, m), 3.0 (3H, bs), 2.41 (1H, m), 2.20-2.04 (3H, m), 1.95-1.76 (5H, m), 1.62 (2H, m), 1.50-1.05 (12H, m), 1.36 (3H, s, isomer 1 (SB)), 1.33 (3H, s, isomer 2 (SC)).

To the above SB:SC mixture (1.18 g, 3.1 mmol) and toluene (20 mL) was added acetic acid (0.2 mL, 3.41 mmol) followed by diethyl 2-oxomalonate (0.72 mL, 4.66 mmol). The reaction mixture was refluxed for 4 h, cooled, diluted with EtOAc (100 mL), washed with 1M aqueous K$_2$CO$_3$ solution (100 mL), dried (MgSO$_4$), and evaporated to dryness under reduced pressure to provide a yellow gum. Flash chromatography of the gum with a silica gel column eluting with 400:100:10:1 hexanes:EtOAc:MeOH:ammonia provided 420 mg of Substituted-Quinoxaline-Type Piperidine Compound 264 (yield 28%).

The identity of Substituted-Quinoxaline-Type Piperidine Compound 264, endo-N-[8-(3,5-dimethyl-adamantan-1-yl)-8-aza-bicyclo[3.2.1]oct-3-yl]-benzene-1,2-diamine, was confirmed by $^1$H NMR and TLC.

Substituted-Quinoxaline-Type Piperidine Compound 264: $^1$H NMR: $\delta_H$ (400 MHz, CDCl$_3$): 7.92 (1H, dd, J=8, 1 Hz), 7.62 (1H, t, J=8 Hz), 7.53 (1H, d, J=8 Hz), 7.34 (1H, dt, J=8, 1 Hz), 4.50 (2H, q, J=8.9 Hz), 3.86 (1H, m), 2.23 (4H, m), 2.12 (1H, m), 1.83 (4H, m), 1.46 (2H, m), 1.43 (3H, t, J=8.9 Hz), 1.26 (9H, m), 1.10 (2H, m), 0.86 (6H, s); TLC (SiO$_2$) 400:100:10:1 hexanes:EtOAc:MeOH:ammonia: Rf=0.26 with UV detection, Dragendorffs reagent.

Further elution with 300:100:10:1 hexanes:EtOAc:MeOH:ammonia provided 300 mg of Substituted-Quinoxaline-Type Piperidine Compound 265 (yield 20%).

The identity of Substituted-Quinoxaline-Type Piperidine Compound 265, exo-N-[8-(3,5-dimethyl-adamantan-1-yl)-8-aza-bicyclo[3.2.1]oct-3-yl]-benzene-1,2-diamine, was confirmed by $^1$H NMR and TLC.

Substituted-Quinoxaline-Type. Piperidine Compound 265: $^1$H NMR: $\delta_H$ (400 MHz, CDCl$_3$): 8.34 (1H, bs), 7.91 (1H, dd, J=9.2, 1.2 Hz), 7.60 (1H, dt, J=9.2, 1.2 Hz), 7.33 (1H, dt, J=9.2, 1.2 Hz), 4.50 (2H, q, J=8 Hz), 3.91 (2H, m), 2.63 (2H, t, J=16 Hz), 2.15 (1H, m), 1.88-1.72 96H, m), 1.56 (4H, m), 1.52 (2H, m), 1.43 (3H, t, J=8 Hz), 1.37-1.24 (8H, m), 1.13 (2H, m); TLC (SiO$_2$) 300:100:10:1 hexanes:EtOAc:MeOH:ammonia: Rf=0.19 with UV detection, Dragendorffs reagent.

Substituted-Quinoxaline-Type Piperidine Compound 266 was prepared from Substituted-Quinoxaline-Type Piperidine Compound 264 in a manner similar to the preparation of Substituted-Quinoxaline-Type Piperidine Compound 111 in Example 5 (yield 83%).

The identity of Substituted-Quinoxaline-Type Piperidine Compound 266, endo-8-aza-bicyclo[3.2.1]oct-3-yl]-3-oxo-3,4-dihydro-quinoxaline-2-carboxylic acid, was confirmed using $^1$H NMR.

Substituted-Quinoxaline-Type Piperidine Compound 266: $^1$H NMR: $\delta_H$ (400 MHz, DMSO-d$_6$): 7.92 (1H, m), 7.80 (1H, m), 7.68 (1H, bs), 7.47 (1H, m), 4.85 (1H, bs), 3.56 (2H, m), 2.49-2.12 (6H, m), 2.12-1.52 (15H, m), 1.35 (2H, m).

5.45 Example 45

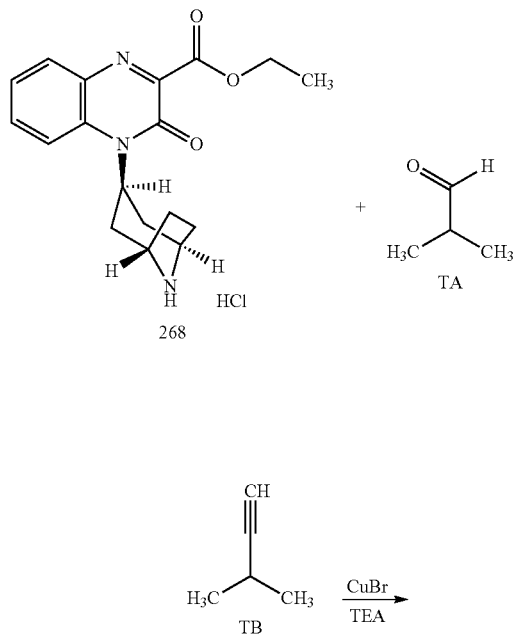

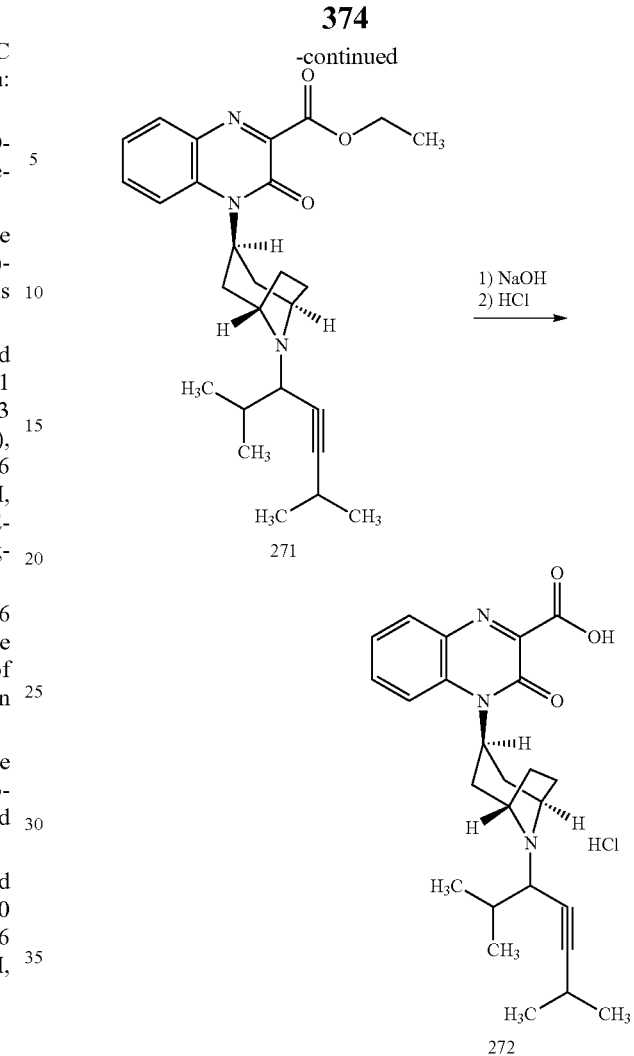

In a dry and argon-flushed 10 mL vial, CuBr (0.05 eq, Sigma-Aldrich) was suspended in dry toluene (2.5 mL) and stirred at a temperature of about 25° C. for 30 min. Thereafter, MS 4 Å molecular sieves (200 mg) were added, followed by 3-methylbut-1-yne (TB, 2.0 eq, Sigma-Aldrich), isobutyraldehyde (TA, 1.5 eq, Sigma-Aldrich), the hydrochloride of Substituted-Quinoxaline-Type Piperidine Compound 268 (200 mg, 1.0 eq), and TEA (1.2 eq). The resulting reaction mixture was warmed to 60° C. and shaken for 2 h. After the molecular sieves were filtered off, the mixture was washed with diethyl ether and the filtrate was concentrated under reduced pressure to provide a residue. The residue was chromatographed with a silica gel column eluted with 2:1 Et$_2$O:hexanes to provide Substituted-Quinoxaline-Type Piperidine Compound 271, ethyl 4-((endo)-8-(2,6-dimethylhept-4-yn-3-yl)-8-azabicyclo[3.2.1]octan-3-yl)-3-oxo-3,4-dihydroquinoxaline-2-carboxylate.

To a mixture of Substituted-Quinoxaline-Type Piperidine Compound 271 and EtOH (2 mL) at 0° C. was added 2N aqueous NaOH (0.3 mL). The resulting reaction mixture was stirred for 1 h as its temperature warmed from 0° C. to about 25° C. Thereafter, the reaction mixture was diluted with CHCl$_3$ (20 mL) and neutralized with 1N aqueous HCl. The organic portion was separated, concentrated under reduced pressure, and dried to provide 50 mg of the hydrochloride of Substituted-Quinoxaline-Type Piperidine Compound 272 as a white solid (yield 20% for two steps).

The identity of Substituted-Quinoxaline-Type Piperidine Compound 272, 4-((endo)-8-(2,6-dimethylhept-4-yn-3-yl)-8-azabicyclo[3.2.1]octan-3-yl)-3-oxo-3,4-dihydroquinoxaline-2-carboxylic acid, was confirmed using $^1$H NMR and LC/MS.

Substituted-Quinoxaline-Type Piperidine Compound 272: $^1$H NMR: $\delta_H$ (400 MHz, CDCl$_3$): 11.4 (br, 1H, HCl), 8.38 (d, 1H, J=8.9 Hz), 8.14 (d, 1H, J=8.2 Hz), 7.83 (dd, 1H, J=7.2 Hz, 8.8 Hz), 7.48 (dd, 1H, J=8.1 Hz, 8.3 Hz), 6.72-6.78 (m, 1H), 4.35-4.38 (m, 1H), 3.95-3.98 (m, 1H), 3.52-3.53 (m, 1H), 3.0-3.08 (m, 2H), 2.18-2.6 (m, 8H), 1.25 (d, 3H, J=6.8 Hz), 1.13-1.16 (m, 6H), 1.06 (d, 3H, J=6.6 Hz); LC/MS (100%, 0.4=5.897): m/z=423.6 [M+H]$^+$.

azabicyclo[3.2.1]octan-3-yl)-3-oxo-3,4-dihydroquinoxaline-2-carboxylic acid, was confirmed using $^1$H NMR and LC/MS.

Substituted-Quinoxaline-Type Piperidine Compound 274: $^1$H NMR: $\delta_H$ (400 MHz, CDCl$_3$): 12.02 (br, 1H, HCl), 8.44 (d, 1H, J=8.3 Hz), 8.24 (dd, 1H, J=1.5 Hz, 8.2 Hz), 7.93-7.97 (m, 1H), 7.57-7.61 (m, 1H), 6.66-6.71 (m, 1H), 4.55-4.58 (m, 1H), 4.09-4.13 (m, 1H), 3.54-3.59 (m, 1H), 3.02-3.14 (m, 2H), 2.36-2.72 (m, 8H), 1.21-1.26 (m, 6H), 1.16 (t, 3H, J=7.5 Hz); LC/MS (100%, t$_r$=5.506): m/z=408.6 [M+H]$^+$.

5.46 Example 46

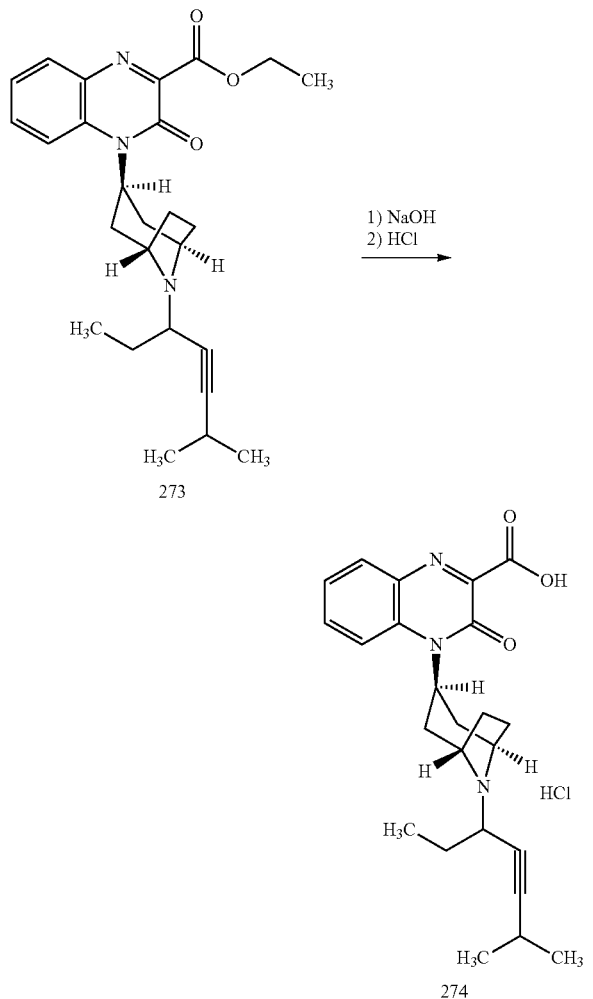

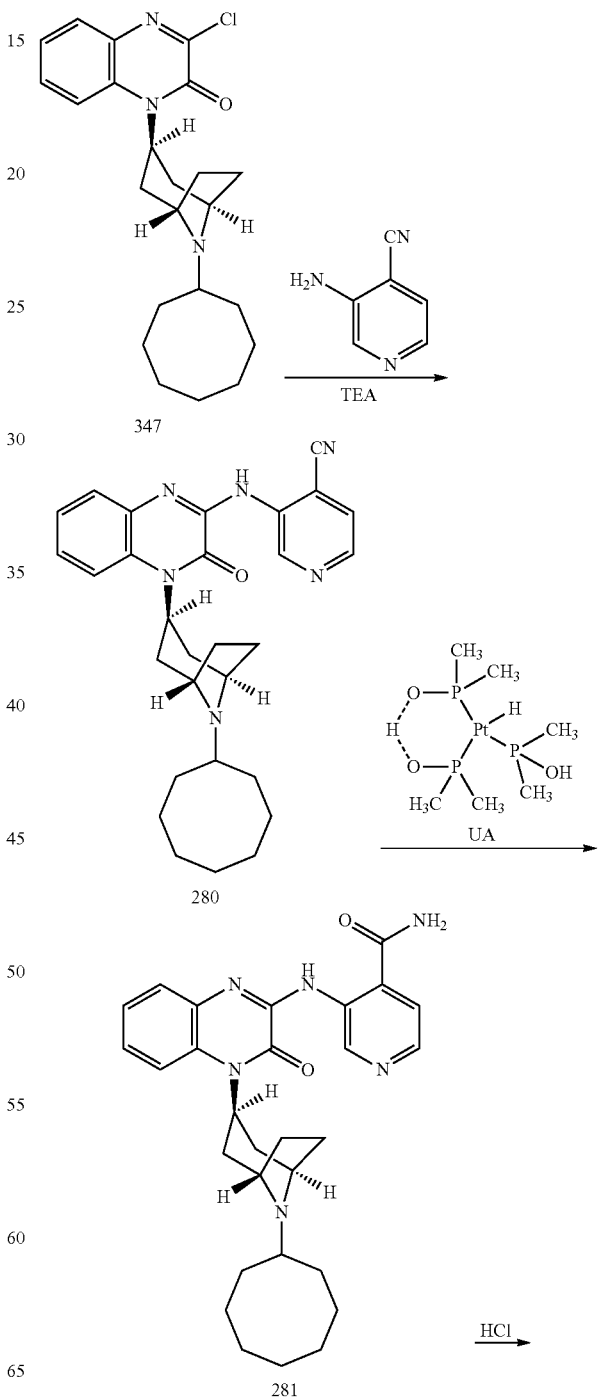

Substituted-Quinoxaline-Type Piperidine Compound 273, ethyl 4-((endo)-8-(6-methylhept-4-yn-3-yl)-8-azabicyclo[3.2.1]octan-3-yl)-3-oxo-3,4-dihydroquinoxaline-2-carboxylate, was prepared from Substituted-Quinoxaline-Type Piperidine Compound 268 by using propionaldehyde (Sigma-Aldrich) in place of isobutyraldehyde. Thereafter, in a manner similar to the preparation of Substituted-Quinoxaline-Type Piperidine Compound 272, the hydrochloride of Substituted-Quinoxaline-Type Piperidine Compound 274 was prepared from Substituted-Quinoxaline-Type Piperidine Compound 273 (yield 30% for two steps).

The identity of Substituted-Quinoxaline-Type Piperidine Compound 274, 4-((endo)-8-(6-methylhept-4-yn-3-yl)-8-

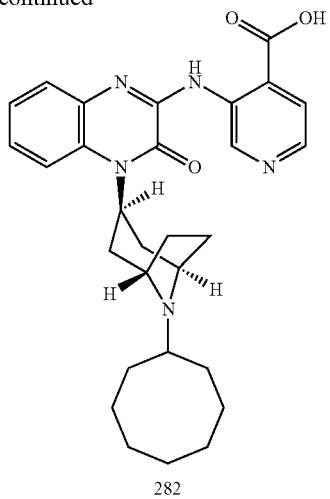

282

In a manner similar to Example 15, Substituted-Quinoxaline-Type Piperidine Compound 280 was prepared from Substituted-Quinoxaline-Type Piperidine Compound 347 by using 3-aminoisonicotinonitrile (Sigma-Aldrich) in place of serine amide hydrochloride (yield 94%).

The identity of Substituted-Quinoxaline-Type Piperidine Compound 280, 3-(4-((endo)-8-cyclooctyl-8-azabicyclo[3.2.1]octan-3-yl)-3-oxo-3,4-dihydroquinoxalin-2-ylamino)isonicotinonitrile, was confirmed using $^1$H NMR and LC/MS.

Substituted-Quinoxaline-Type Piperidine Compound 280: $^1$H NMR: $\delta_H$ (CDCl$_3$): 10.38 (1H, s), 9.00 (1H, s), 8.44 (1H, t, J=2.50 Hz), 7.72 (1H, d, J=8.00 Hz), 7.53 (1H, d, J=8.60 Hz), 7.48 (1H, d, J=5.00 Hz), 7.40 (1H, t, J=8.00 Hz), 7.32 (1H, t, J=8.00 Hz), 5.20 (1H, m), 3.69 (2H, s), 2.31 (5H, m), 2.05 (2H, m), 1.85-1.50 m); LC/MS: m/z=483 [M+H]$^+$ (Calc: 482.6).

To a mixture of Substituted-Quinoxaline-Type Piperidine Compound 280 (327 mg, 0.678 mmol), EtOH (4 mL), and water (2.0 mL) at a temperature of about 25° C. was added the platinum catalyst complex UA (14.5 mg, 0.034 mmol), prepared according to T. Ghaffar and A. W. Parkins, *Tetrahedron Let.*, 36(47):8657-8660 (1995). The resulting reaction mixture was warmed to 80° C. and stirred for 8 h then concentrated under reduced pressure to provide a residue. The residue was chromatographed with a silica gel column eluted with a gradient of from 97%:3% CHCl$_3$:MeOH to 90%:10% CHCl$_3$:MeOH to provide 298 mg of Substituted-Quinoxaline-Type Piperidine Compound 281 as a white solid (yield 88%).

The identity of Substituted-Quinoxaline-Type Piperidine Compound 281, 3-(4-((endo)-8-cyclooctyl-8-azabicyclo[3.2.1]octan-3-yl)-3-oxo-3,4-dihydroquinoxalin-2-ylamino)isonicotinamide, was confirmed using $^1$H NMR and LC/MS.

Substituted-Quinoxaline-Type Piperidine Compound 281: $^1$H NMR: $\delta_H$ (DMSO-d$_6$): 11.76 (1H, s), 10.36 (1H, s), 8.49 (1H, s), 8.38 (1H, t, J=2.40 Hz), 7.97 (1H, s), 7.68 (2H, m), 7.44 (2H, m), 7.31 (1H, t, J=7.20 Hz), 5.20 (1H, br), 3.65 (2H, s), 2.50-1.90 (7H, m), 1.90-1.30 (16H, m); LC/MS: m/z=501 [M+H]$^+$ (Calc: 500.6).

To a mixture of Substituted-Quinoxaline-Type Piperidine Compound 281 (150 mg, 0.300 mmol) and water (1.0 mL) at 0° C. was added concentrated aqueous HCl (2 mL, 65.8 mmol). The resulting reaction mixture was warmed to 80° C. and stirred for 3 h. Thereafter, upon neutralizing the reaction mixture with cold (0° C.) 2N aqueous NaOH a white precipitate formed. The precipitate was filtered, washed with water, washed with MeOH, and dried under reduced pressure to provide 80 mg of Substituted-Quinoxaline-Type Piperidine Compound 282 as a white solid (yield 53%).

The identity of Substituted-Quinoxaline-Type Piperidine Compound 282, 3-(4-((endo)-8-cyclooctyl-8-azabicyclo[3.2.1]octan-3-yl)-3-oxo-3,4-dihydroquinoxalin-2-ylamino)isonicotinic acid, was confirmed using $^1$H NMR and LC/MS.

Substituted-Quinoxaline-Type Piperidine Compound 282: $^1$H NMR: $\delta_H$ (DMSO-d$_6$): 11.66 (1H, s), 10.54 (1H, s), 10.45 (0.9H, s) 9.60 (0.1H, m), 8.44 (1H, d, J=5.00 Hz), 7.97 (2H, m), 7.70 (1H, d, J=8.00 Hz), 7.44 (1H, t, J=8.00 Hz), 7.36 (1H, t, J=8.00 Hz), 5.96 (1H, m), 4.22 (2H, m), 2.95 (1H, m), 2.70 (2H, m), 2.50-1.40 (20H, m); LC/MS (97%, t$_r$=1.35 min): m/z=502 [M+H]$^+$ (Calc: 501.6).

5.47 Example 47

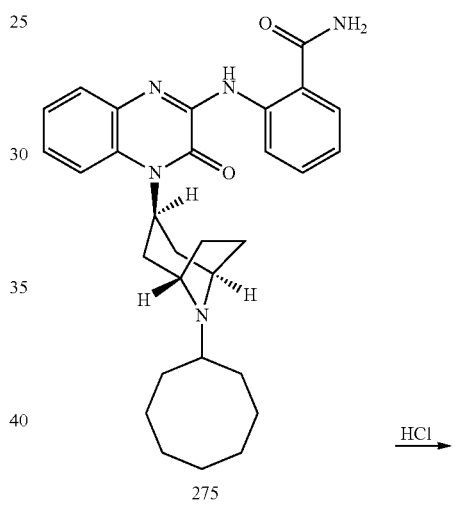

275

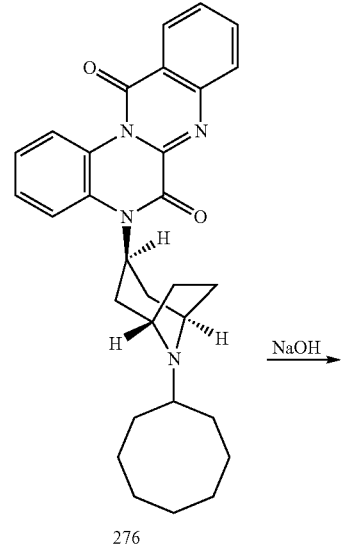

276

-continued

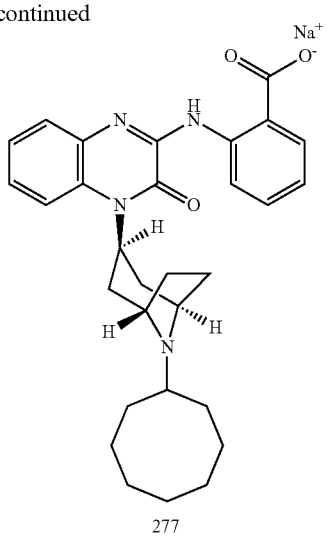

277

In a manner similar to the preparation of Substituted-Quinoxaline-Type Piperidine Compound 281 in Example 46, Substituted-Quinoxaline-Type Piperidine Compound 275, 2-(4-((endo)-8-cyclooctyl-8-azabicyclo[3.2.1]octan-3-yl)-3-oxo-3,4-dihydroquinoxalin-2-ylamino)benzamide, was prepared except that 2-aminobenzonitrile was used in place of 3-aminoisonicotinonitrile.

To a mixture of Substituted-Quinoxaline-Type Piperidine Compound 275 (165 mg, 0.330 mmol) and water (4 mL) at 0° C. was added concentrated aqueous HCl (4 mL, 47.4 mmol). The resulting reaction mixture was warmed to a temperature of about 25° C. and stirred for 1 h. Thereafter, upon neutralizing the reaction mixture with cold (0° C.) 2N aqueous NaOH a white precipitate formed. The precipitate was filtered, washed with water, and dried under reduced pressure to provide 138 mg of the compound of formula 276 as a white solid (yield 81%).

The identity of the compound of formula 276, 5-((endo)-8-cyclooctyl-8-azabicyclo[3.2.1]octan-3-yl)-5H-quinoxalino[2,1-b]quinazoline-6,12-dione, was confirmed using $^1$H NMR and LC/MS.

Compound 276: $^1$H NMR: $\delta_H$ (400 MHz, DMSO): 10.05 (0.8H, s), 9.34 (0.2H, s), 8.77 (1H, d, J=8.0 Hz), 8.32 (1H, d, J=8.0 Hz), 7.98 (1H, t, J=8.0 Hz), 7.88 (1H, d, J=8.0 Hz), 7.71 (1H, t, J=8.0 Hz), 7.66 (1H, d, J=8.0 Hz), 7.50 (1H, t, J=8.0 Hz), 7.30 (1H, t, J=8.0 Hz), 5.48 (0.8H, m), 4.93 (0.2H, m), 4.26 (2H, m), 2.96 (1H, m), 2.76 (2H, m), 2.50-1.40 (20H, m); LC/MS (97%, $t_r$=1.73 min): m/z=483 [M+H]$^+$ (Calc: 482.3).

To a mixture of the compound of formula 276 (90 mg, 0.186 mmol) and MeOH (4 mL) at a temperature of about 25° C. was added 2N aqueous NaOH (1.86 mL, 3.73 mmol). The resulting reaction mixture was warmed to a temperature of 80° C., stirred for 66 h, concentrated under reduced pressure, and diluted with water (5 mL) to precipitate a white solid. The precipitate was filtered and rinsed with water to provide 86 mg of the sodium salt of Substituted-Quinoxaline-Type Piperidine Compound 277 (yield 88%).

The identity of Substituted-Quinoxaline-Type Piperidine Compound 277, 2-(4-((endo)-8-cyclooctyl-8-azabicyclo[3.2.1]octan-3-yl)-3-oxo-3,4-dihydroquinoxalin-2-ylamino)benzoic acid, was confirmed using $^1$H NMR and LC/MS.

Substituted-Quinoxaline-Type Piperidine Compound 277: $^1$H NMR: $\delta_H$ (400 MHz, DMSO-d$_6$): 14.48 (1H, s), 9.15 (1H, d, J=8.0 Hz), 8.02 (1H, d, J=8.0 Hz), 7.55 (1H, d, J=8.0 Hz), 7.40 (1H, d, J=8.0 Hz), 7.30 (2H, m), 7.23 (1H, d, J=8.0 Hz), 6.93 (1H, t, J=8.0 Hz), 5.10 (1H, br), 3.65 (2H, m), 3.00 (1H, m), 2.50-1.40 (22H, m); LC/MS (100%, $t_r$=2.24 min): m/z=501 [M+H]$^+$ (Calc: 500.3).

5.48 Example 48

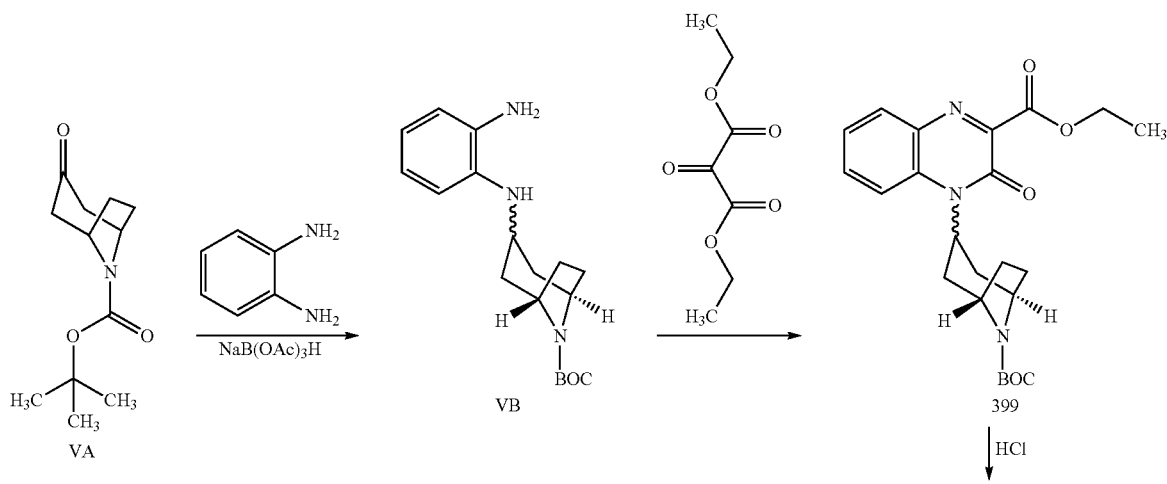

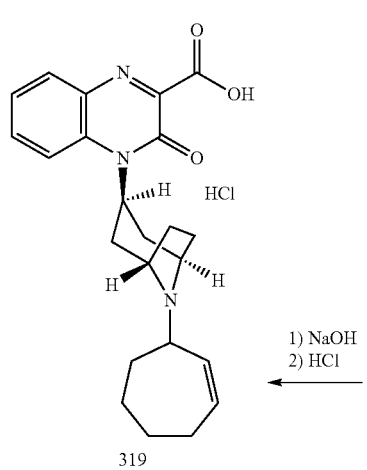
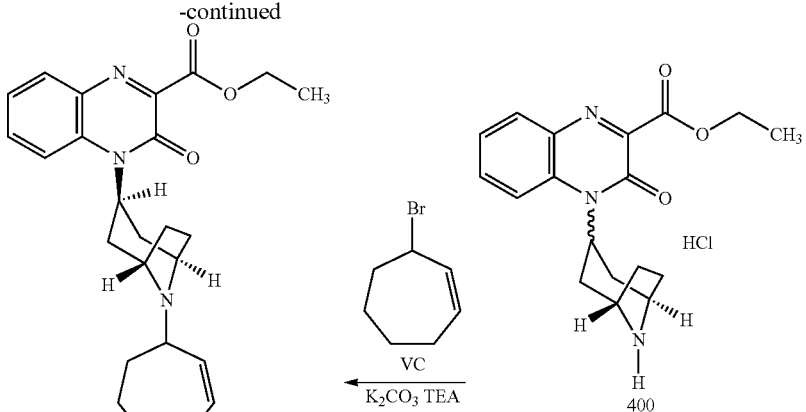

Under an argon atmosphere, a mixture of tert-butyl 3-oxo-8-azabicyclo[3.2.1]octane-8-carboxylate (VA, 9 g, 3B Scientific Corp., Libertyville, Ill.), 1,2-phenylenediamine (9 g), and sodium triacetoxyborohydride (20 g) was stirred at about 25° C. To this mixture, acetic acid (4 mL) was added and the resulting reaction mixture was stirred at a temperature of about 25° C. for 5 h. The reaction mixture was quenched with water (20 mL) and MeOH (1 mL) to provide the compound of formula VB, a mixture of the endo and exo isomers, which mixture was used as follows. The organic portion was separated, concentrated under reduced pressure, and redissolved in toluene (100 mL) and AcOH (6 mL). To this, diethyl 2-oxomalonate (16 mL) at a temperature of 0° C. was added, then the reaction mixture was warmed to 100° C. and stirred for 3 h. After cooling to about 25° C., the mixture was filtered over sea sand, washed with diethyl ether (50 mL), and concentrated under reduced pressure to provide a residue. Chromatography of the residue with a silica gel column eluting with 1:1 hexanes:Et$_2$O provided 13.0 g of Substituted-Quinoxaline-Type Piperidine Compound 399, a mixture of the endo and exo isomers of ethyl 4-(8-(tert-butoxycarbonyl)-8-azabicyclo[3.2.1]octan-3-yl)-3-oxo-3,4-dihydroquinoxaline-2-carboxylate, as a brown oil. The oil was dissolved in 1,4-dioxane (150 mL), treated with 4N HCl in 1,4-dioxane (15 mL), and kept at 40° C. for 24 h. The reaction mixture was concentrated under reduced pressure and titrated with diethyl ether to provide 7.0 g of the hydrochloride of Substituted-Quinoxaline-Type Piperidine Compound 400, a mixture of the endo and exo isomers of ethyl 4-(8-azabicyclo[3.2.1]octan-3-yl)-3-oxo-3,4-dihydroquinoxaline-2-carboxylate, as a white solid (yield 48% for three steps).

A reaction mixture of Substituted-Quinoxaline-Type Piperidine Compound 400 (200 mg), 3-bromocyclohept-1-ene (VC, 2 eq), K$_2$CO$_3$ (1.0 g), TEA (1 mL), and acetonitrile (4 mL) was shaken at 60° C. for 12 h. The reaction mixture was diluted with EtOAc (10 mL), filtered, and concentrated under reduced pressure to provide a residue. Chromatography of the residue with a silica gel column eluting with 1:1 hexanes:Et$_2$O then 1:2 hexanes:Et$_2$O provided 150 mg of Substituted-Quinoxaline-Type Piperidine Compound 401, ethyl 4-((endo)-8-(cyclohept-2-enyl)-8-azabicyclo[3.2.1]octan-3-yl)-3-oxo-3,4-dihydroquinoxaline-2-carboxylate, as an oil (yield 65%).

In a manner similar to the preparation of Substituted-Quinoxaline-Type Piperidine Compound 174 in Example 7, the hydrochloride of Substituted-Quinoxaline-Type Piperidine Compound 319 was prepared from Substituted-Quinoxaline-Type Piperidine Compound 401 (yield 64%).

The identity of Substituted-Quinoxaline-Type Piperidine Compound 319, 4-((endo)-8-(cyclohept-2-enyl)-8-azabicyclo[3.2.1]octan-3-yl)-3-oxo-3,4-dihydroquinoxaline-2-carboxylic acid, was confirmed using $^1$H NMR and LC/MS.

Substituted-Quinoxaline-Type Piperidine Compound 319: $^1$H NMR: $\delta_H$ (400 MHz, CDCl$_3$): 13.8 (br, 1H, COOH), 12.18 (br, 1H, HCl), 8.43 (d, 1H, 8.8 Hz), 8.24 (dd, 11-1, 1.5 Hz, 8.2 Hz), 7.96 (ddd, 1H, 1.5, 7.2 Hz, 8.8 Hz), 7.61 (ddd, 1H, 0.8, 8.1 Hz, 8.3 Hz), 6.6-6.68 (m, 1H), 6.12-6.24 (m, 2H), 4.22-4.28 (m, 2H), 3.54-3.58 (m, 1H), 3.02-3.12 (m, 2H), 2.42-2.55 (m, 4H), 2.32-2.36 (m, 2H), 2.18-2.24 (m, 2H), 2.06-2.12 (m, 2H), 1.4-1.72 (m, 4H); LC/MS (100%, t$_r$=4.881 min): m/z=394.5 [M+H]$^+$.

The compound of formula VC was prepared as follows:

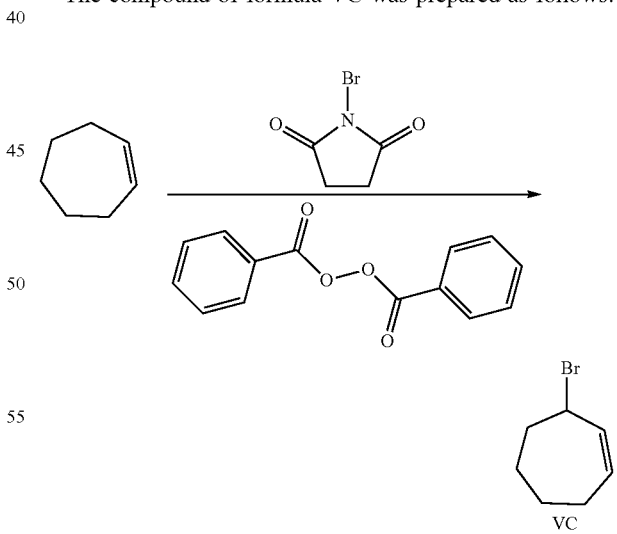

A reaction mixture of cycloheptene (12 g, Sigma-Aldrich), N-bromosuccinimide (23 g, Sigma-Aldrich), and benzoyl peroxide (0.5 g, Sigma-Aldrich) in 100 mL of CCl$_4$ was heated at 80° C. for 2 h. After cooling to about 25° C., the mixture was filtered, washed twice with NaHCO$_3$ (40 mL for each wash), concentrated under reduced pressure, and distilled at 40° C. under a pressure of 2 mmHg to provide 15 g of the compound of formula VC as colorless oil.

5.49 Example 49

In Vitro ORL-1 Receptor Binding Assay

ORL-1 Receptor Binding Assay Procedures: Membranes from recombinant HEK-293 cells expressing the human opioid receptor-like receptor (ORL-1) (Receptor Biology) were prepared by lysing cells in ice-cold hypotonic buffer (2.5 mM $MgCl_2$, 50 mM HEPES, pH 7.4) (10 mL/10 cm dish) followed by homogenization with a tissue grinder/Teflon pestle. Membranes were collected by centrifugation at 30,000×g for 15 min at 4° C. and pellets resuspended in hypotonic buffer to a final concentration 1-3 mg/mL. Protein concentrations were determined using the BioRad protein assay reagent with bovine serum albumen as a standard. Aliquots of the ORL-1 receptor membranes were stored at −80° C.

Radioligand binding assays (screening and dose-displacement) used 0.1 nM [$^3$H]-nociceptin (NEN; 87.7 Ci/mmole) with 10-20 µg membrane protein in a final volume of 500 µ, binding buffer (10 mM $MgCl_2$, 1 mM EDTA, 5% DMSO, 50 mM HEPES, pH 7.4). Non-specific binding was determined in the presence of 10 nM unlabeled nociceptin (American Peptide Company). All reactions were performed in 96-deep well polypropylene plates for 1 h at about 25° C. Binding reactions were terminated by rapid filtration onto 96-well Unifilter GF/C filter plates (Packard) presoaked in 0.5% polyethylenimine (Sigma). Harvesting was performed using a 96-well tissue harvester (Packard) followed by three filtration washes with 500 µ ice-cold binding buffer. Filter plates were subsequently dried at 50° C. for 2-3 hours. Fifty µL/well scintillation cocktail (BetaScint; Wallac) was added and plates were counted in a Packard Top-Count for 1 min/well. The data from screening and dose-displacement experiments were analyzed using Microsoft Excel and the curve fitting functions in GraphPad PRISM™, v. 3.0, respectively, or an in-house function for one-site competition curve-fitting.

ORL-1 Receptor Binding Data: The Substituted-Quinoxaline-Type Piperidine Compounds will have a binding affinity (K) for the human ORL-1 receptor of about 1000 nM or less in one embodiment, or about 500 nM or less in another embodiment. Typically, the Substituted-Quinoxaline-Type Piperidine Compounds will have a $K_i$ (nM) of about 300 or less for binding to ORL-1 receptors. In one embodiment, the Substituted-Quinoxaline-Type Piperidine Compounds will have a $K_i$ (nM) of about 100 or less. In another embodiment, the Substituted-Quinoxaline-Type Piperidine Compounds of the invention will have a $K_i$ (nM) of about 35 or less. In another embodiment, the Substituted-Quinoxaline-Type Piperidine Compounds of the invention will have a $K_i$ (nM) of about 20 or less. In another embodiment, the Substituted-Quinoxaline-Type Piperidine Compounds of the invention will have a $K_i$ (nM) of about 15 or less. In another embodiment, the Substituted-Quinoxaline-Type Piperidine Compounds of the invention will have a $K_i$ (nM) of about 10 or less. In another embodiment, the Substituted-Quinoxaline-Type Piperidine Compounds of the invention will have a $K_i$ (nM) of about 4 or less. In another embodiment, the Substituted-Quinoxaline-Type Piperidine Compounds of the invention will have a $K_i$ (nM) of about 1 or less. In another embodiment, the Substituted-Quinoxaline-Type Piperidine Compounds of the invention will have a $K_i$ (nM) of about 0.4 or less. In another embodiment, the Substituted-Quinoxaline-Type Piperidine Compounds of the invention will have a $K_i$ (nM) of about 0.1 or less.

5.50 Example 50

In Vitro ORL-1 Receptor Functional Assay

ORL-1 Receptor [$^{35}$S]GTPγS Binding Assay Procedures: Membranes from recombinant HEK-293 cells expressing the human opioid receptor-like (ORL-1) (Receptor Biology) were prepared by lysing cells in ice-cold hypotonic buffer (2.5 mM $MgCl_2$, 50 mM HEPES, pH 7.4) (10 mL/10 cm dish) followed by homogenization with a tissue grinder/Teflon pestle. Membranes were collected by centrifugation at 30,000×g for 15 min at 4° C., and pellets resuspended in hypotonic buffer to a final concentration of 1-3 mg/mL. Protein concentrations were determined using the BioRad protein assay reagent with bovine serum albumen as a standard. Aliquots of the ORL-1 receptor membranes were stored at −80° C.

Functional binding assays were conducted as follows. ORL-1 membrane solution was prepared by sequentially adding final concentrations of 0.066 µg/µL ORL-1 membrane protein, 10 µg/mL saponin, 3 µM GDP and 0.20 nM [35S]GTPγS to binding buffer (100 mM NaCl, 10 mM $MgCl_2$, 20 mM HEPES, pH 7.4) on ice. The prepared membrane solution (190 µL/well) was transferred to 96-shallow well polypropylene plates containing 10 µL of 20× concentrated stock solutions of agonist/nociceptin prepared in DMSO. Plates were incubated for 30 min at about 25° C. with shaking. Reactions were terminated by rapid filtration onto 96-well Unifilter GF/B filter plates (Packard) using a 96-well tissue harvester (Packard) and followed by three filtration washes with 200 µL ice-cold binding buffer (10 mM $NaH_2PO_4$, 10 mM $Na_2HPO_4$, pH 7.4). Filter plates were subsequently dried at 50° C. for 2-3 hours. Fifty µL/well scintillation cocktail (BetaScint; Wallac) was added and plates were counted in Packard Top-Count for 1 min/well. Data are analyzed using the sigmoidal dose-response curve fitting functions in GraphPad PRISM v. 3.0, or an in-house function for non-linear, sigmoidal dose-response curve-fitting.

ORL-1 Receptor Functional Data: ORL-1 GTP $EC_{50}$ is the concentration of a compound providing 50% of the maximal response for the compound at an ORL-1 receptor. Substituted-Quinoxaline-Type Piperidine Compounds typically will have an ORL-1 GTP $EC_{50}$ (nM) of about 5000 or less to stimulate ORL-1 receptor function. In one embodiment, the Substituted-Quinoxaline-Type Piperidine Compounds of the invention will have an ORL-1 GTP $EC_{50}$ (nM) of about 1000 or less. In another embodiment, the Substituted-Quinoxaline-Type Piperidine Compounds of the invention will have an ORL-1 GTP $EC_{50}$ (nM) of about 100 or less. In another embodiment, the Substituted-Quinoxaline-Type Piperidine Compounds of the invention will have an ORL-1 GTP $EC_{50}$ (nM) of about 80 or less. In another embodiment, the Substituted-Quinoxaline-Type Piperidine Compounds of the invention will have an ORL-1 GTP $EC_{50}$ (nM) of about 50 or less. In another embodiment, the Substituted-Quinoxaline-Type Piperidine Compounds of the invention will have an ORL-1 GTP $EC_{50}$ (nM) of about 35 or less. In another embodiment, the Substituted-Quinoxaline-Type Piperidine Compounds of the invention will have an ORL-1 GTP $EC_{50}$ (nM) of about 15 or less. In another embodiment, the Substituted-Quinoxaline-Type Piperidine Compounds of the invention will have an ORL-1 GTP $EC_{50}$ (nM) of about 10 or less. In another embodiment, the Substituted-Quinoxaline-Type Piperidine Compounds will have an ORL-1 GTP $EC_{50}$ (nM) of about 4 or less. In another embodiment, the Substituted-Quinoxaline-Type Piperidine Compounds will have an ORL-1 GTP $EC_{50}$ (nM) of about 1 or less. In another embodiment, the Substituted-Quinoxaline-Type Piperidine Compounds will have an ORL-1 GTP $EC_{50}$ (nM) of about 0.4 or less. In another embodiment, the Substituted-Quinoxaline-Type Piperidine Compounds will have an ORL-1 GTP $EC_{50}$ (nM) of about 0.1 or less.

ORL-1 GTP Emax (%) is the maximal effect elicited by a compound relative to the effect elicited by nociceptin, a standard ORL-1 agonist. Typically, the Substituted-Quinoxaline-Type Piperidine Compounds of the invention will have an ORL-1 GTP Emax (%) of greater than about 50%. In one embodiment, the Substituted-Quinoxaline-Type Piperidine Compound Substituted-Quinoxaline-Type Piperidine Compounds will have an ORL-1 GTP Emax (%) of greater than about 75%. In another embodiment, the Substituted-Quinoxaline-Type Piperidine Compounds will have an ORL-1 GTP Emax (%) of greater than about 85%. In another embodiment, the Substituted-Quinoxaline-Type Piperidine Compounds will have an ORL-1 GTP Emax (%) of greater than about 95%. In another embodiment, the Substituted-Quinoxaline-Type Piperidine Compounds will have an ORL-1 GTP Emax (%) of about 100% or greater. In another embodiment, the Substituted-Quinoxaline-Type Piperidine Compounds will have an ORL-1 GTP Emax (%) of about 110% or greater. Typically, a Substituted-Quinoxaline-Type Piperidine Compound of the invention acting as a partial agonist will have an ORL-1 GTP Emax (%) of less than about 10%. In one embodiment, partial agonist Substituted-Quinoxaline-Type Piperidine Compounds will have an ORL-1 GTP Emax (%) of less than about 20%. In another embodiment, partial agonist Substituted-Quinoxaline-Type Piperidine Compounds will have an ORL-1 GTP Emax (%) of less than about 30%. In another embodiment, partial agonist Substituted-Quinoxaline-Type Piperidine Compounds will have an ORL-1 GTP Emax (%) of less than about 40%. In another embodiment, partial agonist Substituted-Quinoxaline-Type Piperidine Compounds will have an ORL-1 GTP Emax (%) of less than about 50%.

5.51 Example 51

In Vitro Mu-Opioid Receptor Binding Assays

μ-Opioid Receptor Binding Assay Procedures: Radioligand dose-displacement binding assays for μ-opioid receptors used 0.2 nM[$^3$H]-diprenorphine (NEN, Boston, Mass.), with 5-20 mg membrane protein/well in a final volume of 500 μL binding buffer (10 mM $MgCl_2$, 1 mM EDTA, 5% DMSO, 50 mM HEPES, pH 7.4). Reactions were carried out in the absence or presence of increasing concentrations of unlabeled naloxone. All reactions were conducted in 96-deep well polypropylene plates for 1-2 hr at about 25° C. Binding reactions were terminated by rapid filtration onto 96-well Unifilter GF/C filter plates (Packard, Meriden, Conn.) presoaked in 0.5% polyethylemimine using a 96-well tissue harvester (Brandel, Gaithersburg, Md.) followed by performing three filtration washes with 5004 of ice-cold binding buffer. Filter plates were subsequently dried at 50° C. for 2-3 hours. BetaScint scintillation cocktail (Wallac, Turku, Finland) was added (50 μL/well), and plates were counted using a Packard Top-Count for 1 min/well. The data were analyzed using the one-site competition curve fitting functions in GraphPad PRISM v. 3.0 (San Diego, Calif.), or an in-house function for one-site competition curve-fitting.

μ-Opioid Receptor Binding Data: Typically, the Substituted-Quinoxaline-Type Piperidine Compounds will have a $K_i$ (nM) of about 3000 or less for binding to μ-opioid receptors. In one embodiment, the Substituted-Quinoxaline-Type Piperidine Compounds will have a $K_i$ (nM) of about 1000 or less. In another embodiment, the Substituted-Quinoxaline-Type Piperidine Compounds of the invention will have a $K_i$ (nM) of about 650 or less. In another embodiment, the Substituted-Quinoxaline-Type Piperidine Compounds of the invention will have a $K_i$ (nM) of about 525 or less. In another embodiment, the Substituted-Quinoxaline-Type Piperidine Compounds of the invention will have a $K_i$ (nM) of about 250 or less. In another embodiment, the Substituted-Quinoxaline-Type Piperidine Compounds of the invention will have a $K_i$ (nM) of about 100 or less. In another embodiment, the Substituted-Quinoxaline-Type Piperidine Compounds of the invention will have a $K_i$ (nM) of about 10 or less. In another embodiment, the Substituted-Quinoxaline-Type Piperidine Compounds of the invention will have a $K_i$ (nM) of about 1 or less. In another embodiment, the Substituted-Quinoxaline-Type Piperidine Compounds of the invention will have a $K_i$ (nM) of about 0.1 or less.

5.52 Example 52

In Vitro Mu-Opioid Receptor Functional Assays

μ-Opioid Receptor Functional Assay Procedures: [$^{35}$S] GTPγS functional assays were conducted using freshly thawed μ-receptor membranes. Assay reactions were prepared by sequentially adding the following reagents to binding buffer (100 mM NaCl, 10 mM $MgCl_2$, 20 mM HEPES, pH 7.4) on ice (final concentrations indicated): membrane protein (0.026 mg/mL), saponin (10 mg/mL), GDP (3 mM) and [$^{35}$S]GTPγS (0.20 nM; NEN). The prepared membrane solution (190 μL/well) was transferred to 96-shallow well polypropylene plates containing 104 of 20× concentrated stock solutions of the agonist DAMGO ([D-Ala2, N-methyl-Phe4 Gly-ol5]-enkephalin) prepared in dimethyl sulfoxide (DMSO). Plates were incubated for 30 min at about 25° C. with shaking. Reactions were terminated by rapid filtration onto 96-well Unifilter GF/B filter plates (Packard, Meriden, Conn.) using a 96-well tissue harvester (Brandel, Gaithersburg, Md.) followed by three filtration washes with 200 μl of ice-cold wash buffer (10 mM $NaH_2PO_4$, 10 mM $Na_2HPO_4$, pH 7.4). Filter plates were subsequently dried at 50° C. for 2-3 hr. BetaScint scintillation cocktail (Wallac, Turku, Finland) was added (50 μL/well) and plates were counted using a Packard Top-Count for 1 min/well. Data were analyzed using the sigmoidal dose-response curve fitting functions in GraphPad PRISM v. 3.0, or an in-house function for non-linear, sigmoidal dose-response curve-fitting.

μ-Opioid Receptor Functional Data: μ GTP $EC_{50}$ is the concentration of a compound providing 50% of the maximal response for the compound at a μ-opioid receptor. Substituted-Quinoxaline-Type Piperidine Compounds typically will have a μ GTP $EC_{50}$ (nM) of about 5000 or less to stimulate μ-opioid receptor function. In one embodiment, the Substituted-Quinoxaline-Type Piperidine Compounds of the invention will have a μ GTP $EC_{50}$ (nM) of about 4100 or less. In one embodiment, the Substituted-Quinoxaline-Type Piperidine Compounds of the invention will have a μ GTP $EC_{50}$ (nM) of about 3100 or less. In another embodiment, the Substituted-Quinoxaline-Type Piperidine Compounds of the invention will have a μ GTP $EC_{50}$ (nM) of about 2000 or less. In another embodiment, the Substituted-Quinoxaline-Type Piperidine Compounds of the invention will have a μ GTP $EC_{50}$ (nM) of about 1000 or less. In another embodiment, the Substituted-Quinoxaline-Type Piperidine Compounds of the invention will have a μ GTP $EC_{50}$ (nM) of about 100 or less. In another embodiment, the Substituted-Quinoxaline-Type Piperidine Compounds of the invention will have a μ GTP $EC_{50}$ (nM) of about 10 or less. In another embodiment, the Substituted-Quinoxaline-Type Piperidine Compounds will have a μ GTP $EC_{50}$ (nM) of about 1 or less. In another embodiment, the Substituted-Quinoxaline-Type Piperidine Compounds will have a μ GTP $EC_{50}$ (nM) of about 0.4 or less. In another embodiment, the Substituted-Quinoxaline-Type Piperidine Compounds will have a μ GTP $EC_{50}$ (nM) of about 0.1 or less.

μ GTP Emax (%) is the maximal effect elicited by a compound relative to the effect elicited by DAMGO, a standard μ agonist. Typically, the Substituted-Quinoxaline-Type Piperidine Compounds of the invention will have a μ GTP Emax (%) of greater than about 10%. In one embodiment, the Substituted-Quinoxaline-Type Piperidine Compounds will have a μ GTP Emax (%) of greater than about 20%. In another embodiment, the Substituted-Quinoxaline-Type Piperidine Compounds will have a μ GTP Emax (%) of greater than about 50%. In another embodiment, the Substituted-Quinoxaline-Type Piperidine Compounds will have a μ GTP Emax (%) of greater than about 65%. In another embodiment, the Substituted-Quinoxaline-Type Piperidine Compounds will have a μ GTP Emax (%) of greater than about 75%. In another embodiment, the Substituted-Quinoxaline-Type Piperidine Compounds will have a μ GTP Emax (%) of greater than about 88%. In another embodiment, the Substituted-Quinoxaline-Type Piperidine Compounds will have a μ GTP Emax (%) of about 100% or greater.

5.53 Example 53

In Vitro Kappa-Opioid Receptor Binding Assays

μ-Opioid Receptor Binding Assay Procedures: Membranes from recombinant HEK-293 cells expressing the human kappa opioid receptor (kappa) (cloned in house) were prepared by lysing cells in ice cold hypotonic buffer (2.5 mM $MgCl_2$, 50 mM HEPES, pH 7.4) (10 mL/10 cm dish) followed by homogenization with a tissue grinder/Teflon pestle. Membranes were collected by centrifugation at 30,000×g for 15 min at 4° C. and pellets resuspended in hypotonic buffer to a final concentration of 1-3 mg/mL. Protein concentrations were determined using the BioRad protein assay reagent with bovine serum albumen as a standard. Aliquots of kappa receptor membranes were stored at −80° C.

Radioligand dose displacement assays used 0.4-0.8 nM [$^3$H]-U69,593 (NEN; 40 Ci/mmole) with 10-20 μg membrane protein (recombinant kappa opioid receptor expressed in HEK 293 cells; in-house prep) in a final volume of 200 μL binding buffer (5% DMSO, 50 mM Trizma base, pH 7.4). Non-specific binding was determined in the presence of 10 μM unlabeled naloxone or U69,593. All reactions were performed in 96-well polypropylene plates for 1 h at a temperature of about 25° C. Binding reactions were determined by rapid filtration onto 96-well Unifilter GF/C filter plates (Packard) presoaked in 0.5% polyethylenimine (Sigma). Harvesting was performed using a 96-well tissue harvester (Packard) followed by five filtration washes with 200 μL ice-cold binding buffer. Filter plates were subsequently dried at 50° C. for 1-2 hours. Fifty μL/well scintillation cocktail (MicroScint20, Packard) was added and plates were counted in a Packard Top-Count for 1 min/well.

κ-Opioid Receptor Binding Data: In one embodiment, the Substituted-Quinoxaline-Type Piperidine Compounds will have substantially activity at κ receptors. Typically, the Substituted-Quinoxaline-Type Piperidine Compounds will have a Ki (nM) of about 20,000 or less for κ receptors. In one embodiment, the Substituted-Quinoxaline-Type Piperidine Compounds will have a Ki (nM) of about 10,000 or less. In another embodiment, the Substituted-Quinoxaline-Type Piperidine Compounds will have a Ki (nM) of about 5000 or less. In another embodiment, the Substituted-Quinoxaline-Type Piperidine Compounds will have a Ki (nM) of about 1000 or less. In another embodiment, the Substituted-Quinoxaline-Type Piperidine Compounds will have a Ki (nM) of about 500 or less. In another embodiment, the Substituted-Quinoxaline-Type Piperidine Compounds will have a Ki (nM) of about 300 or less. In another embodiment, the Substituted-Quinoxaline-Type Piperidine Compounds will have a Ki (nM) of about 100 or less. In another embodiment, the Substituted-Quinoxaline-Type Piperidine Compounds will have a Ki (nM) of about 50 or less. In another embodiment, the Substituted-Quinoxaline-Type Piperidine Compounds will have a Ki (nM) of about 20 or less. In another embodiment, the Substituted-Quinoxaline-Type Piperidine Compounds will have a Ki (nM) of about 15 or less. In another embodiment, the Substituted-Quinoxaline-Type Piperidine Compounds will have a Ki (nM) of about 10 or less.

5.54 Example 54

In Vitro Kappa-Opioid Receptor Functional Assays

κ-Opioid Receptor Functional Assay Procedures: Functional [$^{35}$S]GTPγS binding assays were conducted as follows. Kappa opioid receptor membrane solution was prepared by sequentially adding final concentrations of 0.026 μg/μL kappa membrane protein (in-house), 10 μg/mL saponin, 3 μM GDP and 0.20 nM [$^{35}$S]GTPγS to binding buffer (100 mM NaCl, 10 mM $MgCl_2$, 20 mM HEPES, pH 7.4) on ice. The prepared membrane solution (1904/well) was transferred to 96-shallow well polypropylene plates containing 104 of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Packard) using a 96-well tissue harvester (Packard) and followed by three filtration washes with 200 μL ice-cold binding buffer (10 mM $NaH_2PO_4$, 10 mM $Na_2HPO_4$, pH 7.4). Filter plates were subsequently dried at 50° C. for 2-3 hours. Fifty 4/well scintillation cocktail (MicroScint20, Packard) was added and plates were counted in a Packard Top-Count for 1 min/well.

κ-Opioid Receptor Functional Data: κ GTP $EC_{50}$ is the concentration of a compound providing 50% of the maximal response for the compound at a κ receptor. Substituted-Quinoxaline-Type Piperidine Compounds typically will have a κ GTP $EC_{50}$ (nM) of about 20,000 or less to stimulate κ opioid receptor function. In one embodiment, the Substituted-Quinoxaline-Type Piperidine Compounds will have a κ GTP $EC_{50}$ (nM) of about 10,000 or less. In another embodiment, the Substituted-Quinoxaline-Type Piperidine Compounds will have a κ GTP $EC_{50}$ (nM) of about 5000 or less. In another embodiment, the Substituted-Quinoxaline- Type Piperidine Compounds will have a κ GTP $EC_{50}$ (nM) of about 2000 or less. In another embodiment, the Substituted-Quinoxaline-Type Piperidine Compounds will have a κ GTP $EC_{50}$ (nM) of about 1500 or less. In another embodiment, the Substituted-Quinoxaline-Type Piperidine Compounds will have a κ GTP $EC_{50}$ (nM) of about 800 or less. In another embodiment, the Substituted-Quinoxaline-Type Piperidine Compounds will have a κ GTP $EC_{50}$ (nM) of about 500 or less. In another embodiment, the Substituted-Quinoxaline-Type Piperidine Compounds will have a κ GTP $EC_{50}$ (nM) of about 300 or less. In another embodiment, the Substituted-Quinoxaline-Type Piperidine Compounds will have a κ GTP $EC_{50}$ (nM) of about 100 or less. In another embodiment, the Substituted-Quinoxaline-Type Piperidine Compounds will have a κ GTP $EC_{50}$ (nM) of about 50 or less. In another embodiment, the Substituted-Quinoxaline-Type Piperidine Compounds will have a κ GTP $EC_{50}$ (nM) of about 25 or less. In another embodiment, the Substituted-Quinoxaline-Type Piperidine Compounds will have a κ GTP $EC_{50}$ (nM) of about 10 or less.

κ GTP Emax (%) is the maximal effect elicited by a compound relative to the effect elicited by U69,593. Typically, the Substituted-Quinoxaline-Type Piperidine Compounds of the invention will have a κ GTP Emax (%) of greater than about 10%. In one embodiment, the Substituted-Quinoxaline-Type Piperidine Compounds will have a κ GTP Emax (%) of greater than about 15%. In another embodiment, the Substituted-Quinoxaline-Type Piperidine Compounds will have a κ GTP Emax (%) of greater than about 30%. In another embodiment, the Substituted-Quinoxaline-Type Piperidine Compounds will have a κ GTP Emax (%) of greater than about 40%. In another embodiment, the Substituted-Quinoxaline-Type Piperidine Compounds will have a κ GTP Emax (%) of greater than about 45%. In another embodiment, the Substituted-Quinoxaline-Type Piperidine Compounds will have a κ GTP Emax (%) of greater than about 75%. In another embodiment, the Substituted-Quinoxaline-Type Piperidine Compounds will have a κ GTP Emax (%) of greater than about 90%. In another embodiment, the Substituted-Quinoxaline-Type Piperidine Compounds will have a κ GTP Emax (%) of about 100% or greater.

5.55 Example 55

In Vitro Delta-Opioid Receptor Binding Assays

δ-Opioid Receptor Binding Assay Procedures: Radioligand dose-displacement assays used 0.2 nM [$^3$H]-Naltrindole (NEN; 33.0 Ci/mmole) with 10-20 μg membrane protein (recombinant delta opioid receptor expressend in CHO-K1 cells; Perkin Elmer) in a final volume of 500 μL binding buffer (5 mM $MgCl_2$, 5% DMSO, 50 mM Trizma base, pH 7.4). Non-specific binding was determined in the presence of 25 μM unlabeled naloxone. All reactions were performed in 96-deep well polypropylene plates for 1 h at a temperature of about 25° C. Binding reactions were determined by rapid filtration onto 96-well Unifilter GF/C filter plates (Packard) presoaked in 0.5% polyethylenimine (Sigma). Harvesting was performed using a 96-well tissue harvester (Packard) followed by five filtration washes with 500 μL ice-cold binding buffer. Filter plates were subsequently dried at 50° C. for 1-2 hours. Fifty μL/well scintillation cocktail (MicroScint20, Packard) was added and plates were counted in a Packard Top-Count for 1 min/well.

δ-Opioid Receptor Binding Data: In one embodiment, the Substituted-Quinoxaline-Type Piperdine Compounds will have substantially no activity at δ receptors. Typically, the Substituted-Quinoxaline-Type Piperidine Compounds will have a Ki (nM) of about 20,000 or less for δ receptors. In one embodiment, the Substituted-Quinoxaline-Type Piperidine Compounds will have a Ki (nM) of about 10,000 or less. In another embodiment, the Substituted-Quinoxaline-Type Piperidine Compounds will have a Ki (nM) of about 7500 or less. In another embodiment, the Substituted-Quinoxaline-Type Piperidine Compounds will have a Ki (nM) of about 6500 or less. In another embodiment, the Substituted-Quinoxaline-Type Piperidine Compounds will have a Ki (nM) of about 5000 or less. In another embodiment, the Substituted-Quinoxaline-Type Piperidine Compounds will have a Ki (nM) of about 3000 or less. In another embodiment, the Substituted-Quinoxaline-Type Piperidine Compounds will have a Ki (nM) of about 2500 or less. In another embodiment, the Substituted-Quinoxaline-Type Piperidine Compounds will have a Ki (nM) of about 1000 or less. In another embodiment, the Substituted-Quinoxaline-Type Piperidine Compounds will have a Ki (nM) of about 500 or less. In another embodiment, the Substituted-Quinoxaline-Type Piperidine Compounds will have a Ki (nM) of about 350 or less. In another embodiment, the Substituted-Quinoxaline-Type Piperidine Compounds will have a Ki (nM) of about 250 or less. In another embodiment, the Substituted-Quinoxaline-Type Piperidine Compounds will have a Ki (nM) of about 100 or less. In another embodiment, the Substituted-Quinoxaline-Type Piperidine Compounds will have a Ki (nM) of about 10 or less.

5.56 Example 56

In Vitro Delta-Opioid Receptor Functional Assays

δ-Opioid Receptor Functional Assay Procedures: Functional [$^{35}$S]GTPγS binding assays were conducted as follows. Delta opioid receptor membrane solution was prepared by sequentially adding final concentrations of 0.026 μg/μL delta membrane protein (Perkin Elmer), 10 μg/mL saponin, 3 μM GDP and 0.20 nM [$^{35}$S]GTPγS to binding buffer (100 mM NaCl, 10 mM $MgCl_2$, 20 mM HEPES, pH 7.4) on ice. The prepared membrane solution (190 μL/well) was transferred to 96-shallow well polypropylene plates containing 10 μL of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Packard) using a 96-well tissue harvester (Packard) and followed by three filtration washes with 200 μL ice-cold binding buffer (10 mM $NaH_2PO_4$, 10 mM $Na_2HPO_4$, pH 7.4). Filter plates were subsequently dried at 50° C. for 1-2 hours. Fifty μL/well scintillation cocktail (MicroScint20, Packard) was added and plates were counted in a Packard Top-count for 1 min/well.

δ-Opioid Receptor Functional Data: δ GTP $EC_{50}$ is the concentration of a compound providing 50% of the maximal response for the compound at a δ receptor. Substituted-Quinoxaline-Type Piperidine Compounds typically will have a δ GTP $EC_{50}$ (nM) of about 20,000 or less to stimulate δ opioid receptor function. In one embodiment, the Substituted-Quinoxaline-Type Piperidine Compounds will have a δ GTP $EC_{50}$ (nM) of about 10,000 or less. In another embodiment, the Substituted-Quinoxaline-Type Piperidine Compounds will have a δ GTP $EC_{50}$ (nM) of about 100 or less. In another embodiment, the Substituted-Quinoxaline-Type Piperidine Compounds will have a δ GTP $EC_{50}$ (nM) of about 1000 or less. In another embodiment, the Substituted-Quinoxaline-Type Piperidine Compounds will have a δ GTP $EC_{50}$ (nM) of about 90 or less. In another embodiment, the Substituted-Quinoxaline-Type Piperidine Compounds will have a δ GTP $EC_{50}$ (nM) of about 50 or less. In another embodiment, the Substituted-Quinoxaline-Type Piperidine Compounds will have a δ GTP $EC_{50}$ (nM) of about 25 or less. In another embodiment, the Substituted-Quinoxaline-Type Piperidine Compounds will have a δ GTP $EC_{50}$ (nM) of about 10 or less.

δ GTP Emax (%) is the maximal effect elicited by a compound relative to the effect elicited by met-enkephalin. Typically, the Substituted-Quinoxaline-Type Piperidine Compounds of the invention will have a δ GTP Emax (%) of greater than about 10%. In one embodiment, the Substituted-Quinoxaline-Type Piperidine Compounds will have a δ GTP Emax (%) of greater than about 30%. In another embodiment, the Substituted-Quinoxaline-Type Piperidine Compounds will have a δ GTP Emax (%) of greater than about 50%. In another embodiment, the Substituted-Quinoxaline-Type Piperidine Compounds will have a δ GTP Emax (%) of greater than about 75%. In another embodiment, the Substituted-Quinoxaline-Type Piperidine Compounds will have a δ GTP Emax (%) of greater than about 90%. In another embodiment, the Substituted-Quinoxaline-Type Piperidine Compounds will have a δ GTP Emax (%) of about 100% or greater. In another embodiment, the Substituted-Quinoxaline-Type Piperidine Compounds will have a δ GTP Emax (%) of about 110% or greater.

5.57 Example 57

Efficacy of Receptor Binding and Activity Response

The following Tables provide results on the efficacy of binding and activity response of several Substituted-Quinoxaline-Type Piperidine Compounds to the ORL-1 receptor and, for certain Substituted-Quinoxaline-Type Piperidine Compounds, the mu-opioid receptor, the kappa-opioid receptor, and/or the delta-opioid receptor.

In Table 1, binding efficacy to the ORL-1 receptor was determined by the procedure in Example 49. Binding efficacy to the mu-opioid receptor was determined by the procedure in Example 51. Binding efficacy to the kappa-opioid receptor was determined by the procedure in Example 53. Binding efficacy to the delta-opioid receptor was determined by the procedure in Example 55.

In Table 2, activity response to the ORL-1 receptor was determined by the procedure in Example 50. Activity response to the mu-opioid receptor was determined by the procedure in Example 52. Activity response to the kappa-opioid receptor was determined by the procedure in Example 54. Activity response to the delta-opioid receptor can be determined by the procedure in Example 56.

TABLE 1

Efficacy of Receptor Binding of Substituted-Quinoxaline-Type Piperidine Compounds

| | | $K_i$ [Average ± Std Deviation] (nM) | | | |
|---|---|---|---|---|---|
| Ref | | | Opioid Receptor | | |
| No. | Compound | ORL-1 | Mu | Kappa | Delta |
| 1 | | 326.1 ± 34.6 | 13470 ± 1595 | | 76337 |
| 2 | | 67.2 ± 112.0 | 2053 ± 343 | 257.0 ± 122.0 | 28064 |
| 3 | | 153.7 ± 7.0 | 17060 ± 12280 | 888 ± 1173 | $>10^5$ |
| 4 | | 117.5 ± 112.1 | 3869 ± 1724 | 135.8 ± 115.0 | 8918± 2238 |
| 5 | | 19.4 ± 12.5 | 4340 ± 1155 | 22.5 ± 15.8 | 23220 |
| 6 | | 152 ± 125 | 1145 ± 1104 | 165.2 ± 123.1 | 11122 |
| 7 | | 156 ± 24 | 1074 ± 1182 | 296 ± 45 | 19610 |
| 8 | | 322 ± 79 | 1634 ± 115 | | 7556 ± 363 |
| 9 | | 14.2 ± 13.3 | 1397 ± 1108 | 167.6 ± 15.2 | 47271 |
| 10 | | 72.1 ± 19.1 | 1480 ± 120 | 73.5 ± 118.2 | 27675 |
| 11 | | 114.9 ± 24.2 | 1530 ± 185 | 905 ± 177 | 44071 |
| 12 | | 20.9 ± 3.9 | 2391 ± 261 | 15.1 ± 2.2 | 519741 |
| 13 | | 96.5 ± 18.8 | 3278 ± 270 | 283 ± 155 | 43483 |
| 14 | | 301 ± 29 | 3157 ± 197 | | 15188 |
| 15 | | 15.4 ± 1.8 | 1199 ± 173 | 92.9 ± 16.4 | 24560 |

TABLE 1-continued

Efficacy of Receptor Binding of Substituted-Quinoxaline-Type Piperidine Compounds

| Ref No. | Compound | $K_i$ [Average ± Std Deviation] (nM) | | | |
| --- | --- | --- | --- | --- | --- |
| | | | Opioid Receptor | | |
| | | ORL-1 | Mu | Kappa | Delta |
| 16 | (structure) | 97.8 ± 5.0 | 2313 ± 247 | 328 ± 11.3 | 34024 |
| 17 | | 181.8 ± 1.6 | 5254 ± 208 | 622 ± 102 | 37800 |
| 18 | | 182 ± 29 | 2078 ± 57 | 303 ± 9 | 55229 |
| 19 | | 16.8 ± 0.8 | 26627 | 11500 ± 1090 | 545749 |
| 20 | (structure) | 547 ± 90.0 | | | |

TABLE 1-continued

Efficacy of Receptor Binding of Substituted-Quinoxaline-Type Piperidine Compounds

| Ref No. | Compound | K_i [Average ± Std Deviation] (nM) | | | |
|---|---|---|---|---|---|
| | | | Opioid Receptor | | |
| | | ORL-1 | Mu | Kappa | Delta |
| 21 | | 74.8 ± 3.5 | 3396 ± 362 | 151 ± 20 | 22592 |
| 22 | | 35.2 ± 2.3 | 3037 ± 579 | 30.4 ± 2.2 | 19407 |
| 23 | | 60.8 ± 5.1 | 3942 ± 1253 | 514 ± 70 | 52099 |
| 24 | | 27.0 ± 5.2 | 5281 ± 1532 | 852 ± 61 | 60848 |
| 25 | | 65.7 ± 10.0 | 5979 ± 937 | 1300 ± 360 | 82251 |

TABLE 1-continued
Efficacy of Receptor Binding of Substituted-Quinoxaline-Type Piperidine Compounds
| Ref No. | Compound | $K_i$ [Average ± Std Deviation] (nM) | | | |
| --- | --- | --- | --- | --- | --- |
| | | Opioid Receptor | | | |
| | | ORL-1 | Mu | Kappa | Delta |
| 26 | 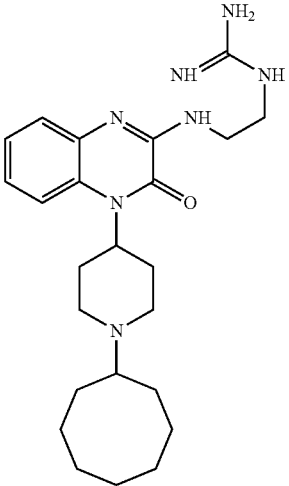 [SMILES: N=C(N)NCCNc1nc2ccccc2n(C2CCN(C3CCCCCCC3)CC2)c1=O] | 7.1 ± 0.3 | 629 ± 24 | 191.4 ± 30.4 | 35858 |
| 27 | 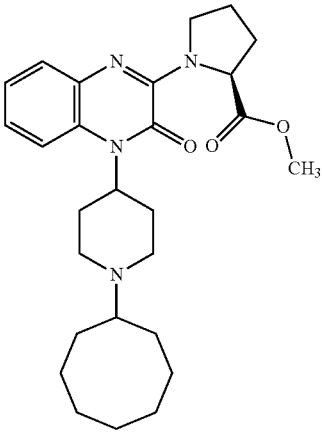 [SMILES: COC(=O)[C@@H]1CCCN1c1nc2ccccc2n(C2CCN(C3CCCCCCC3)CC2)c1=O] | 48.5 ± 7.0 | 2438 ± 493 | 583 ± 155.2 | 27790 |
| 28 | 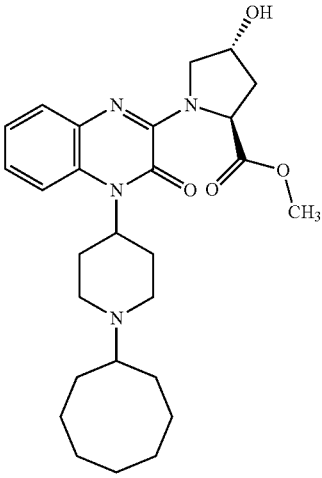 [SMILES: COC(=O)[C@@H]1C[C@@H](O)CN1c1nc2ccccc2n(C2CCN(C3CCCCCCC3)CC2)c1=O] | 156.3 ± 9.4 | 5244 ± 939 | 1038 ± 252 | 66315 |

TABLE 1-continued
Efficacy of Receptor Binding of Substituted-Quinoxaline-Type Piperidine Compounds
| Ref No. | Compound | $K_i$ [Average ± Std Deviation] (nM) | | | |
|---|---|---|---|---|---|
| | | | Opioid Receptor | | |
| | | ORL-1 | Mu | Kappa | Delta |
| 29 | 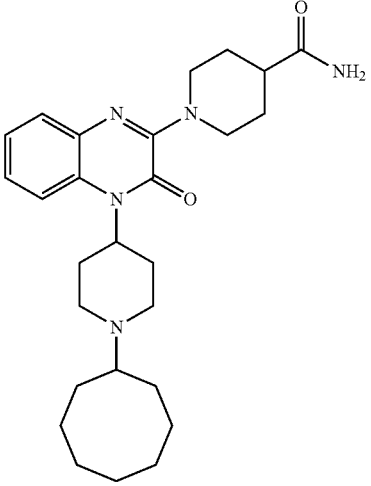 [SMILES: NC(=O)C1CCN(c2nc3ccccc3n(C3CCN(C4CCCCCCC4)CC3)c2=O)CC1] | 39.8 ± 2.6 | 3780 ± 1098 | 481 ± 87 | inactive |
| 30 | 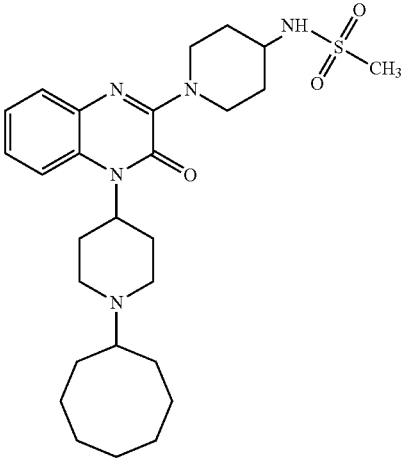 [SMILES: CS(=O)(=O)NC1CCN(c2nc3ccccc3n(C3CCN(C4CCCCCCC4)CC3)c2=O)CC1] | 57.9 ± 1.3 | 1895 ± 309 | 378 ± 62.4 | 61698 |
| 31 | 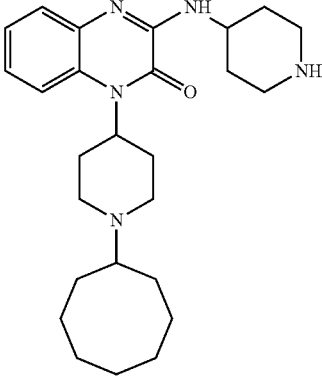 [SMILES: O=c1c(NC2CCNCC2)nc2ccccc2n1C1CCN(C2CCCCCCC2)CC1] | 36.9 ± 3.0 | 1488 ± 321 | 67.5 ± 7.6 | 34671 |

TABLE 1-continued

Efficacy of Receptor Binding of Substituted-Quinoxaline-Type Piperidine Compounds

| | | $K_i$ [Average ± Std Deviation] (nM) | | | |
| --- | --- | --- | --- | --- | --- |
| | | | Opioid Receptor | | |
| Ref No. | Compound | ORL-1 | Mu | Kappa | Delta |
| 32 | | 37.4 ± 7.5 | 6403 ± 1943 | 354 ± 28.2 | 548766 |
| 33 | | 22.9 ± 4.9 | 3341 ± 1068 | 1282.6 ± 212.1 | 96003 |
| 34 | | 153 ± 36 | 627 ± 137 | 46.34 ± 5.96 | 26105 |

TABLE 1-continued

Efficacy of Receptor Binding of Substituted-Quinoxaline-Type Piperidine Compounds

| Ref No. | Compound | $K_i$ [Average ± Std Deviation] (nM) | | | |
|---|---|---|---|---|---|
| | | | Opioid Receptor | | |
| | | ORL-1 | Mu | Kappa | Delta |
| 37 | | 18.6 ± 3.7 | 2064 ± 346 | 222.01 ± 34.1 | 56989 |
| 38 | | 5.7 ± 1.3 | 1451 ± 313 | 375 ± 79.5 | 6673 |
| 39 | | 8.6 ± 1.9 | 624 ± 22 | 57.3 ± 7.43 | 52574 |

TABLE 1-continued
Efficacy of Receptor Binding of Substituted-Quinoxaline-Type Piperidine Compounds
| Ref No. | Compound | $K_i$ [Average ± Std Deviation] (nM) | | | |
| --- | --- | --- | --- | --- | --- |
| | | Opioid Receptor | | | |
| | | ORL-1 | Mu | Kappa | Delta |
| 40 | 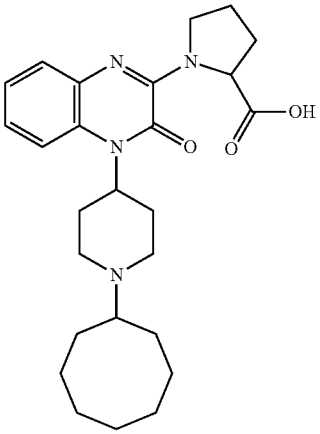 [SMILES: O=C(O)C1CCCN1c1nc2ccccc2n(C2CCN(C3CCCCCCC3)CC2)c1=O] | 309 ± 33 | | | |
| 41 | 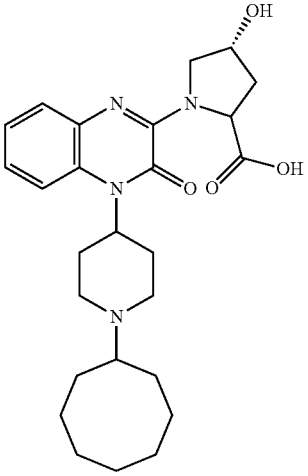 [SMILES: O=C(O)C1C[C@@H](O)CN1c1nc2ccccc2n(C2CCN(C3CCCCCCC3)CC2)c1=O] | 426 ± 85 | | | |
| 42 | 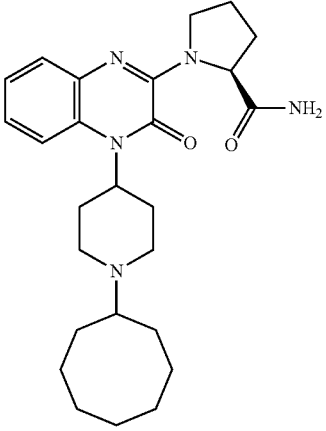 [SMILES: NC(=O)[C@@H]1CCCN1c1nc2ccccc2n(C2CCN(C3CCCCCCC3)CC2)c1=O] | 36.9 ± 4.5 | 1866 ± 27 | 611.9 ± 37.1 | 81321 |

TABLE 1-continued
Efficacy of Receptor Binding of Substituted-Quinoxaline-Type Piperidine Compounds
| Ref No. | Compound | $K_i$ [Average ± Std Deviation] (nM) | | | |
| --- | --- | --- | --- | --- | --- |
| | | Opioid Receptor | | | |
| | | ORL-1 | Mu | Kappa | Delta |
| 43 | 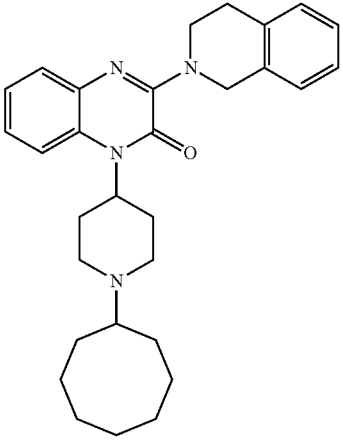 [SMILES: O=c1c(N2CCc3ccccc3C2)nc2ccccc2n1C1CCN(C2CCCCCCC2)CC1] | 42.3 ± 6.1 | 809 ± 57 | 544.2 ± 57 | 38851 |
| 44 | 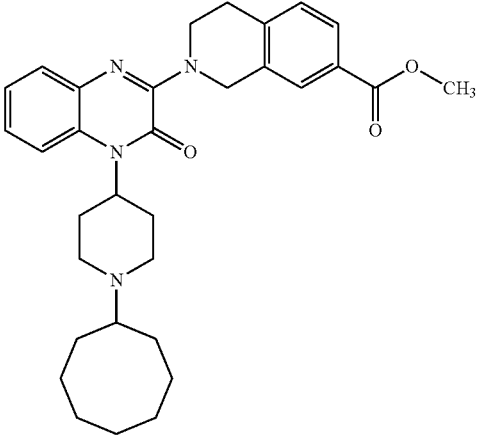 [SMILES: COC(=O)c1ccc2c(c1)CN(c1nc3ccccc3n(C3CCN(C4CCCCCCC4)CC3)c1=O)CC2] | 111 ± 24 | 513 ± 27 | 301 ± 68.4 | 45038 |
| 45 | 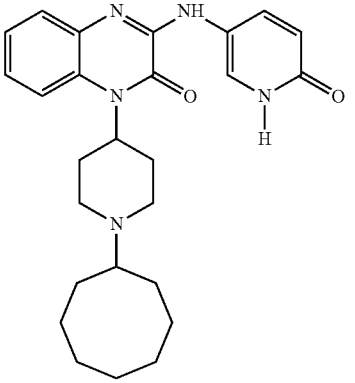 [SMILES: O=c1ccc(Nc2nc3ccccc3n(C3CCN(C4CCCCCCC4)CC3)c2=O)c[nH]1] | 46.3 ± 3.0 | 3986 ± 1172 | 805 ± 97.4 | 46719 |

TABLE 1-continued
Efficacy of Receptor Binding of Substituted-Quinoxaline-Type Piperidine Compounds
| Ref No. | Compound | $K_i$ [Average ± Std Deviation] (nM) | | | |
| --- | --- | --- | --- | --- | --- |
| | | | Opioid Receptor | | |
| | | ORL-1 | Mu | Kappa | Delta |
| 46 | 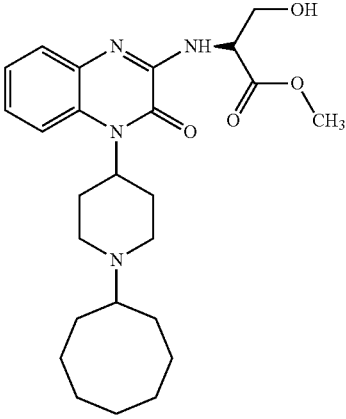 | 32.1 ± 3.7 | 1414 ± 337 | 191 ± 34.5 | 518930 |
| 47 | 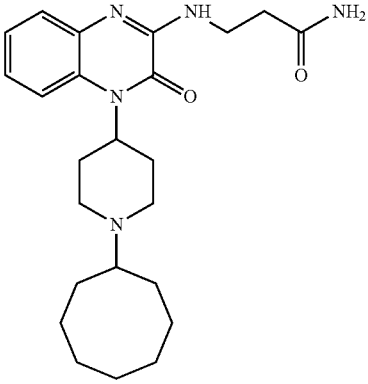 [SMILES: NC(=O)CCNc1nc2ccccc2n(C2CCN(C3CCCCCCC3)CC2)c1=O] | 42.4 ± 2.7 | 2368 ± 245 | 731 ± 55.1 | >10$^5$ |
| 48 | 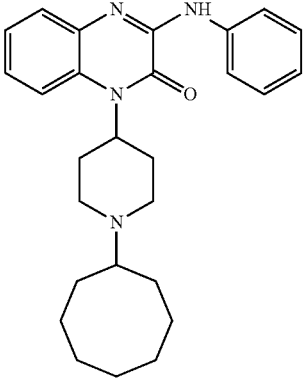 [SMILES: O=c1c(Nc2ccccc2)nc2ccccc2n1C1CCN(C2CCCCCCC2)CC1] | 355 ± 31 | | | |

TABLE 1-continued

Efficacy of Receptor Binding of Substituted-Quinoxaline-Type Piperidine Compounds

| Ref No. | Compound | $K_i$ [Average ± Std Deviation] (nM) | | | |
|---|---|---|---|---|---|
| | | Opioid Receptor | | | |
| | | ORL-1 | Mu | Kappa | Delta |
| 49 | | 70.9 ± 7.2 | 1345 ± 153 | 971 ± 50.6 | 531427 |
| 50 | | 35.2 ± 2.1 | 634 ± 28 | | 59230 |
| 51 | | 4.0 ± 0.6 | 512 ± 79 | 22 ± 2.1 | 28106 |

TABLE 1-continued

Efficacy of Receptor Binding of Substituted-Quinoxaline-Type Piperidine Compounds

| Ref No. | Compound | K$_i$ [Average ± Std Deviation] (nM) Opioid Receptor ||||
| | | ORL-1 | Mu | Kappa | Delta |
|---|---|---|---|---|---|
| 52 | | 92 ± 16 | 3557 ± 1293 | 712 ± 177 | 43207 |
| 53 | | 332 ± 77 | | | |
| 54 | | 31.9 ± 4.8 | 5414 ± 591 | 1195 ± 151 | 528011 |

TABLE 1-continued
Efficacy of Receptor Binding of Substituted-Quinoxaline-Type Piperidine Compounds
| Ref No. | Compound | $K_i$ [Average ± Std Deviation] (nM) | | | |
| --- | --- | --- | --- | --- | --- |
| | | Opioid Receptor | | | |
| | | ORL-1 | Mu | Kappa | Delta |
| 55 | 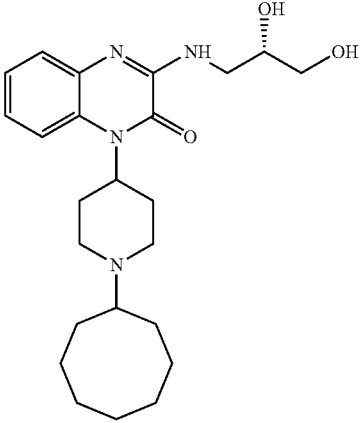 [SMILES: O=c1c(NC[C@H](O)CO)nc2ccccc2n1C1CCN(C2CCCCCCC2)CC1] | 24.1 ± 7.0 | 2109 ± 765 | 929 ± 152 | 530892 |
| 56 | 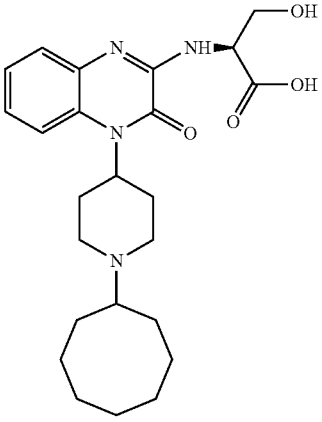 [SMILES: O=C(O)[C@H](CO)Nc1nc2ccccc2n(C2CCN(C3CCCCCCC3)CC2)c1=O] | 36.5 ± 6.9 | 5056 ± 1453 | 544 ± 30.7 | 19145 |
| 57 | 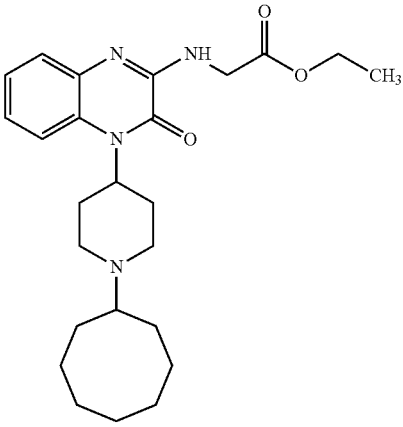 [SMILES: CCOC(=O)CNc1nc2ccccc2n(C2CCN(C3CCCCCCC3)CC2)c1=O] | 45 ± 13 | 1360 ± 468 | 379 ± 48.3 | 532394 |

TABLE 1-continued
Efficacy of Receptor Binding of Substituted-Quinoxaline-Type Piperidine Compounds
| Ref No. | Compound | $K_i$ [Average ± Std Deviation] (nM) | | | |
|---|---|---|---|---|---|
| | | | Opioid Receptor | | |
| | | ORL-1 | Mu | Kappa | Delta |
| 58 | 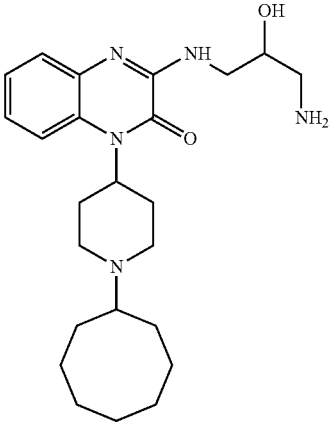 [SMILES: NCC(O)CNc1nc2ccccc2n(C2CCN(C3CCCCCCC3)CC2)c1=O] | 14.8 ± 2.0 | 524 ± 107 | 175 ± 11.6 | 45883 |
| 59 | 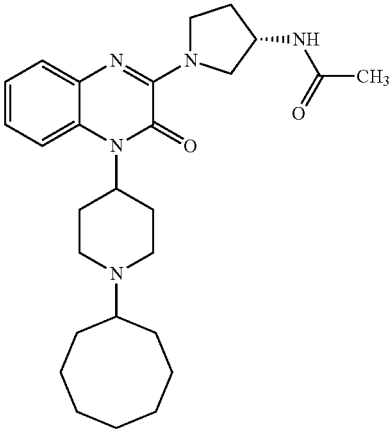 [SMILES: CC(=O)N[C@H]1CCN(c2nc3ccccc3n(C3CCN(C4CCCCCCC4)CC3)c2=O)C1] | 29.9 ± 1.4 | 3183 ± 1005 | 457 ± 72 | 53164 |
| 60 | 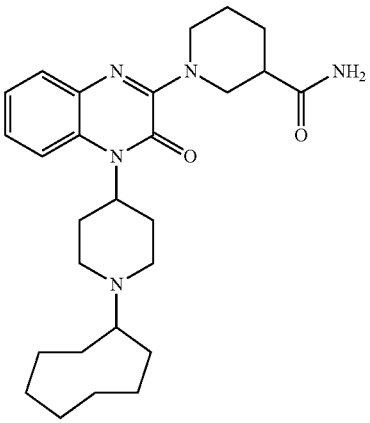 [SMILES: NC(=O)C1CCCN(c2nc3ccccc3n(C3CCN(C4CCCCCCC4)CC3)c2=O)C1] | 130 ± 29 | 6657 ± 2010 | 510 ± 125 | 38477 |

TABLE 1-continued
Efficacy of Receptor Binding of Substituted-Quinoxaline-Type Piperidine Compounds
| Ref No. | Compound | $K_i$ [Average ± Std Deviation] (nM) | | | |
|---|---|---|---|---|---|
| | | Opioid Receptor | | | |
| | | ORL-1 | Mu | Kappa | Delta |
| 61 | 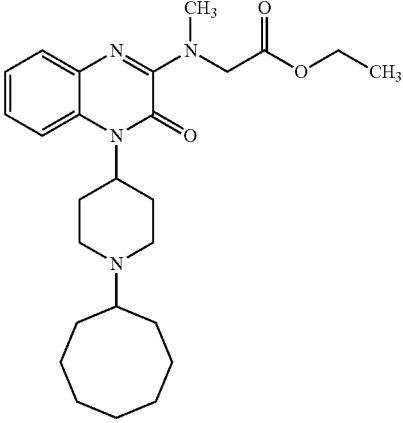 [SMILES: CCOC(=O)CN(C)c1nc2ccccc2n(C2CCN(C3CCCCCCC3)CC2)c1=O] | 130 ± 10 | 4412 ± 953 | 810 ± 170 | 28131 |
| 62 | 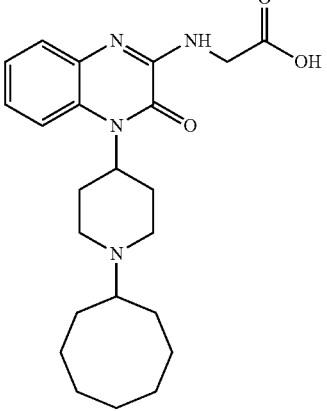 | 368 ± 39 | | | |
| 63 | 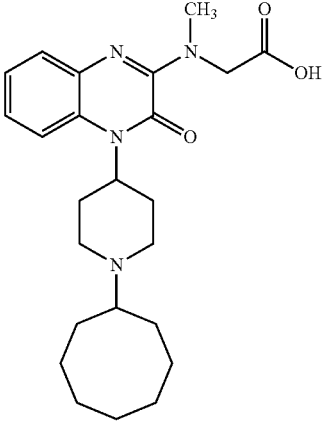 [SMILES: CN(CC(=O)O)c1nc2ccccc2n(C2CCN(C3CCCCCCC3)CC2)c1=O] | 438 ± 36 | | | |

TABLE 1-continued

Efficacy of Receptor Binding of Substituted-Quinoxaline-Type Piperidine Compounds

| | | $K_i$ [Average ± Std Deviation] (nM) | | | |
|---|---|---|---|---|---|
| Ref | | | Opioid Receptor | | |
| No. | Compound | ORL-1 | Mu | Kappa | Delta |
| 64 | | 54.8 ± 1.3 | 9284 ± 2250 | 4359 ± 796 | inactive |
| 65 | | 85.3 ± 4.5 | 3642 ± 704 | 1149 ± 121 | 85587 |
| 66 | | 15.5 ± 1.3 | 1523 ± 106 | 587 ± 131 | 28211 |

TABLE 1-continued
Efficacy of Receptor Binding of Substituted-Quinoxaline-Type Piperidine Compounds
| Ref No. | Compound | $K_i$ [Average ± Std Deviation] (nM) Opioid Receptor |  |  |  |
|---|---|---|---|---|---|
| | | ORL-1 | Mu | Kappa | Delta |
| 67 | 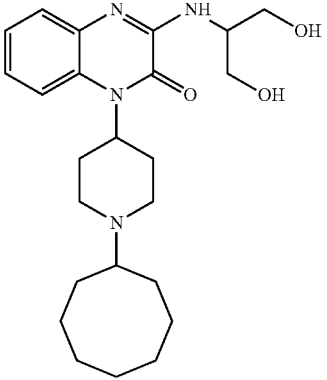 [SMILES: O=c1c(NC(CO)CO)nc2ccccc2n1C1CCN(C2CCCCCCC2)CC1] | 19.1 ± 0.8 | 3296 ± 722 | 666 ± 74 | 86219 |
| 68 | 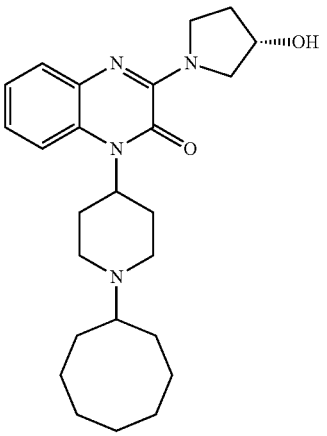 [SMILES: O=c1c(N2CC[C@H](O)C2)nc2ccccc2n1C1CCN(C2CCCCCCC2)CC1] | 49.8 ± 3.7 | 6155 ± 354 | 1486 ± 180 | 54999 |
| 69 | 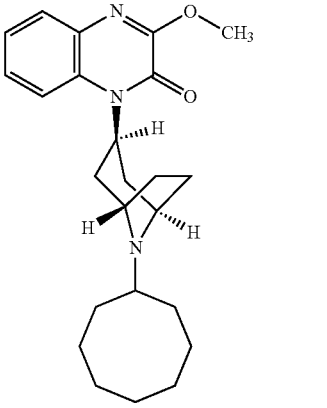 [SMILES: COc1nc2ccccc2n([C@H]2C[C@H]3CC[C@@H](C2)N3C2CCCCCCC2)c1=O] | 4.2 ± 0.9 | 248 ± 33 | 161 ± 47 | 13091 |
| 70 | | 109 ± 7 | 2511 ± 193 | 141 ± 10 | 13080 |
| 71 | | 111 ± 6.7 | 7426 ± 254 | 1034 ± 232 | 31727 |
| 72 | | 220 ± 17 | 887 ± 84 | 23.4 ± 1.1 | |
| 73 | | 52.8 ± 7.5 | | | |

TABLE 1-continued

Efficacy of Receptor Binding of Substituted-Quinoxaline-Type Piperidine Compounds

| Ref No. | Compound | $K_i$ [Average ± Std Deviation] (nM) | | | |
|---|---|---|---|---|---|
| | | | Opioid Receptor | | |
| | | ORL-1 | Mu | Kappa | Delta |
| 74 | (structure) | 12.6 ± 0.8 | 678 ± 9 | 630 ± 218 | 47391 |
| 75 | (structure) | 273 ± 13 | | | |
| 76 | (structure) | 375 ± 115 | | | |

TABLE 1-continued

Efficacy of Receptor Binding of Substituted-Quinoxaline-Type Piperidine Compounds

| Ref No. | Compound | $K_i$ [Average ± Std Deviation] (nM) | | | |
|---|---|---|---|---|---|
| | | Opioid Receptor | | | |
| | | ORL-1 | Mu | Kappa | Delta |
| 77 | (structure with -C(O)NH₂, quinoxalinone, piperidine, cyclooctyl) | 10.9 ± 1.8 | 1239 ± 162 | 418 ± 42 | 21144 |
| 78 | (structure with -C(O)NH-CH₃, quinoxalinone, piperidine, cyclooctyl) | 40.7 ± 4.1 | 1723 ± 313 | 618 ± 107 | 16831 |
| 79 | (structure with -C(O)NH-CH₂-CH(OH)-CH₂OH, quinoxalinone, piperidine, cyclooctyl) | 51 ± 12 | 2727 ± 260 | 994 ± 92 | 20971 |

TABLE 1-continued

Efficacy of Receptor Binding of Substituted-Quinoxaline-Type Piperidine Compounds

| Ref No. | Compound | $K_i$ [Average ± Std Deviation] (nM) | | | |
| --- | --- | --- | --- | --- | --- |
| | | Opioid Receptor | | | |
| | | ORL-1 | Mu | Kappa | Delta |
| 80 | | 13.7 ± 4.1 | 871 ± 196 | 132 ± 18 | 23741 |
| 81 | | 44 ± 12 | 2787 ± 843 | 669 ± 88 | 20507 |
| 82 | | 16.2 ± 4.4 | 2144 ± 549 | 391 ± 71 | 15770 |

TABLE 1-continued

Efficacy of Receptor Binding of Substituted-Quinoxaline-Type Piperidine Compounds

| Ref No. | Compound | $K_i$ [Average ± Std Deviation] (nM) Opioid Receptor | | | |
|---|---|---|---|---|---|
| | | ORL-1 | Mu | Kappa | Delta |
| 83 | (quinoxaline-piperidine-cyclooctyl with C(O)NH-O-CH₃) | 44 ± 20 | 1918 ± 621 | 586 ± 97 | 10177 |
| 84 | (quinoxaline-piperidine-cyclooctyl with C(O)NH-O-CH₂-phenyl) | 12.7 ± 0.5 | 1914 ± 277 | 245 ± 46 | 2712 ± 258 |
| 85 | | 92.2 ± 10.6 | 4089 ± 1450 | 182 ± 26 | 17850 ± 3075 |
| 86 | | 179.4 ± 37.3 | 6758 ± 810 | 83.5 ± 12.8 | 9670 ± 2065 |
| 87 | | 338 ± 6 | | | |
| 88 | (quinoxaline-piperidine-cyclooctyl with CN) | 20.8 ± 4.3 | 1663 ± 590 | 536 ± 56 | 15584 |

TABLE 1-continued

Efficacy of Receptor Binding of Substituted-Quinoxaline-Type Piperidine Compounds

| Ref No. | Compound | K$_i$ [Average ± Std Deviation] (nM) ||||
| | | Opioid Receptor ||||
| | | ORL-1 | Mu | Kappa | Delta |
| --- | --- | --- | --- | --- | --- |
| 89 | | 75.2 ± 6.1 | 10180 ± 2530 | 4490 ± 1110 | 535200 |
| 90 | | 6.42 ± 0.71 | 459.3 ± 8.9 | 253 ± 39 | 38310 |
| 91 | | 5.54 ± 0.23 | 394.3 ± 4.2 | 224 ± 14 | 21860 |

TABLE 1-continued

Efficacy of Receptor Binding of Substituted-Quinoxaline-Type Piperidine Compounds

| Ref No. | Compound | $K_i$ [Average ± Std Deviation] (nM) | | | |
|---|---|---|---|---|---|
| | | Opioid Receptor | | | |
| | | ORL-1 | Mu | Kappa | Delta |
| 92 | | 41.2 ± 0.5 | 4650 ± 657 | 688 ± 189 | 34954 |
| 93 | | 299 ± 19 | | | |
| 94 | | 4.42 ± 0.43 | 819 ± 29 | 154 ± 19 | 25250 |

TABLE 1-continued

Efficacy of Receptor Binding of Substituted-Quinoxaline-Type Piperidine Compounds

| Ref No. | Compound | $K_i$ [Average ± Std Deviation] (nM) | | | |
|---|---|---|---|---|---|
| | | | Opioid Receptor | | |
| | | ORL-1 | Mu | Kappa | Delta |
| 95 | | 10.71 ± 0.64 | 5570 ± 981 | 2728 ± 785 | 53540 |
| 98 | | 8.6 ± 0.2 | 196 ± 21 | 130 ± 15 | 29200 |
| 99 | | 109 ± 10 | 1670 ± 36 | 657 ± 26 | 4470 ± 170 |
| 100 | | 8.2 ± 1.2 | | | |
| 101 | | 1.6 ± 0.2 | 590 ± 47 | 14.9 ± 2.0 | 13970 |
| 102 | | 6.5 ± 0.5 | 576 ± 46 | 156 ± 20 | 49120 |

TABLE 1-continued

Efficacy of Receptor Binding of Substituted-Quinoxaline-Type Piperidine Compounds

| Ref No. | Compound | $K_i$ [Average ± Std Deviation] (nM) | | | |
|---|---|---|---|---|---|
| | | | Opioid Receptor | | |
| | | ORL-1 | Mu | Kappa | Delta |
| 103 | (structure) | 233.7 ± 7.8 | 6700 ± 700 | 4330 ± 700 | 26460 |
| 104 | | 120.1 ± 9.2 | 12100 ± 1315 | 5350 ± 1000 | 29775 |
| 105 | | 288 ± 39 | | | |
| 106 | | 61.4 ± 7.3 | 1172 ± 35 | 2840 ± 340 | 12882 |
| 107 | | 285 ± 33 | | | |
| 108 | (structure) | 607.4 ± 9.9 | | | |
| 109 | | 493 ± 34 | | | |
| 110 | | 1716 ± 177 | | | |
| 111 | | 189 ± 16 | 12825 ± 600 | 19250 | 35615 |
| 112 | | 500 ± 10 | | | |
| 113 | | 785 ± 72 | | | |
| 114 | | 52.1 ± 1.0 | 2510 ± 65 | 1203 ± 200 | 24072 |
| 115 | | 23.8 ± 0.9 | 770 ± 55 | 998 ± 92 | 57741 |
| 116 | | 836 ± 34 | | | |
| 117 | | 1342 ± 71 | | | |
| 118 | | 561 ± 75 | | | |

TABLE 1-continued
Efficacy of Receptor Binding of Substituted-Quinoxaline-Type Piperidine Compounds
| Ref No. | Compound | $K_i$ [Average ± Std Deviation] (nM) Opioid Receptor ||||
| | | ORL-1 | Mu | Kappa | Delta |
|---|---|---|---|---|---|
| 119 | | 73.2 ± 7.1 | 3330 ± 350 | 381 ± 50 | >10$^5$ |
| 120 | | 3.1 ± 0.3 | 210 ± 16 | 55.8 ± 6.3 | 1710 ± 340 |
| 121 | | 18.9 ± 1.3 | 743 ± 22 | 460 ± 71 | 13563 |
| 122 | | 7.5 ± 0.4 | 373.7 ± 1.6 | 161 ± 29 | 17516 |
| 123 | | 127.7 ± 8.0 | 2700 ± 250 | 743 ± 148 | 13745 |
| 124 | | 103 ± 10 | 9840 ± 422 | 2600 ± 165 | >10$^5$ |
| 125 | | 12.0 ± 0.3 | 391.0 ± 4.4 | 380 ± 51 | 42000 |
| 126 | | 43.7 ± 5.2 | 422 ± 25 | 422 ± 21 | 25970 |
| 127 | | 2.7 ± 0.4 | 188 ± 19 | 480 ± 80 | >10$^5$ |
| 128 | | 15.7 ± 2.4 | 488 ± 60 | 250 ± 15 | 17638 ± 320 |
| 129 | | 13.5 ± 1.1 | 462 ± 30 | 180 ± 13 | 26095 |
| 130 | | 11.9 ± 1.1 | 1320 ± 270 | 2430 ± 578 | 28211 |
| 131 | | 275 ± 10 | | | |
| 133 | 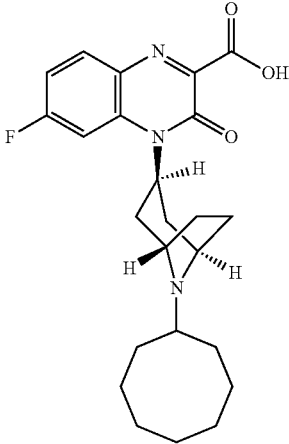 [SMILES: O=C(O)c1nc2ccc(F)cc2n([C@H]2C[C@H]3CC[C@@H](C2)N3C2CCCCCCC2)c1=O] | 135.9 ± 13.6 | 1217 ± 115 | 501 ± 80 | 25020 |
| 168 | | >10$^5$ | | | |
| 171 | | 44.6 ± 2.3 | | | |
| 226 | | 20.4 ± 4.0 | 3200 ± 125 | 707 ± 51 | >10$^5$ |
| 228 | | 4.4 ± 1.4 | 1083 ± 61 | 3320 ± 600 | >20,000 |
| 205 | | 437 ± 36 | | | |
| 207 | | 39.6 ± 5.7 | 1300 ± 57 | 346 ± 62 | >20,000 |
| 209 | | 78.8 ± 2.6 | 377 ± 36 | 534 ± 62 | 1870 |
| 188 | | 16.3 ± 2.0 | 723 ± 126 | 871 ± 90 | 16400 |
| 189 | | 10.9 ± 1.6 | 644.2 ± 11.9 | 67.0 ± 9.5 | 11430 |

TABLE 1-continued
Efficacy of Receptor Binding of Substituted-Quinoxaline-Type Piperidine Compounds
| Ref No. | Compound | $K_i$ [Average ± Std Deviation] (nM) | | | |
|---|---|---|---|---|---|
| | | | Opioid Receptor | | |
| | | ORL-1 | Mu | Kappa | Delta |
| 337 | 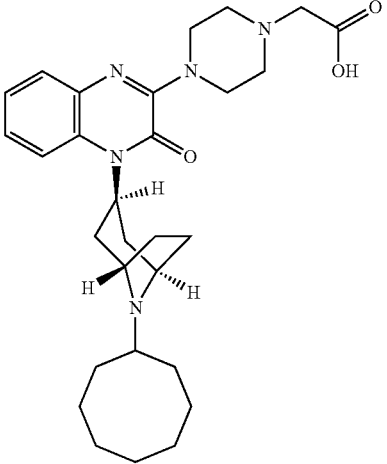 [SMILES: O=C(O)CN1CCN(c2nc3ccccc3n([C@H]3C[C@H]4CC[C@@H](C3)N4C3CCCCCCC3)c2=O)CC1] | 26.5 ± 1.6 | 706 ± 121 | 220.0 ± 7.7 | 8840 |
| 211 | | 34.7 ± 2.9 | 713 ± 48 | 568 ± 29 | >20,000 |
| 191 | | 60.4 ± 3.4 | 1990 ± 289 | 1493 ± 154 | 37410 |
| 193 | | 11.1 ± 0.3 | 6100 ± 56 | 224 ± 21 | >20,000 |
| 212 | | 14.6 ± 0.4 | 1140 ± 60 | 25.9 ± 1.8 | >20,000 |
| 218 | | 10.6 ± 0.5 | 2530 ± 270 | 863 ± 45 | >20,000 |
| 194 | | 158.0 ± 9.7 | 3920 ± 915 | 256 ± 38 | >20,000 |
| 196 | | 46.1 ± 1.4 | 5200 ± 370 | 1650 ± 203 | 8880 ± 970 |
| 221 | | 16.8 ± 0.4 | 10900 ± 1150 | 740 ± 145 | >20,000 |
| 197 | | 74.5 ± 5.7 | 8900 ± 410 | 890 ± 230 | >20,000 |
| 199 | | 237.3 ± 8.4 | >20,000 | 920 ± 360 | >20,000 |
| 201 | | 44.8 ± 1.8 | 1600 ± 260 | 1360 ± 170 | 2740 ± 850 |
| 216 | | 15.8 ± 1.1 | 2250 ± 530 | 134 ± 22 | >20,000 |
| 203 | | 140 ± 20 | 1470 ± 210 | 750 ± 58 | >20,000 |
| 180 | | 456 ± 74 | | | |

TABLE 1-continued

Efficacy of Receptor Binding of Substituted-Quinoxaline-Type Piperidine Compounds

| Ref No. | Compound | $K_i$ [Average ± Std Deviation] (nM) | | | |
|---|---|---|---|---|---|
| | | | Opioid Receptor | | |
| | | ORL-1 | Mu | Kappa | Delta |
| 305 | | 149 ± 23 | 4420 ± 250 | 780 ± 53 | >20,000 |
| 174 | | 71.4 ± 2.5 | 2918 ± 37 | 488 ± 21 | >20,000 |
| 176 | | 101.9 ± 4.5 | 4700 ± 238 | 1153 ± 165 | 1305 ± 39 |
| 178 | | 10.60 ± 0.02 | 2807 ± 307 | 429 ± 75 | >20,000 |
| 277 | | 538 ± 40 | | | |
| 231 | | 61.7 ± 0.7 | 11942 ± 294 | 2032 ± 286 | 547704 |
| 306 | | 114.9 ± 16.8 | 1458 ± 173 | 350 ± 13 | 22330 |

TABLE 1-continued

Efficacy of Receptor Binding of Substituted-Quinoxaline-Type Piperidine Compounds

| Ref No. | Compound | $K_i$ [Average ± Std Deviation] (nM) | | | |
| --- | --- | --- | --- | --- | --- |
| | | | Opioid Receptor | | |
| | | ORL-1 | Mu | Kappa | Delta |
| 307 | | 170 ± 24 | 1375 ± 182 | 478 ± 45 | 23090 |
| 308 | | 77.5 ± 17.1 | 60.2 ± 5.8 | 144 ± 16 | 12160 |
| 309 | | 62.9 ± 9.8 | 784 ± 43 | 210 ± 11 | 2045 |

TABLE 1-continued
Efficacy of Receptor Binding of Substituted-Quinoxaline-Type Piperidine Compounds
| Ref No. | Compound | $K_i$ [Average ± Std Deviation] (nM) | | | |
| --- | --- | --- | --- | --- | --- |
| | | | Opioid Receptor | | |
| | | ORL-1 | Mu | Kappa | Delta |
| 310 |  | 127.6 ± 9.3 | 770 ± 37 | 229 ± 23 | 8680 |
| 311 | 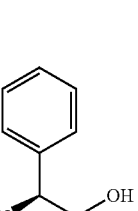 | 24.6 ± 3.0 | 400 ± 48 | 49.3 ± 2.4 | 2570 |
| 240 | | 40.3 ± 3.3 | 480 ± 40 | 46.3 ± 3.8 | 41190 |

TABLE 1-continued
Efficacy of Receptor Binding of Substituted-Quinoxaline-Type Piperidine Compounds
| Ref No. | Compound | $K_i$ [Average ± Std Deviation] (nM) | | | |
| --- | --- | --- | --- | --- | --- |
| | | | Opioid Receptor | | |
| | | ORL-1 | Mu | Kappa | Delta |
| 312 | 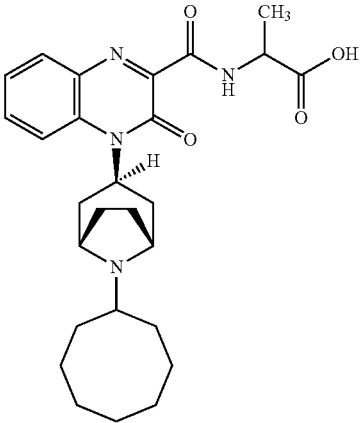 [SMILES: CC(NC(=O)c1nc2ccccc2n([C@H]2C[C@H]3CC[C@@H](C2)N3C2CCCCCCC2)c1=O)C(=O)O] | 35.9 ± 6.6 | 263 ± 11 | 172 ± 41 | 14500 |
| 313 | 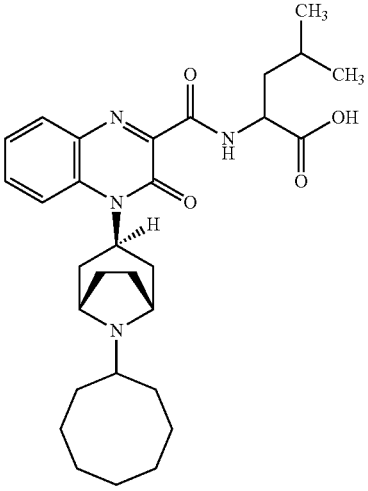 [SMILES: CC(C)CC(NC(=O)c1nc2ccccc2n([C@H]2C[C@H]3CC[C@@H](C2)N3C2CCCCCCC2)c1=O)C(=O)O] | 35.8 ± 9.1 | 452 ± 49 | 35.3 ± 1.3 | 2220 |
| 241 | | 17.7 ± 3.6 | 679 ± 69 | 440 ± 79 | 10900 |
| 253 | | 131.4 ± 9.2 | 5300 ± 900 | 2055 ± 427 | 68750 |
| 257 | | 1187 ± 103 | | | |
| 248 | | 911 ± 139 | | | |
| 249 | | 260 ± 14 | 46010 | 6000 ± 2040 | 533100 |
| 259 | | 962 ± 62 | | | |
| 255 | | 400 ± 22 | | | |
| 251 | | 3294 ± 219 | | | |

TABLE 1-continued

Efficacy of Receptor Binding of Substituted-Quinoxaline-Type Piperidine Compounds

| Ref No. | Compound | $K_i$ [Average ± Std Deviation] (nM) | | | |
|---|---|---|---|---|---|
| | | | Opioid Receptor | | |
| | | ORL-1 | Mu | Kappa | Delta |
| 314 | | 59.7 ± 4.1 | 1792 ± 112 | 909 ± 49 | 4925 |
| 153 | | 22.2 ± 1.8 | 459 ± 18 | 66.0 ± 15.6 | 530900 |
| 261 | | 596 ± 16 | | | |
| 245 | | 912 ± 72 | | | |
| 243 | | 1345 ± 67 | | | |
| 247 | | 89.9 ± 81 | 10970 | 3500 ± 623 | 533800 |
| 316 | | 632 ± 114 | | | |

TABLE 1-continued

Efficacy of Receptor Binding of Substituted-Quinoxaline-Type Piperidine Compounds

| Ref No. | Compound | K$_i$ [Average ± Std Deviation] (nM) | | | |
|---|---|---|---|---|---|
| | | | Opioid Receptor | | |
| | | ORL-1 | Mu | Kappa | Delta |
| 317 | | 157 ± 29 | 1160 ± 19 | 1720 ± 210 | >20,000 |
| 272 | | 740 ± 105 | | | |
| 274 | | 383 ± 45 | | | |
| 270 | | 52.1 ± 7.4 | 2660 ± 256 | 1600 ± 307 | >20 000 |
| 235 | | 18.1 ± 0.8 | 14300 ± 2650 | 1116 ± 18 | >20,000 |
| 318 | | 60.8 ± 7.9 | 1930 ± 335 | 835 ± 83 | 7730 ± 255 |
| 319 | | 611 ± 78 | | | |

TABLE 1-continued

Efficacy of Receptor Binding of Substituted-Quinoxaline-Type Piperidine Compounds

| Ref No. | Compound | $K_i$ [Average ± Std Deviation] (nM) | | | |
|---|---|---|---|---|---|
| | | | Opioid Receptor | | |
| | | ORL-1 | Mu | Kappa | Delta |
| 320 | | 15.4 ± 4.0 | 1865 ± 240 | 3090 ± 1300 | 15010 ± 380 |
| 321 | | >20,000 | | | |

TABLE 1-continued
Efficacy of Receptor Binding of Substituted-Quinoxaline-Type Piperidine Compounds
| Ref No. | Compound | $K_i$ [Average ± Std Deviation] (nM) | | | |
|---|---|---|---|---|---|
| | | | Opioid Receptor | | |
| | | ORL-1 | Mu | Kappa | Delta |
| 322 | 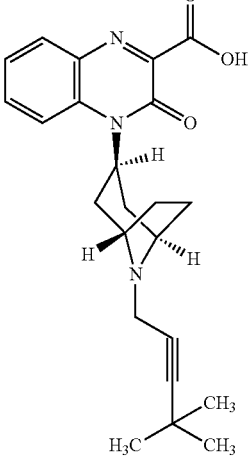 | 2841 ± 961 | | | |
| 323 | 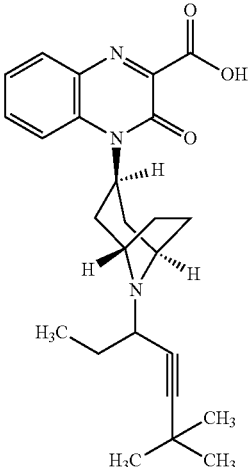 [SMILES: CCC(C#CC(C)(C)C)N1[C@@H]2CC[C@H]1C[C@@H](n1c(=O)c(C(=O)O)nc3ccccc31)C2] | 205 ± 35 | 2800 ± 450 | >20,000 | >20,000 |
| 324 | 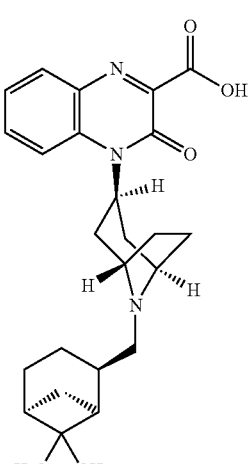 | 398 ± 59 | | | |

TABLE 1-continued

Efficacy of Receptor Binding of Substituted-Quinoxaline-Type Piperidine Compounds

| Ref No. | Compound | $K_i$ [Average ± Std Deviation] (nM) | | | |
|---|---|---|---|---|---|
| | | Opioid Receptor | | | |
| | | ORL-1 | Mu | Kappa | Delta |
| 233 | | 144 ± 37 | | | |
| 325 | | 82 ± 24 | | | |
| 266 | | 4.1 ± 0.6 | 679 ± 54 | 1430 ± 86 | >20,000 |
| 263 | | 47.5 ± 6.1 | 39554 | 5625 ± 1424 | 525570 |
| 237 | | 30.2 ± 0.4 | 16252 ± 3179 | 2473 ± 85 | 524333 |
| 239 | | 45.5 ± 4.4 | 57791 | 3272 ± 398 | 537763 |
| 326 | | 24.6 ± 1.2 | 10098 | 16.2 ± 2.2 | >20,000 |
| 279 | | 29.9 ± 0.7 | 16913 | 447 ± 79 | >20,000 |

TABLE 1-continued

Efficacy of Receptor Binding of Substituted-Quinoxaline-Type Piperidine Compounds

| Ref No. | Compound | K$_i$ [Average ± Std Deviation] (nM) | | | |
|---|---|---|---|---|---|
| | | | Opioid Receptor | | |
| | | ORL-1 | Mu | Kappa | Delta |
| 327 | | 104.2 ± 5.8 | 37211 | 72.5 ± 182.5 | >20,000 |
| 282 | | 502 ± 82 | 1445 ± 106 | 64.2 ± 8.5 | 32209 |
| 284 | | 21.5 ± 1.5 | 8927 ± 524 | 223.4 ± 12.1 | 72511 |
| 328 | | 7.7 ± 0.1 | 3877 ± 261 | 102.0 ± 6.9 | 18818 ± 507 |
| 329 | | 62.2 ± 7.5 | 7122 ± 605 | 31.2 ± 8.4 | 67102 |

TABLE 1-continued
Efficacy of Receptor Binding of Substituted-Quinoxaline-Type Piperidine Compounds
| Ref No. | Compound | $K_i$ [Average ± Std Deviation] (nM) | | | |
|---|---|---|---|---|---|
| | | | Opioid Receptor | | |
| | | ORL-1 | Mu | Kappa | Delta |
| 330 | 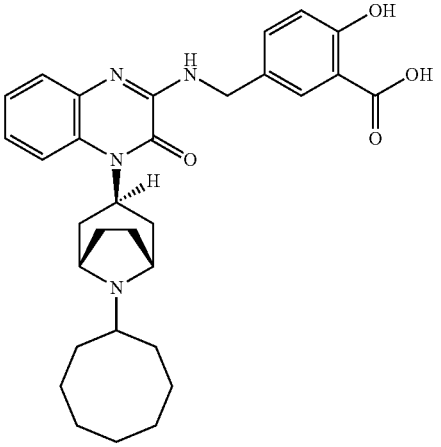 [SMILES: O=C(O)c1cc(CNc2nc3ccccc3n([C@H]3C[C@H]4CC[C@@H](C3)N4C3CCCCCCC3)c2=O)ccc1O] | 66.1 ± 5.4 | | | |
| 331 | 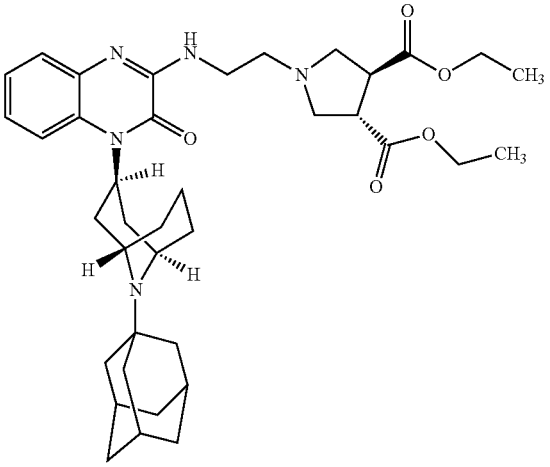 [SMILES: CCOC(=O)[C@@H]1CN(CCNc2nc3ccccc3n([C@H]3C[C@H]4CCC[C@@H](C3)N4C34CC5CC(CC(C5)C3)C4)c2=O)C[C@H]1C(=O)OCC] | 493.3 ± 60.2 | | | |
| 332 | 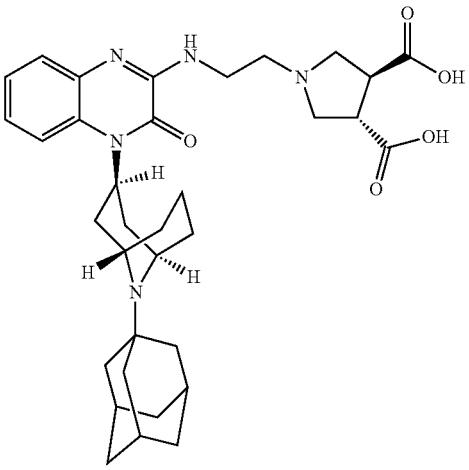 [SMILES: O=C(O)[C@@H]1CN(CCNc2nc3ccccc3n([C@H]3C[C@H]4CCC[C@@H](C3)N4C34CC5CC(CC(C5)C3)C4)c2=O)C[C@H]1C(=O)O] | 587.2 ± 38.3 | | | |
| 333 | | 29.1 ± 2.1 | 17180 ± 6501 | 5035 ± 984 | 39396 |

TABLE 1-continued

Efficacy of Receptor Binding of Substituted-Quinoxaline-Type Piperidine Compounds

| Ref No. | Compound | $K_i$ [Average ± Std Deviation] (nM) | | | |
|---|---|---|---|---|---|
| | | | Opioid Receptor | | |
| | | ORL-1 | Mu | Kappa | Delta |
| 334 | | 38.1 ± 7.2 | 4750 ± 262 | 6866 ± 1903 | 16831 ± 820 |
| 335 | | 8.6 ± 0.7 | >20,000 | 5154 ± 809 | >20,000 |
| 286 | | 2.8 ± 0.8 | >20,000 | 16760 ± 1446 | >20,000 |
| 288 | | 1.8 ± 0.3 | 2060 ± 199 | 565 ± 62 | >20,000 |
| 336 | | 3.6 ± 0.6 | 3291 ± 186 | 365 ± 98 | 5437 ± 796 |
| 290 | | 1.4 ± 0.1 | 699 ± 100 | 375 ± 157 | 3155 ± 1282 |
| 292 | | 8.5 ± 0.9 | 3429 ± 865 | 4470 ± 160 | 2141 ± 507 |
| 294 | | 2.5 ± 0.1 | 709 ± 94 | 425 ± 112 | 1606 ± 155 |

TABLE 1-continued

Efficacy of Receptor Binding of Substituted-Quinoxaline-Type Piperidine Compounds

| Ref No. | Compound | K_i [Average ± Std Deviation] (nM) | | | |
| --- | --- | --- | --- | --- | --- |
| | | Opioid Receptor | | | |
| | | ORL-1 | Mu | Kappa | Delta |
| 299 | | 289 ± 15 | | | |
| 300 | | 9.0 ± 1.5 | 443 | 63.4 ± 8.8 | 106 ± 30 |
| 296 | | 4.8 ± 0.9 | 1029 ± 108 | 1547 ± 604 | 1970 ± 259 |
| 298 | | 2.0 ± 0.1 | 396 ± 5.5 | 469 ± 157 | 1523 ± 523 |

TABLE 1-continued
Efficacy of Receptor Binding of Substituted-Quinoxaline-Type Piperidine Compounds
| Ref No. | Compound | $K_i$ [Average ± Std Deviation] (nM) Opioid Receptor | | | |
|---|---|---|---|---|---|
| | | ORL-1 | Mu | Kappa | Delta |
| 301 | 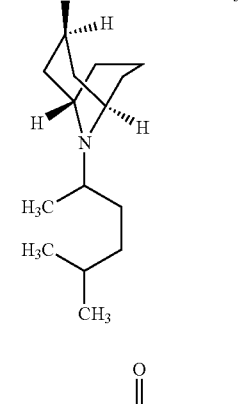 | 29.8 ± 4.0 | 487 ± 61 | 162 ± 35 | 1396 ± 241 |
| 302 | 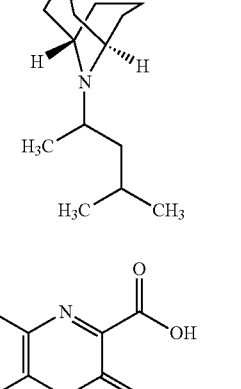 | 9.9 ± 0.8 | 160 ± 18 | 85.4 ± 18.8 | 2863 ± 334 |
| 303 | 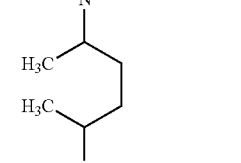 | 35.4 ± 0.6 | 664 ± 79 | 1582 ± 393 | 1102 ± 456 |

TABLE 1-continued

Efficacy of Receptor Binding of Substituted-Quinoxaline-Type Piperidine Compounds

| Ref No. | Compound | K$_i$ [Average ± Std Deviation] (nM) | | | |
|---|---|---|---|---|---|
| | | ORL-1 | Mu | Kappa | Delta |
| | | | Opioid Receptor | | |
| 304 | (structure) | 13.8 ± 2.1 | 397 ± 71 | 523 ± 75 | 667 ± 232 |
| 222 | (structure) | 30.2 ± 2.8 | 1862 ± 433 | 2889 ± 593 | 2027 ± 582 |
| 350 | | 382 ± 74 | | | |
| 351 | | 33.5 ± 3.3 | 368 ± 97 | 129.5 ± 14.4 | 11275 |
| 352 | | 11.5 ± 1.3 | 307.1 ± 4.0 | 49.7 ± 3.8 | 1743 ± 57 |
| 353 | (structure) | 22.9 ± 1.6 | 689 ± 64 | 589 ± 211 | 1159 ± 260 |

TABLE 1-continued

Efficacy of Receptor Binding of Substituted-Quinoxaline-Type Piperidine Compounds

| Ref No. | Compound | K_i [Average ± Std Deviation] (nM) Opioid Receptor | | | |
|---|---|---|---|---|---|
| | | ORL-1 | Mu | Kappa | Delta |
| 354 | | 10.5 ± 2.2 | 292 ± 81 | 20.6 ± 1.1 | 386 ± 73 |
| 355 | | 128.0 ± 7.9 | 5490 ± 85 | 3891 ± 920 | >20,000 |
| 356 | | 43.1 ± 3.4 | 1436 ± 215 | 76 ± 21 | 18180 |

TABLE 1-continued

Efficacy of Receptor Binding of Substituted-Quinoxaline-Type Piperidine Compounds

| Ref No. | Compound | $K_i$ [Average ± Std Deviation] (nM) | | | |
| --- | --- | --- | --- | --- | --- |
| | | Opioid Receptor | | | |
| | | ORL-1 | Mu | Kappa | Delta |
| 357 | | 364 ± 18 | | | |
| 358 | | 9.0 ± 1.1 | 1600 ± 55 | 640 ± 126 | 8900 ± 2390 |
| 359 | | 11.6 ± 1.5 | 407 ± 33 | 1756 ± 308 | 1011 ± 239 |

TABLE 1-continued

Efficacy of Receptor Binding of Substituted-Quinoxaline-Type Piperidine Compounds

| Ref No. | Compound | $K_i$ [Average ± Std Deviation] (nM) | | | |
|---|---|---|---|---|---|
| | | | Opioid Receptor | | |
| | | ORL-1 | Mu | Kappa | Delta |
| 360 | | 202.8 ± 7.1 | 3825 ± 576 | 2691 ± 189 | >20,000 |
| 361 | | 5.7 ± 0.4 | 4450 ± 1224 | 6143 ± 1617 | >20,000 |
| 362 | | 2.4 ± 0.2 | 1631 ± 77 | 2280 ± 213 | 4763 ± 509 |
| 363 | | 250 ± 22 | 14374 | 10240 ± 2400 | 7100 ± 1560 |

TABLE 1-continued

Efficacy of Receptor Binding of Substituted-Quinoxaline-Type Piperidine Compounds

| Ref No. | Compound | K$_i$ [Average ± Std Deviation] (nM) | | | |
| --- | --- | --- | --- | --- | --- |
| | | ORL-1 | Opioid Receptor | | |
| | | | Mu | Kappa | Delta |
| 364 | (structure) | 1.4 ± 0.1 | 670 ± 220 | 63 ± 15 | 758 ± 95 |
| 365 | | 1828 ± 123 | | | |
| 366 | (structure) | 50.0 ± 4.7 | 1759 ± 276 | 480.5 ± 26.5 | 2856 ± 763 |
| 367 | (structure) | 374 ± 73 | | | |

TABLE 1-continued
Efficacy of Receptor Binding of Substituted-Quinoxaline-Type Piperidine Compounds
| Ref No. | Compound | K$_i$ [Average ± Std Deviation] (nM) ||||
| | | Opioid Receptor ||||
| | | ORL-1 | Mu | Kappa | Delta |
|---|---|---|---|---|---|
| 368 | 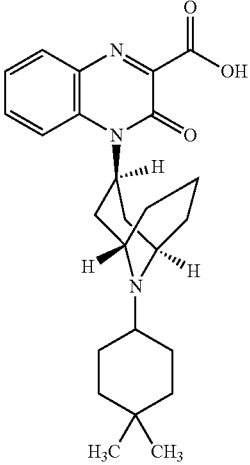 [SMILES: CC1(C)CCC(N2[C@@H]3CCC[C@H]2C[C@@H](n2c(=O)c(C(=O)O)nc4ccccc42)C3)CC1] | 828 ± 126 | | | |
| 369 | | 178 ± 17 | 4032 ± 1010 | 5345 ± 1725 | >20,000 |
| 370 | 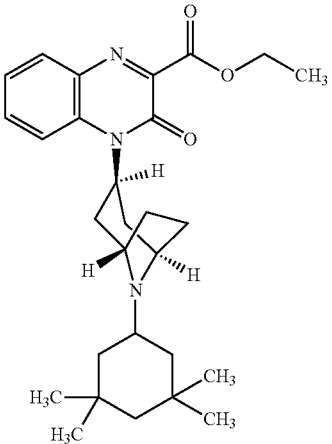 [SMILES: CCOC(=O)c1nc2ccccc2n([C@H]2C[C@H]3CC[C@@H](C2)N3C2CC(C)(C)CC(C)(C)C2)c1=O] | 1300 ± 50 | | | |
| 371 | 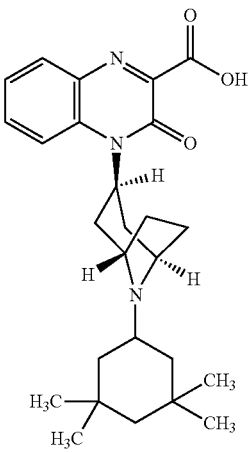 [SMILES: CC1(C)CC(N2[C@@H]3CC[C@H]2C[C@@H](n2c(=O)c(C(=O)O)nc4ccccc42)C3)CC(C)(C)C1] | 496 ± 68 | | | |

TABLE 1-continued

Efficacy of Receptor Binding of Substituted-Quinoxaline-Type Piperidine Compounds

| Ref No. | Compound | K$_i$ [Average ± Std Deviation] (nM) ORL-1 | Mu | Kappa | Delta |
|---|---|---|---|---|---|
| 372 | (structure) | 188 ± 17 | | | |

TABLE 2

Activity Response of Substituted-Quinoxaline-Type Piperidine Compounds

GTPγS (EC$_{50}$: nM, Emax: %) [mean ± SEM]

| Ref No. | ORL-1 EC$_{50}$ | ORL-1 E$_{max}$ | Mu EC$_{50}$ | Mu E$_{max}$ | Kappa EC$_{50}$ | Kappa E$_{max}$ |
|---|---|---|---|---|---|---|
| 1 | 1850 ± 190 | 43 ± 1.7 | | | | |
| 2 | 580 ± 92 | 47.3 ± 2.0 | | | 2110 ± 424 | 14.7 ± 1.5 |
| 3 | 602 ± 95 | 51.7 ± 3.7 | | | | |
| 4 | 1001 ± 105 | 83 ± 1.5 | | | 846 ± 80 | 30.5 ± 2.9 |
| 5 | 293 ± 47 | 73 ± 3.5 | | | 801 ± 208 | 13 ± 0.6 |
| 6 | 76 ± 74 | 85.3 ± 4.4 | | | 1643 ± 150 | 34.7 ± 1.7 |
| 7 | 979 ± 40 | 67.3 ± 1.9 | | | 9777 ± 2022 | 14.7 ± 1.5 |
| 8 | 4560 ± 1120 | 55.7 ± 4.2 | | | | |
| 9 | 79.1 ± 6.9 | 39 ± 1.5 | | | 1523 ± 153 | 12 ± 0.6 |
| 10 | 553 ± 59 | 34 ± 1.5 | | | 2227 ± 565 | 39.8 ± 4.8 |
| 11 | 900 ± 48 | 45.7 ± 1.8 | | | | |
| 12 | 452 ± 66 | 47.7 ± 3.5 | | | 1404 ± 86 | 28 ± 2.1 |
| 13 | 1690 ± 166 | 68.7 ± 2.4 | | | | |
| 14 | 4650 ± 238 | 54.7 ± 2.6 | | | | |
| 15 | 179 ± 24 | 93.7 ± 5.4 | | | 794 ± 14 | 28.3 ± 3.2 |
| 16 | 3745 ± 93 | 61 ± 2 | | | 10810 ± 3960 | 16 ± 3.1 |
| 17 | 7871 ± 2230 | 100 ± 9 | | | 6663 ± 286 | 7 ± 1.2 |
| 18 | 1284 ± 84 | 69.0 ± 2.7 | | | 5125 ± 716 | 28.3 ± 3.4 |
| 19 | 286 ± 30 | 115.3 ± 6.7 | | | | |
| 21 | 1466 ± 50 | 71.7 ± 1.2 | | | 460 ± 130 | 13 ± 1.2 |
| 22 | 440 ± 39 | 64 ± 3.6 | | | 690 ± 86 | 31 ± 1.2 |
| 23 | 950 ± 94 | 73.7 ± 2.3 | | | 1896 ± 380 | 6.83 ± 0.6 |
| 24 | 611 ± 71 | 78 ± 2.3 | | | 7122 ± 1182 | 15.7 ± 2.6 |
| 25 | 781 ± 26 | 79 ± 2.5 | | | | |
| 26 | 108.6 ± 5.9 | 85.3 ± 2.7 | 2883 ± 1286 | | 2076 ± 302 | 17.3 ± 0.9 |
| 27 | 969 ± 89 | 92.3 ± 0.9 | | | | |
| 28 | 1880 ± 285 | 80.3 ± 1.2 | | | | |
| 29 | 468 ± 81 | 85 ± 0.6 | | | 3812 ± 747 | 8.25 ± 0.48 |
| 30 | 699 ± 19 | 92.7 ± 3.5 | | | 3967 ± 1203 | 9.67 ± 1.5 |
| 31 | 335 ± 32 | 76.3 ± 3.9 | | | 1400 ± 49 | 39.3 ± 2.0 |
| 32 | 406 ± 42 | 76 ± 0.6 | | | 7031 ± 662 | 29 ± 3.5 |
| 33 | 211 ± 21 | 71.3 ± 3.7 | | | | |
| 34 | 1077 ± 140 | 43 ± 2.1 | | | 187 ± 41.6 | 26 ± 7 |

TABLE 2-continued

Activity Response of Substituted-Quinoxaline-Type Piperidine Compounds

GTPγS (EC$_{50}$: nM, Emax: %) [mean ± SEM]

| Ref No. | ORL-1 EC$_{50}$ | ORL-1 E$_{max}$ | Opioid Receptor Mu EC$_{50}$ | Mu E$_{max}$ | Kappa EC$_{50}$ | Kappa E$_{max}$ |
|---|---|---|---|---|---|---|
| 37 | 265 ± 31 | 97.7 ± 4.8 | | | 1499 ± 281 | 29 ± 5.1 |
| 38 | 71.2 ± 8.1 | 119.7 ± 2.7 | | | 8763 ± 1214 | 7 ± 1.2 |
| 39 | 88 ± 30 | 78 ± 10 | | | 285 ± 54 | 12.7 ± 4.1 |
| 42 | 543 ± 27 | 86.3 ± 2.4 | | | 4367 ± 1002 | 8.67 ± 0.33 |
| 43 | 474 ± 67 | 88.3 ± 2.7 | 6439 ± 1518 | 1.77 ± 0.4 | 311.2 ± 39.6 | 12.67 ± 1.5 |
| 44 | 392.2 ± 6.6 | 38 ± 3.8 | 8696 ± 3404 | 4 ± 1 | 980 ± 155 | 20.33 ± 1.9 |
| 45 | 169 ± 58 | 98.7 ± 9.5 | | | 5331 ± 608 | 10 ± 0.6 |
| 46 | 399 ± 56 | 112.7 ± 2.3 | | | 4105 ± 223 | 30 ± 1.5 |
| 47 | 418.7 ± 12.7 | 98.7 ± 4.4 | | | 3515 ± 466 | 10.67 ± 1.2 |
| 49 | 808 ± 110 | 76.3 ± 5.4 | | | 5398 ± 125 | 9.33 ± 0.7 |
| 50 | 367 ± 11 | 68 ± 2.5 | 689761 | 6 ± 4 | | |
| 51 | 49.1 ± 8.2 | 107 ± 3.1 | 6125 ± 419 | 2.33 ± 0.7 | 276 ± 42 | 11 ± 2.5 |
| 52 | 957 ± 35 | 99 ± 4.6 | | | 2816 ± 93 | 9 ± 0.6 |
| 54 | 464 ± 28 | 100.3 ± 3.3 | | | | |
| 55 | 421 ± 50 | 106.7 ± 3.7 | | | 4862 ± 1205 | 9.33 ± 0.9 |
| 56 | 113 ± 11 | 48.7 ± 1.9 | | | 2545 ± 960 | 14 ± 1 |
| 57 | 486 ± 34 | 85.3 ± 5.0 | | | 5238 ± 1981 | 12 ± 1 |
| 58 | 151.4 ± 7.9 | 96 ± 2.9 | 13779 ± 5344 | 4.67 ± 0.3 | 5930 ± 1751 | 13 ± 1.5 |
| 59 | 383 ± 63 | 106.5 ± 3.8 | | | 5040 ± 774 | 12 ± 0.6 |
| 60 | 2137 ± 661 | 88.7 ± 6.3 | | | 6901 ± 1020 | 16.67 ± 0.7 |
| 61 | 1234 ± 238 | 73.3 ± 2.3 | | | 7826 ± 1712 | 7.67 ± 1.8 |
| 64 | 457 ± 90 | 87.7 ± 2.3 | | | | |
| 65 | 348 ± 22 | 107.7 ± 3.3 | | | | |
| 66 | 107.6 ± 15.1 | 109.3 ± 5.4 | | | 3543 ± 1799 | 13.7 ± 1.2 |
| 67 | 84.9 ± 4.3 | 78.3 ± 3.8 | | | 6571 ± 1028 | 16.7 ± 0.3 |
| 68 | 478 ± 6.4 | 101 ± 5.9 | | | | |
| 70 | 788 ± 44 | 54.7 ± 1.3 | | | 2103 ± 403 | 12.7 ± 0.9 |
| 71 | 964 ± 116 | 65.3 ± 2.6 | | | | |
| 72 | 1479 ± 116 | 42.0 ± 2.9 | | | 297 ± 195 | 47.0 ± 1.2 |
| 73 | 377 ± 115 | 15.7 ± 1.7 | | | | |
| 74 | 184 ± 21 | 113.3 ± 3.3 | 4066 ± 137 | 10.0 ± 0.6 | 1222 ± 349 | 11.3 ± 1.5 |
| 77 | 97.8 ± 9.7 | 128 ± 4.7 | | | | |
| 78 | 363 ± 20 | 102.3 ± 5.7 | | | 3463 ± 1057 | 11.3 ± 1.3 |
| 79 | 703 ± 39 | 88.3 ± 2.4 | | | 3885 ± 1542 | 11.3 ± 1.2 |
| 81 | 469 ± 8 | 79.3 ± 3.2 | | | 1709 ± 376 | 4.7 ± 0.7 |
| 82 | 181.4 ± 9.8 | 102 ± 3.2 | | | 3019 ± 559 | 8 |
| 83 | 558 ± 77 | 79 ± 2.5 | | | 1981 ± 152 | 11.3 ± 1.5 |
| 84 | 182 ± 22 | 105.3 ± 1.7 | | | 4013 ± 406 | 33.3 ± 0.9 |
| 85 | 197 ± 35 | 67.0 ± 3.2 | 3118 ± 525 | 22 ± 2 | 1936 ± 141 | 27.0 ± 1.7 |
| 86 | 422 ± 40 | 116.7 ± 7.4 | 529310 | | 362 ± 54 | 11.8 ± 0.6 |
| 88 | 201 ± 27 | 110.7 ± 2.9 | | | 2278 ± 266 | 16 ± 0.6 |
| 89 | 806 ± 85 | 74.3 ± 3.4 | | | | |
| 90 | 72.7 ± 13.7 | 104.7 ± 3.8 | 3569 ± 1391 | 9.7 ± 0.3 | 6001 ± 444 | 9.3 ± 1.4 |
| 91 | 51.7 ± 14.3 | 113.7 ± 2.0 | 6198 ± 677 | 16.3 ± 1.2 | 4145 ± 457 | 10.3 ± 0.9 |
| 92 | 510 ± 100 | 74.3 ± 6.0 | | | 2267 ± 101 | 3.3 ± 0.7 |
| 94 | 61.3 ± 5.6 | 113 ± 8 | 7001 ± 3621 | 13 ± 2.1 | 1125 ± 434 | 17 ± 2.7 |
| 95 | 92 ± 14 | 103.3 ± 5.2 | | | | |
| 98 | 93.1 ± 8.3 | 83.3 ± 8.0 | 2150 ± 390 | 14 | 3150 ± 860 | 12.7 ± 2.7 |
| 99 | 1230 ± 158 | 74.7 ± 4.5 | | | >10$^5$ | 0.7 ± 0.9 |
| 100 | 19.1 ± 3.6 | 29 ± 2 | | | | |
| 101 | 17.0 ± 4.2 | 105.7 ± 5.0 | 4900 ± 2050 | 9.7 ± 0.7 | 32770 | 15.3 ± 4.1 |
| 102 | 103 ± 18 | 112.3 ± 6.3 | 4500 ± 1500 | 8.7 ± 3.4 | 960 ± 167 | 5.7 ± 0.3 |
| 103 | 3240 ± 400 | 73.7 ± 4.4 | | | | |
| 104 | 2428 ± 219 | 86.3 ± 5.2 | | | | |
| 106 | 400 ± 44 | 55.3 ± 5.8 | | | | |
| 111 | 3024 ± 477 | 84 ± 10 | | | | |
| 114 | 924 ± 42 | 73 ± 2 | | | | |
| 115 | 43.6 ± 0.9 | 35.3 ± 2.3 | 1061 ± 52 | 93 | 3512 ± 647 | 18 ± 2 |
| 119 | 3663 ± 171 | 62.0 ± 1.5 | | | 5997 ± 517 | 59.3 ± 2.3 |
| 120 | 41.3 ± 4.2 | 94.0 ± 3.6 | 79340 | | 831 ± 86 | 8.7 ± 0.3 |
| 121 | 265 ± 27 | 89.7 ± 5.4 | 3485 ± 445 | 9.7 ± 1.2 | 2930 ± 132 | 10.7 ± 1.2 |
| 122 | 67.6 ± 3.0 | 87.3 ± 3.9 | 5111 ± 1661 | 8.7 ± 0.3 | 1365 ± 285 | 8.3 ± 0.9 |
| 123 | 2351 ± 369 | 110.5 ± 6.5 | | | 3779 ± 1268 | 9.0 ± 1.2 |
| 124 | 1358 ± 89 | 115 ± 5 | | | | |
| 125 | 66.9 ± 7.1 | 107.3 ± 2.4 | 3600 ± 825 | 10.8 ± 2.1 | 2560 ± 470 | 10.3 ± 1.8 |
| 126 | 594 ± 83 | 105.0 ± 0.6 | 3580 ± 140 | 10.6 ± 1.2 | 4680 ± 975 | 8.3 ± 0.9 |
| 127 | 31.3 ± 3.8 | 127.0 ± 5.3 | 1365 ± 250 | 12.5 ± 1.4 | 2450 ± 490 | 17 |
| 128 | 209 ± 31 | 102.7 ± 2.7 | 1350 ± 125 | 12.0 ± 0.8 | 4340 ± 610 | 12.7 ± 1.5 |
| 129 | 182.6 ± 7.5 | 107.7 ± 3.7 | 1750 ± 40 | 9.7 ± 0.6 | 3855 ± 572 | 8.3 ± 0.3 |
| 130 | 40.6 ± 2.4 | 59.7 ± 0.3 | 336 ± 47 | 23 ± 1 | | |

TABLE 2-continued

Activity Response of Substituted-Quinoxaline-Type Piperidine Compounds

GTPγS (EC$_{50}$: nM, Emax: %) [mean ± SEM]

| Ref No. | ORL-1 | | Opioid Receptor | | | |
|---|---|---|---|---|---|---|
| | | | Mu | | Kappa | |
| | EC$_{50}$ | E$_{max}$ | EC$_{50}$ | E$_{max}$ | EC$_{50}$ | E$_{max}$ |
| 133 | 473 ± 27 | 81.3 ± 3.0 | 1138 ± 281 | 9 ± 1 | 1138 ± 281 | 9 ± 1 |
| 226 | 357 ± 84 | 83 | | | 4567 ± 1257 | 7.7 ± 0.3 |
| 228 | 53.6 ± 8.4 | 101.3 | | | | |
| 207 | 946 ± 85 | 60 | | | 1943 ± 548 | 6.0 ± 1.5 |
| 209 | 1211 ± 54 | 69 | 1750 ± 76 | 10.5 | 9700 ± 3550 | 3.7 |
| 188 | 103.7 ± 14.3 | 36.5 | 4940 ± 525 | 11.5 | 3340 ± 1590 | 3.3 |
| 189 | 175 ± 13 | 90 | >20,000 | 21 | >20,000 | 0.25 |
| 337 | 438 ± 15 | 78 | 7120 ± 380 | 9.1 | >20,000 | 10.7 |
| 211 | 337 ± 20 | 38 | 1080 ± 235 | 4.2 | 2260 ± 480 | 9 |
| 191 | 956 ± 67 | 67 ± 1.5 | | | | |
| 193 | 94.4 ± 19.0 | 34.5 ± 1.6 | | | 4727 ± 1215 | 13 ± 2.1 |
| 212 | 195 ± 13 | 78.7 ± 3 | | | 382 ± 97 | 6.7 ± 1.8 |
| 218 | 85 ± 17 | 53.7 ± 2.3 | | | 4839 ± 2411 | 9.7 ± 1.8 |
| 194 | 1760 ± 119 | 46.7 ± 1.9 | | | >20,000 | 0 |
| 196 | 293 ± 23 | 40.3 ± 2.3 | | | | |
| 221 | 277.1 ± 5.6 | 80.3 ± 3.8 | | | 4458 ± 865 | 9.3 ± 1.3 |
| 197 | 517 ± 48 | 31.3 ± 1.8 | | | 5960 ± 561 | 7.7 ± 1.2 |
| 199 | 1774 ± 296 | 39 ± 1 | | | >20,000 | 0 |
| 201 | 1299 ± 240 | 84 ± 1.2 | | | | |
| 216 | 397 ± 26 | 81 ± 3 | | | >20,000 | 0.3 |
| 203 | 3856 ± 15 | 73.3 ± 1.7 | | | 4587 ± 1293 | 6.3 |
| 305 | 394 ± 53 | 42.3 ± 2.9 | | | >20,000 | 1.0 |
| 174 | 1619 ± 224 | 69.7 ± 5.2 | | | >20,000 | 0.3 |
| 176 | 1519 ± 105 | 50.3 ± 4.4 | | | | |
| 178 | 125.0 ± 8.4 | 83.3 ± 5.4 | | | 3206 ± 379 | 6.3 ± 0.9 |
| 306 | 548 ± 57 | 82.3 ± 3.7 | | | 2194 ± 744 | 5.7 ± 0.3 |
| 307 | 400 ± 72 | 54.0 ± 2.3 | | | 4787 ± 336 | 11.3 ± 1.2 |
| 308 | 379 ± 58 | 97.7 ± 2.9 | 63410 | 10.3 ± 0.3 | 28900 | 24.7 ± 8.7 |
| 309 | 659 ± 155 | 92.7 ± 2.3 | 7780 ± 689 | 33.2 ± 4.3 | 24960 | 32.3 ± 9.2 |
| 310 | 419 ± 62 | 81.3 ± 3.2 | 7406 ± 723 | 16.0 ± 1.7 | 8526 ± 2196 | 14.0 ± 6.7 |
| 311 | 78.6 ± 12.5 | 74.7 ± 1.8 | 20640 | 14.0 | 28150 | 31.3 ± 3.8 |
| 240 | 103 ± 23 | 58.3 ± 1.9 | 9871 ± 1430 | 7.7 ± 0.6 | 6241 ± 2805 | 10.3 ± 5.3 |
| 312 | 138.2 ± 8.1 | 56.5 ± 2.3 | 10896 ± 666 | 17.7 ± 0.7 | 11751 ± 4518 | 20.3 ± 2.6 |
| 313 | 269 ± 53 | 67 ± 53 | 21190 | 12.3 ± 0.3 | 3946 ± 2100 | 12.0 ± 4.0 |
| 241 | 114 ± 16 | 87.3 ± 5.0 | 3922 ± 139 | 11.0 ± 0.6 | 450 ± 180 | 3.7 ± 0.3 |
| 253 | 3573 ± 302 | 67.8 ± 1.9 | | | | |
| 249 | 4252 ± 181 | 95.8 ± 3.6 | | | | |
| 314 | 453 ± 66 | 61.0 ± 0.6 | | | 4425 ± 1516 | 10.3 ± 0.9 |
| 153 | 210 ± 21 | 58.3 ± 1.6 | 643 ± 13 | 3.0 ± 0.4 | 667025 | 1.0 ± 2.0 |
| 247 | 271 ± 16 | 33.3 ± 2.2 | | | | |
| 317 | 647 ± 27 | 58.3 ± 3.9 | | | | |
| 270 | 1016 ± 203 | 99.3 ± 1.3 | | | | |
| 235 | 207 ± 10 | 88 ± 5 | | | | |
| 318 | 236 ± 13 | 44 ± 1.7 | | | 2177 ± 656 | 6.7 ± 1.9 |
| 320 | 103.6 ± 7.8 | 80 ± 4.8 | | | | |
| 233 | 503 ± 105 | 29 ± 3 | | | | |
| 325 | 109 ± 14 | 15 ± 1.2 | | | | |
| 266 | 33.8 ± 1.0 | 80 ± 2.2 | 395.4 ± 43.3 | 6.6 ± 0.7 | | |
| 263 | 298 ± 26 | 69 ± 2.9 | | | | |
| 326 | 214 ± 31 | 68 ± 3 | | | 429 ± 62 | 11.7 ± 0.3 |
| 279 | 471 ± 54 | 59 ± 2 | | | >20,000 | 4.3 ± 1.3 |
| 282 | 211.7 ± 0.9 | 58 ± 1.2 | | | 13444 ± 962 | 10.0 ± 1.2 |
| 284 | 618 ± 47 | 73.3 ± 3.7 | | | >20,000 | 8.0 ± 1.1 |
| 328 | 101.6 ± 5.2 | 75.3 ± 1.9 | | | 4397 ± 1592 | 15.0 ± 2.5 |
| 329 | 321 ± 28 | 66.3 ± 2.4 | | | 552 ± 77 | 13.0 ± 1.7 |
| 330 | 75.4 ± 9.1 | 19 ± 1.5 | | | | |
| 333 | 1831 ± 159 | 60.0 ± 1.7 | | | | |
| 334 | 293 ± 15 | 68.7 ± 3.4 | | | | |
| 335 | 174 ± 10 | 117 ± 5 | | | | |
| 286 | 17 ± 2.7 | 105.3 ± 5.7 | | | | |
| 288 | 11.6 ± 0.6 | 104 ± 4.6 | | | >20,000 | 3.3 ± 1.9 |
| 336 | 32.0 ± 5.0 | 80.3 ± 2.2 | | | >20,000 | 6.0 ± 1.5 |
| 290 | 11.1 ± 1.0 | 96.5 ± 1.9 | 3389 ± 838 | 17.3 ± 2.9 | 1770 ± 421 | 12.7 |
| 292 | 106.0 ± 3.8 | 97.5 ± 1.3 | | | | |
| 294 | 28.1 ± 2.1 | 106.3 ± 0.9 | 5705 ± 574 | 14.7 ± 1.5 | 1258 ± 258 | 20.0 |
| 300 | 53.1 ± 8.5 | 57.7 ± 2 | 5265 ± 1497 | 12 ± 1.8 | 208 ± 70 | 8.7 ± 1.3 |
| 301 | 208 ± 16 | 82.0 ± 2 | 6181 ± 1252 | 40.7 ± 3.2 | 1506 ± 494 | 10 ± 0.6 |
| 302 | 85 ± 4 | 98.3 ± 1.7 | 1365 ± 251 | 56 ± 6.5 | 1484 ± 367 | 7 ± 0.6 |
| 303 | 298 ± 23 | 90.0 ± 2 | 5468 ± 552 | 45.7 ± 7.8 | | |
| 304 | 150 ± 6 | 102.7 ± 2.7 | 1727 ± 402 | 50.7 ± 2.9 | 3269 ± 939 | 6.7 ± 1.2 |

TABLE 2-continued

Activity Response of Substituted-Quinoxaline-Type Piperidine Compounds

GTPγS (EC$_{50}$: nM, Emax: %) [mean ± SEM]

| | | | Opioid Receptor | | | |
|---|---|---|---|---|---|---|
| Ref | ORL-1 | | Mu | | Kappa | |
| No. | EC$_{50}$ | E$_{max}$ | EC$_{50}$ | E$_{max}$ | EC$_{50}$ | E$_{max}$ |
| 351 | 361 ± 58 | 53.3 ± 0.6 | 36425 | 20.0 ± 0.6 | 46490 | 63 ± 11 |
| 352 | 199 ± 40 | 80.0 ± 1.7 | 1727 ± 321 | 8.9 ± 0.5 | 3734 ± 971 | 13.0 ± 2.3 |
| 353 | 219 ± 20 | 57.0 | 6980 ± 1255 | 31.7 | 7660 ± 1140 | 20.0 |
| 354 | 37.55 ± 1.31 | 87.0 | 1409 ± 248 | 21.7 | >20,000 | 5.3 |
| 355 | 1855 ± 414 | 74.7 ± 3.8 | | | | |
| 356 | 686 ± 41 | 93.3 ± 8 | | | >20,000 | 3.3 ± 1.2 |
| 358 | 62.6 ± 14.1 | 101.3 ± 5.7 | | | 1960 ± 806 | 11.7 ± 2.3 |
| 359 | 133.7 ± 2.7 | 89.7 ± 5.2 | 3615 ± 730 | 28.7 ± 1.2 | | |
| 360 | 1667.1 ± 18.4 | 57.3 ± 4.1 | | | | |
| 361 | 57.2 ± 3.1 | 58.7 ± 2.4 | | | | |
| 362 | 4.0 ± 0.9 | 47.8 | | | | |
| 363 | 4088 ± 1164 | 67.0 ± 5.8 | | | | |
| 364 | 9.22 ± 0.44 | 61.8 | 571.8 | 9.5 | >20,000 | 9.8 |
| 366 | 925 ± 101 | 86.5 ± 2.6 | | | 1169 ± 368 | 30.3 |
| 369 | 545 ± 85 | 37.7 ± 0.7 | | | | |
| 372 | 214 ± 57 | 20.7 ± 3.8 | | | | |

5.58 Example 58

In Vivo Assays for Prevention or Treatment of Pain

Test Animals: Each experiment uses rats weighing between 200-260 g at the start of the experiment. The rats are group-housed and have free access to food and water at all times, except prior to oral administration of a Substituted-Quinoxaline-Type Piperidine Compound when food is removed for 16 hours before dosing. A control group acts as a comparison to rats treated with a Substituted-Quinoxaline-Type Piperidine Compound. The control group is administered the carrier for the Substituted-Quinoxaline-Type Piperidine Compound. The volume of carrier administered to the control group is the same as the volume of carrier and Substituted-Quinoxaline-Type Piperidine Compound administered to the test group.

Acute Pain: To assess the actions of a Substituted-Quinoxaline-Type Piperidine Compound for the treatment or prevention of acute pain, the rat tail flick test can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Substituted-Quinoxaline-Type Piperidine Compound. Data are expressed as tail flick latency(s) and the percentage of the maximal possible effect (% MPE), i.e., 20 seconds, is calculated as follows:

$$\% \text{ MPE} = \frac{[(\text{post administration latency}) - (\text{pre-administration latency})]}{(20 s \text{ pre-administration latency})} \times 100$$

The rat tail flick test is described in F. E. D'Amour et al., "A Method for Determining Loss of Pain Sensation," *J. Pharmacol. Exp. Ther.* 72:74-79 (1941).

Inflammatory Pain: To assess the actions of a Substituted-Quinoxaline-Type Piperidine Compound for the treatment or prevention of inflammatory pain, the Freund's complete adjuvant ("FCA") model of inflammatory pain was used. FCA-induced inflammation of the rat hind paw is associated with the development of persistent inflammatory mechanical hyperalgesia and provides reliable prediction of the anti-hyperalgesic action of clinically useful analgesic drugs (L. Bartho et al., "Involvement of capsaicin-sensitive neurons in hyperalgesia and enhanced opioid antinociception in inflammation," *Naunyn-Schmiedeberg's Archives of Pharmacol.* 342:666-670 (1990)). The left hind paw of each animal was administered a 50 μL intraplantar injection of 50% FCA. 24 hour post injection, the animal was assessed for response to noxious mechanical stimuli by determining the PWT, as described below. Rats were then administered a single injection of 1, 3, 10 or 30 mg/kg of either a Substituted-Quinoxaline-Type Piperidine Compound; 30 mg/kg of a control selected from Celebrex, indomethacin or naproxen; or carrier. Responses to noxious mechanical stimuli were then determined 1, 3, 5 and 24 hours post administration. Percentage reversal of hyperalgesia for each animal was defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

Assessments of the actions of the Substituted-Quinoxaline-Type Piperidine Compounds that were tested revealed these compounds were efficacious, e.g., Substituted-Quinoxaline-Type Piperidine Compounds significantly reduced FCA-induced thermal hyperalgesia, with ED$_{50}$ values of from about 0.1 mg/kg to about 20 mg/kg and maximum % reversal values of from about 20% to about 100%. For example, for Substituted-Quinoxaline-Type Piperidine Compound 241 the $ED_{50}$ value for reversal of thermal hyperalgesia was 2.7 mg/kg at 1 hour after administration, 3.8 mg/kg at 3 hours after administration, and 2.3 mg/kg at 5 hours after administration of Substituted-Quinoxaline-Type Piperidine Compound 241. Additionally, the maximum % reversal of thermal hyperalgesia was about 80% at 3 hours after administration of Substituted-Quinoxaline-Type Piperidine Compound 241. And, for Substituted-Quinoxaline-Type Piperidine Compound 74 the $ED_{50}$ value for reversal of thermal hyperalgesia was 8.5 mg/kg at 1 hour after administration, 4.0 mg/kg at 3 hours after administration, and 7.8 mg/kg at 5 hours after administration of Substituted-Quinoxaline-Type Piperidine Compound 74. Additionally, the maximum % reversal of thermal hyperalgesia was about 80% at 3 hours after administration of Substituted-Quinoxaline-Type Piperidine Compound 74.

Moreover, for the Substituted Quinoxaline-Type Piperidine Compound 362, the $ED_{50}$ value for reversal of thermal hyperalgesia was 0.8 mg/kg at 1 hour after administration, 1.5 mg/kg at 3 hours after administration, and 3.0 mg/kg at 5 hours after administration of Substituted Quinoxaline-Type Piperidine Compound 362. Additionally, the % reversal of thermal hyperalgesia after administration of a 3 mg/kg dose was 86% at 1 hour after administration, 51% at 3 hours after administration, and 27% at 5 hours after administration of Substituted Quinoxaline-Type Piperidine Compound 362. And, for Substituted Quinoxaline-Type Piperidine Compound 361, upon administration of a 5 mg/kg dose, the % reversal of thermal hyperalgesia was 36% reversal at 1 hour after administration, 90% reversal at 3 hours after administration, and 70% reversal at 5 hours after administration of Substituted Quinoxaline-Type Piperidine Compound 361. And, for Substituted Quinoxaline-Type Piperidine Compound 358, upon administration of 5 mg/kg dose, the % reversal of thermal hyperalgesia was 34% reversal at 1 hour after administration, 46% reversal at 3 hours after administration, and 79% reversal at 5 hours after administration of Substituted Quinoxaline-Type Piperidine Compound 358.

Substituted Quinoxaline-Type Piperidine Compounds 358, 361, and 362 also have surprisingly and desirably reduced abnormal behavioral side effects, such as reduced sedation, hyperactivity and/or hypoactivity. Additionally and surprisingly, Substituted Quinoxaline-Type Piperidine Compound 362 has reduced cardiovascular side effects. These side effects were determined using known methods: an in vitro hERG (human ether a-go-go gene) assay as disclosed in Z. Zhou et al., "Properties of HERG Channels Stably Expressed in HEK 293 Cells Studied at Physiological Temperature," *Biophysical J.* 74:230-241 (1998); and APD (action potential duration) in guinea pig purkinje fibers as disclosed in J. A. Hey, "The Guinea Pig Model for Assessing Cardiotoxic Proclivities of Second Generation Antihistamines," *Arzneimittelforschung* 46(8):834-837 (1996).

Neuropathic Pain: To assess the actions of a Substituted-Quinoxaline-Type Piperidine Compound for the treatment or prevention of neuropathic pain, either the Seltzer model or the Chung model can be used.

In the Seltzer model, the partial sciatic nerve ligation model of neuropathic pain is used to produce neuropathic hyperalgesia in rats (Z. Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration for rear paw of the animal. Percentage reversal of neuropathic hyperalgesia is defined as:

$$\% \text{ Reversal} = \frac{[(\text{post administration } PWT) - (\text{pre-administration } PWT)]}{[(\text{baseline } PWT) - (\text{pre-administration } PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Substituted-Quinoxaline-Type Piperidine Compound for the left rear paw of the animal. The animal can also be assessed for response to noxious thermal stimuli or for tactile allodynia, as described below. The Chung model for neuropathic pain is described in S. H. Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia: The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in C. Stein, "Unilateral Inflammation of the Hind-paw in Rats as a Model of Prolonged Noxious Stimulation: Alterations in Behavior and Nociceptive Thresholds," *Pharmacol. Biochem. and Behavior* 31:451-455 (1988). The maximum weight that can be applied to the hind paw is set at 250 g and the end point is taken as complete withdrawal of the paw. PWT is determined once for each rat at each time point and either only the affected (ipsilateral) paw is tested, or both the ipsilateral and contralateral (non-injured) paw are tested.

Response to Thermal Stimuli as an Assessment of Thermal Hyperalgesia: The plantar test can be used to assess thermal hyperalgesia. For this test, hind paw withdrawal latencies to a noxious thermal stimulus are determined using a plantar test apparatus (commercially available from Ugo Basile of Italy) following the technique described by K. Hargreaves et al., "A New and Sensitive Method for Measuring Thermal Nociception in Cutaneous Hyperalgesia," Pain 32(1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia: To assess tactile allodynia, rats are placed in clear, plexiglass compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

The invention is not to be limited in scope by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

A number of references have been cited, the entire disclosures of which are incorporated herein by reference for all purposes.

What is claimed:
1. A compound of Formula (IIE):

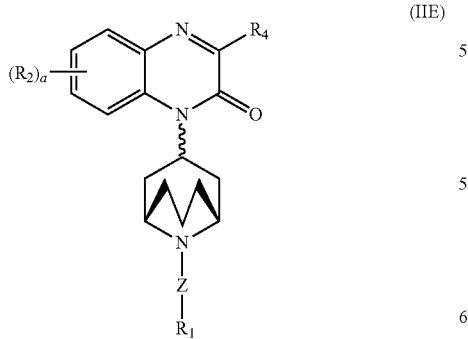

(IIE)

or a pharmaceutically acceptable salt thereof wherein:
each $R_2$ is independently:
(a) -halo, —CN, —$NO_2$, —$OT_3$, —C(=O)$T_3$, —C(=O)$OT_3$, —C(=O)N($T_1$)($T_2$), —S(=O)$_2$OH, —S(=O)$T_3$, —S(=O)$_2T_3$, —S(=O)$_2$N($T_1$)($T_2$), —N($T_1$)($T_2$), —N($T_3$)C(=O)$T_3$, —N($T_3$)C(=O)N($T_1$)($T_2$), —N($T_3$)S(=O)$_2T_3$, or —N($T_3$)S(=O)$_2$N($T_1$)($T_2$); or
(b) —($C_1$-$C_6$)alkyl, —($C_2$-$C_6$)alkenyl, —($C_2$-$C_6$)alkynyl, —($C_1$-$C_6$)alkoxy, —($C_3$-$C_7$)cycloalkyl, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(5- or 6-membered)heterocycle, or -(7- to 10-membered)bicycloheterocycle, each of which is unsubstituted or substituted with 1, 2 or 3 independently selected $R_8$ groups; or
(c) -phenyl, -naphthalenyl, —($C_{14}$)aryl, or -(5- or 6-membered)heteroaryl, each of which is unsubstituted or substituted with 1, 2 or 3 independently selected $R_7$ groups;
a is an integer selected from 0, 1, and 2;
each $R_4$ is independently:
(a) —H; or
(b) -halo, —CN, or —$NO_2$; or
(c) —X, —($C_1$-$C_6$)alkyl-X, -(5- or 6-membered)heterocycle-X, or -(5- or 6-membered)heterocycle-($C_1$-$C_6$)alkyl-X; or
(d) —C(=Y)CN, —C(=Y)X, —C(=Y)$T_3$, —C(=Y)YX, —C(=Y)$YT_3$, —C(=Y)N($T_1$)($T_2$), —C(=Y)N($R_9$)CN, —C(=Y)N($R_9$)X, —C(=Y)N($R_9$)YH, —C(=Y)N($R_9$)YX, —C(=Y)N($R_9$)YCH$_2$X, —C(=Y)N($R_9$)YCH$_2$CH$_2$X, or —C(=Y)N($R_9$)S(=O)$_2T_3$; or
(e) —N($R_9$)X, —N($R_9$)—CH$_2$X, —N($R_9$)—CH$_2$CH$_2$X, —N($R_9$)CH$_2$N($R_9$)C(=N($R_{12}$))N($R_{12}$)$_2$, —N($R_9$)—CH$_2$CH$_2$N($R_9$)C(=N($R_{12}$))N($R_{12}$)$_2$, —N($T_1$)($T_2$), —N($T_3$)C(=Y)$T_3$, —N($T_3$)C(=Y)$YT_3$, —N($T_3$)C(=Y)N($T_1$)($T_2$), —N($T_3$)S(=O)$_2T_3$, or —N($T_3$)S(=O)$_2$N($T_1$)($T_2$); or
(f) —YH, —CH$_2$YH, —CH$_2$CH$_2$YH, —YX, or —$YT_3$; or
(g) —S(=O)$T_3$, —S(=O)$_2T_3$, —S(=O)N($T_1$)($T_2$), —S(=O)$_2$N($T_1$)($T_2$), —S(=O)X, or —S(=O)$_2$X;
X is:
(a) —H, —($C_1$-$C_6$)alkyl, —($C_2$-$C_6$)alkenyl, —($C_2$-$C_6$)alkynyl, —($C_1$-$C_6$)alkoxy, —($C_3$-$C_7$)cycloalkyl, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(5- or 6-membered)heterocycle, or -(7- to 10-membered)bicycloheterocycle, each of which is unsubstituted or substituted with 1, 2 or 3 independently selected $R_8$ groups; or
(b) -phenyl, -naphthalenyl, —($C_{14}$)aryl, or -(5- or 6-membered)heteroaryl, each of which is unsubstituted or substituted with 1, 2 or 3 independently selected $R_7$ groups;
each Y is independently O or S;
Z is —[($C_1$-$C_{10}$)alkyl optionally substituted by $R_1$]$_h$—, wherein h is 0 or 1; or —($C_1$-$C_{10}$)alkyl-NR$_6$C(=Y)—;
each $R_1$ is independently:
(a) -halo, —CN, —OH, —CH$_2$OH, —CH$_2$CH$_2$OH, —$NO_2$, —N($R_6$)$_2$, —S(=O)NH$_2$, —S(=O)$_2$NH$_2$, —C(=O)$OV_1$, or —C(=O)CN; or
(b) —($C_1$-$C_{10}$)alkyl, —($C_2$-$C_{10}$)alkenyl, —($C_2$-$C_{10}$)alkynyl, —O($C_1$-$C_6$)alkyl, —($C_3$-$C_7$)cycloalkoxy, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, or -(3- to 7-membered)heterocycle, each of which is unsubstituted or substituted with 1, 2 or 3 independently selected $R_8$ groups; or (c)

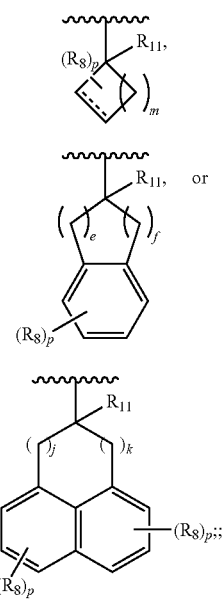

or (d) -phenyl, -naphthalenyl, or —(C$_{14}$)aryl, each of which is unsubstituted or substituted with an R$_7$ group; or —Z—R$_1$ is 3,3-diphenylpropyl- optionally substituted at the 3 carbon of the propyl with —CN, —C(=O)N(R$_6$)$_2$, —C(=O)OV$_1$, or -tetrazolyl; or —Z—R$_1$ is —(C$_1$-C$_4$)alkyl substituted with tetrazolyl;

each R$_5$ is independently —(C$_1$-C$_4$)alkyl, —(C$_2$-C$_6$)alkenyl, —(C$_2$-C$_6$)alkynyl, -(5- or 6-membered)heteroaryl, —(C$_1$-C$_6$)alkyl-C(=O)OR$_9$, —OR$_9$, —SR$_9$, —C(halo)$_3$, —CH(halo)$_2$, —CH$_2$(halo), —CN, =O, =S, -halo, —N$_3$, —NO$_2$, —CH=N(R$_9$), —N(R$_9$)(C$_1$-C$_6$)alkyl-C(=O)OR$_9$, —N(R$_9$)$_2$, —N(R$_9$)OH, —N(R$_9$)S(=O)R$_{12}$, —N(R$_9$)S(=O)$_2$R$_{12}$, —N(R$_9$)C(=O)R$_{12}$, —N(R$_9$)C(=O)OR$_{12}$, —C(=O)R$_9$, —C(=O)OR$_9$, —OC(=O)R$_9$, —OC(=O)OR$_9$, —S(=O)R$_9$, or —S(=O)$_2$R$_9$;

each R$_6$ is independently —H, —(C$_1$-C$_6$)alkyl, or —(C$_3$-C$_7$)cycloalkyl, or two R$_6$ groups attached to the same nitrogen atom can together form a 5- to 8-membered ring, wherein the number of atoms in the ring includes the nitrogen atom, and in which one of the 5- to 8-membered ring carbon atoms is optionally replaced by O, S, or N(T$_3$);

each R$_7$ is independently —(C$_1$-C$_4$)alkyl, —(C$_2$-C$_6$)alkenyl, —(C$_2$-C$_6$)alkynyl, —OR$_9$, —SR$_9$, —C(halo)$_3$, —CH(halo)$_2$, —CH$_2$(halo), —CN, -halo, —N$_3$, —NO$_2$, —CH=N(R$_9$), —N(R$_9$)$_2$, —N(R$_9$)OH, —N(R$_9$)S(=O)R$_{12}$, —N(R$_9$)S(=O)$_2$R$_{12}$, —N(R$_9$)C(=O)R$_{12}$, —N(R$_9$)C(=O)N(T$_1$)(T$_2$), —N(R$_9$)C(=O)OR$_{12}$, —C(=O)R$_9$, —C(=O)N(T$_1$)(T$_2$), —C(=O)OR$_9$, —OC(=O)R$_9$, —OC(=O)N(T$_1$)(T$_2$), —OC(=O)OR$_9$, —S(=O)R$_9$, or —S(=O)$_2$R$_9$;

each R$_8$ is independently —(C$_1$-C$_4$)alkyl, —(C$_2$-C$_6$)alkenyl, —(C$_2$-C$_6$)alkynyl, -(5- or 6-membered)heteroaryl, —(C$_1$-C$_6$)alkyl-C(=O)OR$_9$, —OR$_9$, —SR$_9$, —C(halo)$_3$, —CH(halo)$_2$, —CH$_2$(halo), —CN, =O, =S, -halo, —N$_3$, —NO$_2$, —CH=N(R$_9$), —N(R$_9$)(C$_1$-C$_6$)alkyl-C(=O)OR$_9$, —N(R$_9$)$_2$, —N(R$_9$)OH, —N(R$_9$)S(=O)R$_{12}$, —N(R$_9$)S(=O)$_2$R$_{12}$, —N(R$_9$)C(=O)R$_{12}$, —N(R$_9$)C(=O)N(T$_1$)(T$_2$), —N(R$_9$)C(=O)OR$_{12}$, —C(=O)R$_9$, —C(=O)N(T$_1$)(T$_2$), —C(=O)OR$_9$, —OC(=O)R$_9$, —OC(=O)N(T$_1$)(T$_2$), —OC(=O)OR$_9$, —S(=O)R$_9$, or —S(=O)$_2$R$_9$;

each R$_9$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -benzyl, -(3- to 6-membered)heterocycle, —C(halo)$_3$, —CH(halo)$_2$, or —CH$_2$(halo);

if h is 0, then R$_{11}$ can be —H, —CN, —C(=O)OR$_9$, or —C(=O)N(R$_6$)$_2$ or R$_{11}$ can be —(C$_1$-C$_4$)alkyl which is unsubstituted or substituted with —OH, —(C$_1$-C$_4$)alkoxy, —N(R$_6$)$_2$, —C(=O)OR$_9$, or —C(=O)N(R$_6$)$_2$;

if h is 1, then R$_{11}$ can be —H, —CN, —OH, -halo, —C(=O)OR$_9$, or —C(=O)N(R$_6$)$_2$ or R$_{11}$ can be —(C$_1$-C$_4$)alkyl which is unsubstituted or substituted with —OH, —(C$_1$-C$_4$)alkoxy, —N(R$_6$)$_2$, —C(=O)OR$_9$, or —C(=O)N(R$_6$)$_2$;

otherwise, wherein Z is —(C$_1$-C$_{10}$)alkyl-NR$_6$C(=Y)—, then R$_{11}$ can be —H, —CN, —C(=O)OR$_9$, or —C(=O)N(R$_6$)$_2$ or R$_{11}$ can be —(C$_1$-C$_4$)alkyl which is unsubstituted or substituted with —OH, —(C$_1$-C$_4$)alkoxy, —N(R$_6$)$_2$, —C(=O)OR$_9$, or —C(=O)N(R$_6$)$_2$;

each R$_{12}$ is independently —H or —(C$_1$-C$_4$)alkyl;

m is an integer selected from 0, 1, 2, 3, 4, 5, 6, 7, 8, 9, 10, and 11;

e and f are each an integer independently selected from 0, 1, 2, 3, 4, and 5 provided that 2≤(e+f) ≤5;

j and k are each an integer independently selected from 0, 1, 2, 3, and 4 provided that 1≤(j+k)≤4;

each p is an integer independently selected from 0 and 1;

each T$_1$ and T$_2$ is independently —H or —(C$_1$-C$_{10}$)alkyl which is unsubstituted or substituted with 1, 2 or 3 independently selected R$_5$ groups and, optionally, in which any —(C$_1$-C$_{10}$)alkyl carbon atom except the carbon atom bonded directly to the atom to which T$_1$ or T$_2$ is attached is independently replaced by O, S, or N(R$_6$), or T$_1$ and T$_2$ can together form a 5- to 8-membered ring wherein the number of atoms in the ring includes the nitrogen atom to which T$_1$ and T$_2$ are bonded, said 5- to 8-membered ring is unsubstituted or substituted with 1, 2 or 3 independently selected R$_5$ groups and, optionally, any carbon atom in said 5- to 8-membered ring is independently replaced by O, S, or N(R$_6$);

each T$_3$ is independently —H or —(C$_1$-C$_{10}$)alkyl which is unsubstituted or substituted with 1, 2 or 3 independently selected R$_5$ groups and, optionally, in which any —(C$_1$-C$_{10}$)alkyl carbon atom except the carbon atom bonded directly to the atom to which T$_3$ is attached is independently replaced by O, S, or N(R$_{12}$);

each V$_1$ is independently —H, —(C$_1$-C$_6$)alkyl, —(C$_3$-C$_7$)cycloalkyl, -phenyl, or benzyl; and each halo is independently —F, —Cl, —Br, or —I;

provided that if Z is —[(C$_1$-C$_{10}$)alkyl optionally substituted by R$_1$]$_h$— and h is 0 then R$_4$ is not COOH.

2. The compound of claim 1 or a pharmaceutically acceptable salt thereof, wherein a is 0.

3. The compound of claim 2 or a pharmaceutically acceptable salt thereof, wherein h is 0 and R$_1$ is:

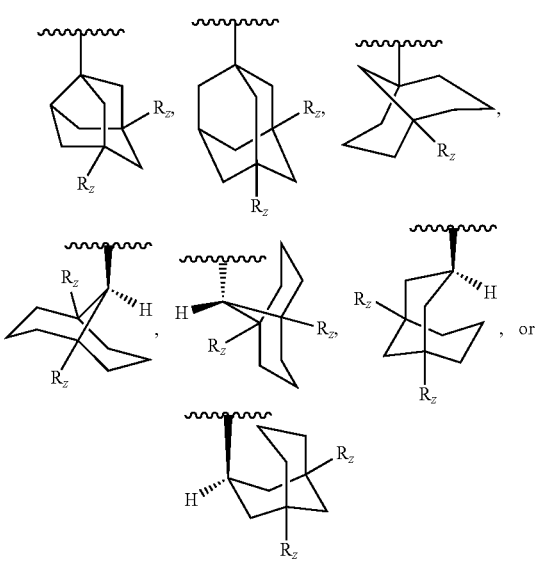

wherein each $R_z$ is independently —H, —$(C_1$-$C_4)$alkyl, —OH, or —CN.

4. The compound of claim 3 or a pharmaceutically acceptable salt thereof, wherein $R_1$ is optionally substituted bicyclo[3.3.1]nonyl.

5. The compound of claim 3 or a pharmaceutically acceptable salt thereof, wherein $R_1$ is:

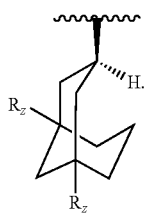

6. The compound of claim 5 or a pharmaceutically acceptable salt thereof, wherein each $R_z$ is —H.

7. The compound of claim 2 or a pharmaceutically acceptable salt thereof, wherein $R_4$ is:
(a) —C(=Y)YX; or
(b) —N($R_9$)X.

8. The compound of claim 7 or a pharmaceutically acceptable salt thereof, wherein X of —N($R_9$)X is —$(C_1$-$C_6)$alkyl substituted with one $R_8$ group, -(5- or 6-membered) heterocycle substituted with one $R_8$ group, -phenyl substituted with one $R_7$ group, or -(5- or 6-membered)heteroaryl substituted with one $R_7$ group and each $R_7$ or $R_8$ is —C(=O) O$R_9$.

9. The compound of claim 7 or a pharmaceutically acceptable salt thereof, wherein each Y is O.

10. The compound of claim 2 or a pharmaceutically acceptable salt thereof, wherein $R_4$ is X and X is -tetrazolyl.

11. The compound of claim 1 or a pharmaceutically acceptable salt thereof, wherein a is 1 and $R_2$ is selected from -halo.

12. A method for modulating ORL-1 receptor function in a cell, comprising contacting a cell capable of expressing the ORL-1 receptor with an effective amount of the compound or a pharmaceutically acceptable salt of the compound of claim 1.

13. A method for treating pain in an animal, comprising administering to an animal in need thereof an effective amount of the compound or a pharmaceutically acceptable salt of the compound of claim 1.

14. The compound of claim 1, wherein the compound of Formula (IIE) is a compound of Formula (IIE1):

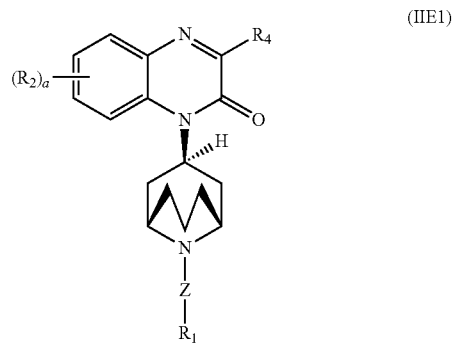

or a pharmaceutically acceptable salt thereof.

15. The compound of claim 14 or a pharmaceutically acceptable salt thereof, wherein a is 0.

16. The compound of claim 15 or a pharmaceutically acceptable salt thereof, wherein h is 0 and $R_1$ is:

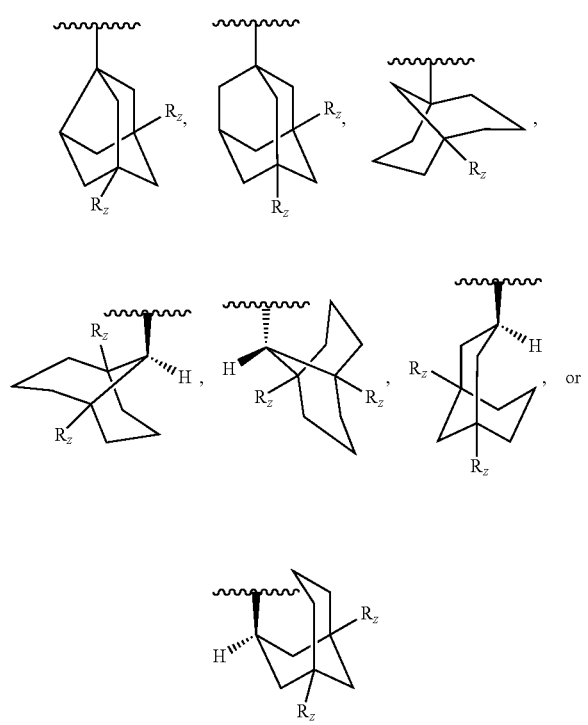

wherein each $R_z$ is independently —H, —$(C_1$-$C_4)$alkyl, —OH, or —CN.

17. The compound of claim 16 or a pharmaceutically acceptable salt thereof, wherein $R_1$ is optionally substituted bicyclo[3.3.1]nonyl.

18. The compound of claim 16 or a pharmaceutically acceptable salt thereof, wherein $R_1$ is:

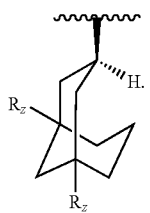
19. The compound of claim 18 or a pharmaceutically acceptable salt thereof, wherein each $R_z$ is —H.
20. The compound of claim 15 or a pharmaceutically acceptable salt thereof, wherein $R_4$ is:
(a) —C(=Y)YX; or
(b) —N($R_9$)X.
* * * * *